US012122787B2

(12) United States Patent
Guo et al.

(10) Patent No.: US 12,122,787 B2
(45) Date of Patent: *Oct. 22, 2024

(54) FUSED PYRIDONE COMPOUND, AND PREPARATION METHOD THEREFOR AND USE THEREOF

(71) Applicants: SHANGHAI JEMINCARE PHARMACEUTICALS CO., LTD, Shanghai (CN); JIANGXI JEMINCARE GROUP CO., LTD, Nanchang (CN)

(72) Inventors: Shuchun Guo, Shanghai (CN); Jun Fan, Shanghai (CN); Yang Liu, Shanghai (CN); Fang Bao, Shanghai (CN); Jianbiao Peng, Shanghai (CN); Haibing Guo, Shanghai (CN)

(73) Assignees: SHANGHAI JEMINCARE PHARMACEUTICALS CO., LTD (CN); JIANGXI JEMINCARE GROUP CO., LTD (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,515

(22) Filed: Jan. 25, 2023

(65) Prior Publication Data

US 2023/0227472 A1 Jul. 20, 2023

Related U.S. Application Data

(63) Continuation of application No. 17/761,983, filed as application No. PCT/CN2020/016510 on Sep. 21, 2020.

(30) Foreign Application Priority Data

| Sep. 20, 2019 | (CN) | 201910892032.X |
| Nov. 18, 2019 | (CN) | 201911129688.2 |
| Nov. 22, 2019 | (CN) | 201911157939.8 |
| Jan. 17, 2020 | (CN) | 202010054188.3 |
| Feb. 19, 2020 | (CN) | 202010102546.3 |
| Mar. 27, 2020 | (CN) | 202010230303.8 |
| Apr. 17, 2020 | (CN) | 202010306926.9 |
| Apr. 30, 2020 | (CN) | 202010367694.8 |
| Sep. 15, 2020 | (CN) | 202010967317.8 |

(51) Int. Cl.
| C07D 471/22 | (2006.01) |
| A61P 35/00 | (2006.01) |
| C07D 471/14 | (2006.01) |
| C07D 498/14 | (2006.01) |
| C07D 498/22 | (2006.01) |

(52) U.S. Cl.
CPC ............ C07D 498/22 (2013.01); A61P 35/00 (2018.01); C07D 471/14 (2013.01); C07D 471/22 (2013.01); C07D 498/14 (2013.01)

(58) Field of Classification Search
CPC ............ C07D 471/22; A61K 31/4985

USPC .......................................... 544/343; 514/250
See application file for complete search history.

(56) References Cited

U.S. PATENT DOCUMENTS

| 9,745,631 B2 | 8/2017 | DePinho et al. |
| 9,840,516 B2 | 12/2017 | Li et al. |
| 9,901,079 B2 | 2/2018 | Bar-Sagi et al. |
| 9,988,357 B2 | 6/2018 | Mani et al. |
| 10,111,874 B2 | 10/2018 | Janes et al. |
| 10,238,650 B2 | 3/2019 | Huang |

(Continued)

FOREIGN PATENT DOCUMENTS

| CN | 106488910 A | 3/2017 |
| CN | 107849022 A | 3/2018 |

(Continued)

OTHER PUBLICATIONS

Halford, Bethany, "Amgen unveils its KRas covalent inhibitor AMG 510." *Chemical & Engineering News* 9.14 (2019): 4-4.
Third Party Observation for application No. EP20200865331, mailed Jun. 5, 2023, 28 Pages. (English).
First Office Action for CN202010769535, mailed Jun. 18, 2021 (7 pages, English).
Search Report for CN202010769535, mailed Jun. 10, 2021 (1 page).
Supplementary Search Report for CN202010769535, mailed Nov. 17, 2021 (1 page).

(Continued)

*Primary Examiner* — Jeffrey H Murray
(74) *Attorney, Agent, or Firm* — Eversheds Sutherland (US) LLP

(57) ABSTRACT

Disclosed in the present invention are a fused pyridone compound, and a preparation method therefor and a use thereof. Specifically, the present invention discloses a compound of formula (I-B), an optical isomer thereof and a pharmaceutically acceptable salt thereof, and the use of the compound as a KRAS inhibitor.

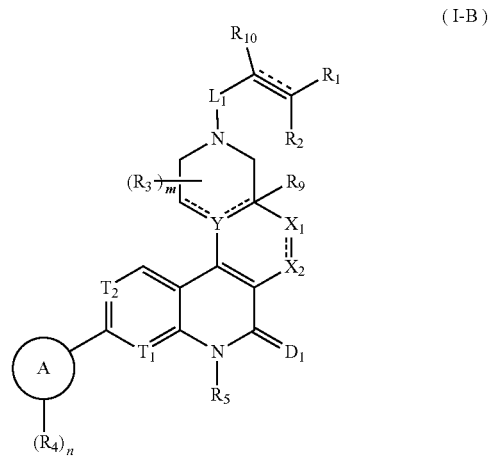

(I-B)

13 Claims, 1 Drawing Sheet

(56) References Cited

U.S. PATENT DOCUMENTS

| | | |
|---|---|---|
| 10,246,424 B2 | 4/2019 | Li et al. |
| 10,344,026 B2 | 7/2019 | Tao et al. |
| 10,428,064 B2 | 10/2019 | Li et al. |
| 10,519,146 B2 | 12/2019 | Lanman et al. |
| 10,532,042 B2 | 1/2020 | Lanman et al. |
| 10,556,906 B2 | 2/2020 | Kuramoto et al. |
| 10,588,894 B2 | 3/2020 | Hadari et al. |
| 10,597,405 B2 | 3/2020 | Kettle et al. |
| 10,640,504 B2 | 5/2020 | Lanman et al. |
| 10,662,204 B2 | 5/2020 | Planken et al. |
| 10,689,377 B2 | 6/2020 | Blake et al. |
| 10,837,015 B2 | 11/2020 | Kimmelman et al. |
| 10,968,214 B2 | 4/2021 | Barda et al. |
| 11,053,226 B2 | 7/2021 | Shin et al. |
| 11,091,481 B2 | 8/2021 | Dai |
| 11,141,418 B1 | 10/2021 | Abebe et al. |
| 11,439,645 B2 | 9/2022 | Lipford et al. |
| 2004/0121384 A1 | 6/2004 | Gelb et al. |
| 2005/0227929 A1 | 10/2005 | Masferrer |
| 2013/0231346 A1 | 9/2013 | Gilmer et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0214994 A1 | 7/2016 | Xu |
| 2016/0297774 A1 | 10/2016 | Li et al. |
| 2016/0317519 A1 | 11/2016 | Saha et al. |
| 2017/0015680 A1 | 1/2017 | Chen et al. |
| 2017/0022184 A1 | 1/2017 | Li et al. |
| 2017/0173033 A1 | 6/2017 | Brake et al. |
| 2017/0197945 A1 | 7/2017 | Li et al. |
| 2017/0247376 A1 | 8/2017 | Li et al. |
| 2017/0281633 A1 | 10/2017 | Boylan et al. |
| 2017/0283418 A1 | 10/2017 | Chen et al. |
| 2018/0086753 A1 | 3/2018 | Li et al. |
| 2018/0127396 A1 | 5/2018 | Li et al. |
| 2018/0155348 A1 | 6/2018 | Li et al. |
| 2018/0177767 A1 | 6/2018 | Lanman et al. |
| 2018/0273515 A1 | 9/2018 | Li et al. |
| 2018/0273523 A1 | 9/2018 | Li et al. |
| 2018/0282307 A1 | 10/2018 | Li et al. |
| 2018/0282308 A1 | 10/2018 | Li et al. |
| 2018/0319775 A1 | 11/2018 | Li et al. |
| 2018/0334454 A1 | 11/2018 | Lanman et al. |
| 2019/0055211 A1 | 2/2019 | Li et al. |
| 2019/0062313 A1 | 2/2019 | Li et al. |
| 2019/0062314 A1 | 2/2019 | Li et al. |
| 2019/0077801 A1 | 3/2019 | Lanman et al. |
| 2019/0092767 A1 | 3/2019 | Li et al. |
| 2019/0127336 A1 | 5/2019 | Li et al. |
| 2019/0177338 A1 | 6/2019 | Kettle et al. |
| 2019/0336514 A1 | 11/2019 | Wurz et al. |
| 2019/0343838 A1 | 11/2019 | Allen et al. |
| 2019/0345158 A1 | 11/2019 | Li et al. |
| 2019/0345169 A1 | 11/2019 | Minatti et al. |
| 2019/0367489 A1 | 12/2019 | Li et al. |
| 2019/0374542 A1 | 12/2019 | Allen et al. |
| 2019/0375749 A1 | 12/2019 | Chen et al. |
| 2019/0382377 A1 | 12/2019 | Li et al. |
| 2019/0389851 A1 | 12/2019 | Li et al. |
| 2020/0010454 A1 | 1/2020 | Li et al. |
| 2020/0010479 A1 | 1/2020 | Redinbo et al. |
| 2020/0030324 A1 | 1/2020 | Booker et al. |
| 2020/0109153 A1 | 4/2020 | Kettle et al. |
| 2020/0115363 A1 | 4/2020 | Li et al. |
| 2020/0140834 A1 | 5/2020 | Wang et al. |
| 2020/0165231 A1 | 5/2020 | Shin et al. |
| 2020/0181118 A1 | 6/2020 | Malhotra et al. |
| 2020/0222407 A1 | 7/2020 | Lipford et al. |
| 2020/0368238 A1 | 11/2020 | Nichols et al. |
| 2020/0369662 A1 | 11/2020 | Chaves et al. |
| 2020/0385364 A1 | 12/2020 | Li et al. |
| 2021/0085683 A1 | 3/2021 | Briere et al. |
| 2021/0122764 A1 | 4/2021 | Bharathan et al. |
| 2021/0130303 A1 | 5/2021 | Koltun et al. |
| 2021/0130326 A1 | 5/2021 | Aggen et al. |
| 2021/0130369 A1 | 5/2021 | Koltun et al. |
| 2021/0317127 A1 | 10/2021 | Li et al. |
| 2021/0322405 A1 | 10/2021 | Ding et al. |
| 2021/0380595 A1 | 12/2021 | Li et al. |
| 2021/0401845 A1 | 12/2021 | Abebe et al. |
| 2022/0062260 A1 | 3/2022 | Peng et al. |
| 2022/0079947 A1 | 3/2022 | Christensen et al. |
| 2022/0112192 A1 | 4/2022 | Li et al. |
| 2022/0186227 A1 | 6/2022 | Green et al. |

FOREIGN PATENT DOCUMENTS

| | | | |
|---|---|---|---|
| CN | 112047937 A | 12/2020 | |
| CN | 112225734 A | 1/2021 | |
| CN | 112300196 A | 2/2021 | |
| CN | 112390818 A | 2/2021 | |
| CN | 113061132 A | 7/2021 | |
| CN | 112300195 A | 12/2021 | |
| CN | 12300194 B * | 1/2022 | ............ C07D 498/22 |
| CN | 112300194 A | 1/2022 | |
| WO | WO2016025639 A1 | 2/2016 | |
| WO | WO2016025648 A1 | 2/2016 | |
| WO | WO2016049565 A1 | 3/2016 | |
| WO | WO2016141492 A1 | 9/2016 | |
| WO | WO2016168540 A1 | 10/2016 | |
| WO | WO2017100546 A1 | 6/2017 | |
| WO | WO2017201161 A1 | 11/2017 | |
| WO | WO2018112420 A1 | 6/2018 | |
| WO | WO2018119183 A2 | 6/2018 | |
| WO | WO2018140513 A1 | 8/2018 | |
| WO | WO2018140598 A1 | 8/2018 | |
| WO | WO2018142365 A1 | 8/2018 | |
| WO | WO2018195439 A2 | 10/2018 | |
| WO | WO2018206539 A1 | 11/2018 | |
| WO | WO2018217651 A1 | 11/2018 | |
| WO | WO2019051291 A1 | 3/2019 | |
| WO | WO2019099524 A1 | 5/2019 | |
| WO | WO2019141250 A1 | 7/2019 | |
| WO | WO2019217307 A1 | 11/2019 | |
| WO | WO2020027083 A1 | 2/2020 | |
| WO | WO2020027084 A1 | 2/2020 | |
| WO | WO2020028706 A1 | 2/2020 | |
| WO | WO2020035031 A1 | 2/2020 | |
| WO | WO2020039123 A1 | 2/2020 | |
| WO | WO2020047192 A1 | 3/2020 | |
| WO | WO2020055755 A1 | 3/2020 | |
| WO | WO2020055756 A1 | 3/2020 | |
| WO | WO2020055758 A1 | 3/2020 | |
| WO | WO2020055760 A1 | 3/2020 | |
| WO | WO2020055761 A1 | 3/2020 | |
| WO | WO2020086739 A1 | 4/2020 | |
| WO | WO2020097537 A2 | 5/2020 | |
| WO | WO2020113071 A1 | 6/2020 | |
| WO | WO2020118066 A1 | 6/2020 | |
| WO | WO2020128878 A1 | 6/2020 | |
| WO | WO2020146613 A1 | 7/2020 | |
| WO | WO2020156285 A1 | 8/2020 | |
| WO | WO2020214537 A1 | 10/2020 | |
| WO | WO2020232130 A1 | 11/2020 | |
| WO | WO2020236948 A1 | 11/2020 | |
| WO | WO2020239077 A1 | 12/2020 | |
| WO | WO2020247914 A1 | 12/2020 | |
| WO | WO2020259432 A1 | 12/2020 | |
| WO | WO2020259513 A1 | 12/2020 | |
| WO | WO2020259573 A1 | 12/2020 | |
| WO | WO2021023247 A1 | 2/2021 | |
| WO | WO2021052499 A1 | 3/2021 | |
| WO | WO2021055728 A1 | 3/2021 | |
| WO | WO2021061749 A1 | 4/2021 | |
| WO | WO2021076655 A1 | 4/2021 | |
| WO | WO2021081212 A1 | 4/2021 | |
| WO | WO2021083167 A1 | 5/2021 | |
| WO | WO2021088458 A1 | 5/2021 | |
| WO | WO2021108683 A1 | 6/2021 | |
| WO | WO2021121367 A1 | 6/2021 | |
| WO | WO2021126816 A1 | 6/2021 | |
| WO | WO2021141628 A1 | 7/2021 | |
| WO | WO2021142252 A1 | 7/2021 | |

(56) References Cited

FOREIGN PATENT DOCUMENTS

| WO | WO2021154929 A1 | 8/2021 |
| --- | --- | --- |
| WO | WO2021155716 A1 | 8/2021 |
| WO | WO2021169963 A1 | 9/2021 |
| WO | WO2021169990 A1 | 9/2021 |
| WO | WO2022036285 A1 | 2/2022 |
| WO | WO2022061202 A1 | 3/2022 |
| WO | WO2022076917 A1 | 4/2022 |
| WO | WO2022081912 A2 | 4/2022 |
| WO | WO2022087270 A1 | 4/2022 |
| WO | WO2022087624 A1 | 4/2022 |
| WO | WO2022109485 A1 | 5/2022 |
| WO | WO2022109487 A1 | 5/2022 |
| WO | WO2022125962 A1 | 6/2022 |
| WO | WO2022125971 A1 | 6/2022 |
| WO | WO2022150628 A1 | 7/2022 |
| WO | WO2022187411 A1 | 9/2022 |
| WO | WO2022197865 A1 | 9/2022 |

OTHER PUBLICATIONS

Written Opinion of the International Search Authority from PCT/CN2020/106573, mailed Jun. 11, 2020 (7 pages, English).

International Search Report from PCT/CN2020/106573, mailed Nov. 6, 2020 (8 Pages, English Translation).

Written Opinion of the International Search Authority from PCT/CN2020/116510, mailed Nov. 25, 2020 (3pages, English).

International Search Report from PCT/CN2020/116510, mailed Nov. 25, 2020 (9 Pages, English Translation).

Ostrem, Jonathan M., et al. "K-Ras (G12C) inhibitors allosterically control GTP affinity and effector interactions." *Nature* 503.7477 (2013): 548-551.

Parada, Luis F., et al. "Human EJ bladder carcinoma oncogene is homologue of Harvey sarcoma virus ras gene." *Nature* 297.5866 (1982): 474-478.

\* cited by examiner

FUSED PYRIDONE COMPOUND, AND PREPARATION METHOD THEREFOR AND USE THEREOF

CROSS-REFERENCE TO RELATED APPLICATIONS

This application is a continuation of U.S. application Ser. No. 17/761,983, filed Mar. 18, 2022, which is a National Stage Application of International Application PCT/CN2020/077391, filed Sep. 21, 2020, which claims priority to CN201910892032.X, filed Sep. 20, 2019, CN201911129688.2, filed Nov. 18, 2019, CN201911157939.8, filed Nov. 22, 2019, CN202010054188.3, filed Jan. 17, 2020, CN202010102546.3, filed Feb. 19, 2020, CN202010230303.8, filed Mar. 27, 2020, CN202010306926.9, filed Apr. 17, 2020, CN202010367694.8, filed Apr. 30, 2020, CN202010967317.8, filed Sep. 15, 2020, the content each of which is incorporated herein by reference in their entireties.

FIELD OF THE INVENTION

The present disclosure relates to a compound represented by formula (I-B), an optical isomer thereof and a pharmaceutically acceptable salt thereof, and a use of the compound as a KRAS inhibitor.

BACKGROUND

Cancer has been ranked first among the top ten causes of death in China for 31 years, wherein lung cancer is one of the tumors with the highest incidence, and its non-small cell lung cancer accounts for more than 80%, at the same time, the incidence of lung cancer is high and there are many kinds of mutations. In order to enrich the company's R&D pipeline and focus on unmet medical needs, it is necessary for the company's long-term development to develop innovative drugs for cancer treatment, which has important economic and social significance.

About 30% of cancer patients have RAS gene mutations. In the research of cancer genes, scientists found more than 20 years ago that RAS gene is the key gene of cancers such as lung cancer, colorectal cancer and pancreatic cancer.

In the United States, the three cancers with the highest mortality rate (pancreatic cancer, colorectal cancer and lung cancer) happen to be the three cancers with the most common RAS mutations, accounting for 95%, 52% and 31% of the patients of these three cancers respectively. In pancreatic cancer, colorectal cancer and lung cancer, KRAS mutation accounts for the absolute majority, while NRAS mutation is more common in melanoma and acute myeloid leukemia, and HRAS mutation is more common in bladder cancer and head and neck cancer.

The mutation rate of KRAS gene in Asian population is 10-15%, KRAS is one of the major oncogenes, which can mutate in many cancers. KRAS mutant tumor is the most potential targeted molecular subtype of non-small cell lung cancer (NSCLC), and its mutation rate is about 15%-25% in non-small cell lung cancer (NSCLC). In NSCLC cases, KRAS mutations mainly occur at codon 12 and codon 13. The most common codon variation accounted for about 39% of the mutant NSCLCs of KRAS, which is the KRAS-G12C mutation.

In lung adenocarcinoma, the positive probability of KRAS gene accounts for 1/5-1/4, which is second only to the positive mutation probability of EGFR. The lack of targeted inhibitors makes it very difficult for patients with KRAS-positive non-small cell lung cancer both in terms of treatment and prognosis. The NCCN Clinical Practice Guide for Non-small Cell Lung Cancer in 2013 clearly pointed out that before receiving EGFR-TKI treatment, patients with lung cancer must be tested for KRAS gene, and whether to use EGFR-TKI targeted drugs as a clinical treatment measure should be decided according to the test results. If the KRAS gene is mutated, the patient is not recommended for molecularly targeted therapy with EGFR-TKI.

According to the Thomson Reuters Competitive Intelligence Drug Database (Cortellis For CI), the current number of various drugs directly related to RAS genes/proteins is 162 (data accessed on Aug. 18, 2016), wherein, there are 18 KRAS small molecule drugs, including 10 KRAS GTPase inhibitors, 4 KRAS gene inhibitors, 2 KRAS GTPase modulators and 2 KRAS gene modulators; there is 1 such drug currently under clinical research. In addition, Antroquinonol, the first KRAS inhibitor developed by a Taiwanese company, has entered the Phase II clinical trial of the US FDA, and Selumetinib, an inhibitor developed by AstraZeneca targeting the MEK downstream pathway of KRAS, is also undergoing Phase II clinical trials. KRAS mutation is the most important tumor driver gene. This part of mutation cases accounted for a certain proportion in pancreatic cancer, lung cancer and rectal gastric cancer. At present, there is no specific targeting drug acting on this target. Therefore, the project has important medical research value and clinical application value, and has greater medical value for nation. The molecular mechanism for developing KRAS-G12C small molecule drug has been basically clarified; the molecular structure and pharmacodynamics of the drug have been verified under the existing experimental conditions, and it has the characteristics of high activity and the possibility of becoming a drug.

Content of the Invention

In the first aspect of the present disclosure, the present disclosure provides a compound represented by formula (I-B), an optical isomer thereof and a pharmaceutically acceptable salt thereof,

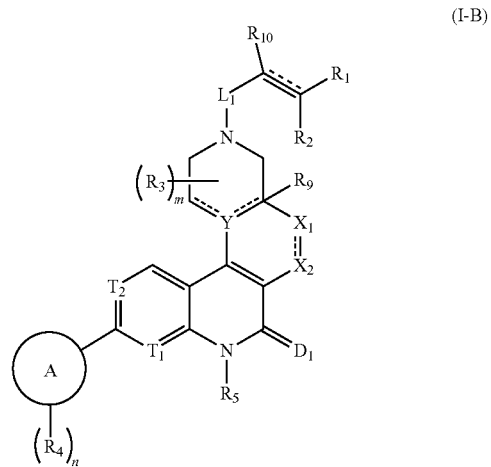

wherein,
R₁, R₂ are independently selected from H, halogen and C_{1-6} alkyl, the C_{1-6} alkyl is optionally substituted by 1, 2 or 3 R;
R₃ is selected from H, halogen, OH, NH₂, CN, C_{1-6} alkyl, C_{1-6} heteroalkyl, 3-6 membered heterocycloalkyl, C_{3-6} cycloalkyl, 3-6 membered heterocycloalkyl-O— and C_{3-6} cycloalkyl-O—, the C_{1-6} alkyl, C_{1-6} heteroalkyl, 3-6 membered heterocycloalkyl, C_{3-6} cycloalkyl, 3-6 membered heterocycloalkyl-O— or C_{3-6} cycloalkyl-O— is optionally substituted by 1, 2 or 3 R;
R₄ is independently selected from H, halogen, OH, NH₂, CN, C_{1-6} alkyl, C_{1-6} heteroalkyl, C_{3-6} cycloalkyl, 3-6 membered heterocycloalkyl, phenyl, 5-10 membered heteroalkyl, benzo 5-6 membered heterocycloalkyl and 5-6 membered heteroaryl-fused 5-6 membered heterocycloalkyl, the C_{1-6} alkyl, C_{1-6} heteroalkyl, C_{3-6} cycloalkyl, 3-6 membered heterocycloalkyl, phenyl, 5-10 membered heteroaryl, benzo 5-6 membered heterocycloalkyl or 5-6 membered heteroaryl-fused 5-6 membered heterocycloalkyl is optionally substituted by 1, 2 or 3 R;
R₅ is selected from H, C_{1-6} alkyl, C_{3-6} cycloalkyl, 5-6 membered heterocycloalkyl-C_{1-3} alkyl-, 3-8 membered heterocycloalkyl, phenyl, naphthyl, 5-10 membered heteroaryl, benzo 5-6 membered heterocycloalkyl and 5-6 membered heteroaryl-fused 5-6 membered heterocycloalkyl, the C_{1-6} alkyl, C_{3-6} cycloalkyl, 5-6 membered heterocycloalkyl-C_{1-3} alkyl-, 3-8 membered heterocycloalkyl, phenyl, naphthyl, 5-10 membered heteroaryl, benzo 5-6 membered heterocycloalkyl or 5-6 membered heteroaryl-fused 5-6 membered heterocycloalkyl is optionally substituted by 1, 2 or 3 R;
L₁ is selected from —C(=O)—, —S(=O)— and —S(=O)₂—;
R₆ is selected from H, CN, C_{1-6} alkyl, C_{1-6} alkyl-S(=O)₂—, 3-6 membered heterocycloalkyl, —C_{1-6} alkyl-3-6 membered heterocycloalkyl and C_{3-6} cycloalkyl-C(=O)—, the C_{1-6} alkyl, C_{1-6} alkyl-S(=O)₂—, 3-6 membered heterocycloalkyl, —C_{1-6} alkyl-3-6 membered heterocycloalkyl or C_{3-6} cycloalkyl-C(=O)— is optionally substituted by 1, 2 or 3 R;
R₇ is independently selected from H, halogen, OH, NH₂, CN, —C(=O)—OH, C_{1-6} alkyl-O—C(=O)—, —C(=O)—NH₂, C_{1-6} alkyl, C_{1-6} heteroalkyl and —C_{1-6} alkyl-3-6 membered heterocycloalkyl, the C_{1-6} alkyl, C_{1-6} heteroalkylC_{1-6} alkyl-O—C(=O)— or —C_{1-6} alkyl-3-6 membered heterocycloalkyl is optionally substituted by 1, 2 or 3 R;
T₁, T₂ are independently selected from N and —C(R₈)—;
R₈ is selected from H, halogen, OH, NH₂, CN, C_{1-6} alkyl, C_{1-6} heteroalkyl, C_{3-6} cycloalkyl and 3-6 membered heterocycloalkyl, the C_{1-6} alkyl, C_{1-6} heteroalkyl, C_{3-6} cycloalkyl or 3-6 membered heterocycloalkyl is optionally substituted by 1, 2 or 3 R;
R₉ is selected from H, halogen, OH, NH₂, CN, C_{1-6} alkyl and C_{1-6} heteroalkyl, the C_{1-6} alkyl or C_{1-6} heteroalkyl is optionally substituted by 1, 2 or 3 R;
R₁₀ is selected from H, halogen, CN, C_{1-6} alkyl, C_{1-6} alkoxy and C_{1-6} alkylamino, the C_{1-6} alkyl, C_{1-6} alkoxy or C_{1-6} alkylamino is optionally substituted by 1, 2 or 3 R;
R is independently selected from H, halogen, OH, NH₂, CN,

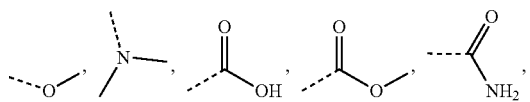

C_{1-6} alkyl, C_{1-6} heteroalkyl, C_{3-6} cycloalkyl, 5-6 membered heterocycloalkyl, C_{3-6} cycloalkyl-O— and 5-6 membered heterocycloalkyl-O—, the C_{1-6} alkyl, C_{1-6} heterocycloalkyl, C_{3-6} cycloalkyl, 5-6 membered heterocycloalkyl, C_{3-6} cycloalkyl-O— or 5-6 membered heterocycloalkyl-O— is optionally substituted by 1, 2 or 3 R';
R' is selected from F, Cl, Br, I, OH, NH₂ and CH₃;
ring A is independently selected from C_{6-10} aryl, 5-10 membered heteroaryl, benzo 5-6 membered heterocycloalkyl and 5-6 membered heteroaryl-fused 5-6 membered heterocycloalkyl;
n is selected from 0, 1, 2, 3 or 4;
m is selected from 0, 1, 2, 3 or 4;
D₁ is selected from O;
Y is selected from N, CH or C;
≈ is ＼ or ⫽, and when ≈ is ⫽, R₂, R₁₀ are not existed;
≈ is ＼ or ⟋;
when in ⟍, ≈ is ＼, X₁, X₂ are independently selected from —N=, —C(R₇)= and —C(R₇)₂—C(R₇)=;
when in ⟍, ≈ is ⟋, X₁, X₂ are independently selected from single bond, —O—, —S—, S(=O), S(=O)₂, —N(R₆)—, —C(=O)—, —C(R₇)₂— and —C(R₇)₂—C(R₇)₂—;
and, Y cannot be connected to two ＼ at the same time, when the bond between Y and R₉ is ＼, R₉ is not existed;
the above 3-6 membered heterocycloalkyl, 5-6 membered heteroaryl, 5-6 membered heterocycloalkyl, 5-10 membered heteroaryl or C_{1-6} heterocycloalkyl comprises 1, 2, or 3 heteroatoms or heteroatomic groups independently selected from —O—, —NH—, —S—, —C(=O)—, —C(=O)O—, —S(=O)—, —S(=O)₂— and N.

In another aspect of the present disclosure, the present disclosure also provides a compound represented by formula (I-A), an optical isomer thereof and a pharmaceutically acceptable salt thereof,

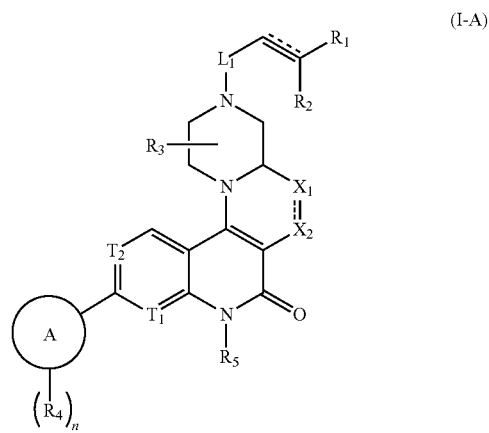

(I-A)

wherein,
R$_1$, R$_2$ are independently selected from H, halogen and C$_{1-6}$ alkyl, the C$_{1-6}$ alkyl is optionally substituted by 1, 2 or 3 R;
R$_3$ is selected from H, halogen, OH, NH$_2$, CN, C$_{1-6}$ alkyl, C$_{1-6}$ heteroalkyl, 3-6 membered heterocycloalkyl, C$_{3-6}$ cycloalkyl, 3-6 membered heterocycloalkyl-O— and C$_{3-6}$ cycloalkyl-O—, the C$_{1-6}$ alkyl, C$_{1-6}$ heteroalkyl, 3-6 membered heterocycloalkyl, C$_{3-6}$ cycloalkyl, 3-6 membered heterocycloalkyl-O— or C$_{3-6}$ cycloalkyl-O— is optionally substituted by 1, 2 or 3 R;
R$_4$ is independently selected from H, halogen, OH, NH$_2$, CN, C$_{1-6}$ alkyl, C$_{1-6}$ heteroalkyl, C$_{3-6}$ cycloalkyl, 3-6 membered heterocycloalkyl, phenyl, 5-10 membered heteroaryl, benzo 5-6 membered heterocycloalkyl and 5-6 membered heteroaryl-fused 5-6 membered heterocycloalkyl, the C$_{1-6}$ alkyl, C$_{1-6}$ heteroalkyl, C$_{3-6}$ cycloalkyl, 3-6 membered heterocycloalkyl, phenyl, 5-10 membered heteroaryl, benzo 5-6 membered heterocycloalkyl or 5-6 membered heteroaryl-fused 5-6 membered heterocycloalkyl is optionally substituted by 1, 2 or 3 R;
R$_5$ is selected from H, C$_{1-6}$ alkyl, C$_{3-6}$ cycloalkyl, 5-6 membered heterocycloalkyl-C$_{1-3}$ alkyl-, 3-8 membered heterocycloalkyl, phenyl, naphthyl, 5-10 membered heteroaryl, benzo 5-6 membered heterocycloalkyl and 5-6 membered heteroaryl-fused 5-6 membered heterocycloalkyl, the C$_{1-6}$ alkyl, C$_{3-6}$ cycloalkyl, 5-6 membered heterocycloalkyl-C$_{1-3}$ alkyl-, 3-8 membered heterocycloalkyl, phenyl, naphthyl, 5-10 membered heteroaryl, benzo 5-6 membered heterocycloalkyl or 5-6 membered heteroaryl-fused 5-6 membered heterocycloalkyl is optionally substituted by 1, 2 or 3 R;
L$_1$ is selected from —C(=O)—, —S(=O)— and —S(=O)$_2$—;
R$_6$ is selected from H, CN, C$_{1-6}$ alkyl, C$_{1-6}$ alkyl-S(=O)$_2$—, 3-6 membered heterocycloalkyl, —C$_{1-6}$ alkyl-3-6 membered heterocycloalkyl and C$_{3-6}$ cycloalkyl-C(=O)—, the C$_{1-6}$ alkyl, C$_{1-6}$ alkyl-S(=O)$_2$—, 3-6 membered heterocycloalkyl, —C$_{1-6}$ alkyl-3-6 membered heterocycloalkyl or C$_{3-6}$ cycloalkyl-C(=O)— is optionally substituted by 1, 2 or 3 R;
R$_7$ is independently selected from H, halogen, OH, NH$_2$, CN, —C(=O)OH, C$_{1-6}$ alkyl-O—C(=O)—, —C(=O)—NH$_2$, C$_{1-6}$ alkyl, C$_{1-6}$ heteroalkyl and —C$_{1-6}$ alkyl-3-6 membered heterocycloalkyl, the C$_{1-6}$ alkyl, C$_{1-6}$ heteroalkyl, C$_{1-6}$ alkyl-O—C(=O)— or —C$_{1-6}$ alkyl-3-6 membered heterocycloalkyl is optionally substituted by 1, 2 or 3 R;
T$_1$, T$_2$ are independently selected from N and —C(R$_8$)—;
R$_8$ is selected from H, halogen, OH, NH$_2$, CN, C$_{1-6}$ alkyl, C$_{1-6}$ heteroalkyl, C$_{3-6}$ cycloalkyl and 3-6 membered heterocycloalkyl, the C$_{1-6}$ alkyl, C$_{1-6}$ heteroalkyl, C$_{3-6}$ cycloalkyl or 3-6 membered heterocycloalkyl is optionally substituted by 1, 2 or 3 R;
R is independently selected from H, halogen, OH, NH$_2$, CN,

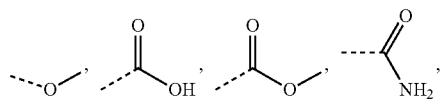

C$_{1-6}$ alkyl, C$_{1-6}$ heteroalkyl, C$_{3-6}$ cycloalkyl, 5-6 membered heterocycloalkyl, C$_{3-6}$ cycloalkyl-O— and 5-6 membered heterocycloalkyl-O—, the C$_{1-6}$ alkyl, C$_{1-6}$ heterocycloalkyl, C$_{3-6}$ cycloalkyl, 5-6 membered heterocycloalkyl, C$_{3-6}$ cycloalkyl-O— or 5-6 membered heterocycloalkyl-O— is optionally substituted by 1, 2 or 3 R';
R' is selected from F, Cl, Br, I, OH, NH$_2$ and CH$_3$;
ring A is independently selected from C$_{6-10}$ aryl, 5-10 membered heteroaryl, benzo 5-6 membered heterocycloalkyl and 5-6 membered heteroaryl-fused 5-6 membered heterocycloalkyl;
n is selected from 0, 1, 2, 3 or 4;
≋ is ≳ or ⌀, and when ≋ is ⌀, R$_2$ is not existed;
≳ is ≳ or ⌇;
when in ⌇$_{X_2}$, ≳ is ≳, X$_1$, X$_2$ are independently selected from —N=, —C(R$_7$)= and —C(R$_7$)$_2$—C(R$_7$)=;
when in ⌇$_{X_2}$, ≳ is ⌇, X$_1$, X$_2$ are independently selected from single bond, —O—, —S—, S(=O), S(=O)$_2$, —N(R$_6$)—, —C(=O)—, —C(R$_7$)$_2$— and —C(R$_7$)$_2$—C(R$_7$)$_2$—;
the above 3-6 membered heterocycloalkyl, 5-6 membered heteroaryl, 5-6 membered heterocycloalkyl, 5-10 membered heteroaryl or C$_{1-6}$ heterocycloalkyl comprises 1, 2, or 3 heteroatoms or heteroatomic groups independently selected from —O—, —NH—, —S—, —C(=O)—, —C(=O)O—, —S(=O)—, —S(=O)$_2$— and N.

In some embodiments of the present disclosure, the above compounds, optical isomers thereof and pharmaceutically acceptable salts thereof are selected from:

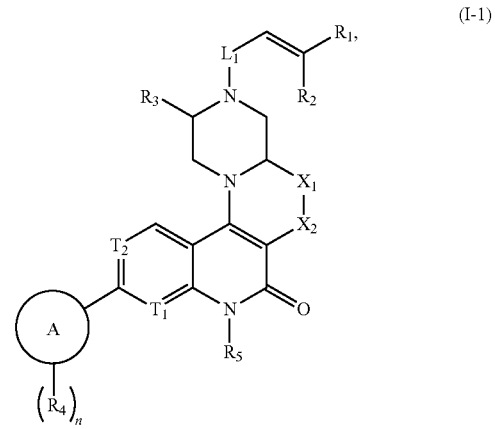

(I-1)

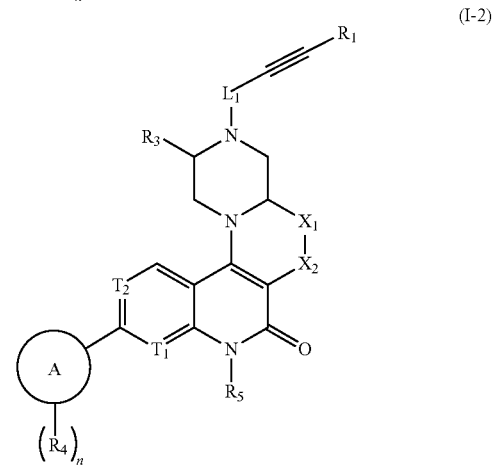

(I-2)

wherein,

X₁, X₂ are independently selected from single bond, —O—, —S—, S(=O), S(=O)₂, —N(R₆)—, —C(=O)—, —C(R₇)₂— and —C(R₇)₂—C(R₇)₂—, R₁, R₂, R₃, R₄, R₅, L₁, R₆, R₇, T₁, T₂, ring A and n are as defined above.

In some embodiments of the present disclosure, the above R is independently selected from H, halogen, OH, NH₂, CN,

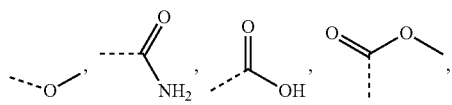

C₁₋₃ alkyl, C₁₋₃ alkoxy, C₁₋₃ alkylthio, C₁₋₃ alkylamino, C₃₋₆ cycloalkyl, 5-6 membered heterocycloalkyl, C₃₋₆ cycloalkyl-O— and –5-6 membered heterocycloalkyl-O—, the C₁₋₃ alkyl, C₁₋₃ alkoxy, C₁₋₃ alkylthio, C₁₋₃ alkylamino, C₃₋₆ cycloalkyl, 5-6 membered heterocycloalkyl, C₃₋₆ cycloalkyl-O— or 5-6 membered heterocycloalkyl-O— is optionally substituted by 1, 2 or 3 R', and other variables are as defined in the present disclosure.

In some embodiments of the present disclosure, the above R is independently selected from H, F, Cl, Br, I, OH, NH₂, CN, Me, CH₂CH₃,

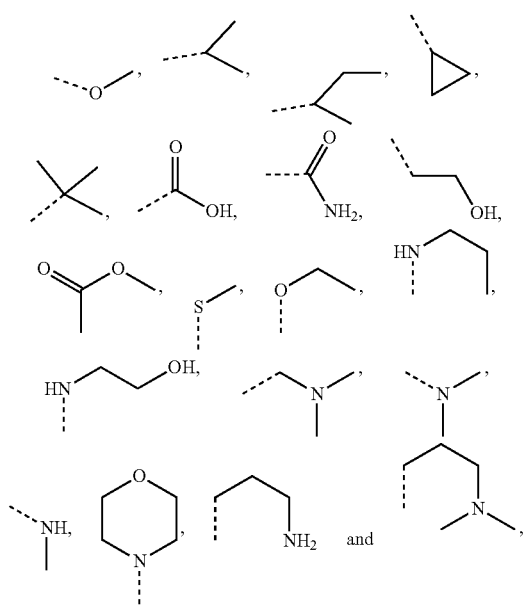

and other variables are as defined in the present disclosure.

In some embodiments of the present disclosure, the above R₁, R₂ are independently selected from H, F, Me, CF₃,

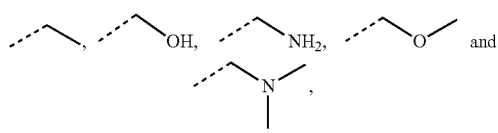

and other variables are as defined in the present disclosure.

In some embodiments of the present disclosure, the above structural moiety

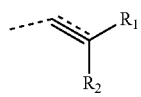

is selected from

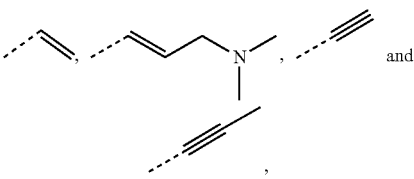

and other variables are as defined in the present disclosure.

In some embodiments of the present disclosure, the above R₃ is selected from H, halogen, OH, NH₂, CN, C₁₋₃ alkyl, C₁₋₃ alkoxy, C₁₋₃ alkylamino, C₁₋₃ alkylthio, 3-6 membered heterocycloalkyl, C₃₋₆ cycloalkyl, 3-6 membered heterocycloalkyl-O— and C₃₋₆ cycloalkyl-O—, the C₁₋₃ alkyl, C₁₋₃ alkoxy, C₁₋₃ alkylamino, C₁₋₃ alkylthio, 3-6 membered heterocycloalkyl, C₃₋₆ cycloalkyl, 3-6 membered heterocycloalkyl-O— or C₃₋₆ cycloalkyl-O— is optionally substituted by 1, 2 or 3 R, and other variables are as defined in the present disclosure.

In some embodiments of the present disclosure, the above R₃ is selected from H, F, Cl, Br, I, OH, NH₂, CN, Me, CF₃,

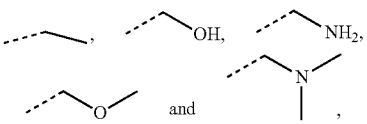

and other variables are as defined in the present disclosure.

In some embodiments of the present disclosure, the above R₄ is independently selected from H, halogen, OH, NH₂, CN, C₁₋₃ alkyl, C₁₋₃ alkoxy, C₁₋₃ alkylamino, C₁₋₃ alkylthio, C₃₋₆ cycloalkyl, 3-6 membered heterocycloalkyl, phenyl, pyridinyl, pyrimidinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl and indolyl, the C₁₋₃ alkyl, C₁₋₃ alkoxy, C₁₋₃ alkylamino, C₁₋₃ alkylthio, C₃₋₆ cycloalkyl, 3-6 membered heterocycloalkyl, phenyl, pyridinyl, pyrimidinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl or indolyl is optionally substituted by 1, 2 or 3 R, and other variables are as defined in the present disclosure.

In some embodiments of the present disclosure, the above R₄ is selected from H, F, Cl, Br, I, OH, NH₂, CN, Me, CF₃,

and other variables are as defined in the present disclosure.

In some embodiments of the present disclosure, the above ring A is selected from phenyl, naphthyl, pyridinyl, pyrimidinyl, pyridazinyl, pyrazinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl, indolyl, indazolyl, benzoimidazolyl, 1H-benzo[d]imidazolyl, benzopyrazolyl, purinyl, quinolinyl, isoquinolinyl, isoquinolin-1 (2H)-one, isoindolin-1-one, benzo[d]oxazol-2(H)-one, benzo[d]oxazol-2(3H)-one, H-benzo[d] [1,2,3]triazolyl, 1H-pyrazolo[3,4-b]pyridinyl, benzo[d]thiazolyl and 1,3-dihydro-2H-benzo[d]imidazolyl-2-one, the phenyl, naphthyl, pyridinyl, pyrimidinyl, pyridazinyl, pyrazinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl, indolyl, indazolyl, benzoimidazolyl, 1H-benzo[d] imidazolyl, benzopyrazolyl, purinyl, quinolinyl, isoquinolinyl, isoquinolin-1(2H)-one, isoindolin-1-one, benzo[d]oxazol-2(H)-one, benzo[d]oxazol-2(3H)-one, H-benzo[d] [1,2,3]triazolyl, 1H-pyrazolo[3,4-b]pyridinyl, benzo[d]thiazolyl or 1,3-dihydro-2H-benzo[d]imidazolyl-2-one is optionally substituted by 1, 2 or 3 R, and other variables are as defined in the present disclosure.

In some embodiments of the present disclosure, the above structural moiety

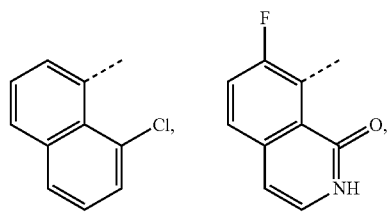

is selected from

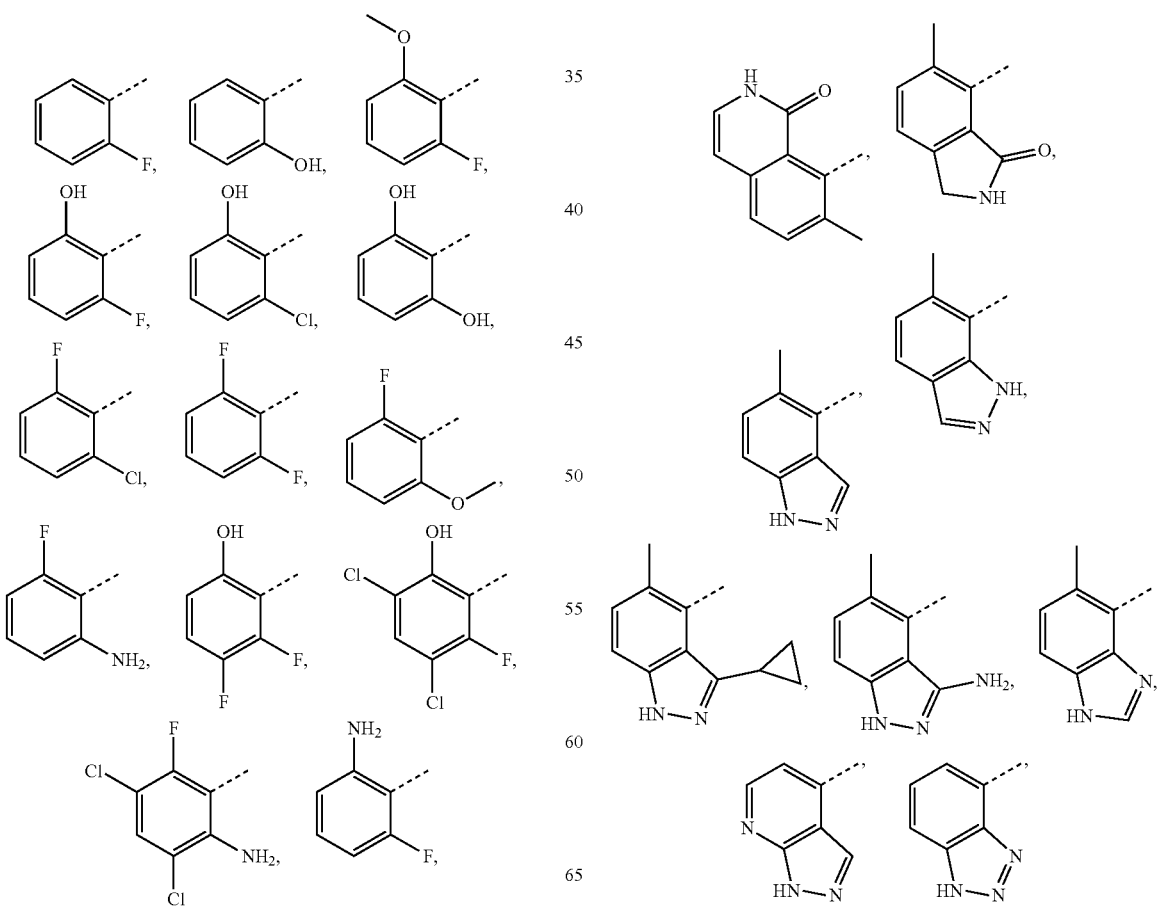

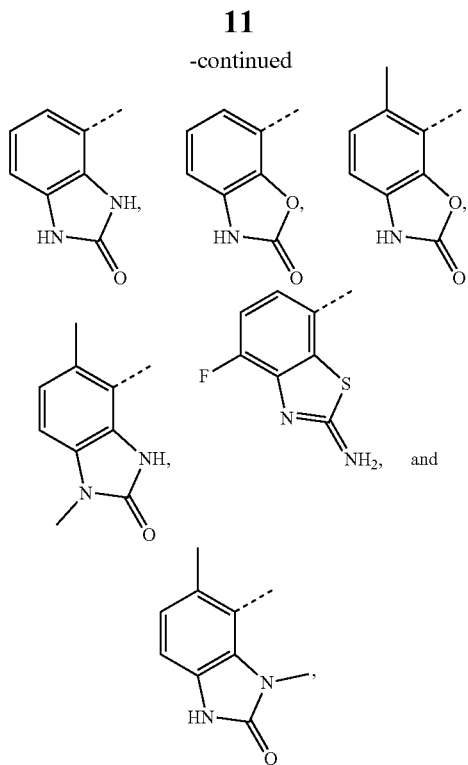

and other variables are as defined in the present disclosure.

In some embodiments of the present disclosure, the above $R_5$ is selected from H, $C_{1-3}$ alkyl, cyclopropyl, cyclobutyl, cyclopentyl, cyclohexyl, tetrahydrofuranyl, pyrrolidinyl, tetrahydro-2H-pyranyl, piperidinyl, piperazinyl, 5-6 membered heterocycloalkyl-$C_{1-3}$ alkyl-, phenyl, naphthyl, pyridinyl, pyrimidinyl, pyridazinyl, pyrazinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl, indolyl, benzoimidazolyl, benzopyrazolyl, purinyl, quinolinyl, isoquinolinyl, isoquinolin-1(2H)-one, isoindolin-1-one, benzo[d]oxazol-2(H)-one and 1,3-dihydro-2H-benzo[d]imidazolyl-2-one, the $C_{1-3}$ alkyl, cyclopropyl, cyclobutyl, cyclopentyl, cyclohexyl, tetrahydrofuranyl, pyrrolidinyl, tetrahydro-2H-pyranyl, piperidinyl, piperazinyl, 5-6 membered heterocycloalkyl-$C_{1-3}$ alkyl-, phenyl, naphthyl, pyridinyl, pyrimidinyl, pyridazinyl, pyrazinyl, thienyl, thiazolyl, isothiazolyl, oxazolyl, isoxazolyl, imidazolyl, pyrazolyl, 1,2,3-triazolyl, 1,2,4-triazolyl, benzofuranyl, benzothienyl, indolyl, benzoimidazolyl, benzopyrazolyl, purinyl, quinolinyl, isoquinolinyl, isoquinolin-1(2H)-one, isoindolin-1-one, benzo[d]oxazol-2(H)-one or 1,3-dihydro-2H-benzo[d]imidazolyl-2-one is optionally substituted by 1, 2 or 3 R, and other variables are as defined in the present disclosure.

In some embodiments of the present disclosure, the above $R_5$ is selected from H, Me,

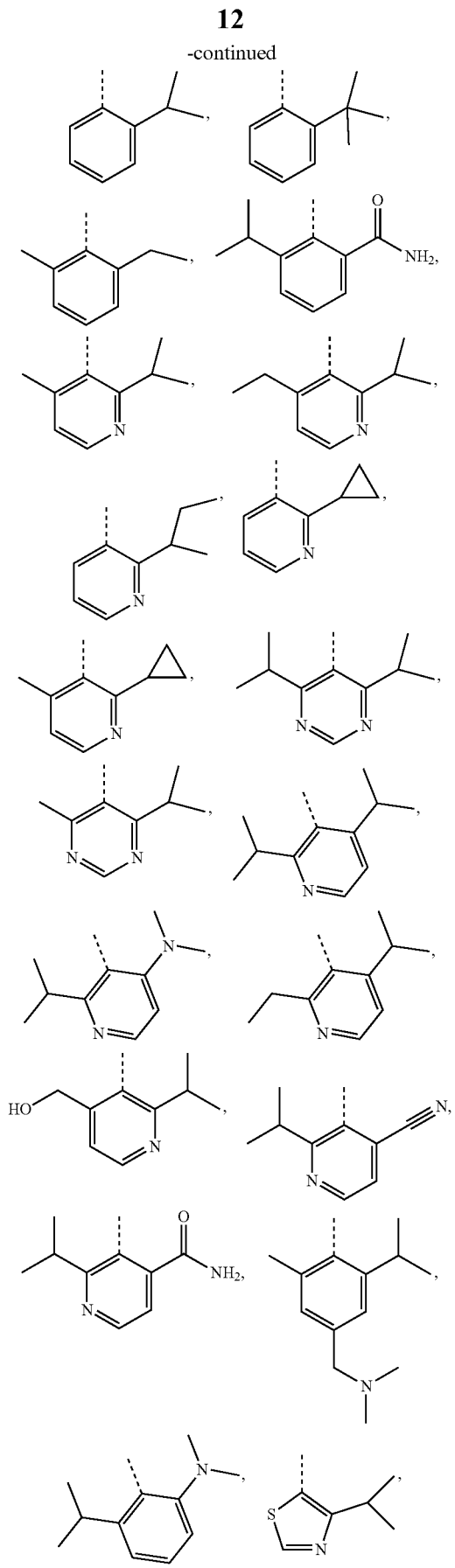

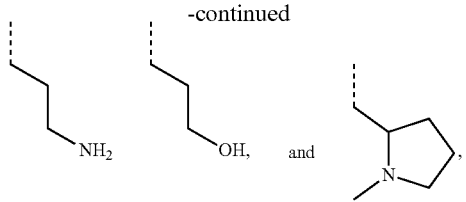

and other variables are as defined in the present disclosure.

In some embodiments of the present disclosure, the above $R_7$ is independently selected from H, halogen, OH, $NH_2$, CN, $C_{1-3}$ alkyl, $C_{1-3}$ alkyl-O—C(=O)—, —C(=O)—$NH_2$, $C_{1-3}$ alkoxy, $C_{1-3}$ alkylamino, $C_{1-3}$ alkylthio and —$C_{1-3}$ alkyl-3-6 membered heterocycloalkyl, the $C_{1-3}$ alkyl, $C_{1-3}$ alkyl-O—C(=O)—, —C(=O)—$NH_2$, $C_{1-3}$ alkoxy, $C_{1-3}$ alkylamino, $C_{1-3}$ alkylthio or —$C_{1-3}$ alkyl-3-6 membered heterocycloalkyl is optionally substituted by 1, 2 or 3 R, and other variables are as defined in the present disclosure.

In some embodiments of the present disclosure, the above $R_7$ is independently selected from H, F, Cl, Br, I, OH, $NH_2$, CN, Me, $CF_3$,

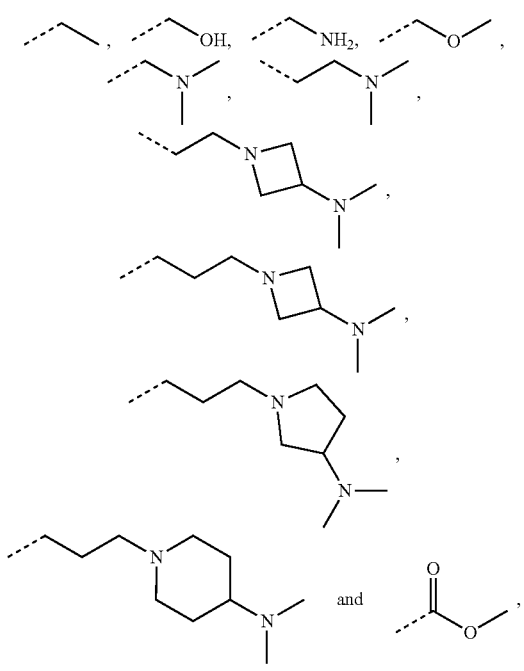

and other variables are as defined in the present disclosure.

In some embodiments of the present disclosure, the above $R_6$ is independently selected from H, CN, $C_{1-3}$ alkyl, $C_{1-3}$ alkyl-S(=O)$_2$—, 3-6 membered heterocycloalkyl, —$C_{1-3}$ alkyl-3-6 membered heterocycloalkyl and $C_{3-6}$ cycloalkyl-C(=O)—, the $C_{1-3}$ alkyl, $C_{1-3}$ alkyl-S(=O)$_2$—, 3-6 membered heterocycloalkyl, —$C_{1-3}$ alkyl 3-6 membered heterocycloalkyl or $C_{3-6}$ cycloalkyl-C(=O)— is optionally substituted by 1, 2 or 3 R, and other variables are as defined in the present disclosure.

In some embodiments of the present disclosure, the above $R_6$ is independently selected from H, CN, Me, $CF_3$,

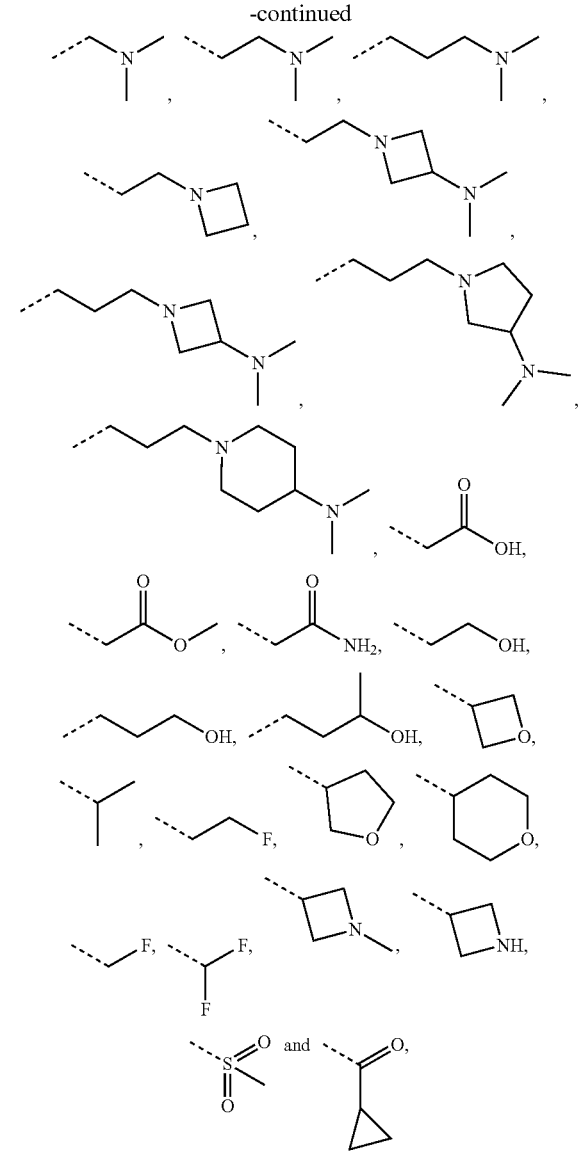

and other variables are as defined in the present disclosure.

In some embodiments of the present disclosure, the above $X_1$, $X_2$ are independently selected from single bond, $CH_2$, $CH_2CH_2$, C(=O), O, S, NH, N($CH_3$), S(=O), S(=O)$_2$,

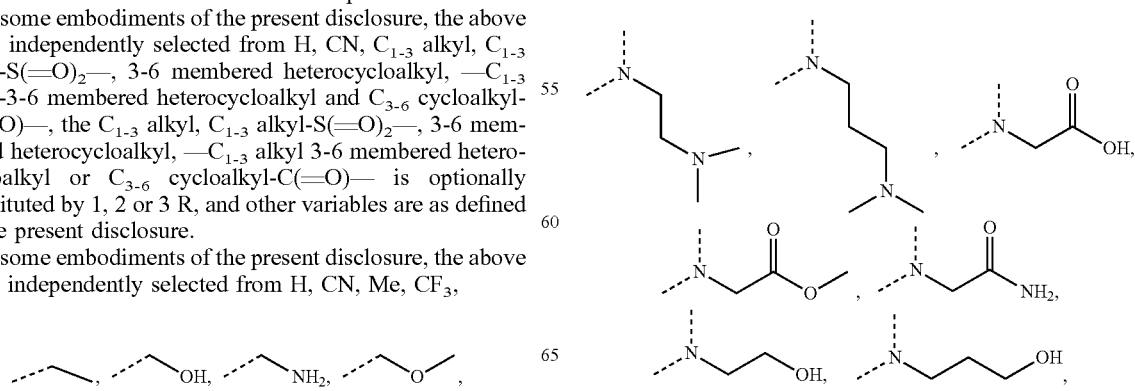

-continued

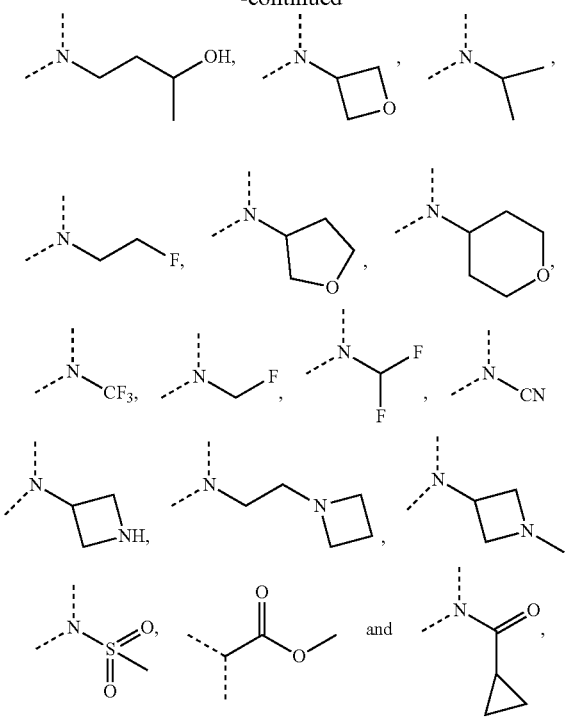

and other variables are as defined in the present disclosure.

In some embodiments of the present disclosure, the above $R_8$ is selected from H, halogen, OH, $NH_2$, CN, $C_{1-3}$ alkyl, $C_{1-3}$ alkoxy, $C_{1-3}$ alkylamino and $C_{1-3}$ alkylthio, the $C_{1-3}$ alkyl, $C_{1-3}$ alkoxy, $C_{1-3}$ alkylamino or $C_{1-3}$ alkylthio is optionally substituted by 1, 2 or 3 R, and other variables are as defined in the present disclosure.

In some embodiments of the present disclosure, the above $R_8$ is selected from H, F, Cl, Br, I, OH, $NH_2$, CN, Me, $CF_3$,

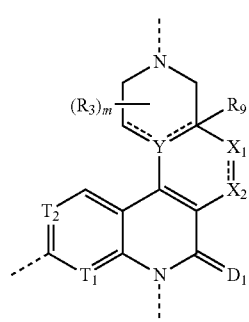

and other variables are as defined in the present disclosure.

In some embodiments of the present disclosure, the above structural moiety

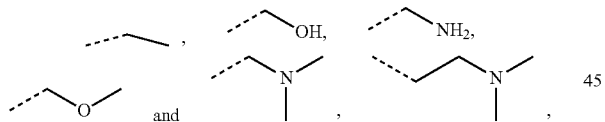

is selected from

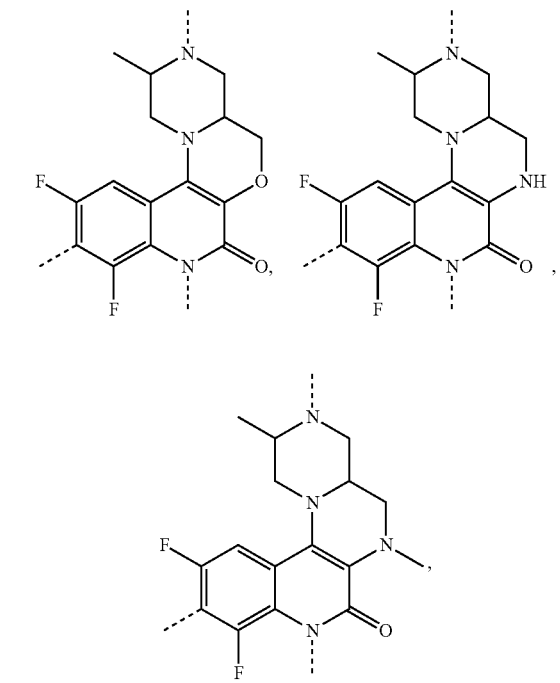

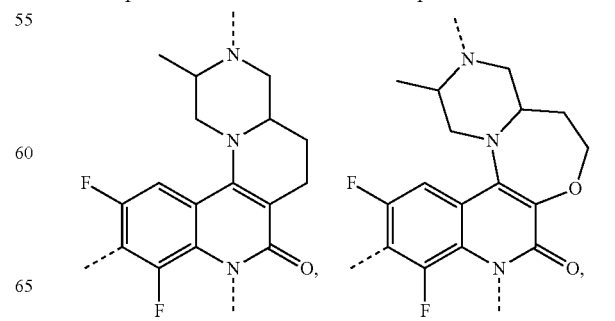

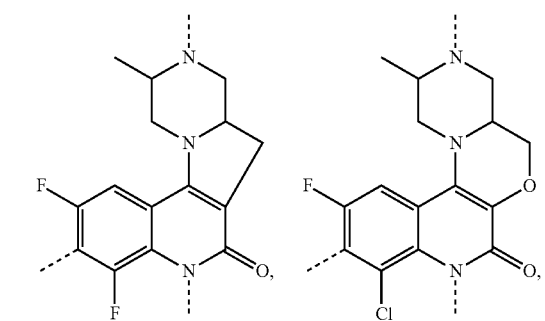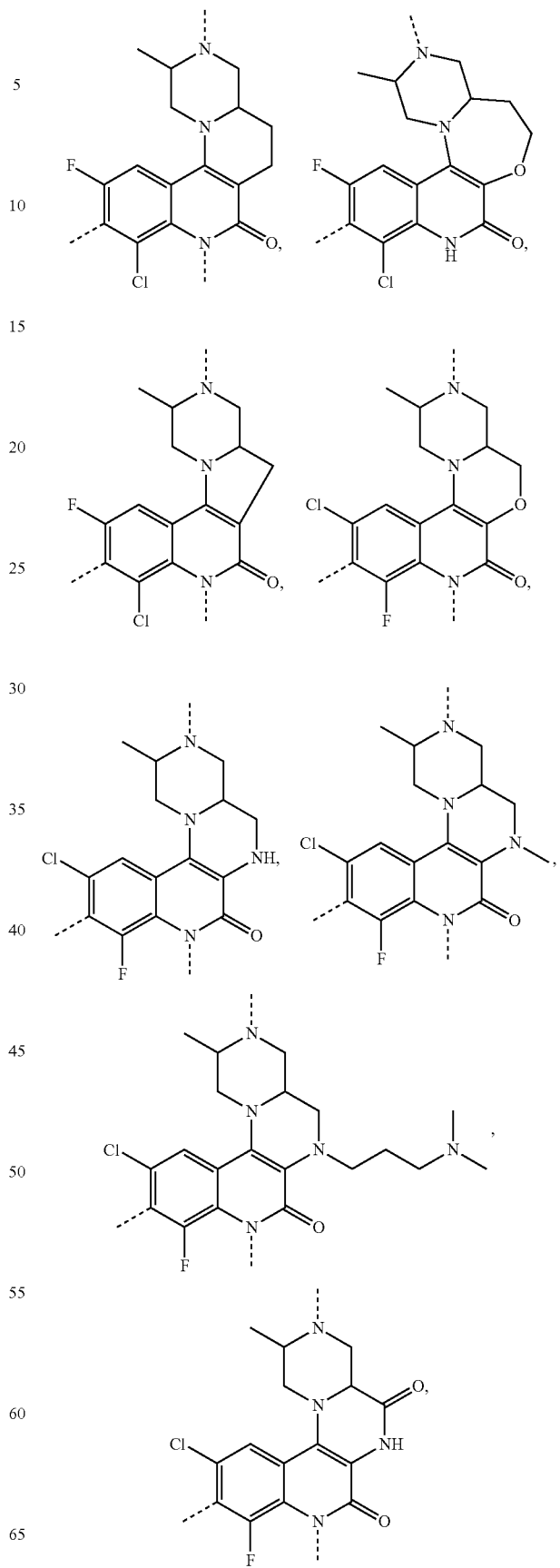

-continued
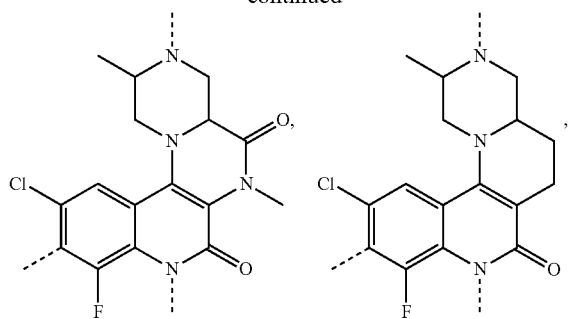 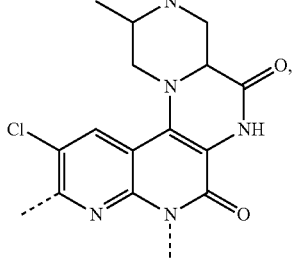
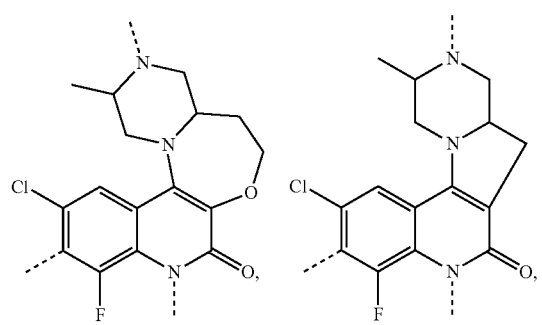 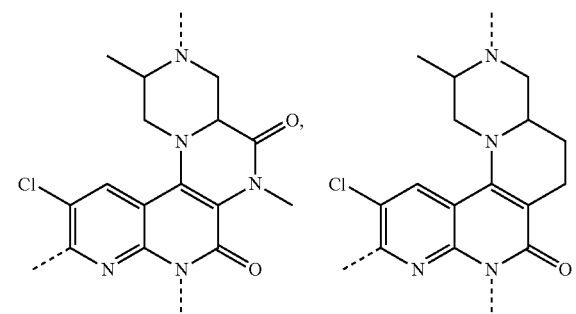
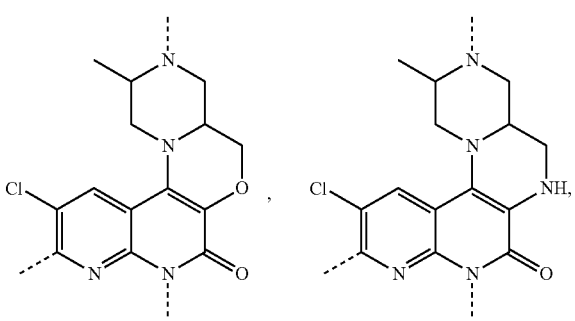 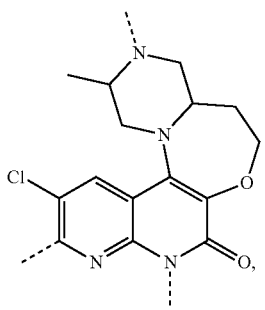
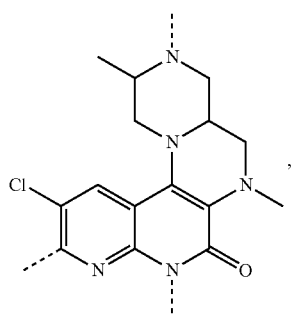 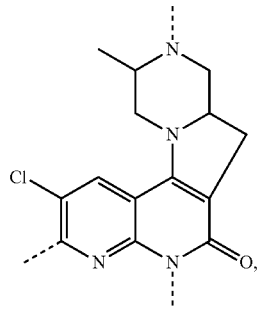
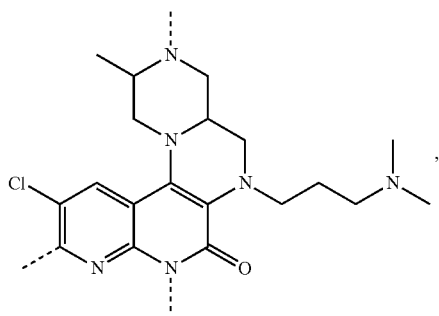 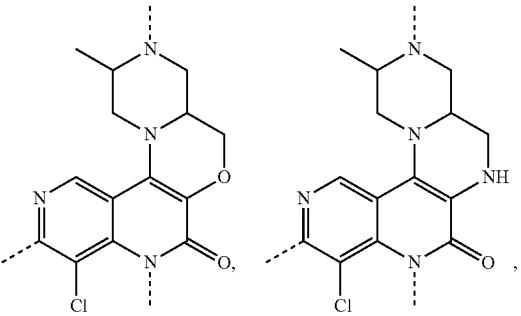

-continued
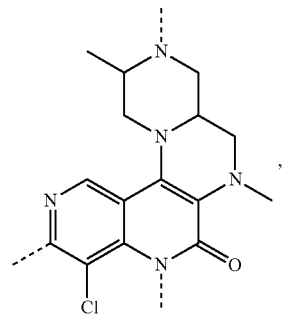
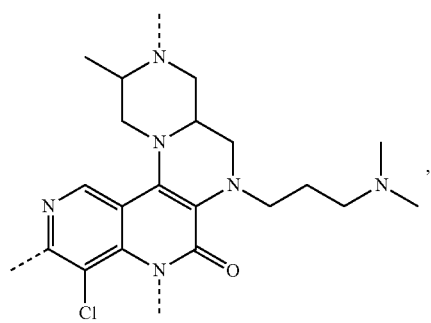
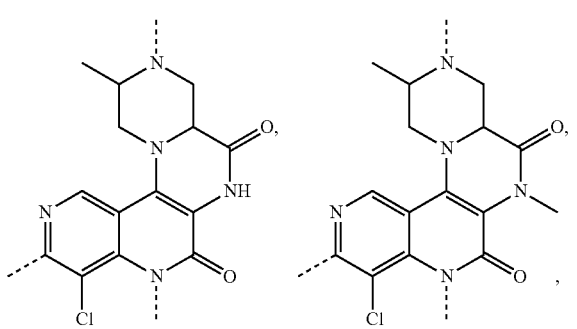
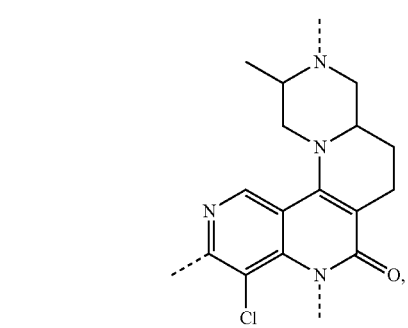
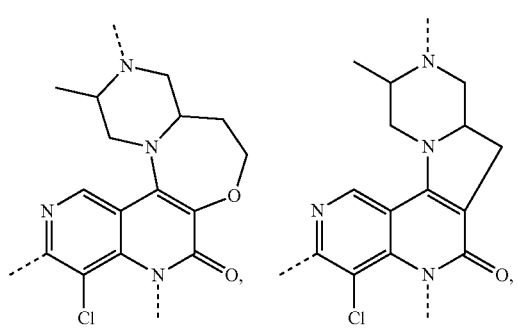
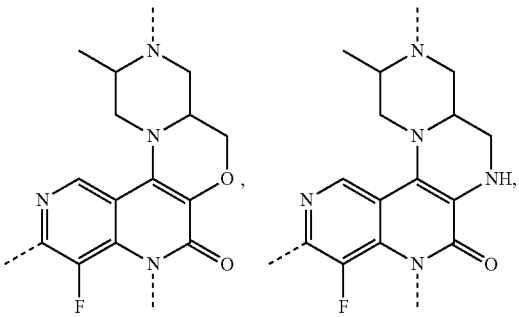
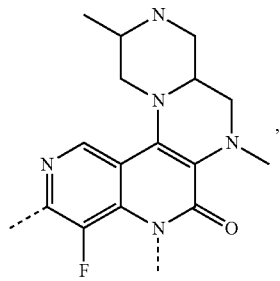
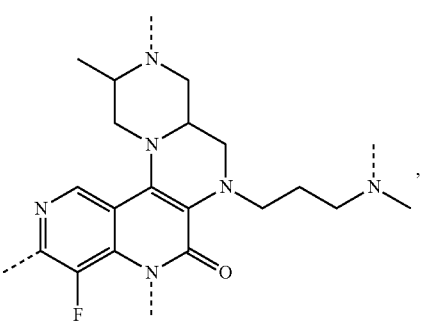
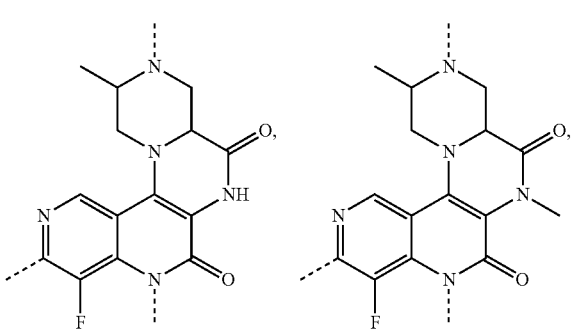
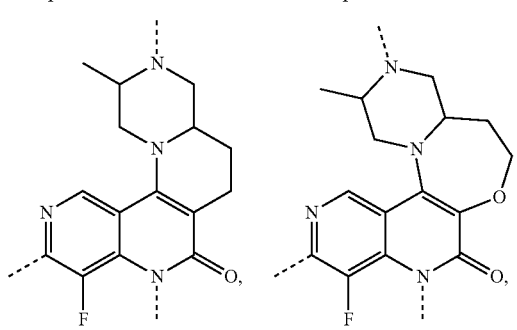

-continued
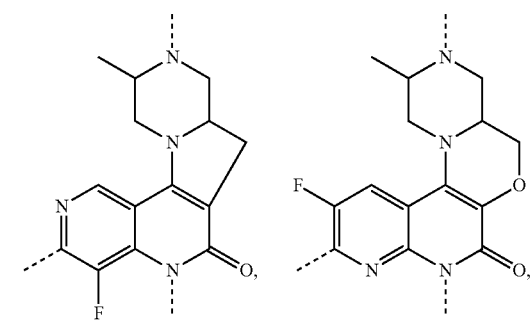
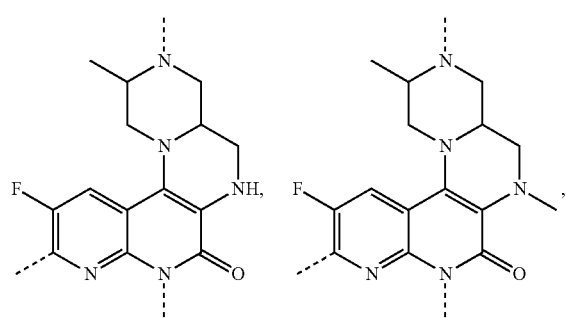
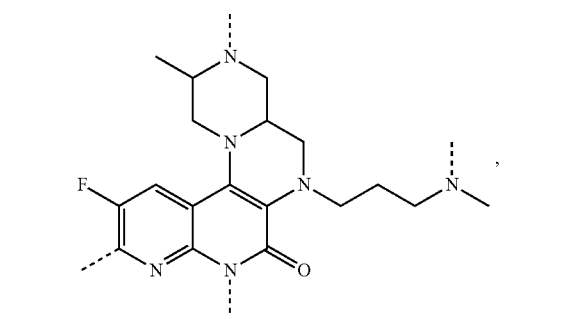
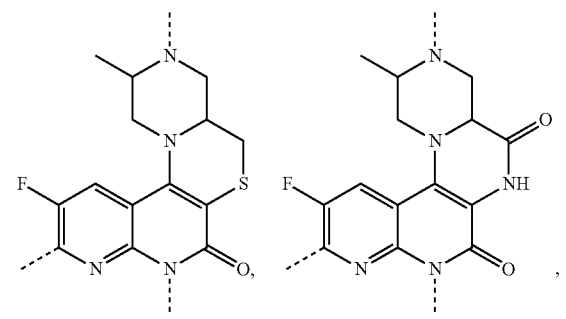
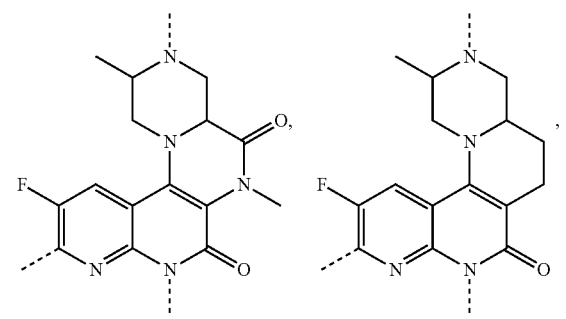
-continued
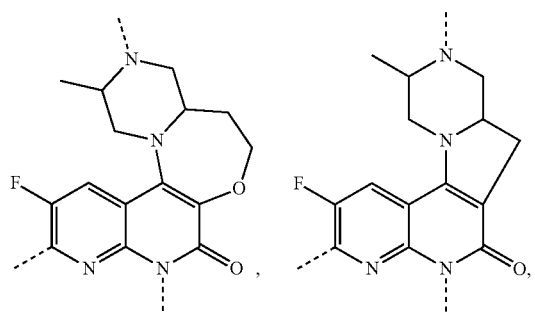
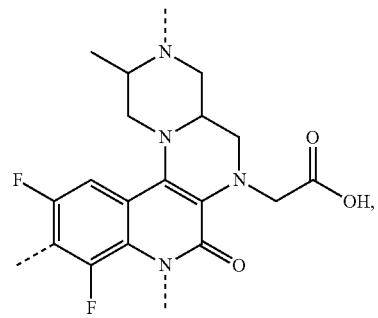
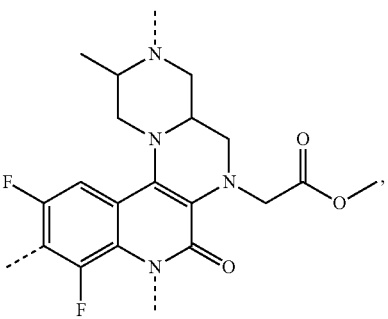
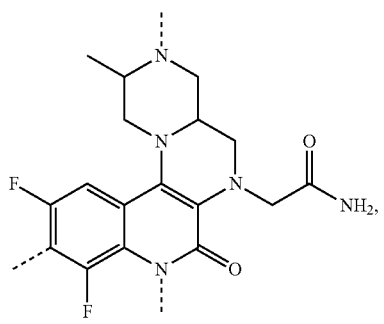
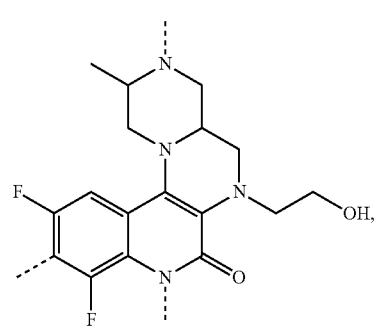

-continued
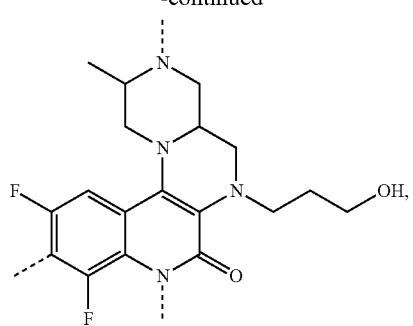
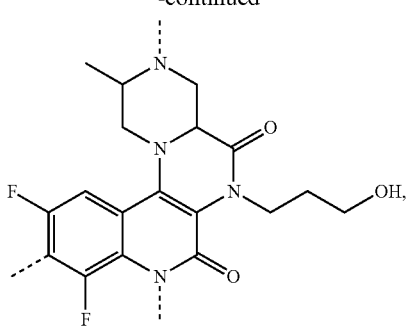
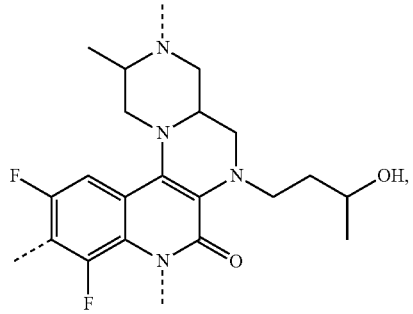
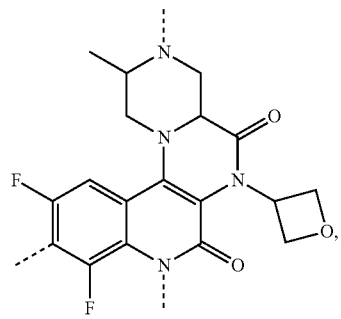
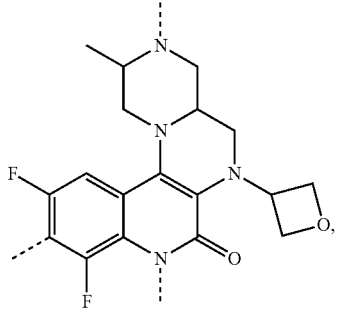
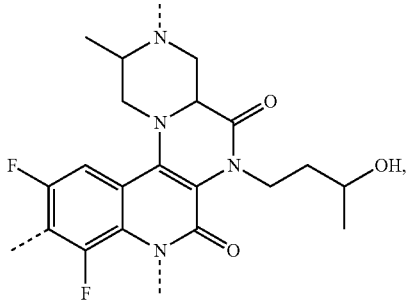
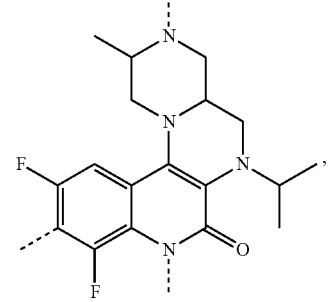
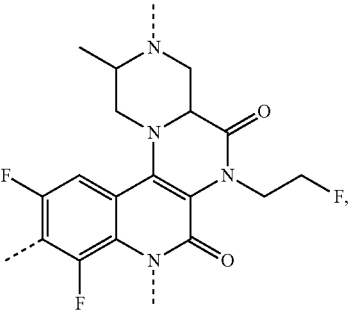
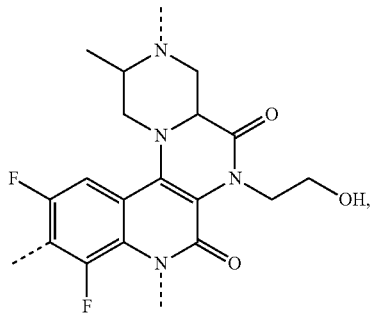
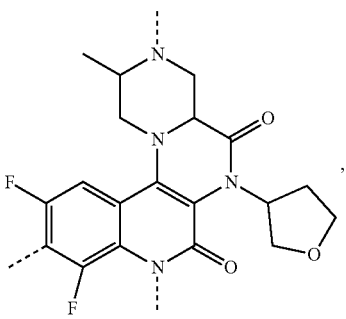

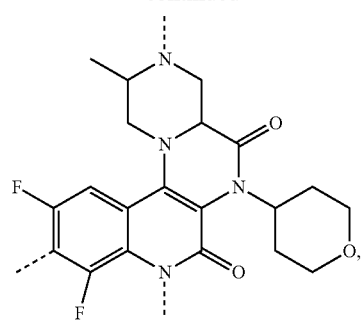
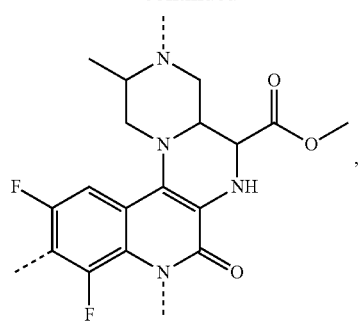
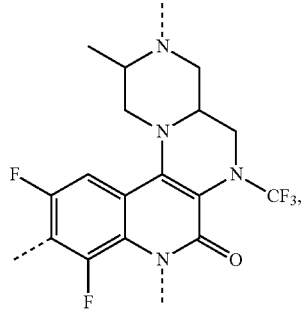
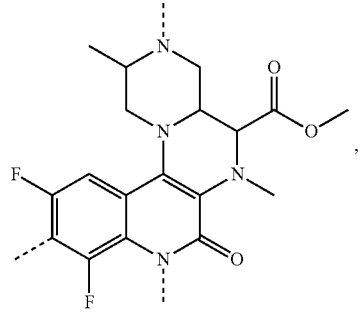
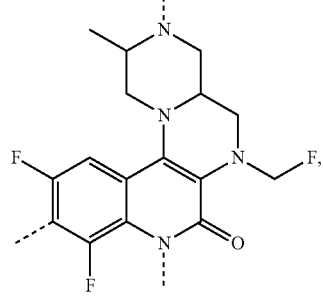
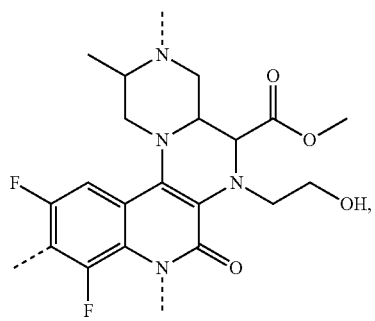
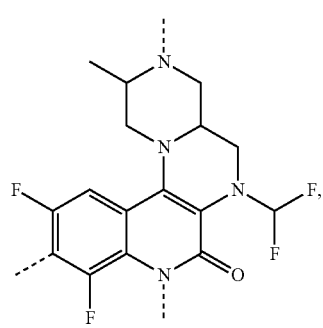
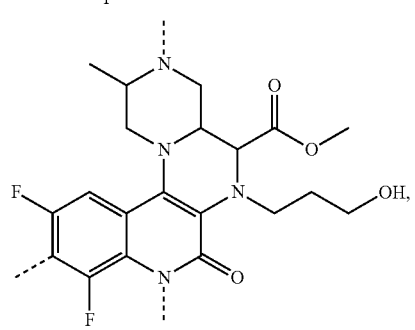
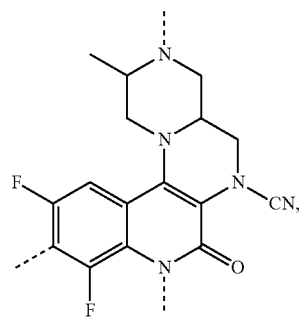
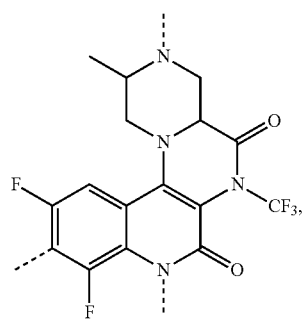

-continued
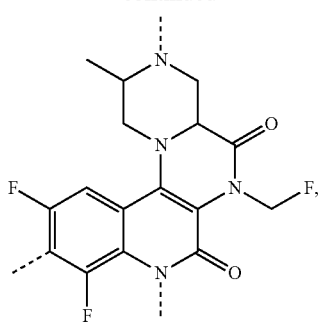
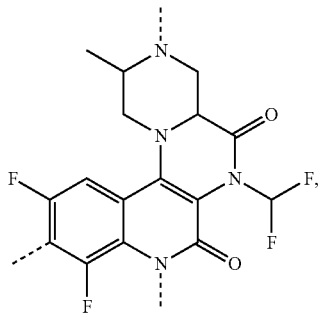
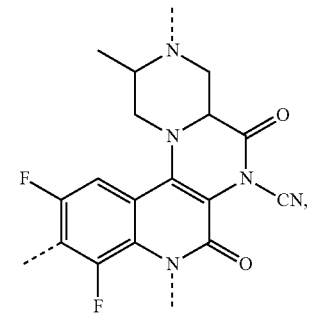
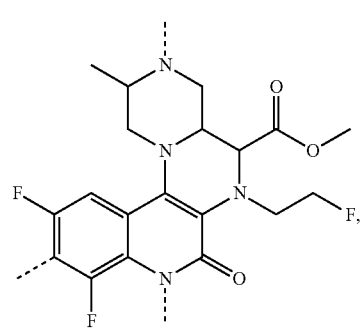
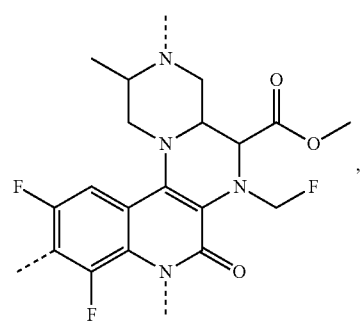
-continued
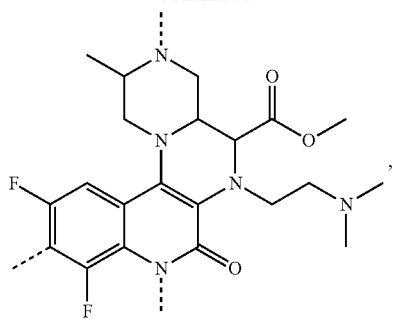
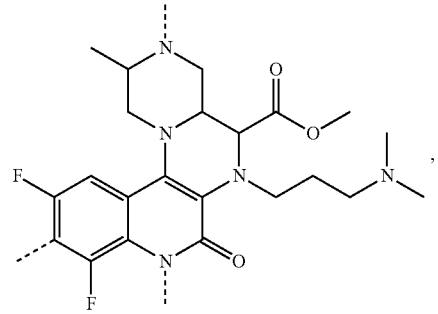
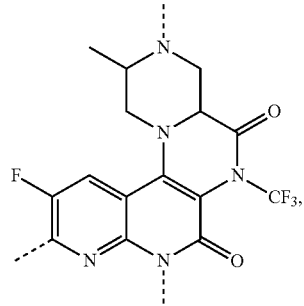
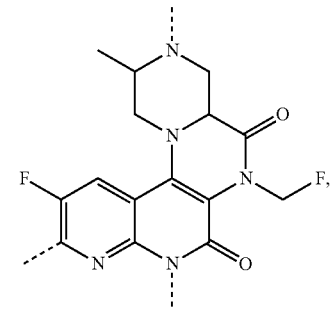
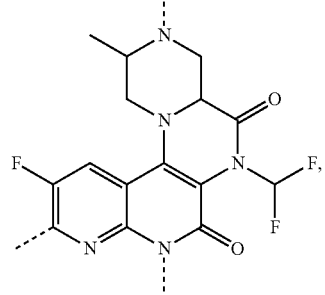

-continued
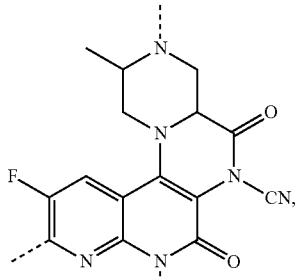
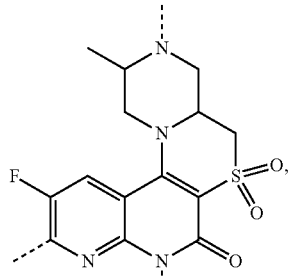
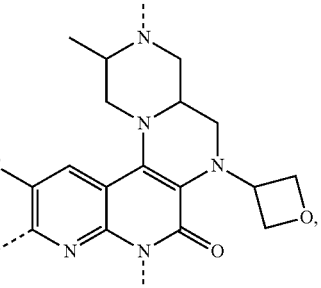
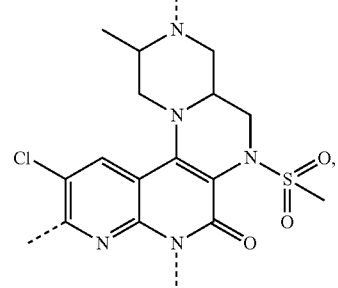
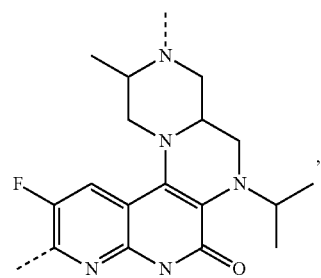
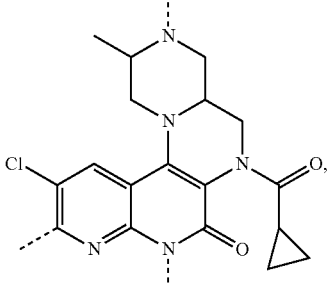
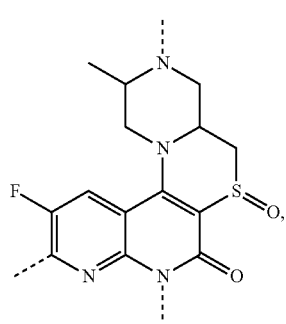
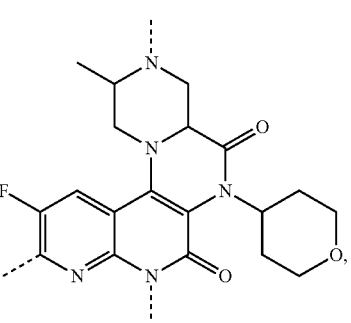

33
-continued
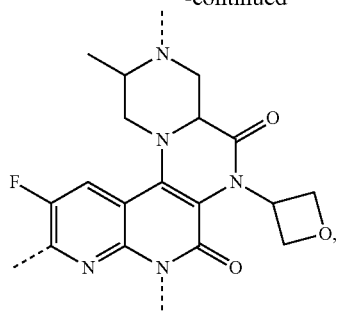
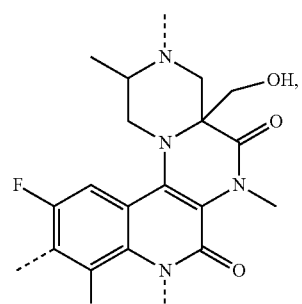
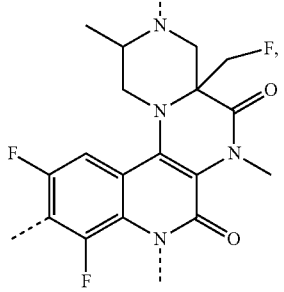
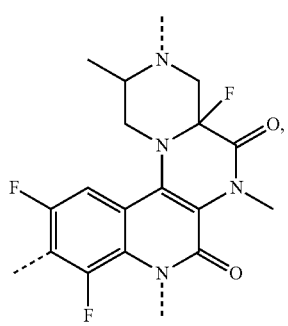
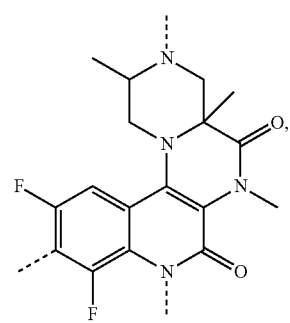
34
-continued
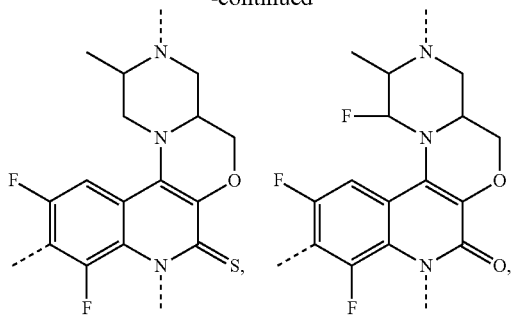
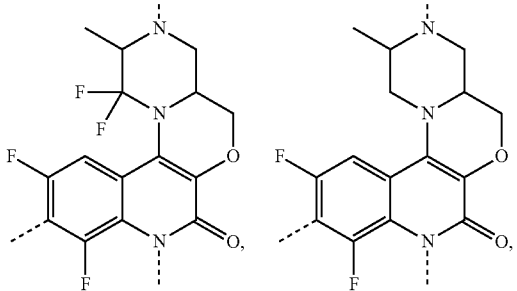
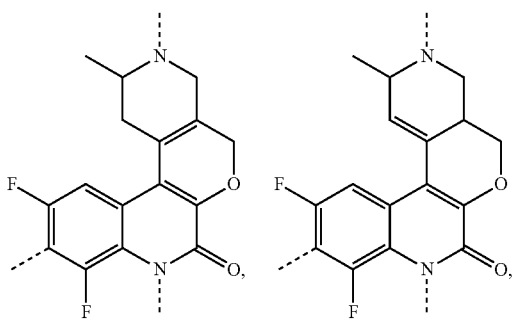
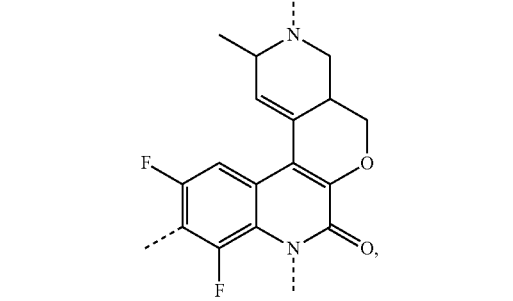
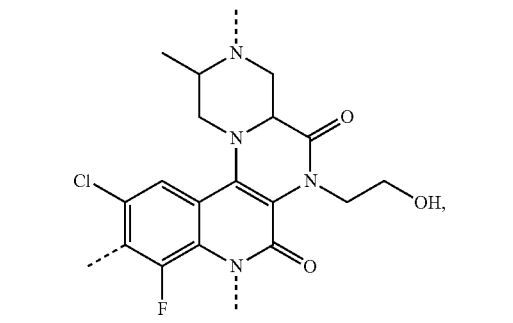

35
-continued
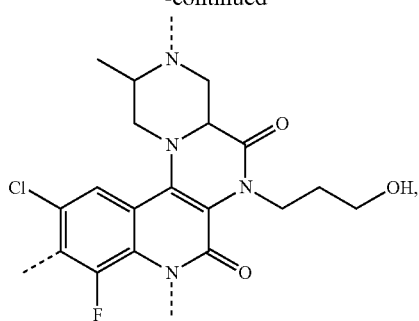
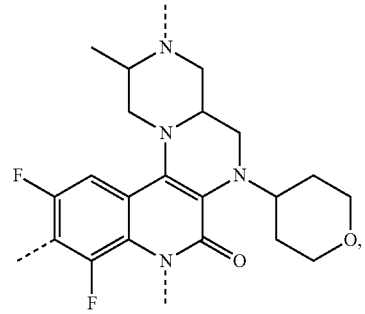
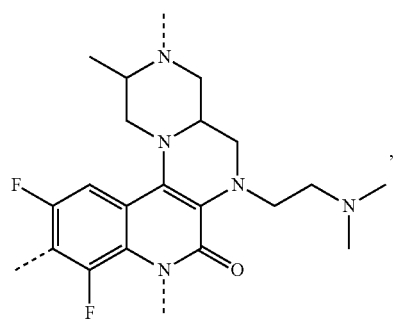
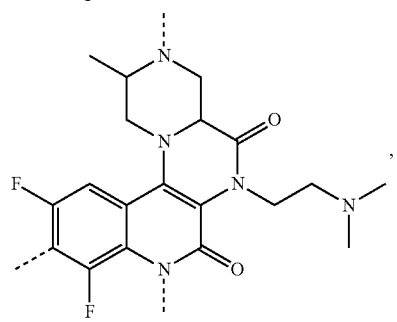
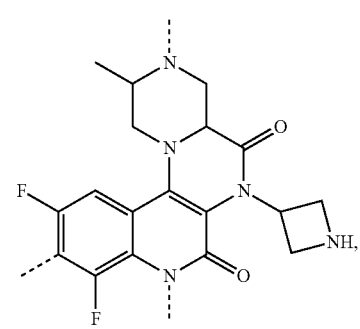
36
-continued
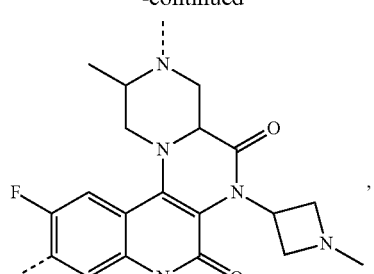
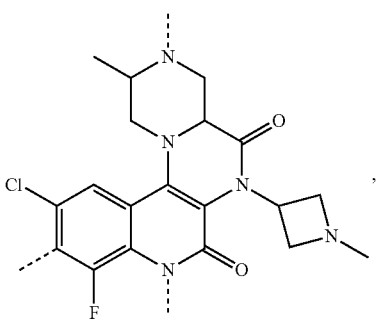
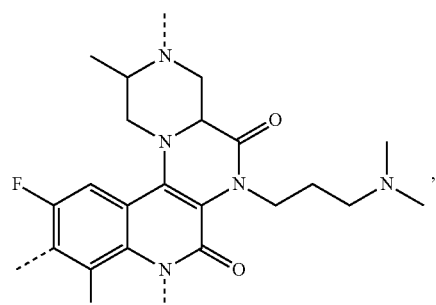
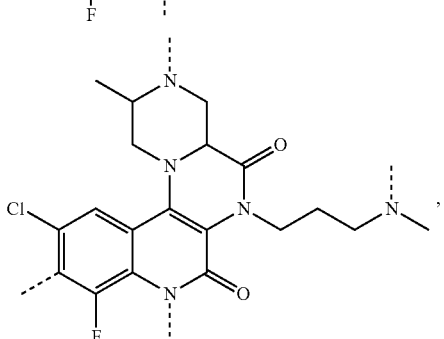
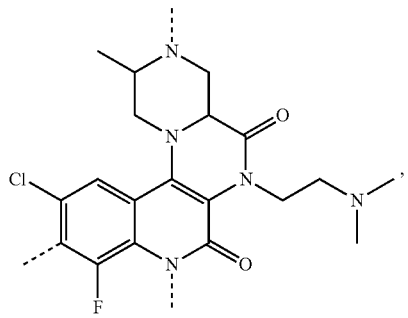

-continued
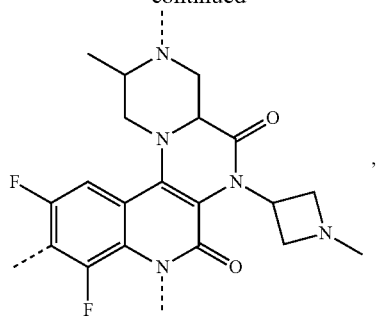
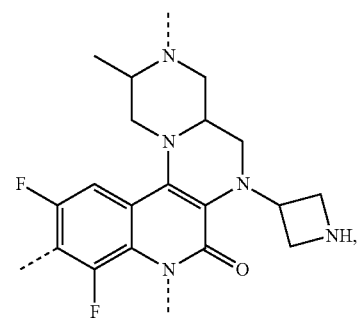
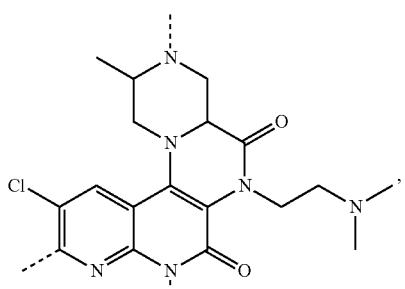
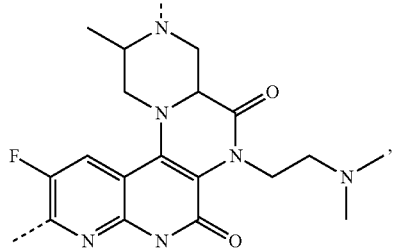
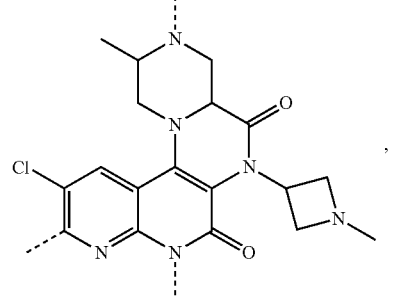
-continued
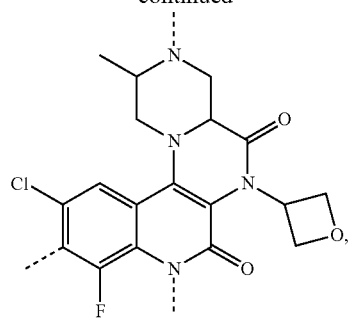
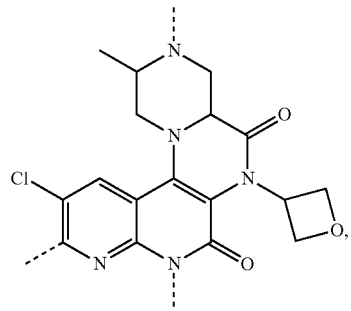
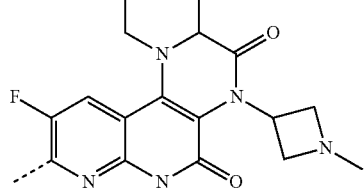
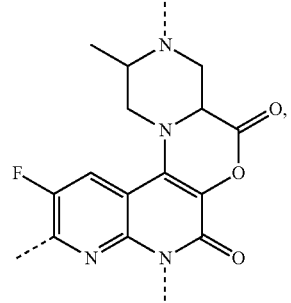
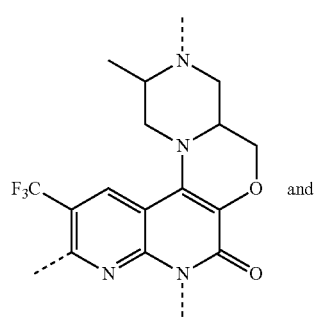 and 39
-continued
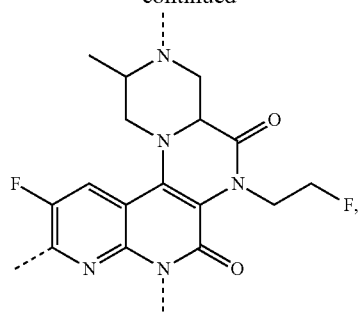
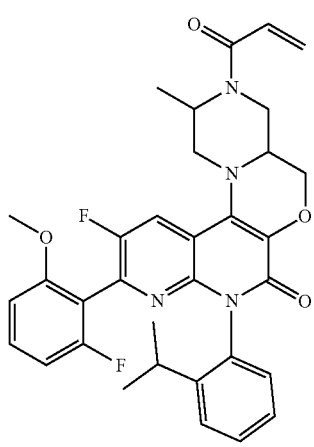
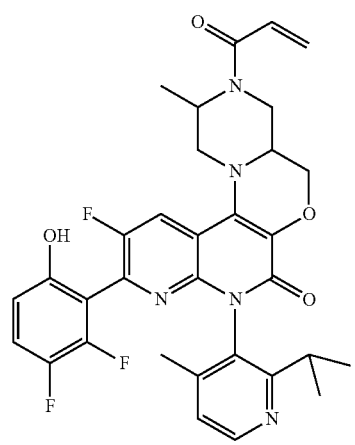
40
-continued
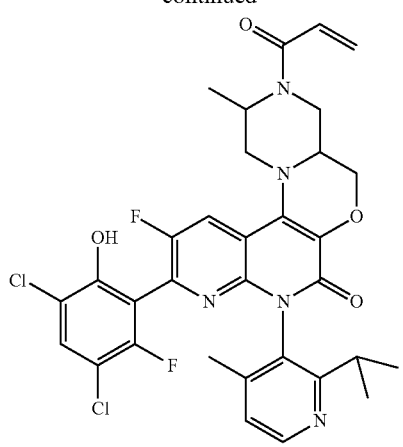
and other variables are as defined in the present disclosure.
In a further aspect of the present disclosure, the disclosure also provides compounds of the following formula, optical isomers thereof and pharmaceutically acceptable salts thereof,
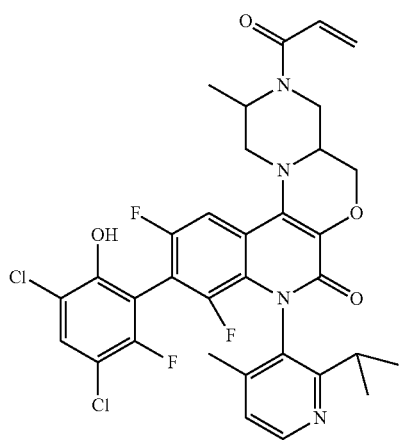
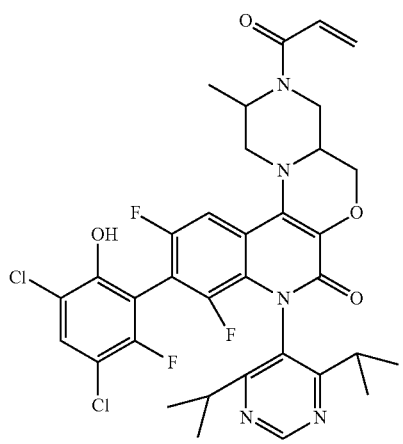

-continued
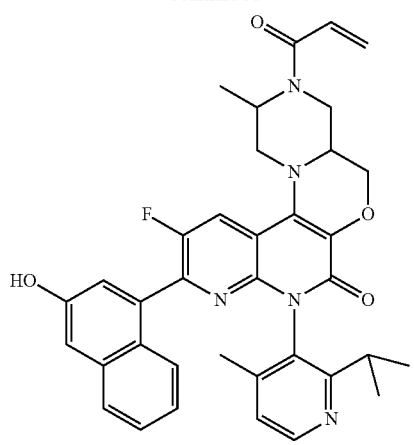
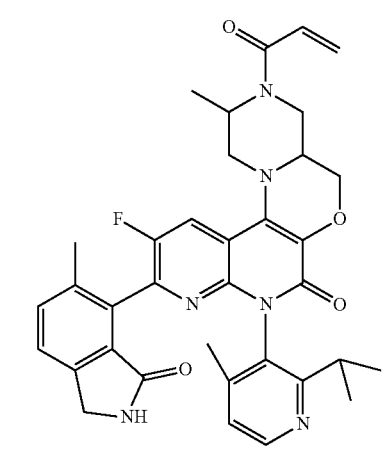
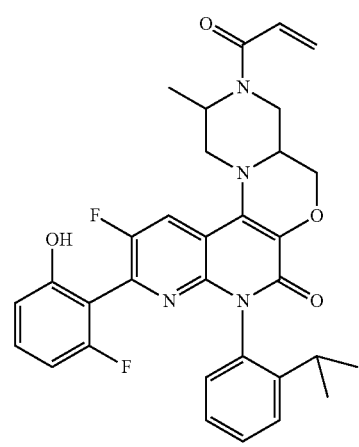
-continued
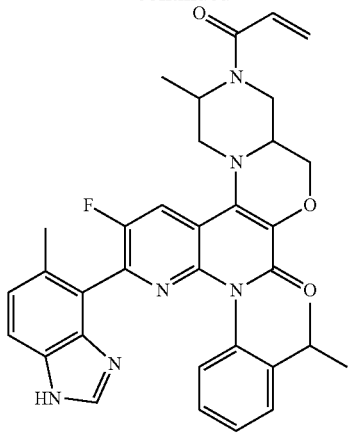
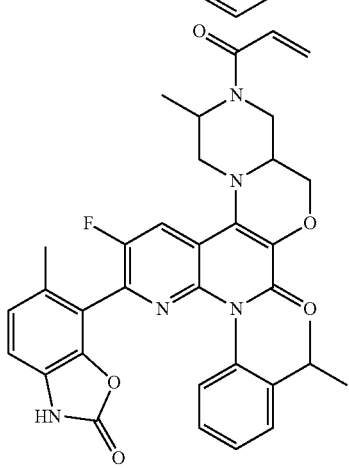
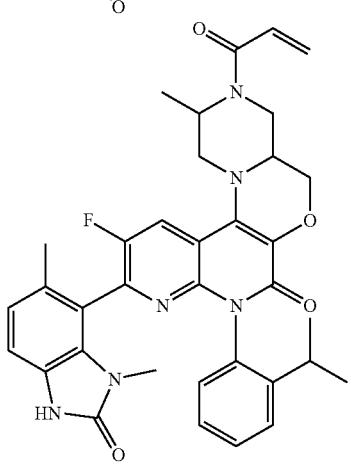
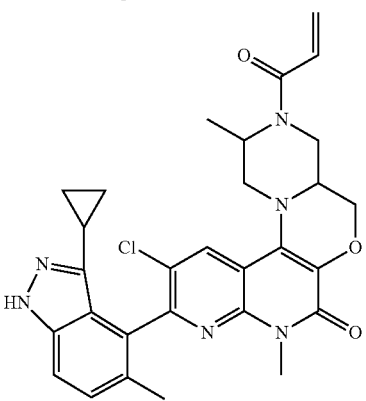

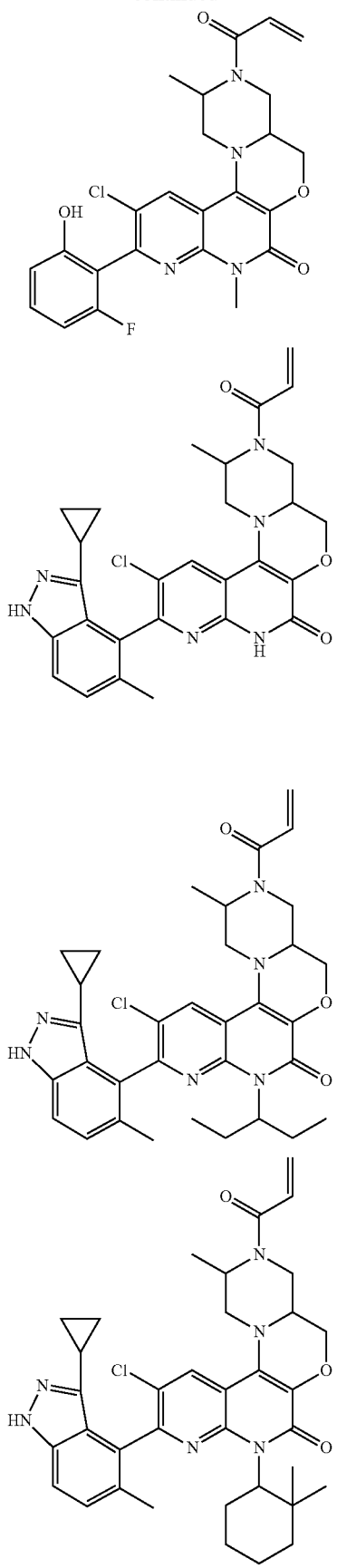
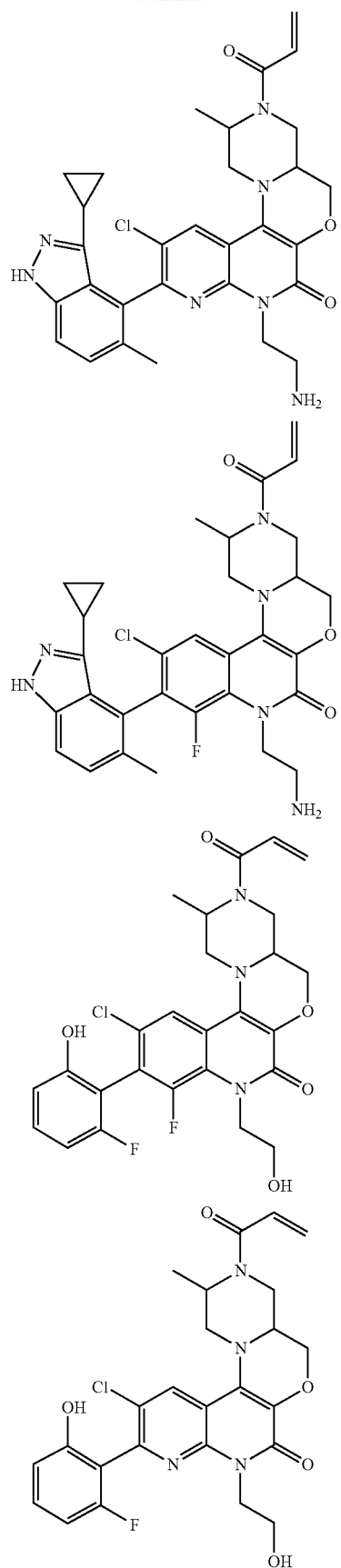

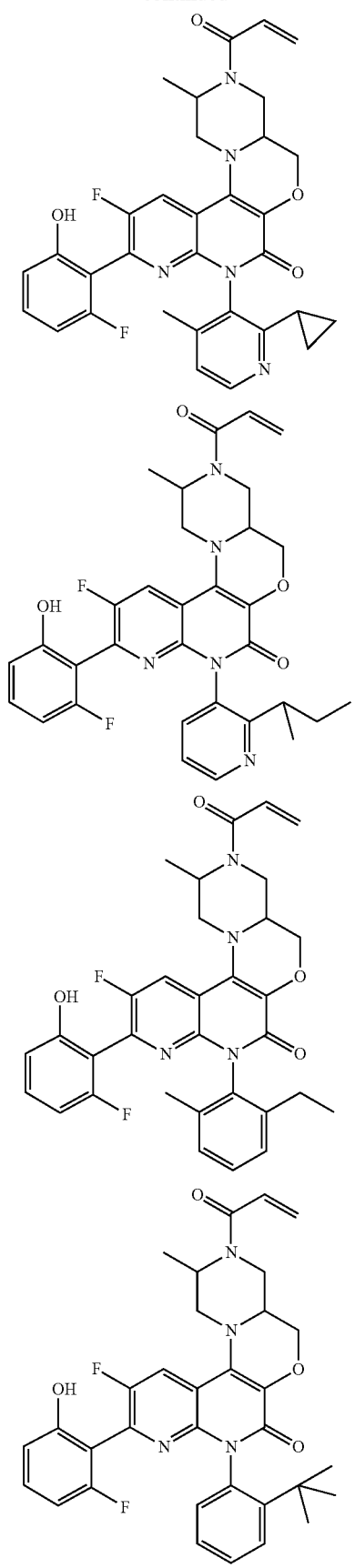
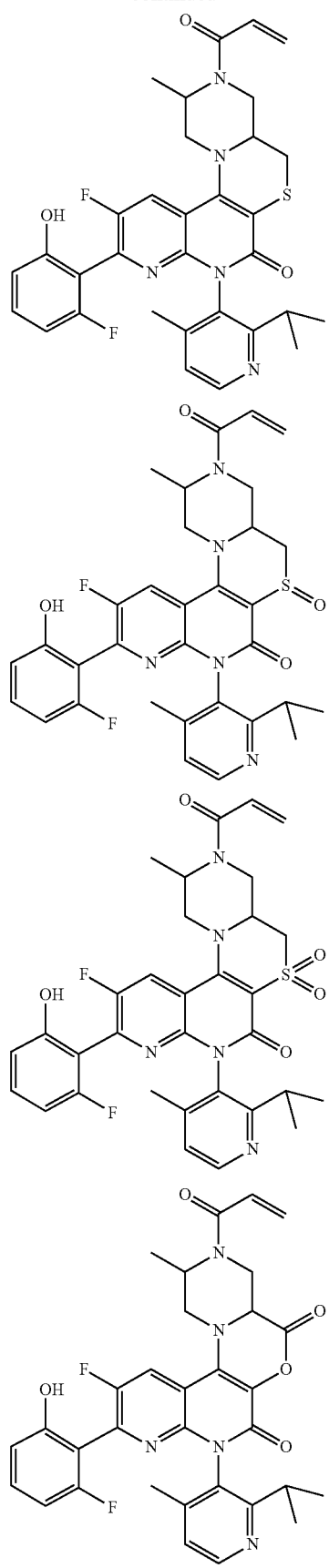

47
-continued
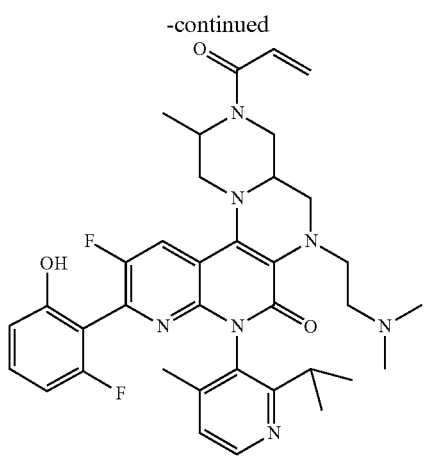
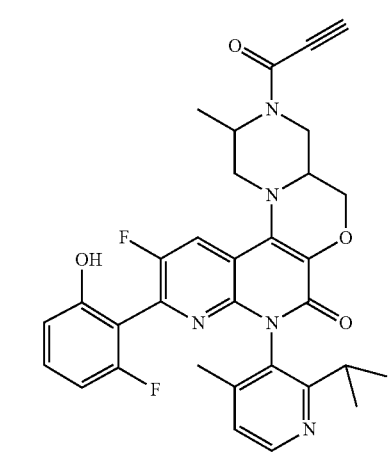
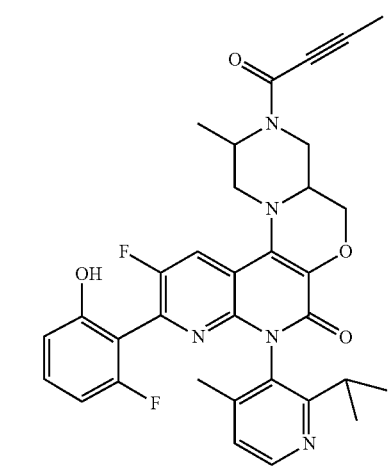
48
-continued
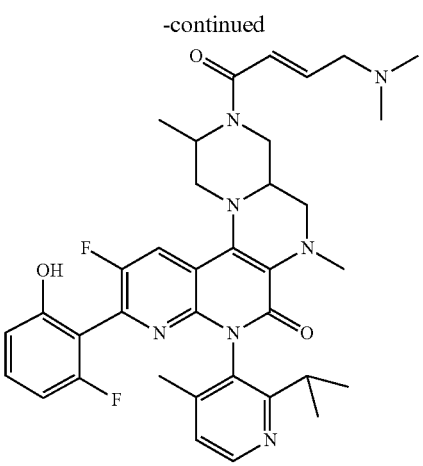
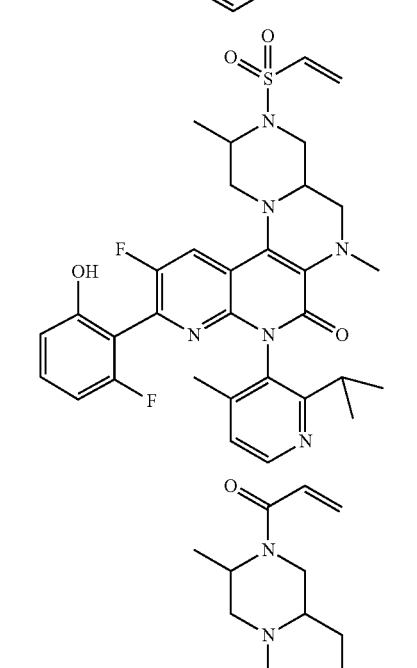
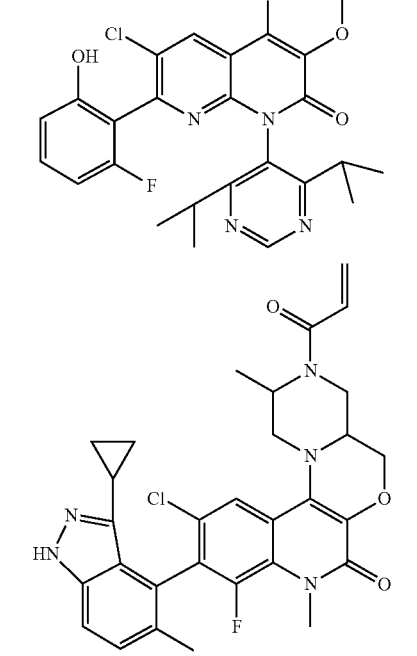

-continued
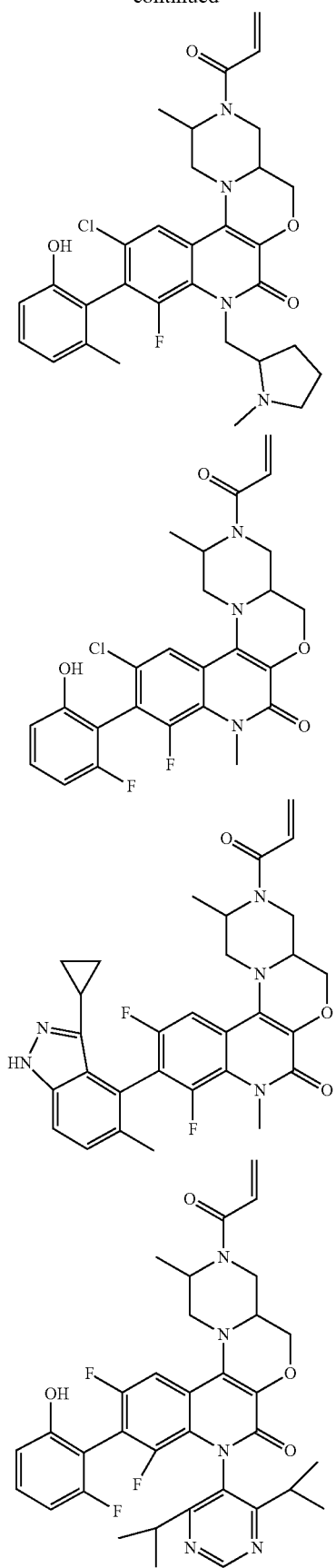
-continued
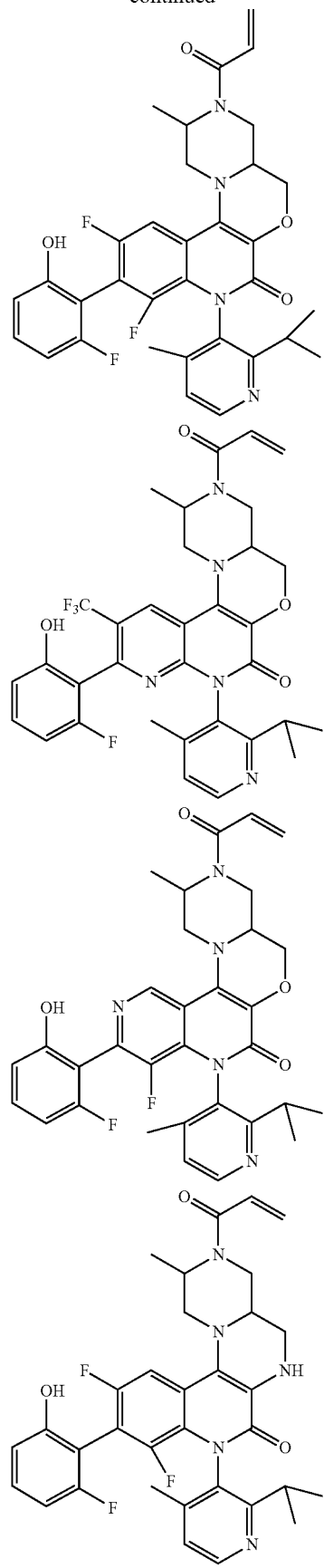

51
-continued
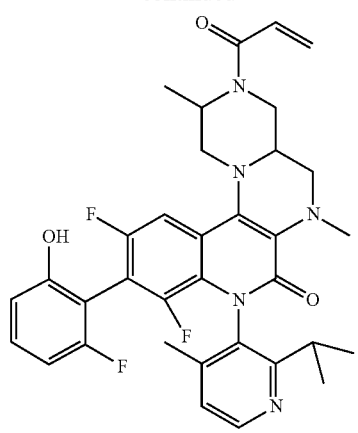
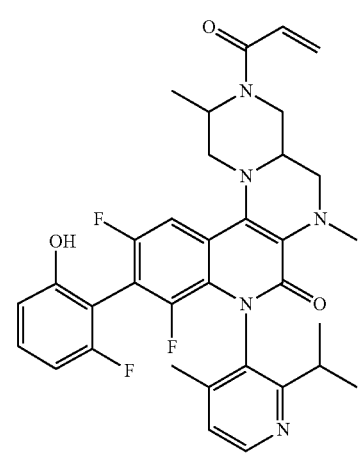
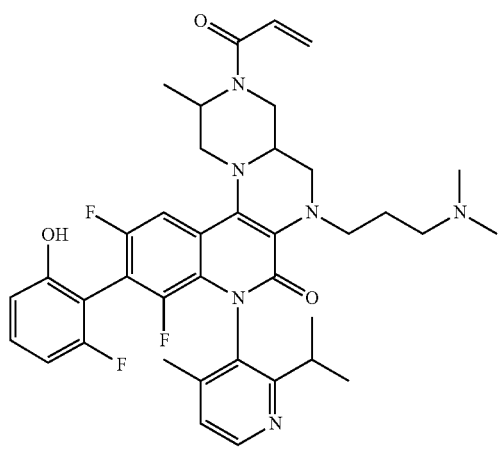
52
-continued
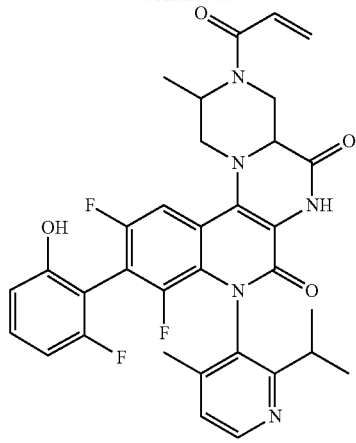
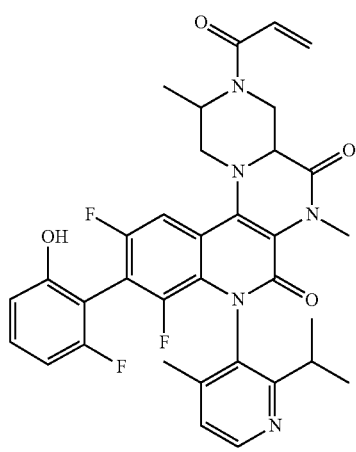
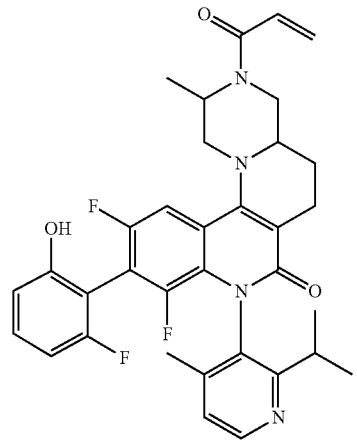

53
-continued
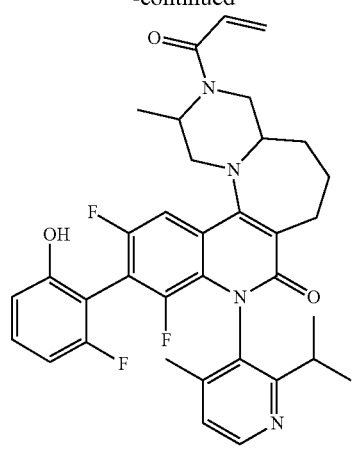
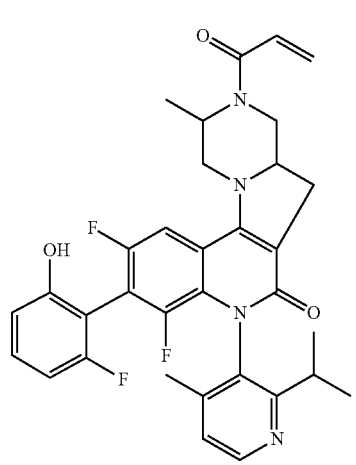
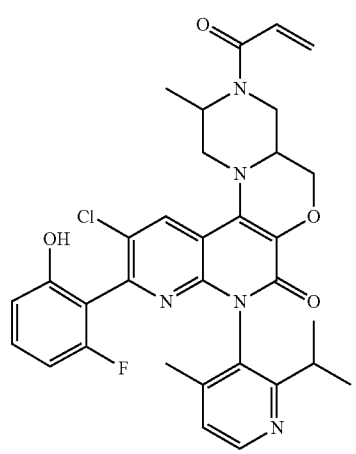
54
-continued
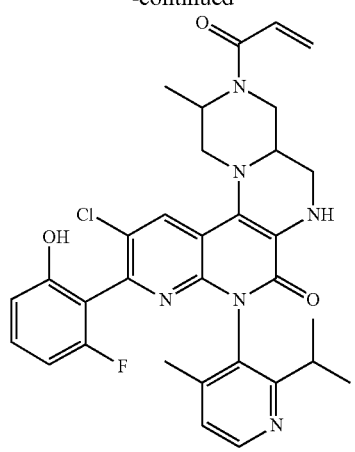
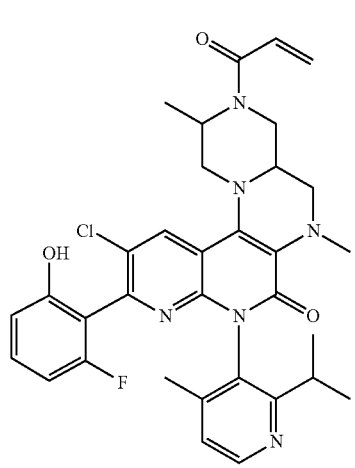
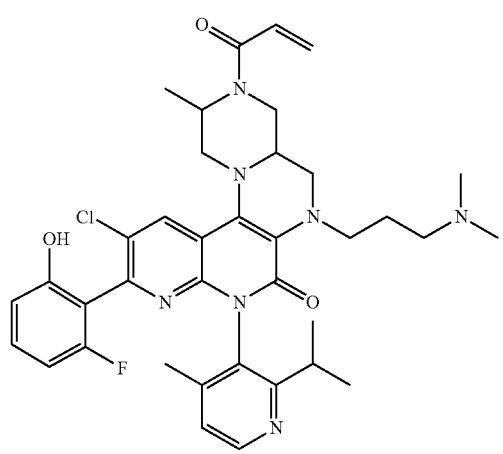

55
-continued
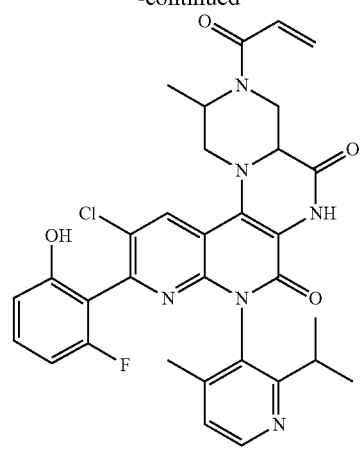
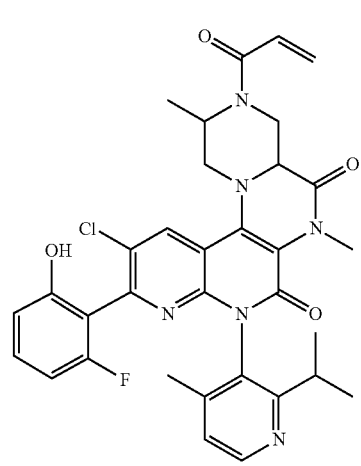
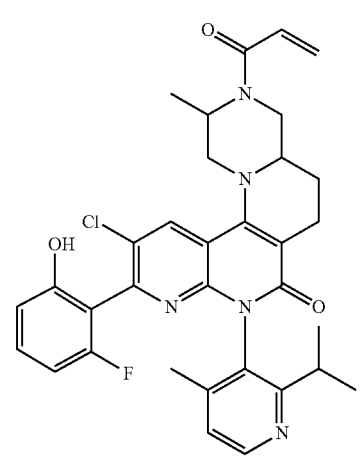
56
-continued
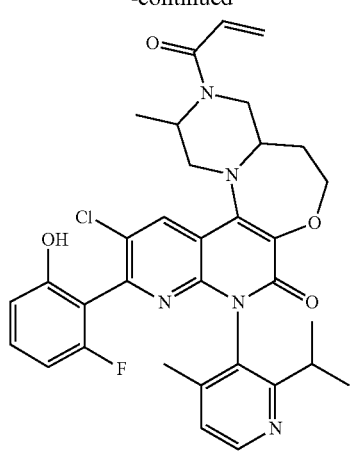
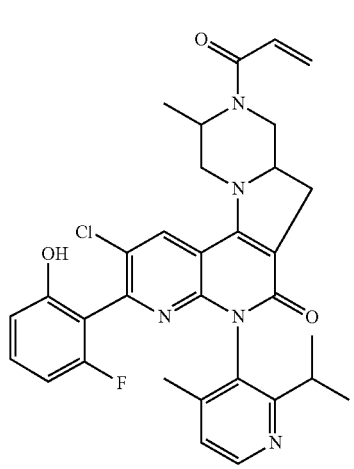
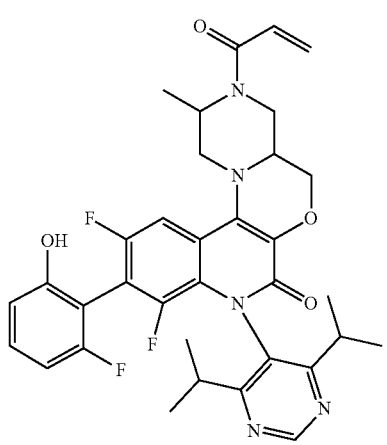

57
-continued
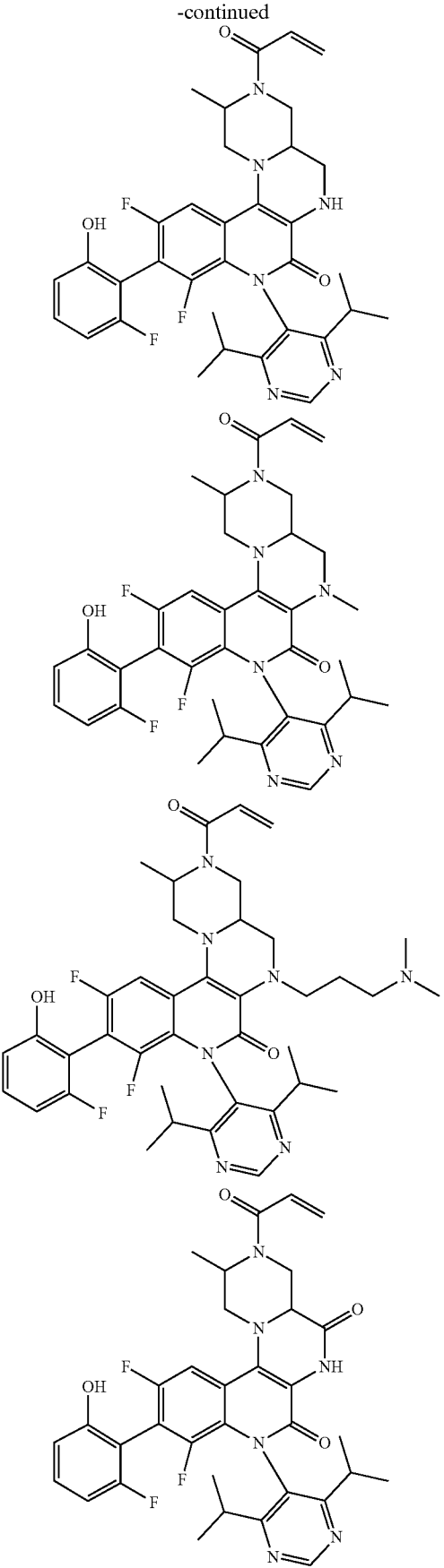
58
-continued
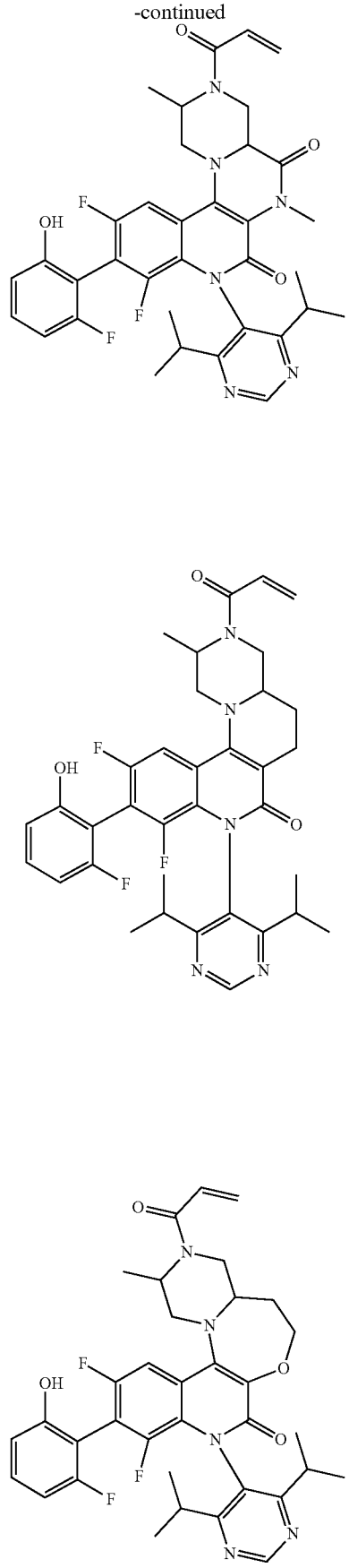

59
-continued
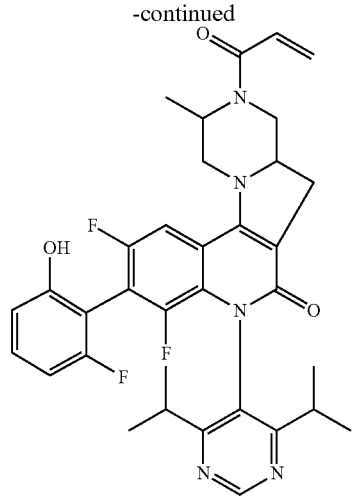
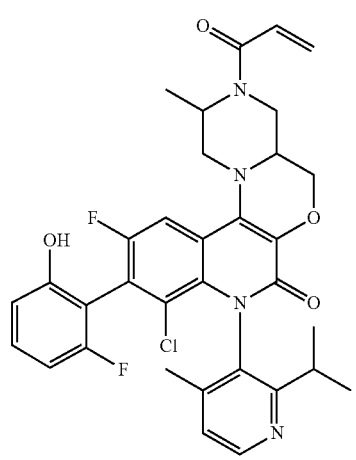
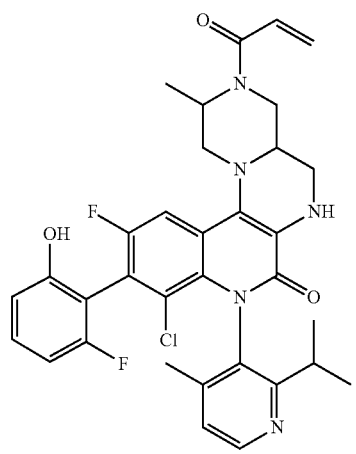
60
-continued
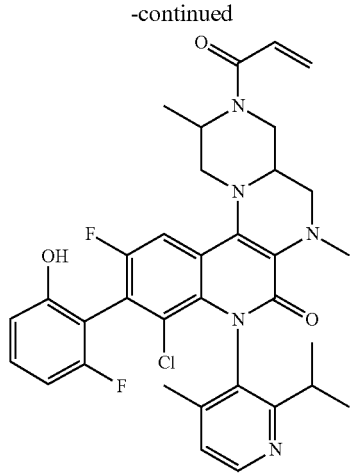
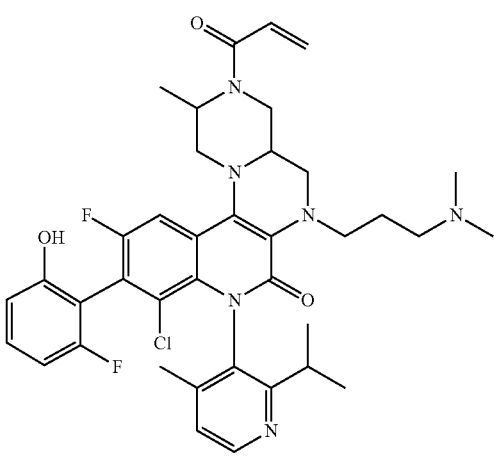
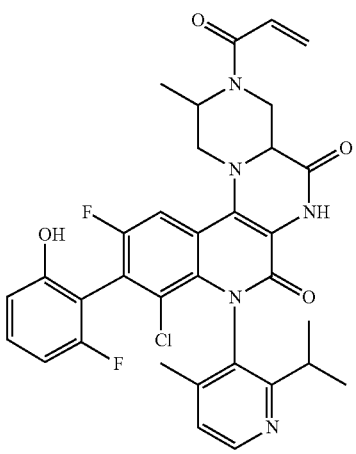

-continued
61
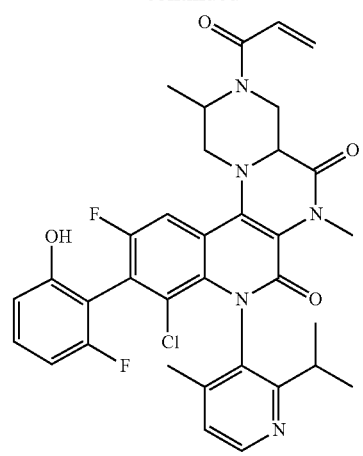
62
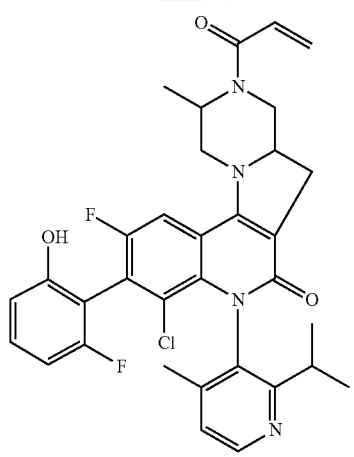
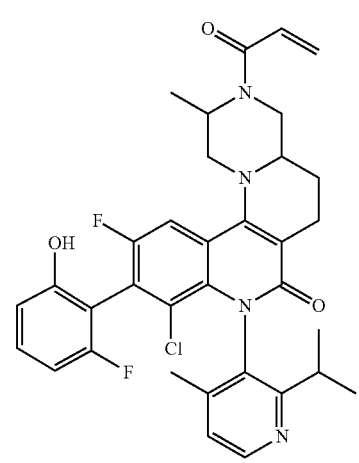
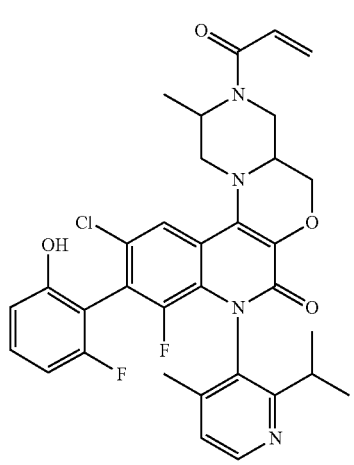
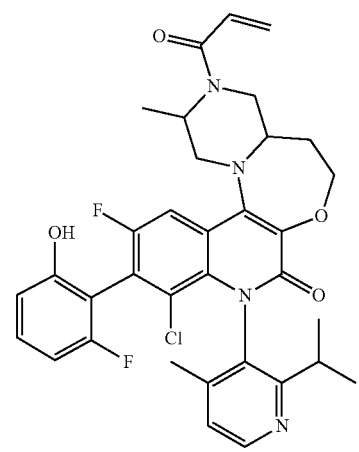
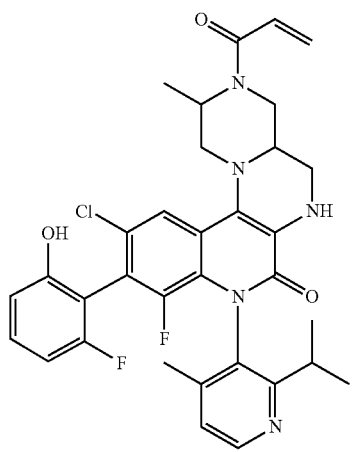

-continued
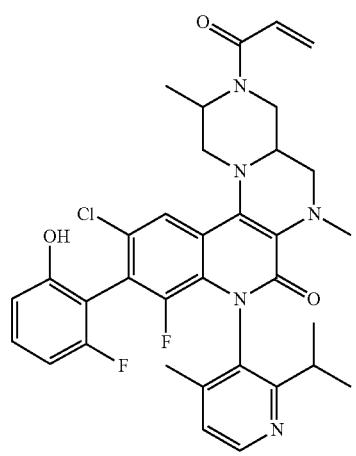
-continued
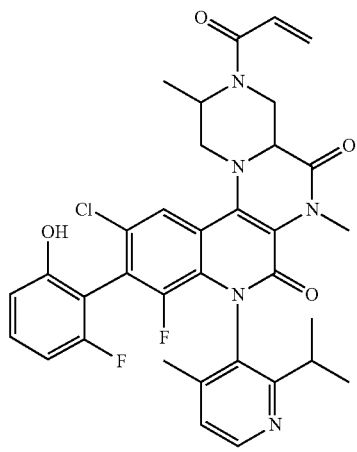
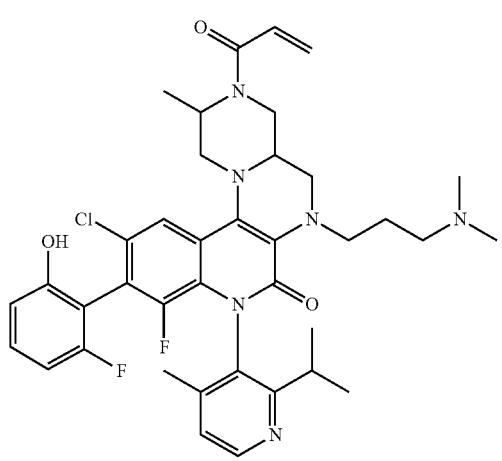
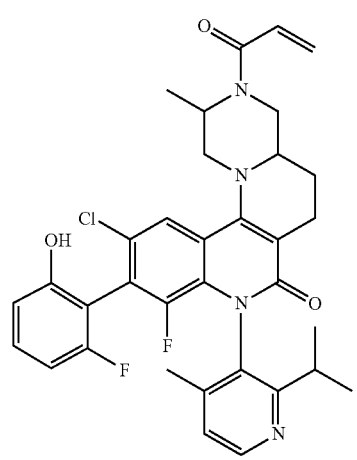
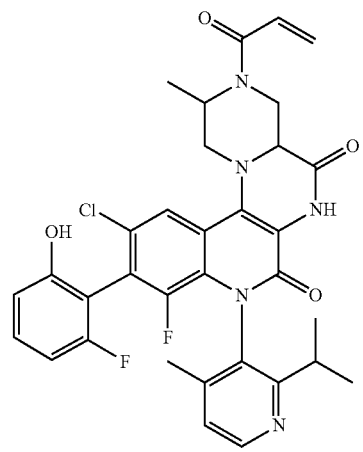
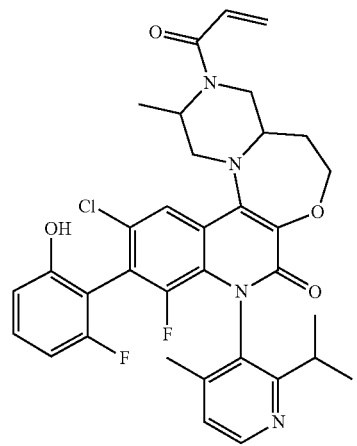

65
-continued
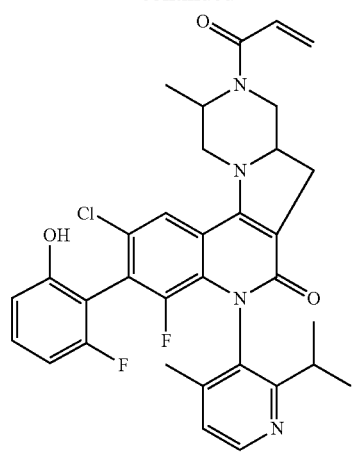
66
-continued
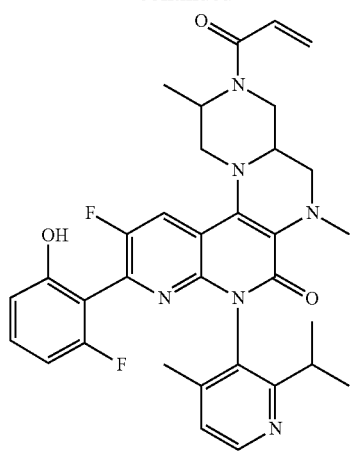
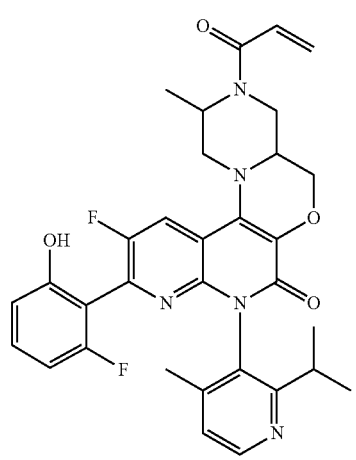
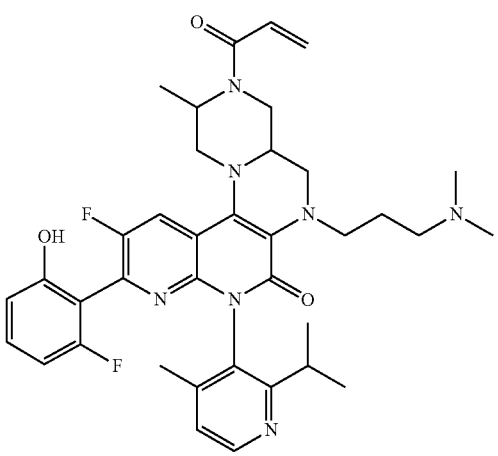
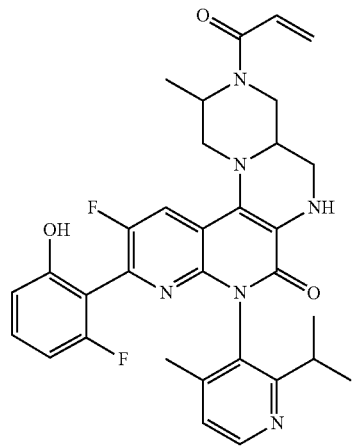
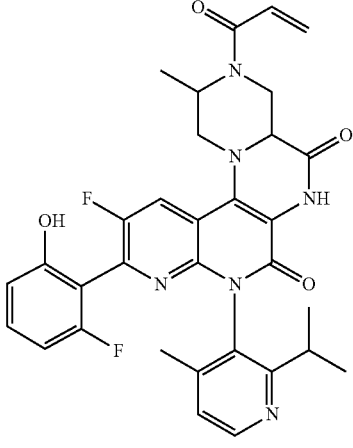

-continued
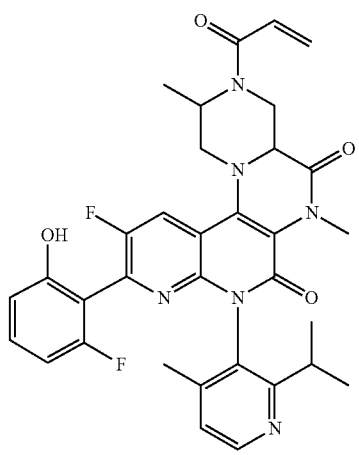
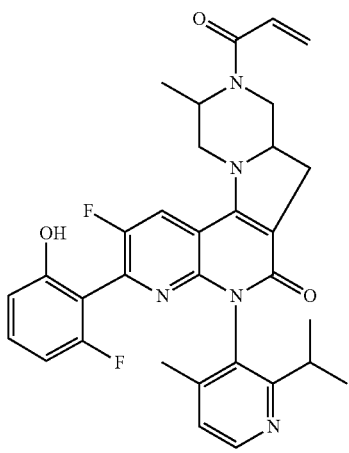
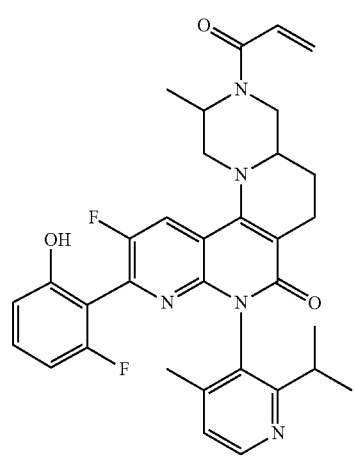
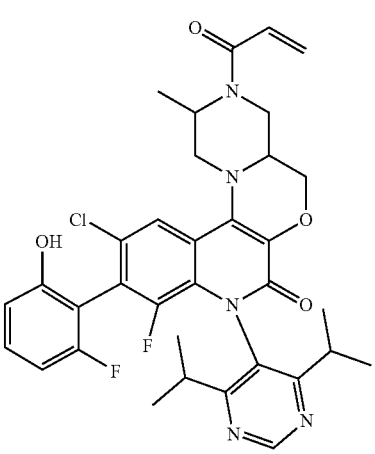
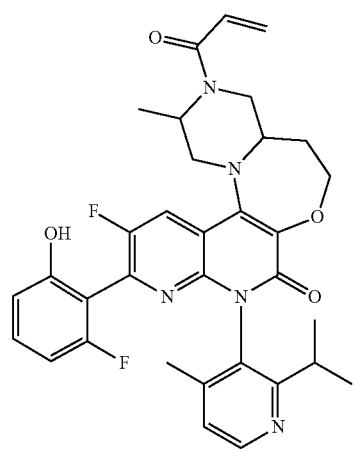
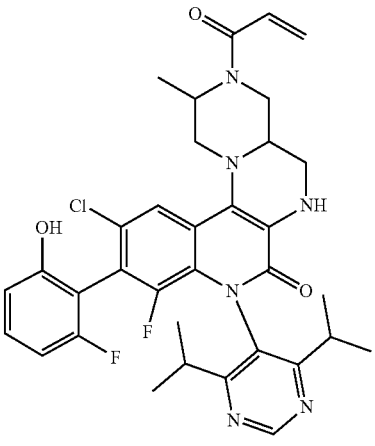

69
-continued
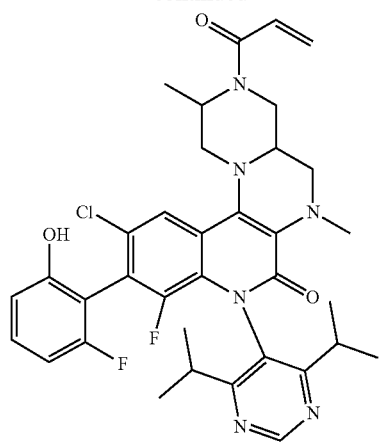
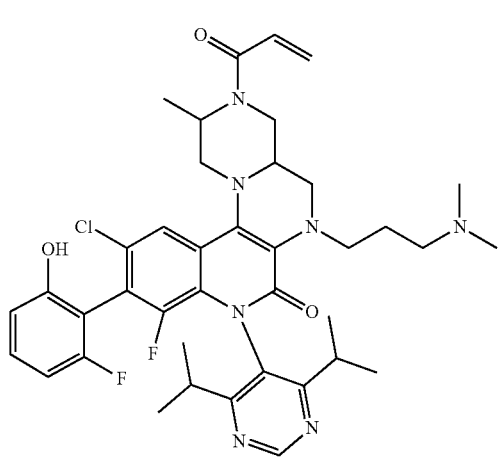
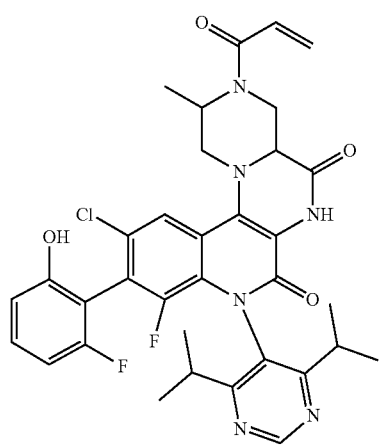
70
-continued

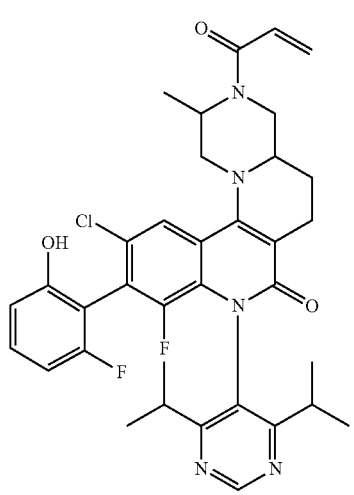
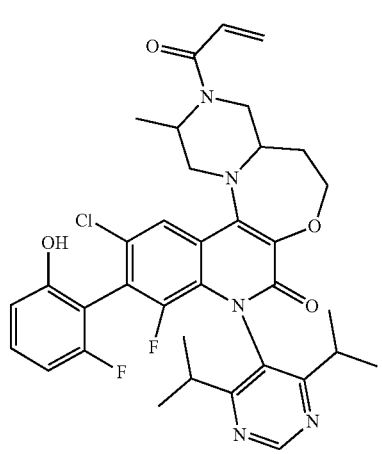

71
-continued
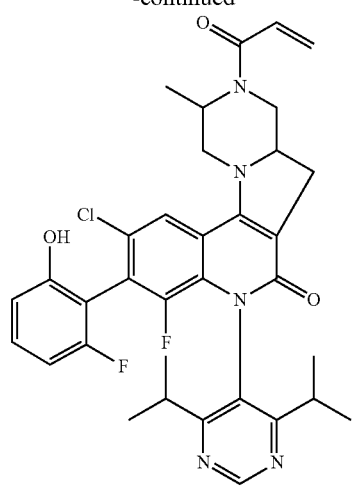
72
-continued
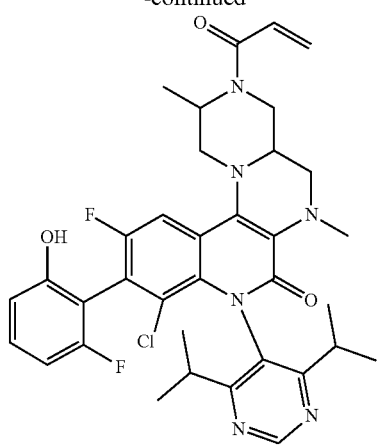
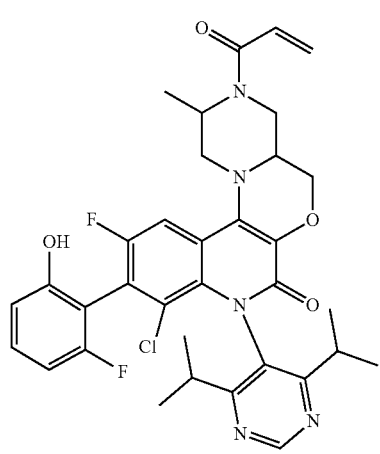
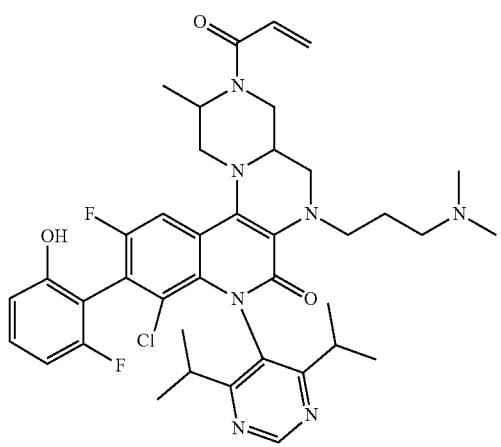
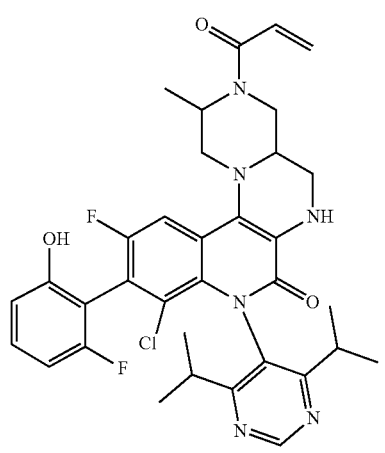
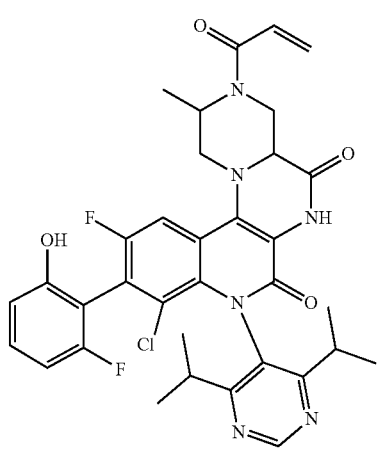

73
-continued
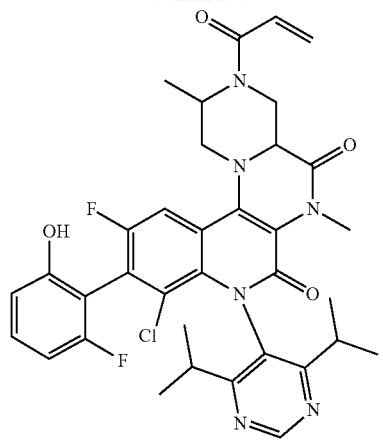
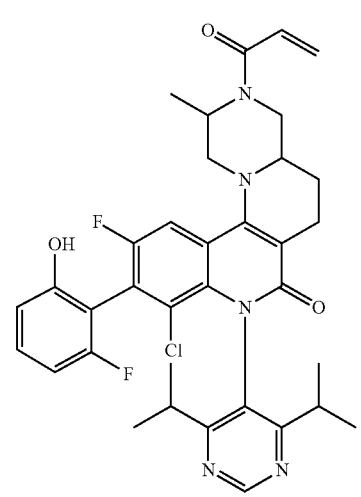
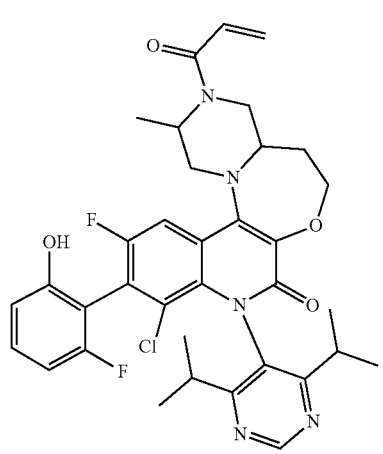
74
-continued
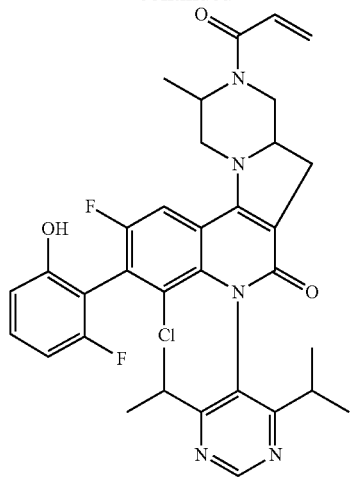
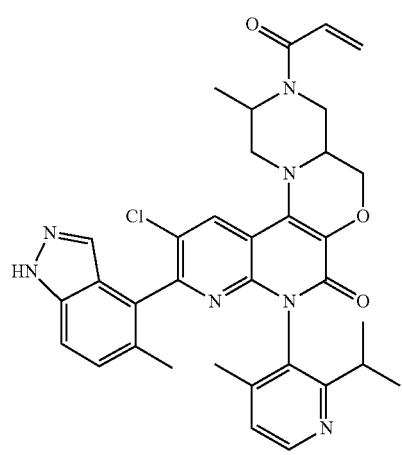
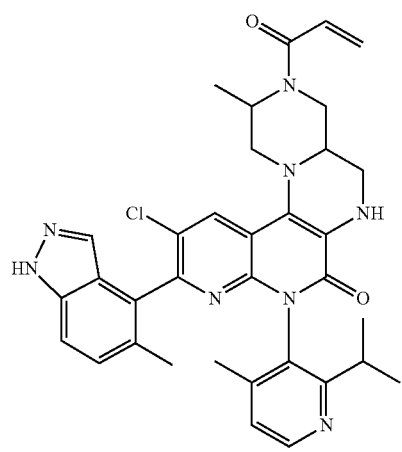

-continued
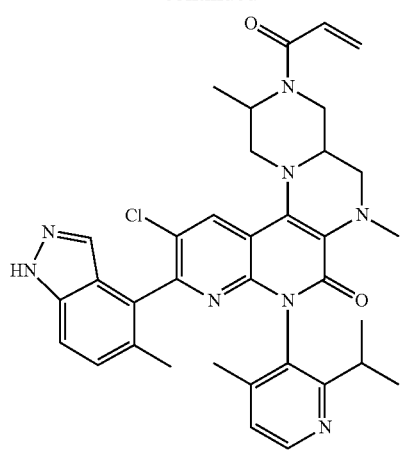
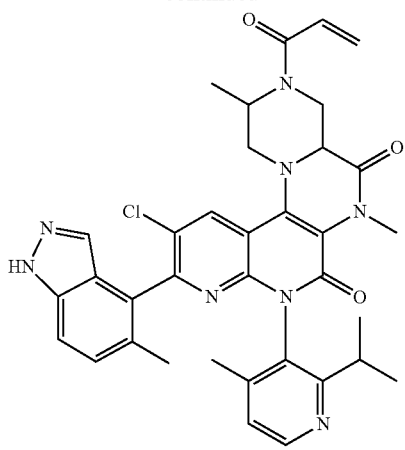
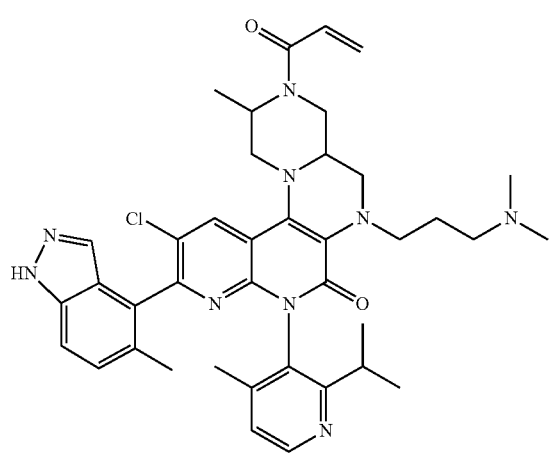
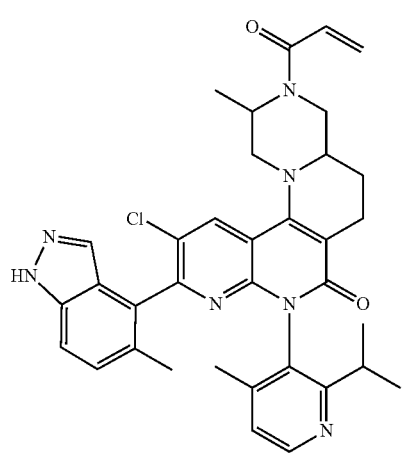
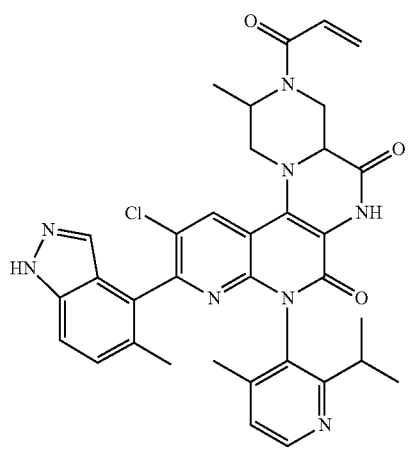
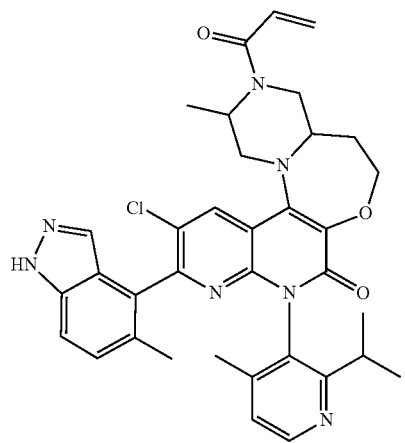

77
-continued
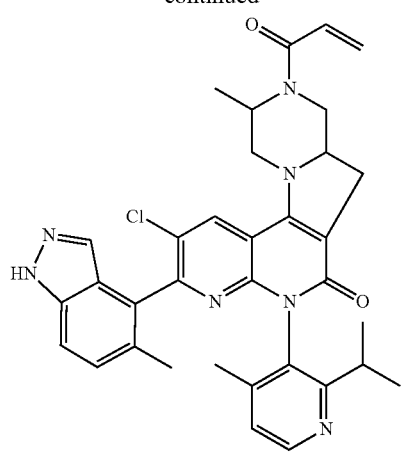
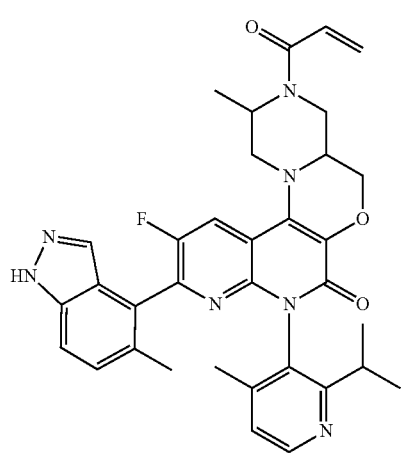
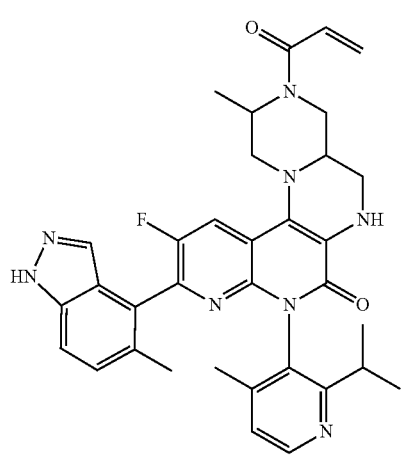
78
-continued
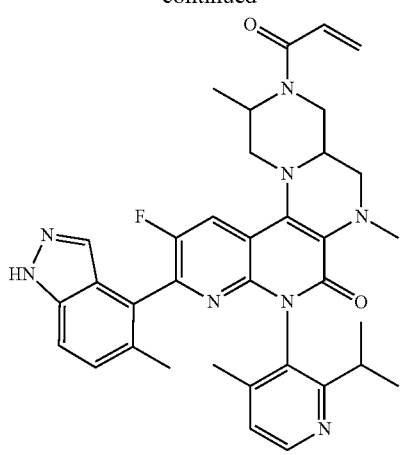
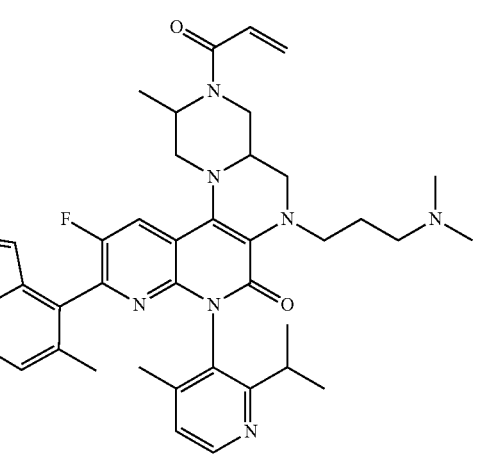
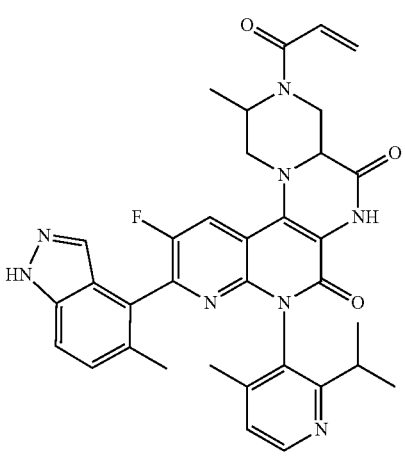

79
-continued
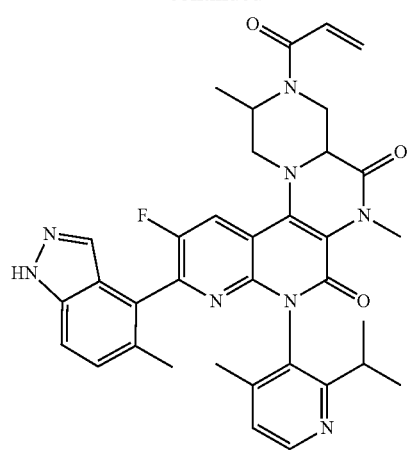
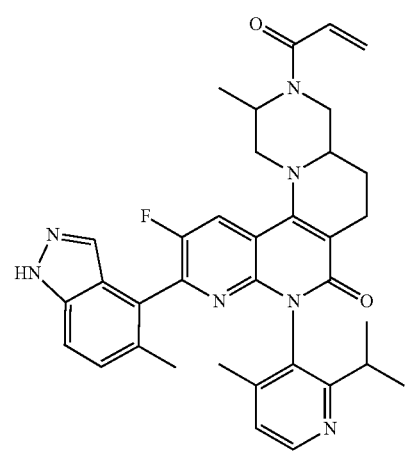
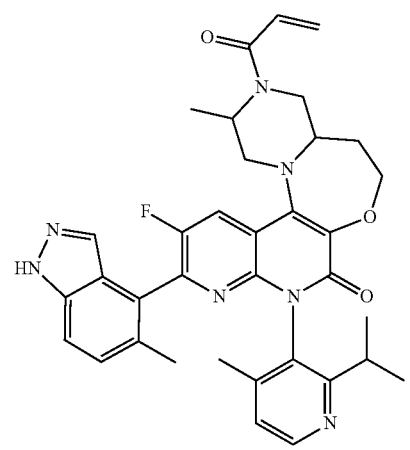
80
-continued
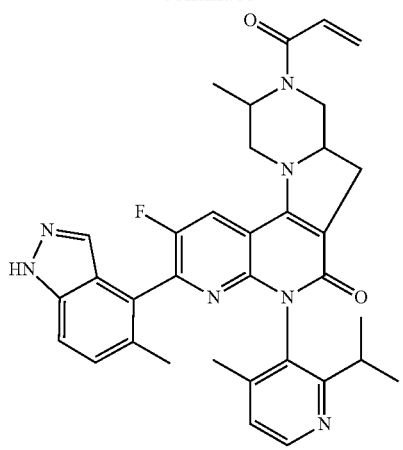
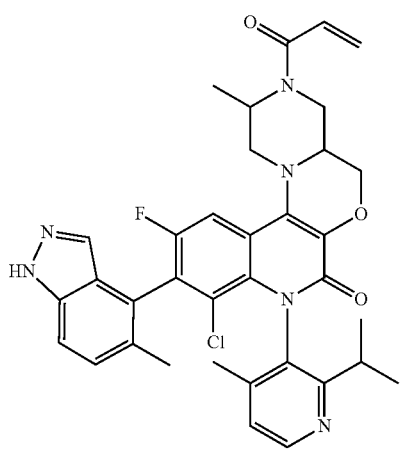
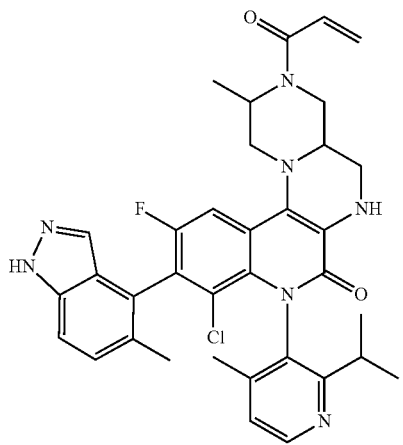

-continued
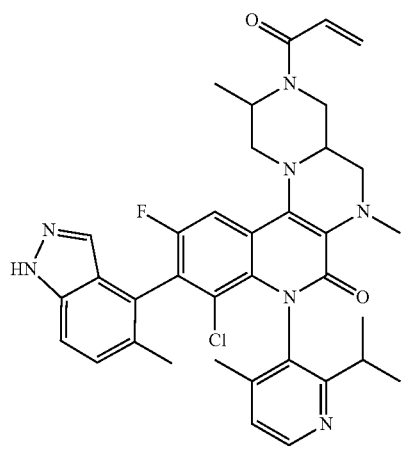
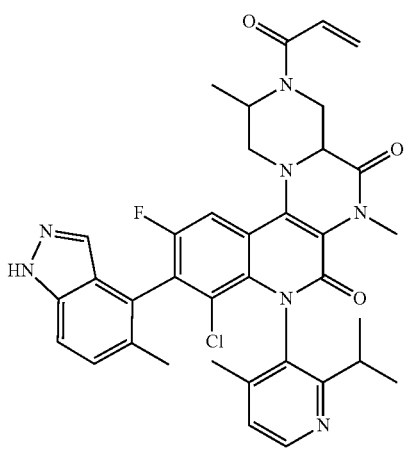
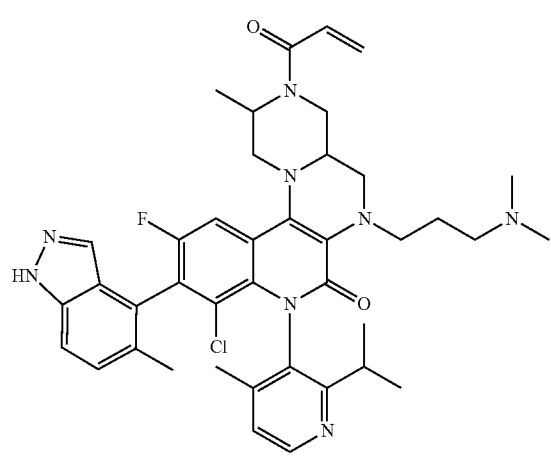
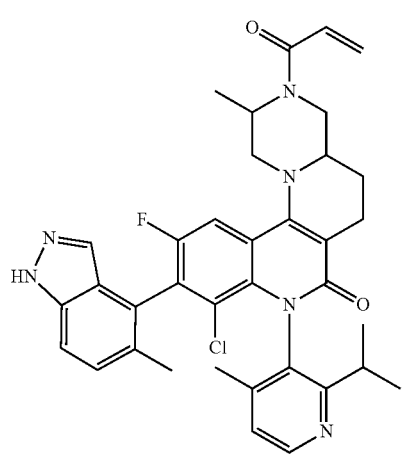
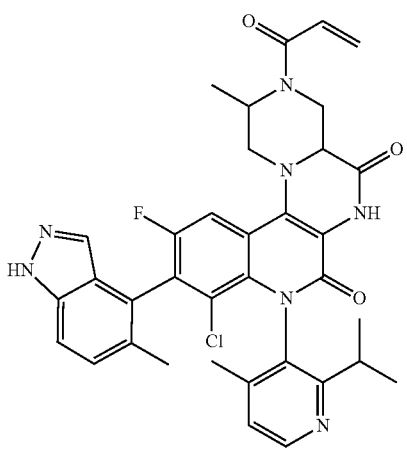
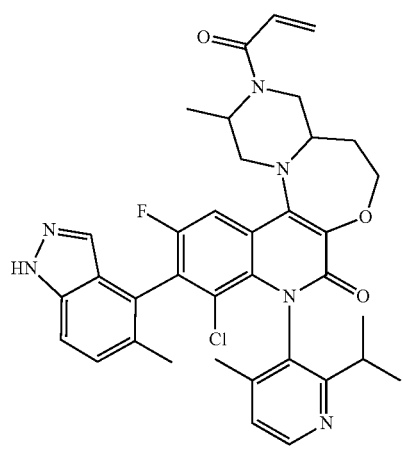

83 84
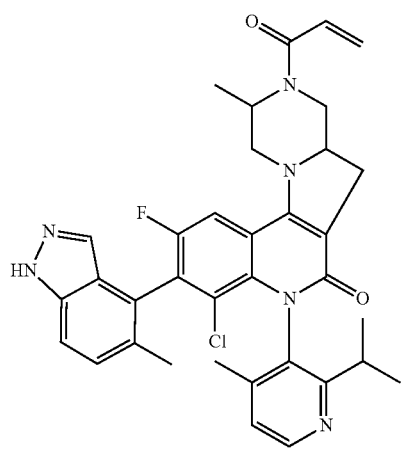
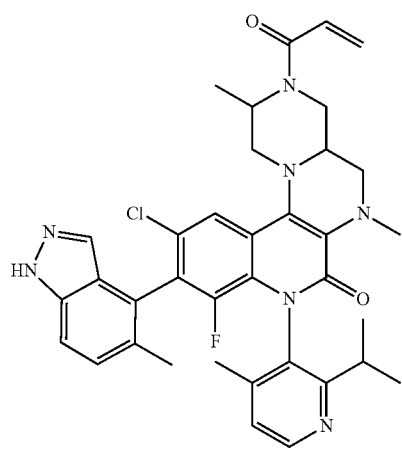
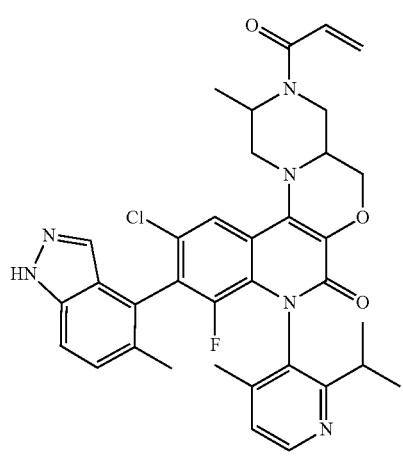
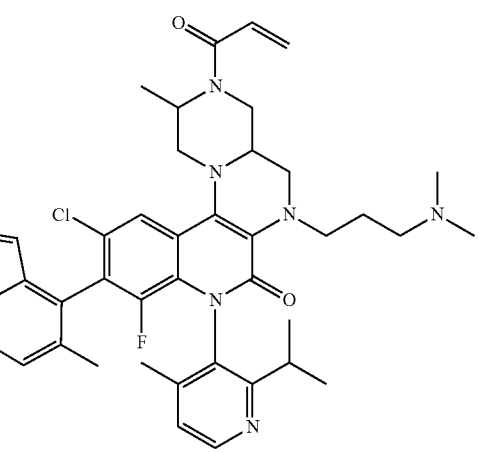
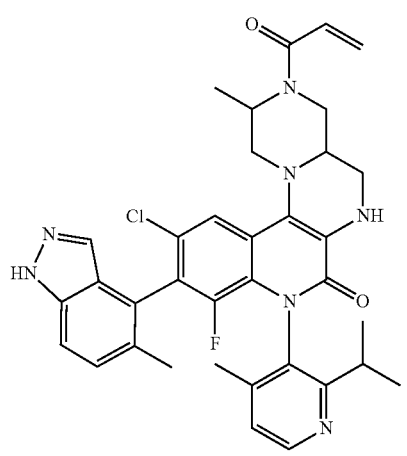
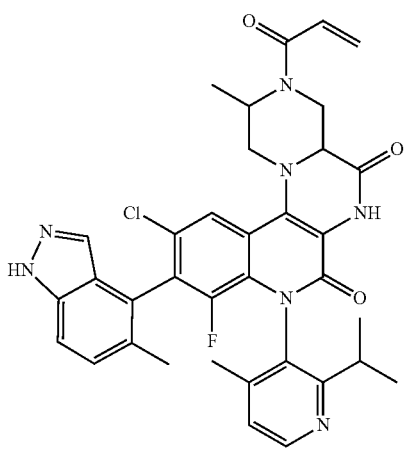

85
-continued
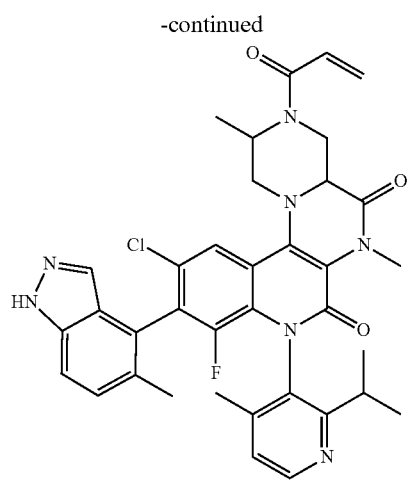
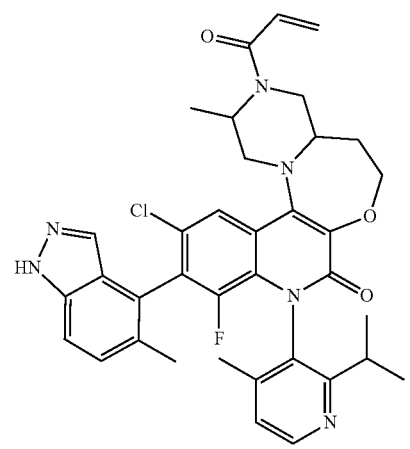
86
-continued
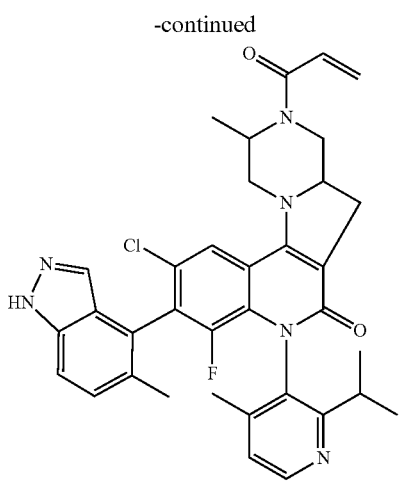
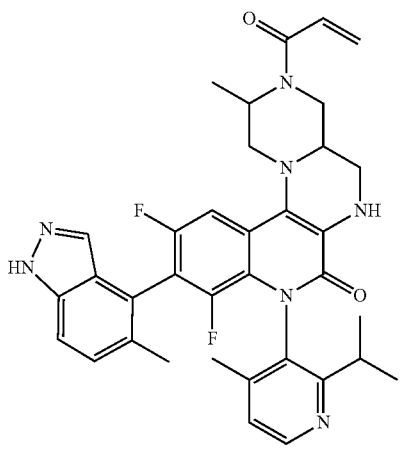

87
-continued
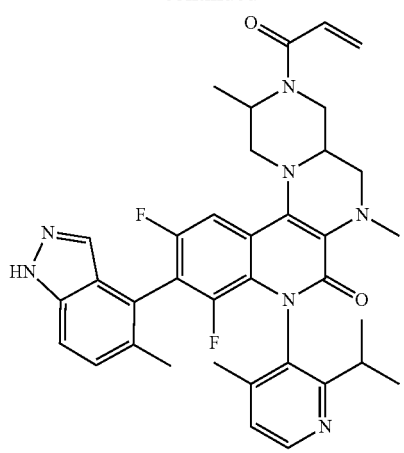
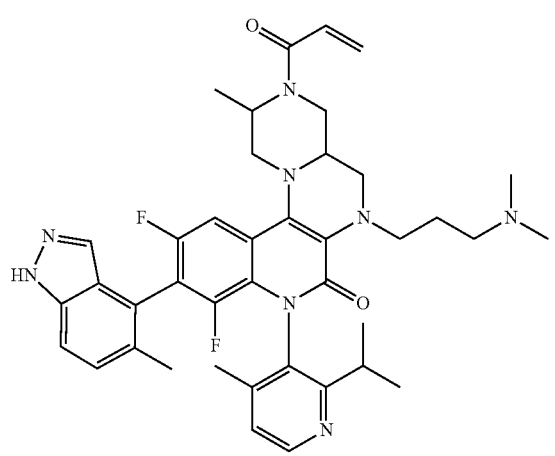
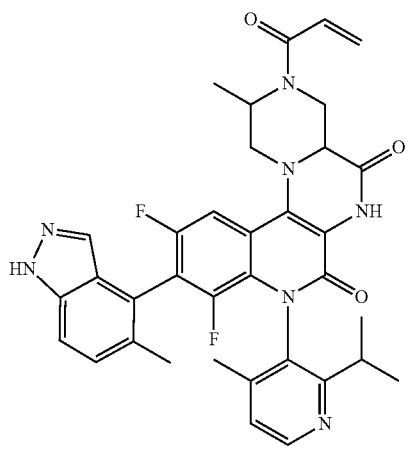
88
-continued
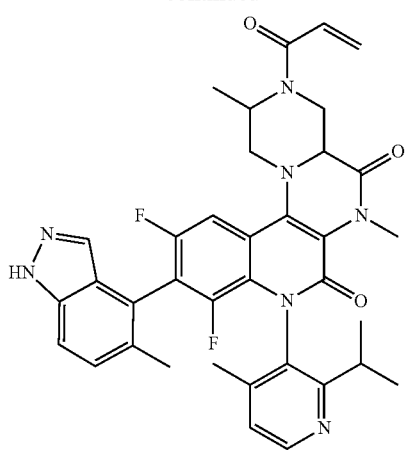
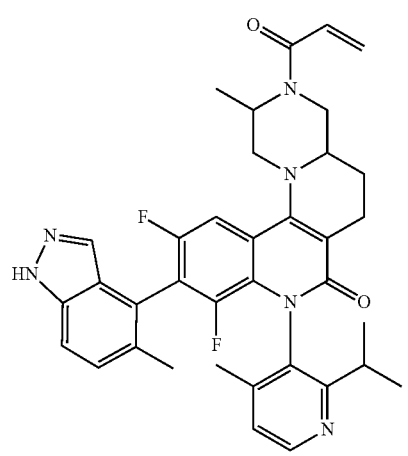
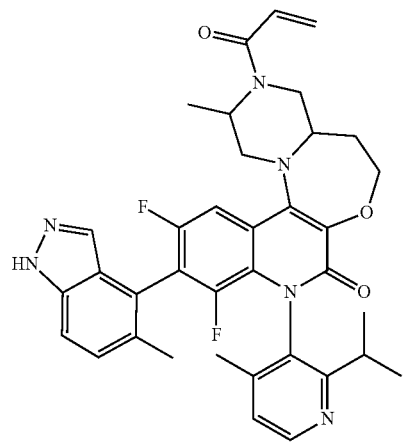

89
-continued
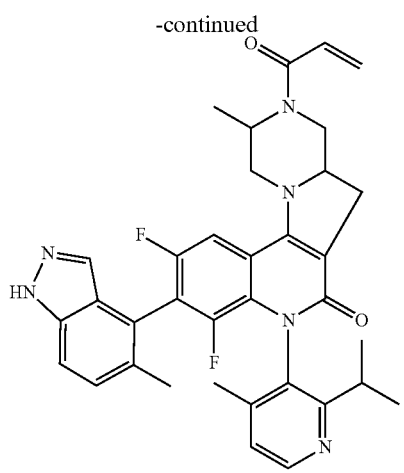
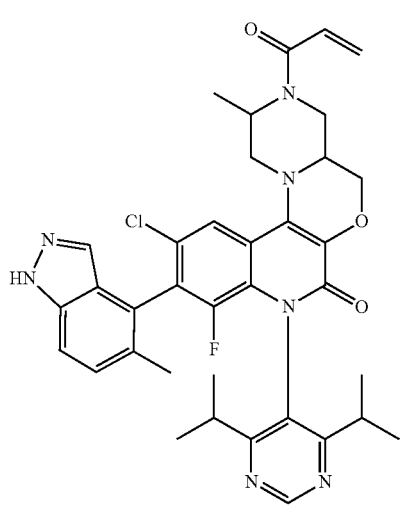
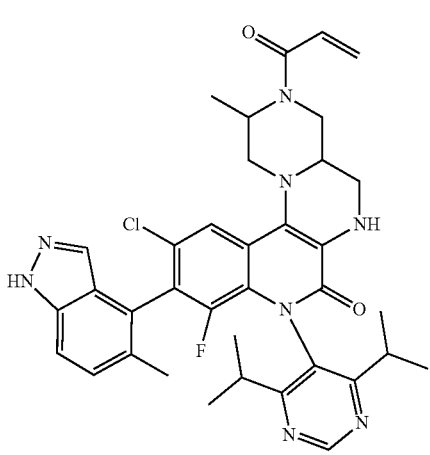
90
-continued
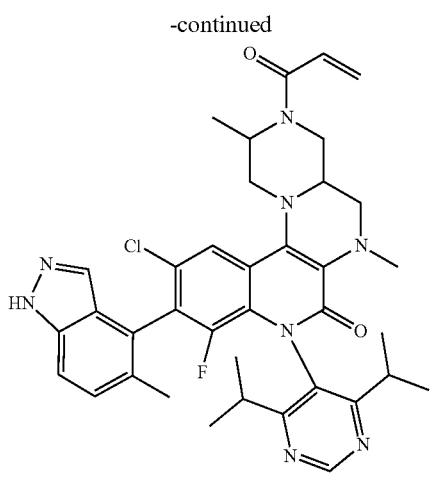
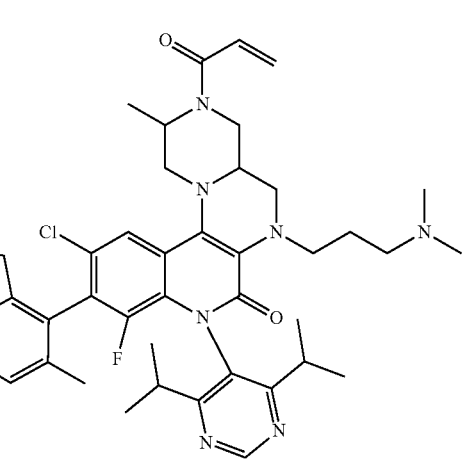
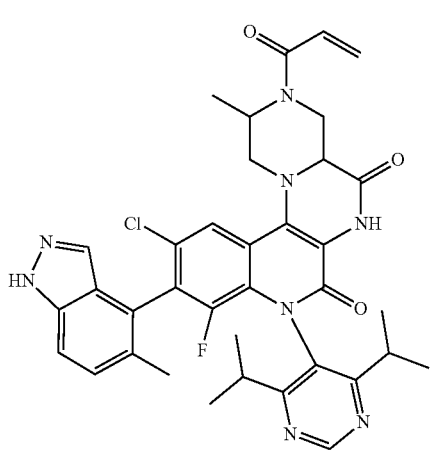

91
-continued
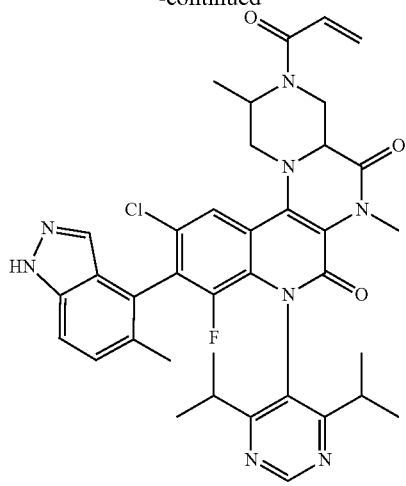
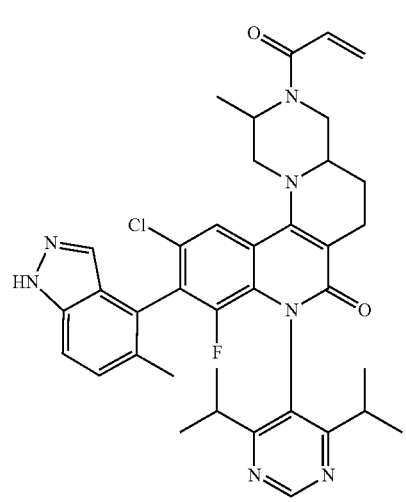
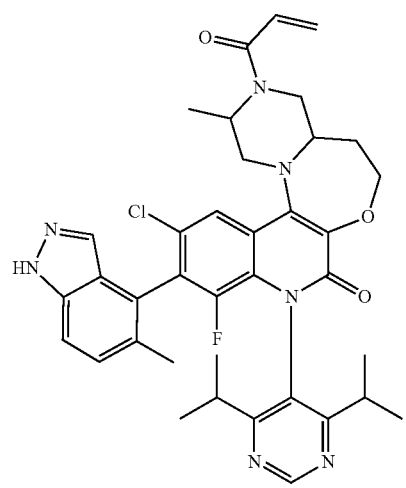
92
-continued
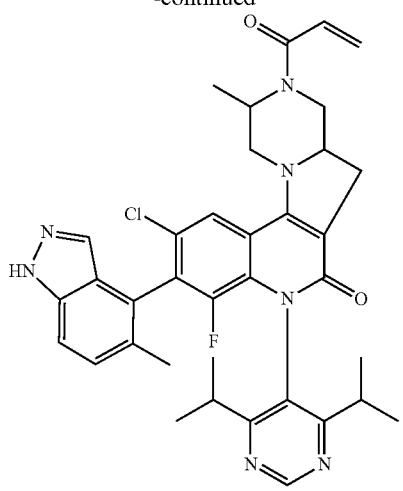
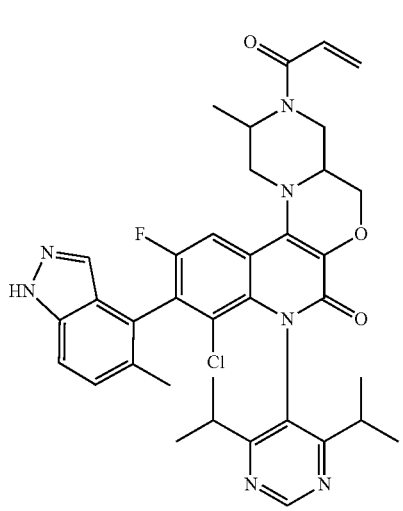
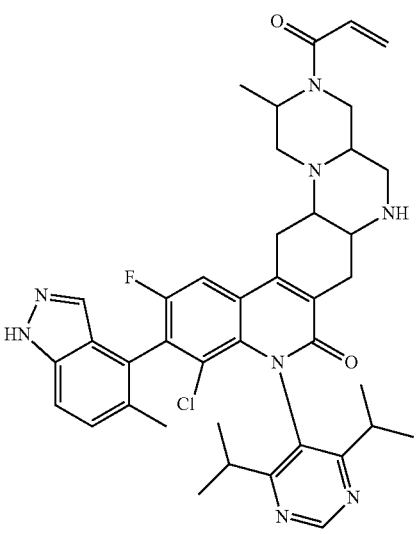

93
-continued
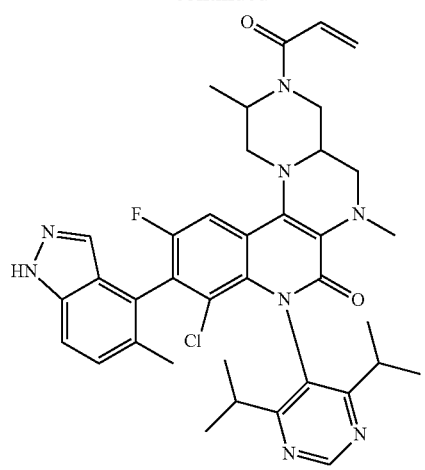
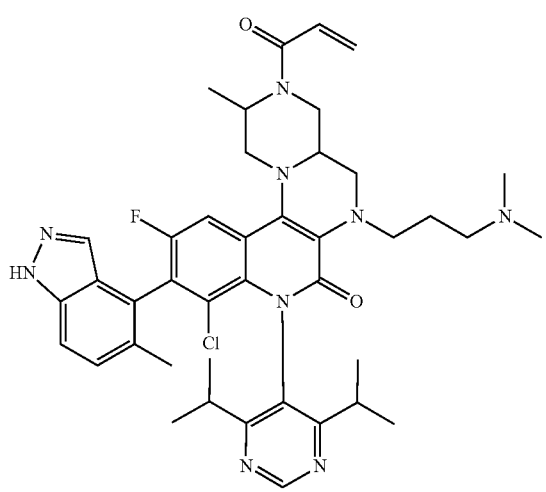
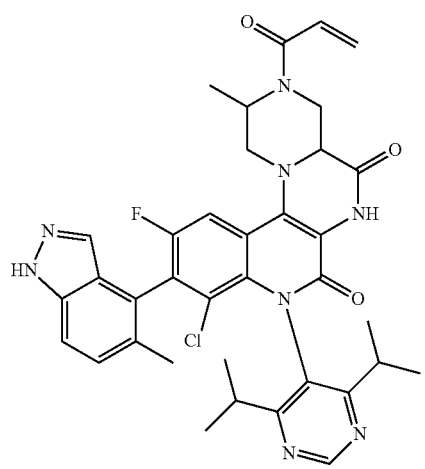
94
-continued
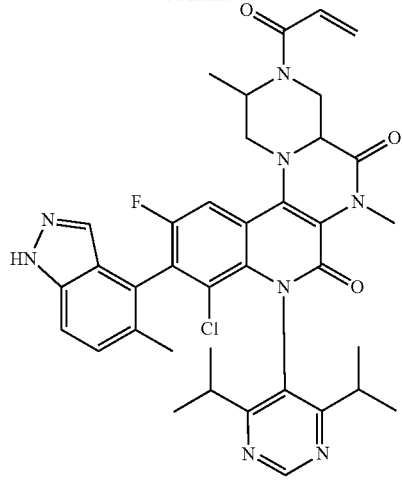
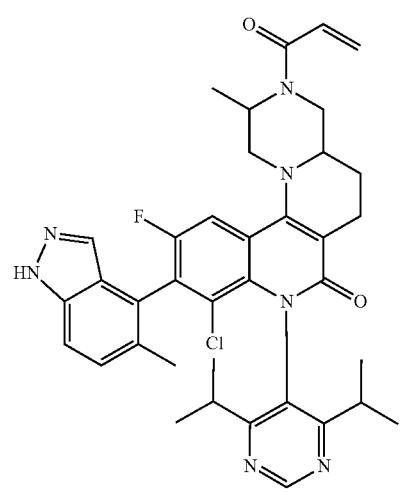
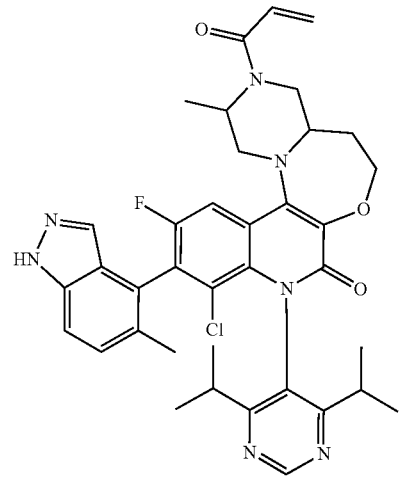

95
-continued
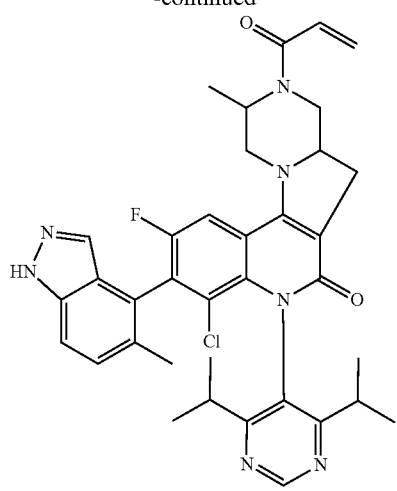
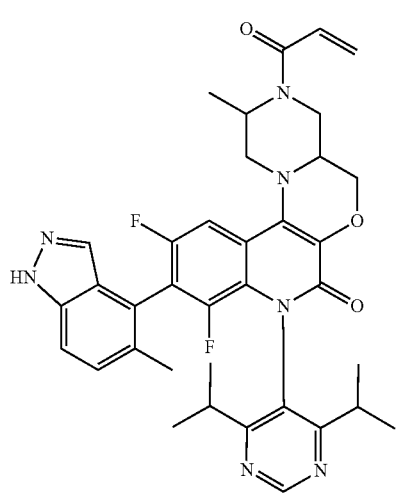
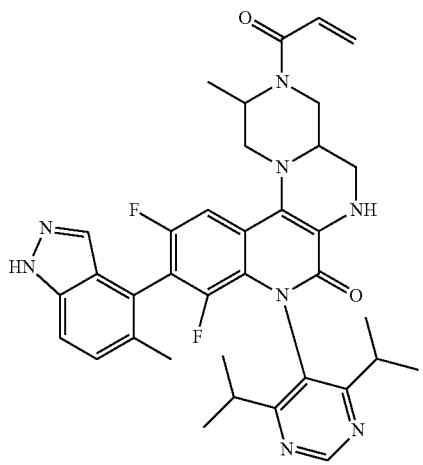
96
-continued
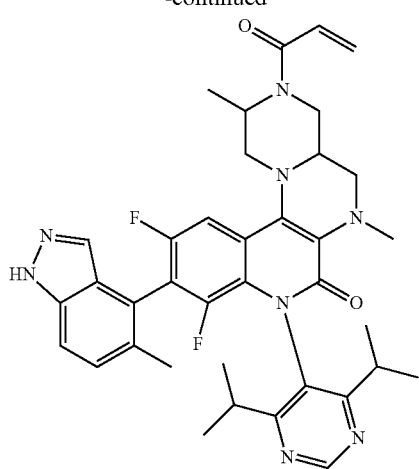
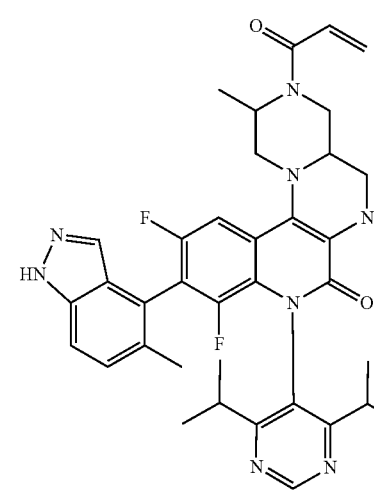
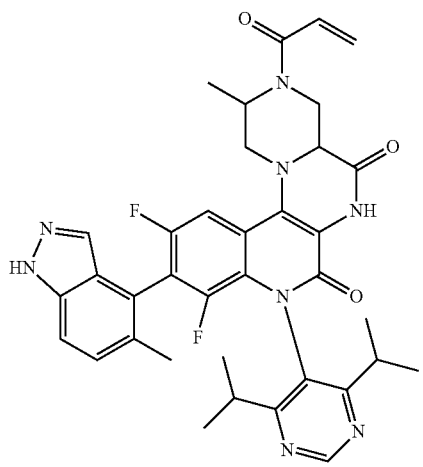

97
-continued
98
-continued
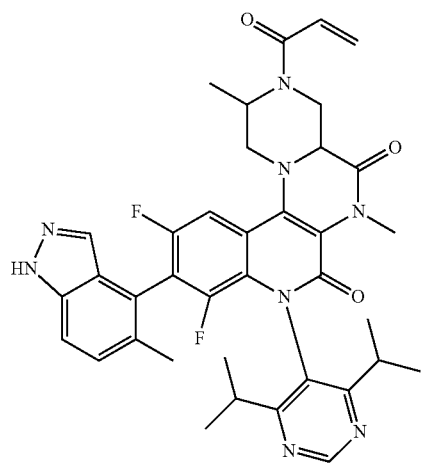
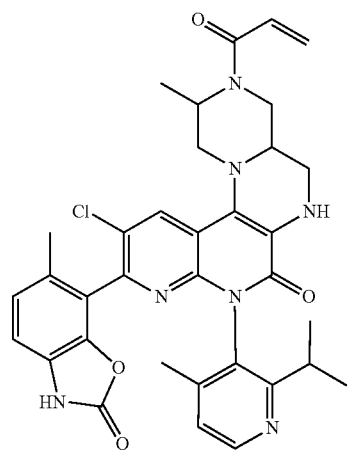
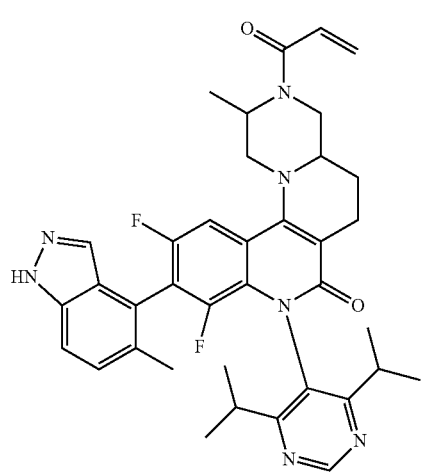
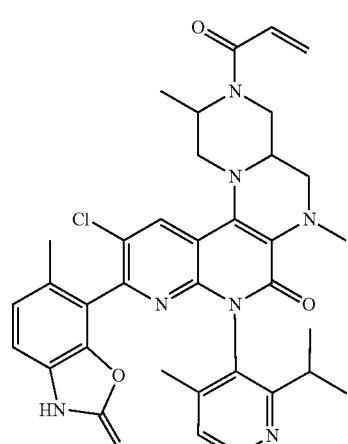
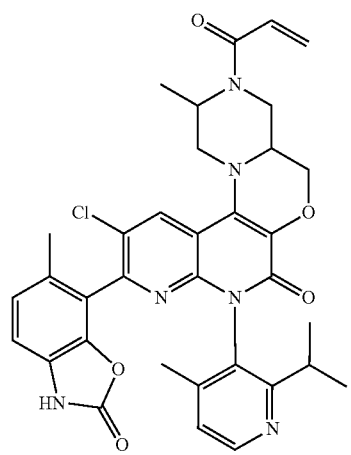
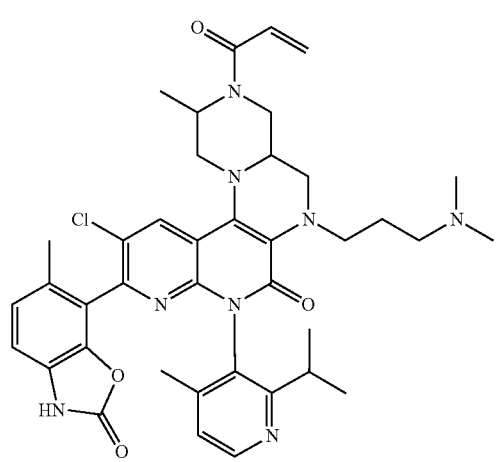

99
-continued

100
-continued

101
-continued
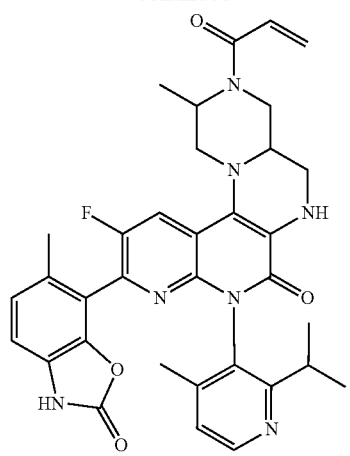
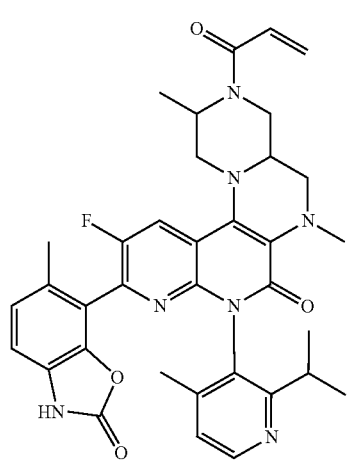
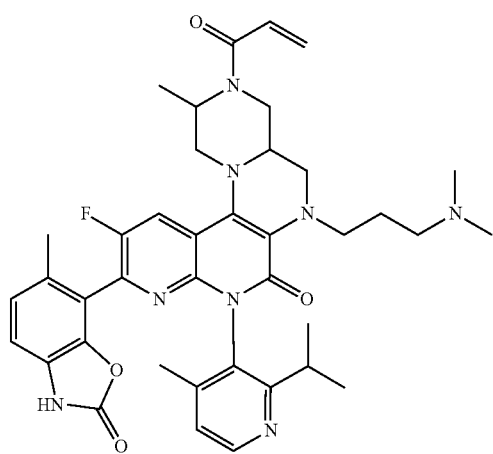
102
-continued
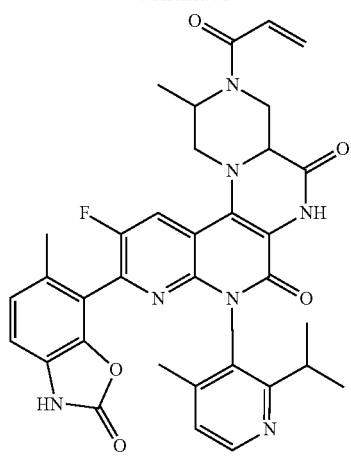
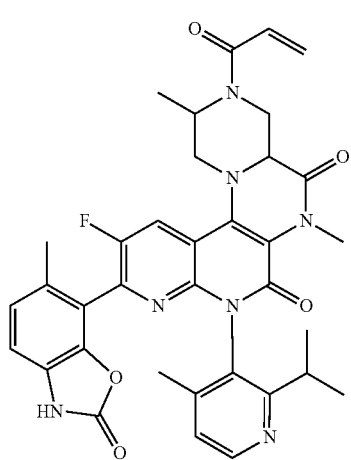
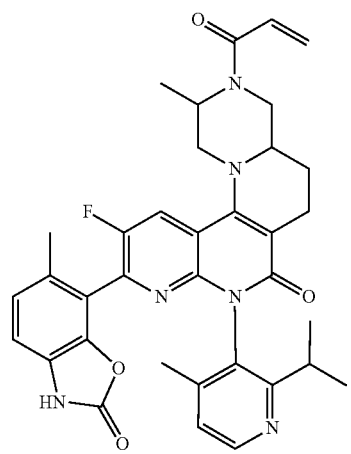

103
-continued
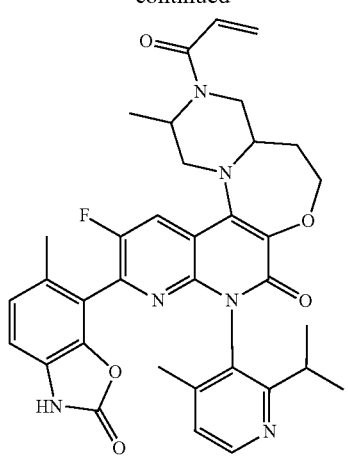
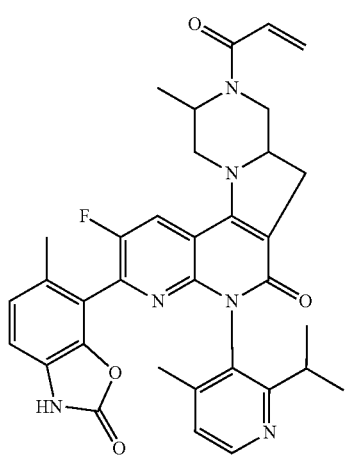
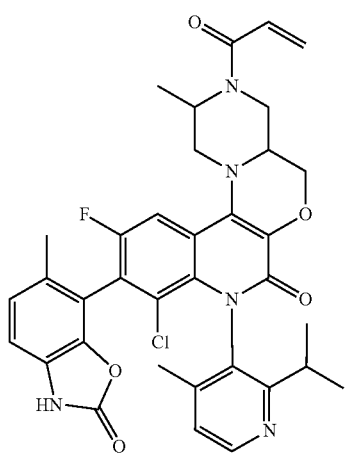
104
-continued
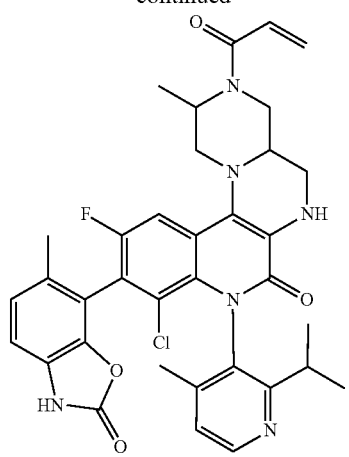
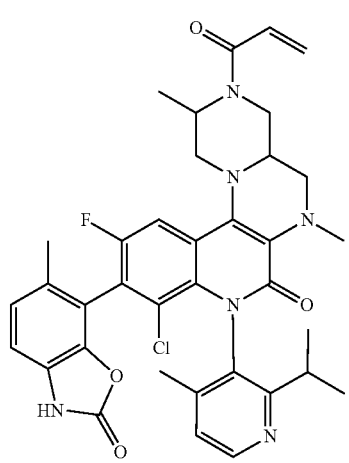
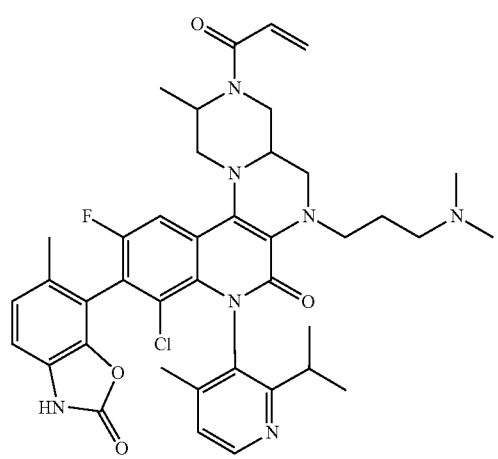

105
-continued
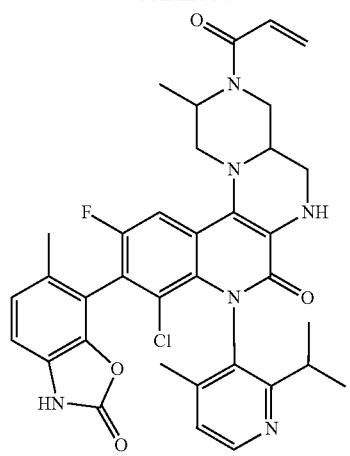
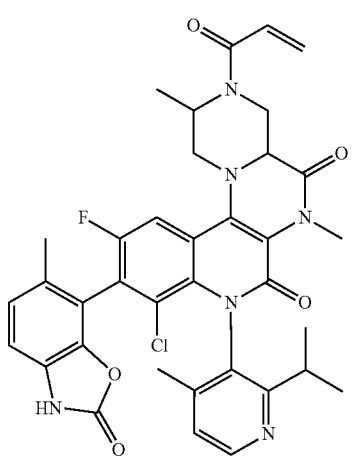
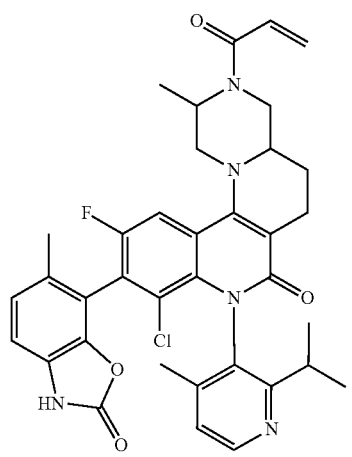
106
-continued
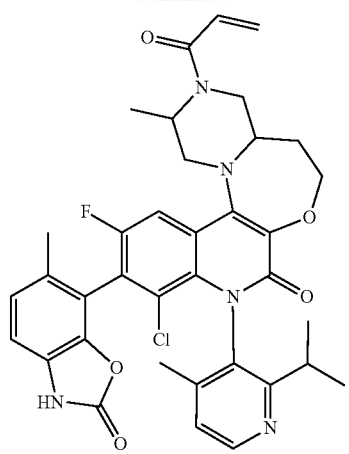
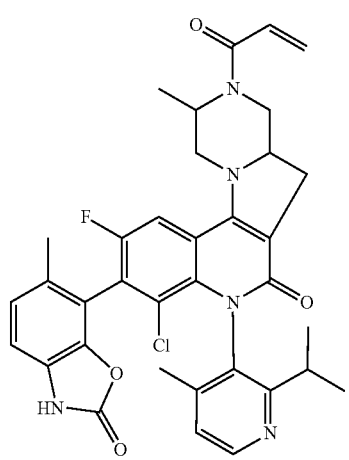
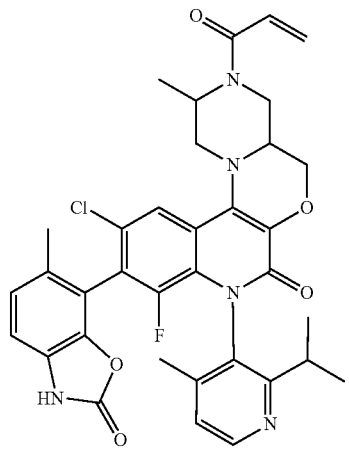

107
-continued
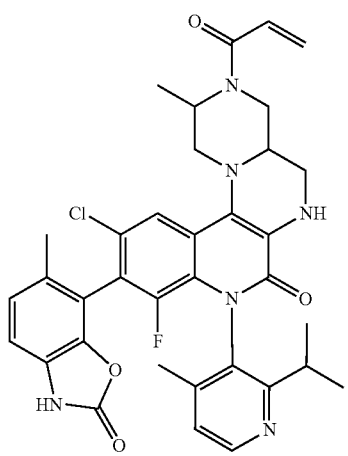
108
-continued
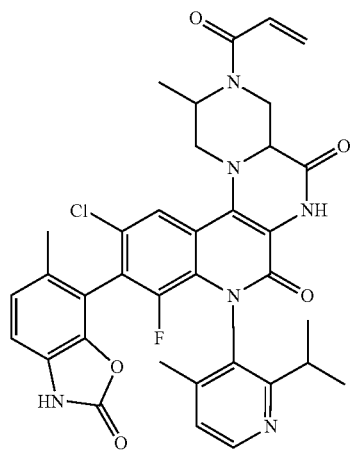
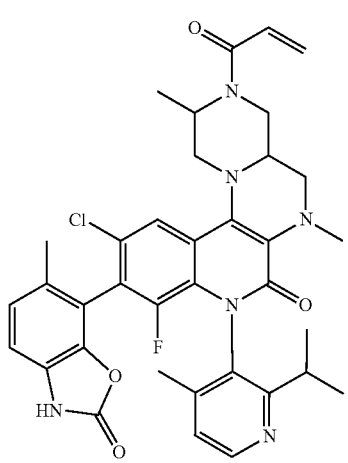
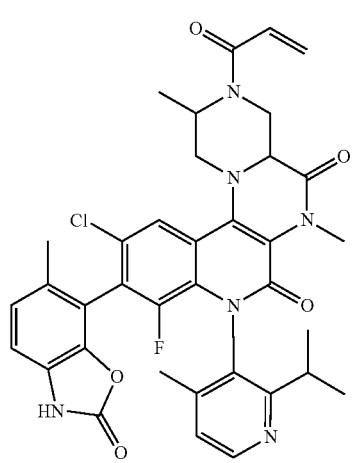
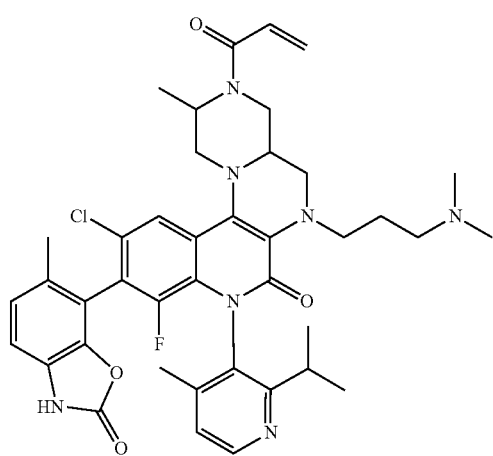
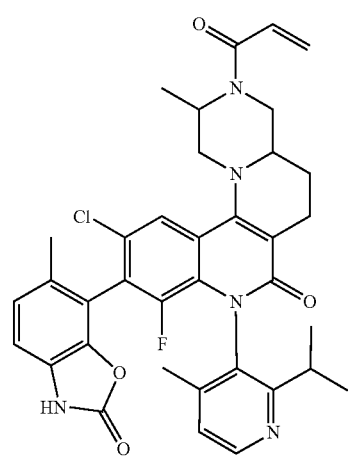

109
-continued
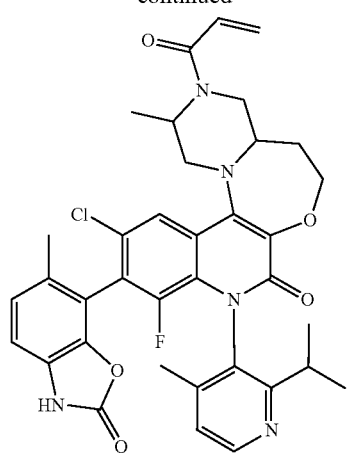
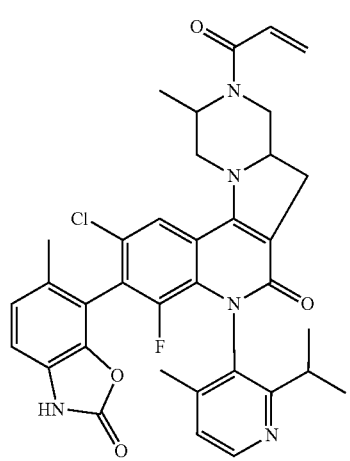 [SMILES: C=CC(=O)N1CC2Cc3c(c4cc(F)c(-c5c(C)ccc6[nH]c(=O)oc56)c(F)c4n(-c4c(C)ccnc4C(C)C)c3=O)N2CC1C]
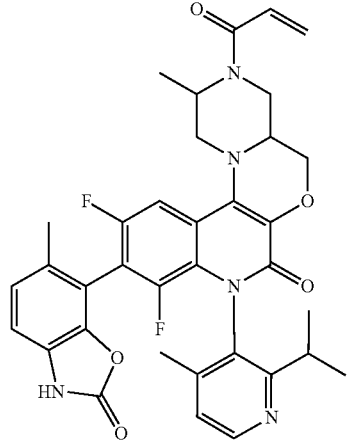
110
-continued
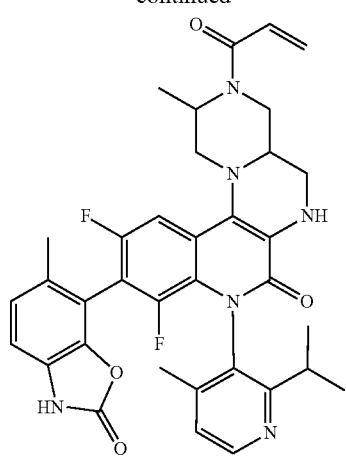
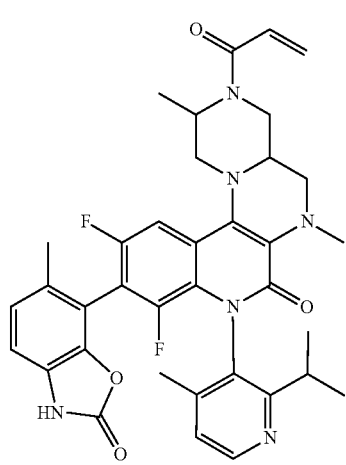
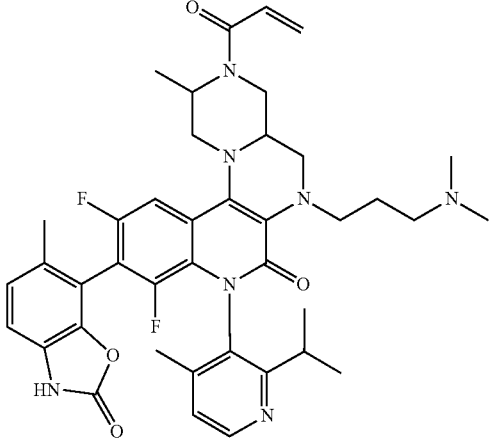

111
-continued
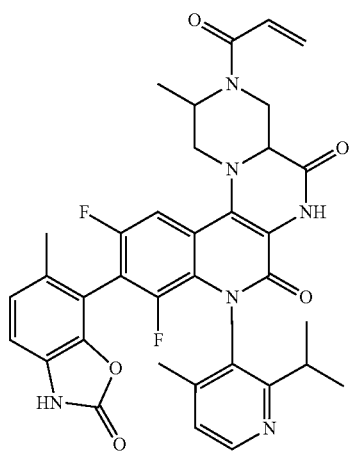
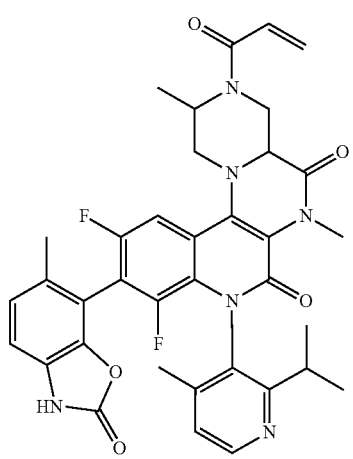
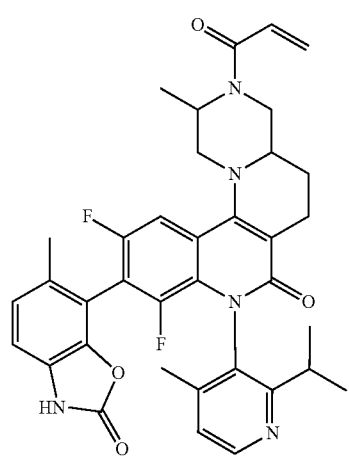
112
-continued
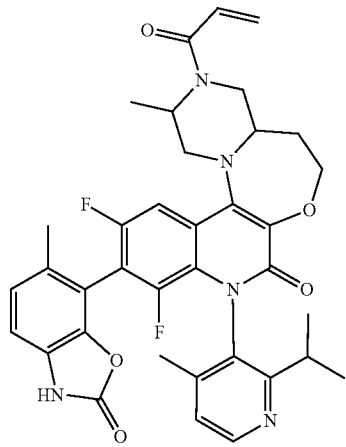
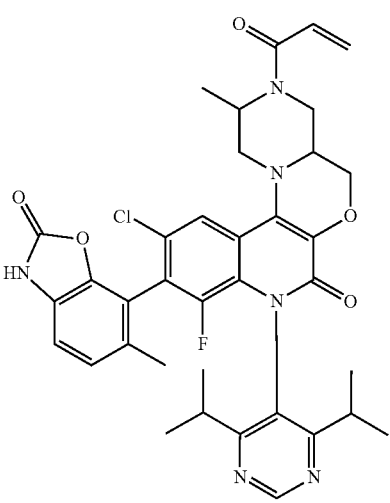

113
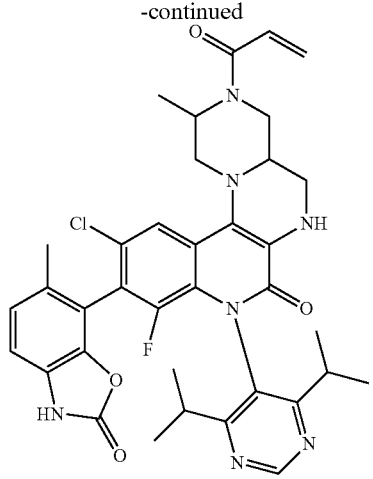
114
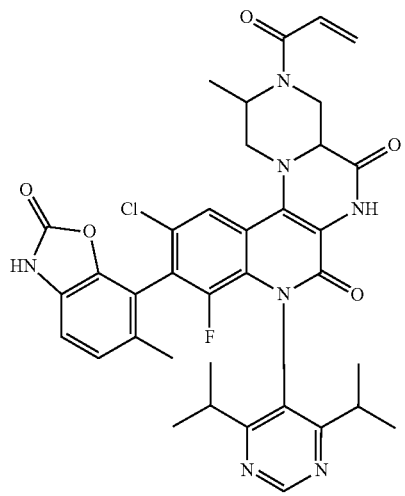
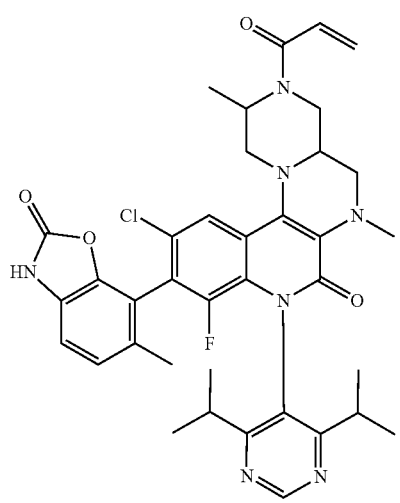
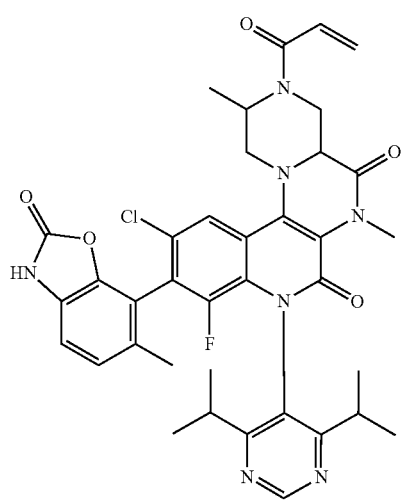
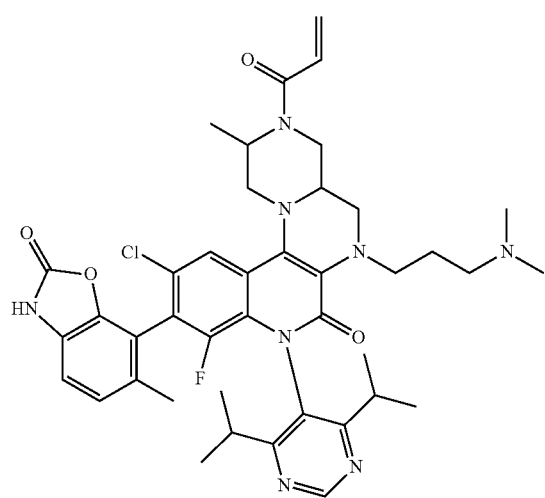
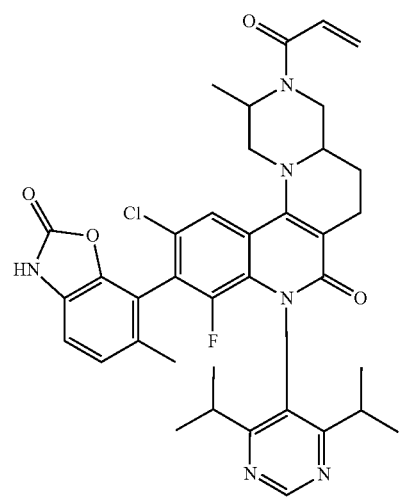

115
-continued
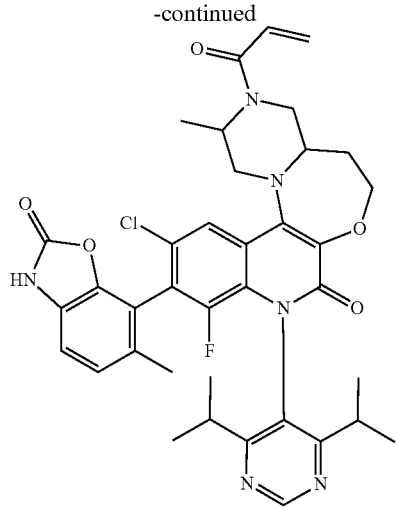
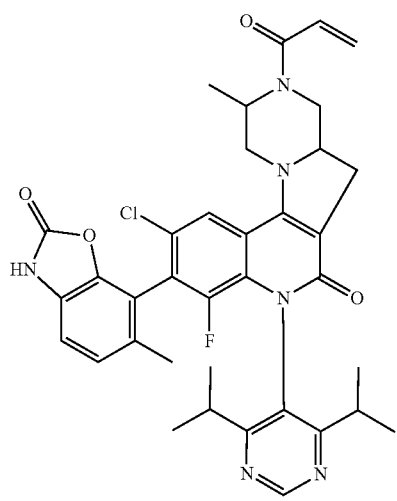
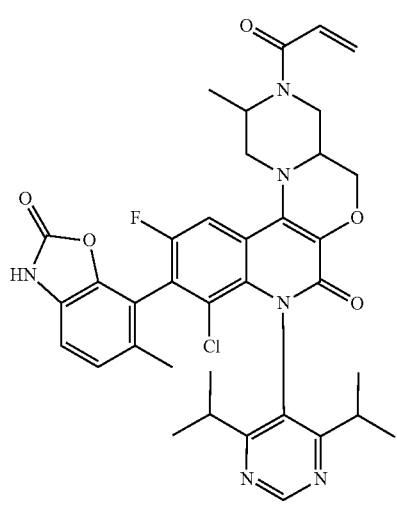
116
-continued
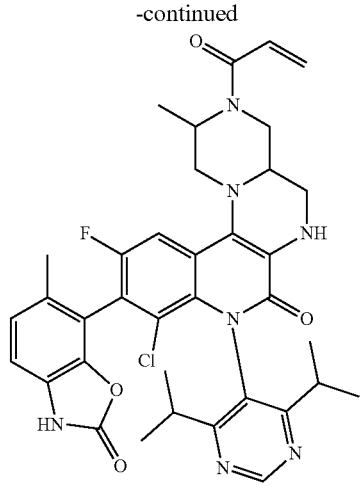
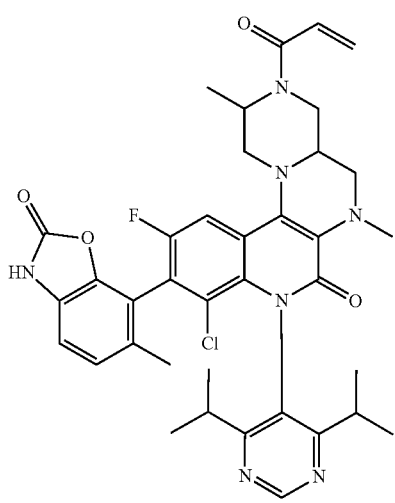
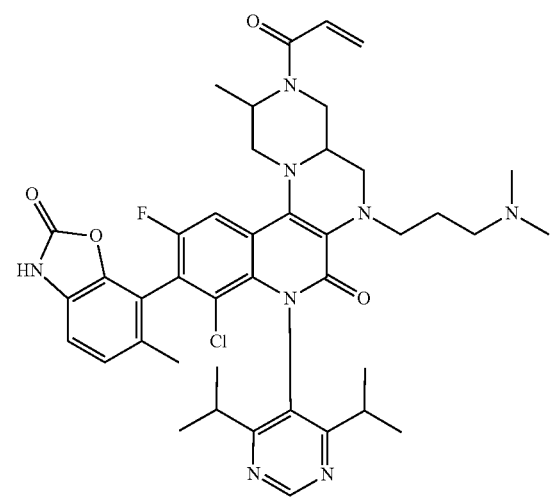

117
-continued
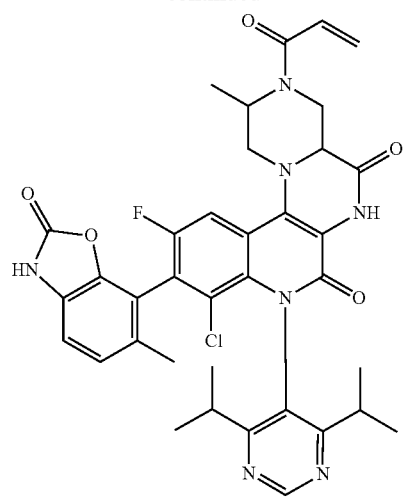
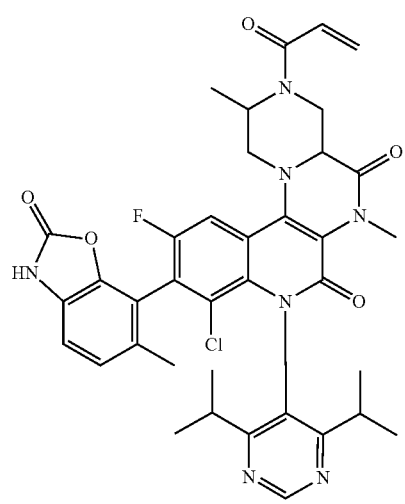
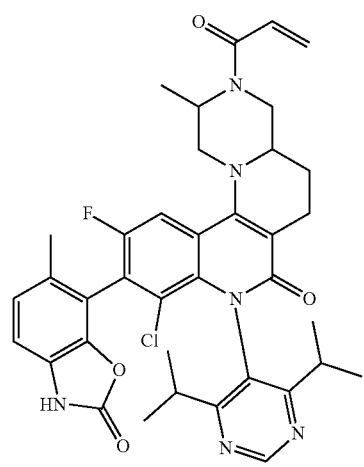
118
-continued
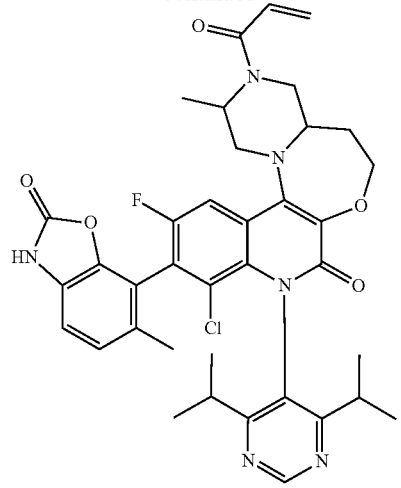
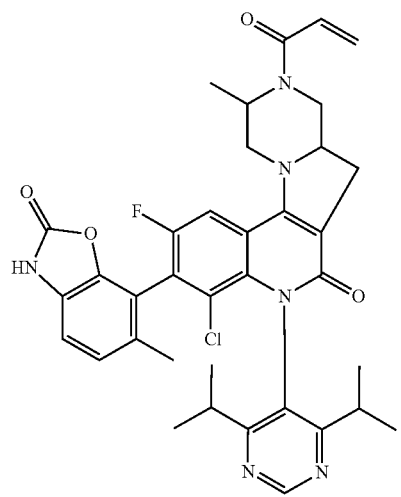
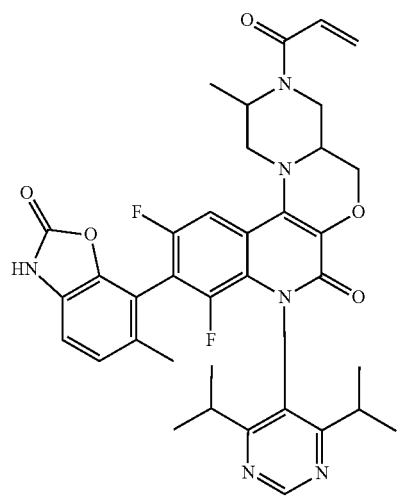

-continued
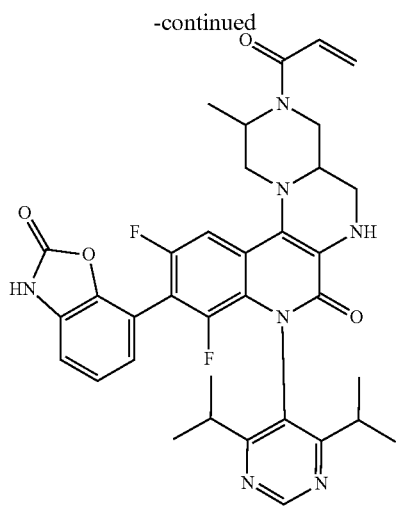
-continued
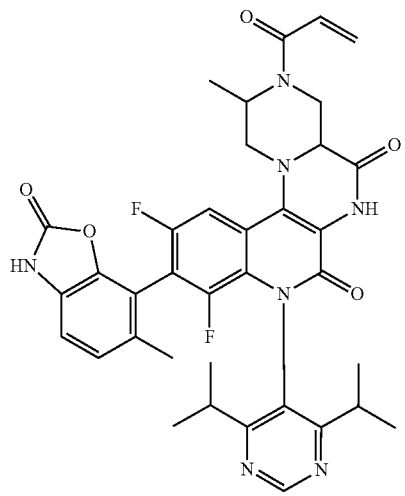
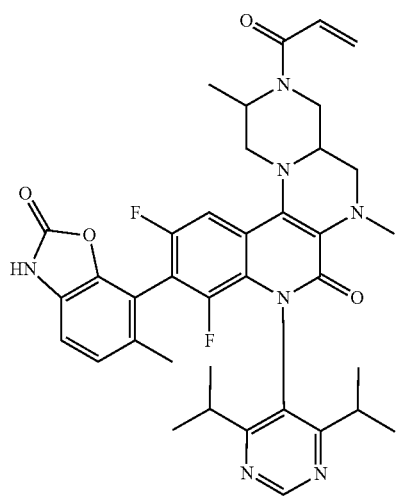
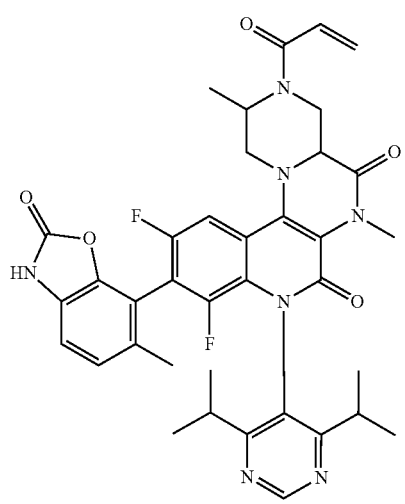
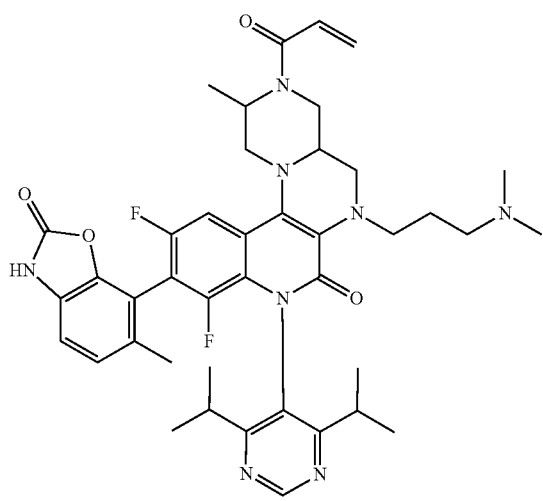
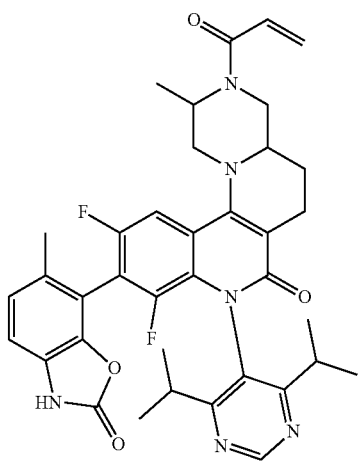

121
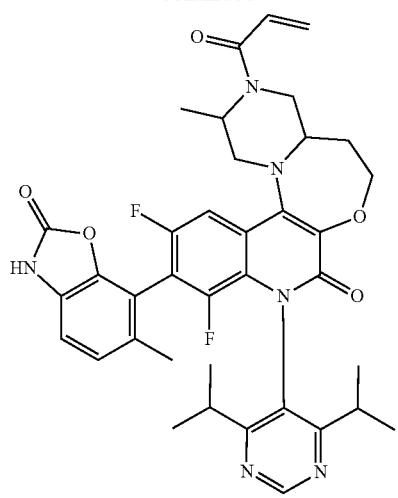
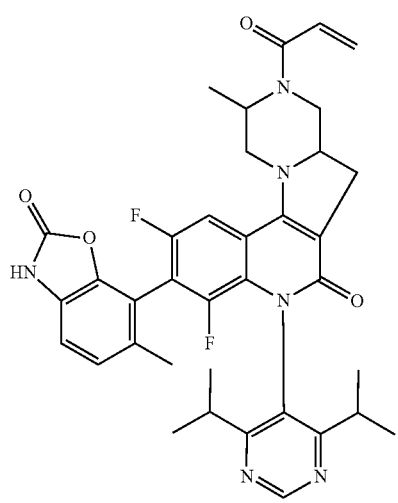
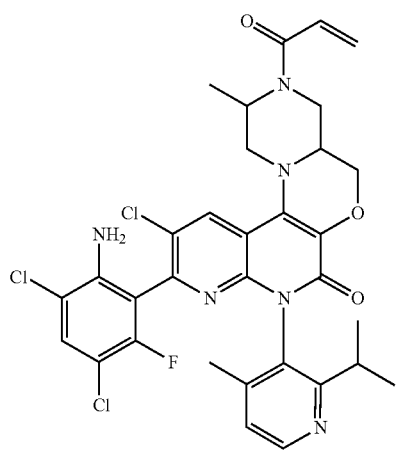
122
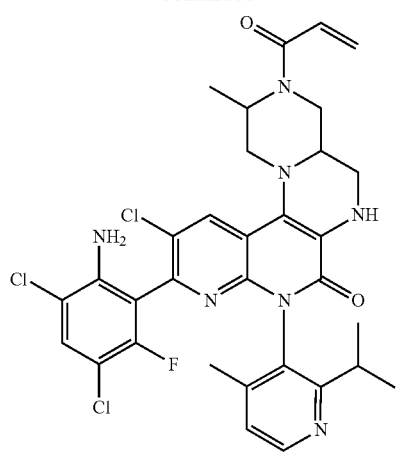
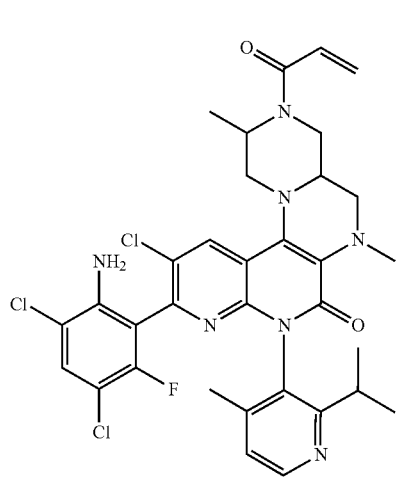
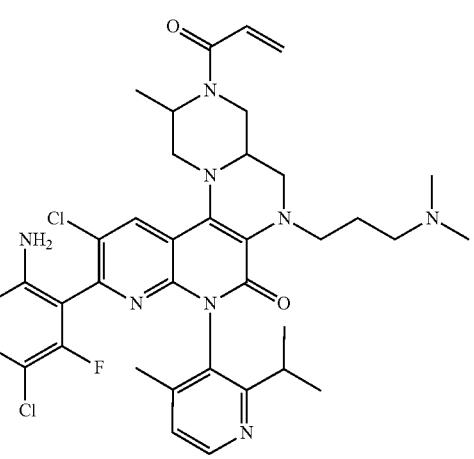

123
-continued
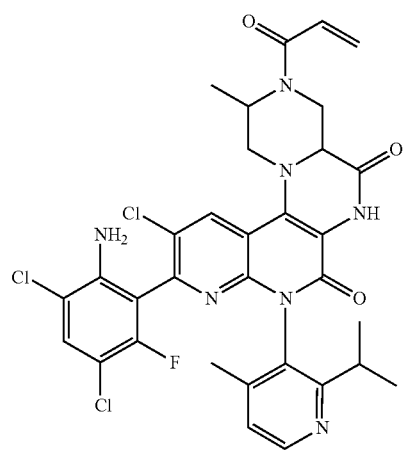
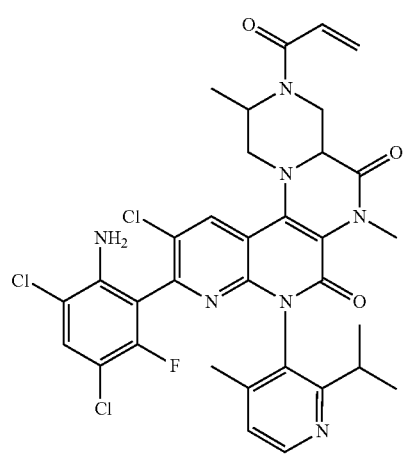
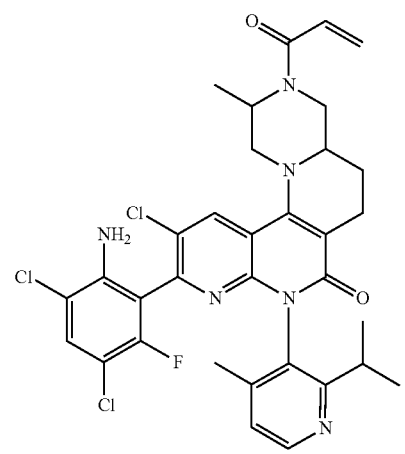
124
-continued
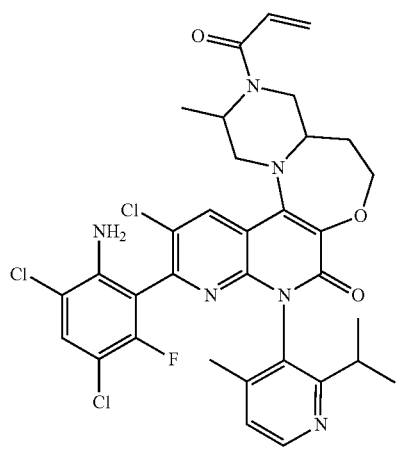
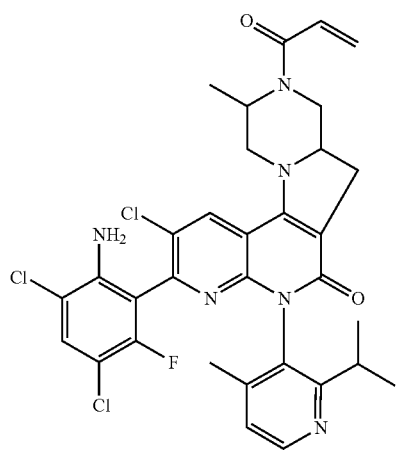
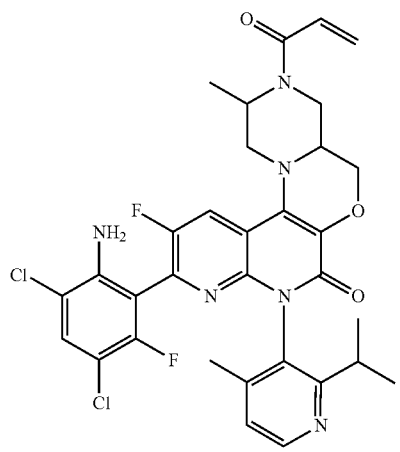

125
-continued
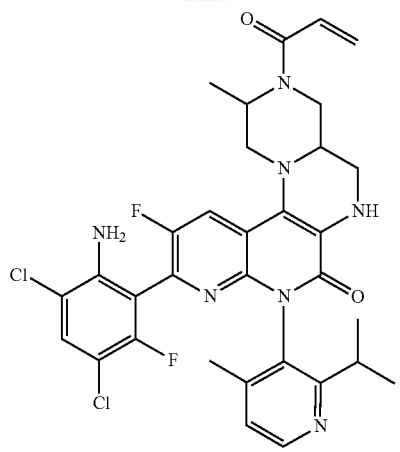
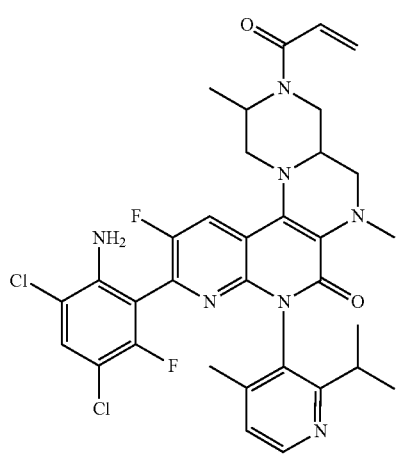
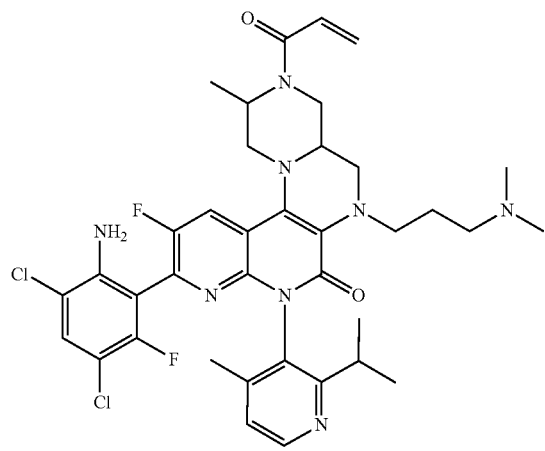
126
-continued
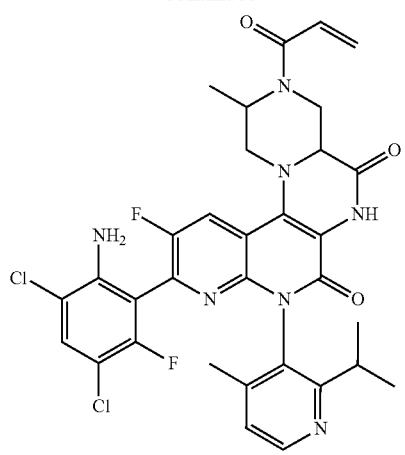
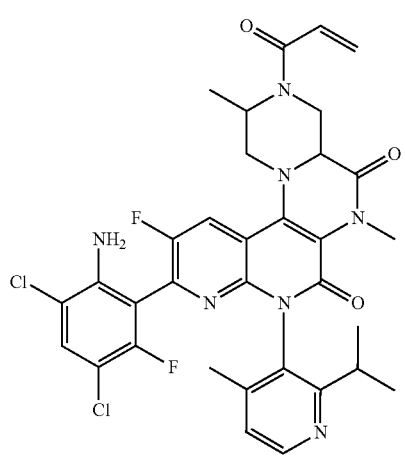
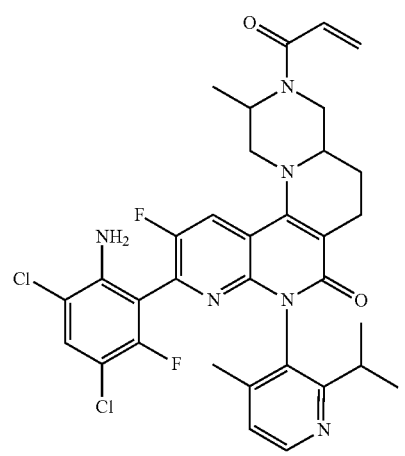

127
-continued
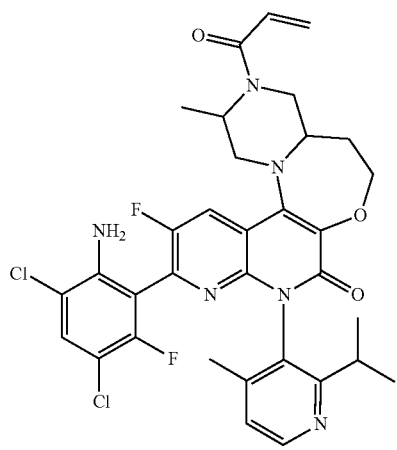
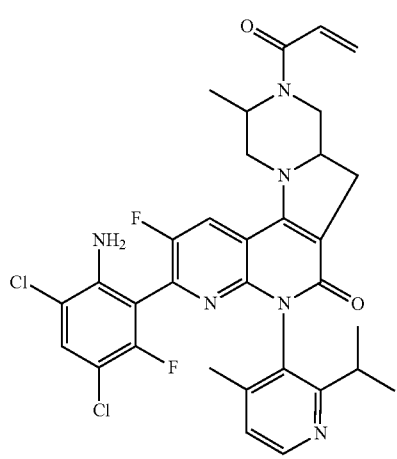
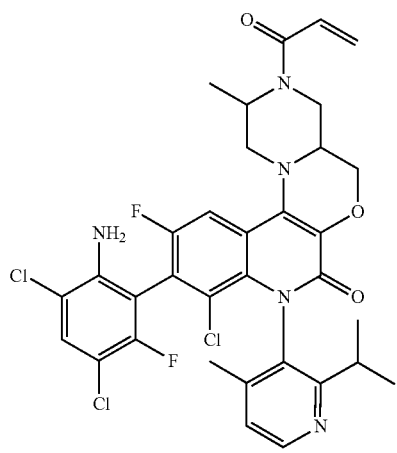
128
-continued
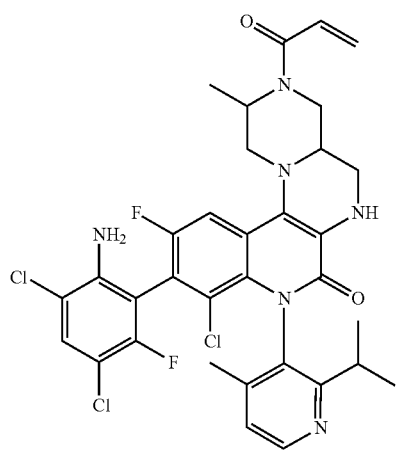
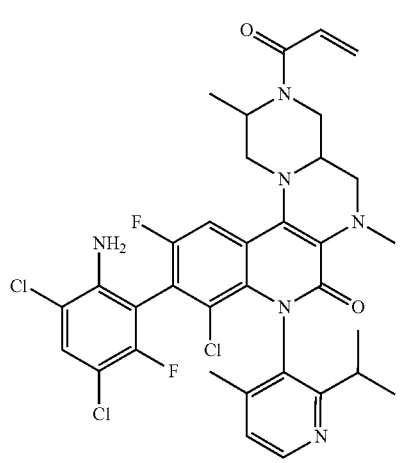
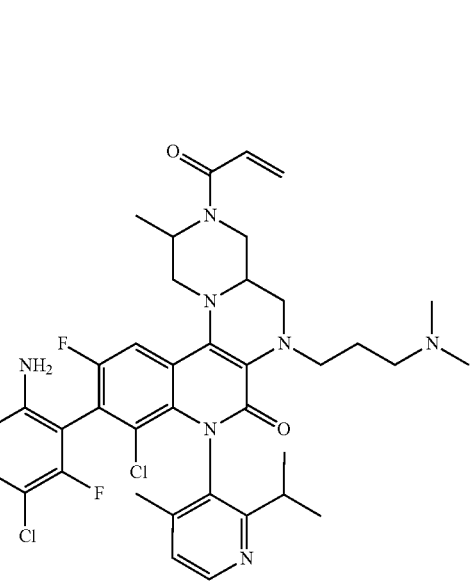

129
-continued
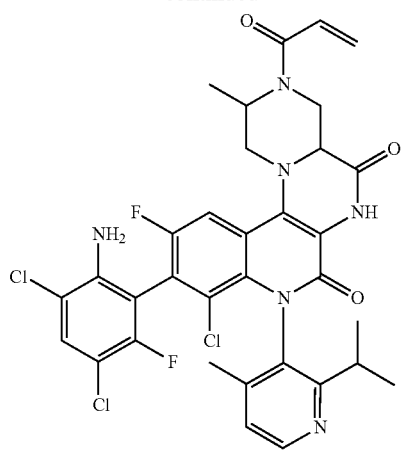
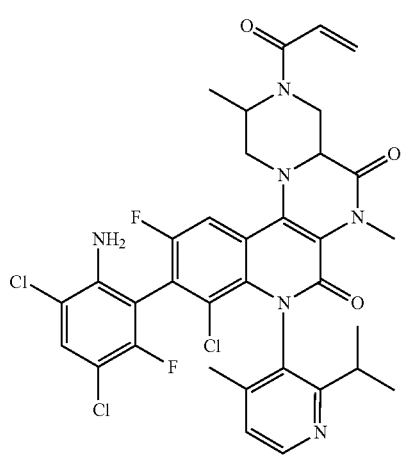
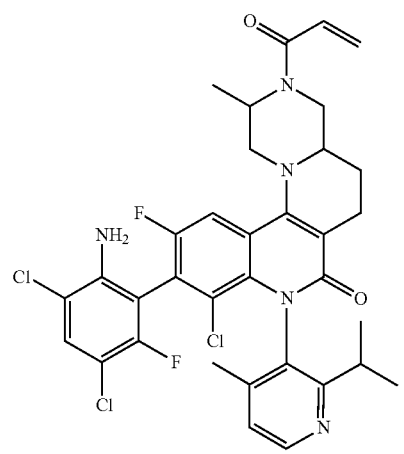
130
-continued
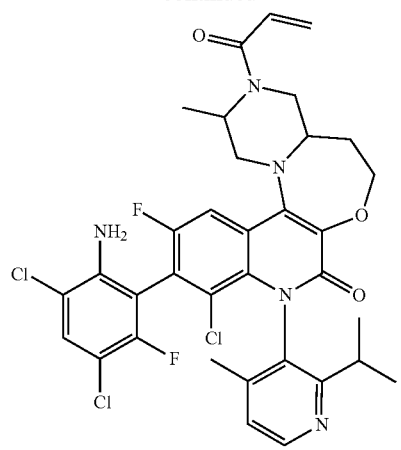
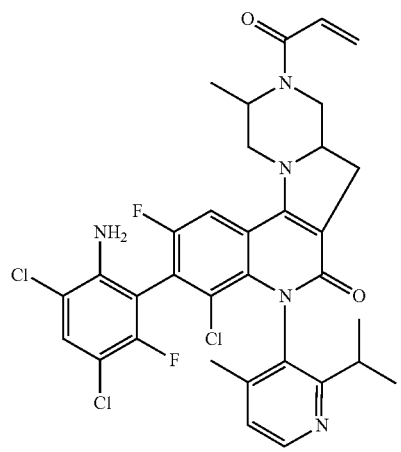
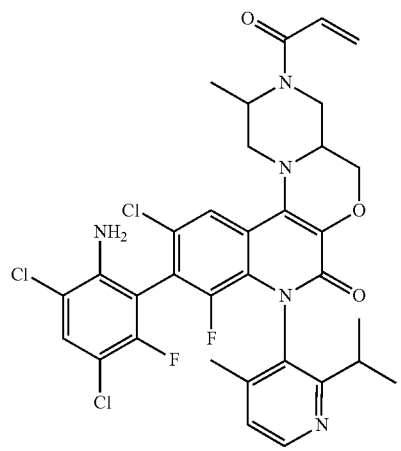

131
-continued
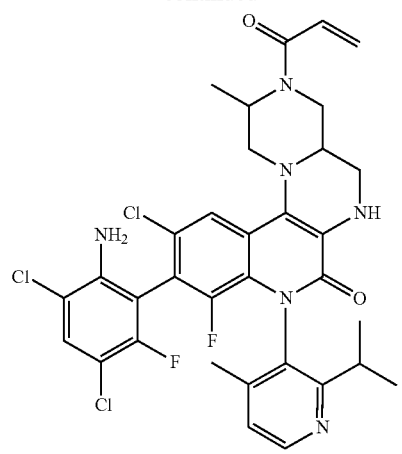
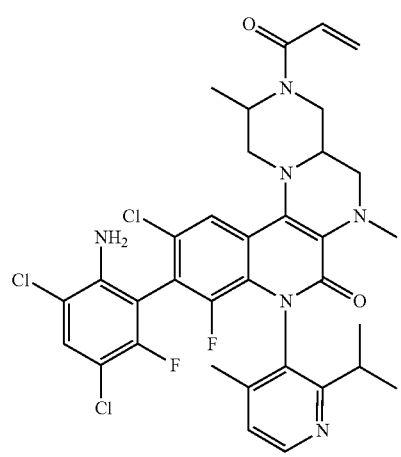
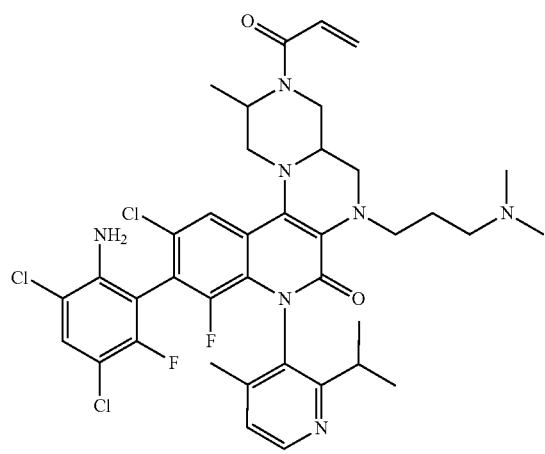
132
-continued
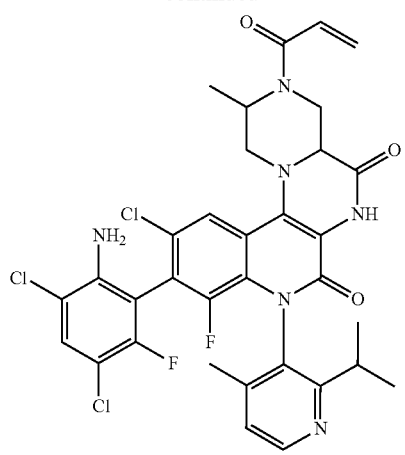
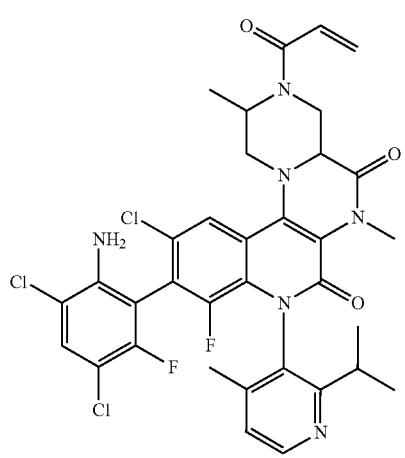
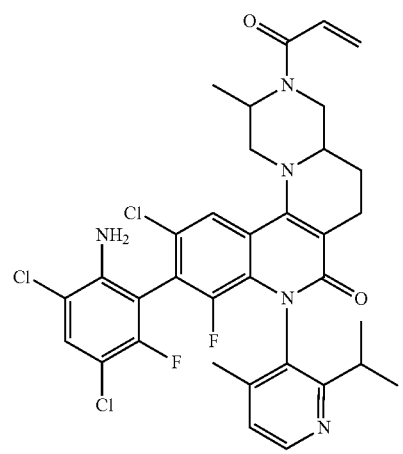

133
-continued
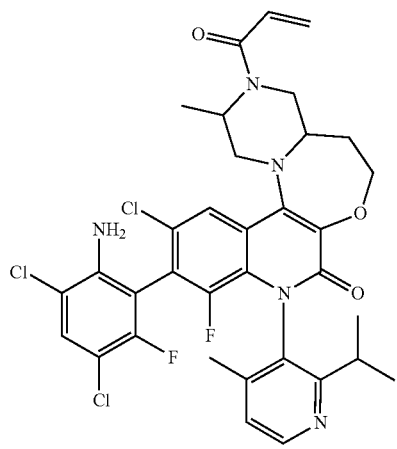
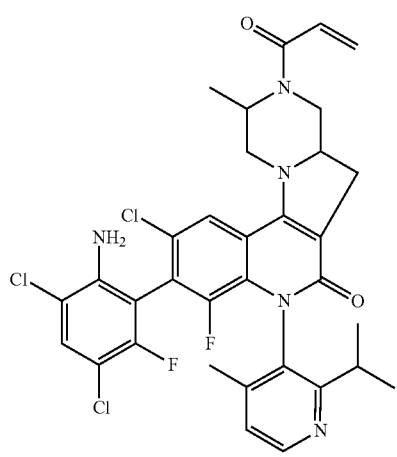
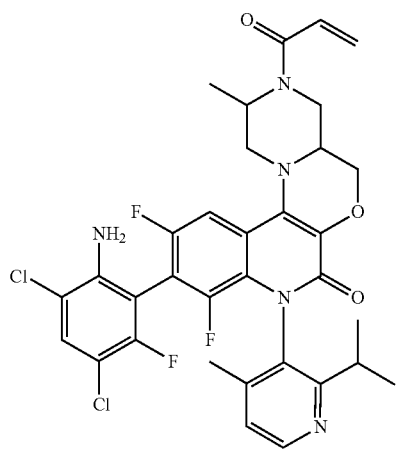
134
-continued
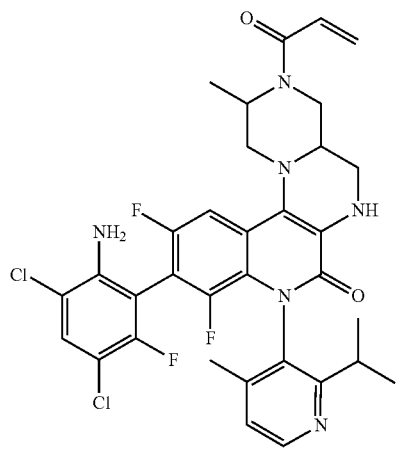
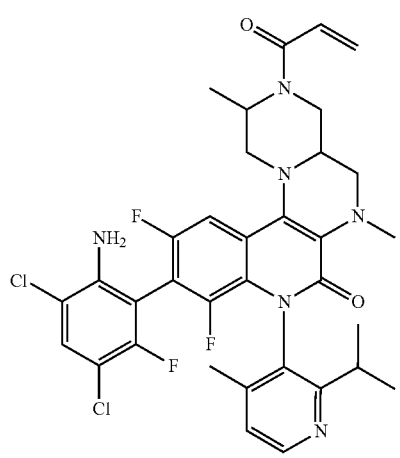
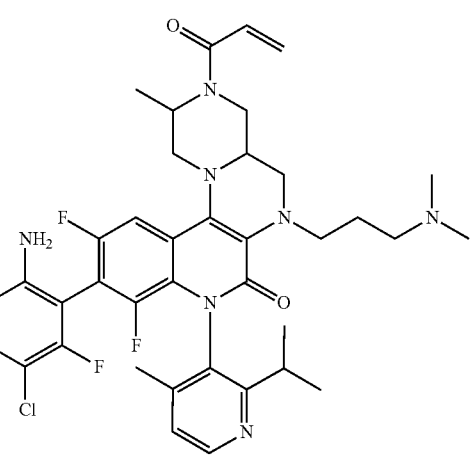

135
-continued
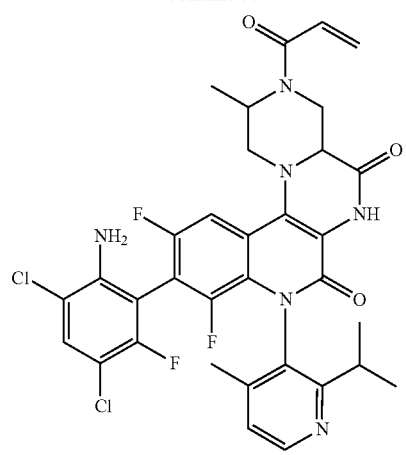
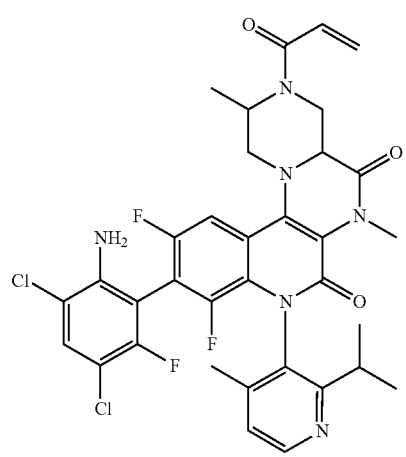
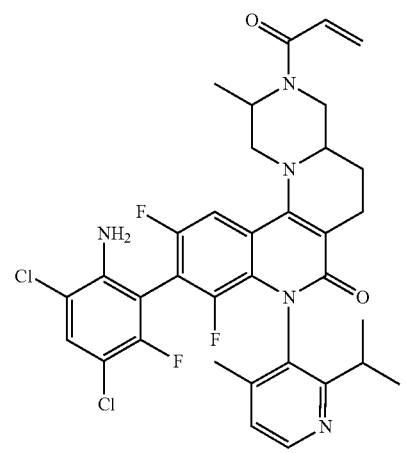
136
-continued
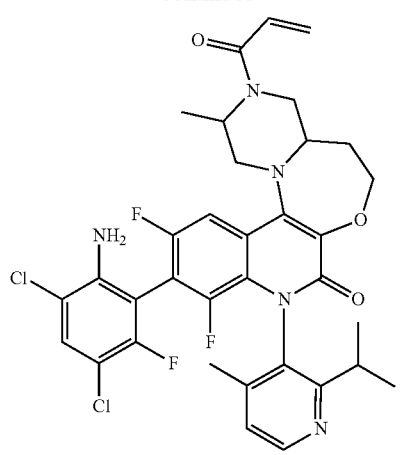
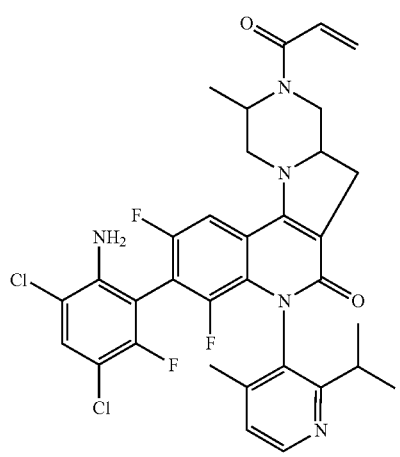
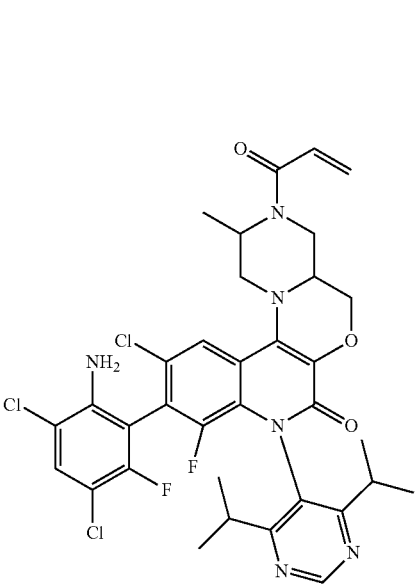

137
-continued
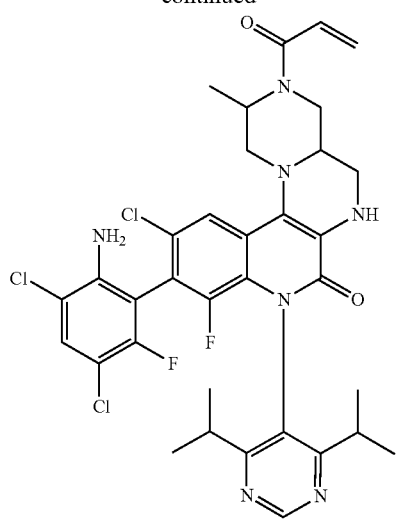
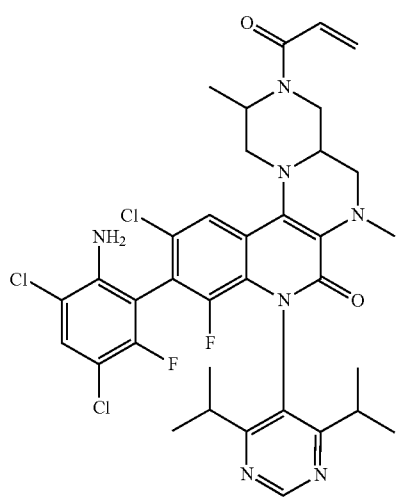
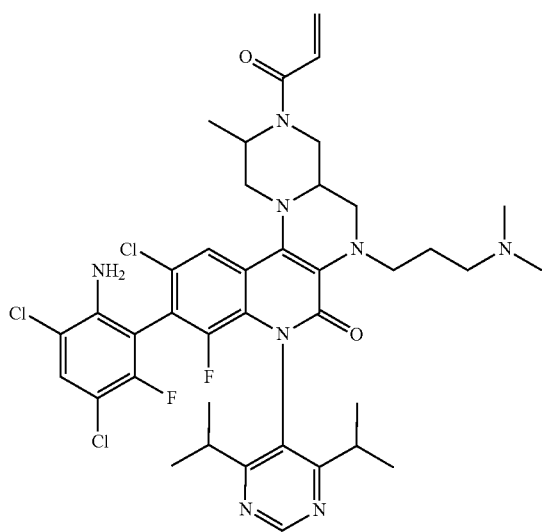
138
-continued
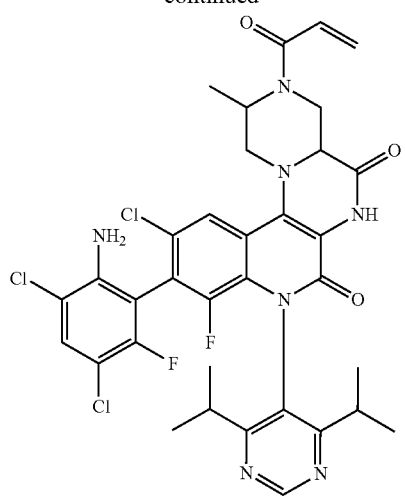
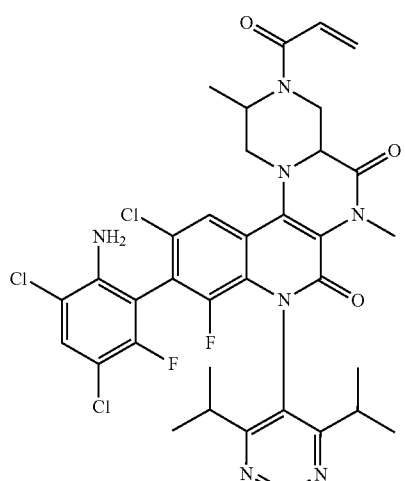
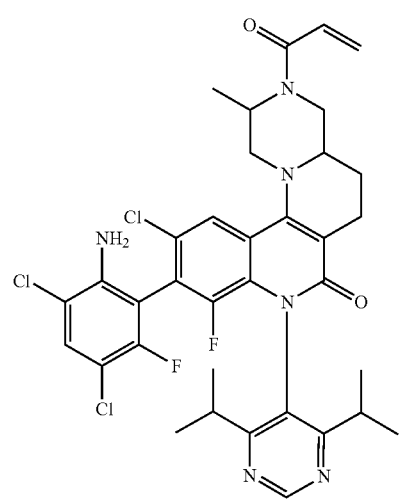

139
-continued
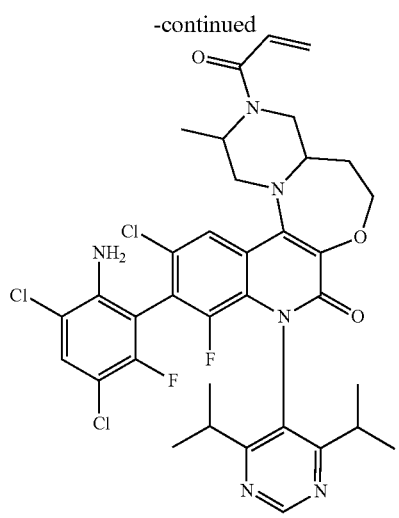
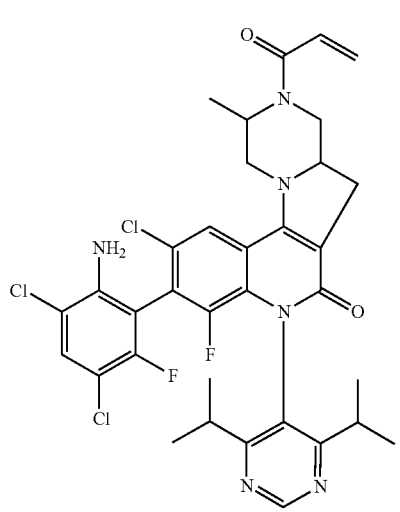
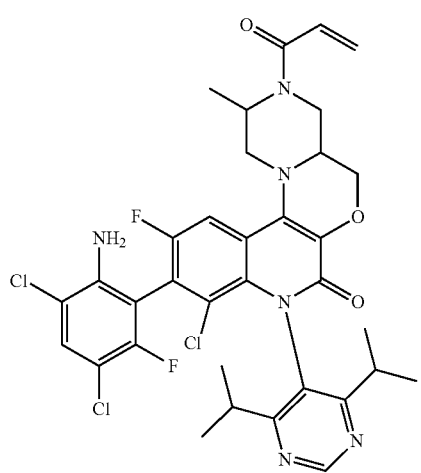
140
-continued
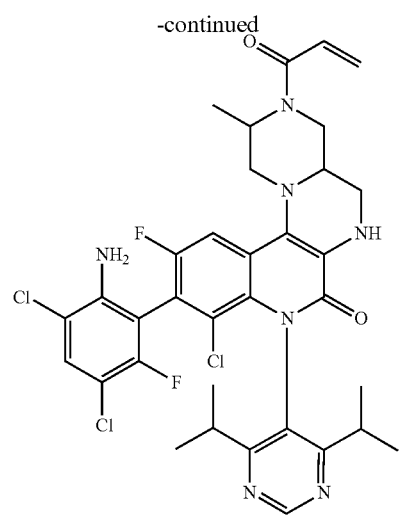
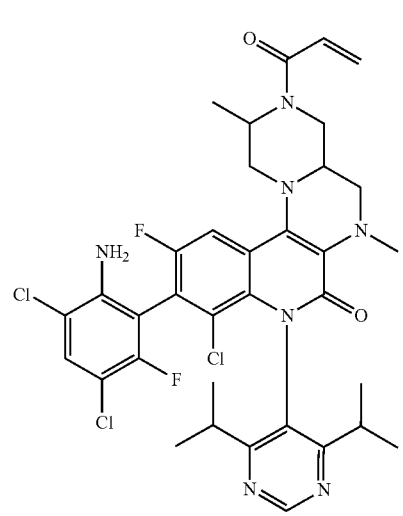
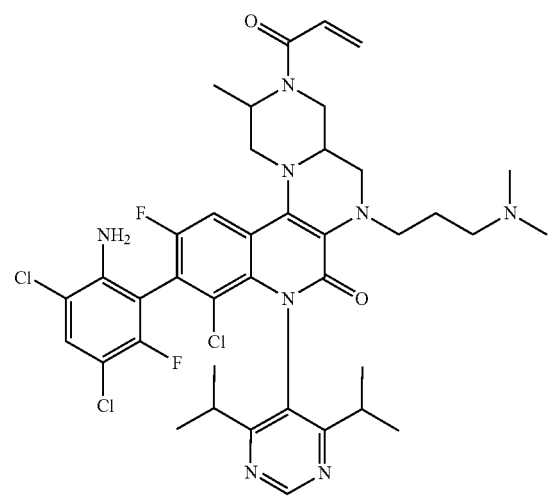

141
-continued
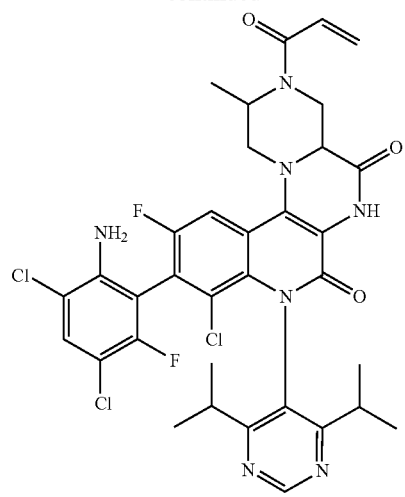
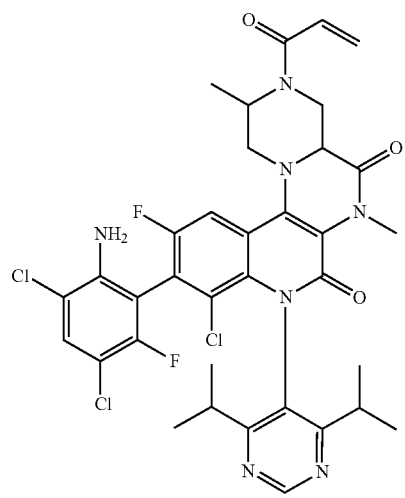
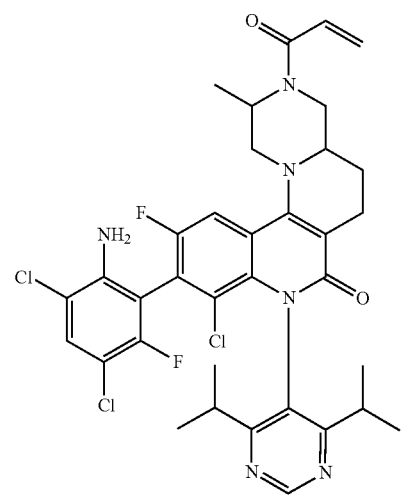
142
-continued
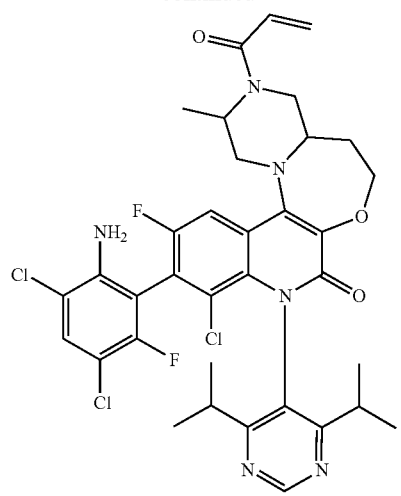
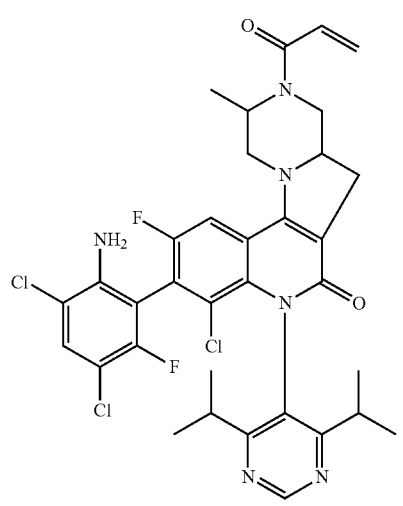
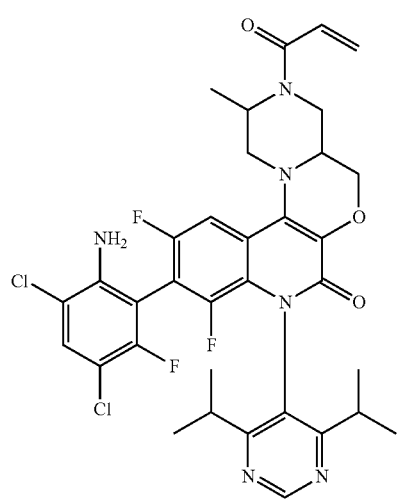

-continued
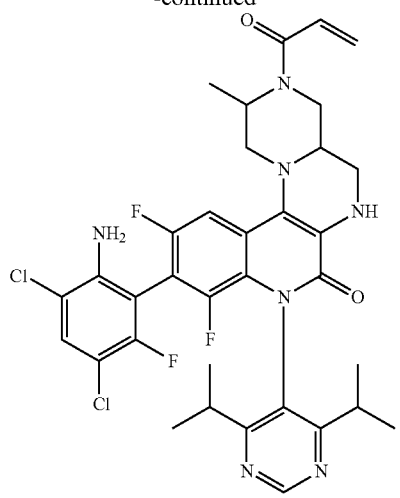
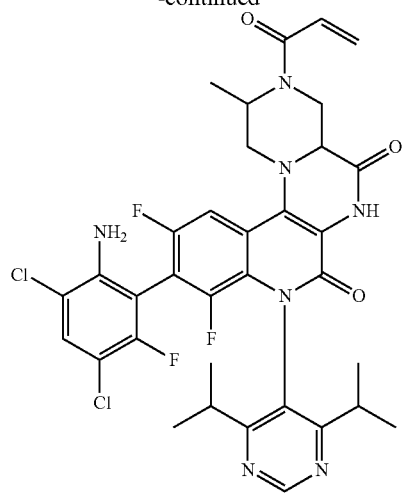
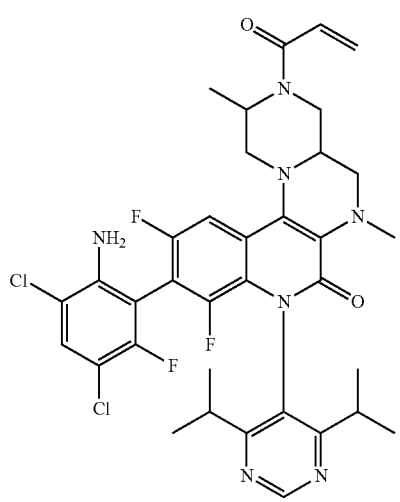
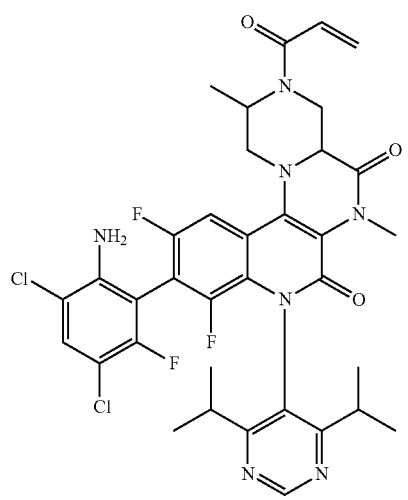
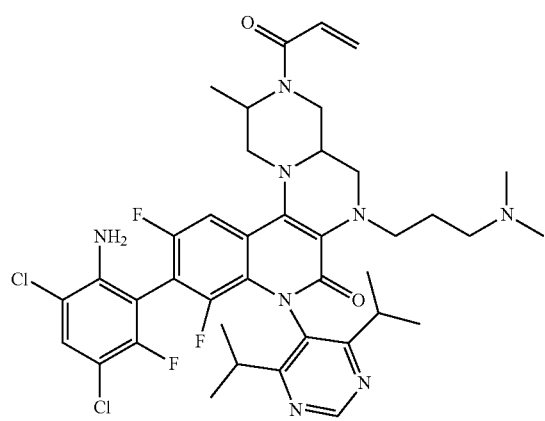
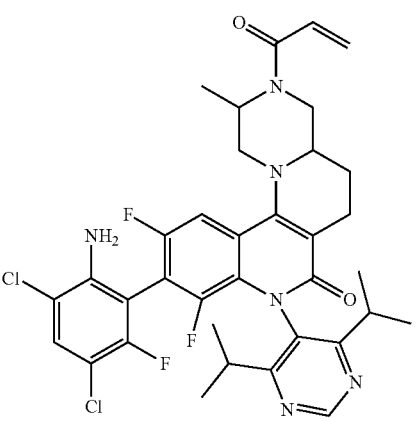

145
-continued
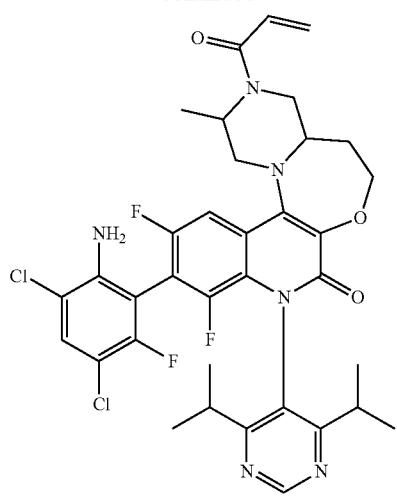
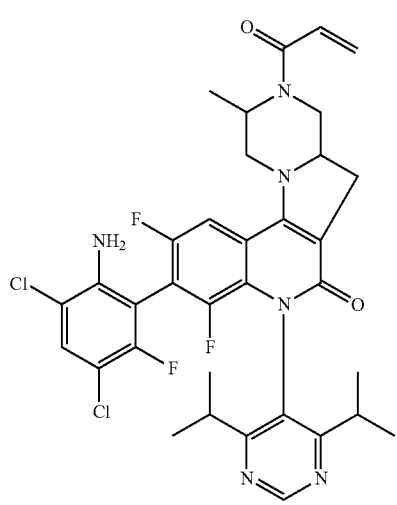
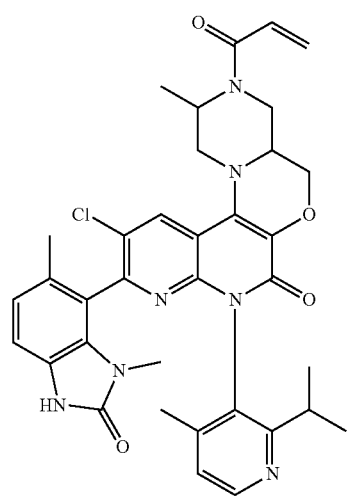
146
-continued
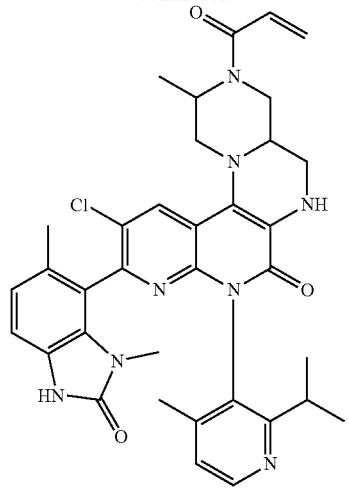
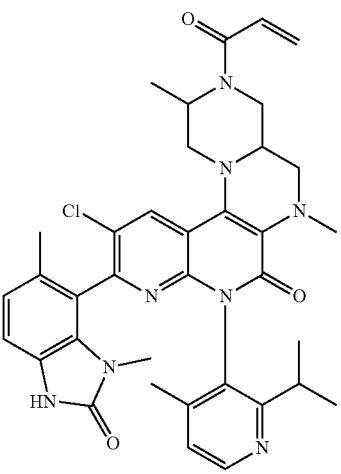
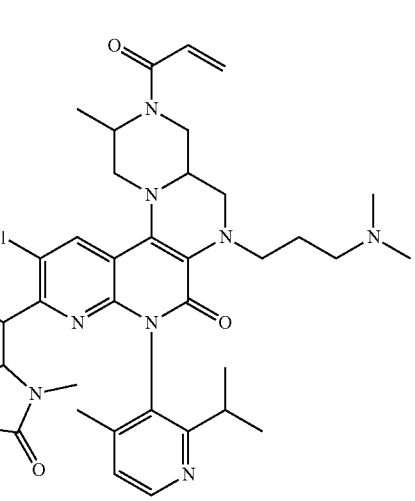

147
-continued
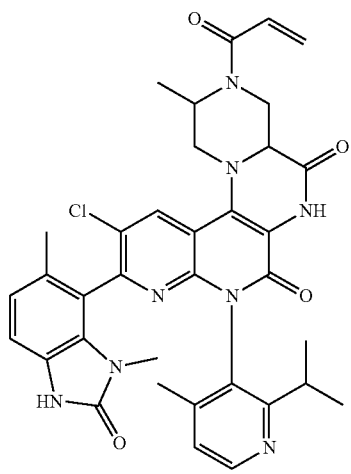
148
-continued
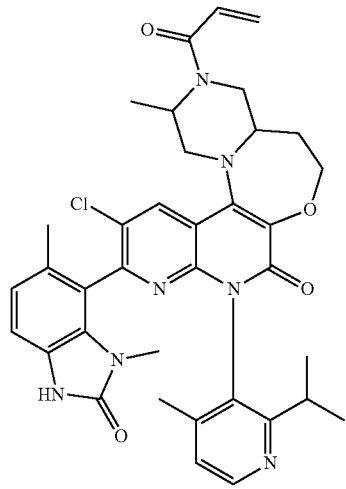
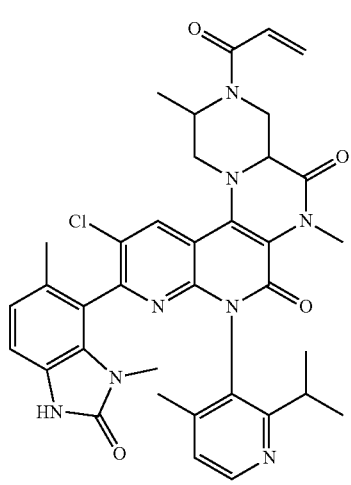
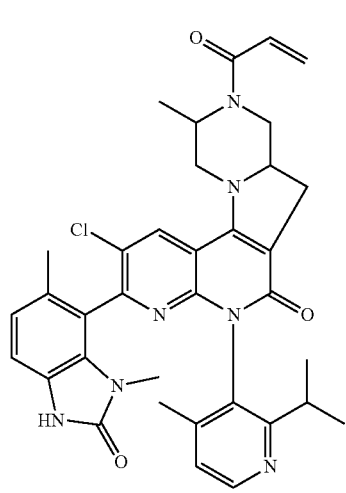
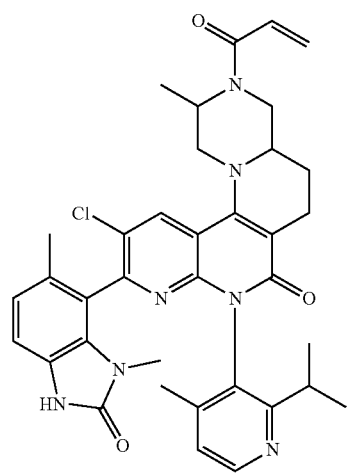
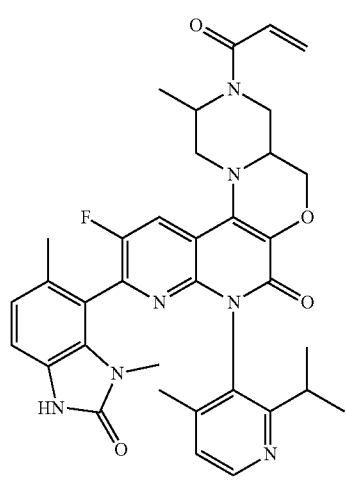

149
-continued
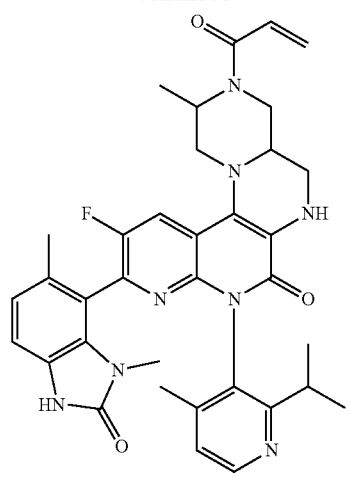
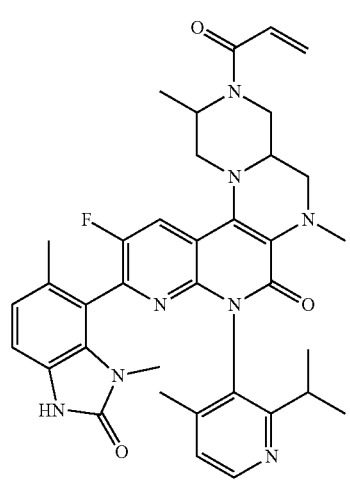
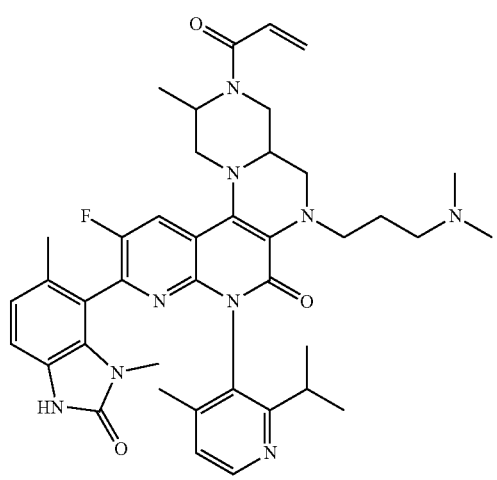
150
-continued
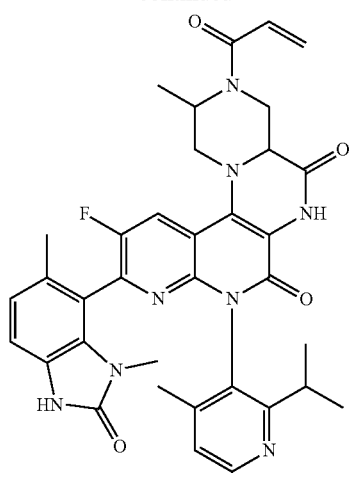
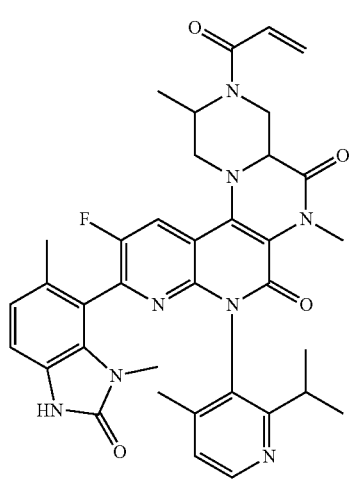
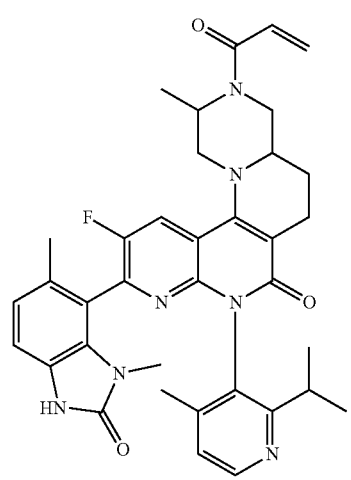

151
-continued
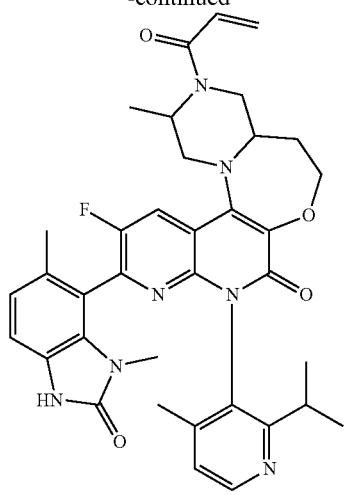
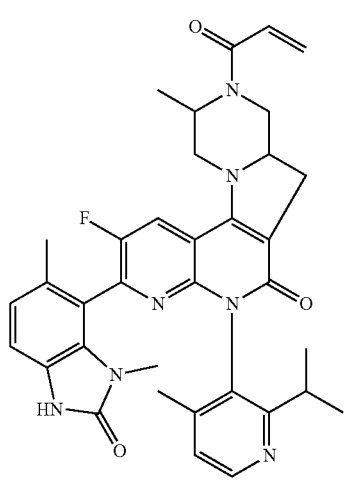
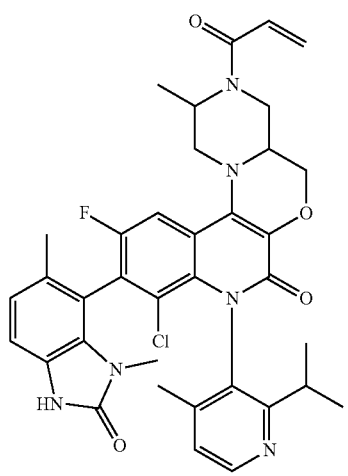
152
-continued
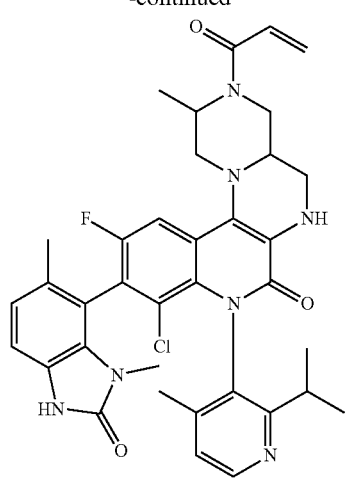
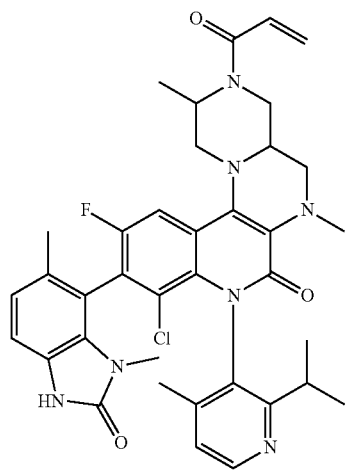
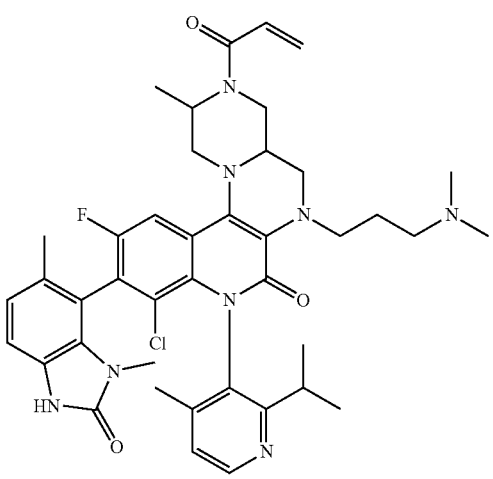

153
-continued
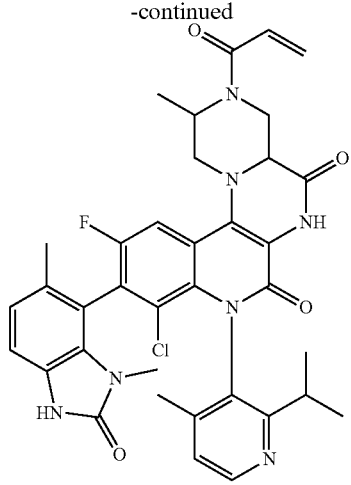
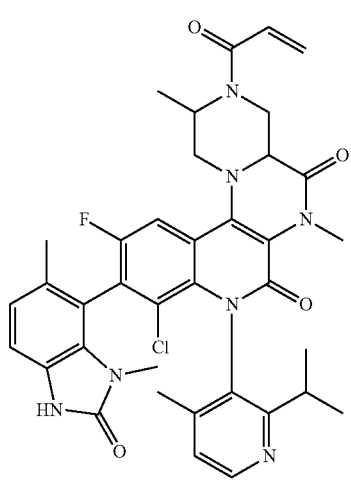
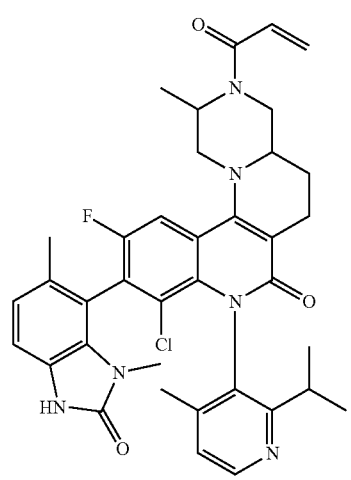
154
-continued
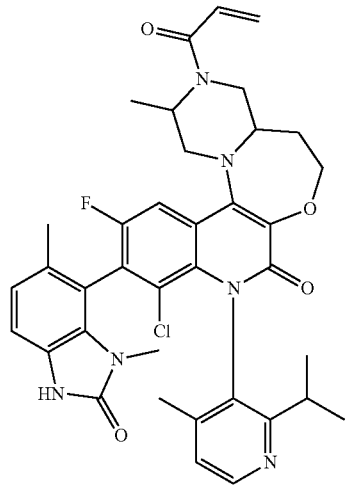
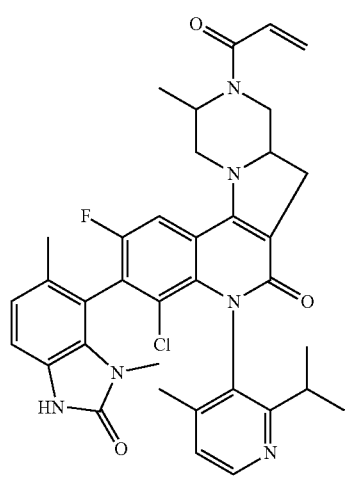
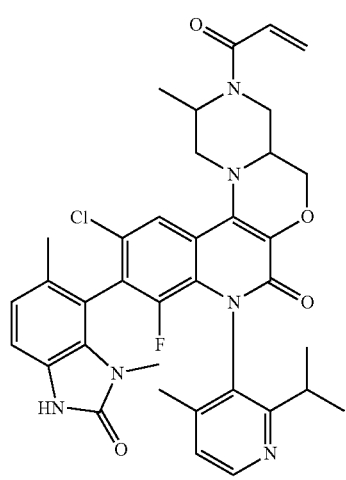

155
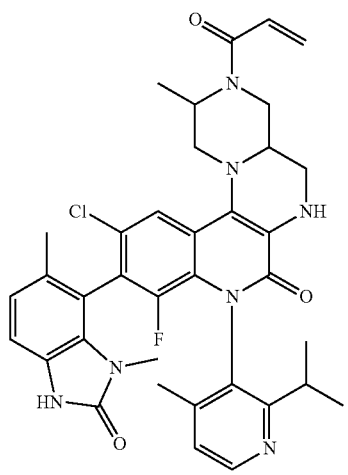
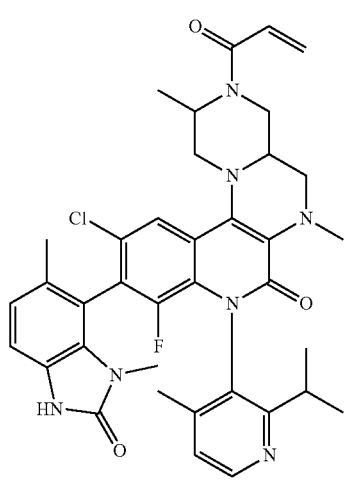
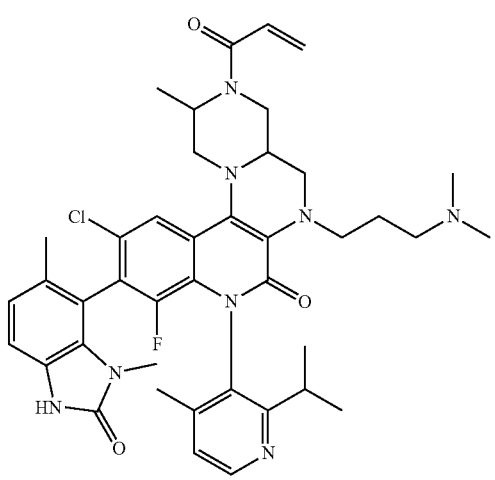
156
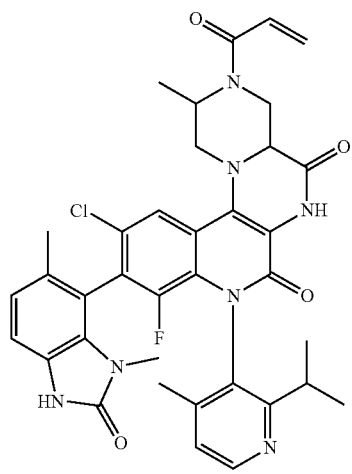
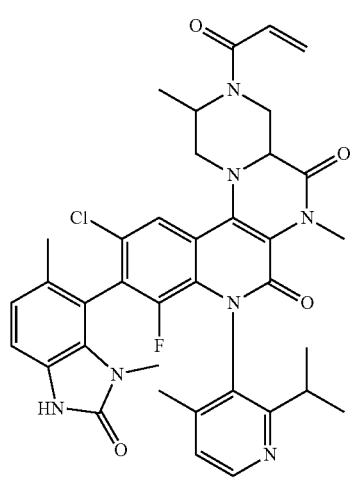
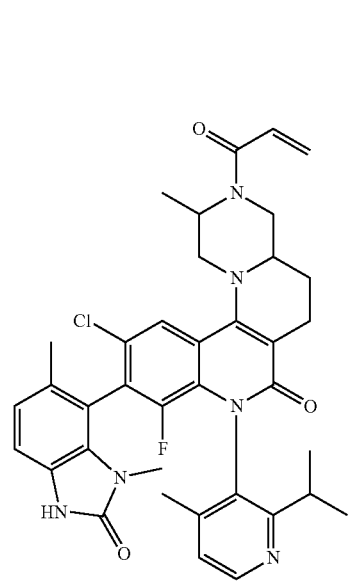

157
-continued
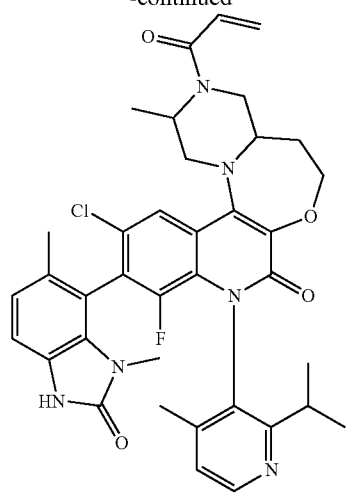
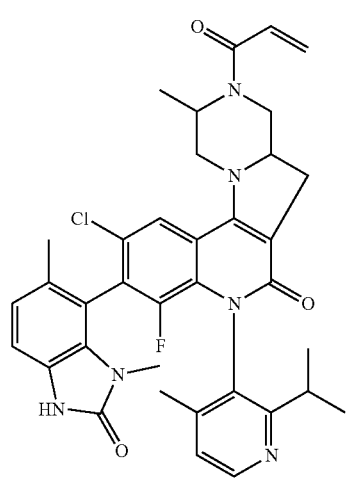
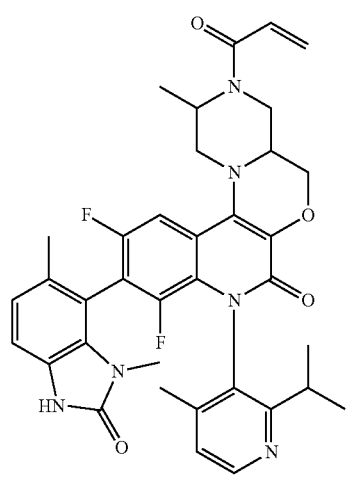
158
-continued
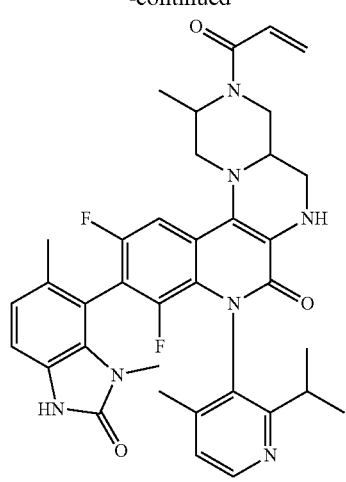
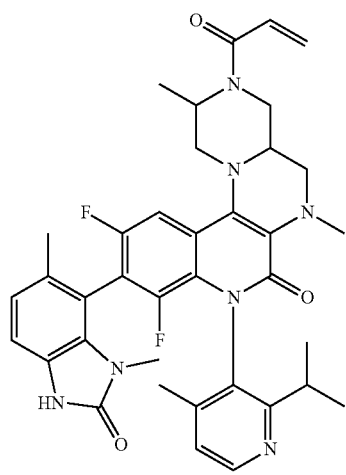
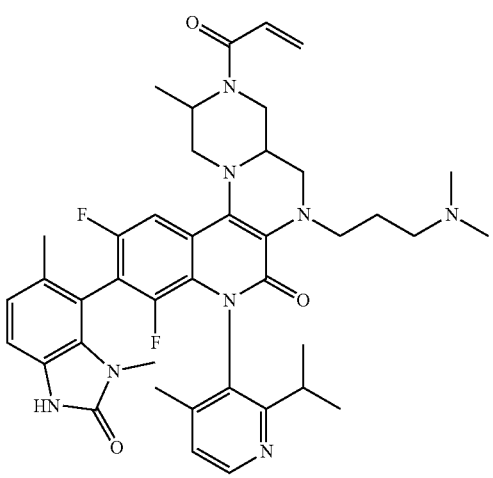

159
-continued
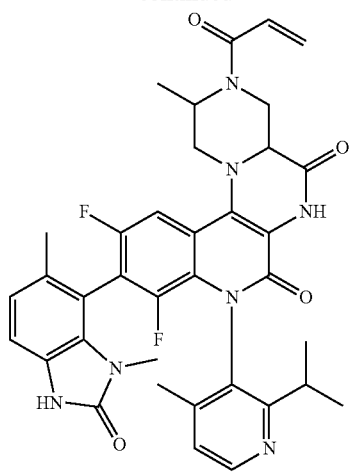
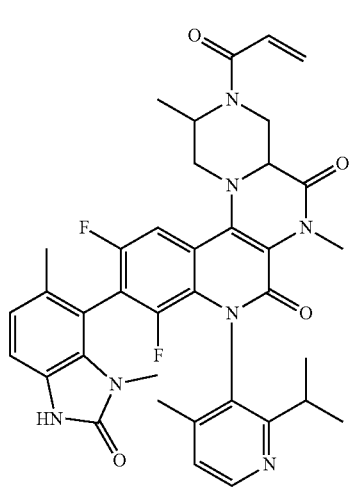
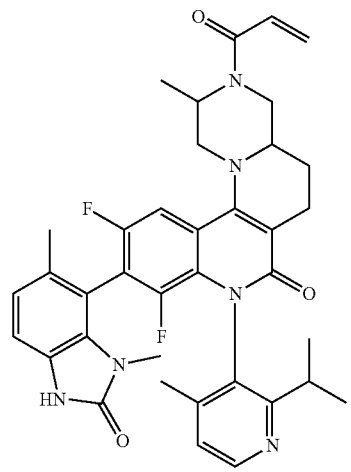
160
-continued
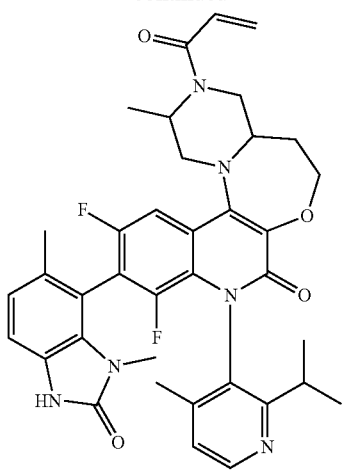
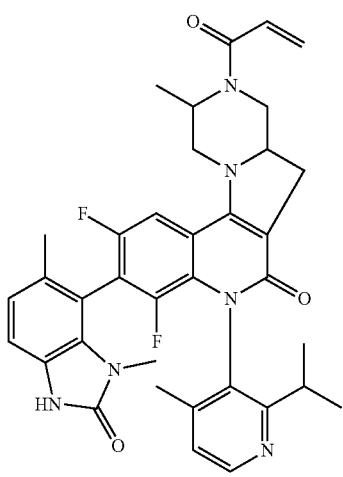
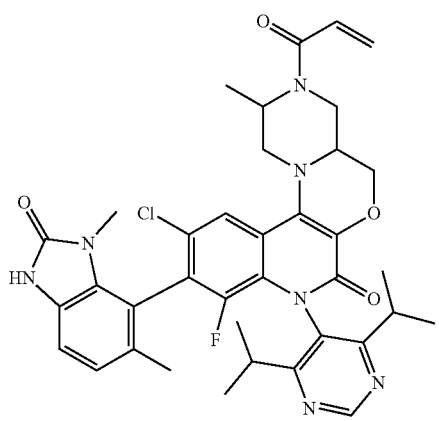

-continued
161
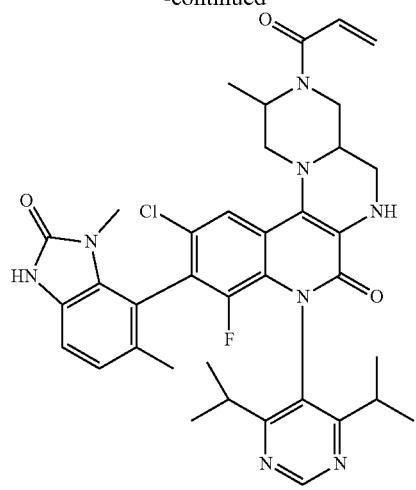
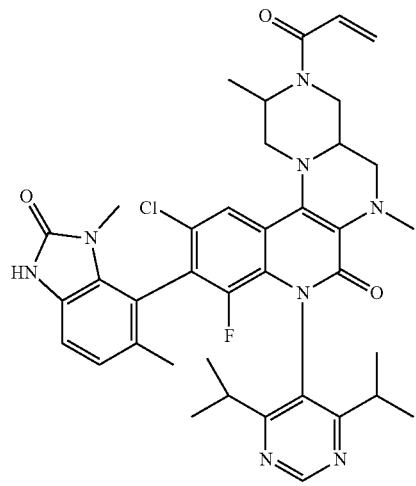
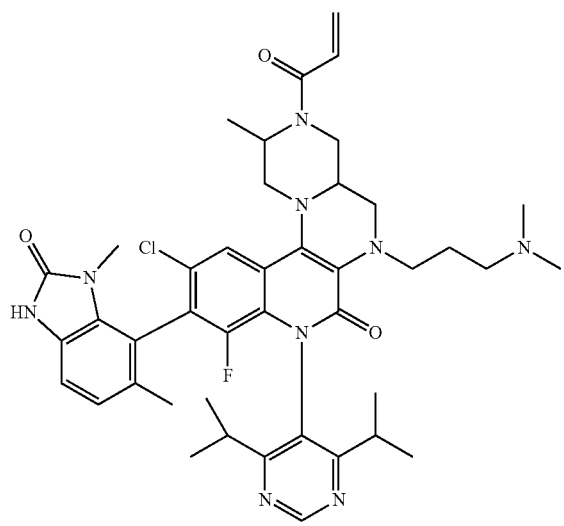
-continued
162
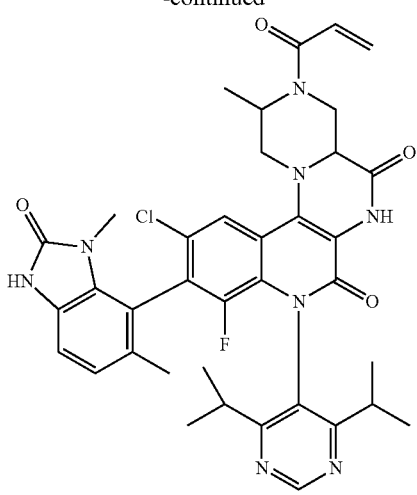
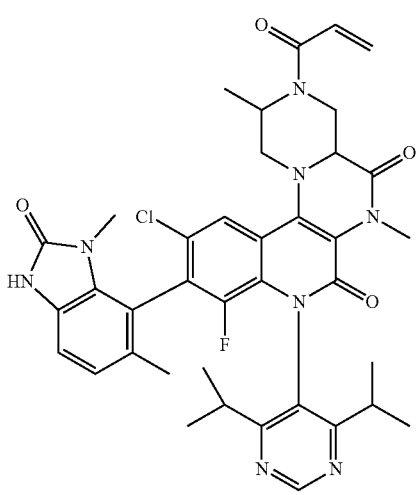
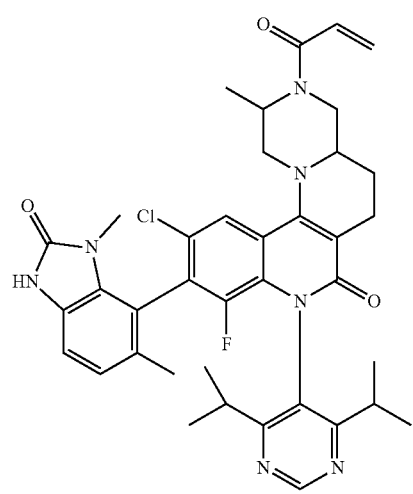

163
-continued
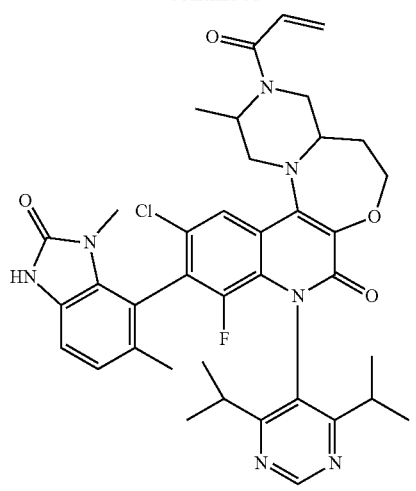
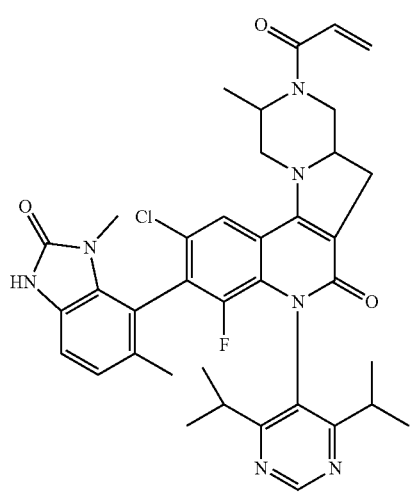
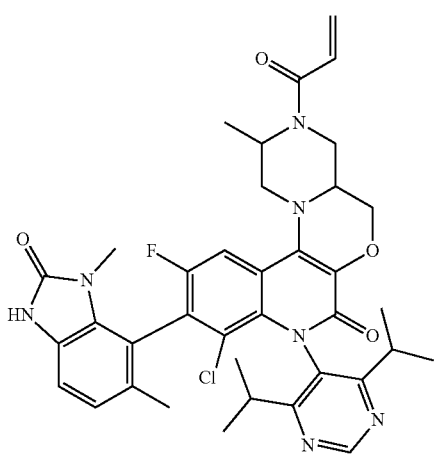
164
-continued
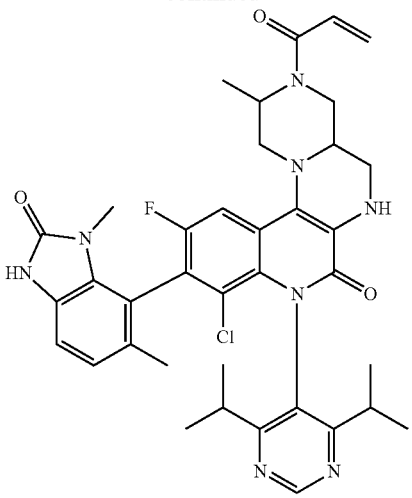
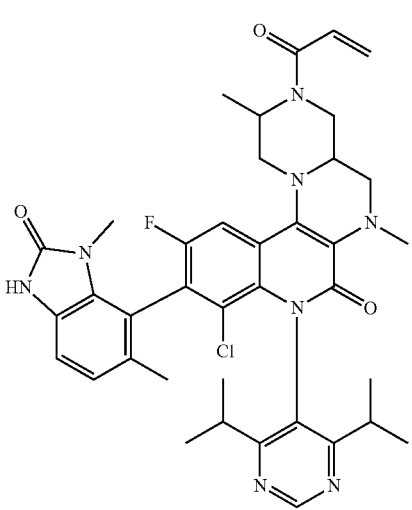
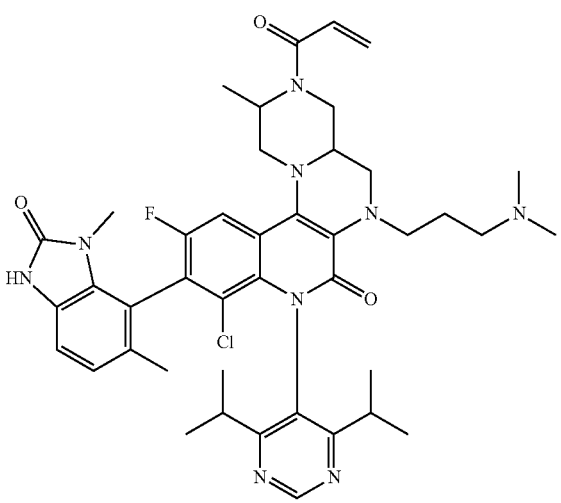

-continued
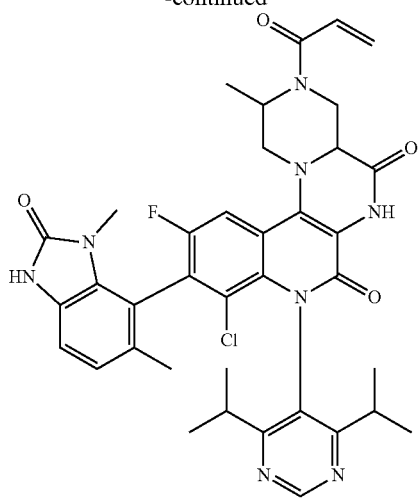
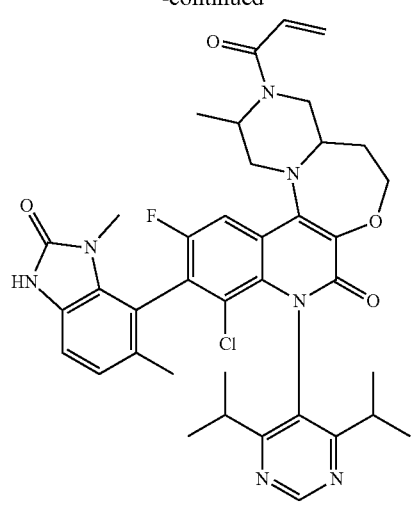
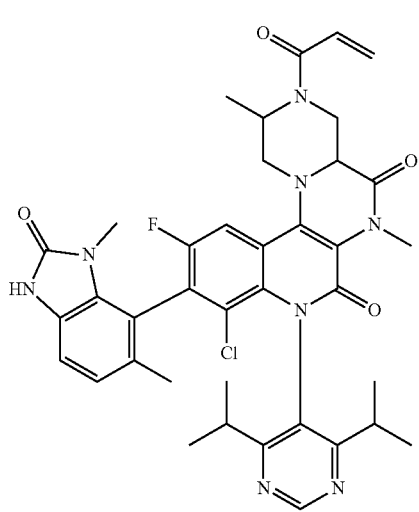
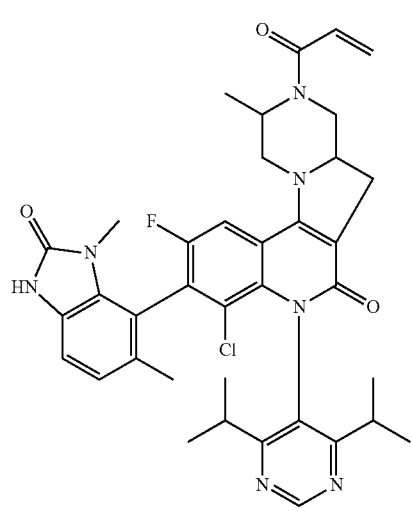
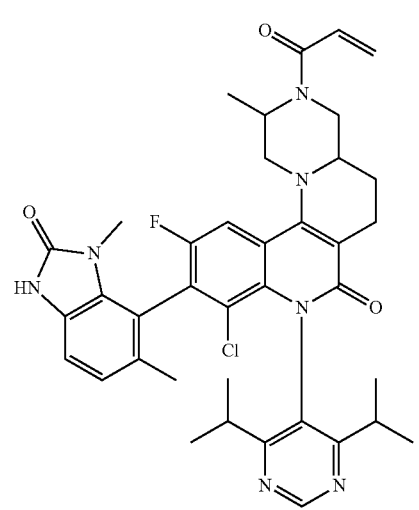
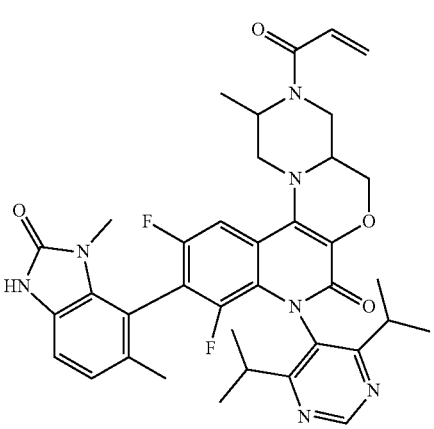

167
-continued
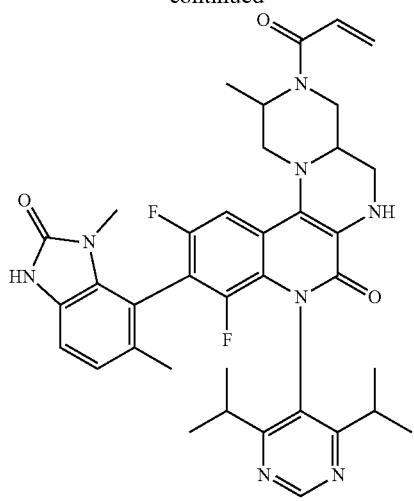
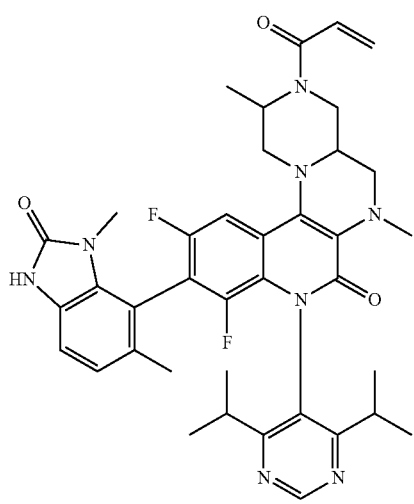
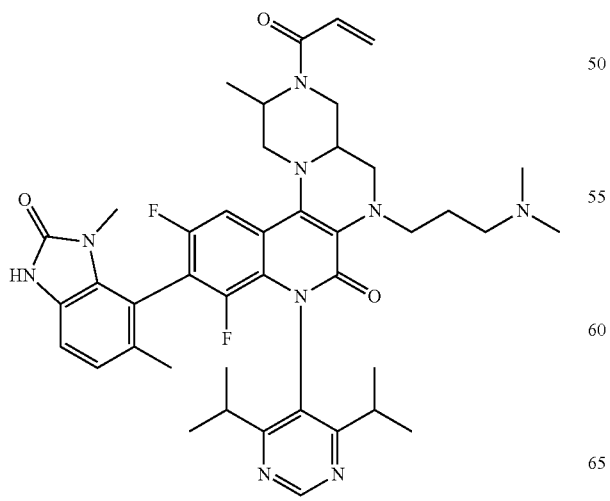
168
-continued
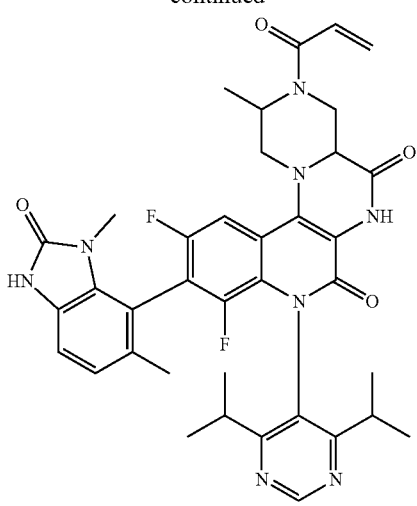
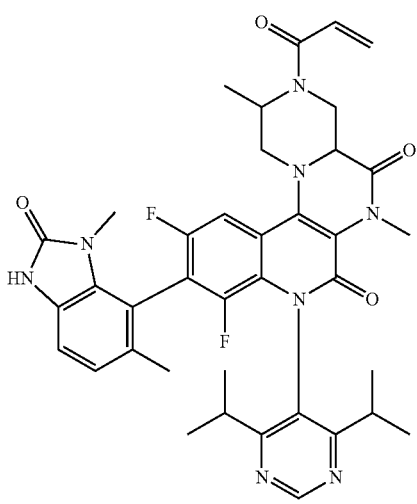
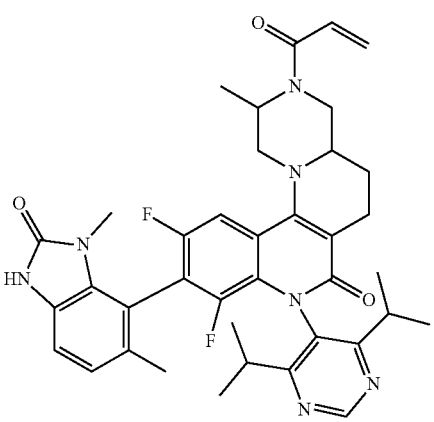

169
-continued
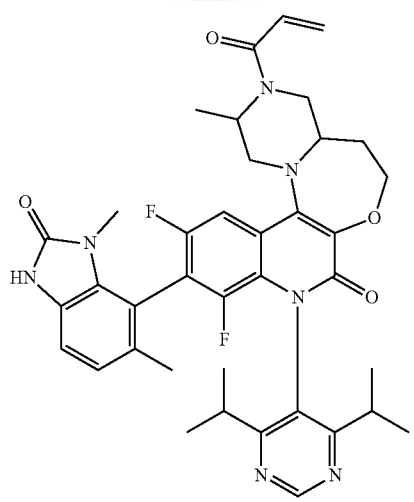
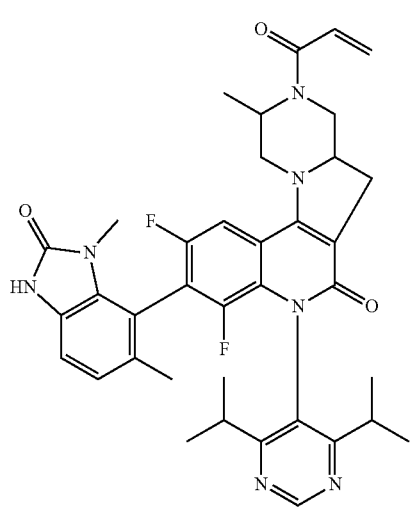
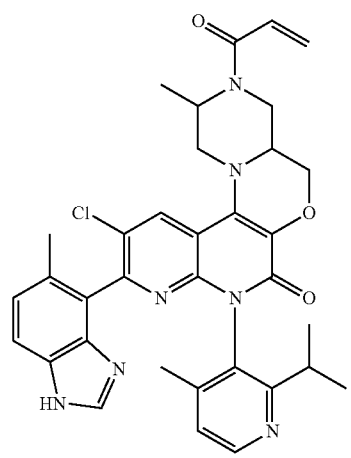
170
-continued
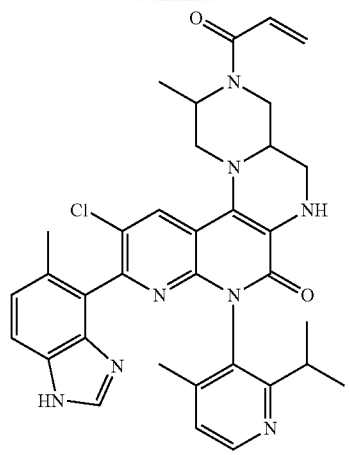
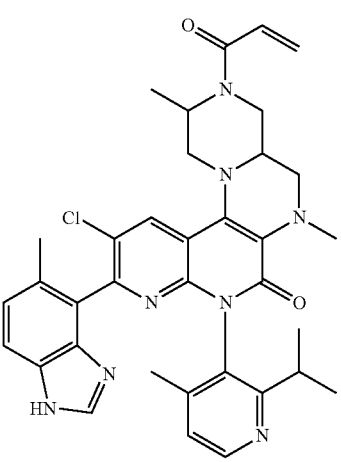
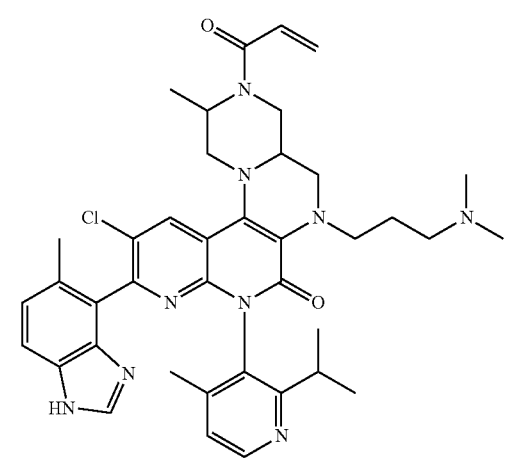

171
-continued
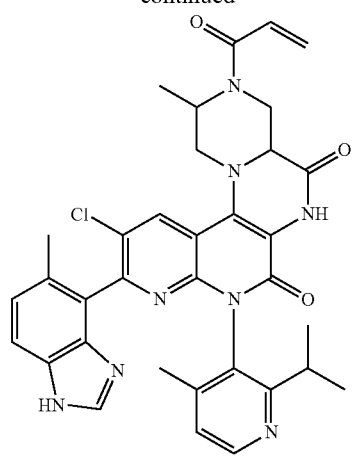
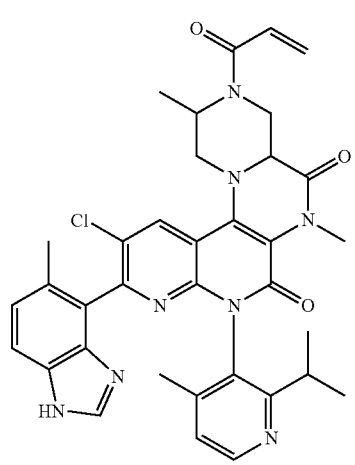
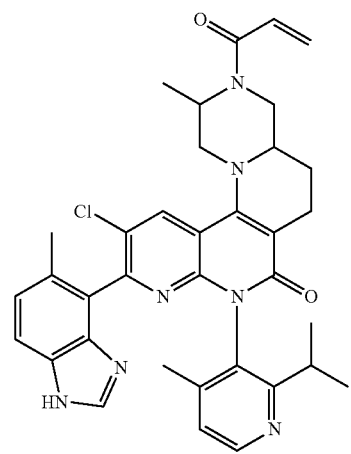
172
-continued
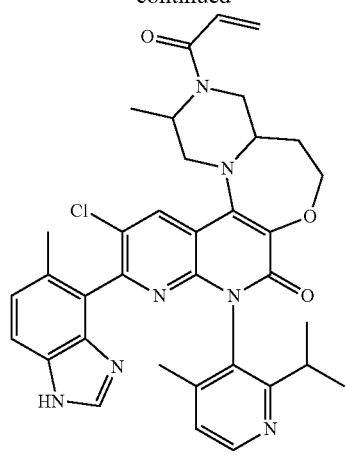
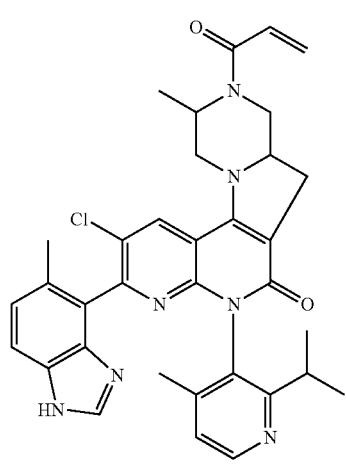

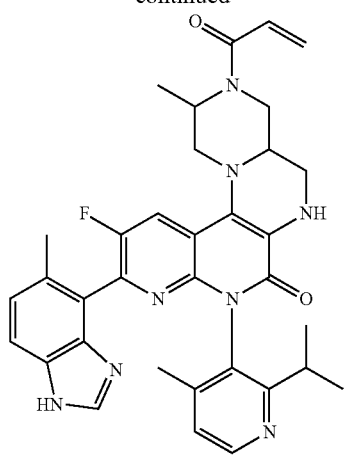
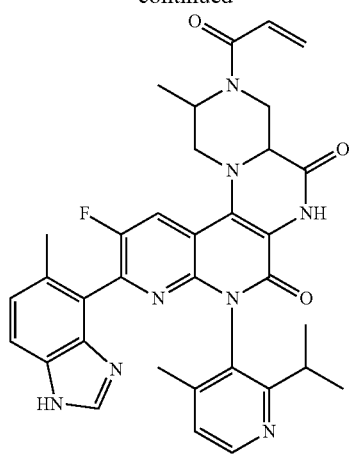
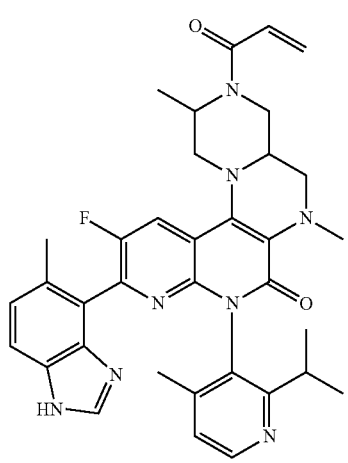
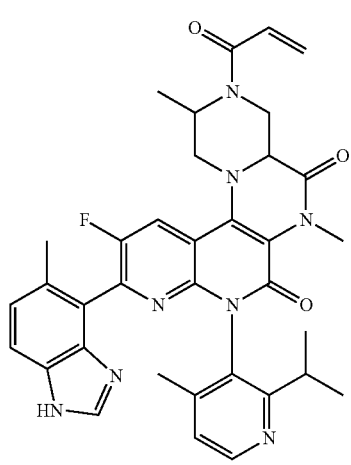
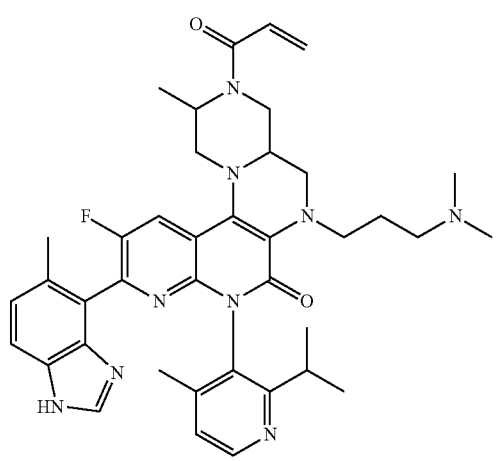
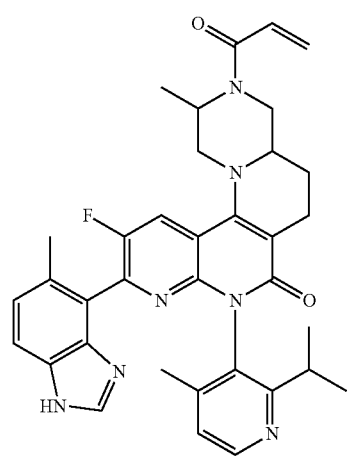

175
-continued
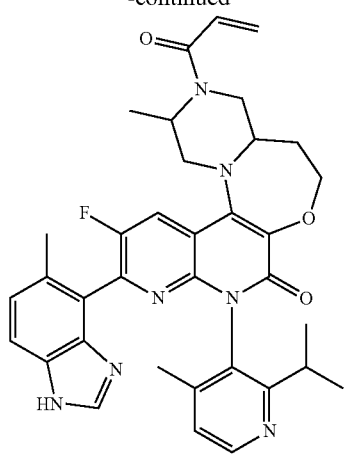
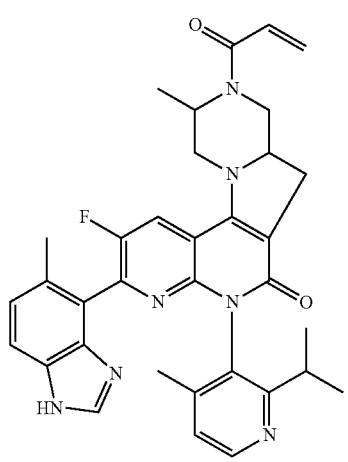
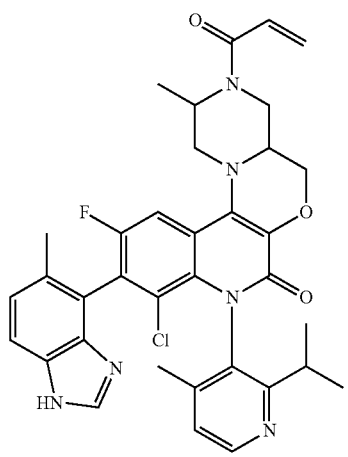
176
-continued
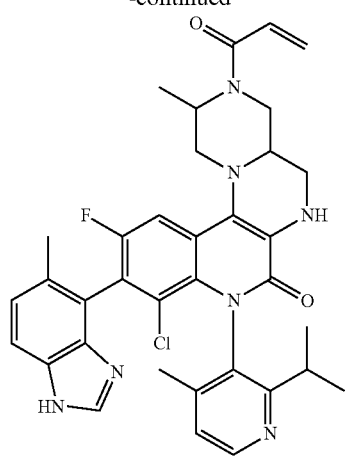
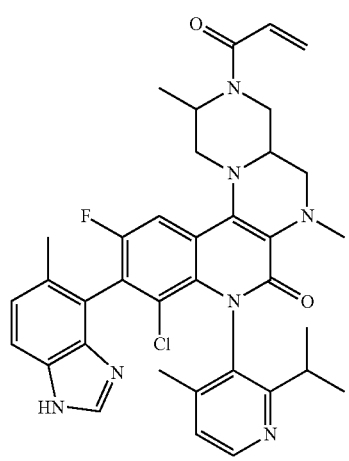
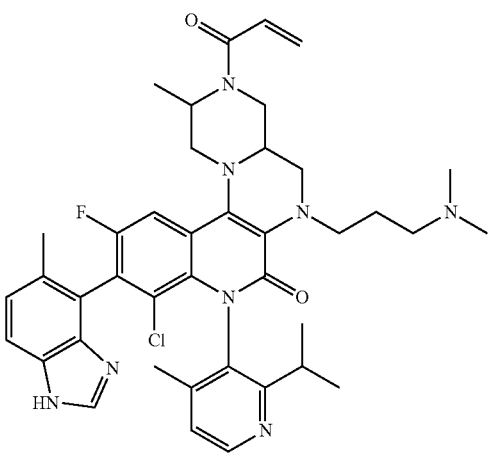

-continued

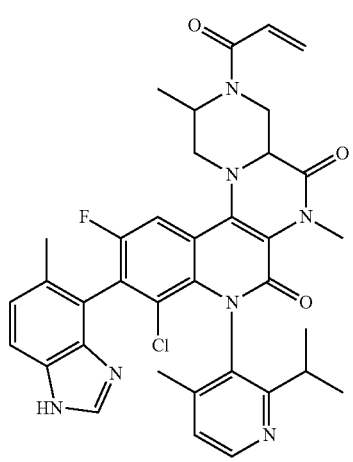
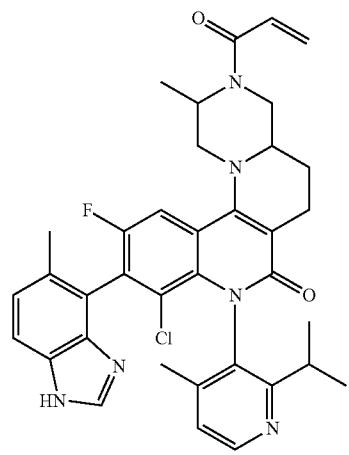
-continued
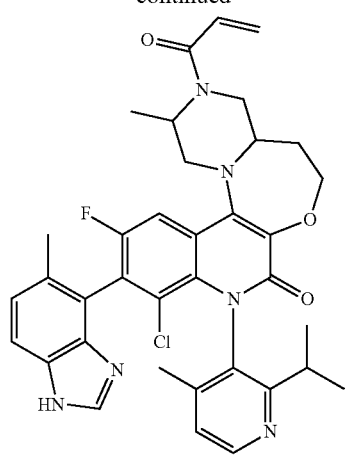
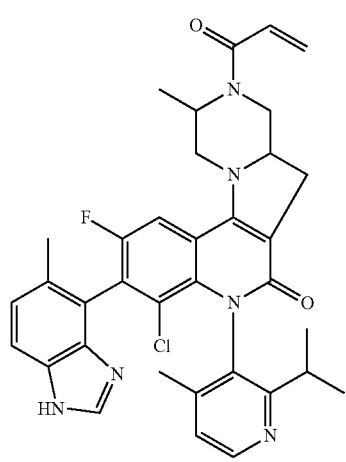
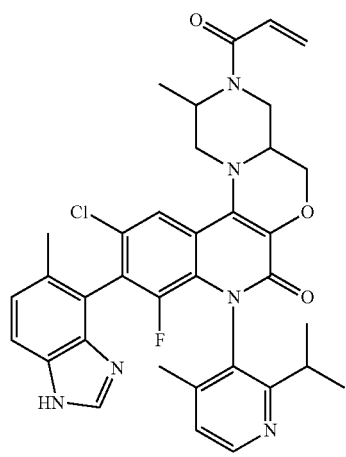

179
-continued
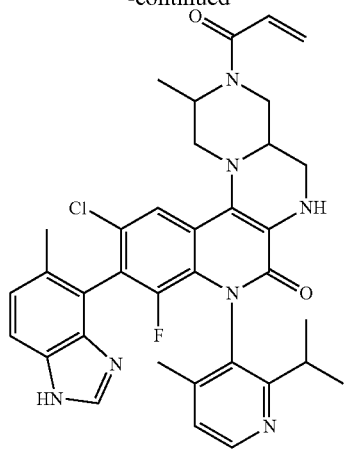
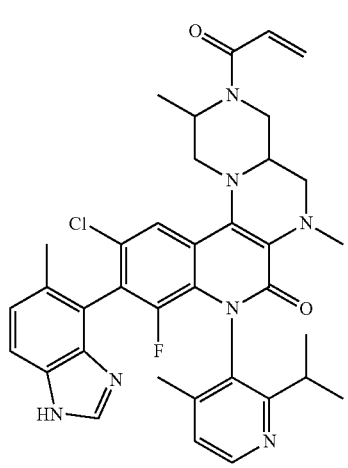
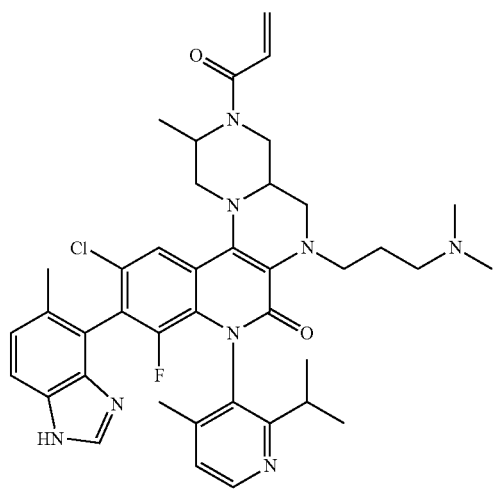
180
-continued
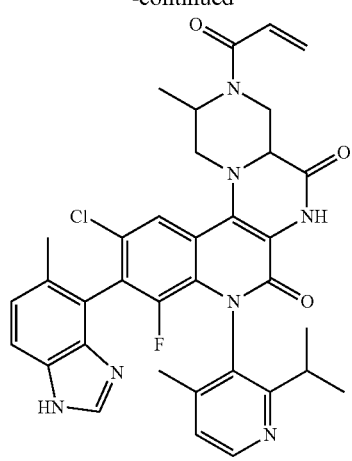
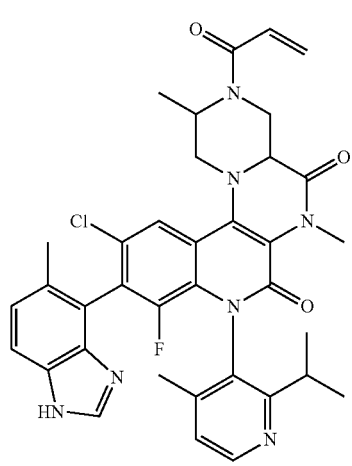
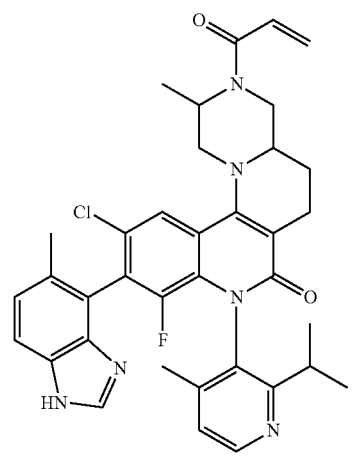

181
-continued
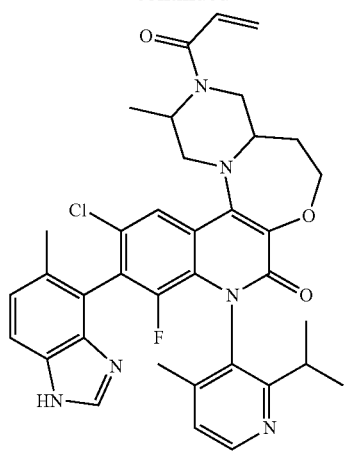
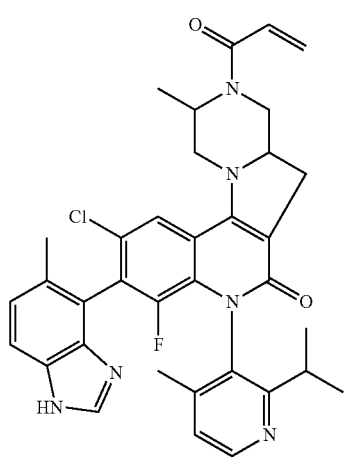
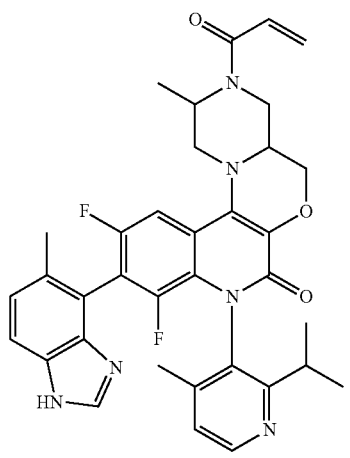
182
-continued
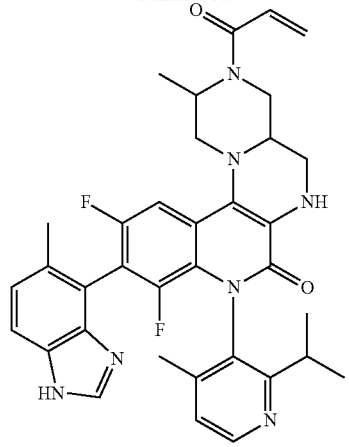
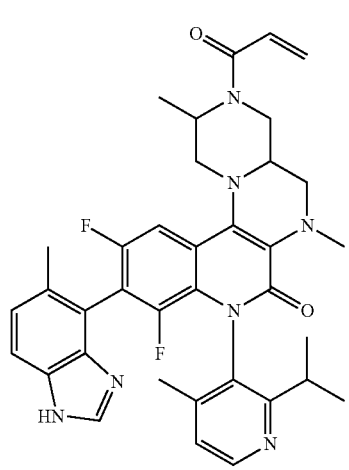
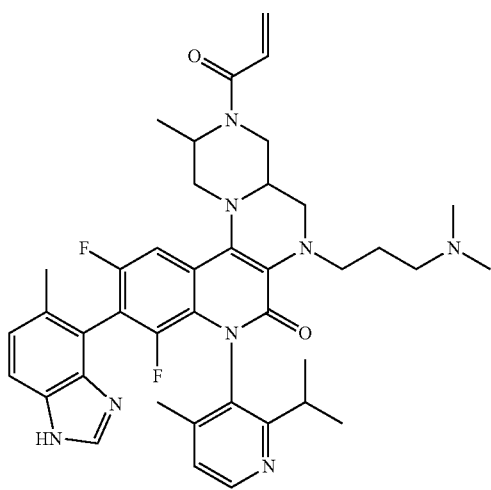

183
-continued
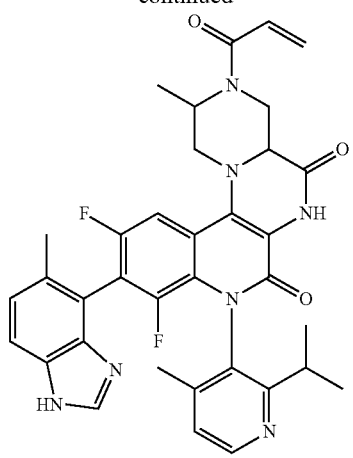
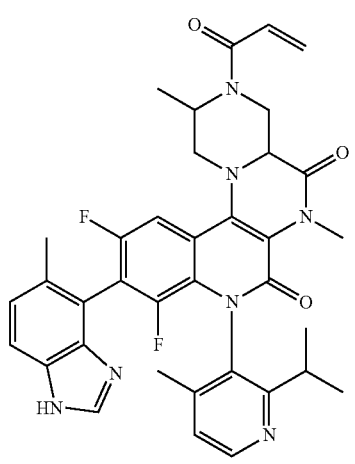
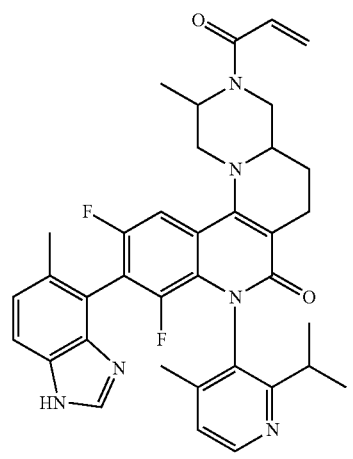
184
-continued
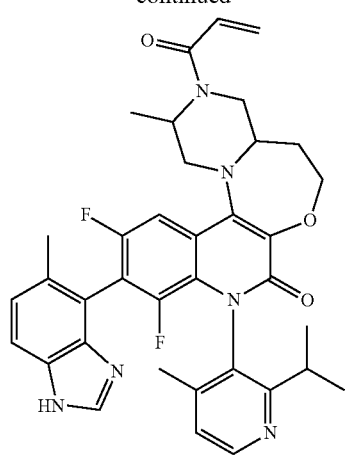
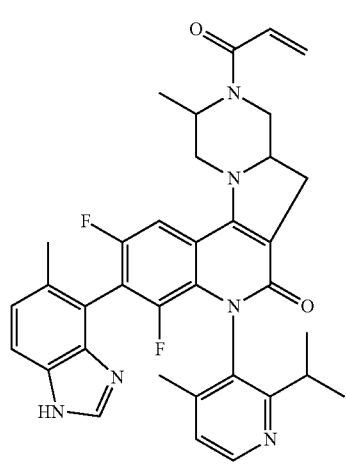
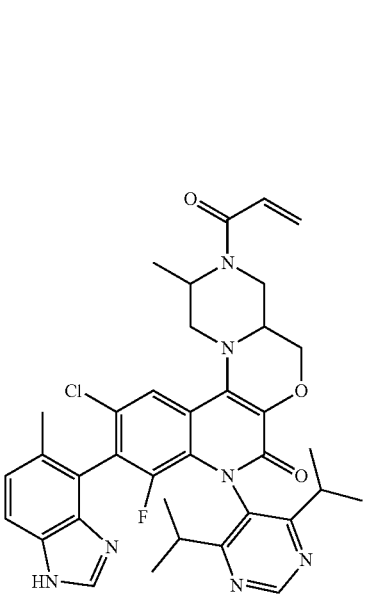

-continued
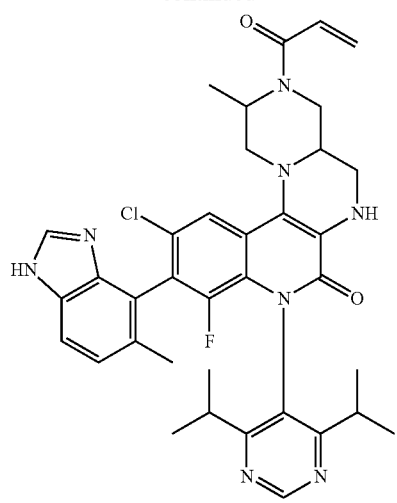
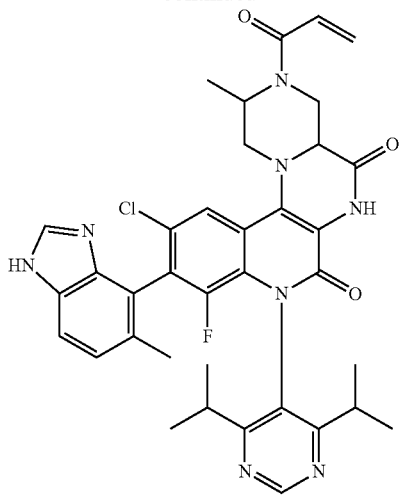
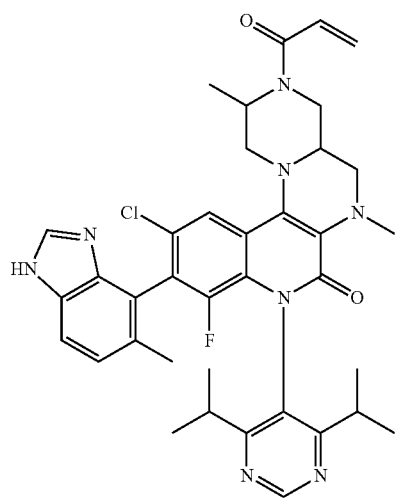
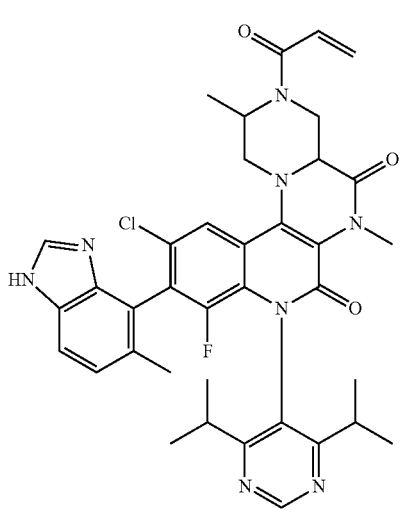
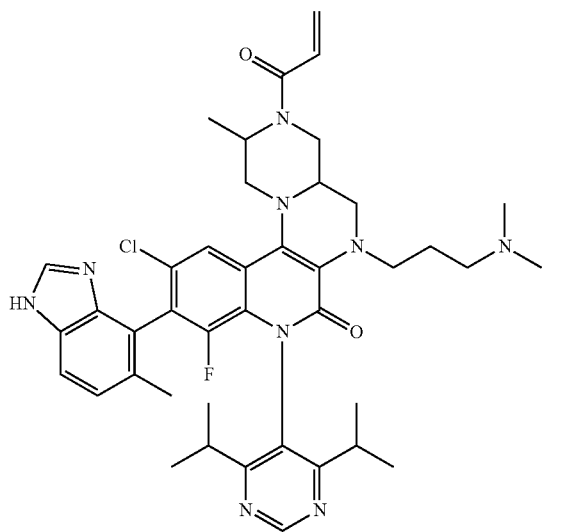
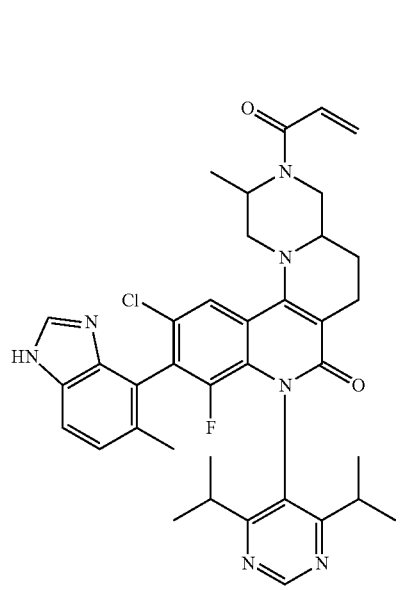

187
-continued
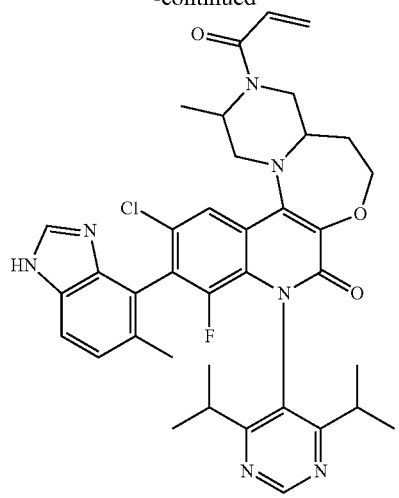
188
-continued
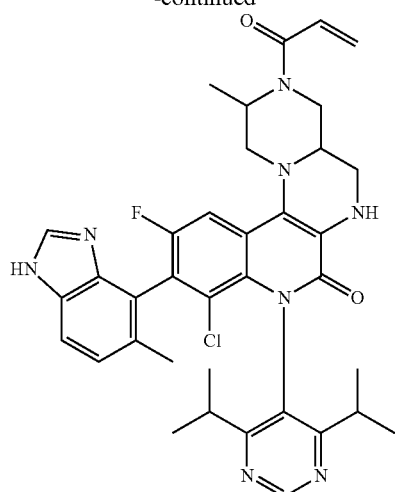
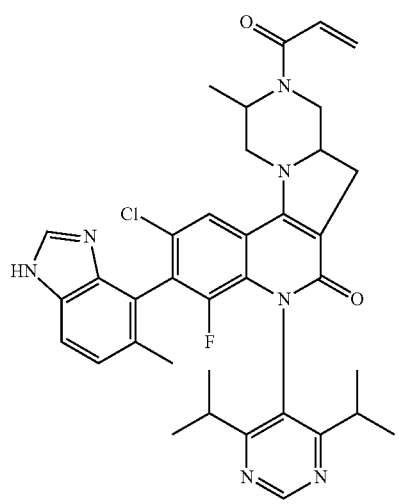
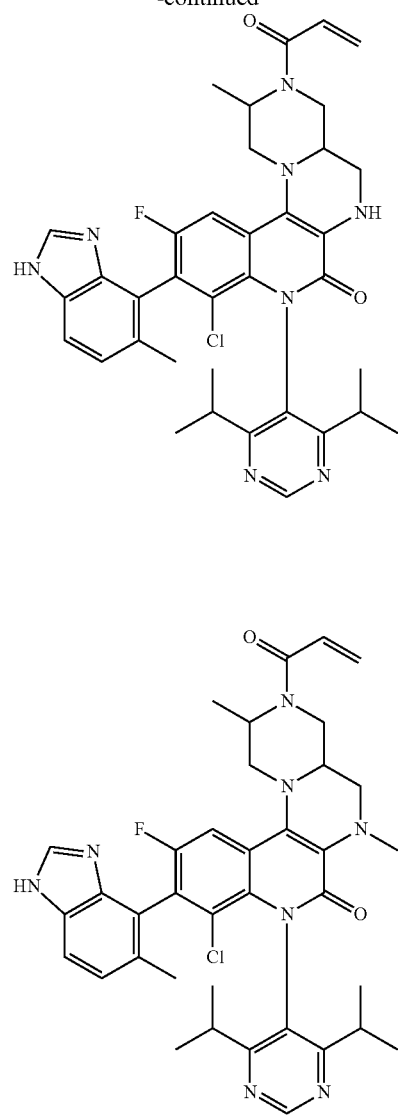
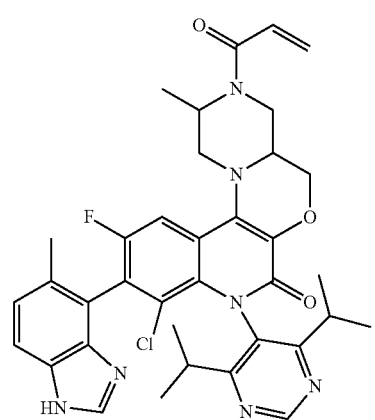
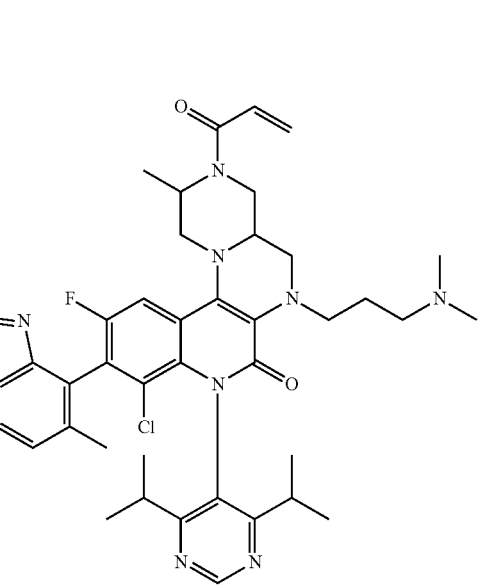

189
-continued
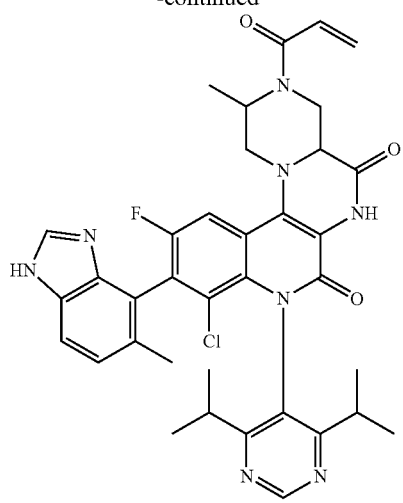
190
-continued
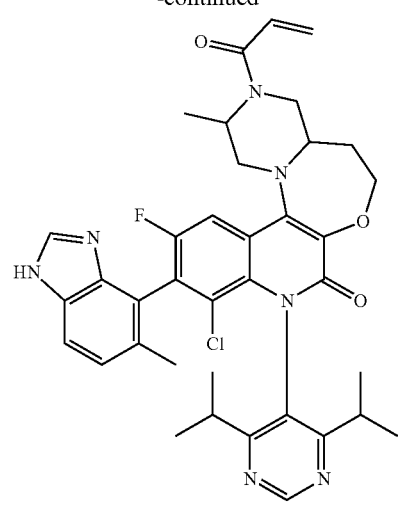
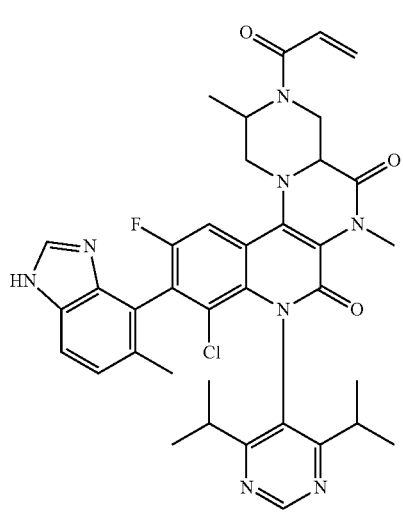
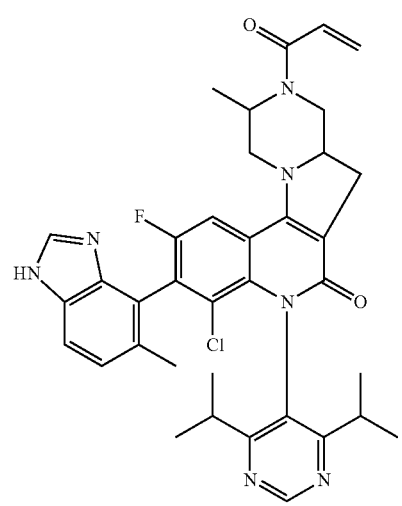
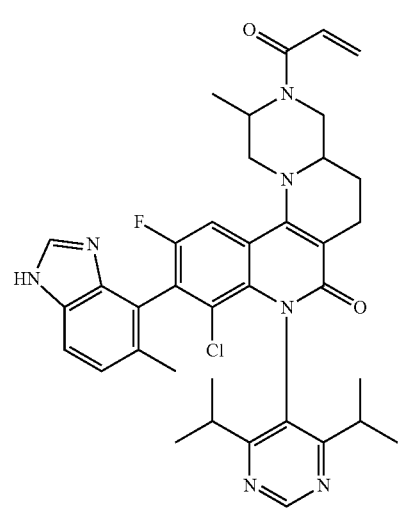
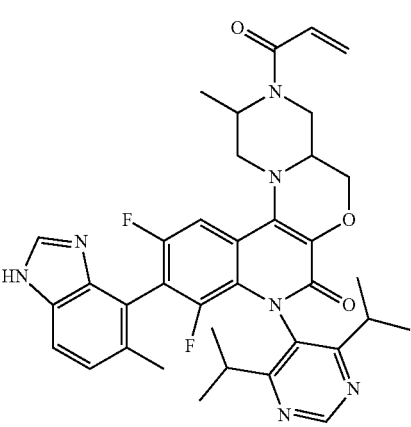

191
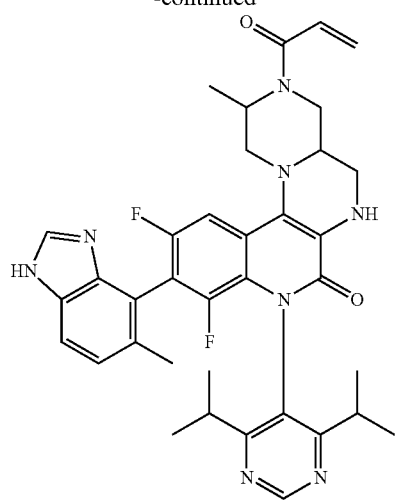
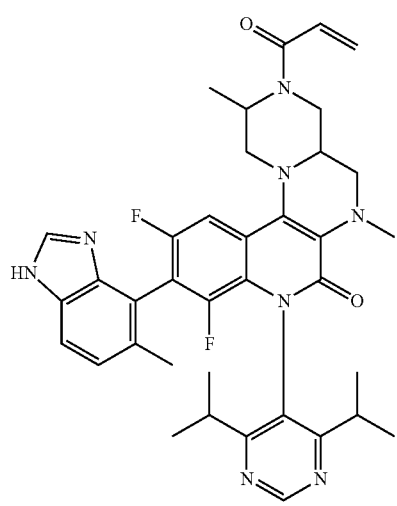
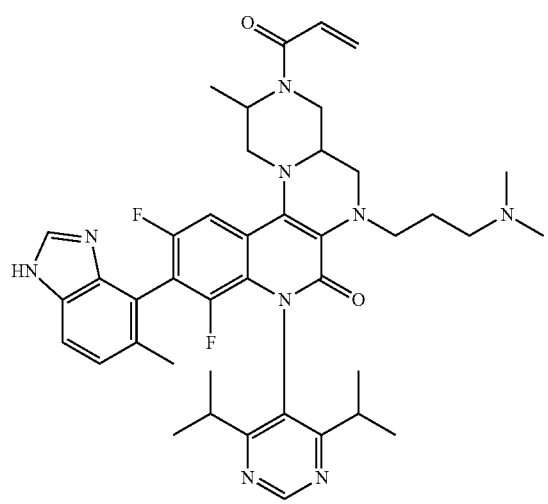
192
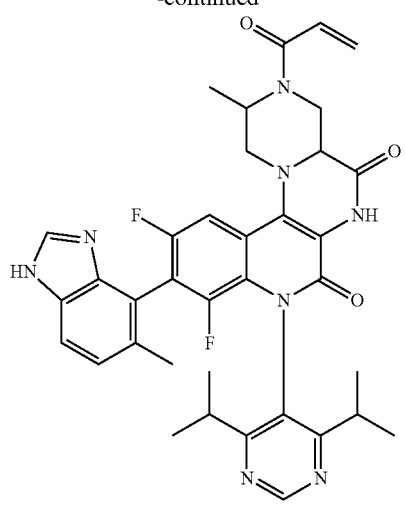
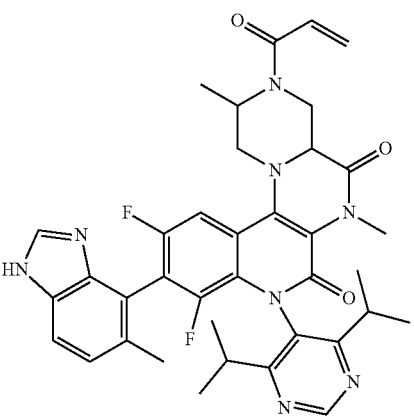
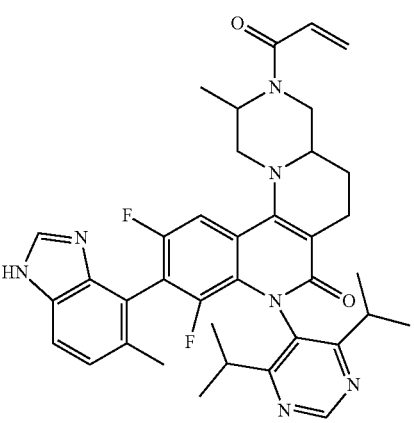

193
-continued
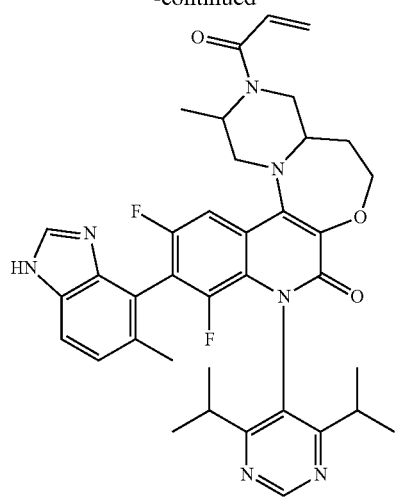
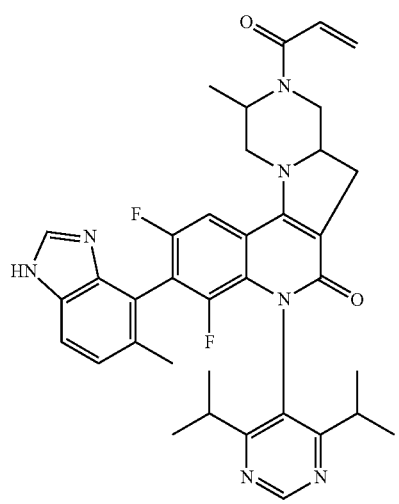
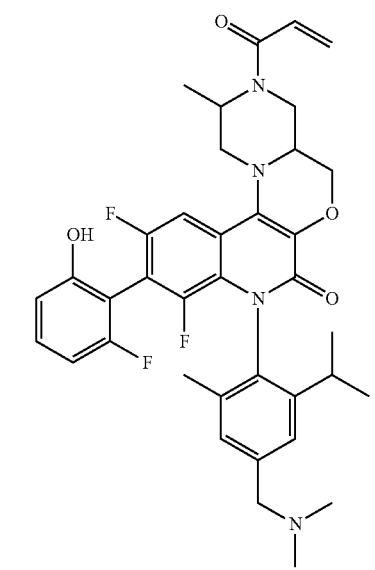
194
-continued
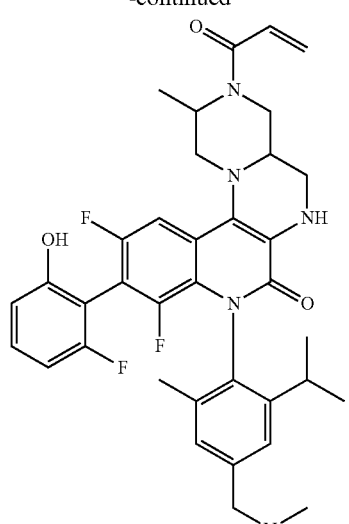
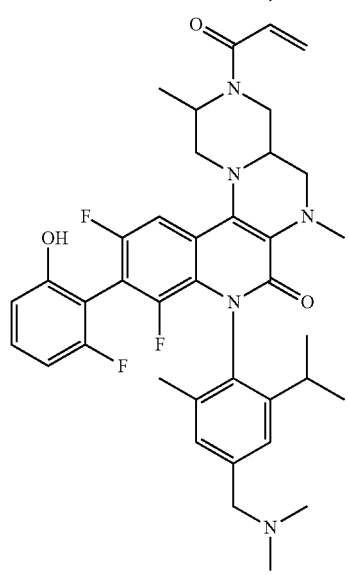
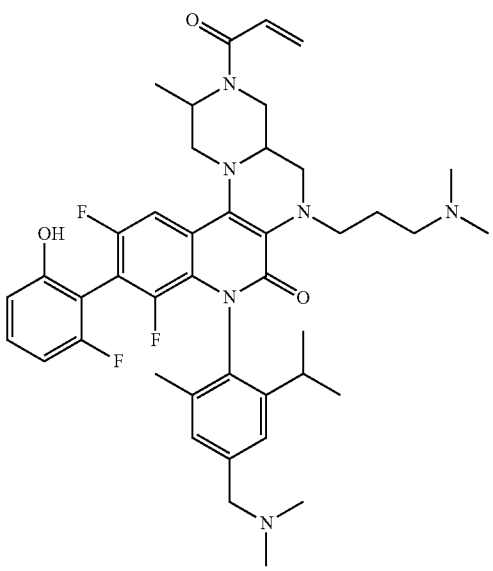

195
-continued
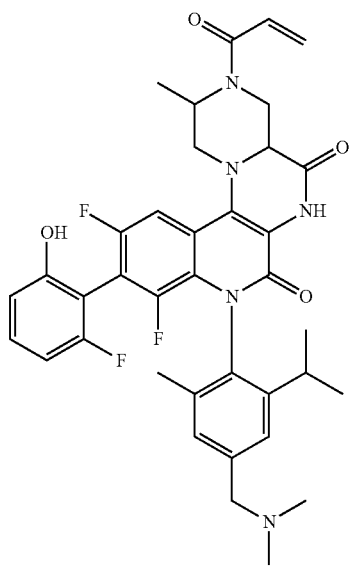
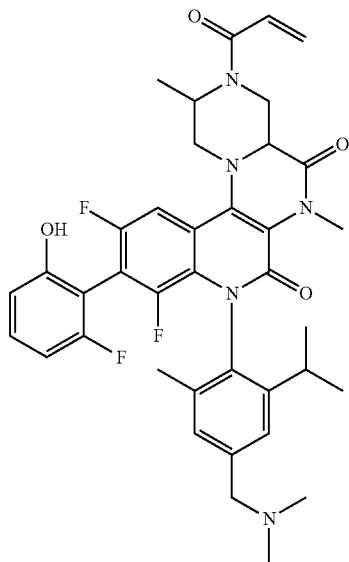
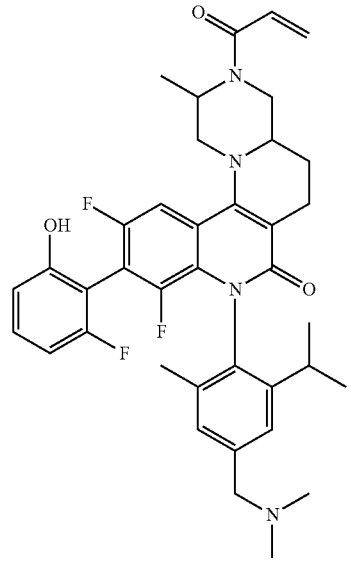
196
-continued
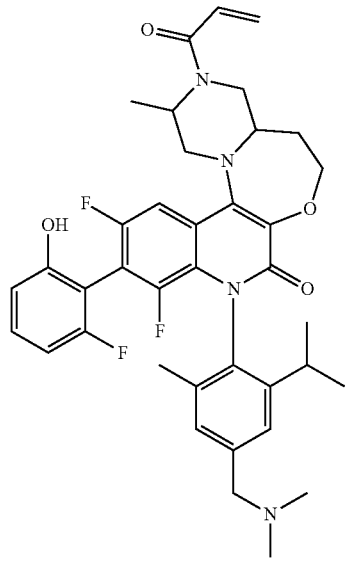
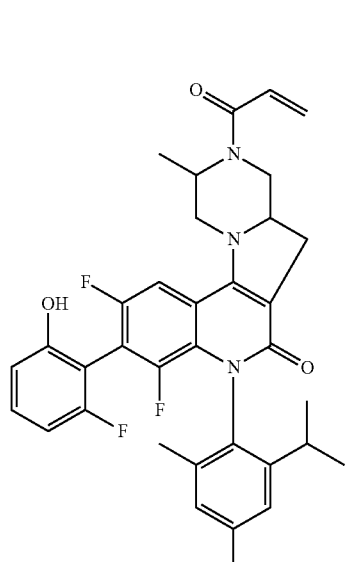
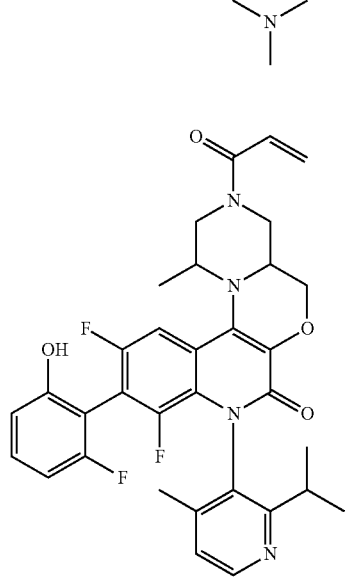

-continued
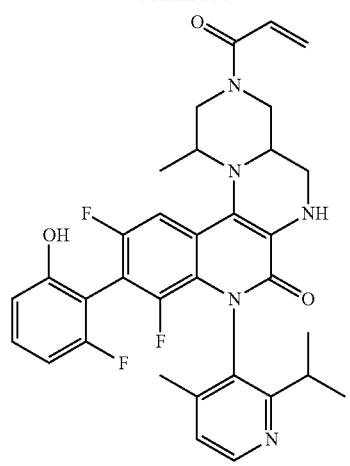
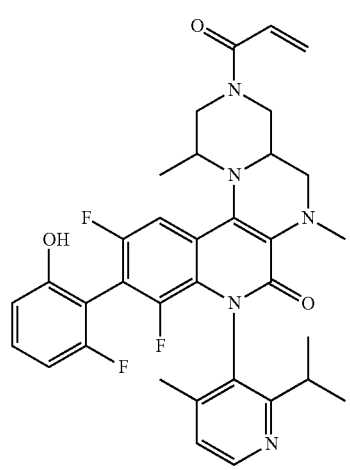
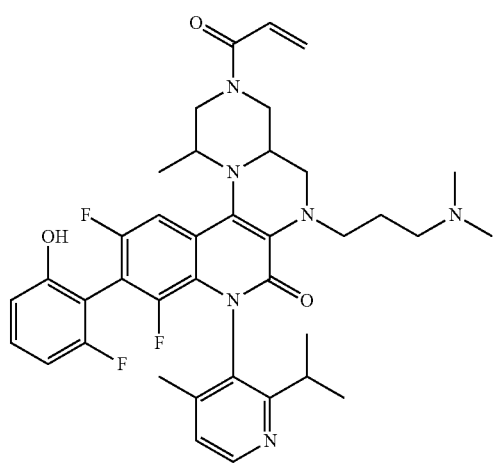
-continued
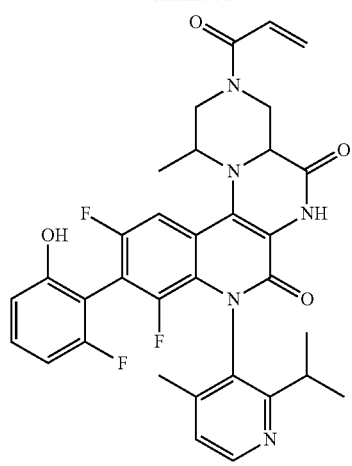
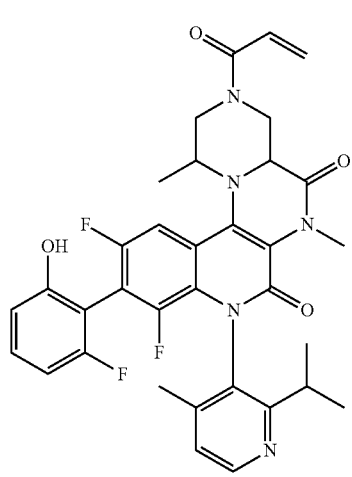
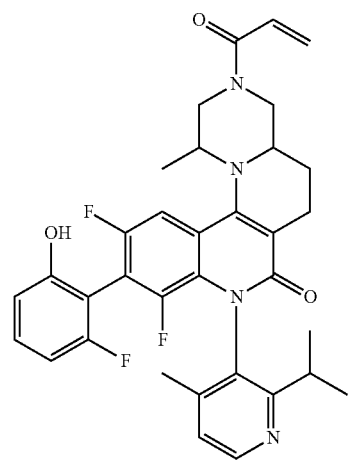

199
-continued
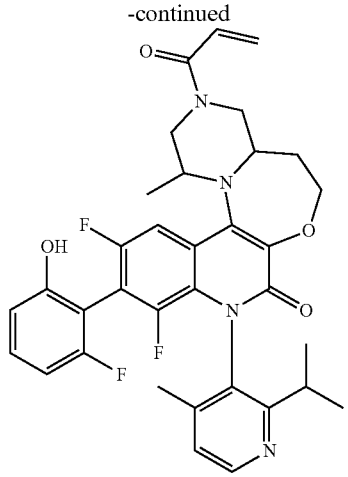
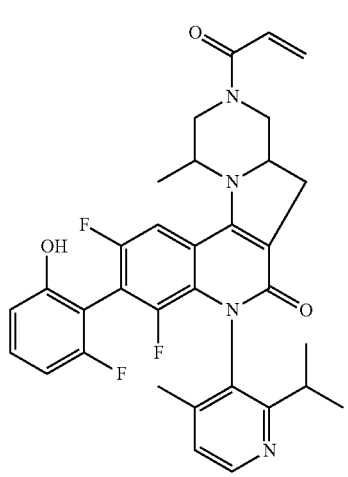
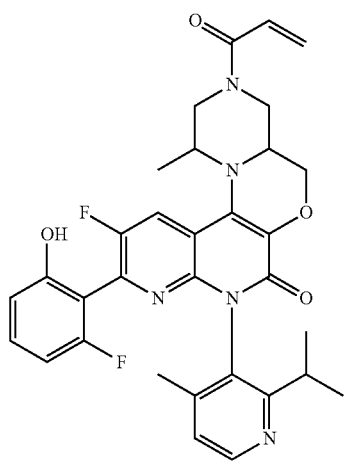
200
-continued
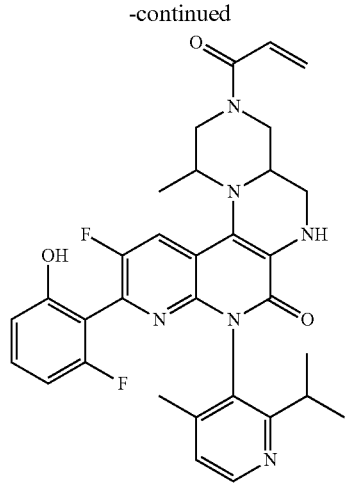
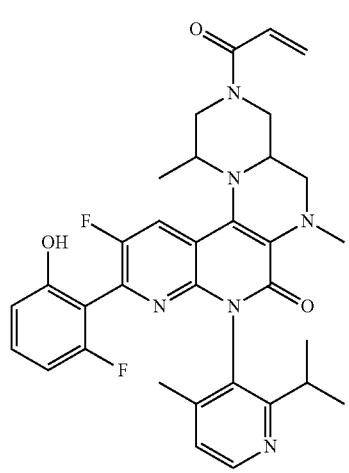
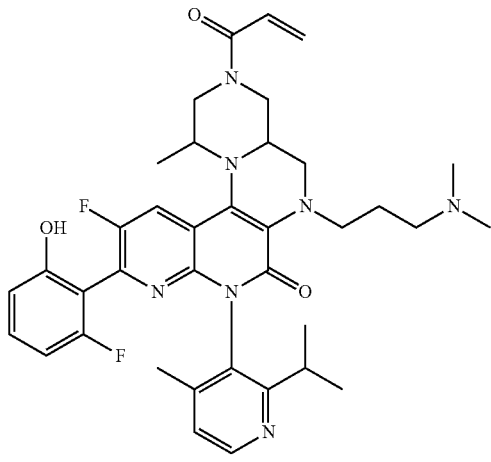

201
-continued
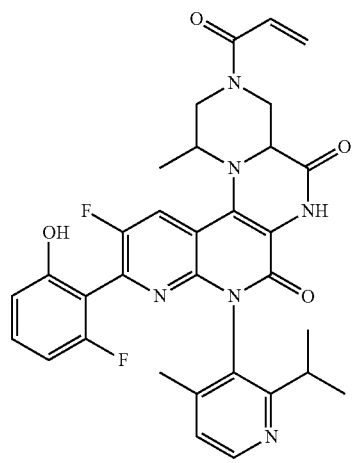
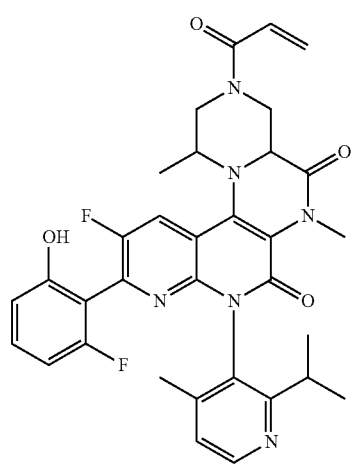
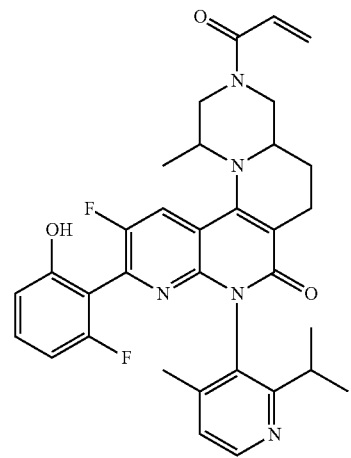
202
-continued
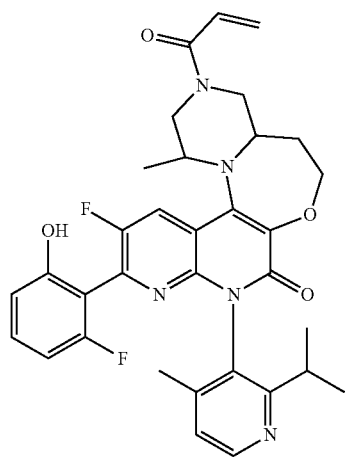
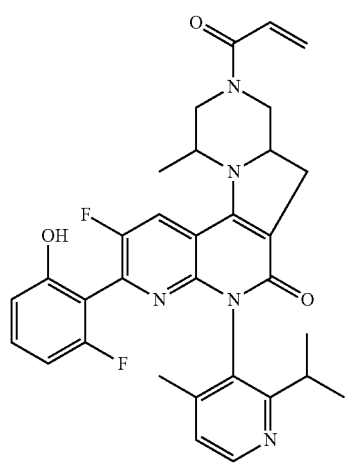
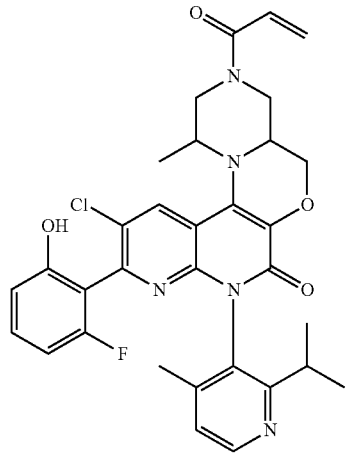

203
-continued
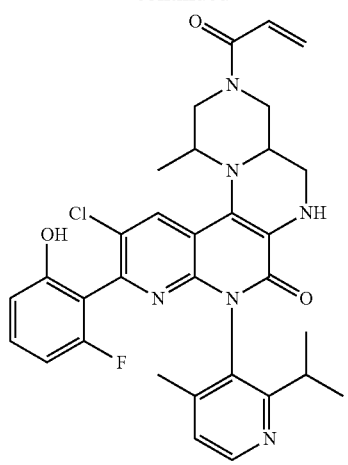
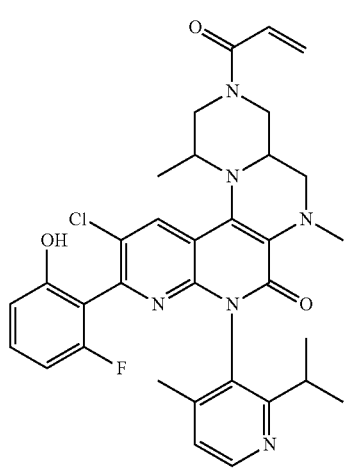
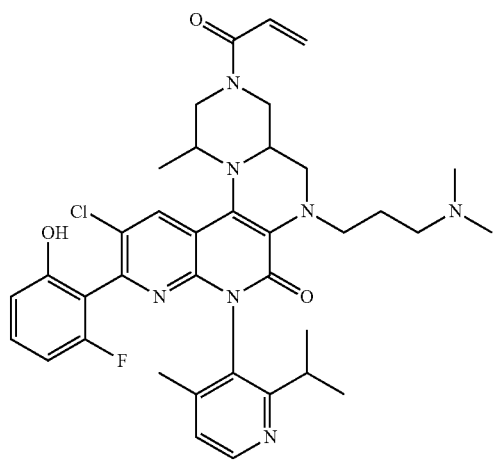
204
-continued
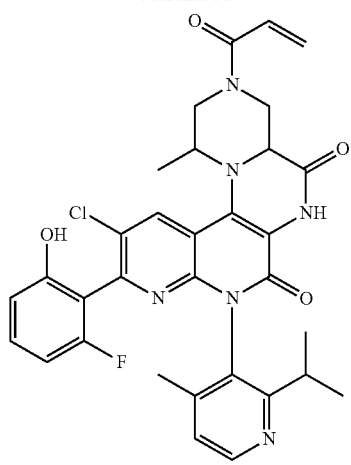
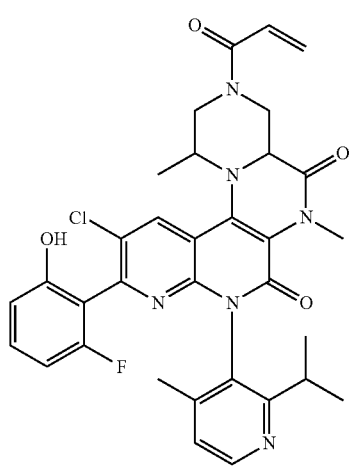
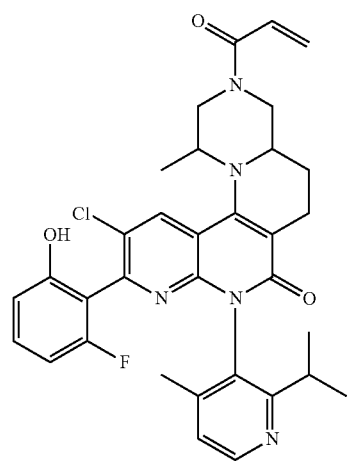

205
-continued
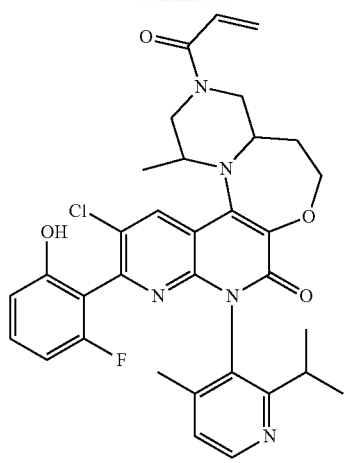
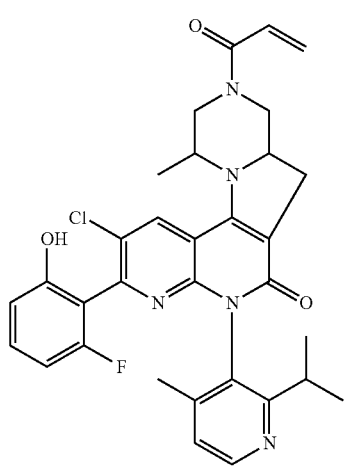
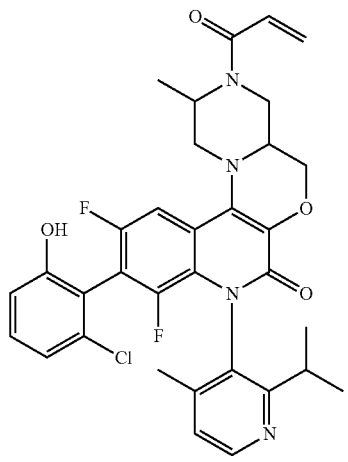
206
-continued
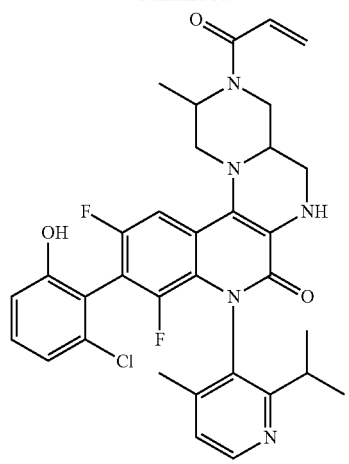
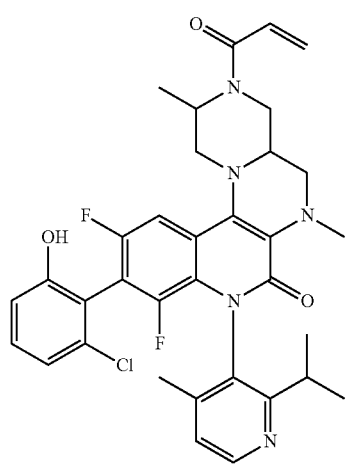
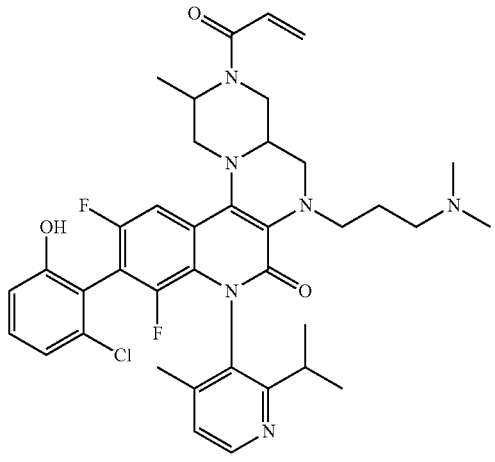

207
-continued
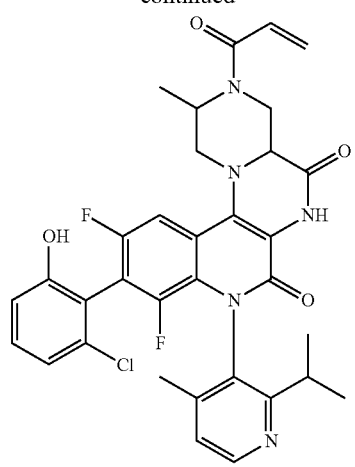
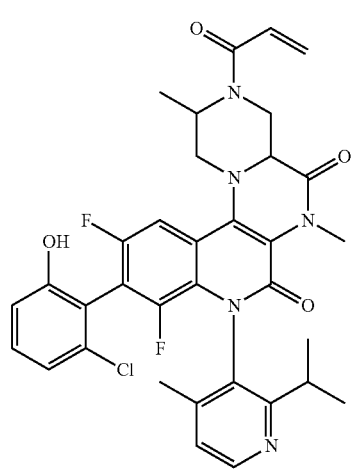
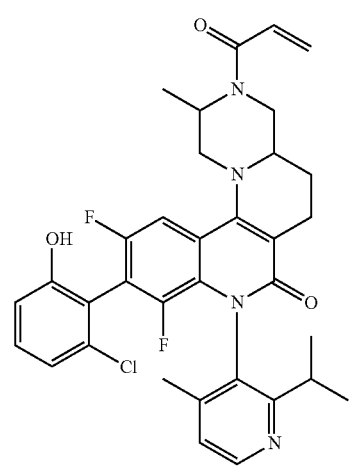
208
-continued
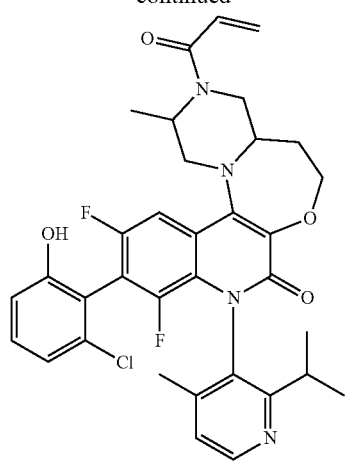
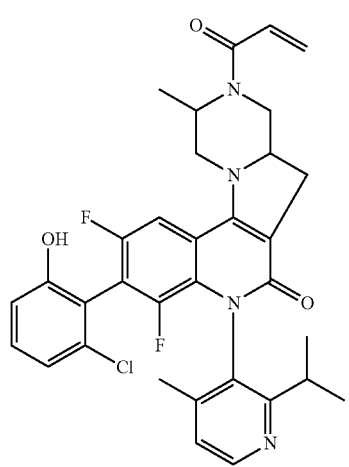
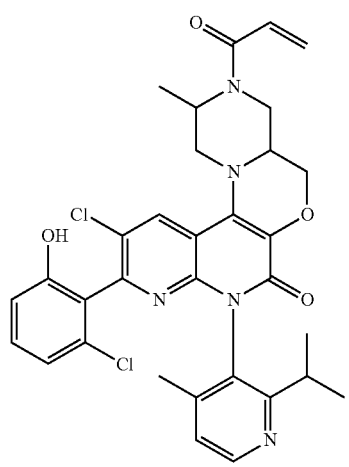

209
-continued
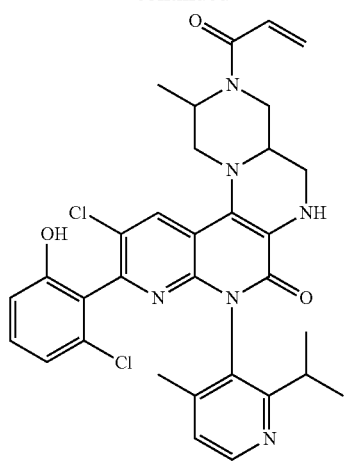
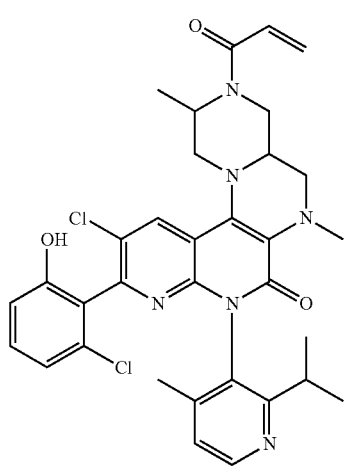
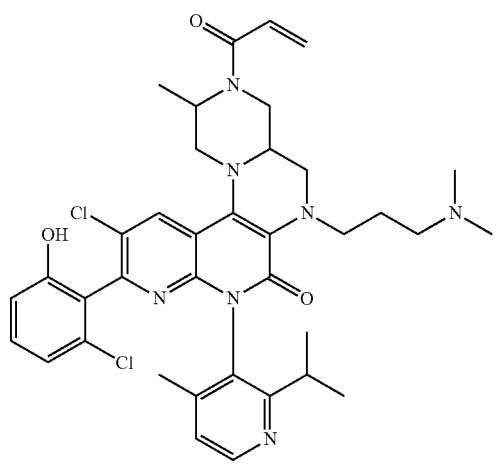
210
-continued
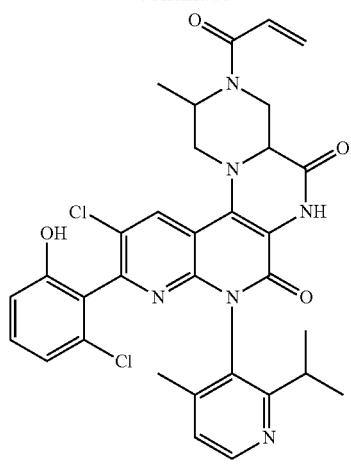
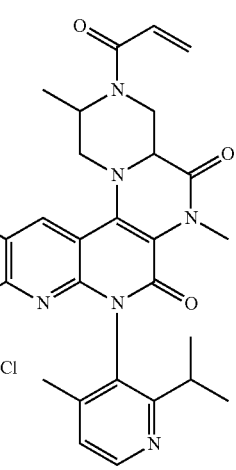
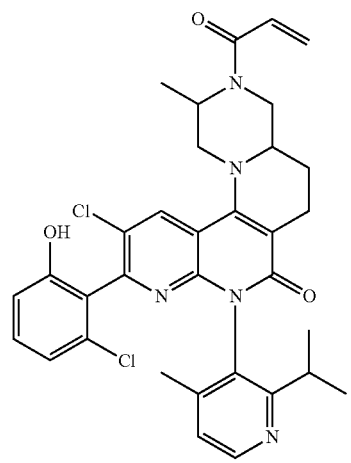

211 -continued
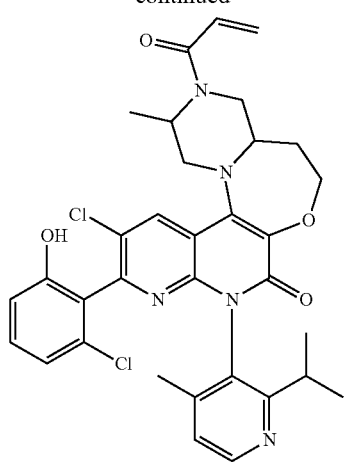
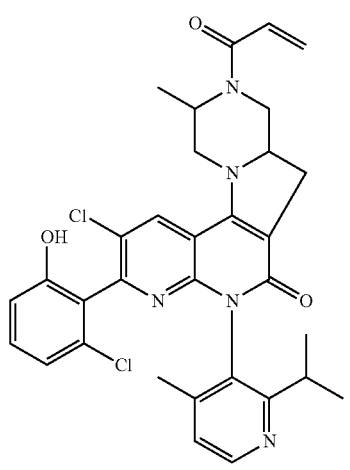
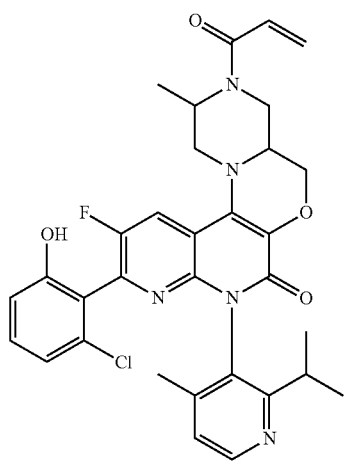
212 -continued
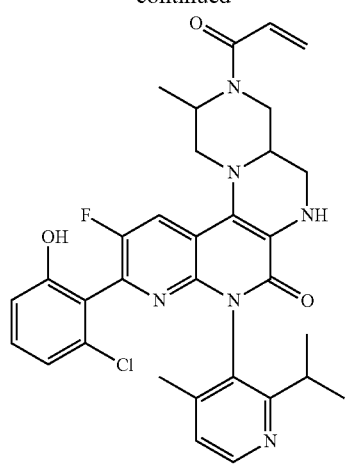
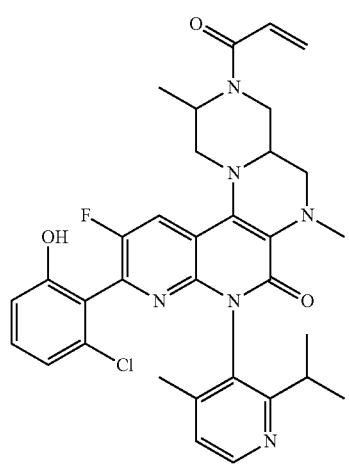
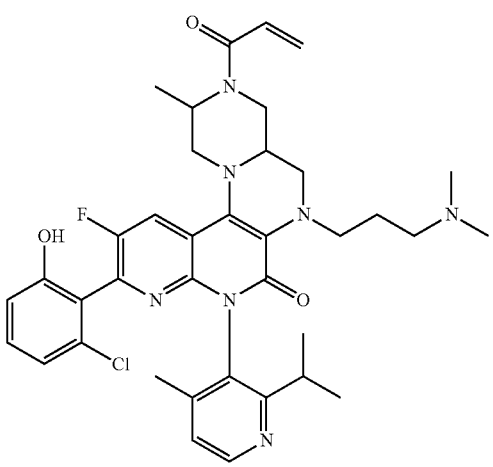

213
-continued
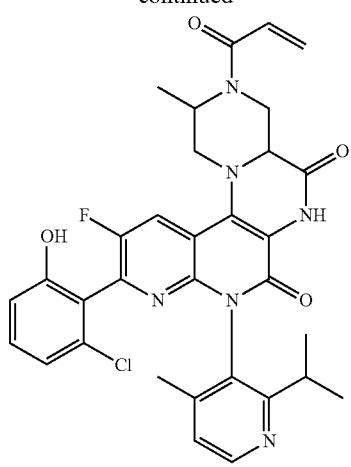
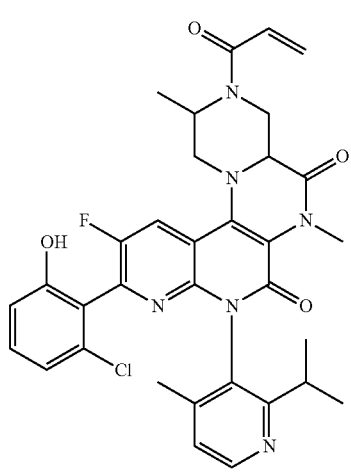
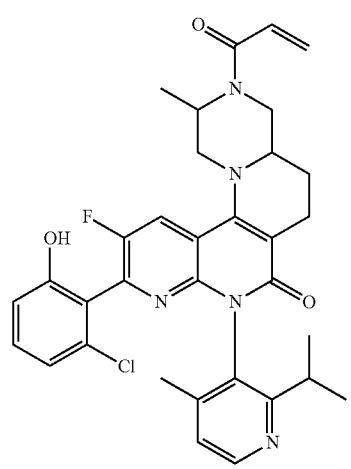
214
-continued
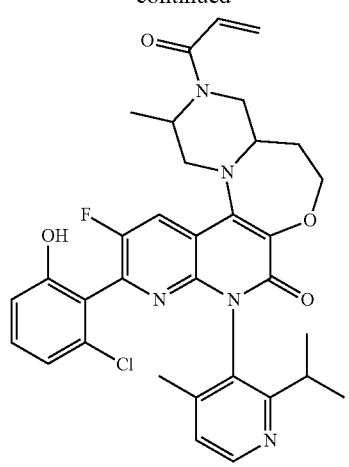
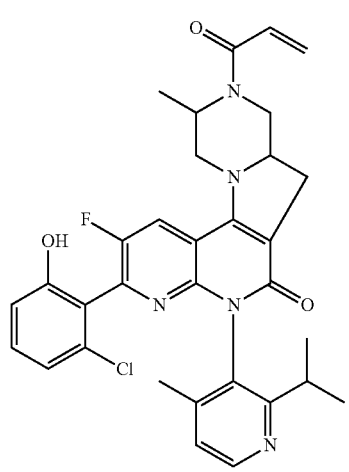
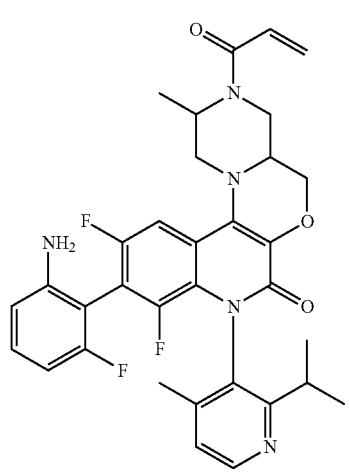

215
-continued
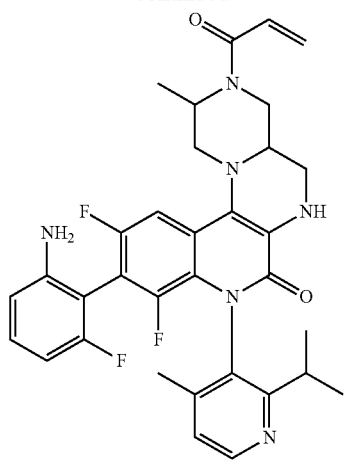
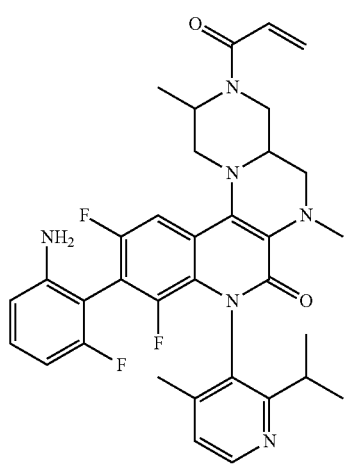
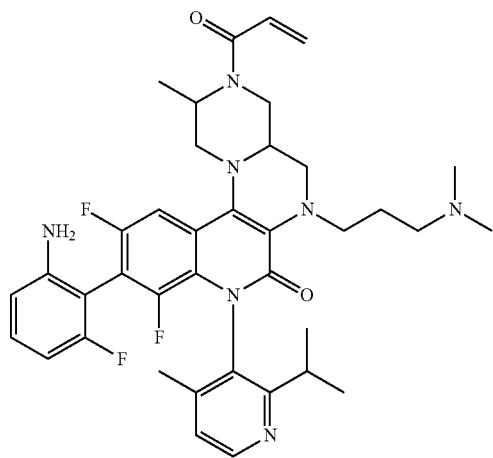
216
-continued
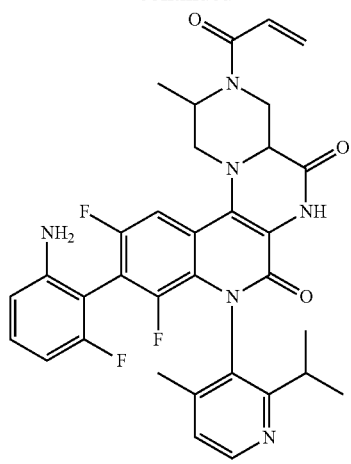
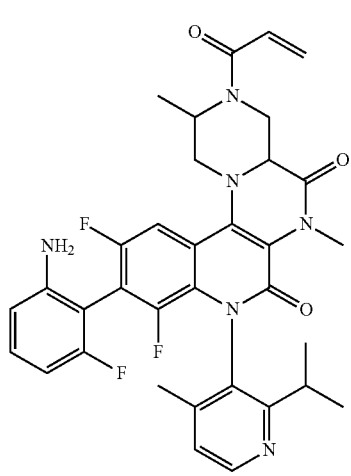
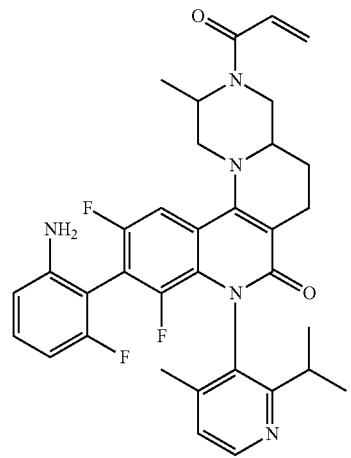

217
-continued
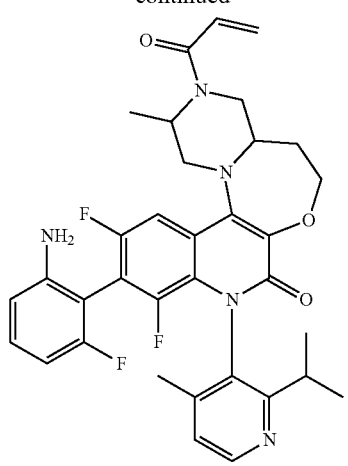
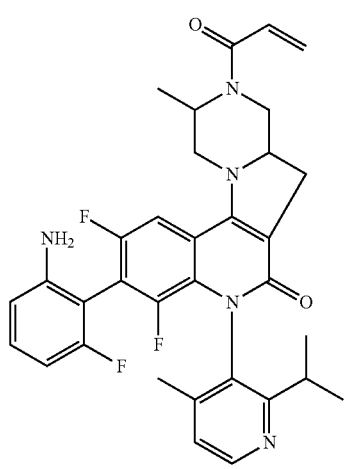
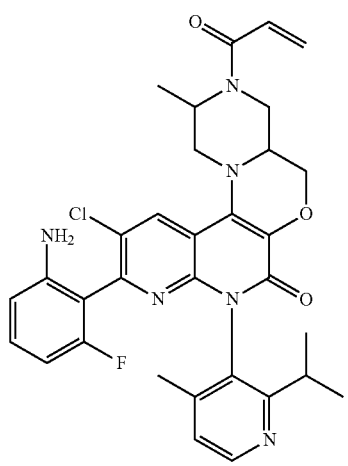
218
-continued
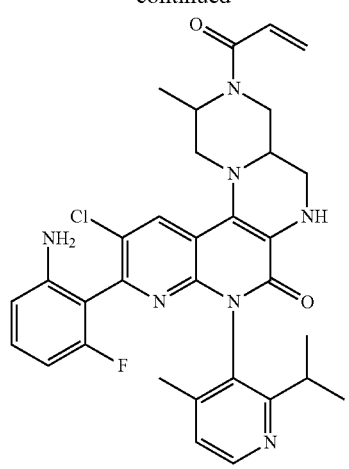
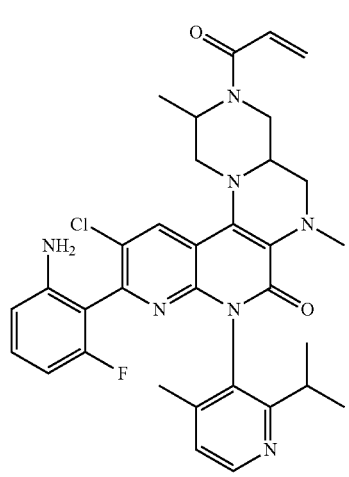
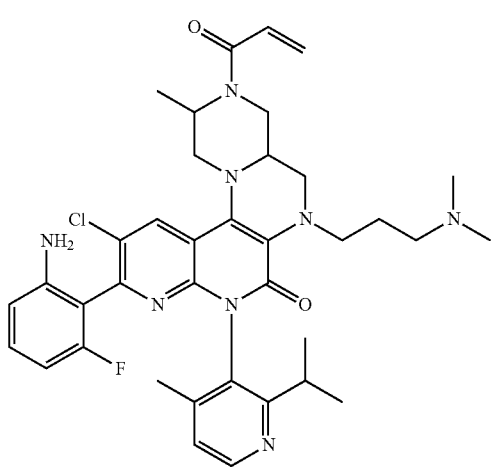

219
-continued
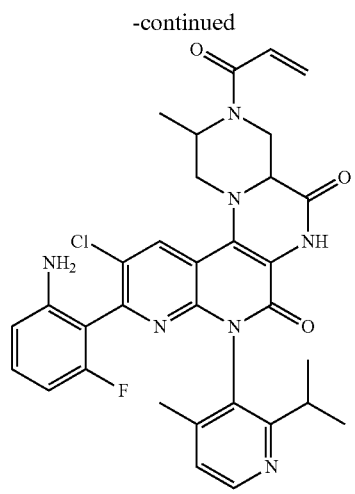
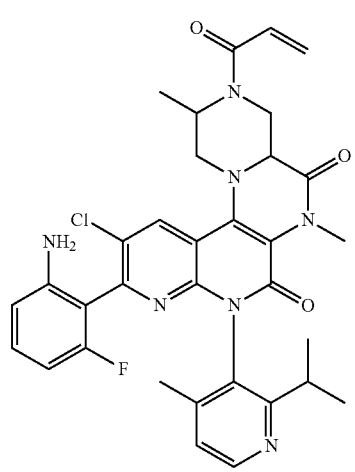
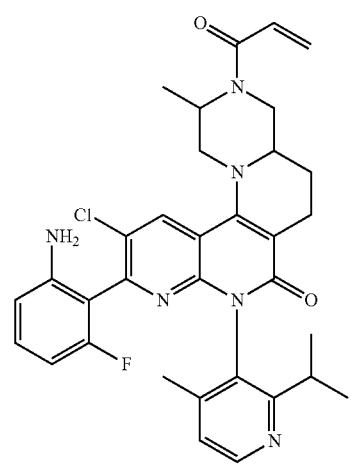
220
-continued
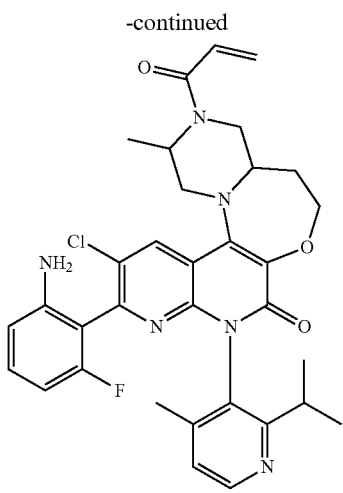
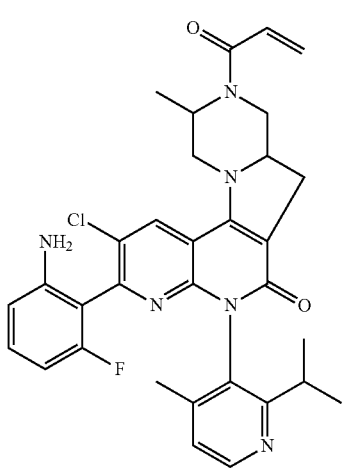
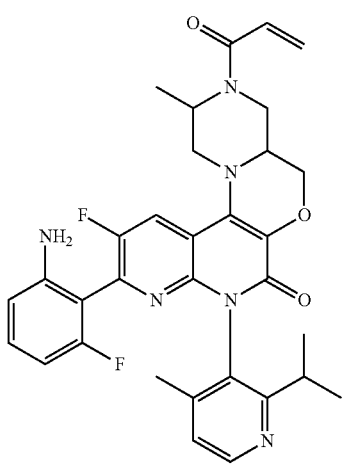

221
-continued
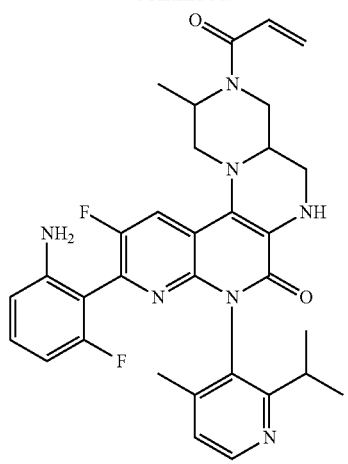
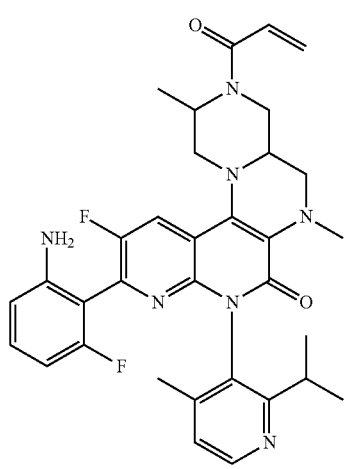
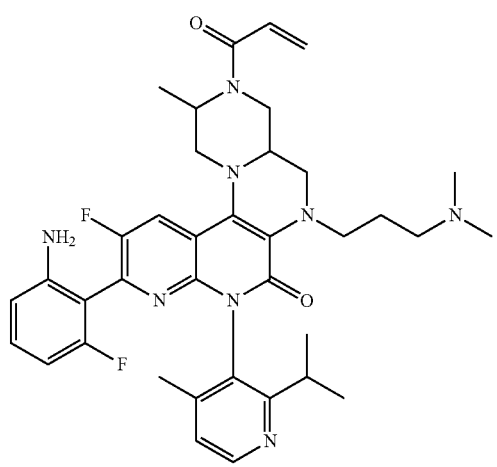
222
-continued
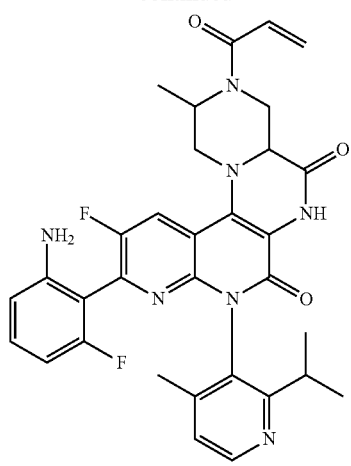
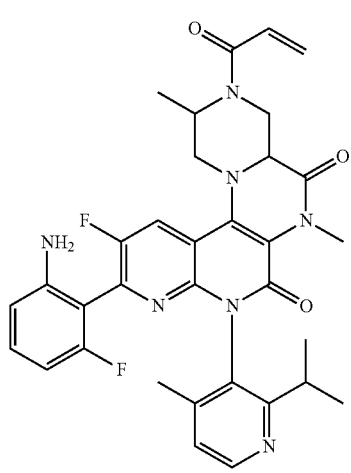
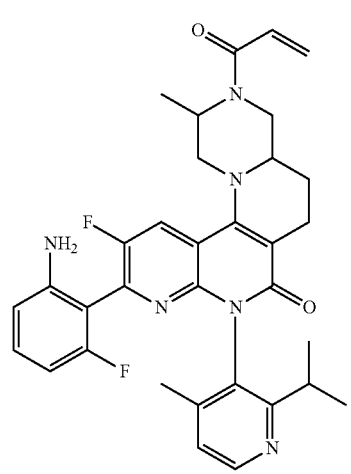

223
-continued
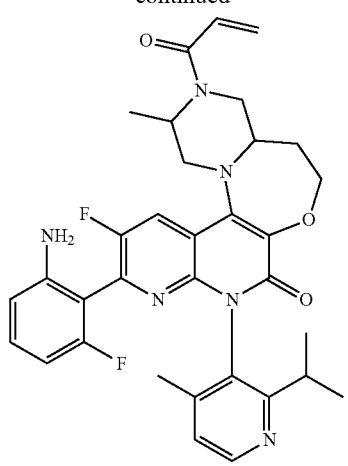
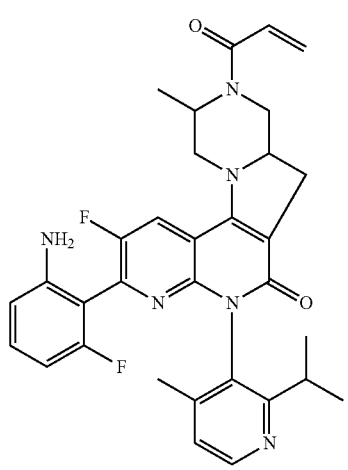
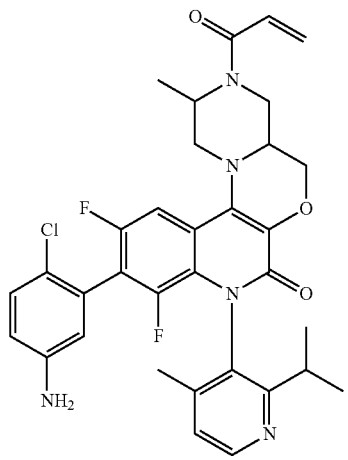
224
-continued
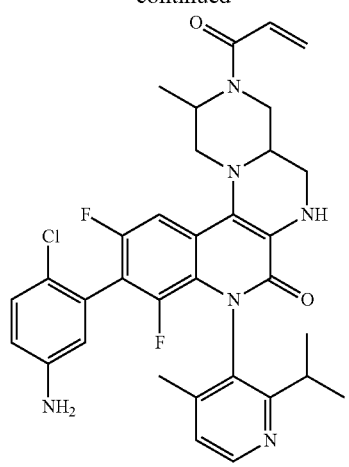
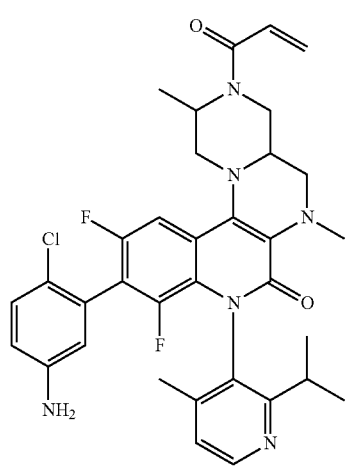
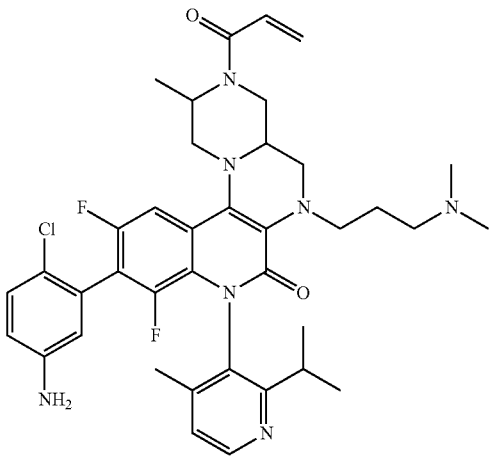

225
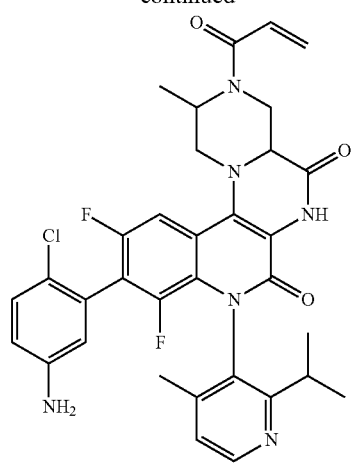
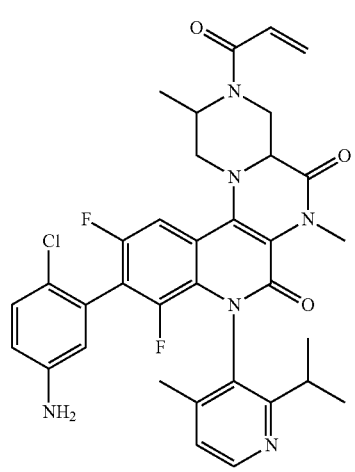
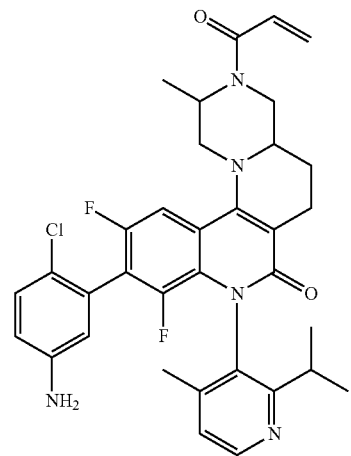
226
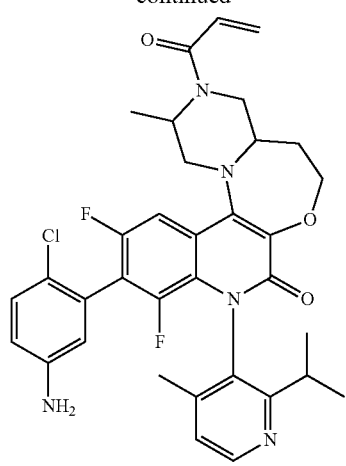
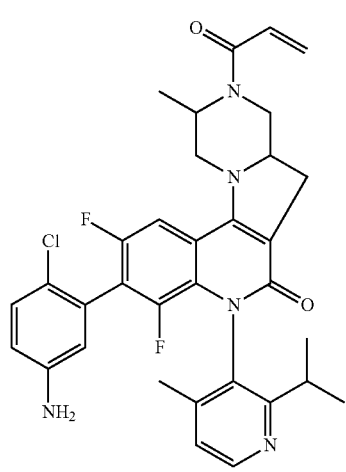
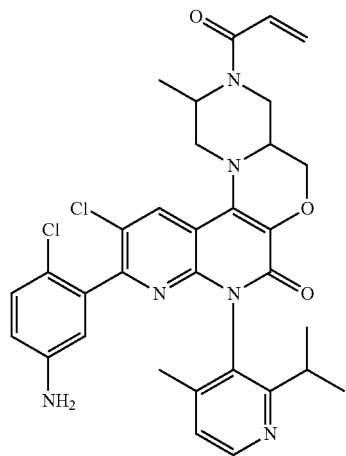

-continued
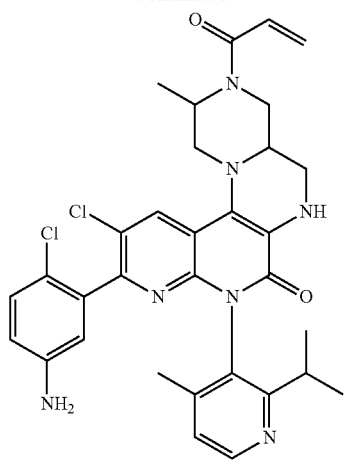
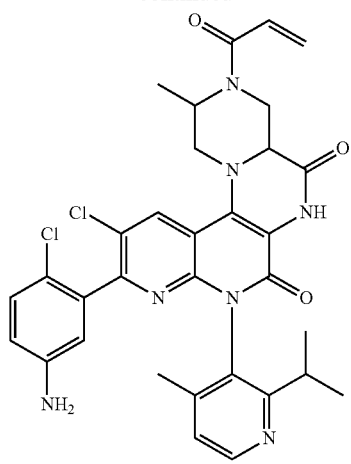
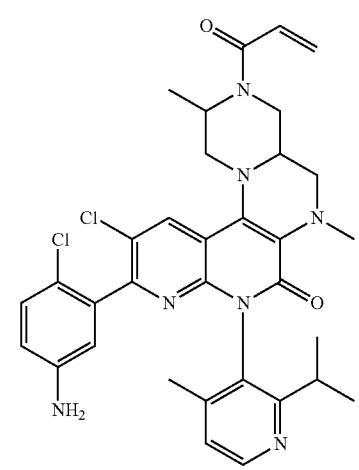
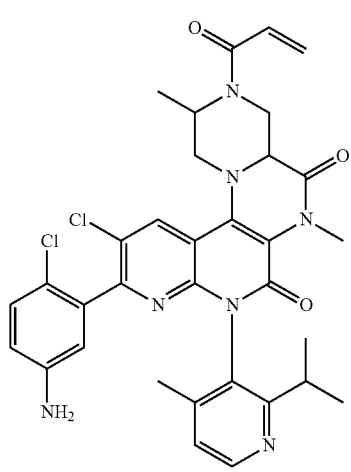
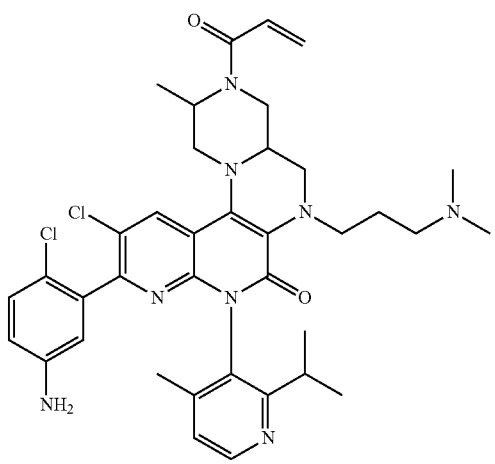
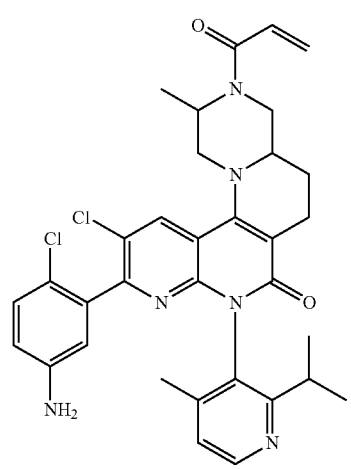

229
-continued
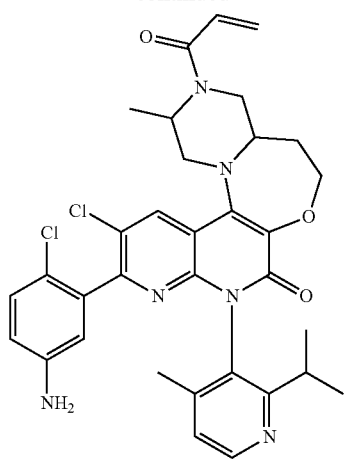
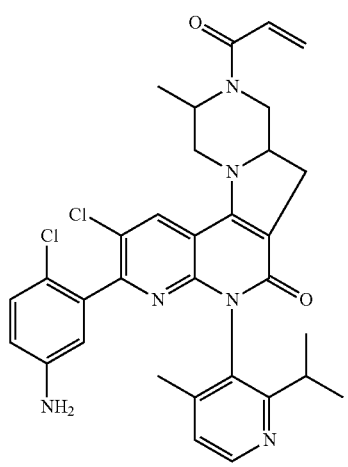
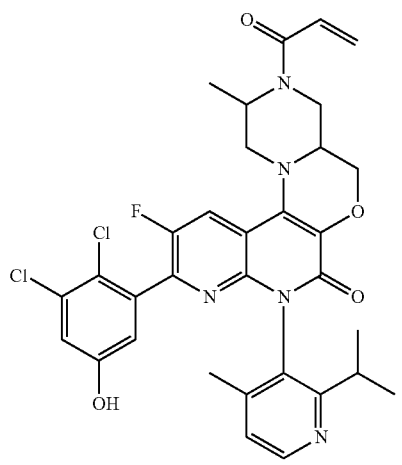
230
-continued
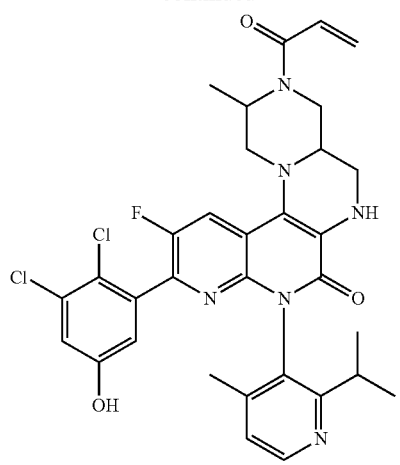
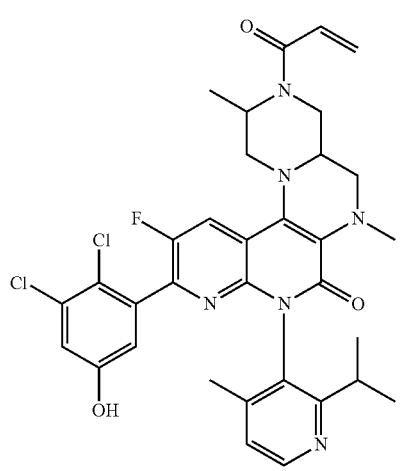
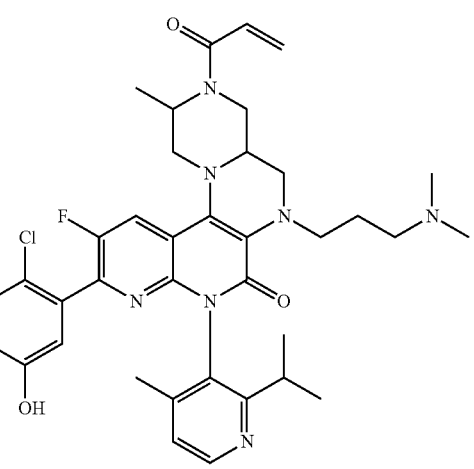

231
-continued
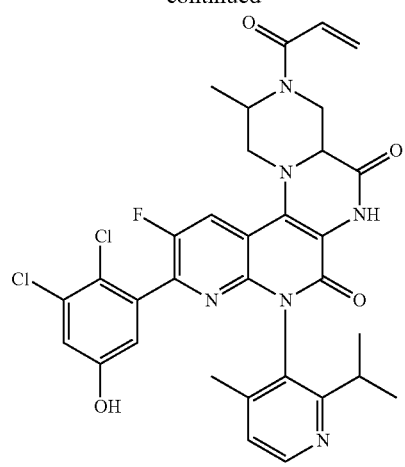
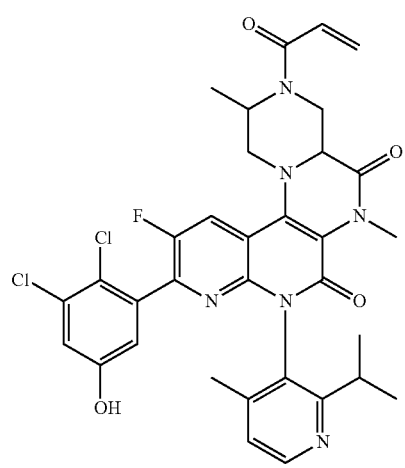
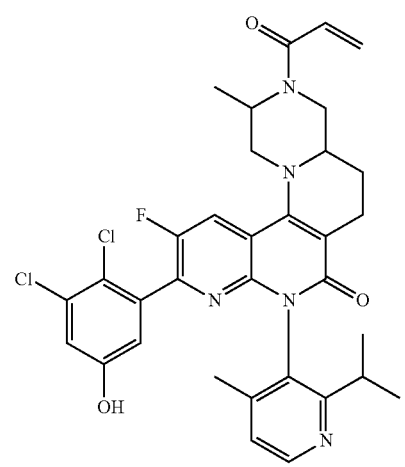
232
-continued
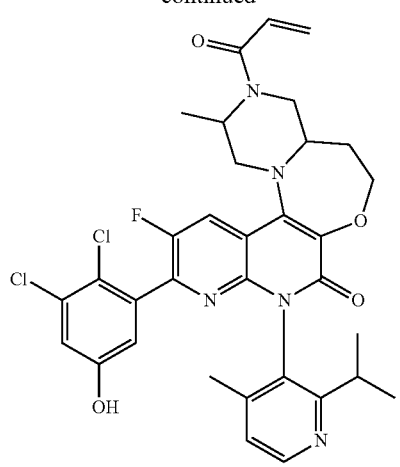
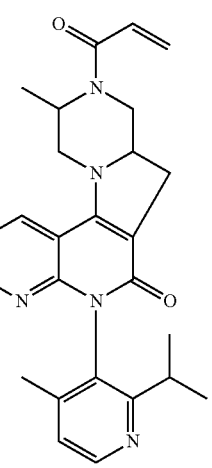
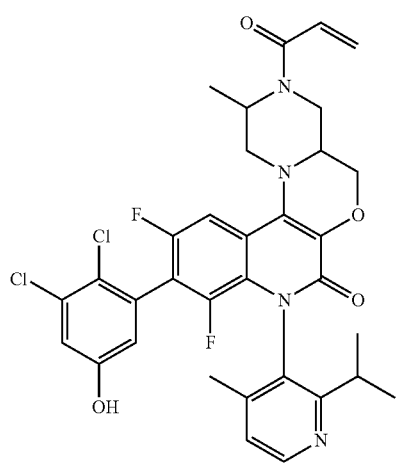

233
-continued
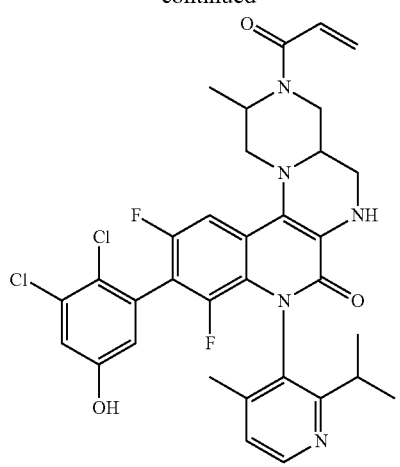
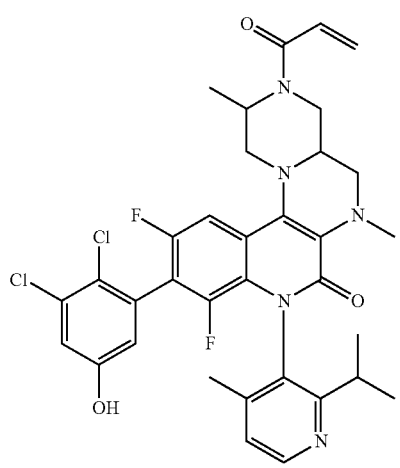
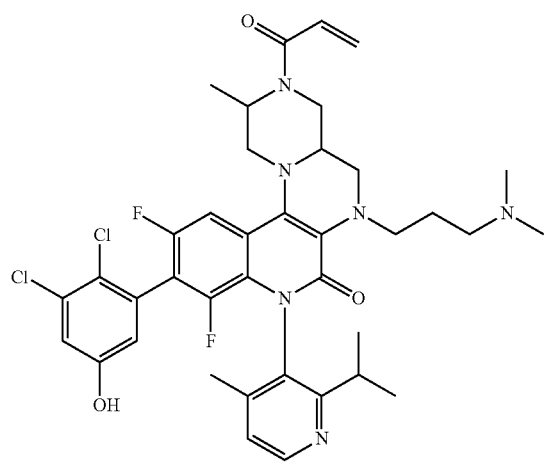
234
-continued
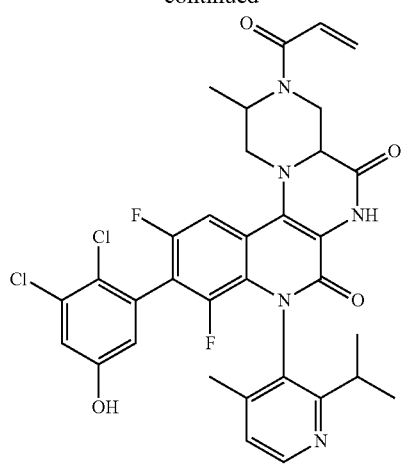
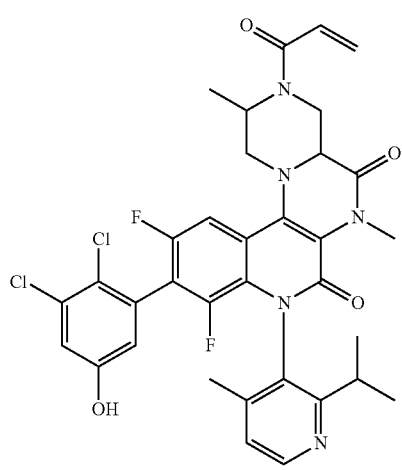
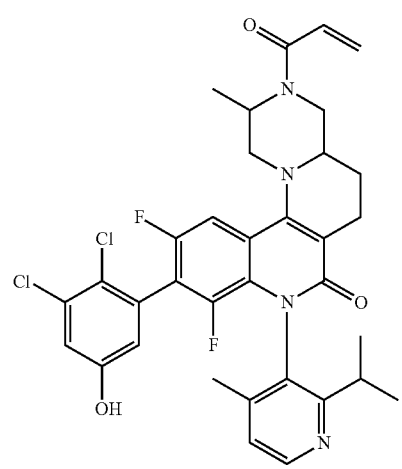

| 235 -continued | 236 -continued |
|---|---|
| 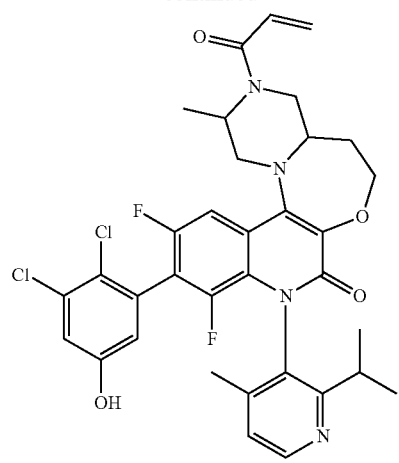 | 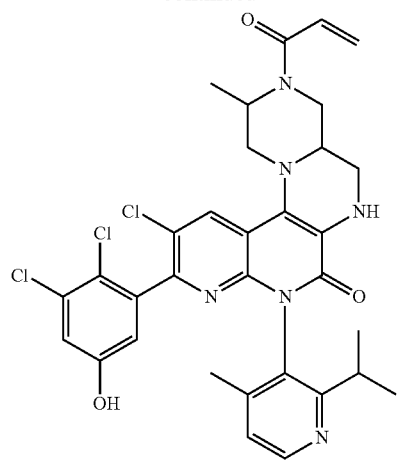 |
| 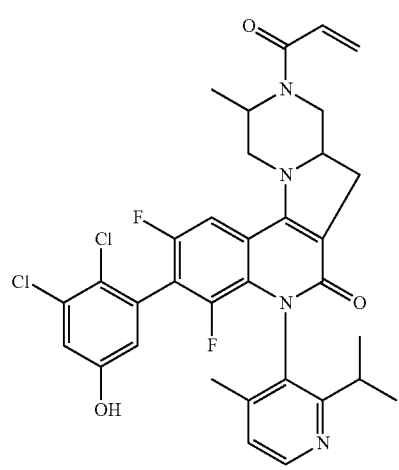 | 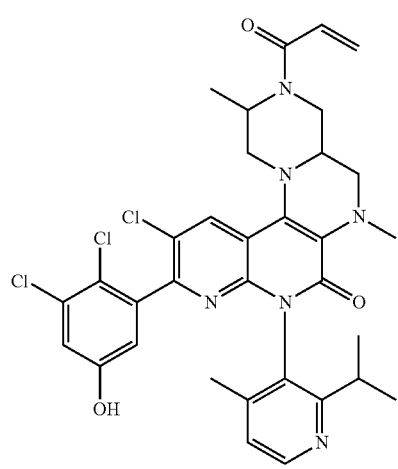 |
| 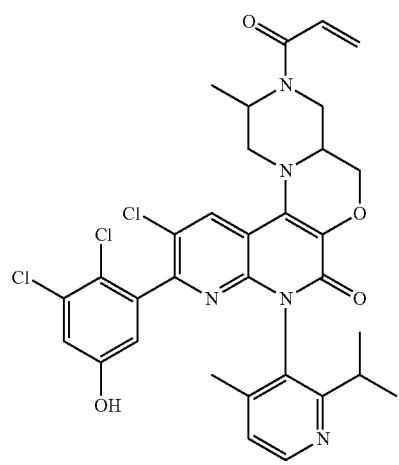 | 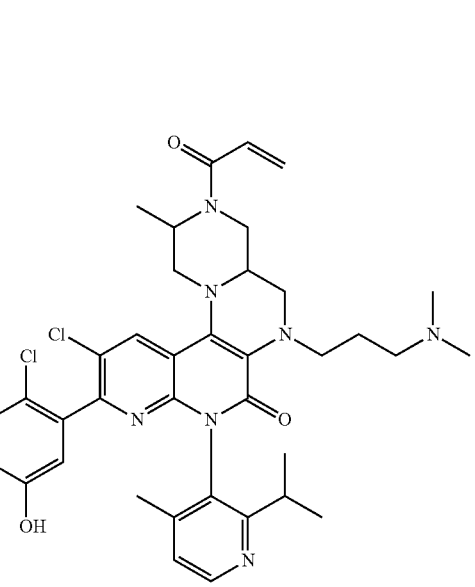 |

237
-continued
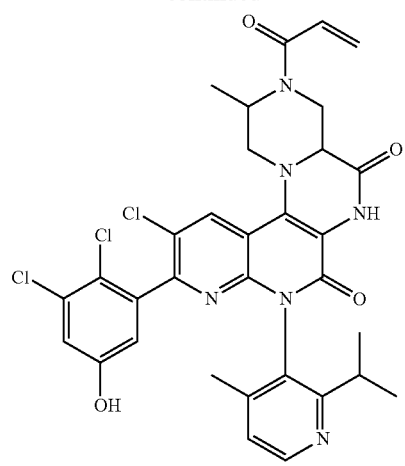
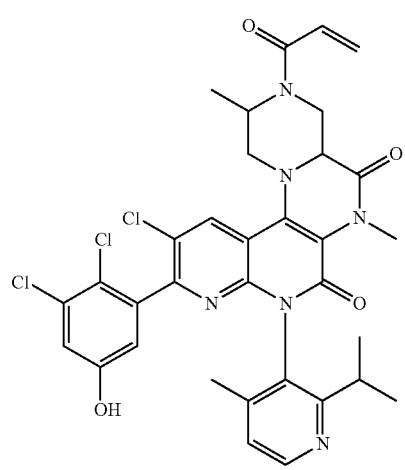
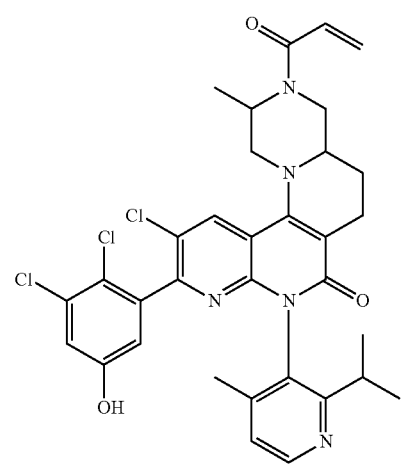
238
-continued
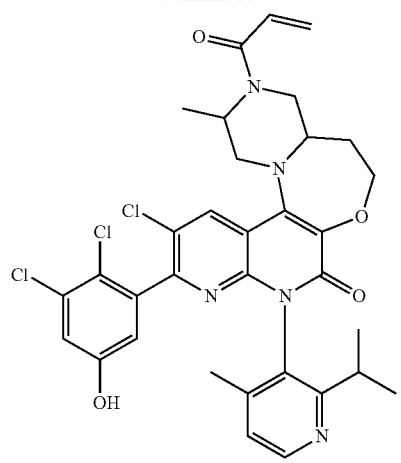
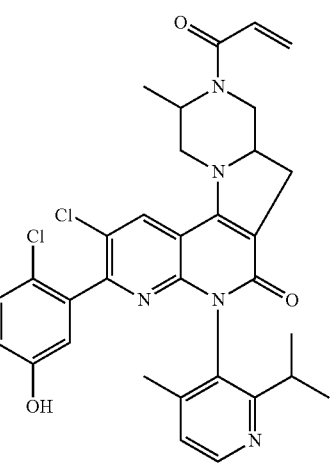
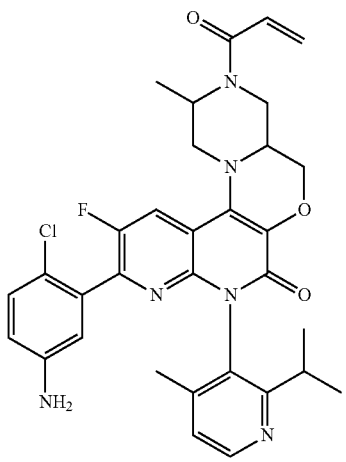

239
-continued
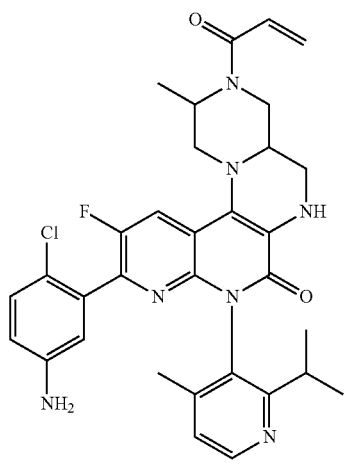
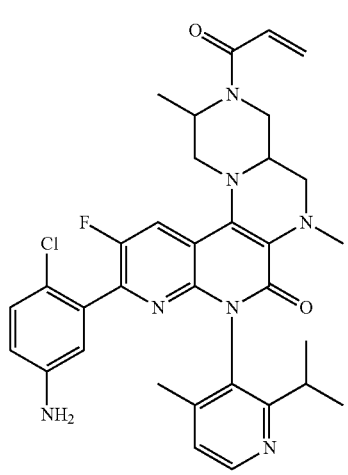
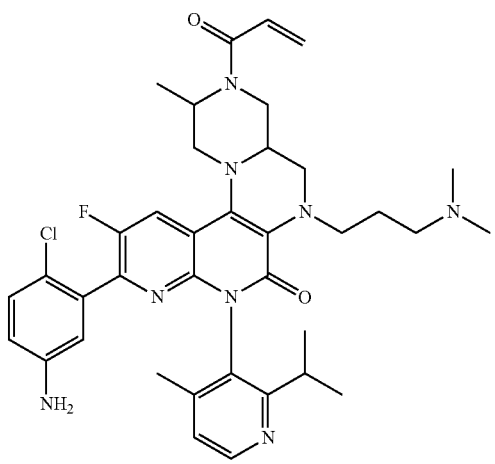
240
-continued
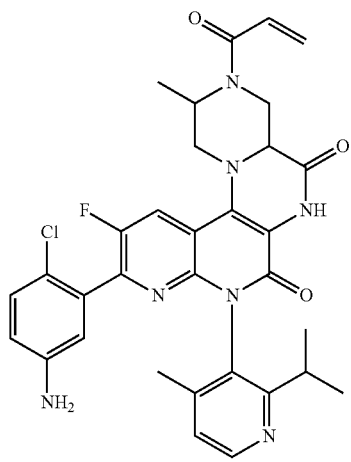
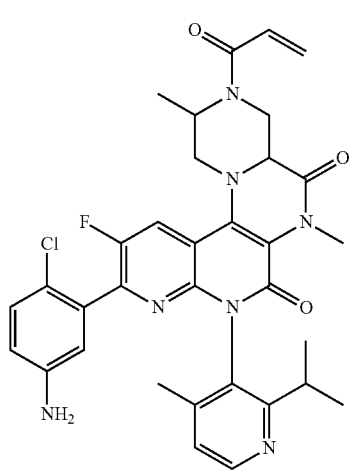
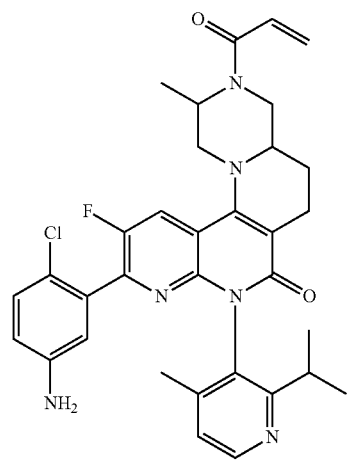

241
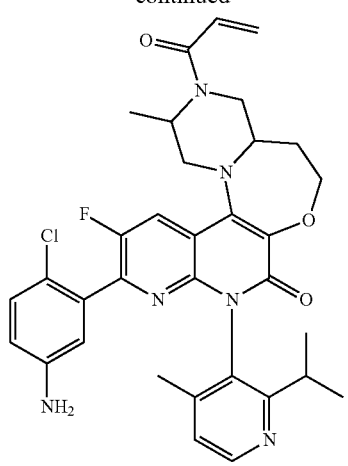
242
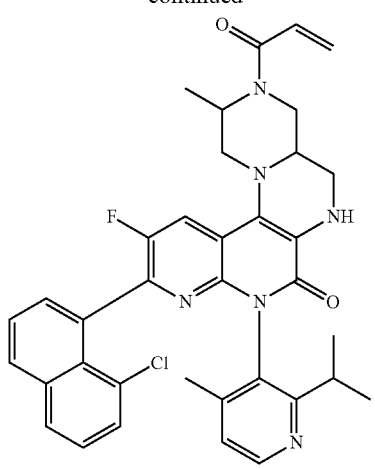
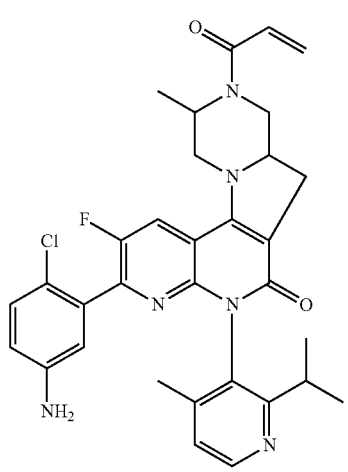
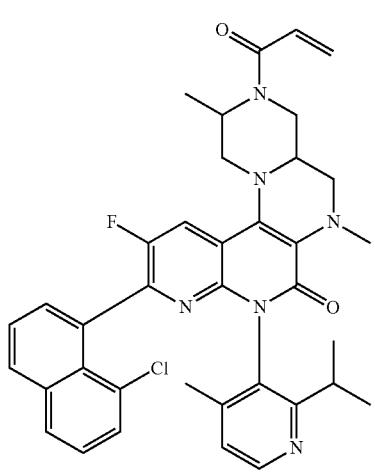
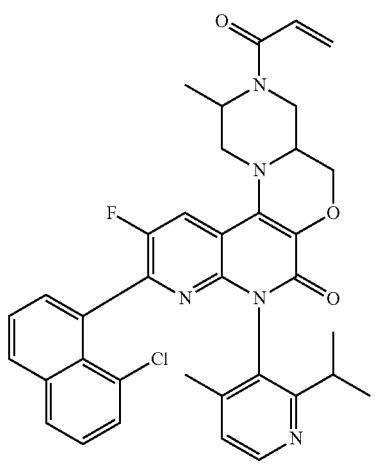
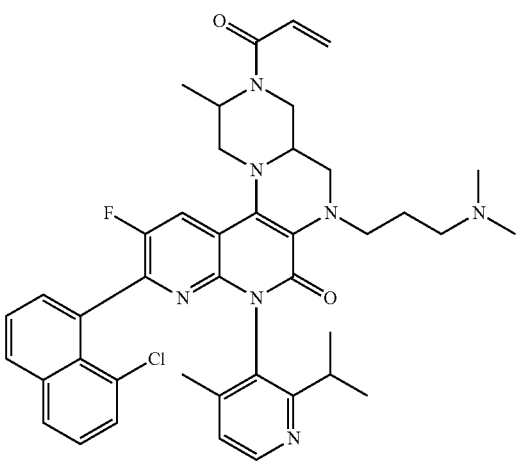

243
-continued
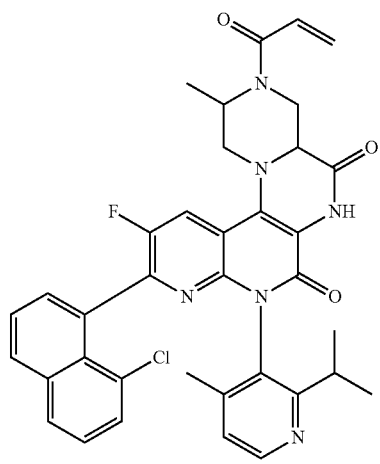
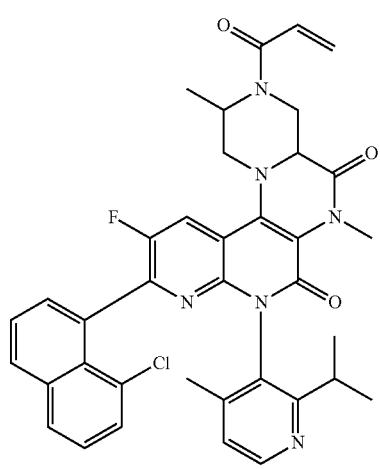
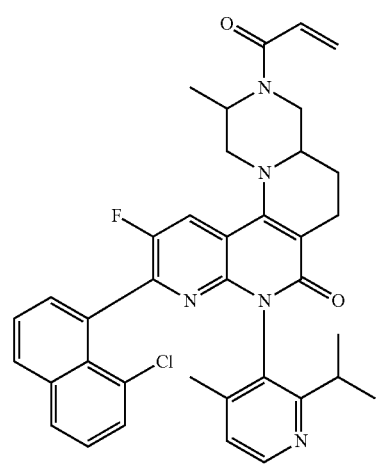
244
-continued
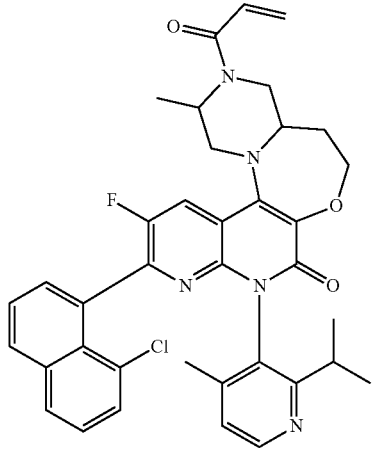
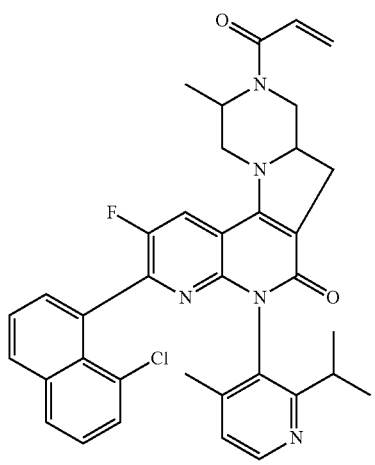
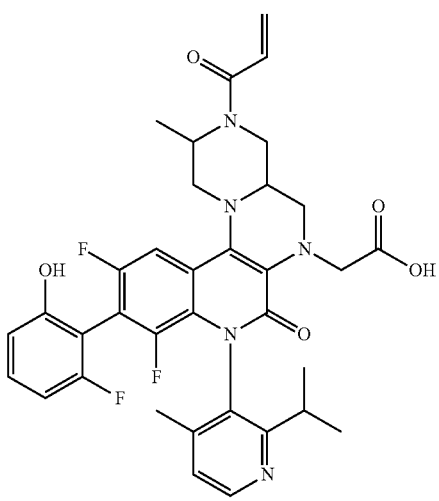

245
-continued
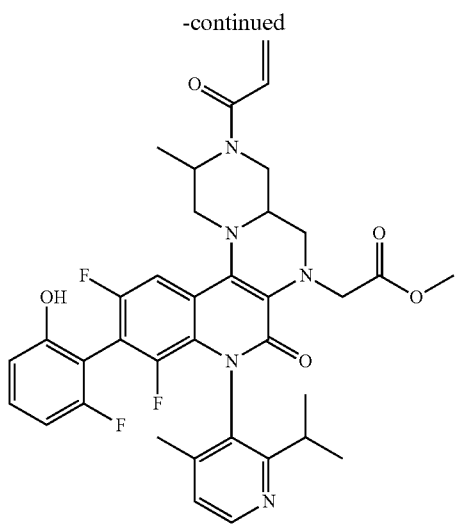
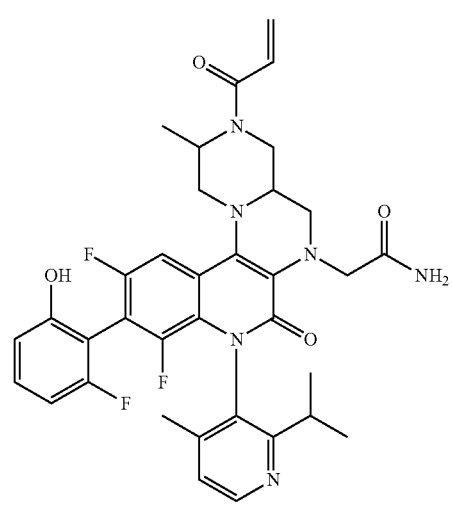
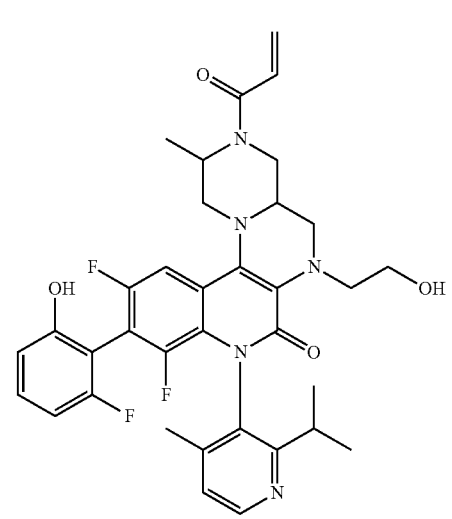
246
-continued
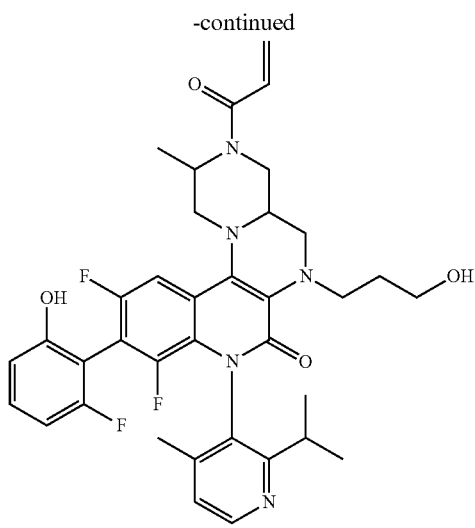
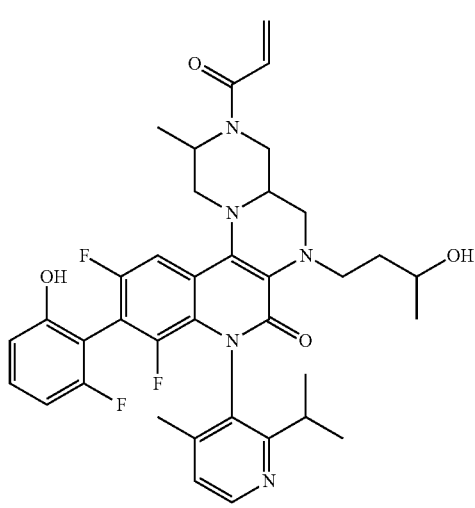
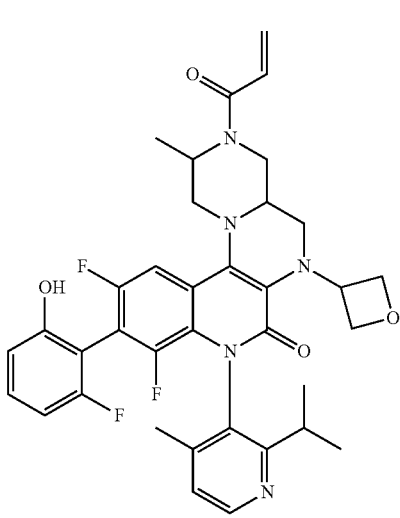

247
-continued
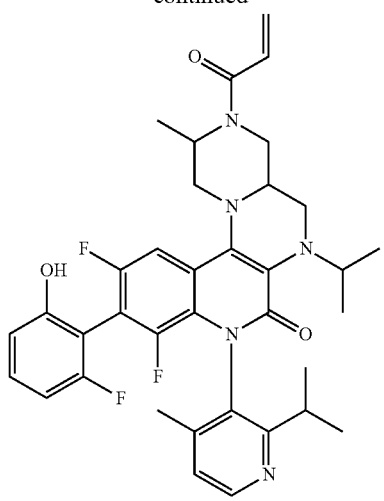
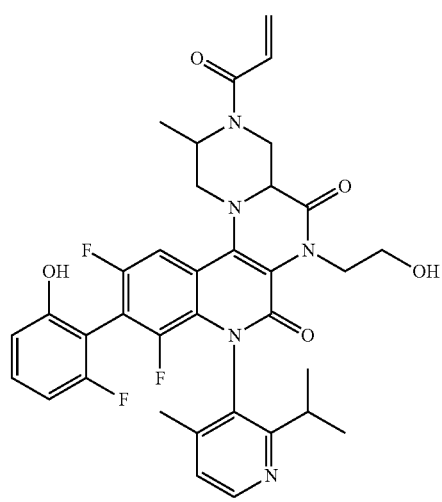
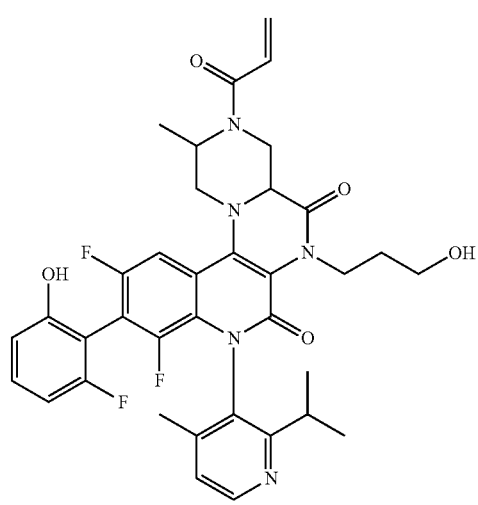
248
-continued
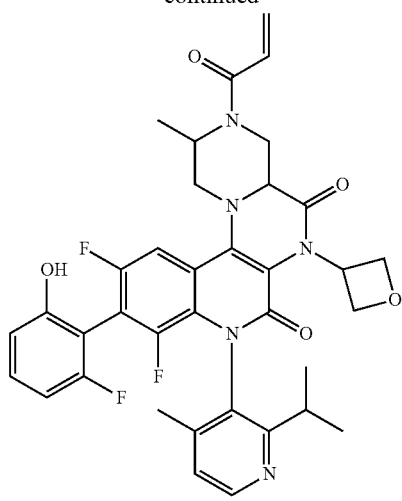
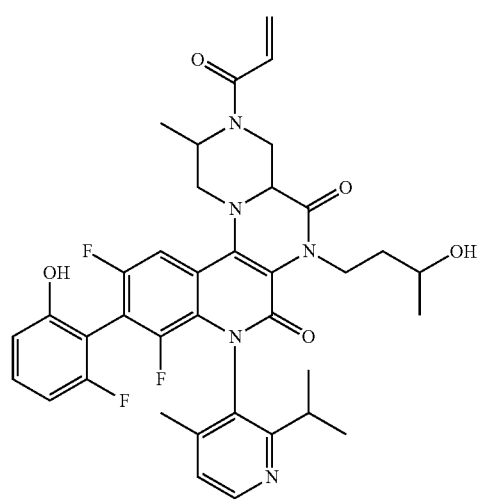
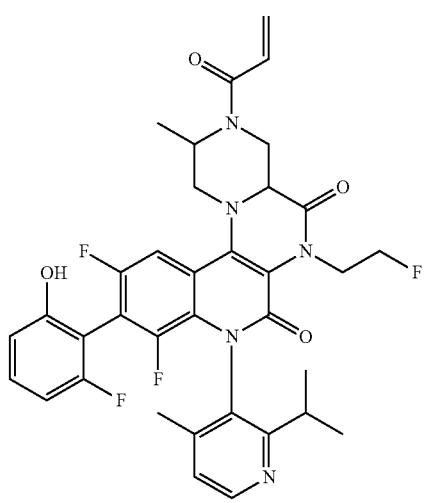

249
-continued
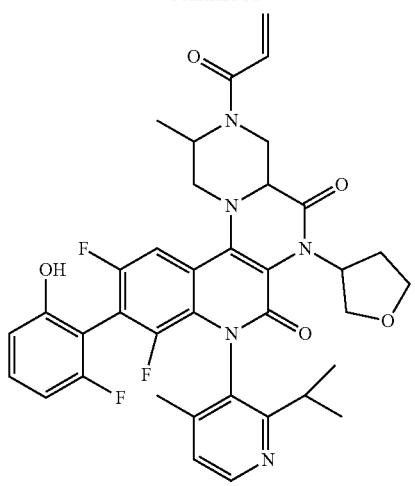
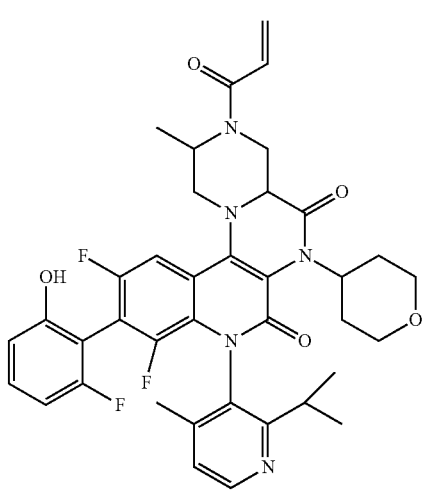
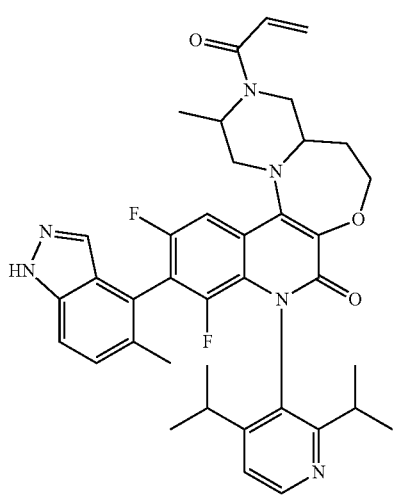
250
-continued
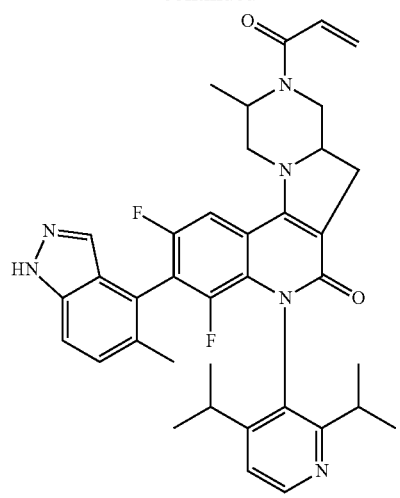
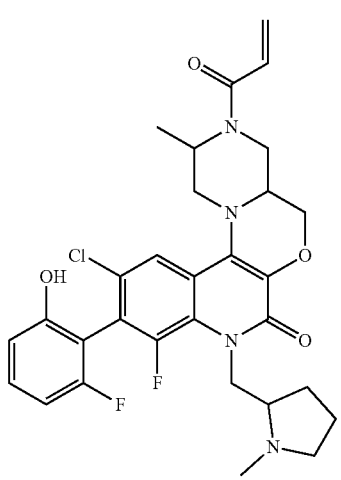
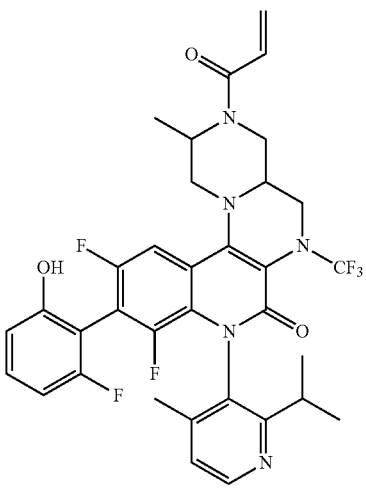

251
-continued
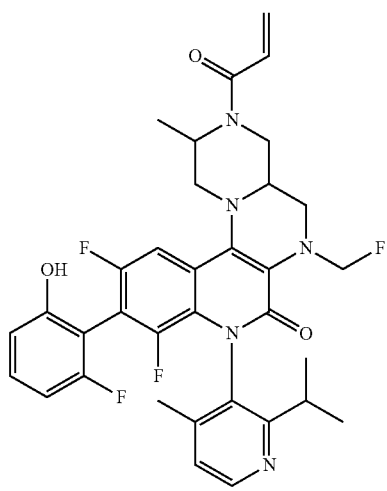
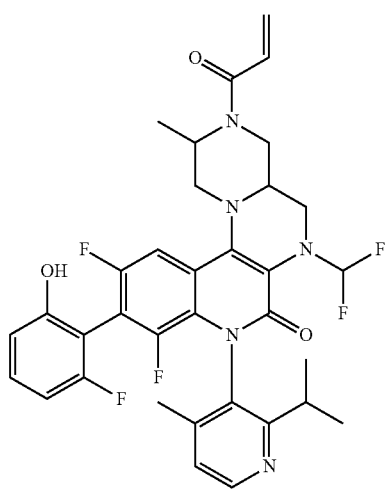
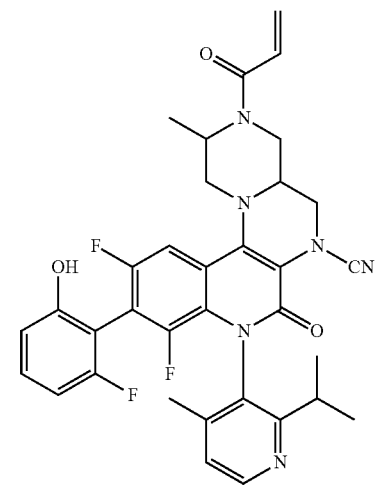
252
-continued
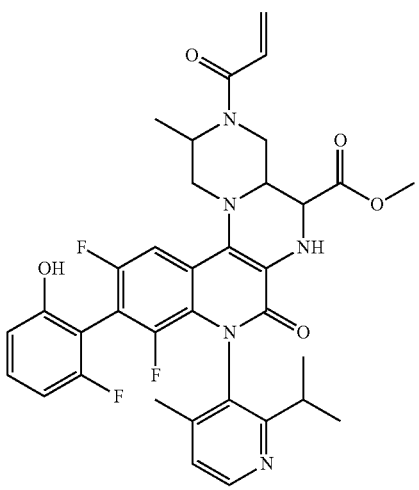
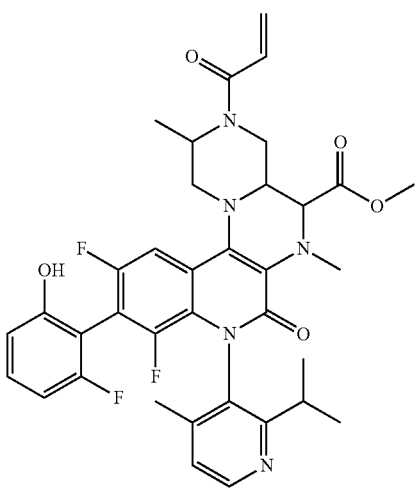
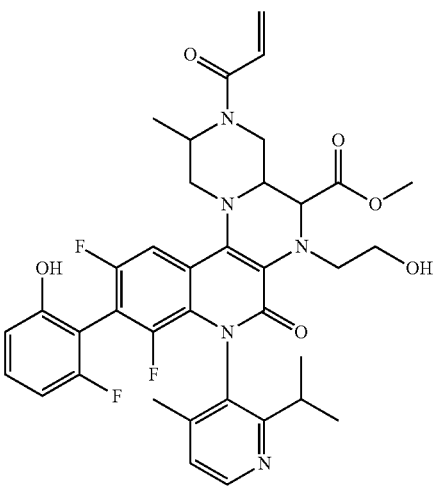

253
-continued
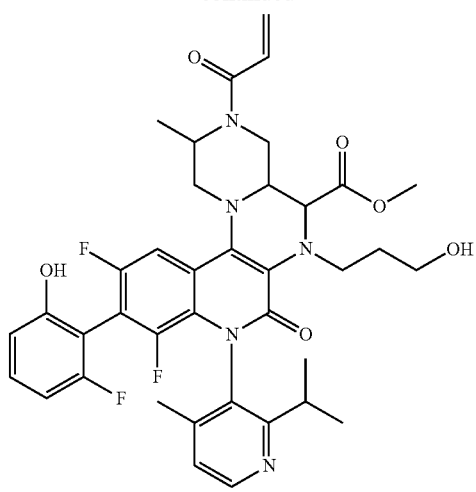
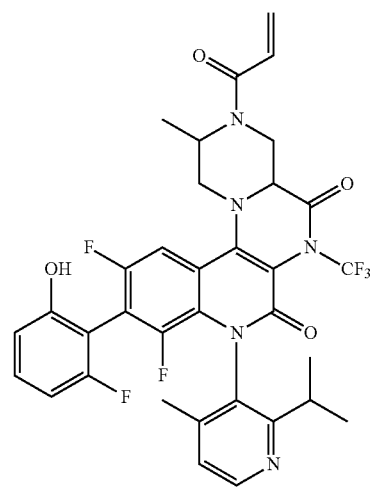
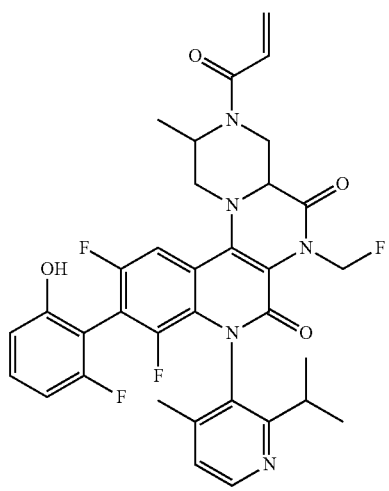
254
-continued
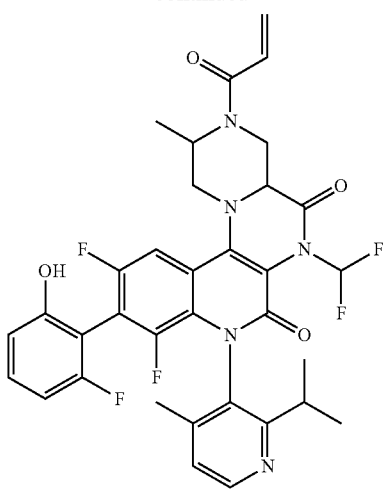
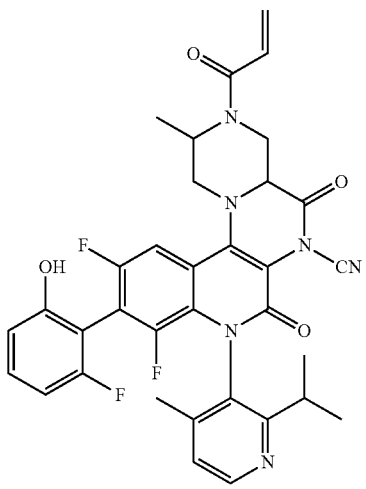
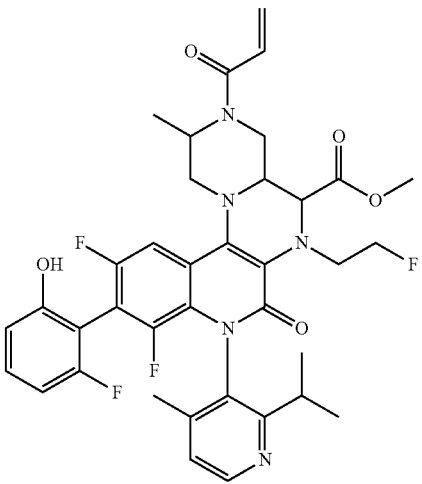

255
-continued
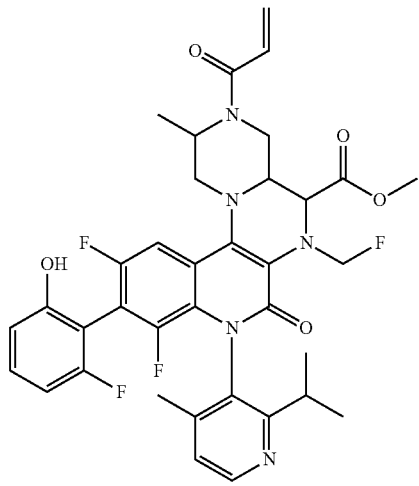
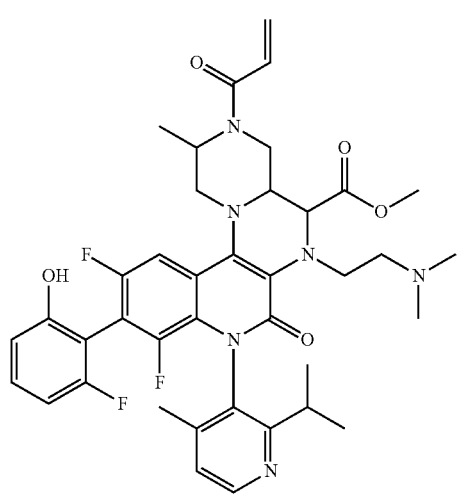
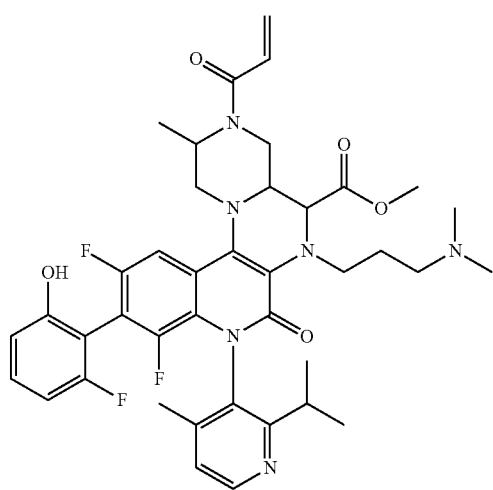
256
-continued
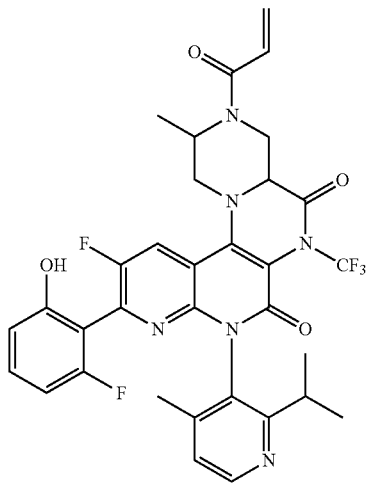
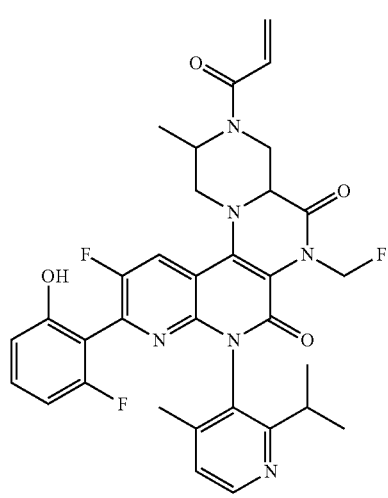
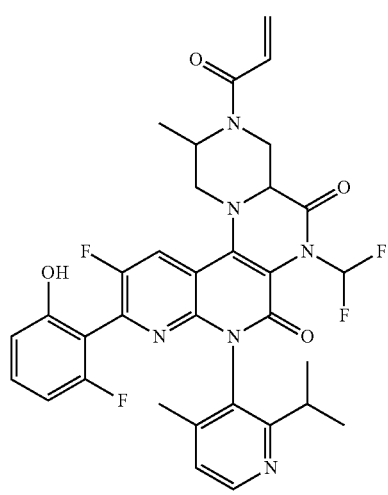

257
-continued
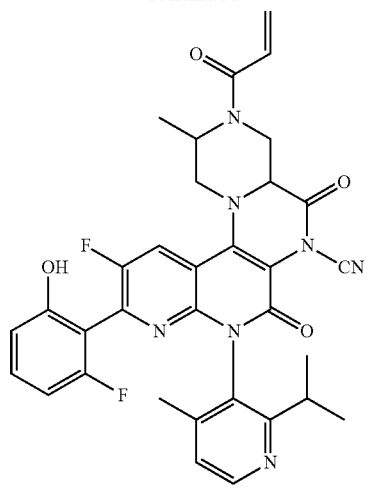
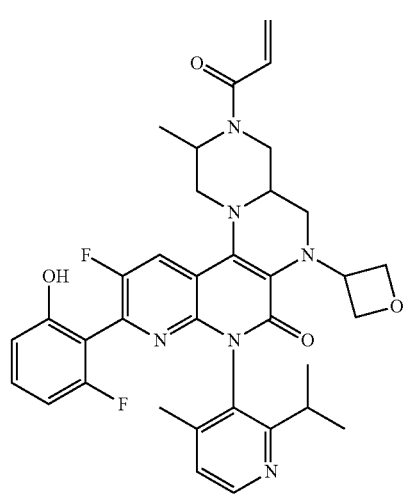
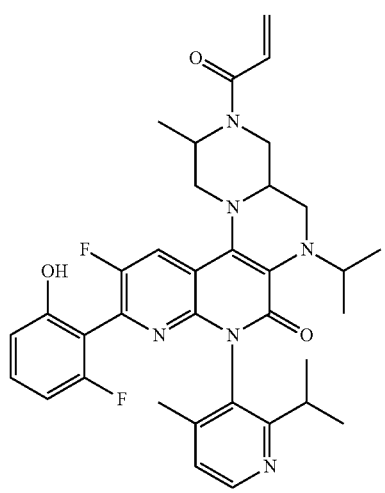
258
-continued
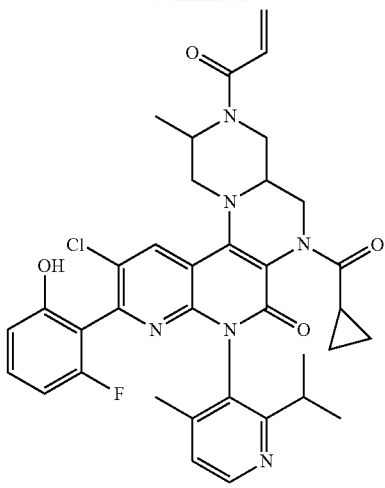
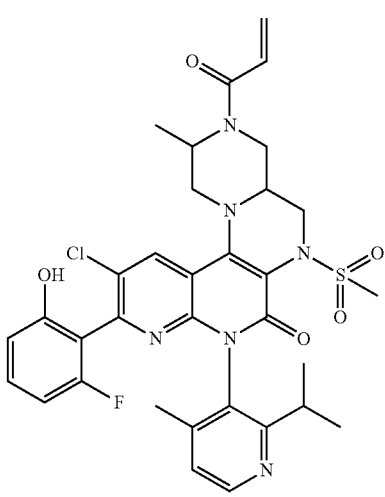
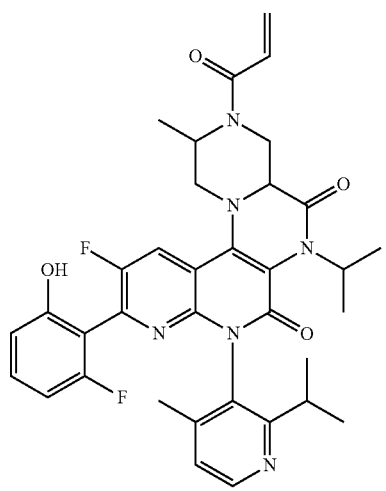

259
-continued
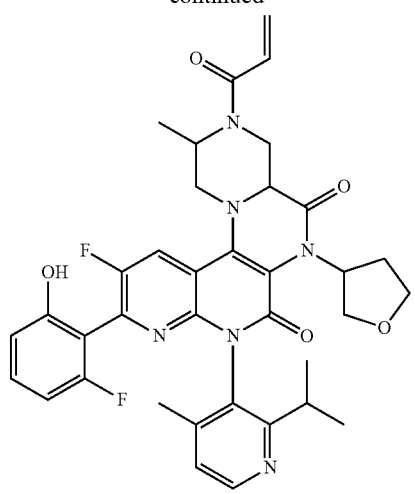
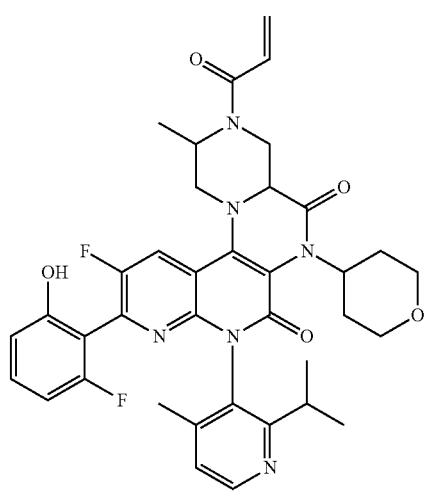
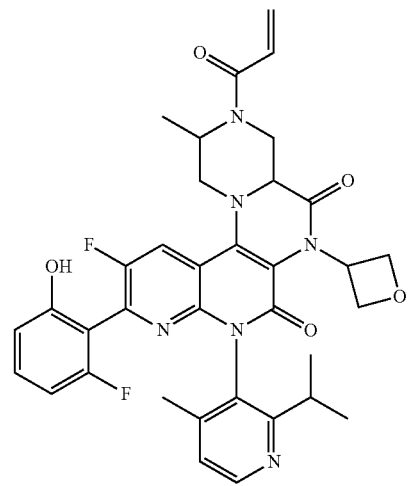
260
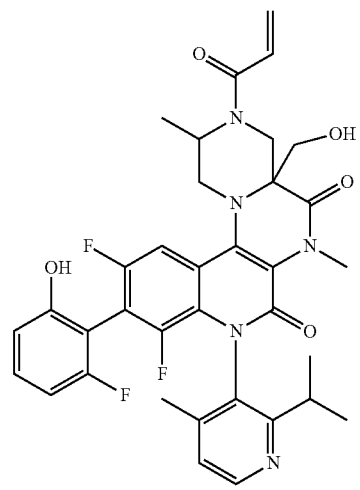
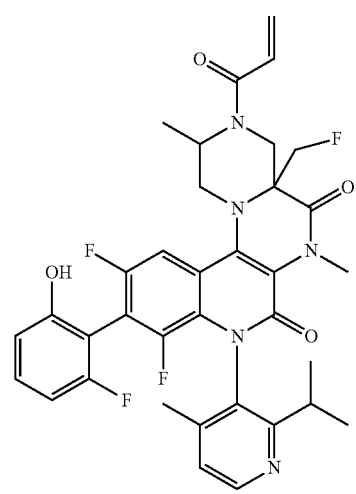
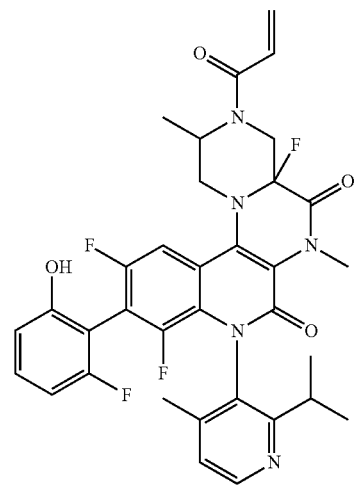

261
-continued
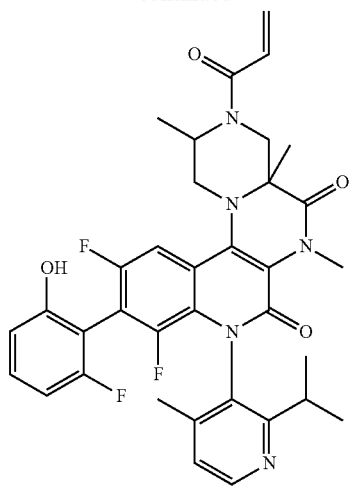
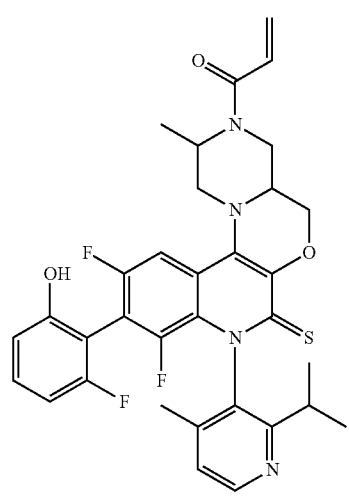
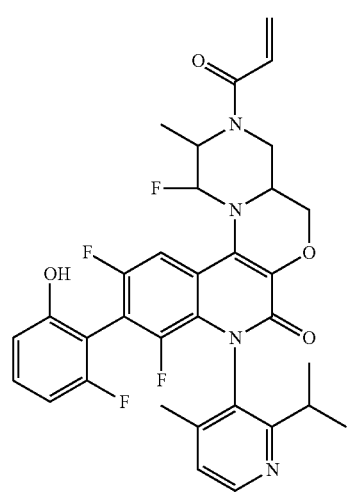
262
-continued
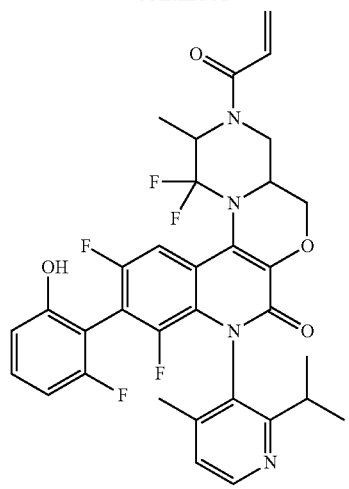
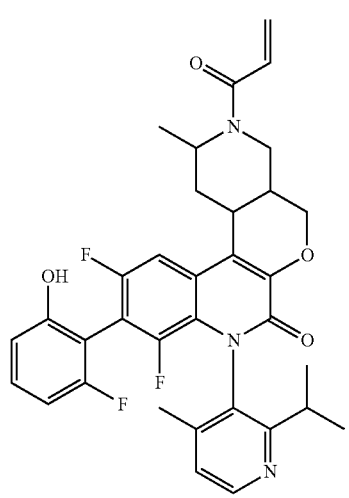

263
-continued
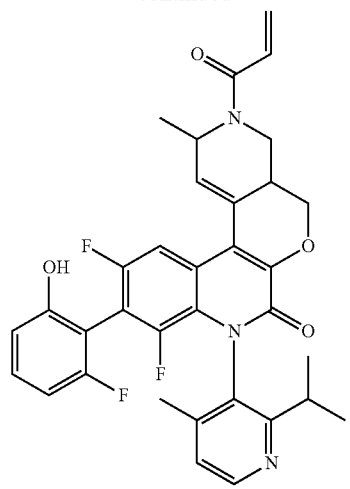
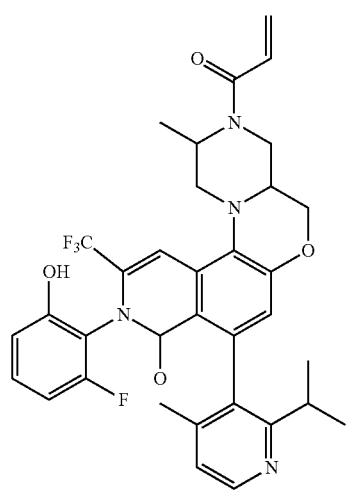
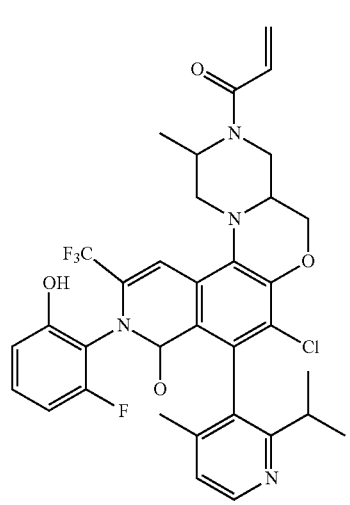
264
-continued
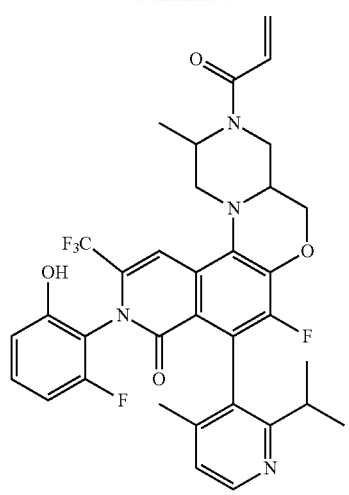
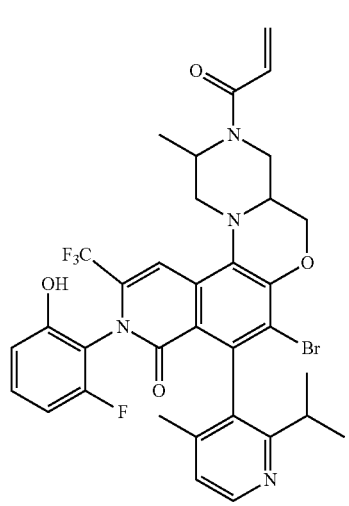
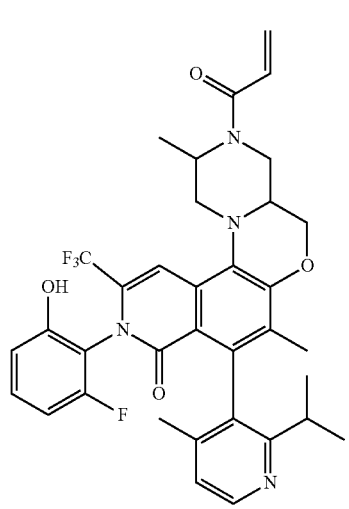

265
-continued
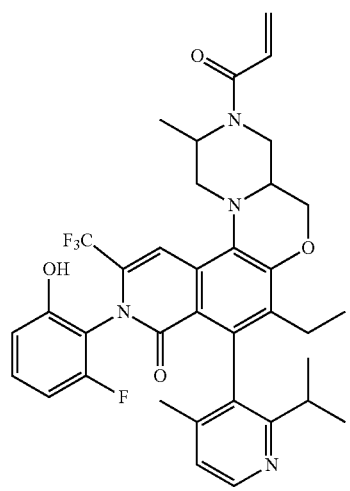
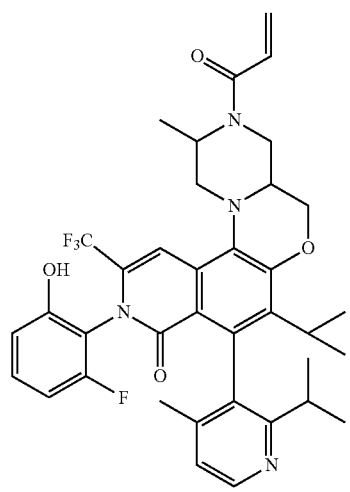
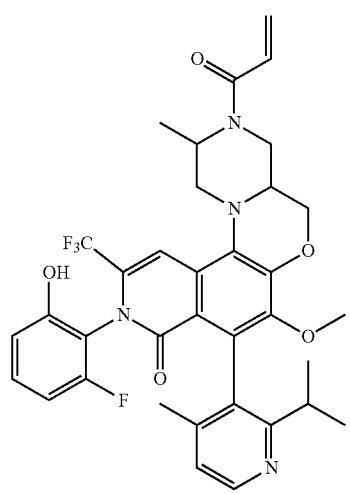
266
-continued
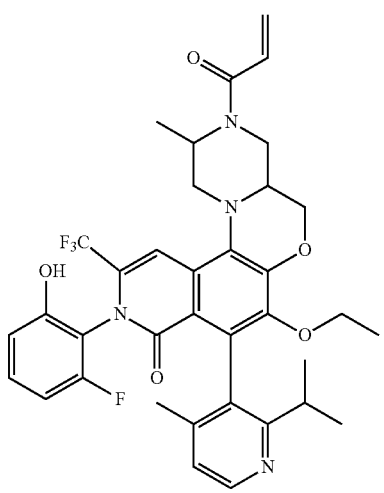
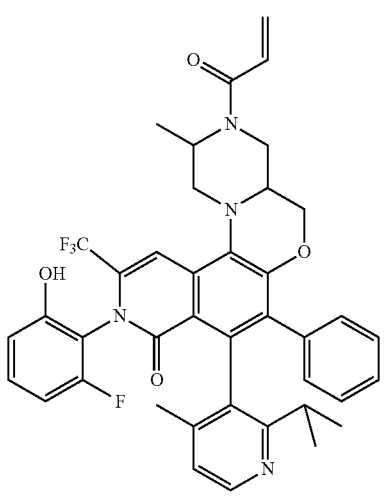
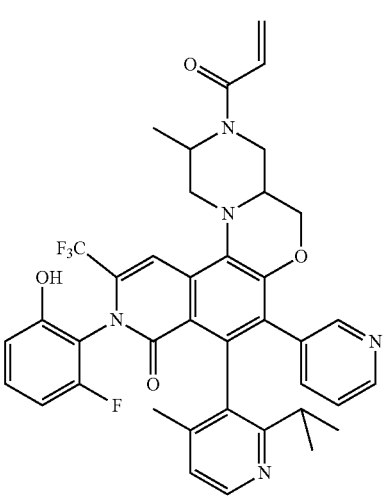

267
-continued
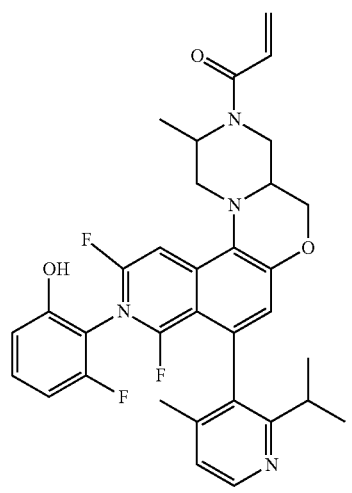
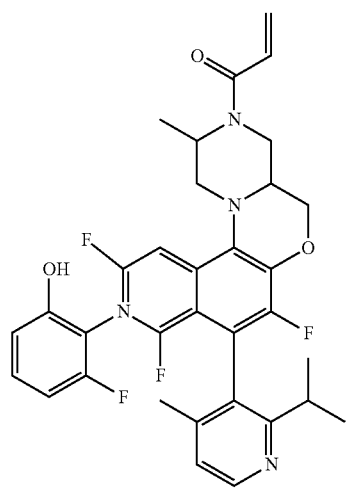
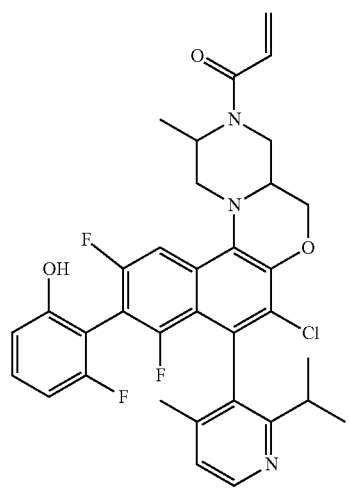
268
-continued
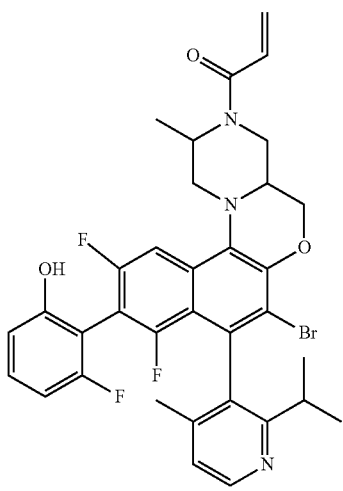
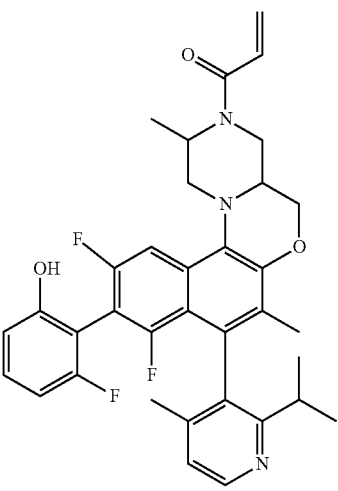
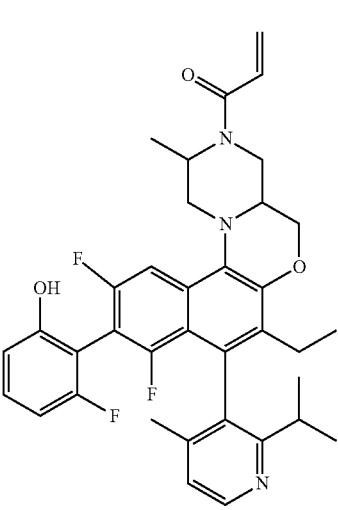

269
-continued
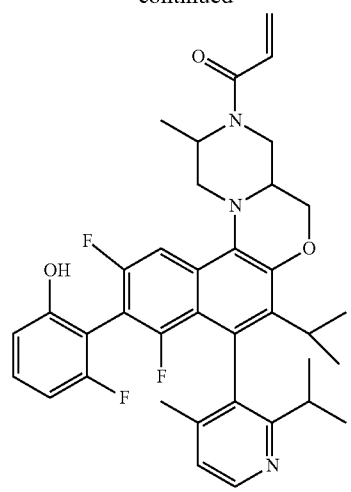
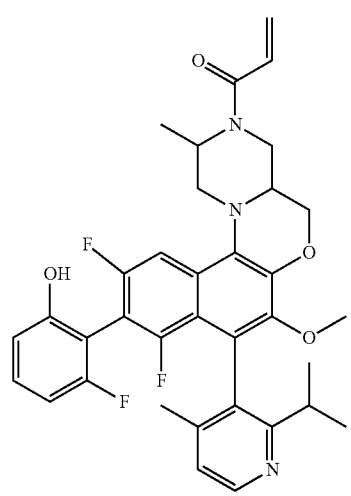
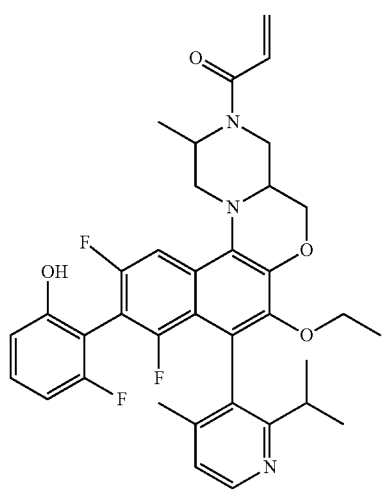
270
-continued
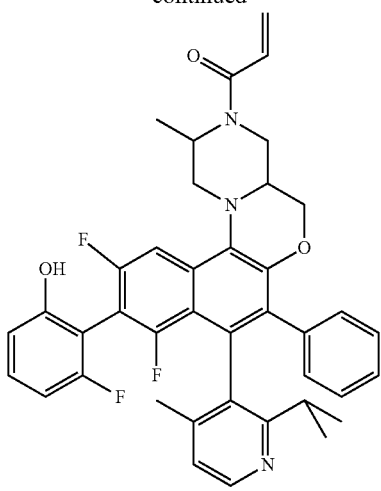
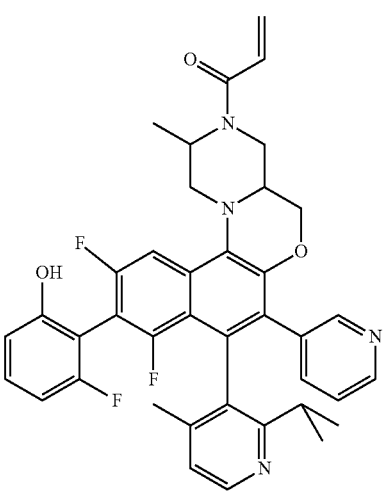
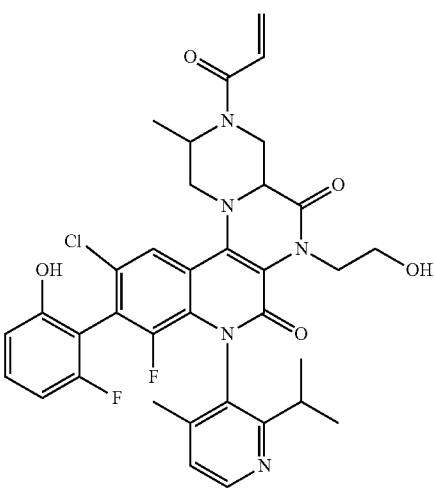

271
-continued
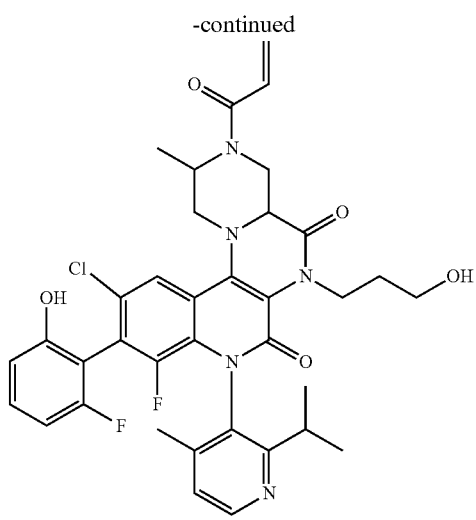
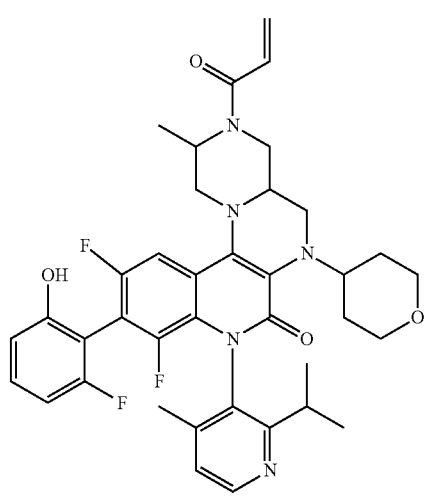
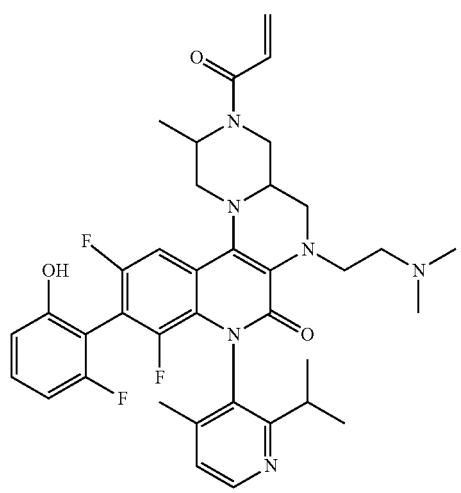
272
-continued
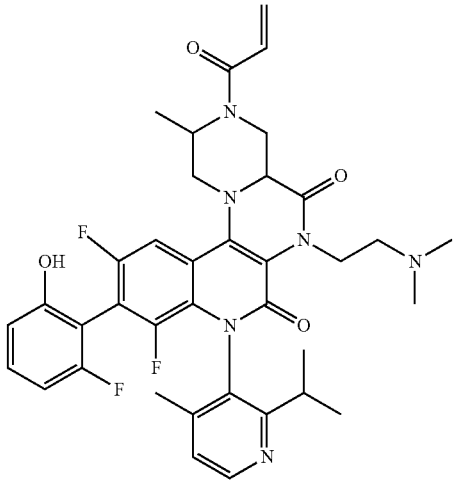
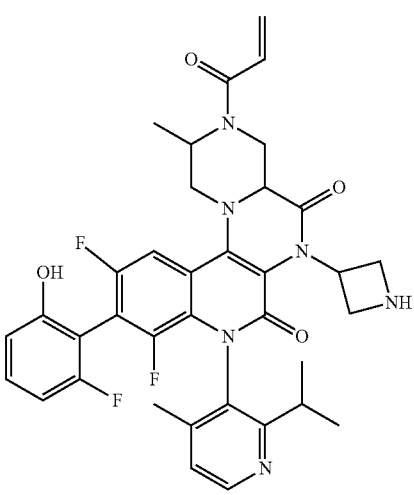
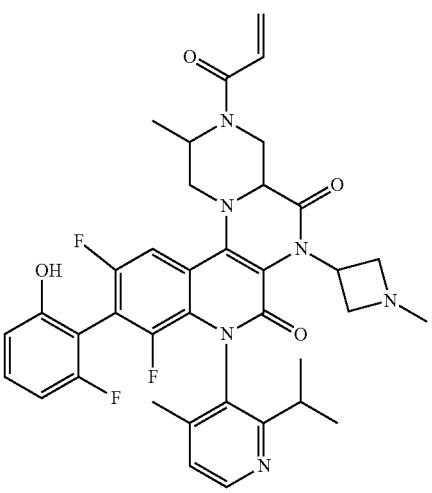

273
-continued
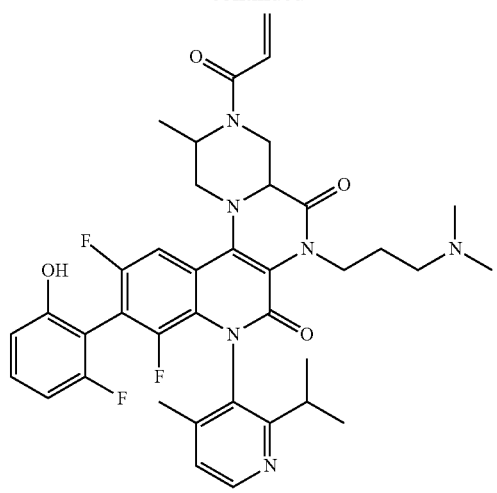
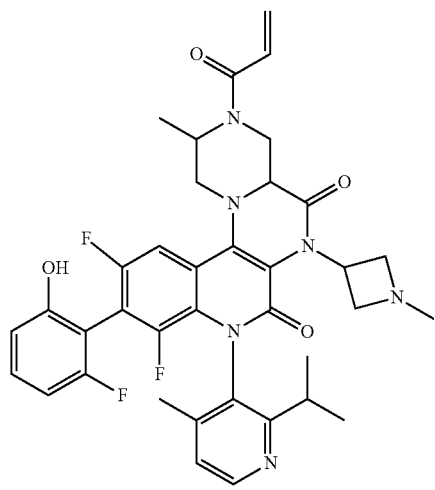
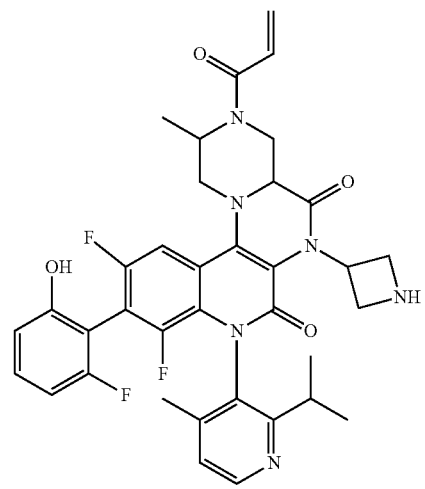
274
-continued
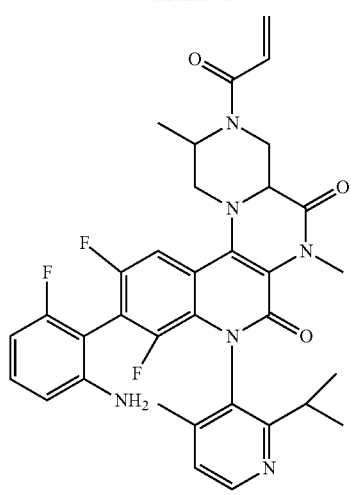
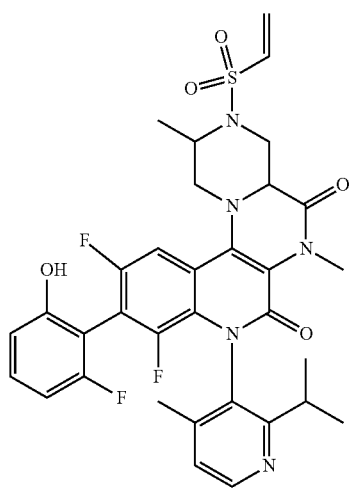
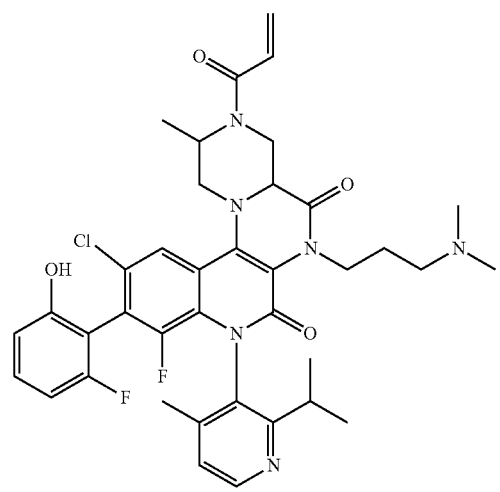

275
-continued
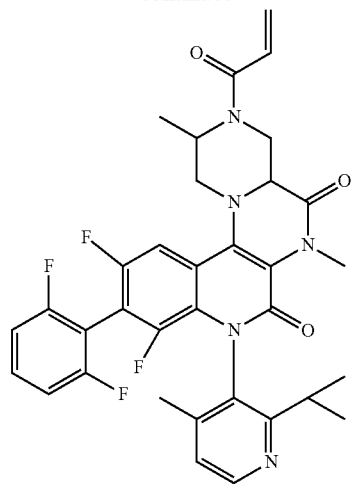
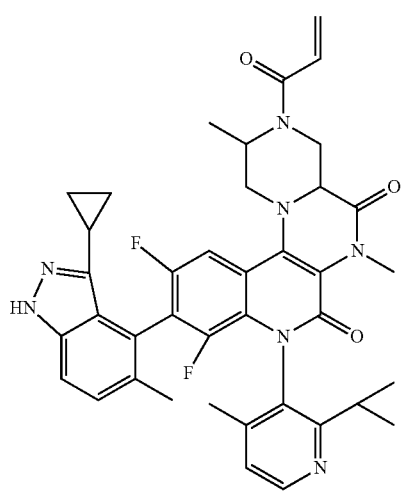
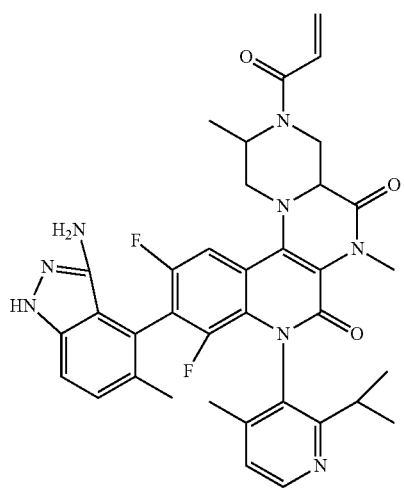
276
-continued
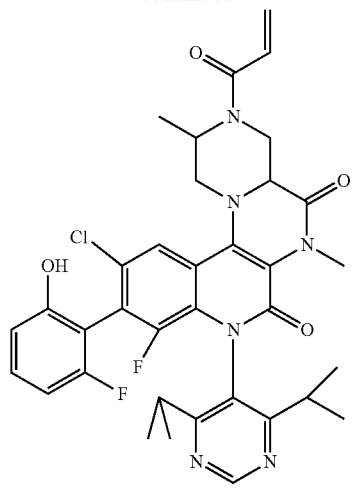
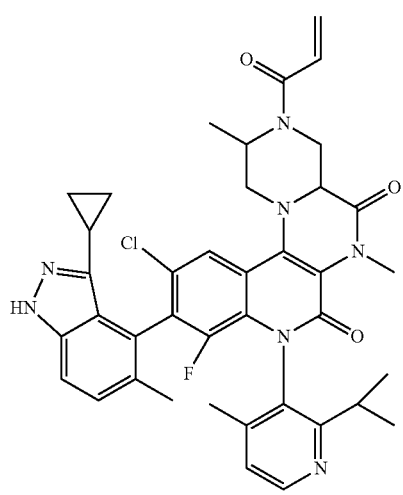
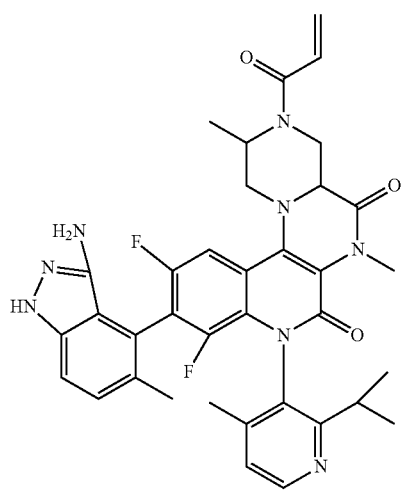

277
-continued
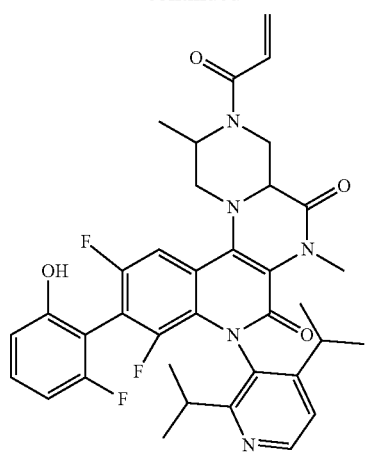
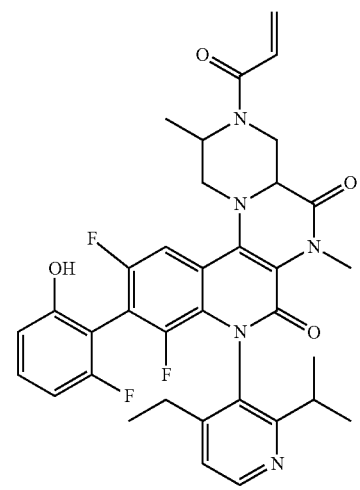
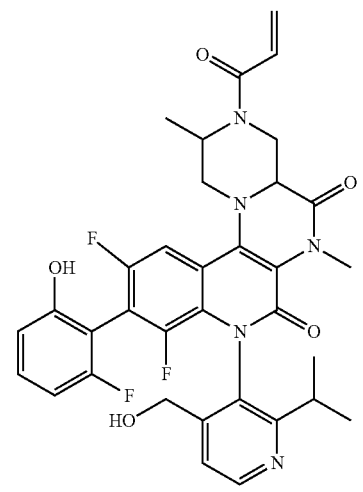
278
-continued
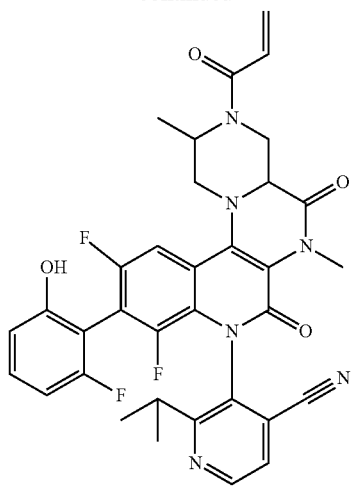
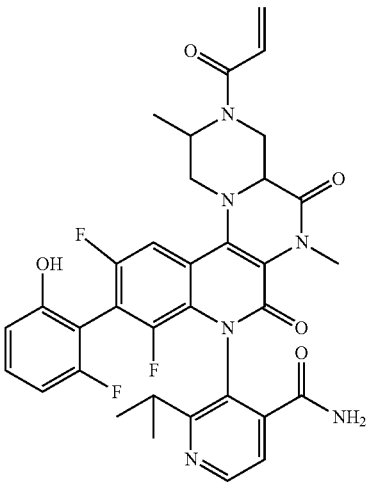
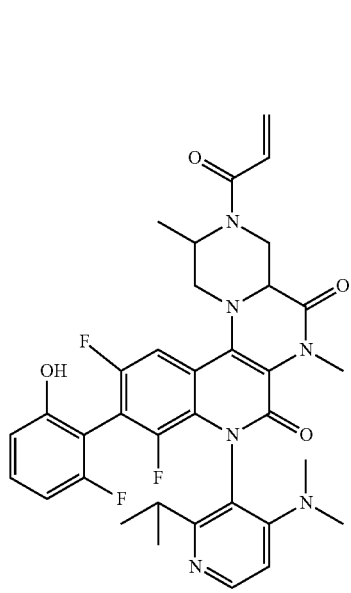

279
-continued
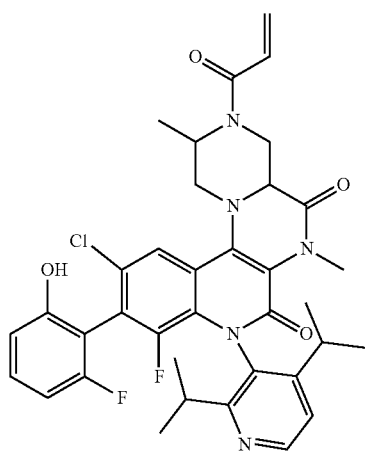
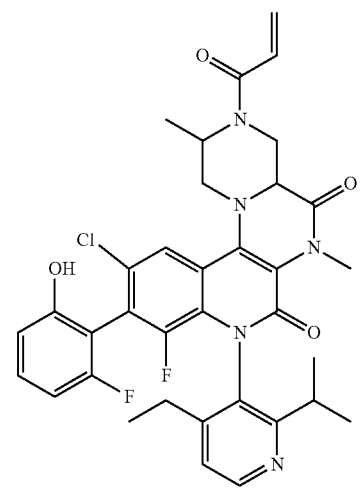
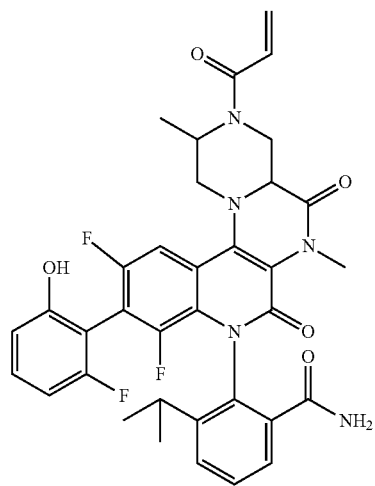
280
-continued
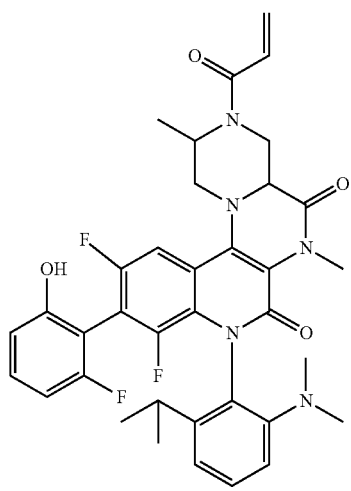
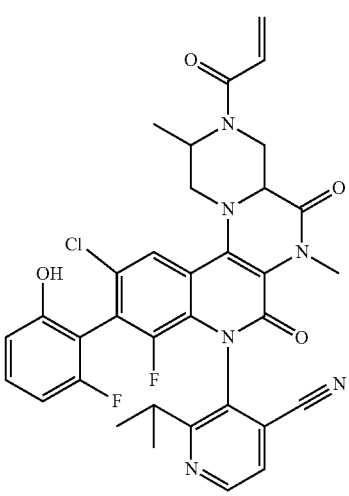
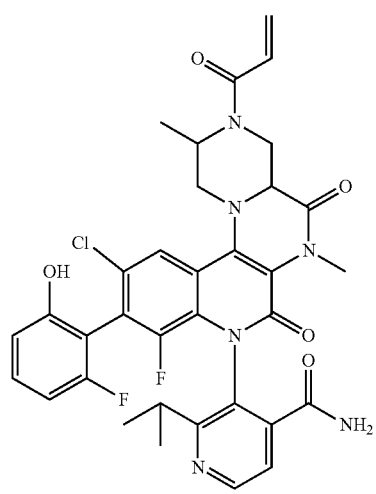

281
-continued
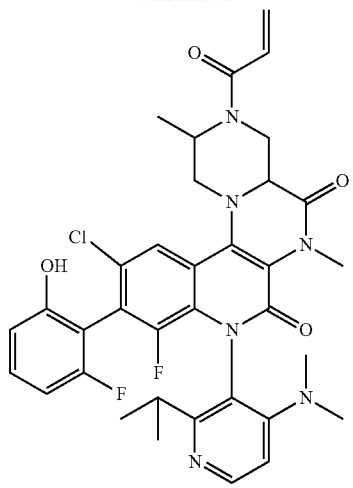
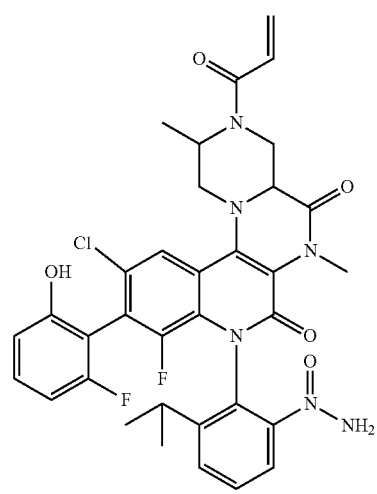
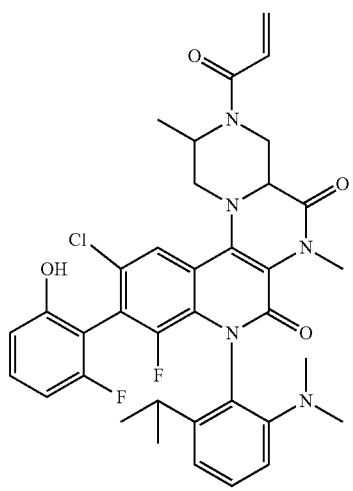
282
-continued
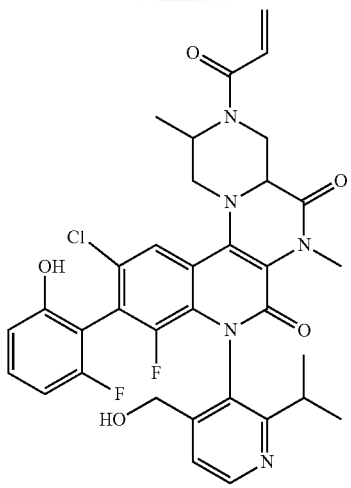
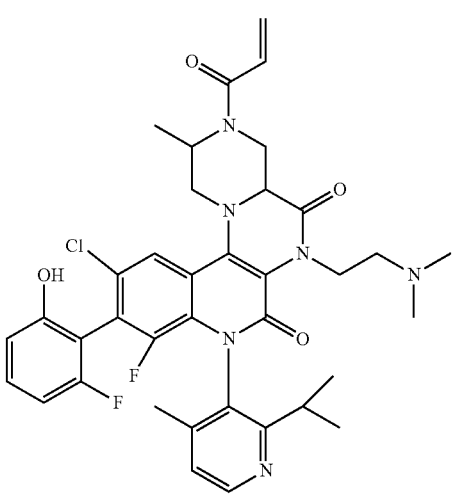
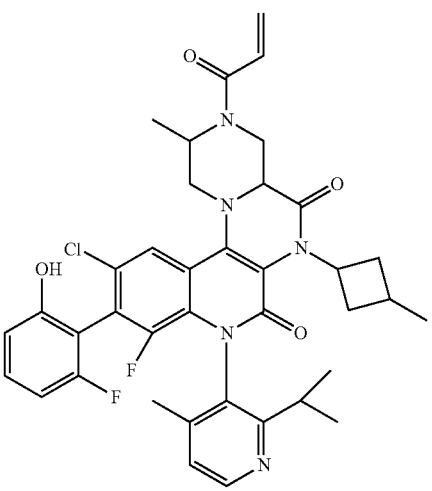

283
-continued
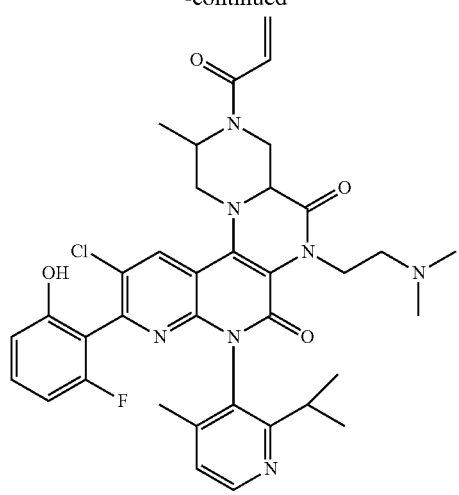
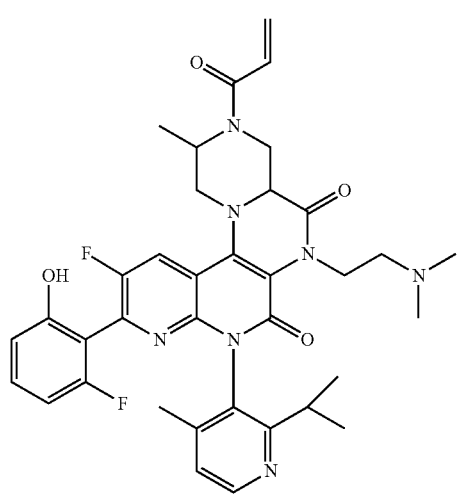
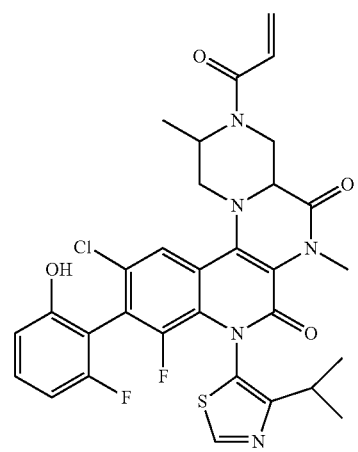
284
-continued
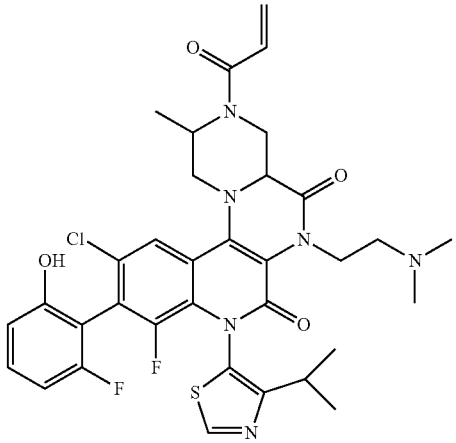
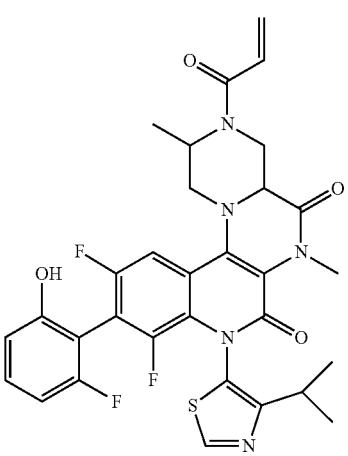
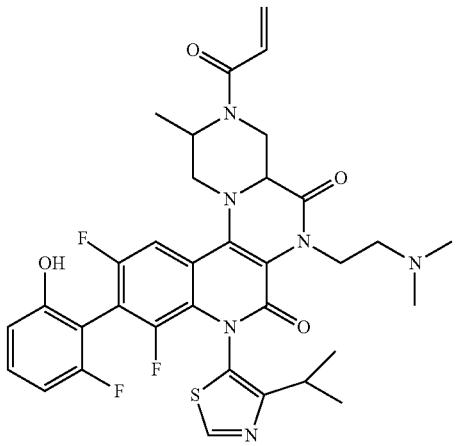

285
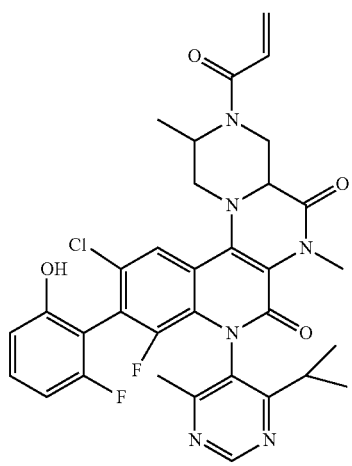
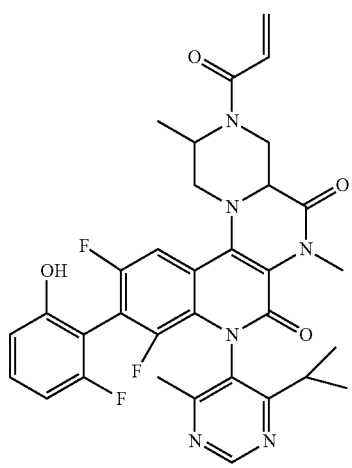
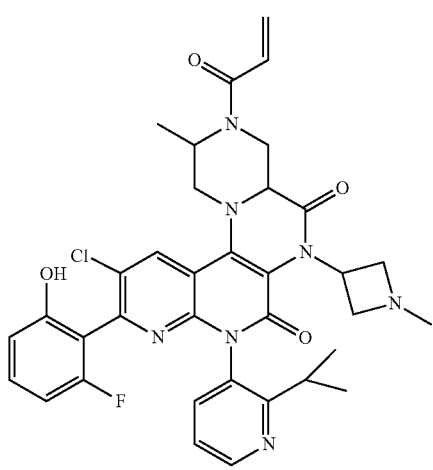
286
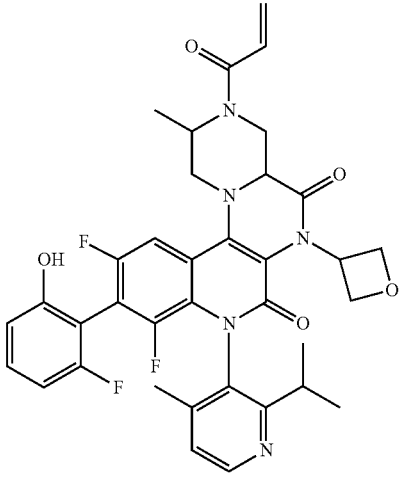
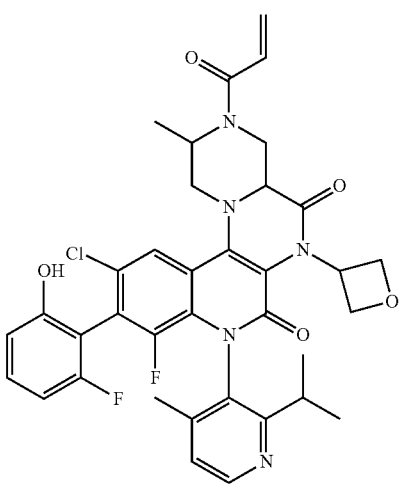
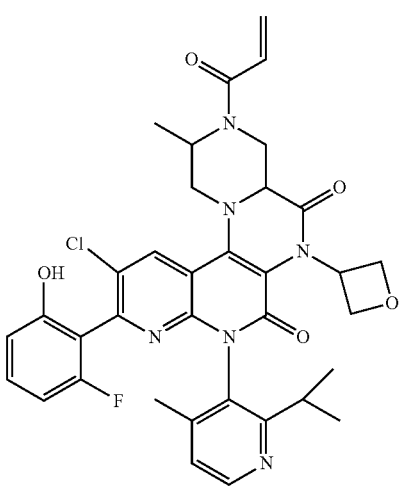

287
-continued
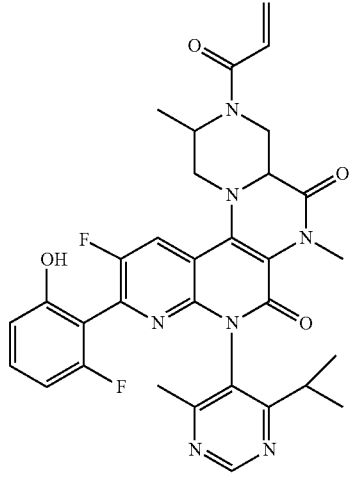
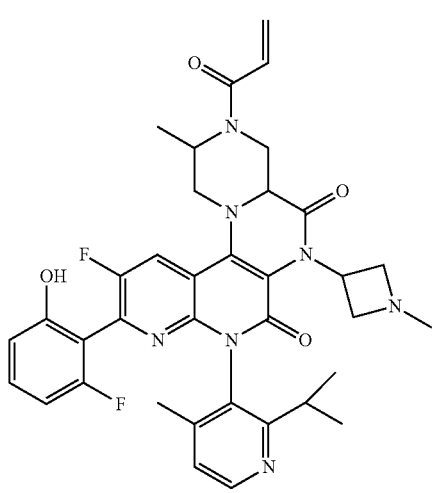
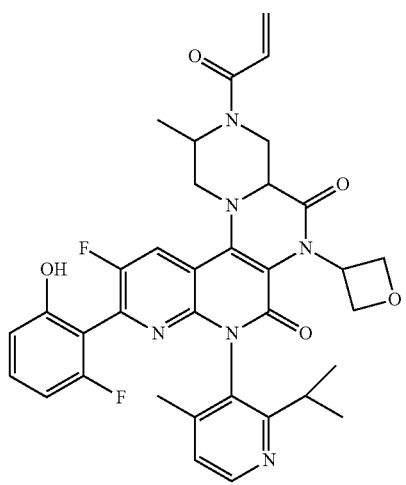
288
-continued
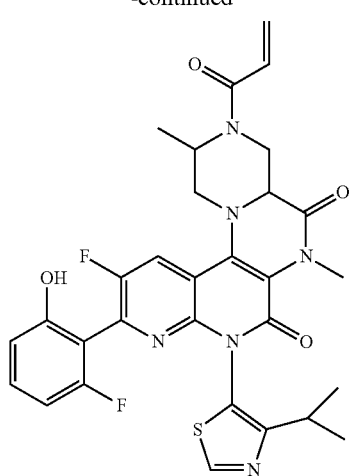
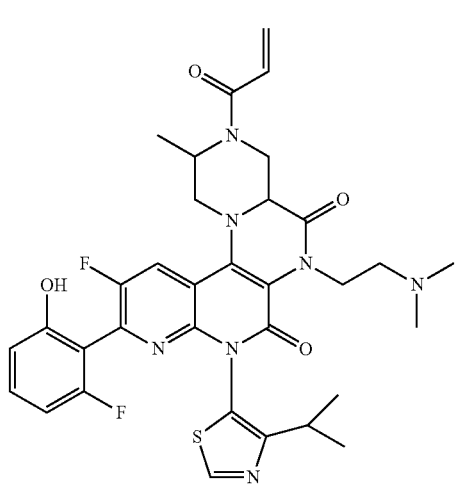
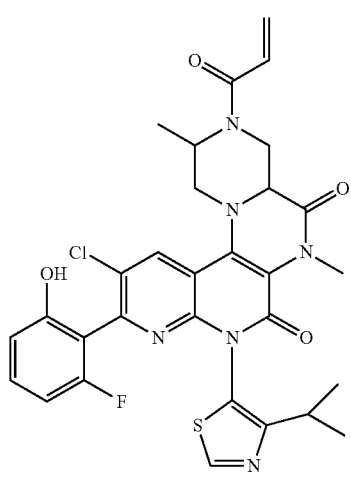

289
-continued
290
-continued
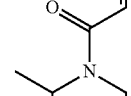
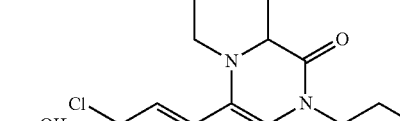
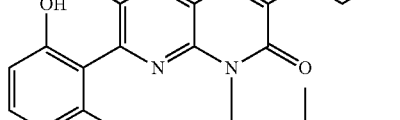
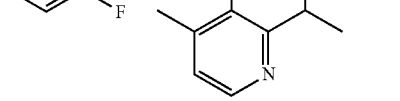

291
-continued
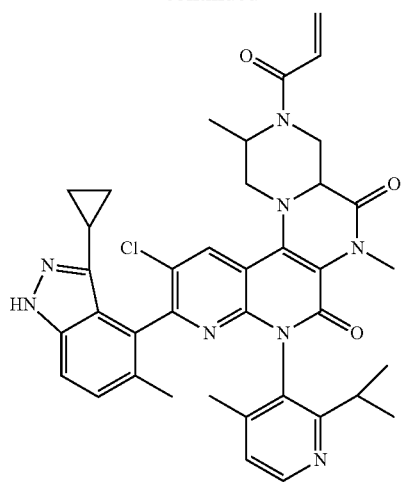
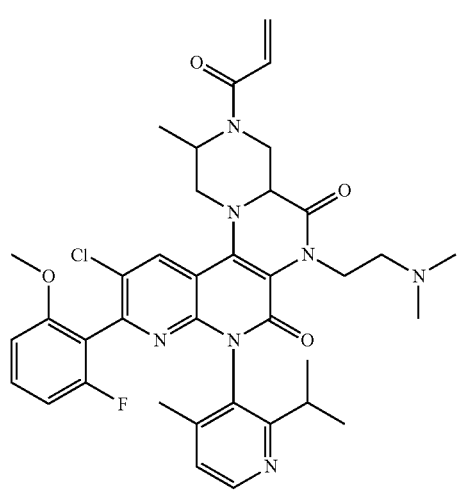
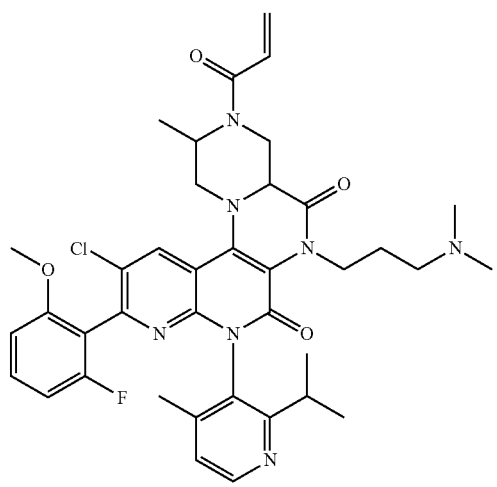
292
-continued
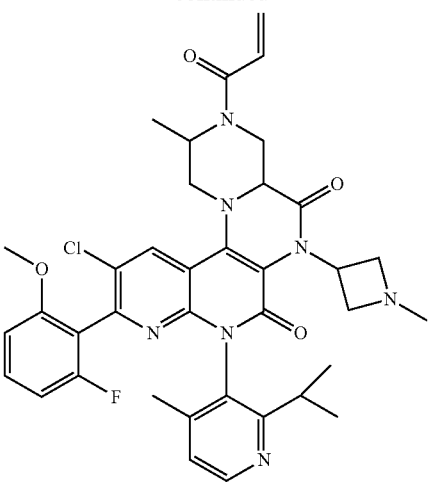
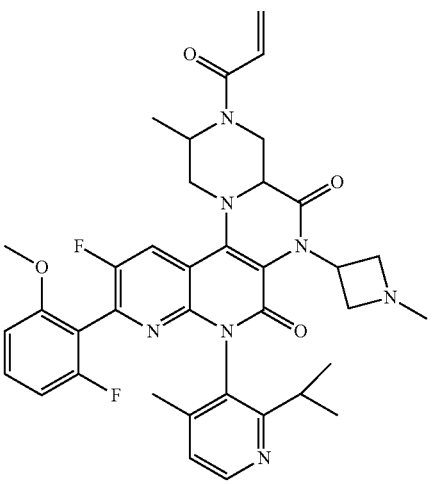
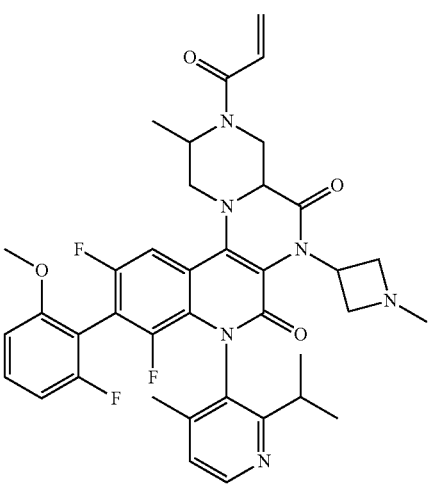

-continued
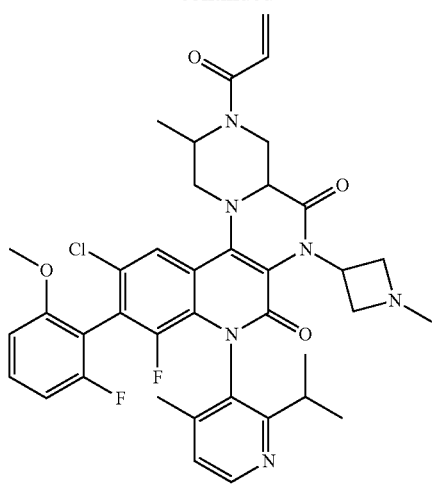
-continued
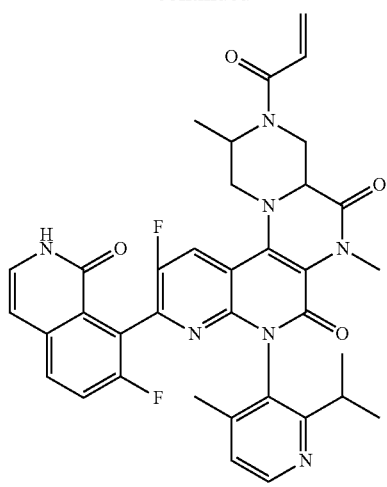
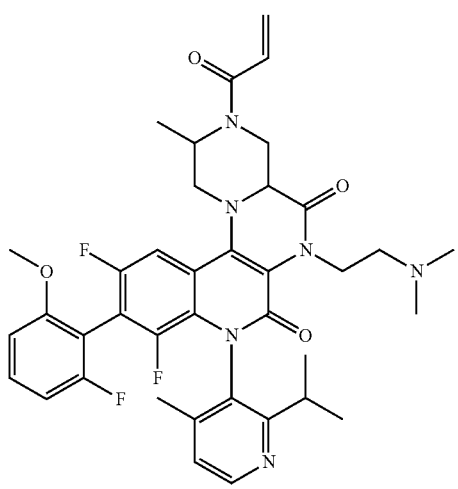
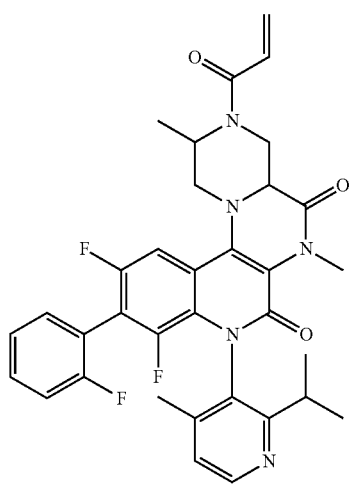
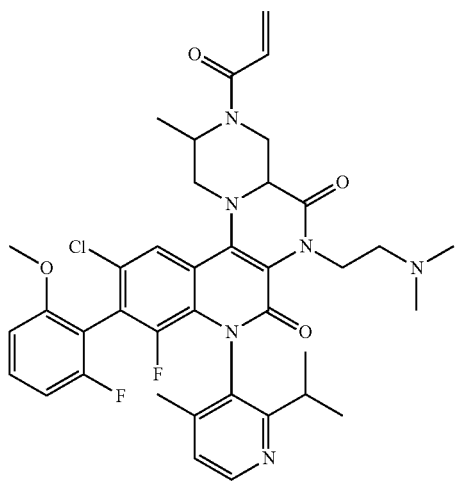
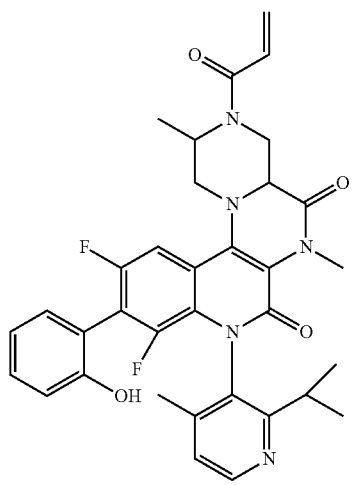

295
-continued
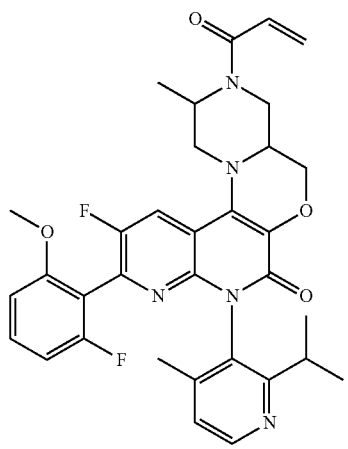
296
-continued
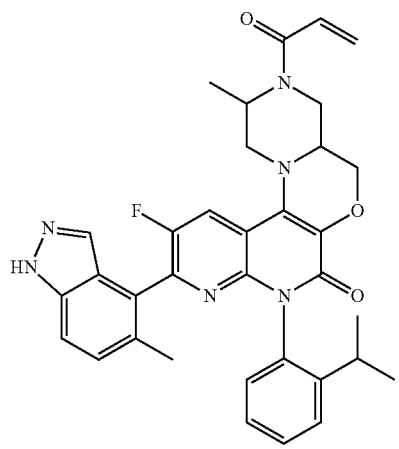
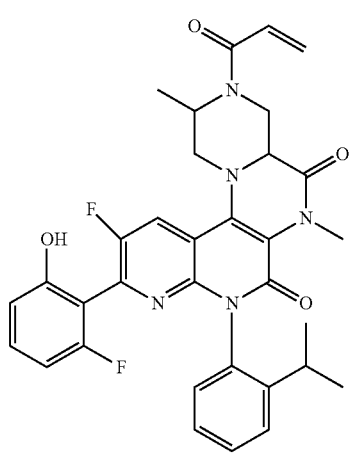
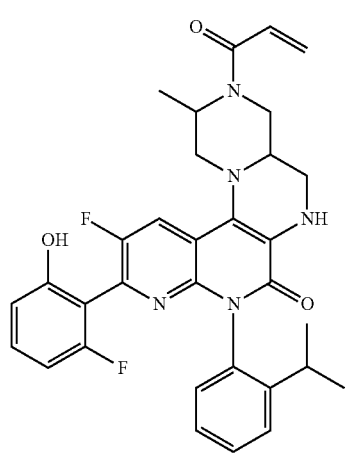
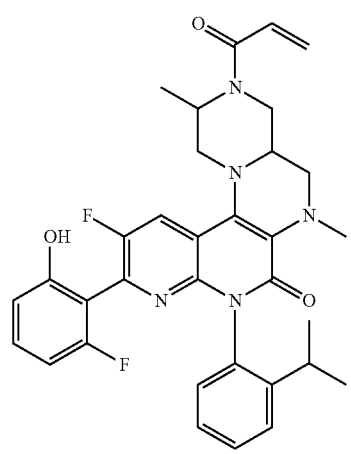
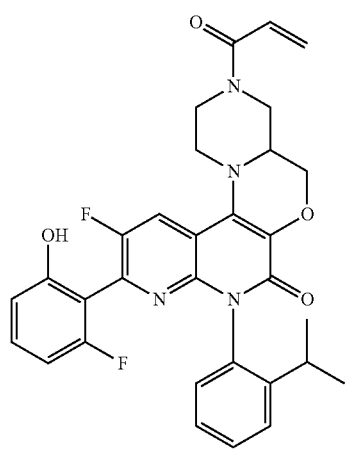

297
-continued
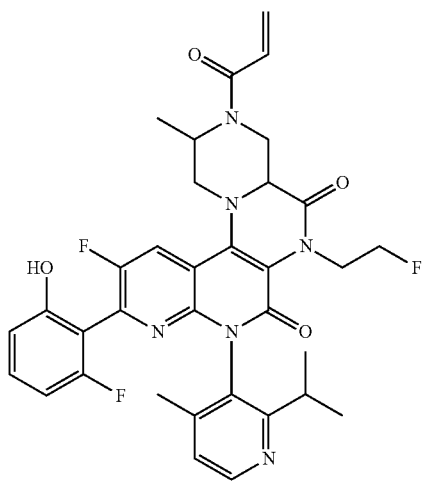
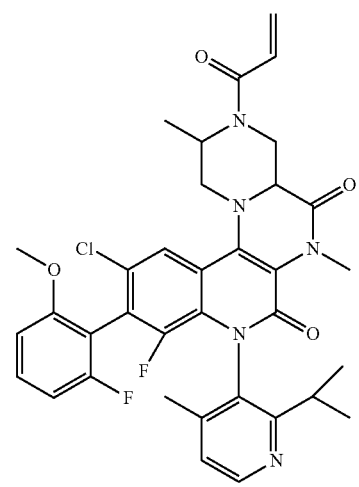
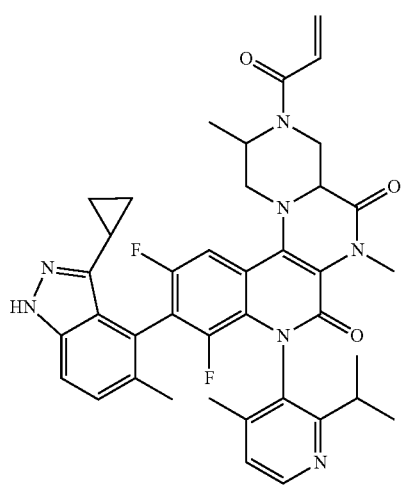
298
-continued
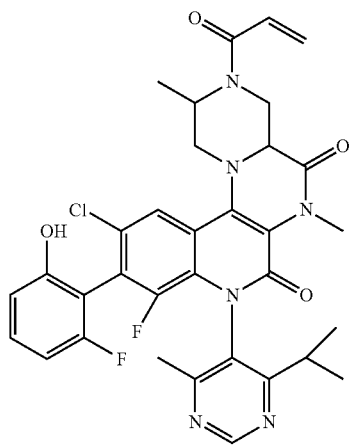
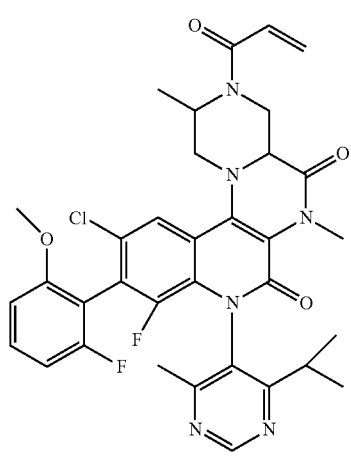
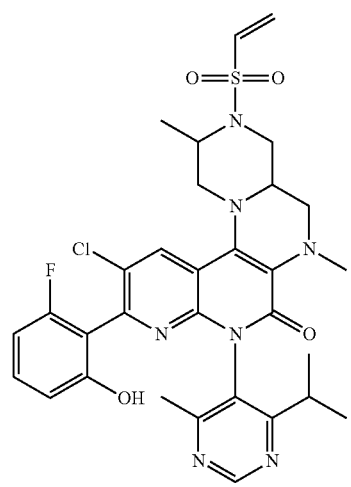

299
-continued
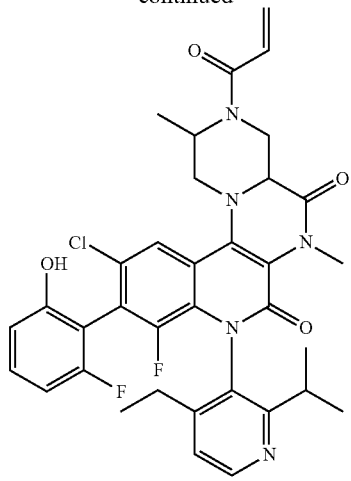
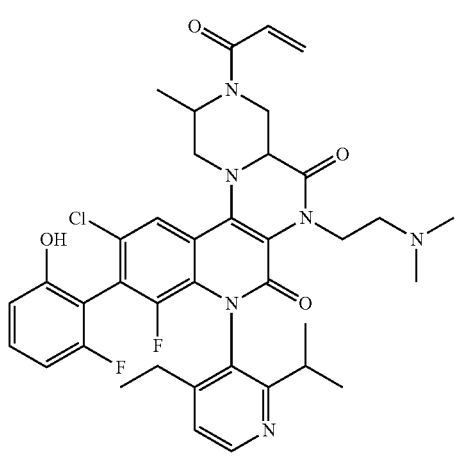
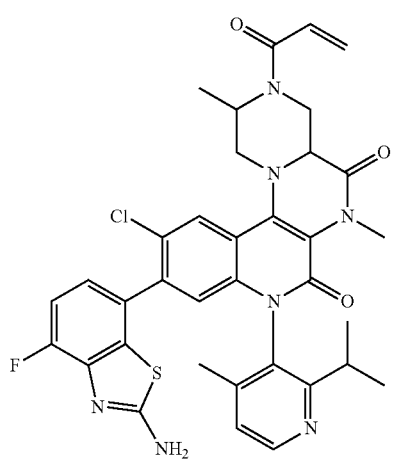
300
-continued
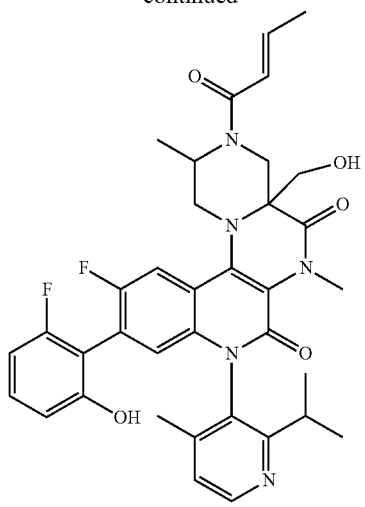
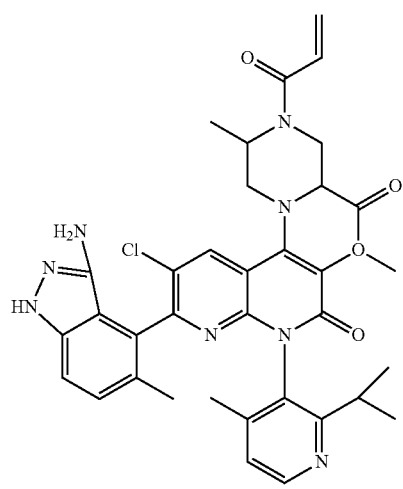
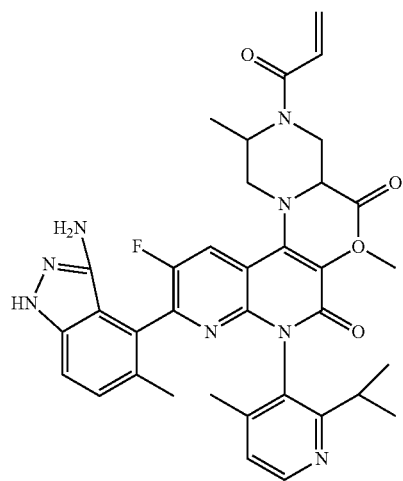

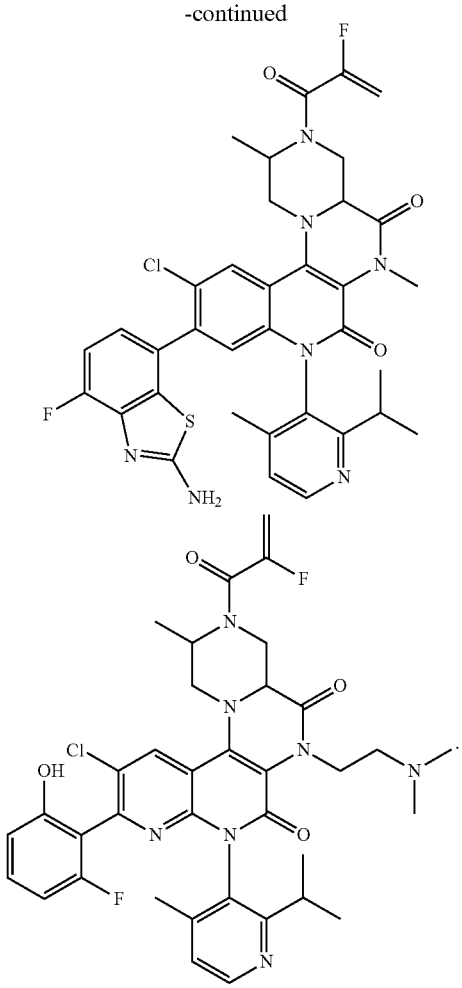

In another aspect of the present disclosure, the present disclosure also provides a pharmaceutical composition, comprising the aforementioned compounds, optical isomers and pharmaceutically acceptable salts thereof, and one or more pharmaceutically acceptable carriers, diluents or excipients.

In another aspect of the present disclosure, the present disclosure also provides a use of the aforementioned compounds, optical isomers thereof and pharmaceutically acceptable salts thereof or the aforementioned pharmaceutical composition in preparing a medicament for preventing and/or treating diseases related to KRAS-G12C.

In some embodiments of the present disclosure, the above diseases related to KRAS-G12C is selected from non-small cell lung cancer, colon cancer and pancreatic cancer.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, and is commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

A short horizontal ("-") that is not between two letters or symbols refers to the site where the substituent is attached. For example, $C_{1-6}$ alkylcarbonyl- refers to $C_{1-6}$ alkyl which is connected to the rest of the molecule through carbonyl. However, when the attachment site of a substituent is obvious to those skilled in the art, for example, a halogen substituent, "-" may be omitted.

When the valence bond of a group is marked with a dashed line " ", for example in

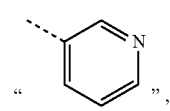

the wavy line indicates the point of attachment of the group to the rest of the molecule.

The compounds of the present disclosure may exist in specific geometric or stereoisomer or optical isomer forms. The present disclosure contemplates all such compounds, including cis and trans isomers, (−)- and (+)-enantiomers, (R)- and (S)-enantiomers, diastereomers isomers, (D)-isomers, (L)-isomers, and racemic mixture and other mixtures thereof, such as enantiomeric or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to stereoisomers in which the molecules have two or more chiral centers and the relationship between the molecules is not mirror images.

Unless otherwise specified, the absolute configuration of a stereocenter is indicated by a wedge-shaped solid line bond ( ⬧ ) and a wedge-shaped dashed line bond ( ⬧ ).

The compounds of the present disclosure may exist in specific. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxicity and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but is not requisite, the term includes the instance in which the event or condition occurs and the instance in which the event or condition does not occur.

Stereochemical definitions and conventions may be followed in S. P. Parker, editor, McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active form, i.e., they have the ability to rotate planes of plane-polarized light. When describing optically active compounds, the prefixes D and L or R and S are used to indicate the absolute configuration of the molecule with respect to its chiral center. The prefixes d and l or (+) and (−) are used to indicate the sign of the compound rotating plane-polarized light, wherein (−) or l indicates that the compound is levorotatory. Compounds prefixed with (+) or d are dextrorotatory. For a given chemical structure, these stereoisomers are identical except that they are mirror images of each other. Specific stereoisomers may also be referred to as enantiomers, the mixtures of such isomers are often referred to as enantiomeric mixtures. A 50:50 mixture of enantiomers is known as a racemic mixture or racemate, which can occur in chemical reactions or methods where there is no stereoselectivity or stereospecificity. The terms "racemic mixture" and "racemate" refer to an equimolar mixture of two enantiomers which have no optical activity.

The racemic mixture may be used in its own form or separated into individual isomers. Through resolution, a stereochemically pure compound or a mixture enriched with one or more isomers can be obtained. Methods for separating isomers are well known (see Arlinger N. L. and Eliel E. L., "Topics in Stereochemistry", Vol. 6, Wiley Interscience, 1971), including physical methods, such as chromatography using chiral adsorbents. Single isomers in chiral form can be prepared from chiral precursors. Or, a single isomer can be obtained by chemical separation from the mixture by forming diastereomer salts with chiral acids (such as single enantiomers of 10-camphor sulfonic acid, camphor acid, α-bromocamphor acid, tartaric acid, diacetyl tartaric acid, malic acid, pyrrolidone-5-carboxylic acid, etc.), and the salt is crystallized in stages, and then one or two of the resolved bases are separated, and this process is optionally repeated; thereby obtaining one or two isomers which do not substantially contain another isomer, i.e., the desired stereoisomer with an optical purity of, for example, at least 91%, 92%, 93%, 94%, 95%, 96%, 97%, 98%, 99% or 99.5% by weight. Or, as well known to those skilled in the art, the racemate can be covalently linked to a chiral compound (auxiliary) to obtain diastereomers.

The term "substituted" means one or more than one hydrogen atom(s) on a specific atom are substituted with a substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with an oxygen. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When one of the variables is selected from a single bond, it means that the two groups connected are directly connected. For example, when $L_3$ represents a single bond in

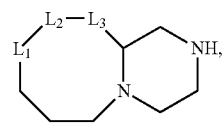

it means that the structure is actually

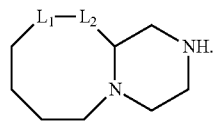

When the listed substituents do not indicate which atom is connected to the substituted group, the substituents can be attached to any atom. For example, pyridyl as a substituent can be connected to the substituted group by any carbon atom on the pyridine ring.

When the enumerative linking group does not indicate the direction for linking, the direction for linking is arbitrary, for example, the linking group L contained in

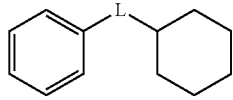

is

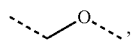

then

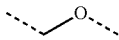

can be linked to the benzene ring and cyclohexane to form

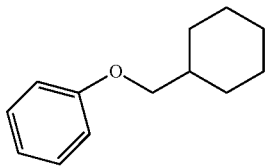 [SMILES: c1ccc(OCC2CCCCC2)cc1]

in the direction same as left-to-right reading order, and can be linked to the benzene ring and cyclohexane to form

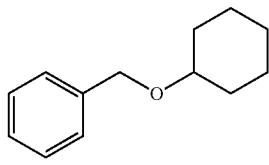 [SMILES: c1ccc(COC2CCCCC2)cc1]

in the direction contrary to left-to-right reading order. A combination of the linking groups, substituents and/or variables thereof is allowed only when such combination can result in a stable compound.

Unless otherwise specified, the number of atoms on a ring is usually defined as the number of elements of the ring, e.g., a "5-7 element ring" is a "ring" having 5-7 atoms in a surrounded arrangement.

Unless otherwise specified, the term "$C_{1-6}$ alkyl" refers to a linear or branched saturated hydrocarbon group containing 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, iso-pentyl and neopentyl), hexyl, etc.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

The term "heteroalkyl", by itself or in combination with another term, refers to a stable straight-chain or branched-chain alkyl radica or a composition thereof composed of a certain number of carbon atoms and at least one heteroatom or heteroatom group. In some embodiments, the heteroatoms are selected from B, O, N, and S, wherein nitrogen and sulfur atoms are optionally oxidized, and nitrogen heteroatoms are optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in other embodiments, the heteroalkyl is $C_{1-3}$ heteroalkyl. The heteroatoms or heteroatom groups may be located at any internal position of a heteroalkyl group, including the position where the alkyl is attached to the rest of the molecule, but the terms "alkoxy", "alkylamino" and "alkylthio" (or thioalkoxy) are customary expressions referring to those alkyl groups that are attached to the rest of the molecule by an oxygen, amino or sulfur atom, respectively. Examples of heteroalkyl include but are not limited to —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$ and —CH$_2$—CH$_2$—S(=O)$_2$—CH$_3$. At most two heteroatoms may be continuous, for example —CH$_2$—NH—OCH$_3$.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentyloxy and neopentyloxy), hexyloxy, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-6}$ alkylamino" refers to an alkyl group containing 1 to 6 carbon atoms that are connected to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino, etc. Examples of $C_{1-6}$ alkylamino include but are not limited to —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "C$_{1-3}$ alkylamino" refers to an alkyl group containing 1 to 3 carbon atoms that are connected to the rest of the molecule through an amino group. The C$_{1-3}$ alkylamino includes C$_{1-2}$, C$_3$ and C$_2$ alkylamino, etc. Examples of C$_{1-3}$ alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, etc.

Unless otherwise specified, the term "C$_{1-6}$ alkylthio" refers to an alkyl group containing 1 to 6 carbon atoms that are connected to the rest of the molecule through a sulfur atom. The C$_{1-6}$ alkylthio includes C$_{1-4}$, C$_{1-3}$, C$_{1-2}$, C$_{2-6}$, C$_{2-4}$, C$_6$, C$_5$, C$_4$, C$_3$ and C$_2$ alkylthio, etc. Examples of C$_{1-6}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, the term "C$_{1-3}$ alkylthio" refers to an alkyl group containing 1 to 3 carbon atoms that are connected to the rest of the molecule through a sulfur atom. The C$_{1-3}$ alkylthio includes C$_{1-3}$, C$_{1-2}$ and C$_3$ alkylthio, etc. Examples of C$_{1-3}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, "C$_{3-6}$ cycloalkyl" refers to saturated cyclic hydrocarbon groups consisting of 3 to 6 carbon atoms in monocyclic and bicyclic systems, the C$_{3-6}$ cycloalkyl including C$_{3-5}$, C$_{4-5}$ and C$_{5-6}$, etc.; it may be monovalent, divalent or polyvalent. Examples of C$_{3-6}$ cycloalkyl include, but are not limited to cyclopropyl, cyclobutyl, cyclopentyl, cyclohexyl, etc.

Unless otherwise specified, the term "3-8-membered heterocycloalkyl" by itself or in combination with other terms refers to a saturated cyclic group consisting of 3 to 8 ring atoms, respectively, wherein 1, 2, 3 or 4 ring atoms are heteroatoms independently selected from O, S and N and the remainder are carbon atoms, wherein the nitrogen atoms are optionally quaternized and the nitrogen and sulfur heteroatoms may optionally oxidized (i.e., NO and S(O)$_p$, p is 1 or 2). It includes monocyclic, bicyclic and tricyclic ring systems, wherein the bicyclic ring system includes spiro, fused, and bridged rings. In addition, in the case of the "3-8-membered heterocycloalkyl", the heteroatom may occupy the position where the heterocycloalkyl is attached to the rest of the molecule. The 3-8-membered heterocycloalkyl includes 3-6 membered, 3-5 membered, 4-6 membered, 5-6 membered, 4 membered, 5 membered and 6 membered heterocycloalkyl, etc. Examples of 3-8 membered heterocycloalkyl include, but are not limited to, azetidinyl, oxetidinyl, thietidinyl, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxolyl, dithianyl, isoxazolidinyl, isothiazolidinyl, 1,2-oxazinyl, 1,2-thiazinyl, hexahydropyridazinyl, homopiperazinyl, homopiperidinyl, or dioxepanyl, etc.

Unless otherwise specified, the term "3-6-membered heterocycloalkyl" by itself or in combination with other terms refers to a saturated cyclic group consisting of 3 to 6 ring atoms, respectively, wherein 1, 2, 3 or 4 ring atoms are heteroatoms independently selected from O, S and N and the remainder are carbon atoms, wherein the nitrogen atoms are optionally quaternized and the nitrogen and sulfur heteroatoms may optionally oxidized (i.e., NO and S(O)$_p$, p is 1 or 2). It includes monocyclic and bicyclic ring systems, wherein the bicyclic ring system includes spiro and bridged rings. In addition, in the case of the "3-6-membered heterocycloalkyl", the heteroatom may occupy the position where the heterocycloalkyl is attached to the rest of the molecule. The 3-6 membered heterocycloalkyl includes 4-6 membered, 5-6 membered, 4 membered, 5 membered and 6 membered heterocycloalkyl, etc. Examples of 3-6 membered heterocycloalkyl include, but are not limited to, azetidinyl, oxetidinyl, thietidinyl, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxolyl, dithianyl, isoxazolidinyl, isothiazolidinyl, 1,2-oxazinyl, 1,2-thiazinyl, hexahydropyridazinyl, homopiperazinyl, or homopiperidinyl, etc.

Unless otherwise specified, the terms "C$_{6-10}$ aromatic ring" and "C$_{6-10}$ aryl" in the present disclosure can be used interchangeably, and the terms "C$_{6-10}$ aromatic ring" or "C$_{6-10}$ aryl" refer to a cyclic hydrocarbon group with conjugated π electron system composed of 6 to 10 carbon atoms, which can be a monocyclic, fused bicyclic or fused tricyclic system, wherein each ring is aromatic. It may be monovalent, divalent or multivalent, and C$_{6-10}$ aryl includes C$_{6-9}$, C$_9$, C$_{10}$ and C$_6$ aryl, etc. Examples of C$_{6-10}$ aryl include, but are not limited to, phenyl and naphthyl (including 1-naphthyl and 2-naphthyl, etc.).

Unless otherwise specified, the terms "5-10 membered heteroaromatic ring" and "5-10 membered heteroaryl" in the present disclosure may be used interchangeably, and the term "5-10 membered heteroaryl" refers to a cyclic group consisting of 5 to 10 ring atoms with conjugated π electronic system, of which 1, 2, 3 or 4 ring atoms are heteroatoms independently selected from O, S and N, and the rest are carbon atoms. It may be a monocyclic, fused bicyclic or fused tricyclic system, wherein each ring is aromatic. Wherein the nitrogen atom is optionally quaternized, and the nitrogen and sulfur heteroatoms are optionally oxidized (i.e., NO and S(O)$_p$, p is 1 or 2). The 5-10 membered heteroaryl may be attached to the rest of the molecule through a heteroatom or a carbon atom. The 5-10 membered heteroaryl includes 5-8 membered, 5-7 membered, 5-6 membered, 5 membered and 6 membered heteroaryl, etc. Examples of the 5-10 membered heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), and thienyl (including 2-thienyl and 3-thienyl, etc.), pyridinyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), and isoquinolinyl (including 1-isoquinolinyl and 5-isoquinolinyl, etc.), quinoxalinyl (including 2-quinoxalinyl and 5-quinoxalinyl, etc.) or quinolinyl (including 3-quinolinyl and 6-quinolinyl, etc.).

Unless otherwise specified, the terms "5-6 membered heteroaromatic ring" and "5-6 membered heteroaryl" in the present disclosure may be used interchangeably, and the term "5-6 membered heteroaryl" refers to a monocyclic group consisting of 5 to 6 ring atoms with conjugated 7E electronic system, of which 1, 2, 3 or 4 ring atoms are heteroatoms independently selected from O, S and N, and the rest are carbon atoms. Wherein the nitrogen atom is optionally quaternized, and the nitrogen and sulfur heteroatoms are optionally oxidized (i.e., NO and $S(O)_p$, p is 1 or 2). The 5-6 membered heteroaryl may be attached to the rest of the molecule through a heteroatom or a carbon atom. The 5-6 membered heteroaryl includes 5 membered and 6 membered heteroaryl. Examples of the 5-6 membered heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), and thienyl (including 2-thienyl and 3-thienyl, etc.), pyridinyl (including 2-pyridyl, 3-pyridyl and 4-pyridyl, etc.), pyrazinyl or pyrimidinyl (including 2-pyrimidinyl and 4-pyrimidinyl, etc.)

Unless otherwise specified, "benzo-5-6 heterocycloalkyl" refers to a double fused cyclic structure formed by combining a phenyl with a heterocyclic ring or combining a phenyl with a 5-6 membered heterocycloalkyl, where the substituent may be attached to other structures through the benzene ring or the 5-6 membered heterocycloalkyl ring. Examples of the benzo 5-6 membered heterocycloalkyl include but are not limited to

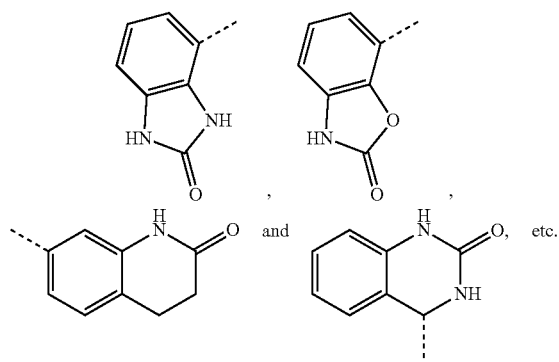

Unless otherwise specified, "5-6 membered heteroaryl-fused 5-6 membered heterocycloalkyl" refers to a double fused cyclic structure formed by combining a 5-6 membered heteroaryl with a heterocyclic ring or combining a 5-6 membered heteroaryl with a 5-6 membered heterocycloalkyl, where the substituent may be attached to other structures through the 5-6 membered heteroaryl or the 5-6 membered heterocycloalkyl ring. Examples of benzo 5-6 membered heterocycloalkyl include but are not limited to

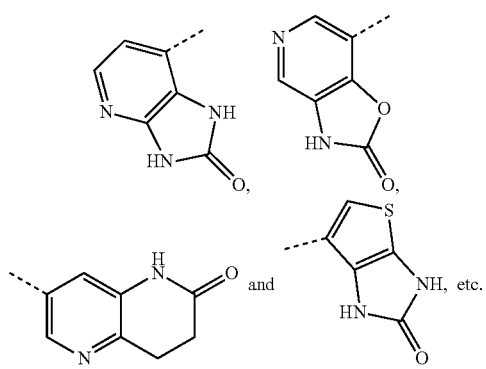

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "treatment" as used herein refers to the administration of one or more pharmaceutical substances, in particular compounds of formula (I) and/or pharmaceutically acceptable salts thereof, to an individual suffering from a disease or having symptoms of the disease, for the purpose of curing, alleviating, mitigating, modifying, healing, improving, ameliorating or affecting the disease or symptoms of the disease. As used herein, the term "prevention" refers to the administration of one or more pharmaceutical substances, especially the compound of formula (I) described herein and/or pharmaceutically acceptable salts thereof, to an individual with a constitution susceptible to the disease, to prevent the individual from suffering from the disease. When referring to chemical reactions, the terms "treating", "contacting" and "reacting" refer to adding or mixing two or more reagents under appropriate conditions to produce the indicated and/or desired products. It should be understood that the reaction to produce the indicated and/or desired products may not necessarily come directly from the combination of the two reagents initially added, i.e. there may be one or more intermediates generated in the mixture, which eventually lead to the formation of the indicated and/or desired products.

As used herein, the term "effective amount" refers to an amount generally sufficient to produce a beneficial effect on an individual. The effective amount of a compound of the present disclosure can be determined by conventional methods (e.g., modeling, dose-escalation studies, or clinical trials) in combination with conventional influencing factors (e.g., mode of administration, pharmacokinetics of the compound, severity and duration of the disease, medical history of the individual, health status of the individual, degree of response of the individual to the drug, etc.).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvent used in the present disclosure is commercially available. The following abbreviations are used in the present disclosure: $CDCl_3$ refers to deuterated chloroform; $CD_3OD$ refers to deuterated methanol; DMSO-$d_6$ refers to deuterated dimethyl sulfoxide; TBS refers to tert-butyldimethylsilyl.

The compounds of the present disclosure are named according to the conventional naming principles in the art or by ChemDraw® software, and the commercially available compounds use the supplier catalog names.

DETAILED DESCRIPTION OF THE INVENTION

Figure 1:
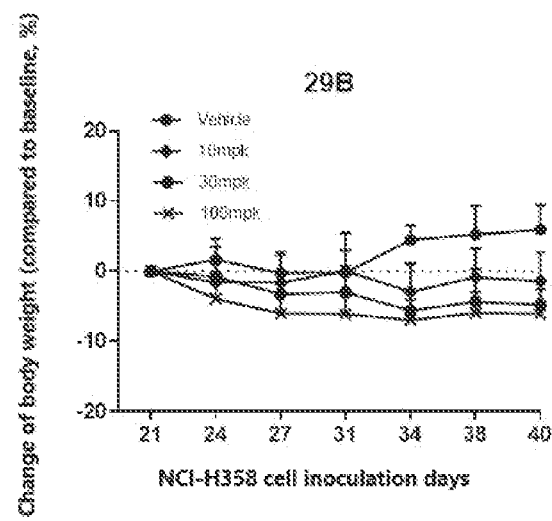
FIG. 1 is a graph showing the relationship between the inoculation days of NCI-H358 cells and the change of body weight after administration of compound 29B of embodiment according to an embodiment of the present disclosure.

The present application is described in detail by the embodiments below, but it does not mean that there are any adverse restrictions on the present application. The present application has been described in detail herein, wherein specific embodiments thereof are also disclosed, and it will be apparent to those skilled in the art that various variations and improvements can be made to specific embodiments of the present application without departing from the spirit and scope of the present application.

Embodiment 1: Preparation of Compound 1

Step 1: Preparation of Compound 1-2

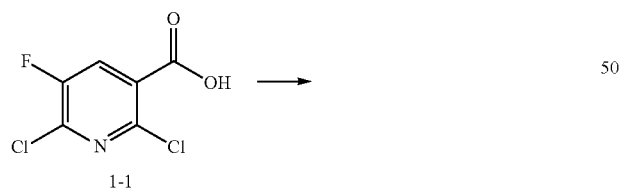

Raw material 1-1 (2.00 g, 9.57 mmol) was dissolved in thionyl chloride (10 mL), and the mixture was heated to 80° C. to react for 16 hours. The system was concentrated to obtain a crude product, and the crude product was dissolved in dioxane (10 mL), then a mixed solution of dioxane (5 mL) and ethanol (5 mL) was added thereto at 0° C., after the addition was completed, the system was stirred at room temperature (20° C.) for 1 hour. The system was dissolved in ethyl acetate (20 mL), washed with saturated potassium carbonate solution, left to stratify, and the organic phase was dried over anhydrous sodium sulfate and concentrated to obtain yellow oily compound 1-2.

Step 2: Preparation of Compound 1-3

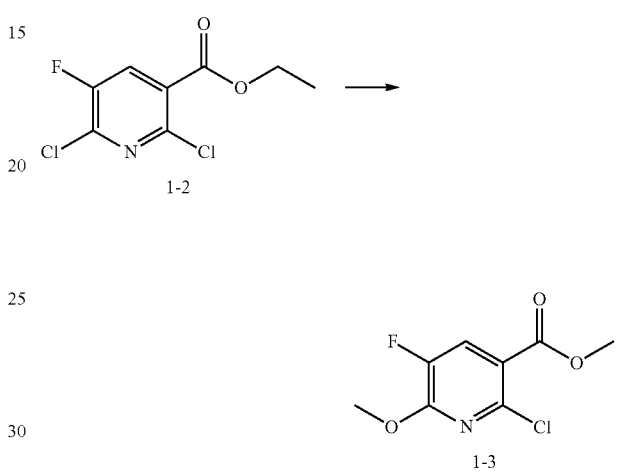

Compound 1-2 (1.5 g, 6.32 mmol) was dissolved in methanol (15 mL), and a methanol solution of sodium methoxide (1.25 g, 6.96 mmol, 30% by weight) was added dropwise thereto at 0° C. After the dropwise addition was completed, the system was stirred at 0° C. for 15 min, and then raised to room temperature (20° C.) and stirred for 1 hour. The system was concentrated under reduced pressure, and the residue was dissolved in ethyl acetate (20 mL), washed with saturated ammonium chloride solution and left to stratify; the organic phase was dried over anhydrous sodium sulfate and concentrated to obtain crude compound 1-3, which was used directly in the next reaction without further purification.

$^1$H NMR (400 MHz, $CDCl_3$) 7.94 (d, 1H, J=12 Hz), 4.09 (s, 3H), 3.93 (s, 3H).

Step 3: Preparation of Compound 1-5

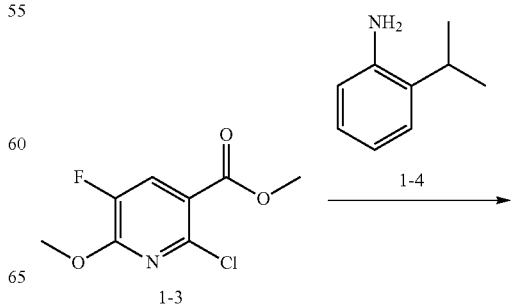

-continued

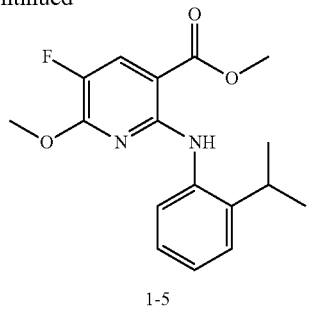

1-5

At room temperature (20° C.), compound 1-3 (1.05 g, 4.79 mmol), compound 1-4 (0.776 g, 5.75 mmol), palladium acetate (107 mg, 0.479 mmol), 4,5-bis(diphenylphosphino)-9,9-dimethylxanthene (275 mg, 0.479 mmol), cesium carbonate (3.142 g, 9.58 mmol) were dissolved in anhydrous dioxane (15 mL), under nitrogen atmosphere, the system was heated to 100° C. and stirred for 3 hours. The system was cooled to room temperature, concentrated, diluted with water (100 mL), extracted with ethyl acetate (3×20 mL); then the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-10%) to obtain white solid compound 1-5.

MS (ESI) m/z (M+H)$^+$=319.2.

Step 4: Preparation of Compound 1-6

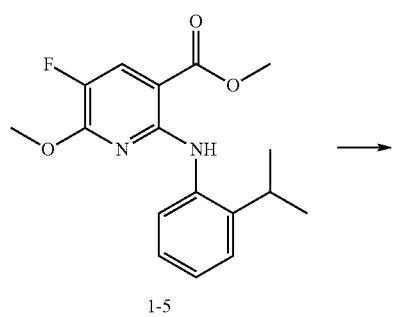

1-5

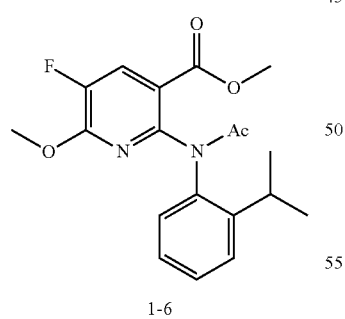

1-6

Compound 1-5 (200 mg, 0.629 mmol) and acetyl chloride (3 mL) were added to a 5 mL microwave tube, and the system was heated to 150° C. for 3 hours under microwave conditions. The system was cooled to room temperature and concentrated to obtain a crude product, the crude product was purified by medium pressure column chromatography (ethyl acetate/petroleum ether (v/v)=0-50%) to obtain reddish brown oily compound 1-6.

MS (ESI) m/z (M+H)$^+$=361.2.

Step 5: Preparation of Compound 1-7

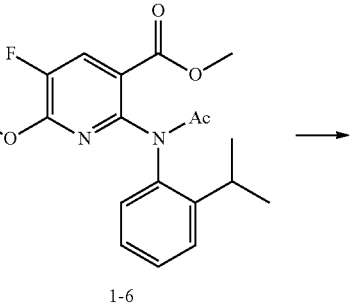

1-6

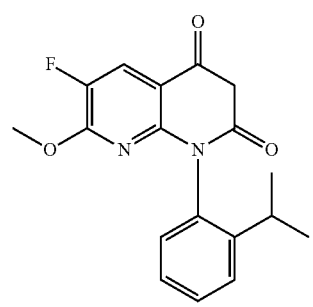

1-7

Compound 1-6 (360 mg, 1 mmol) and potassium tert-butoxide (336 mg, 3 mmol) were dissolved in toluene (5 mL) at room temperature (20° C.), under nitrogen atmosphere, the system was heated to 100° C. and stirred for 3 hours. The system was cooled to room temperature, quenched with dilute hydrochloric acid (1 N, 10 mL), extracted with ethyl acetate (2×10 mL); then the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-50%) to obtain yellow solid compound 1-7.

MS (ESI) m/z (M+H)$^+$=329.2.

Step 6: Preparation of Compound 1-8

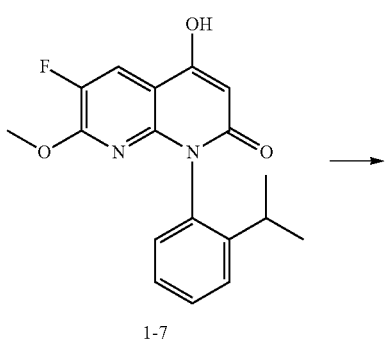

1-7

315

-continued

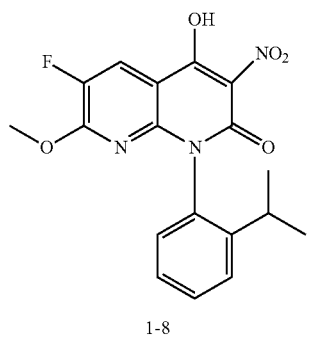

1-8

Compound 1-7 (200 mg, 0.61 mmol) was dissolved in acetic acid (3 mL), and concentrated nitric acid (0.3 mL) was added dropwise thereto at room temperature; after the dropwise addition was completed, the system was stirred at room temperature (20° C.) for 30 min. The system was poured into ice water (100 mL), a yellow solid was precipitated, filtered, and the filter cake was dried under vacuum until the weight was no longer reduced to obtain yellow solid compound 1-8.

MS (ESI) m/z (M+H)$^+$=374.2.

Step 7: Preparation of Compound 1-9

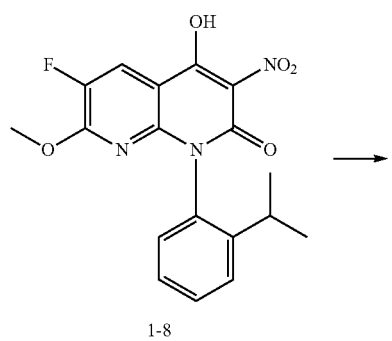

Compound 1-8 (200 mg, 0.54 mmol) was dissolved in acetic acid (2 mL), and hydrobromic acid (48%, 1 mL) was added thereto at room temperature, then the system was heated to 100° C. and stirred for 3 hours. The reaction mixture was concentrated to obtain crude compound 1-9, which was directly used in the next reaction without further purification.

MS (ESI) m/z (M+H)$^+$=360.3.

316

Step 8: Preparation of Compound 1-10

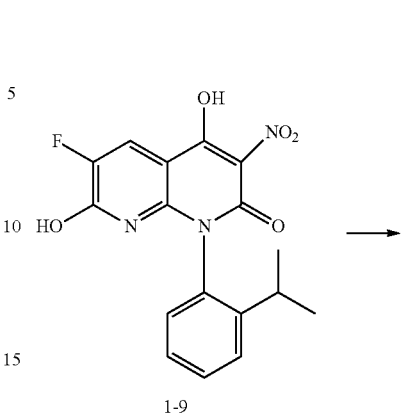

1-9

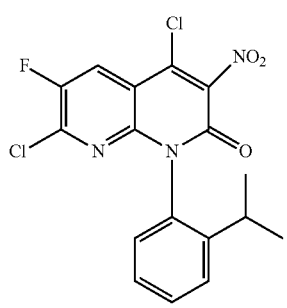

1-10

Compound 1-9 (360 mg, 1 mmol) was added to N,N-diisopropylethylamine (2 mL), and phosphorus oxychloride (1 mL) was added thereto at room temperature, and the reaction system turned black, then the system was heated to 90° C. and stirred for 1 hour. The system was concentrated, and the crude product was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-10%) to obtain yellow solid compound 1-10.

MS (ESI) m/z (M+H)$^+$=396.0.

Step 9: Preparation of Compound 1-12

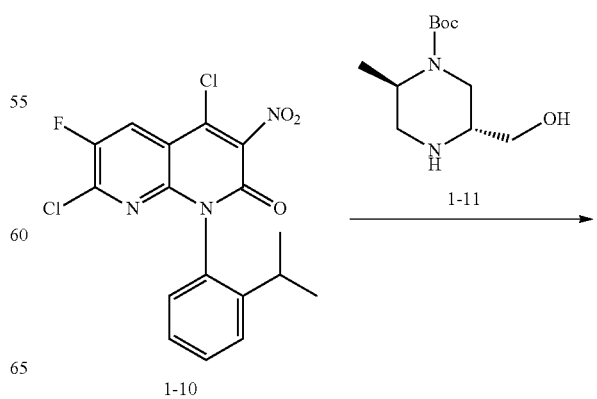

317

-continued

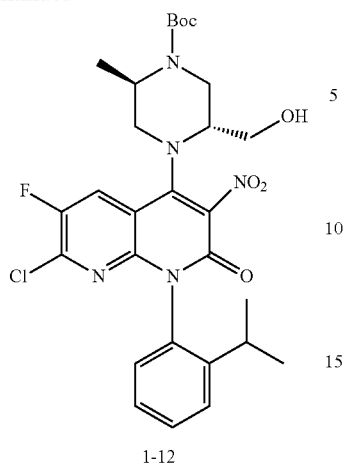

1-12

Compound 1-10 (147 mg, 0.372 mmol), compound 1-11 (102 mg, 0.446 mmol), cuprous iodide (71.0 mg, 0.372 mmol), and cesium carbonate (244 mg, 0.744 mmol) were dissolved in dioxane (4 mL), under nitrogen atmosphere, the system was heated to 100° C. and stirred for 2 hours. The system was filtered by diatomite, and the filtrate was concentrated to obtain a crude product. The crude product was purified by medium pressure column chromatography (ethyl acetate/petroleum ether (v/v)=0-30%) to obtain yellow solid compound 1-12.

MS (ESI) m/z (M+H)⁺=590.2.

Step 10: Preparation of Compound 1-14

318

-continued

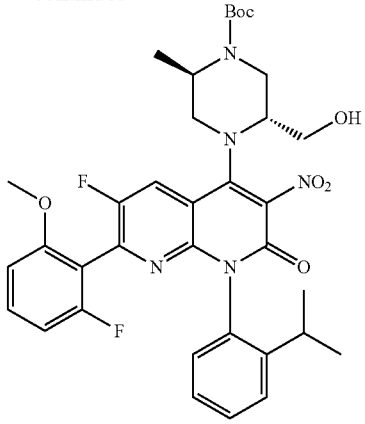

1-14

Compound 1-12 (100 mg, 0.169 mmol), compound 1-13 (34.6 mg, 0.203 mmol), 1,1-bis(diphenylphosphino)ferrocene palladium dichloride (12.3 mg, 0.0169 mmol), potassium carbonate (46.6 mg, 0.338 mmol) were dissolved in a mixed solution of tetrahydrofuran (3 mL) and water (0.3 mL), under nitrogen atmosphere, the system was heated to 80° C. and stirred for 1 hour. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 1-14.

MS (ESI) m/z (M+H)⁺=680.2.

Step 11: Preparation of Compound 1-15

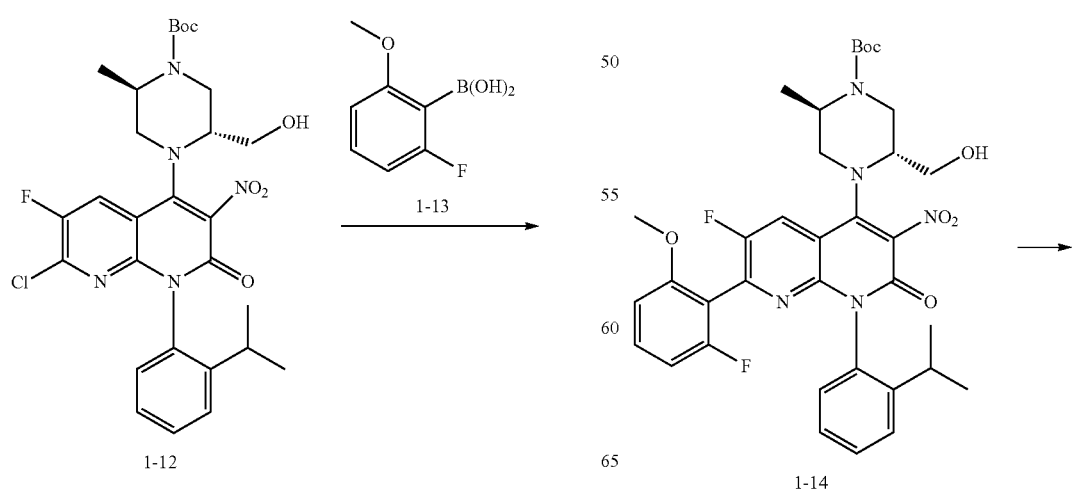

319
-continued

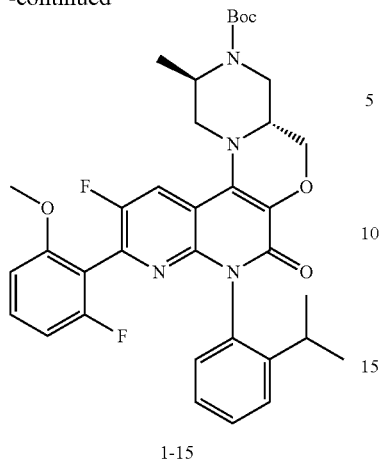

1-15

Compound 1-14 (30 mg, 0.044 mmol) were dissolved in N, N-dimethylacetamide (1 mL), and tetrahydrofuran solution of LiHMDS (24%, 0.1 mL) was added thereto at room temperature, under nitrogen atmosphere, the system was heated to 160° C. and stirred for 4 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 1-15.

MS (ESI) m/z (M+H)$^+$=633.4.

Step 12: Preparation of Compounds 1A and 1B

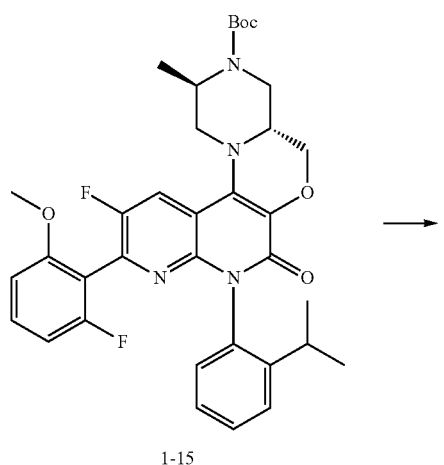

1-15

320
-continued

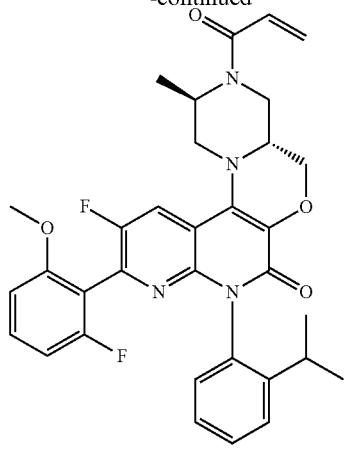

1A or 1B

+

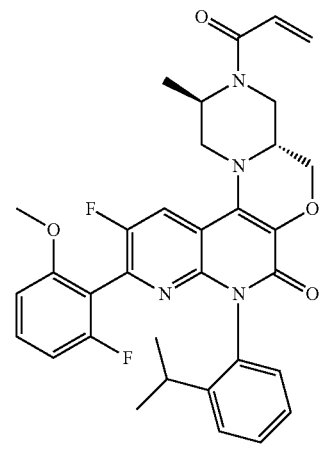

1B or 1A

Compound 1-15 (8 mg, 0.0126 mmol) was dissolved in dichloromethane (1 mL), trifluoroacetic acid (1 mL) was added thereto at room temperature, and the mixture was stirred at room temperature (20° C.) for 1 hour. The system was concentrated and the residue was dissolved in dichloromethane (1 mL); and the system was cooled to 0° C., then triethylamine (2.52 mg, 0.0252 mmol) and acryloyl chloride (2.27 mg, 0.0252 mmol) were added dropwise thereto. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by high performance liquid chromatography (separation conditions: chromatographic column Welch Ultimate XB-C18 10*250 mm, 5 μm, aqueous phase 0.15TFA, organic phase acetonitrile, gradient 52%-70%, time 12 min) to obtain compound 1A and compound 1B.

Compound 1A:
$^1$H NMR (400 MHz, MeOD-d4) 7.83 (d, 1H, J=8 Hz), 7.38-7.07 (m, 3H), 6.93-6.86 (m, 1H), 6.80-6.54 (m, 3H), 6.20 (d, 1H, J=8 Hz), 5.75-5.67 (m, 2H), 4.40-4.27 (m, 2H), 4.21-4.08 (m, 1H), 4.02-3.82 (m, 3H), 3.81-3.69 (m, 2H), 3.58 (d, 3H), 2.44-2.32 (m, 1H), 1.08-0.98 (m, 3H), 0.92-0.85 (m, 3H), 0.84-0.76 (m, 3H).

MS (ESI) m/z (M+H)$^+$=587.42.

Separation conditions: chromatographic column: Waters Xselect CSH C18 3.5 μm, 100*4.6 mm; column temperature: 60° C.; mobile phase: water (0.01% trifluoroacetic acid solution)-acetonitrile (0.01% trifluoroacetic acid solution); acetonitrile: 5%-95% 7 min, 95% 8 min; flow rate: 1.2 mL/min. Retention time was 6.175 min Compound 1B:

$^1$H NMR (400 MHz, MeOD-d4) 7.83 (d, 1H, J=8 Hz), 7.38-7.21 (m, 3H), 7.20-7.12 (m, 1H), 7.0-6.89 (m, 1H), 6.80-6.57 (m, 3H), 6.20-6.11 (m, 1H), 5.73 (d, 1H, J=8.0 Hz), 4.38-4.21 (m, 4H), 4.20-4.08 (m, 2H), 4.07-3.93 (m, 2H), 3.58 (d, 3H), 2.35-2.25 (m, 1H), 1.06-0.99 (m, 3H), 0.92-0.83 (m, 3H), 0.82-0.79 (m, 3H).

MS (ESI) m/z (M+H)$^+$=587.4.

Separation conditions: chromatographic column: Waters Xselect CSH C18 3.5 μm, 100*4.6 mm; column temperature: 60° C.; mobile phase: water (0.01% trifluoroacetic acid solution)-acetonitrile (0.01% trifluoroacetic acid solution); acetonitrile: 5%-95% 7 min, 95% 8 min; flow rate: 1.2 mL/min. Retention time was 6.327 min.

Embodiment 2: Preparation of Compound 2

Step 1: Preparation of Compound 2-2

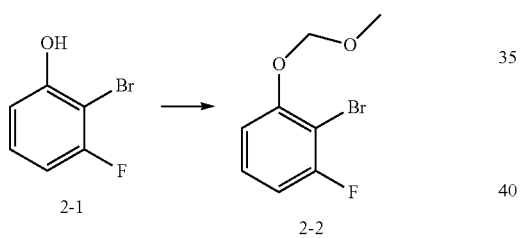

Compound 2-1 (2.87 g, 15 mmol) was dissolved in anhydrous N,N-dimethylacetamide (10 mL), and sodium hydride (60%, 660 mg, 16.5 mol) was added thereto in batches at 0° C., after the addition was completed, the system was raised to room temperature and stirred for 10 min, chloromethyl methyl ether (2.4 g, 30 mmol) was added dropwise to the system, after the dropwise addition was completed, the system was stirred at room temperature for 10 min. The system was quenched by pouring to ice water (50 mL), extracted with methyl tert-butyl ether (3×50 mL); the organic phases were combined, washed once with saturated sodium chloride aqueous solution, and the organic phase was dried over anhydrous sodium sulfate, filtered, and the filtrate was concentrated to obtain a crude product. The crude product was purified by medium pressure column chromatography (ethyl acetate/petroleum ether (v/v)=0-10%) to obtain light yellow viscous compound 2-2.

$^1$H NMR (400 MHz, CDCl$_3$-d$_1$) 7.24-7.18 (m, 1H), 6.95-6.93 (m, 1H), 6.83-6.79 (m, 1H), 5.26 (s, 2H), 3.52 (s, 3H).

Step 2: Preparation of Compound 2-3

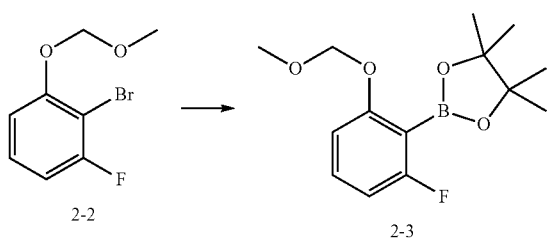

Compound 1-2 (650 mg, 2.77 mmol) was dissolved in anhydrous tetrahydrofuran (5 mL), and n-butyllithium (2.5 N, 1.22 mL, 3.05 mmol) was added dropwise to the system at −78° C., and the system was stirred at −78° C. for 30 min, then isopropyl pinacol borate (567 mg, 3.05 mmol) was added dropwise to the system, and the system was stirred at −78° C. for 30 min. The system was raised to room temperature, quenched with water, extracted with ethyl acetate (10 mL); then the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-20%) to obtain colorless oily compound 2-3.

Step 3: Preparation of Compound 2-4

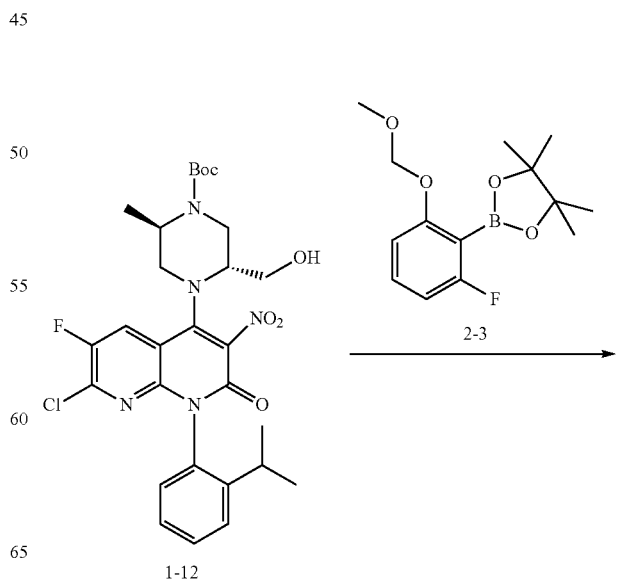

323
-continued

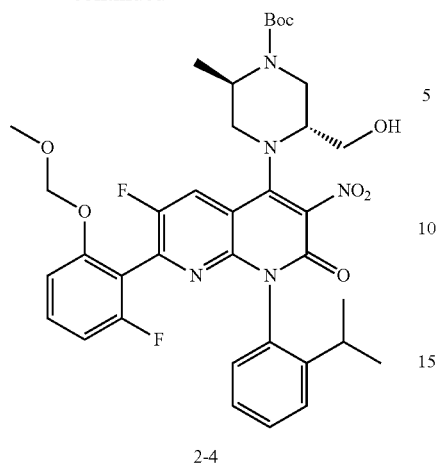

2-4

324
-continued

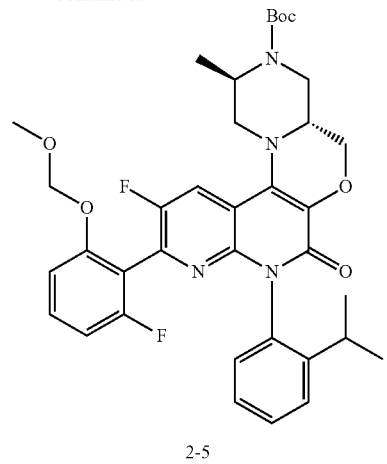

2-5

Compound 1-12 (50 mg, 0.0848 mmol), compound 2-3 (28.7 mg, 0.10 mmol), 1,1-bis(diphenylphosphino)ferrocene palladium dichloride (6.2 mg, 0.00848 mmol), potassium carbonate (23.4 mg, 0.169 mmol) were dissolved in a mixed solution of tetrahydrofuran (2 mL) and water (0.2 mL). Under nitrogen atmosphere, the system was heated to 80° C. and stirred for 2 hours. The system was concentrated to obtain a crude product, the crude product was purified by medium pressure column chromatography (ethyl acetate/petroleum ether (v/v)=0-50%) to obtain yellow solid compound 2-4.

MS (ESI) m/z (M+H)$^+$=710.2.

Step 4: Preparation of Compound 2-5

Compound 2-4 (30 mg, 0.0423 mmol) was dissolved in N,N-dimethylacetamide (1 mL), and tetrahydrofuran solution of lithium bis(trimethylsilyl)amide (24%, 0.1 mL) was added dropwise thereto under nitrogen atmosphere. The system was heated to 160° C. and stirred for 4 hours. The system was cooled to room temperature and concentrated to obtain a crude product. The crude product was purified by medium pressure column chromatography (ethyl acetate/petroleum ether (v/v)=0-50%) to obtain light yellow solid compound 2-5.

MS (ESI) m/z (M+H)$^+$=663.2.

Step 5: Preparation of Compound 2-6

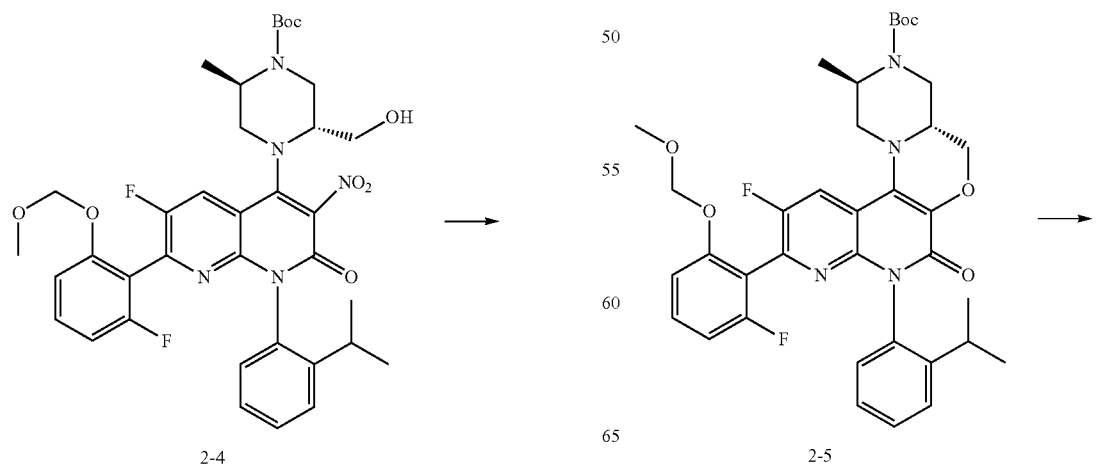

2-4

2-5

-continued

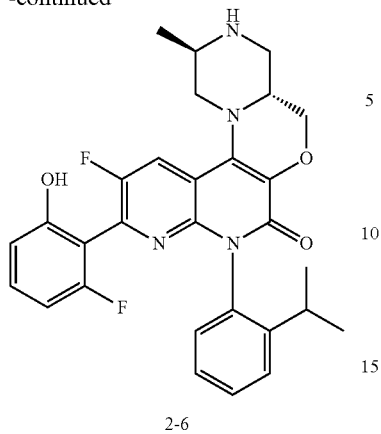

2-6

Compound 2-5 (6 mg, 0.009 mmol), hydrochloric acid (6N, 0.5 mL) were added to a mixed solution of methanol (0.45 mL) and tetrahydrofuran (0.05 mL). The system was heated to 55° C. and stirred for 15 min. The system was concentrated to obtain crude product 2-6, which was directly used in the next reaction without further purification.

MS (ESI) m/z (M+H)$^+$=519.2.

Step 6: Preparation of Product 2A and Product 2B

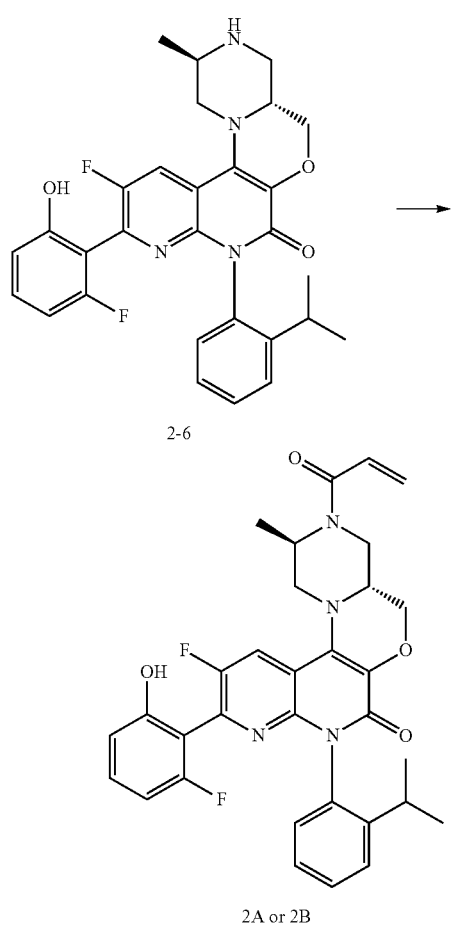

2A or 2B

-continued

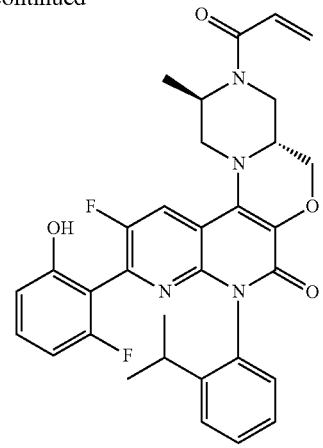

2B or 2A

Compound 2-6 (5 mg, 0.0096 mmol) was dissolved in dichloromethane (1.0 mL), and the system was cooled to 0° C., triethylamine (1.95 mg, 0.0193 mmol) and acryloyl chloride (1.73 mg, 0.0193 mmol) were added dropwise thereto, the reaction was carried out at 0° C. for 1 hour. The system was concentrated to obtain a crude product, the crude product was purified by high performance liquid chromatography (separation conditions: chromatographic column Welch Ultimate XB-C18 10*250 mm, 5 μm, aqueous phase 10 mmol/L ammonium acetate, organic phase acetonitrile, gradient 38%-65%, time 15 min) to obtain compounds 2A and 2B.

Compound 2A:

MS (ESI) m/z (M+H)$^+$=573.4.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min. Retention time was 5.743 min.

Compound 2B:

MS (ESI) m/z (M+H)$^+$=573.4.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min. Retention time was 5.879 min.

Embodiment 3: Preparation of Compound 3

Step 1: Preparation of Compound 3-2

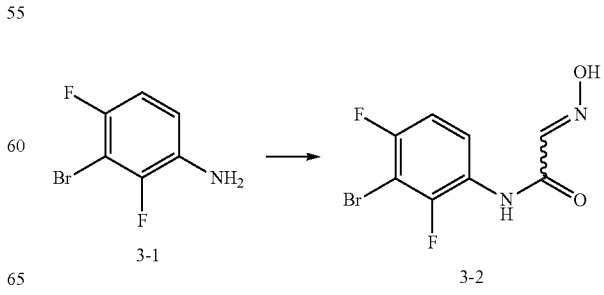

The raw materials chloral hydrate (19.08 g, 115.38 mmol, 15.03 mL) and sodium sulfate (122.92 g, 865.37 mmol) were dissolved in water (360 mL), the system was heated to 35° C., and the aqueous solution (120 mL) of raw material 3-1 (20 g, 96.15 mmol), hydrochloric acid (12 M, 10.82 mL) and hydroxylamine hydrochloride (21.38 g, 307.69 mmol) were added successively. After the addition was completed, the system was heated to 90° C. and reacted for 16 hours. A gray precipitate appeared in the system, the system was cooled to room temperature and filtered to obtain a filter cake, the filter cake was washed with water and dried under vacuum to obtain compound 3-2, which was directly used in the next reaction without further purification.

$^1$H NMR (400 MHz, DMSO-$d_6$) δ 12.34 (s, 1H), 10.01 (s, 1H), 7.78-7.74 (m, 1H), 7.70 (s, 1H), 7.31-7.26 (m, 1H).

Step 2: Preparation of Compound 3-3

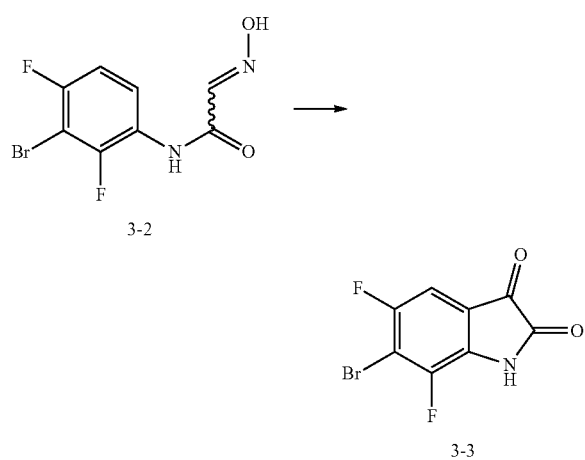

Compound 3-2 (35 g, 125.43 mmol) was added to concentrated sulfuric acid (368.00 g, 3.75 mol, 200 mL) at 60° C. After the addition was completed, the system was heated to 90° C. and stirred for 3 hours. The system was cooled to room temperature, poured into ice water, a black precipitate was precipitated, filtered to obtain a filter cake, and the filter cake was dried to obtain crude product A. The filtrate was extracted with ethyl acetate (500 mL×2), and the organic phases were combined and washed with saturated saline (500 mL), the organic phase was dried over anhydrous sodium sulfate, filtered, and the filtrate was concentrated to obtain crude product B. The crude products A and B were combined to obtain compound 3-3, which was directly used in the next reaction without further purification.

Step 3: Preparation of Compound 3-4

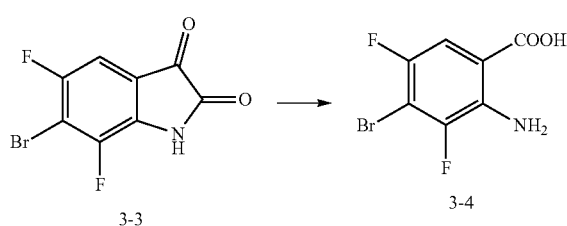 [SMILES: O=C1Nc2c(cc(F)c(Br)c2F)C1=O ; Nc1c(C(=O)O)cc(F)c(Br)c1F]

Compound 3-3 (29 g, 110.68 mmol) was dissolved in sodium hydroxide aqueous solution (2 M, 290.00 mL), and hydrogen peroxide (70.80 g, 624.44 mmol, 60 mL, purity 30%) was added dropwise thereto at 0° C. After the dropwise addition was completed, the system was stirred at 0° C. for 0.5 hours, and then raised to room temperature (20° C.) and stirred for 16 hours. The system was poured into ice water (300 mL), and the pH was adjusted to 6 with concentrated hydrochloric acid, the system was precipitated and filtered to obtain a filter cake, the filter cake was dried to obtain compound 3-4, which was directly used in the next reaction without further purification.

Step 4: Preparation of Compound 3-5

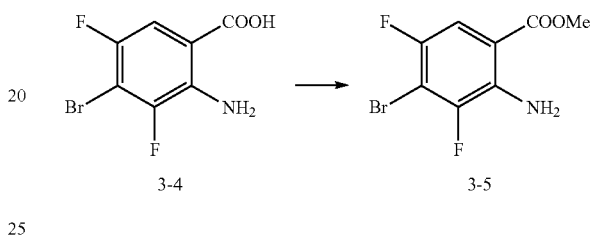

Compound 3-4 (28 g, 111.11 mmol) was dissolved in methanol (300 mL), and concentrated sulfuric acid (18.40 g, 187.60 mmol, 10 mL) was added thereto, under nitrogen atmosphere, the system was heated to 75° C. and the reaction was carried out for 16 hours. The system was concentrated and the obtained crude product was separated and extracted with ethyl acetate (200 mL) and water (300 mL), the organic phase was dried over anhydrous sodium sulfate, filtered and the filtrate was concentrated to obtain a crude product, the crude product was purified by medium pressure column chromatography (ethyl acetate/petroleum ether (v/v)=0-20%) to obtain compound 3-5.

$^1$H NMR (400 MHz, CDCl$_3$) δ 7.46 (d, J=8.6 Hz, 1H), 5.73 (br s, 2H), 3.90 (br d, J=2.0 Hz, 3H)

Step 5: Preparation of Compound 3-6

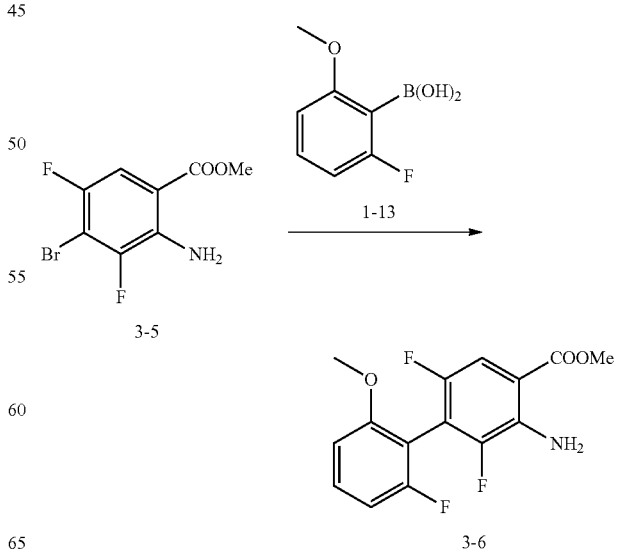

Compound 3-5 (2.3 g, 8.65 mmol), compound 1-13 (2.20 g, 12.97 mmol), methanesulfonato(2-dicyclohexylphosphino-2',6'-di-i-propoxy-1,1'-biphenyl)(2'-amino-1,1'-biphenyl-2-yl)palladium(II) (723 mg, 864.53 μmol), 2-dicyclohexylphosphino-2',6'-di-i-propoxy-1,1'-biphenyl (403 mg, 864.53 μmol) and potassium carbonate (3.58 g, 25.94 mmol) were dissolved in a mixed solution of dioxane (25 mL) and water (5 mL). Under nitrogen atmosphere, the system was heated to 100° C. and stirred for 16 hours. The system was concentrated and dissolved with ethyl acetate (50 mL), filtered and the filtrate was concentrated to obtain a crude product, the crude product was purified by medium pressure column chromatography (ethyl acetate/petroleum ether (v/v)=0-20%) to obtain compound 3-6.

¹H NMR (400 MHz, CDCl₃) δ 7.48 (dd, J=2.0, 9.9 Hz, 1H), 7.42-7.36 (m, 1H), 6.87-6.78 (m, 2H), 5.67 (br s, 2H), 3.92 (s, 3H), 3.82 (s, 3H).

Step 6: Preparation of Compound 3-7

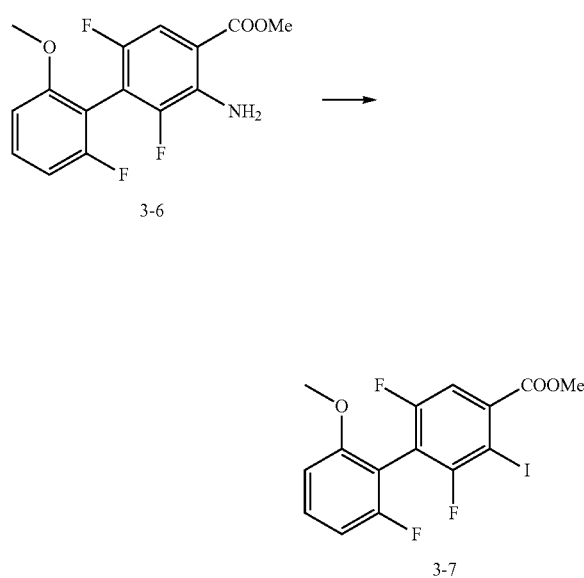

Compound 3-6 (2 g, 6.43 mmol), cuprous iodide (1.24 g, 6.51 mmol), and potassium iodide (2.16 g, 13.01 mmol) were dissolved in acetonitrile (30 mL), and tert-butyl nitrite (1.39 g, 13.45 mmol, 1.60 mL) was added thereto at 0° C. Under nitrogen atmosphere, the system was heated to 80° C. and stirred for 2 hours. The system was filtered, and the filtrate was concentrated to obtain a crude product, the crude product was purified by medium pressure column chromatography (ethyl acetate/petroleum ether (v/v)=0-10%) to obtain compound 3-7.

¹H NMR (400 MHz, CDCl₃) δ 7.50 (dd, J=1.5, 9.0 Hz, 1H), 7.45-7.37 (m, 1H), 6.87-6.78 (m, 2H), 3.98 (s, 3H), 3.86-3.77 (s, 3H).

Step 7: Preparation of Compound 3-8

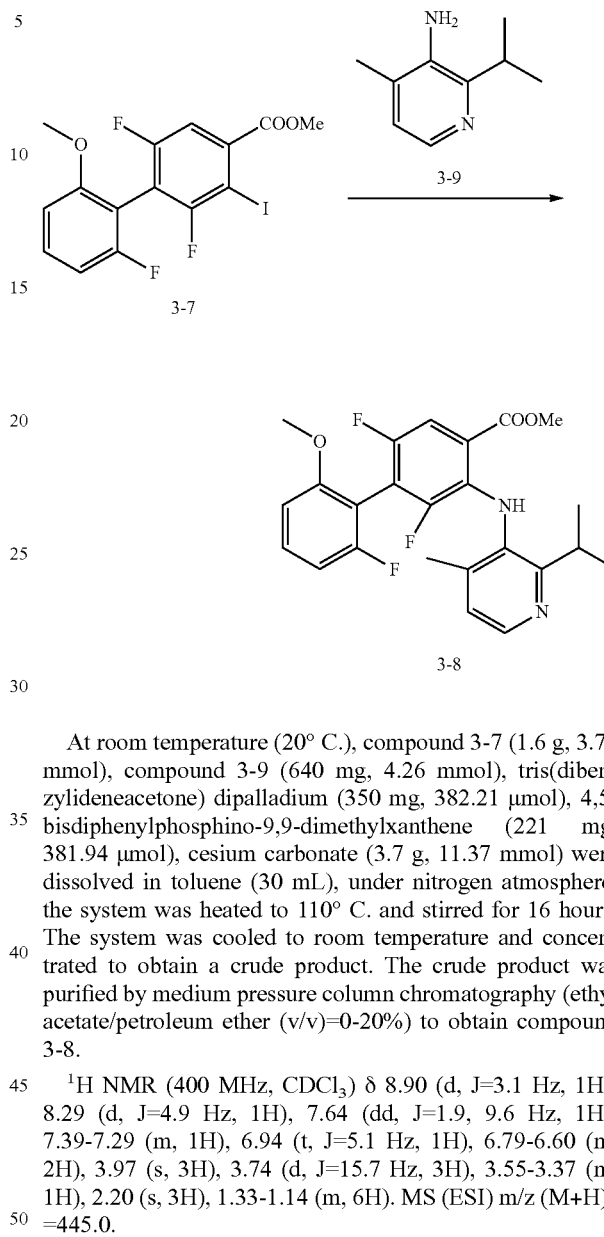

At room temperature (20° C.), compound 3-7 (1.6 g, 3.79 mmol), compound 3-9 (640 mg, 4.26 mmol), tris(dibenzylideneacetone) dipalladium (350 mg, 382.21 μmol), 4,5-bisdiphenylphosphino-9,9-dimethylxanthene (221 mg, 381.94 μmol), cesium carbonate (3.7 g, 11.37 mmol) were dissolved in toluene (30 mL), under nitrogen atmosphere, the system was heated to 110° C. and stirred for 16 hours. The system was cooled to room temperature and concentrated to obtain a crude product. The crude product was purified by medium pressure column chromatography (ethyl acetate/petroleum ether (v/v)=0-20%) to obtain compound 3-8.

¹H NMR (400 MHz, CDCl₃) δ 8.90 (d, J=3.1 Hz, 1H), 8.29 (d, J=4.9 Hz, 1H), 7.64 (dd, J=1.9, 9.6 Hz, 1H), 7.39-7.29 (m, 1H), 6.94 (t, J=5.1 Hz, 1H), 6.79-6.60 (m, 2H), 3.97 (s, 3H), 3.74 (d, J=15.7 Hz, 3H), 3.55-3.37 (m, 1H), 2.20 (s, 3H), 1.33-1.14 (m, 6H). MS (ESI) m/z (M+H)⁺ =445.0.

Step 8: Preparation of Compound 3-10

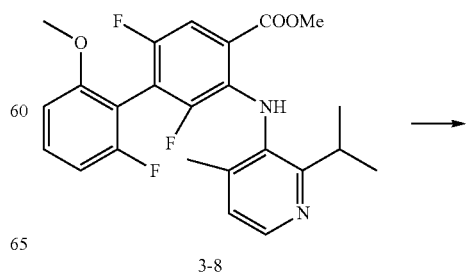

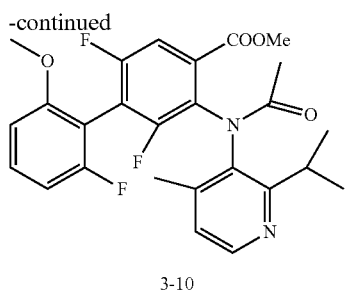

3-10

At room temperature (20° C.), compound 3-8 (1.26 g, 2.83 mmol) was dissolved in N,N-dimethylformamide (15 mL), and sodium hydride (454 mg, 11.35 mmol, purity 60%) was added in batches, after the addition was completed, acetyl chloride (888.59 mg, 11.32 mmol, 807.81 µL) was added dropwise thereto. After the addition was completed, under nitrogen atmosphere, the system was heated to 100° C. and the reaction was carried out for 8 hours. The reaction was quenched by adding saturated ammonium chloride aqueous solution (5 mL) to the system, then added with 30 mL of water and extracted with ethyl acetate (30 mL×2), the organic phase was dried over anhydrous sodium sulfate, filtered and the filtrate was concentrated to obtain a crude product, the crude product was purified by medium pressure column chromatography (ethyl acetate/petroleum ether (v/v)=0-30%) to obtain compound 3-10.

MS (ESI) m/z (M+H)$^+$=487.2.

Step 9: Preparation of Compound 3-11

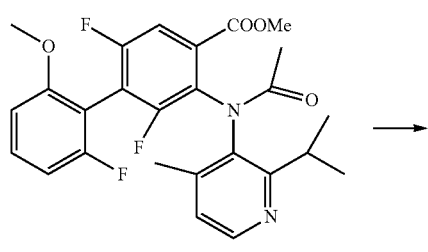

3-10

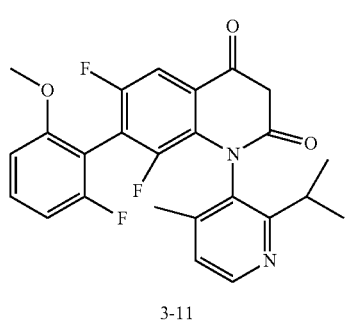

3-11

At room temperature (20° C.), compound 3-10 (800 mg, 1.64 mmol) was dissolved in toluene (15 mL), and potassium tert-butoxide (1 M, 5.33 mL) was added thereto. After the addition was completed, under nitrogen atmosphere, the reaction was carried out at room temperature (20° C.) for 0.5 hours. The reaction was quenched by adding water (20 mL) to the system, the pH was adjusted to neutral with 1N hydrochloric acid; and the mixture was extracted with ethyl acetate (30 mL×3), the organic phase was dried over anhydrous sodium sulfate, filtered, and the filtrate was concentrated to obtain compound 3-11, which were used directly in the next reaction without further purification.

$^1$H NMR (400 MHz, CDCl$_3$) δ 8.55 (t, J=4.5 Hz, 1H), 7.64 (br d, J=8.6 Hz, 1H), 7.39-7.27 (m, 1H), 7.19-7.06 (m, 1H), 6.79-6.65 (m, 2H), 6.41 (s, 1H), 3.72 (s, 1.5H), 3.66 (s, 1.5H), 2.85-2.78 (m, 1H), 2.08 (d, J=5.7 Hz, 3H), 1.31-1.07 (m, 6H).

MS (ESI) m/z (M+H)$^+$=455.1.

Step 10: Preparation of Compound 3-12

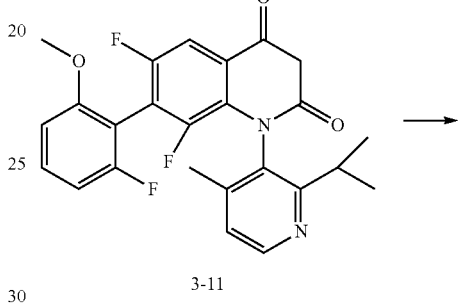

3-11

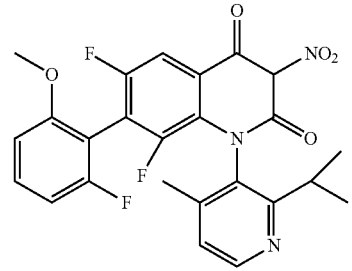

3-12

Compound 3-11 (1 g, 2.20 mmol) was dissolved in glacial acetic acid (20 mL), and nitric acid (2.55 g, 40.40 mmol, 1.82 mL) was added dropwise to the system at room temperature (20° C.). After the dropwise addition was completed, the system was heated to 80° C. and stirred for 2 hours. The system was cooled to room temperature, concentrated to remove most of the glacial acetic acid, and the remainder was poured into ice water (50 mL), precipitated, filtered, and the filter cake was washed with water and dried to obtain compound 3-12, which was used directly in the next step without further purification.

$^1$H NMR (400 MHz, DMSO-d$_6$) δ 8.72 (d, J=5.8 Hz, 1H), 7.97-7.74 (m, 2H), 7.48 (q, J=8.1 Hz, 1H), 7.06-6.83 (m, 2H), 3.74 (s, 1.5H), 3.67 (s, 1.5H), 3.18-3.05 (m, 1H), 2.25 (d, J=7.5 Hz, 3H), 1.30-1.09 (m, 6H).

MS (ESI) m/z (M+H)$^+$=500.5.

Step 11: Preparation of Compound 3-13

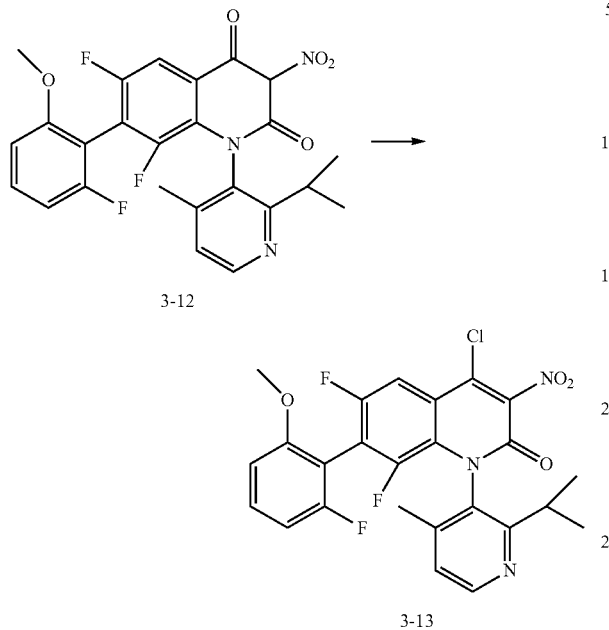

Compound 3-12 (900 mg, 1.80 mmol) and N,N-diisopropylethylamine (1.40 g, 10.81 mmol, 1.88 mL) were dissolved in acetonitrile (10 mL), and at room temperature, phosphorus oxychloride (828.92 mg, 5.41 mmol, 502.38 μL) was added thereto. After the addition was completed, the system was heated to 80° C. and stirred for 2 hours. The system was concentrated to obtain a crude product. The crude product was purified by medium pressure column chromatography (ethyl acetate/petroleum ether (v/v)=0-50%) to obtain compound 3-13.

$^1$H NMR (400 MHz, CDCl$_3$) δ 8.54 (t, J=4.3 Hz, 1H), 7.87-7.84 (m, 1H), 7.42-7.36 (m, 1H), 7.10 (t, J=4.3 Hz, 1H), 6.85-6.67 (m, 2H), 3.76 (s, 1.5H), 3.70 (s, 1.5H), 2.79-2.66 (m, 1H), 2.13 (s, 1.5H), 2.11 (s, 1.5H), 1.28-1.15 (m, 6H).

Step 12: Preparation of Compound 3-14

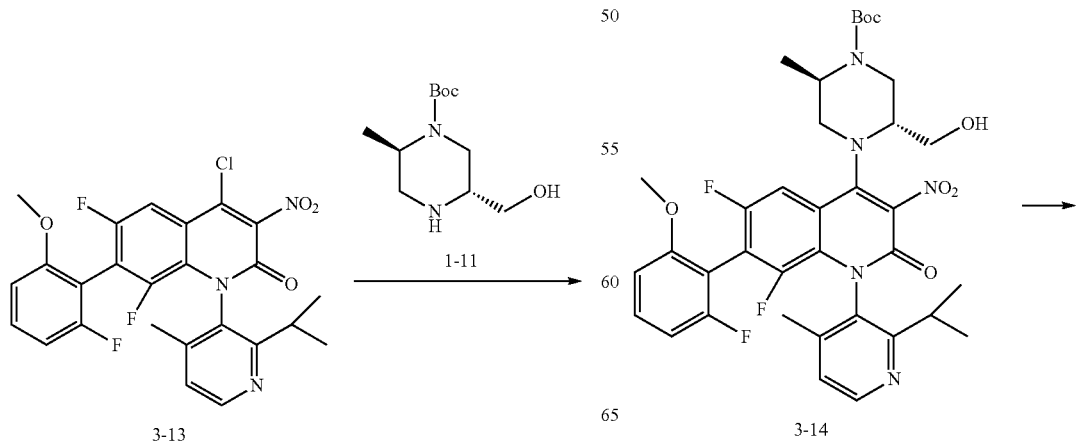

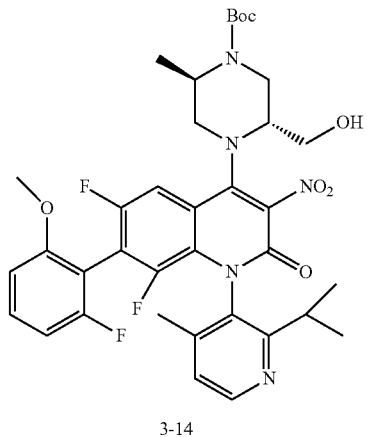

Compound 3-13 (700 mg, 1.35 mmol), compound 1-11 (467 mg, 2.03 mmol), N,N-diisopropylethylamine (873.44 mg, 6.76 mmol, 1.18 mL) were dissolved in acetonitrile (10 mL), under nitrogen atmosphere, the system was heated to 80° C. and stirred for 1 hour. The system was concentrated to obtain a crude product. The crude product was purified by medium pressure column chromatography (ethyl acetate/petroleum ether (v/v)=0-60%) to obtain compound 3-14.

$^1$H NMR (400 MHz, MeOD) δ 8.57-8.36 (m, 1H), 7.77 (br d, J=7.8 Hz, 1H), 7.59-7.41 (m, 1H), 7.33-7.21 (m, 1H), 7.07-6.89 (m, 1H), 6.85-6.75 (m, 1H), 4.45 (br s, 1H), 4.02-3.91 (m, 2H), 3.82-3.65 (m, 6H), 3.16-3.29 (m, 1H), 2.96-2.72 (m, 1H), 2.27-2.07 (m, 3H), 1.60-1.36 (m, 12H), 1.30-1.02 (m, 6H).

MS (ESI) m/z (M+H)$^+$=712.3.

Step 13: Preparation of Compound 3-15

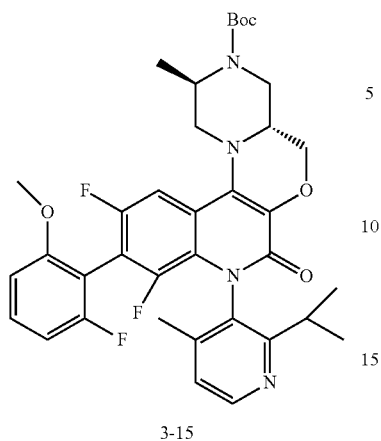

3-15

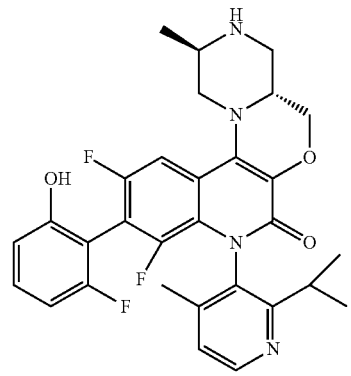

3-16

Compound 3-14 (700 mg, 983.52 μmol) and 4 Å molecular sieve (1 g) were dissolved in N-methylpyrrolidone (10 mL), and tetrahydrofuran solution of lithium bis(trimethylsilyl)amide (1 M, 2.10 mL) was added thereto at room temperature. After the addition was completed, under nitrogen atmosphere, the system was heated to 130° C. and stirred for 24 hours. The system was cooled to room temperature, added with water (50 mL), and then extracted with ethyl acetate (50 mL×2); the organic phase was dried over anhydrous sodium sulfate, filtered, and the filtrate was concentrated to obtain a crude product. The crude product was purified by medium pressure column chromatography (ethyl acetate/petroleum ether (v/v)=0-60%) to obtain compound 3-15.

$^1$H NMR (400 MHz, MeOD) δ 8.42 (d, J=5.1 Hz, 1H), 7.53 (d, J=9.7 Hz, 1H), 7.46-7.34 (m, 1H), 7.24 (br d, J=5.1 Hz, 1H), 6.94-6.85 (m, 1H), 6.79 (t, J=9.0 Hz, 1H), 4.67-4.44 (m, 3H), 4.50-4.35 (m, 1H), 4.21-4.07 (m, 1H), 3.82-3.64 (m, 3H), 3.57-3.39 (m, 2H), 3.14-3.08 (m, 1H), 2.75-2.61 (m, 1H), 2.12-1.98 (m, 3H), 1.64 (br d, J=6.8 Hz, 3H), 1.51 (s, 9H), 1.23-1.04 (m, 6H).

MS (ESI) m/z (M+H)$^+$=665.3.

Step 14: Preparation of Compound 3-16

Compound 3-15 (180 mg, 270.79 μmol) was dissolved in anhydrous dichloromethane (3 mL), and dichloromethane solution of boron tribromide (339.20 mg, 1.35 mmol, 130.46 μL) was added thereto at 0° C. After the addition was completed, under nitrogen atmosphere, the system was raised to room temperature (20° C.) and stirred for 2 hours. Methanol (10 mL) was added to the system and stirred for 10 min. The system was concentrated and lyophilized to obtain compound 3-16 (hydrobromide), which was directly used in the next reaction without further purification.

MS (ESI) m/z (M+H)$^+$=551.3.

Step 15: Preparation of Compounds 3A, 3B, 3C, 3D

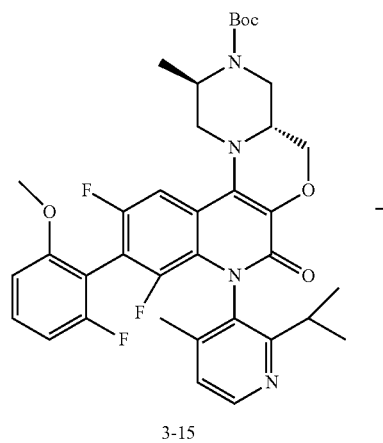

3-15

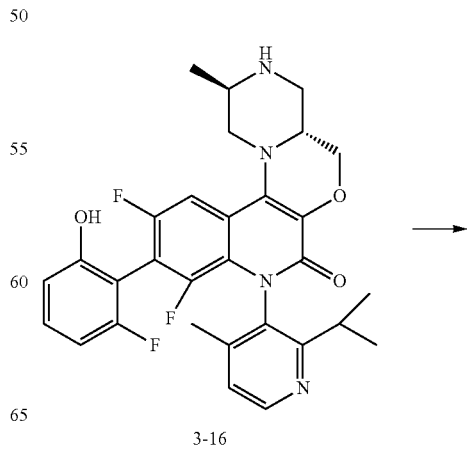

3-16

-continued

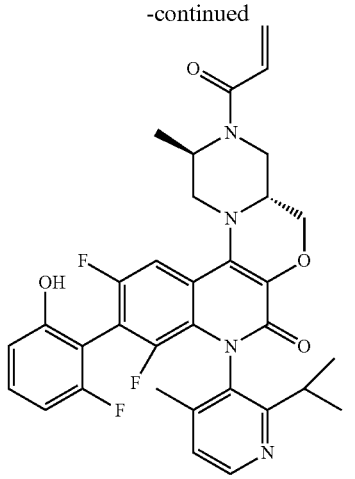

3A or 3B

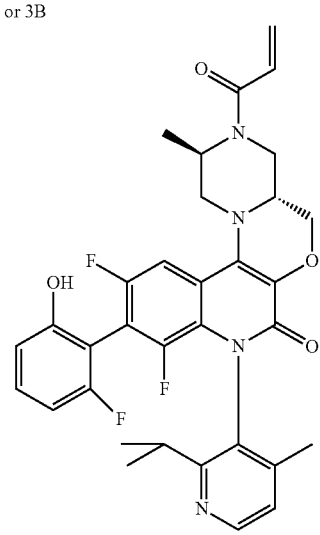

3B or 3A

Compound 3-16 (180 mg, 285.04 μmol, hydrobromide) was dissolved in tetrahydrofuran (5 mL) and saturated sodium bicarbonate aqueous solution (2.62 mL), and acrylic anhydride (43.59 mg, 345.68 μmol) was added thereto at room temperature (20° C.). After the addition was completed, the system was stirred at room temperature (20° C.) for 2 hours. Methanol (3 mL) and lithium hydroxide aqueous solution (21.80 mg, 910.16 μmol) were added to the system, and the mixture was stirred at room temperature (20° C.) for 2 hours. The pH of the system was adjusted to neutral with 1 N hydrochloric acid; and the mixture was extracted with ethyl acetate (10 mL×2), the organic phase was dried over anhydrous sodium sulfate, filtered, and the filtrate was concentrated to obtain a crude product. The crude product was purified by preparative high performance liquid chromatography (Separation conditions: chromatographic column: Phenomenex Gemini-NX 80*30 mm*3 μm; mobile phase: [water (10 mM ammonium bicarbonate solution)-acetonitrile]; acetonitrile %: 41%-51% 9.5 min) to obtain compounds 3A and 3B.

Compound 3A $^1$H NMR (400 MHz, MeOD) δ 8.42 (d, J=4.9 Hz, 1H), 7.54 (br d, J=9.0 Hz, 1H), 7.31-7.16 (m, 2H), 6.86-6.79 (m, 1H), 6.73-6.59 (m, 2H), 6.27 (dd, J=2.0, 16.8 Hz, 1H), 5.81 (d, J=9.7 Hz, 1H), 4.72-4.34 (m, 3H), 4.32-4.09 (m, 1H), 3.82-3.41 (m, 3H), 3.13 (br s, 1H), 2.81-2.60 (m, 1H), 2.20-1.99 (m, 3H), 1.87-1.63 (m, 3H), 1.17-1.04 (m, 6H).

MS (ESI) m/z (M+H)$^+$=605.3.

HPLC 98.77% purity; retention time was 3.72 min.

Separation conditions: chromatographic column: Ultimate C18 3.0*50 mm, 3 μm; column temperature: 40° C.; mobile phase: water (0.0688% trifluoroacetic acid solution)-acetonitrile (0.0625% trifluoroacetic acid solution); acetonitrile: 10%-80% 6 min, 80% 2 min; flow rate: 1.2 mL/min.

Compound 3B $^1$H NMR (400 MHz, MeOD) δ 8.42 (d, J=5.1 Hz, 1H), 7.54 (d, J=7.9 Hz, 1H), 7.33-7.14 (m, 2H), 6.83 (dd, J=10.7, 16.6 Hz, 1H), 6.70-6.53 (m, 2H), 6.27 (dd, J=2.0, 16.8 Hz, 1H), 5.82 (d, J=10.4 Hz, 1H), 4.74-4.33 (m, 3H), 4.31-4.04 (m, 1H), 3.84-3.36 (m, 3H), 3.15 (br s, 1H), 2.87-2.56 (m, 1H), 2.05 (d, J=4.0 Hz, 3H), 1.88-1.59 (m, 3H), 1.23-0.97 (m, 6H).

MS (ESI) m/z (M+H)$^+$=605.3.

HPLC 98.77% purity; retention time was 3.59 min.

Separation conditions: chromatographic column: Ultimate C18 3.0*50 mm, 3 μm; column temperature: 40° C.; mobile phase: water (0.0688% trifluoroacetic acid solution)-acetonitrile (0.0625% trifluoroacetic acid solution); acetonitrile: 10%-80% 6 min, 80% 2 min; flow rate: 1.2 mL/min.

Step 16: Splitting of Isomers of Compound 3A

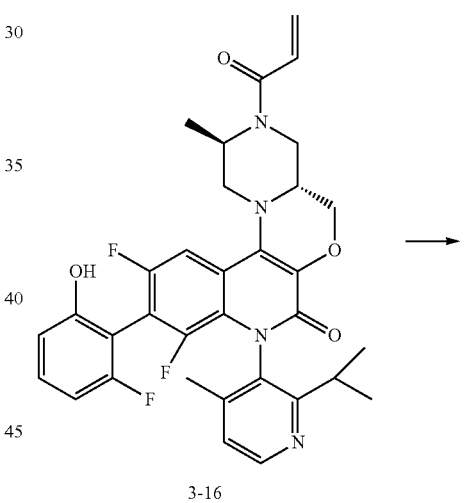

3-16

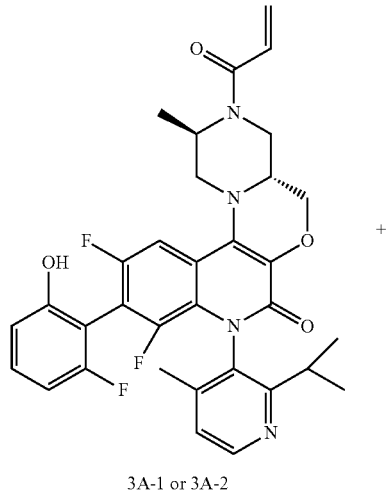

3A-1 or 3A-2

339
-continued

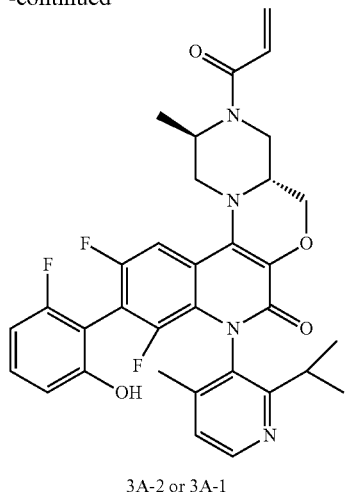

3A-2 or 3A-1

Diastereoisomeric compound 3A was purified by SFC (separation conditions: chromatographic column: DAICEL CHIRALCEL OJ-H (250 mm*30 mm, 5 μm); mobile phase: [0.1% ammonia solution-ethanol]; ethanol %: 30%-30%; flow rate: 60 mL/min). After concentration, compound 3A-1 and compound 3A-2 were obtained.

Compound 3A-1

$^1$H NMR (400 MHz, MeOD) δ 8.42 (d, J=5.1 Hz, 1H), 7.54 (d, J=9.0 Hz, 1H), 7.37-7.10 (m, 2H), 6.82 (dd, J=10.7, 16.6 Hz, 1H), 6.68 (d, J=8.2 Hz, 1H), 6.62 (t, J=8.8 Hz, 1H), 6.27 (dd, J=1.8, 16.8 Hz, 1H), 5.81 (d, J=10.4 Hz, 1H), 4.68-4.54 (m, 2H), 4.50-4.38 (m, 1H), 4.31-4.05 (m, 1H), 3.81-3.37 (m, 3H), 3.17-3.08 (m, 1H), 2.69-2.62 (m, 1H), 2.05 (s, 3H), 1.86-1.52 (m, 3H), 1.15 (d, J=6.8 Hz, 3H), 1.06 (d, J=6.8 Hz, 3H).

MS (ESI) m/z (M+H)$^+$=605.3.

HPLC 97.74% purity; retention time was 3.606 min.

Separation conditions: chromatographic column Xbridge C18, 5 μm, 2.1*50 mm; column temperature: 50° C.; mobile phase: water (0.02% ammonia solution)-acetonitrile; acetonitrile: 10%-80% 6 min, 80% 2 min; flow rate: 0.8 mL/min.

SFC 100% ee. Retention time was 3.864 min.

Compound 3A-2

$^1$H NMR (400 MHz, MeOD) δ 8.42 (d, J=4.9 Hz, 1H), 7.54 (br d, J=7.9 Hz, 1H), 7.33-7.14 (m, 2H), 6.82 (dd, J=10.6, 16.8 Hz, 1H), 6.71-6.56 (m, 2H), 6.27 (dd, J=1.8, 16.8 Hz, 1H), 5.81 (br d, J=10.8 Hz, 1H), 4.61 (br s, 2H), 4.53-4.09 (m, 2H), 3.81-3.40 (m, 3H), 3.14 (br s, 1H), 2.80-2.66 (m, 1H), 2.03 (s, 3H), 1.80-1.66 (m, 3H), 1.15-1.10 (m, 6H).

MS (ESI) m/z (M+H)$^+$=605.3.

HPLC 95.13% purity; retention time was 3.674 min.

Separation conditions: chromatographic column Xbridge C18, 5 μm, 2.1*50 mm; column temperature: 50° C.; mobile phase: water (0.02% ammonia solution)-acetonitrile; acetonitrile: 10%-80% 6 min, 80% 2 min; flow rate: 0.8 mL/min.

SFC 98.88% ee. Retention time was 4.332 min.

340

Step 17: Splitting of Isomers of Compound 3B

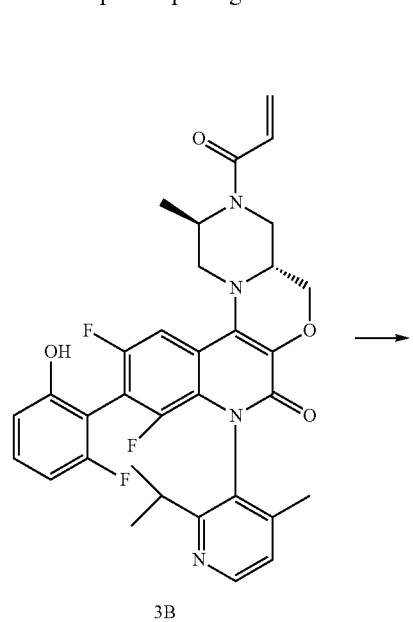

3B

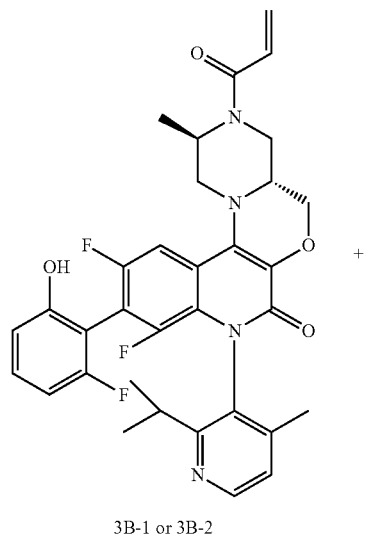

3B-1 or 3B-2

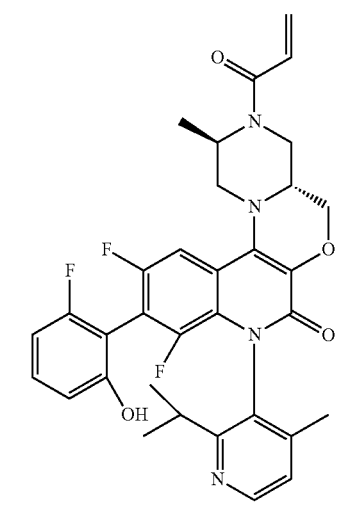

3B-2 or 3B-1

Diastereoisomeric compound 3B was purified by SFC (separation conditions: chromatographic column: DAICEL CHIRALCEL OJ-H (250 mm*30 mm, 5 µm); mobile phase: [0.1% ammonia solution-ethanol]; ethanol %: 30%-30%; flow rate: 60 mL/min). After concentration, compound 3B-1 and compound 3B-2 were obtained.

Compound 3B-1

$^1$H NMR (400 MHz, MeOD) δ 8.42 (d, J=5.1 Hz, 1H), 7.54 (br d, J=9.0 Hz, 1H), 7.34-7.12 (m, 2H), 6.82 (dd, J=10.7, 16.6 Hz, 1H), 6.75-6.51 (m, 2H), 6.27 (dd, J=1.8, 16.8 Hz, 1H), 5.81 (br d, J=10.1 Hz, 1H), 4.74-4.57 (m, 2H), 4.45 (d, J=10.1 Hz, 1H), 4.31-4.09 (m, 1H), 3.74 (br d, J=9.7 Hz, 1H), 3.63-3.43 (m, 2H), 3.15-3.08 (m, 1H), 2.69-2.62 (m, 1H), 2.05 (s, 3H), 1.86-1.61 (m, 3H), 1.13 (dd, J=6.7, 13.1 Hz, 6H).

MS (ESI) m/z (M+H)$^+$=605.3.

HPLC 95.70% purity; retention time was 3.669 min.

Separation conditions: chromatographic column Xbridge C18, 5 µm, 2.1*50 mm; column temperature: 50° C.; mobile phase: water (0.02% ammonia solution)-acetonitrile; acetonitrile: 10%-80% 6 min, 80% 2 min; flow rate: 0.8 mL/min.

SFC 100% ee. Retention time was 3.978 min.

Compound 3B-2

$^1$H NMR (400 MHz, MeOD) δ 8.42 (d, J=4.9 Hz, 1H), 7.54 (br d, J=8.8 Hz, 1H), 7.31-7.14 (m, 2H), 6.82 (dd, J=10.8, 16.8 Hz, 1H), 6.68 (d, J=8.4 Hz, 1H), 6.62 (t, J=8.7 Hz, 1H), 6.27 (br dd, J=1.8, 16.8 Hz, 1H), 5.81 (br d, J=10.6 Hz, 1H), 4.65 (br d, J=13.2 Hz, 1H), 4.56-4.34 (m, 2H), 4.27-4.07 (m, 1H), 3.83-3.43 (m, 3H), 3.15 (br s, 1H), 2.76-2.63 (m, 1H), 2.04 (s, 3H), 1.86-1.59 (m, 3H), 1.15 (d, J=6.6 Hz, 3H), 1.07 (d, J=6.8 Hz, 3H).

MS (ESI) m/z (M+H)$^+$=605.3.

HPLC 98.65% purity; retention time was 3.581 min.

Separation conditions: chromatographic column Xbridge C18, 5 µm, 2.1*50 mm; column temperature: 50° C.; mobile phase: water (0.02% ammonia solution)-acetonitrile; acetonitrile: 10%-80% 6 min, 80% 2 min; flow rate: 0.8 mL/min.

SFC 100% ee. Retention time was 4.607 min.

Embodiment 4: Preparation of Compound 4

Step 1: Preparation of Compound 4-2

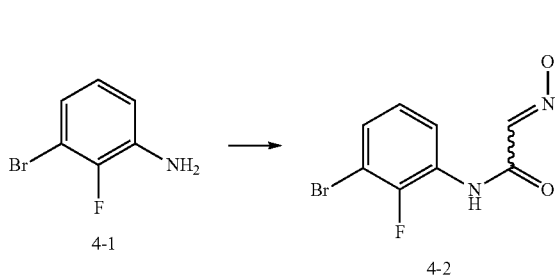

The raw materials chloral hydrate (22 g, 133.01 mmol, 17.32 mL) and sodium sulfate (168.20 g, 1.18 mol, 120.14 mL) were dissolved in water (360 mL), the system was heated to 35° C., and the aqueous solution (120 mL) of raw material 4-1 (25 g, 131.57 mmol), hydrochloric acid (12 M, 14.80 mL) and hydroxylamine hydrochloride (29.26 g, 421.02 mmol) were added successively. After the addition was completed, the system was heated to 90° C. and reacted for 16 hours. A yellow precipitate appeared in the system, the system was cooled to room temperature and filtered to obtain a filter cake, the filter cake was washed with water, dissolved with ethyl acetate (300 mL), filtered, and the filtrate was concentrated to obtain compound 4-2, which was directly used in the next reaction without further purification. MS (ESI) m/z (M+H)$^+$=262.9.

Step 2: Preparation of Compound 4-3

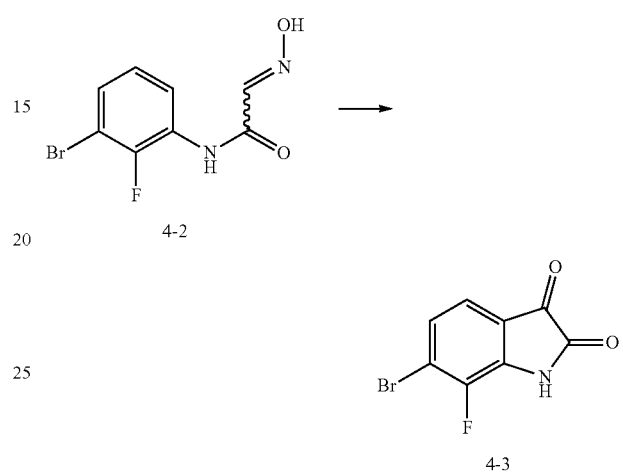

Compound 4-2 (30.8 g, 117.99 mmol) was added to concentrated sulfuric acid (460.00 g, 4.60 mol, 250 mL, purity 98%) at 60° C. After the addition was completed, the system was heated to 90° C. and stirred for 3 hours. The system was cooled to room temperature, poured into ice water, yellow precipitate was precipitated, filtered to obtain yellow solid 4-3, which was directly used in the next reaction without further purification.

Step 3: Preparation of Compound 4-4

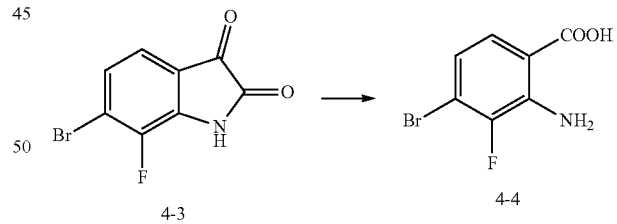

Compound 4-3 (22 g, 90.16 mmol) was dissolved in sodium hydroxide aqueous solution (2 M, 225.39 mL), and hydrogen peroxide (51.11 g, 450.79 mmol, 43.31 mL, purity 30%) was added dropwise thereto at 0° C. After the dropwise addition was completed, the system was stirred at 0° C. for 0.5 hours, and then raised to room temperature (20° C.) and stirred for 16 hours. The system was poured into ice water (400 mL), and the pH was adjusted to 6 with concentrated hydrochloric acid, the system was precipitated and filtered to obtain a filter cake, the filter cake was dried to obtain compound 3-4, which was directly used in the next reaction without further purification.

Step 4: Preparation of Compound 4-5

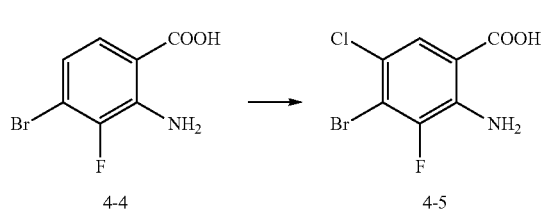 [SMILES: Nc1c(C(=O)O)ccc(Br)c1F ; Nc1c(C(=O)O)cc(Cl)c(Br)c1F]

Compound 4-4 (20.5 g, 87.60 mmol) was dissolved in N,N-dimethylformamide (100 mL), and N-chlorosuccinimide (11.70 g, 87.60 mmol) was added thereto at room temperature (20° C.). After the addition was completed, under nitrogen atmosphere, the system was heated to 70° C. and stirred for 16 hours. The system was cooled to room temperature, then poured into ice water, the system was precipitated, filtered to obtain a filter cake, the filter cake was washed and dried to obtain compound 4-5, which was directly used in the next reaction without further purification.

Step 5: Preparation of Compound 4-6

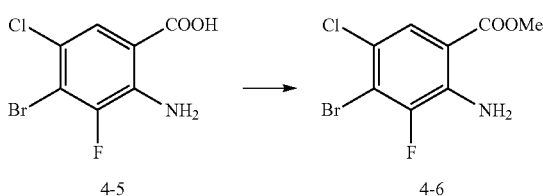 [SMILES: Nc1c(C(=O)O)cc(Cl)c(Br)c1F ; COC(=O)c1cc(Cl)c(Br)c(F)c1N]

Compound 4-5 (15 g, 55.87 mmol) was dissolved in methanol (100 mL), and thionyl chloride (67.50 g, 567.37 mmol, 41.16 mL) was added dropwise thereto, under nitrogen atmosphere, the system was heated to 75° C. and stirred for 16 hours. The system was concentrated and the crude product was dissolved with ethyl acetate (200 mL), the organic phase was washed with saturated sodium bicarbonate aqueous solution (80 mL) and saturated saline (80 mL), dried over anhydrous sodium sulfate, filtered and the filtrate was concentrated to obtain a crude product, the crude product was purified by medium pressure column chromatography (ethyl acetate/petroleum ether (v/v)=0-10%) to obtain compound 4-6.

$^1$H NMR (400 MHz, DMSO-$d_6$) δ 7.68 (d, J=2.0 Hz, 1H), 6.86 (s, 2H), 3.83 (s, 3H).

MS (ESI) m/z (M+H)$^+$=283.8.

Step 6: Preparation of Compound 4-8

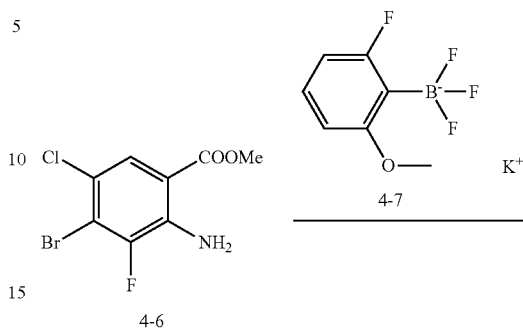

Compound 4-6 (6 g, 21.24 mmol), compound 4-7 (10 g, 43.10 mmol), tris(dibenzylideneacetone)dipalladium (840 mg, 1.46 mmol), 2-dicyclohexylphosphino-2,4,6-triisopropylbiphenyl (2.03 g, 4.25 mmol), and potassium carbonate (7.34 g, 53.10 mmol) were dissolved in a mixed solution of dioxane (100 mL) and water (20 mL). Under nitrogen atmosphere, the system was heated to 100° C. and stirred for 16 hours. The system was concentrated, then separated and extracted with ethyl acetate (50 mL×2) and water (80 mL), the organic phase was dried over anhydrous sodium sulfate, filtered and the filtrate was concentrated to obtain a crude product, the crude product was purified by medium pressure column chromatography (ethyl acetate/petroleum ether (v/v)=0-10%) to obtain compound 4-8.

$^1$H NMR (400 MHz, DMSO-$d_6$) δ 7.83-7.77 (m, 1H), 7.67 (d, J=1.7 Hz, 1H), 7.03 (d, J=8.5 Hz, 1H), 6.96 (t, J=8.7 Hz, 1H), 6.73 (s, 2H), 3.86 (s, 3H), 3.77 (s, 3H).

MS (ESI) m/z (M+H)$^+$=328.0.

Step 7: Preparation of Compound 4-9

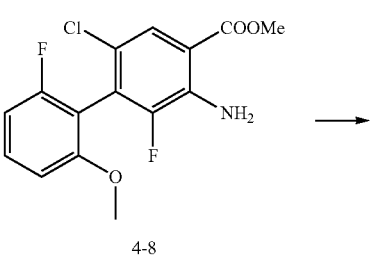

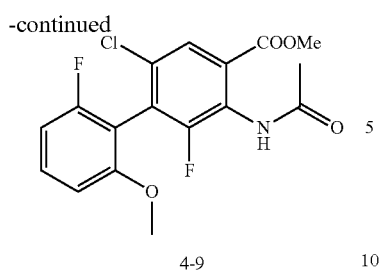

4-9

Compound 4-8 (4.8 g, 14.65 mmol) was dissolved in glacial acetic acid (50 mL), and acetic anhydride (4.49 g, 43.94 mmol, 4.12 mL) was added dropwise at 0° C., and the system was heated to room temperature (20° C.) to react for 36 hours. The system was concentrated to obtain a crude product, the crude product was purified by medium pressure column chromatography (ethyl acetate/petroleum ether (v/v)=0-100%) to obtain compound 4-9.

$^1$H NMR (400 MHz, DMSO-d$_6$) δ 10.05 (s, 1H), 7.71 (s, 1H), 7.54 (q, J=8.1 Hz, 1H), 7.06 (d, J=8.5 Hz, 1H), 6.99 (t, J=8.7 Hz, 1H), 3.79 (s, 3H), 3.77 (s, 3H), 2.03 (s, 3H).

MS (ESI) m/z (M+H)$^+$=370.0.

Step 8: Preparation of Compound 4-10

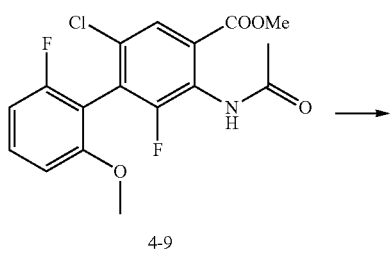

4-9

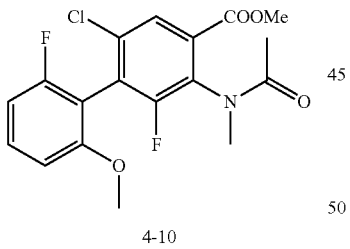

4-10

Compound 4-9 (4 g, 10.82 mmol) and potassium carbonate (4.49 g, 32.45 mmol) were dissolved in N,N-dimethylformamide (40 mL), iodomethane (4.61 g, 32.45 mmol, 2.02 mL) was added thereto. The system was stirred at room temperature (20° C.) for 16 hours. The system was filtered, the filtrate was poured into water (100 mL), extracted with ethyl acetate (100 mL×2); the organic phases were combined, and the organic phase was dried over anhydrous sodium sulfate, filtered and the filtrate was concentrated to obtain a crude product, the crude product was purified by medium pressure column chromatography (ethyl acetate/petroleum ether (v/v)=0-50%) to obtain compound 4-10.

MS (ESI) m/z (M+H)$^+$=384.0.

Step 9: Preparation of Compound 4-11

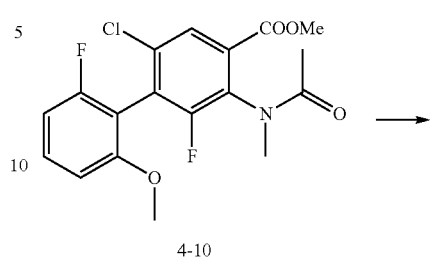

4-10

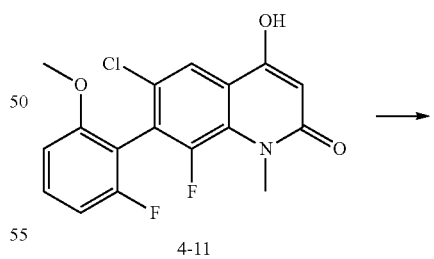

4-11

At room temperature (20° C.), compound 4-10 (4.1 g, 10.68 mmol) was dissolved in toluene (60 mL), and potassium tert-butoxide (1 M, 21.37 mL) was added thereto. After the addition was completed, under nitrogen atmosphere, the reaction was carried out at room temperature (20° C.) for 4 hours. The reaction was quenched by adding 1 M hydrochloric acid to the system, diluted with water (80 mL), extracted with ethyl acetate (80 mL×3), the organic phase was dried over anhydrous sodium sulfate, filtered, and the filtrate was concentrated to obtain a crude product, the crude product was slurried with methanol to obtain compound 4-11, which was directly used in the next reaction without further purification.

$^1$H NMR (400 MHz, DMSO-d$_6$) δ 11.88 (s, 1H), 7.84 (s, 1H), 7.54 (q, J=7.8 Hz, 1H), 7.10-6.95 (m, 2H), 5.98 (s, 1H), 3.78 (s, 3H), 3.65 (d, J=9.3 Hz, 3H).

MS (ESI) m/z (M+H)$^+$=351.9.

Step 10: Preparation of Compound 4-12

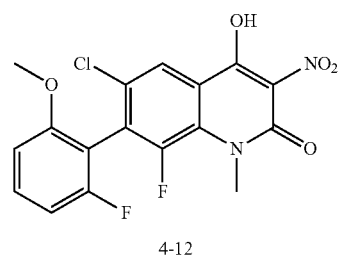

4-12

Compound 4-11 (1 g, 2.84 mmol) was dissolved in glacial acetic acid (20 mL), and nitric acid (2.80 g, 44.44 mmol, 2 mL) was added dropwise to the system at room temperature (20° C.). After the dropwise addition was completed, the system was heated to 80° C. and stirred for 1 hour. The system was cooled to room temperature, concentrated to remove most of the glacial acetic acid; the residue was poured into ice water (25 mL) and extracted with ethyl acetate (20 mL×2); the organic phase was dried over anhydrous sodium sulfate, filtered, and the filtrate was concentrated to obtain compound 4-12, which was used directly in the next step without further purification.

$^1$H NMR (400 MHz, CDCl$_3$) δ 13.53 (br s, 1H), 8.21 (d, J=1.8 Hz, 1H), 7.47 (t, J=6.8, 8.4 Hz, 1H), 6.91-6.83 (m, 2H), 3.87 (d, J=8.8 Hz, 3H), 3.82 (s, 3H).

MS (ESI) m/z (M+H)$^+$=397.0.

Step 11: Preparation of Compound 4-13

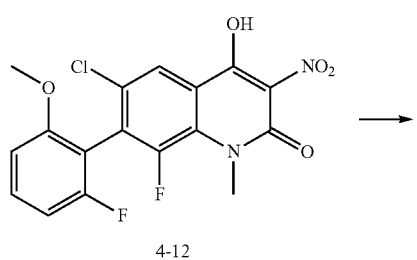

4-12

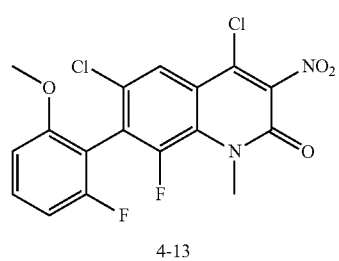

4-13

Compound 4-12 (1.1 g, 2.77 mmol) and N,N-diisopropylethylamine (1.43 g, 11.09 mmol, 1.93 mL) were dissolved in acetonitrile (10 mL), and at room temperature, phosphorus oxychloride (1.32 g, 8.61 mmol, 800 μL) was added thereto. After the addition was completed, the system was heated to 80° C. and stirred for 1 hour. The system was cooled to room temperature and concentrated to obtain a crude product. The crude product was purified by medium pressure column chromatography (ethyl acetate/petroleum ether (v/v)=0-10%) to obtain compound 4-13.

$^1$H NMR (400 MHz, CDCl$_3$) δ 8.07 (d, J=1.8 Hz, 1H), 7.48 (t, J=6.8, 8.4 Hz, 1H), 6.91-6.83 (m, 2H), 3.96 (d, J=9.3 Hz, 3H), 3.82 (s, 3H).

MS (ESI) m/z (M+H)$^+$=414.9.

Step 12: Preparation of Compound 4-14

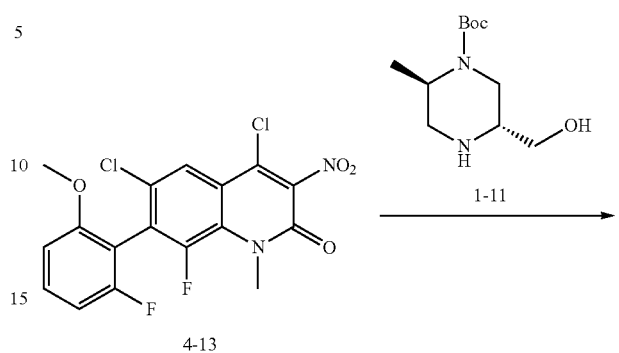

4-13

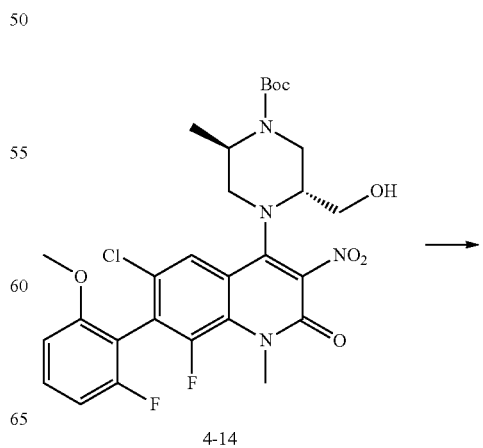

4-14

Compound 4-13 (0.8 g, 1.93 mmol), compound 1-11 (621.28 mg, 2.70 mmol), N,N-diisopropylethylamine (747.10 mg, 5.78 mmol, 1.01 mL) were dissolved in acetonitrile (10 mL), under nitrogen atmosphere, the system was heated to 80° C. and stirred for 3 hours. The system was concentrated to obtain a crude product. The crude product was purified by medium pressure column chromatography (ethyl acetate/petroleum ether (v/v)=0-30%) to obtain compound 4-14.

$^1$H NMR (400 MHz, MeOD) δ 7.91 (s, 1H), 7.52 (dt, J=6.8, 8.4 Hz, 1H), 7.00 (d, J=8.3 Hz, 1H), 6.89 (t, J=8.7 Hz, 1H), 4.38 (br s, 1H), 4.16 (br d, J=13.8 Hz, 1H), 3.88-3.74 (m, 8H), 3.72-3.52 (m, 3H), 2.98 (br d, J=12.3 Hz, 1H), 1.50 (s, 9H), 1.34 (d, J=6.8 Hz, 3H).

MS (ESI) m/z (M+H)$^+$=609.1.

Step 13: Preparation of Compound 4-15

-continued

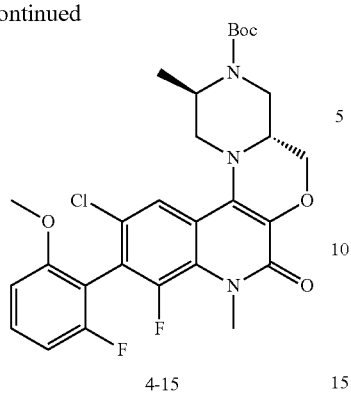

4-15

-continued

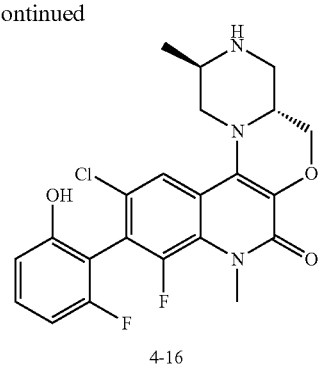

4-16

Compound 4-14 (0.86 g, 1.41 mmol) and 4 Å molecular sieve (0.5 g) were dissolved in N-methylpyrrolidone (10 mL), and tetrahydrofuran solution of lithium bis(trimethylsilyl)amide (1 M, 2.82 mL) was added thereto at room temperature. After the addition was completed, under nitrogen atmosphere, the system was heated to 140° C. and stirred for 5 hours. The system was cooled to room temperature and filtered, the filtrate was diluted with ethyl acetate (80 mL) and washed with water (60 mL×2) and saturated saline (60 mL) successively. The organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain a crude product, the crude product was purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 60%-90% 9.5 min) to obtain compound 4-15.

$^1$H NMR (400 MHz, MeOD) δ 7.76 (s, 1H), 7.51-7.44 (m, 1H), 6.97 (d, J=8.5 Hz, 1H), 6.86 (t, J=8.5 Hz, 1H), 4.60 (s, 1H), 4.51-4.39 (m, 2H), 4.33 (dd, J=2.8, 10.8 Hz, 1H), 4.10 (d, J=14.8 Hz, 1H), 3.92 (br s, 1H), 3.88 (d, J=9.0 Hz, 3H), 3.80 (s, 3H), 3.37 (br d, J=12.5 Hz, 1H), 3.00 (br d, J=12.8 Hz, 1H), 1.60 (d, J=7.0 Hz, 3H), 1.50 (s, 9H).

MS (ESI) m/z (M+H)$^+$=562.1.

Step 14: Preparation of Compound 4-16

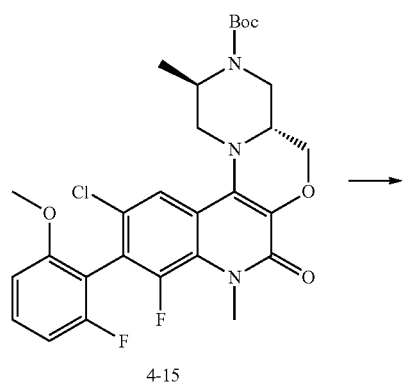

4-15

Compound 4-15 (0.08 g, 142.35 μmol) was dissolved in anhydrous dichloromethane (1 mL), and dichloromethane solution of boron tribromide (260 mg, 1.04 mmol, 0.1 mL) was added thereto at 0° C. After the addition was completed, under nitrogen atmosphere, the system was raised to room temperature (20° C.) and stirred for 2 hours. Methanol (2 mL) was added to the system and stirred for 10 min. The system was concentrated to obtain compound 4-16 (hydrobromide), which was directly used in the next reaction without further purification.

Step 15: Preparation of Compounds 4A and 4B

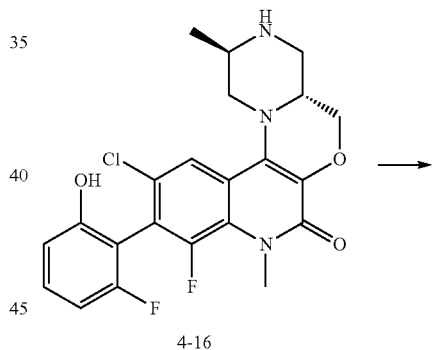

4-16

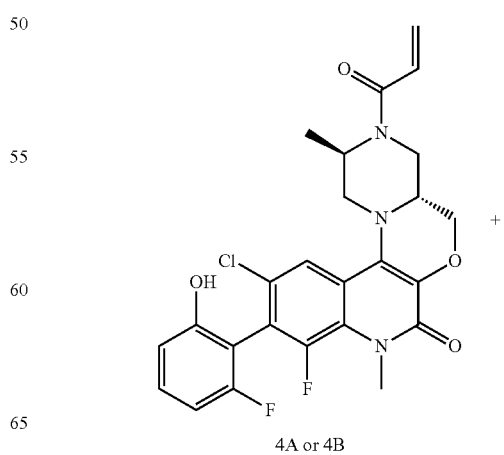

4A or 4B

-continued

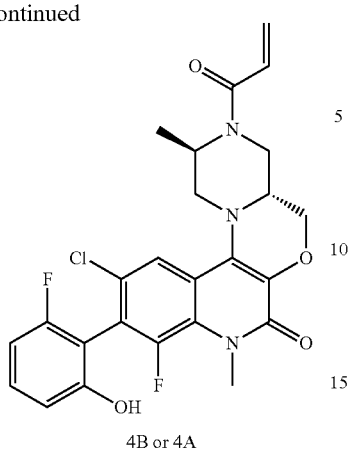

4B or 4A

Compound 3-17 (0.1 g, 189.12 μmol, hydrobromide) was dissolved in tetrahydrofuran (5 mL) and saturated sodium bicarbonate aqueous solution (2.82 mL), and acrylic anhydride (0.02 g, 158.59 μmol) was added thereto at room temperature (20° C.). After the addition was completed, the system was stirred at room temperature (20° C.) for 2 hours. Methanol (3 mL) and aqueous solution of lithium hydroxide (31.74 mg, 756.47 μmol) were added to the system, and the mixture was stirred at room temperature (20° C.) for 2 hours. The pH of the system was adjusted to neutral with 1 N hydrochloric acid; and the mixture was extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 43%-73% 9.5 min) to obtain compounds 4A and 4B.

Compound 4A
$^1$H NMR (400 MHz, MeOD) δ 7.78 (br s, 1H), 7.34-7.26 (m, 1H), 6.87-6.66 (m, 3H), 6.26 (dd, J=1.8, 16.8 Hz, 1H), 5.80 (br d, J=9.5 Hz, 1H), 4.67-4.03 (m, 4H), 3.89 (d, J=9.0 Hz, 3H), 3.72 (br s, 1H), 3.46 (br d, J=14.6 Hz, 2H), 3.03 (br d, J=10.0 Hz, 1H), 1.77-1.61 (m, 3H).

MS (ESI) m/z (M+H)$^+$=502.2.

HPLC 96.17% purity; retention time was 9.28 min.

Separation conditions: chromatographic column: YMC-Pack ODS-A 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 4B
$^1$H NMR (400 MHz, MeOD) δ 7.78 (br s, 1H), 7.35-7.25 (m, 1H), 6.86-6.67 (m, 3H), 6.26 (dd, J=1.9, 16.7 Hz, 1H), 5.81 (br s, 1H), 4.69-4.04 (m, 4H), 3.89 (d, J=9.0 Hz, 3H), 3.70 (br d, J=15.3 Hz, 1H), 3.47 (br d, J=11.8 Hz, 2H), 3.03 (br s, 1H), 1.78-1.62 (m, 3H). MS (ESI) m/z (M+H)$^+$=502.2.

HPLC 97.7% purity; retention time was 9.60 min.

Separation conditions: chromatographic column: YMC-Pack ODS-A 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Embodiment 5: Preparation of Compound 5

Step 1: Preparation of Compound 5-1

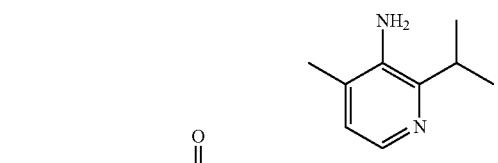

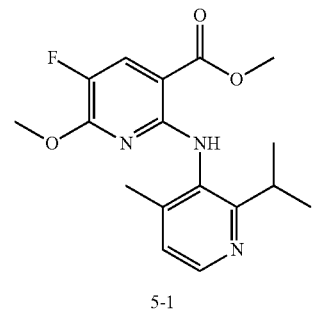

5-1

At room temperature (20° C.), compound 1-3 (29.57 g, 135.0 mmol, 1.0 eq), compound 3-9 (20.25 g, 135.0 mmol, 1.0 eq), palladium acetate (3.038 g, 13.5 mmol, 0.1 eq), 4,5-bis(diphenylphosphino)-9,9-dimethylxanthene (7.817 g, 13.5 mmol, 0.1 eq), cesium carbonate (88.02 g, 270.0 mmol, 2.0 eq) were dissolved in anhydrous dioxane (270 mL), under nitrogen atmosphere, the system was heated to 120° C. and stirred for 3 hours. The system was cooled to room temperature, quenched with saturated ammonium chloride aqueous solution (1 L), extracted with ethyl acetate (3×500 mL); then the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-10%) to obtain compound 5-1.

MS (ESI) m/z (M+H)$^+$=334.1.

Step 2: Preparation of Compound 5-2

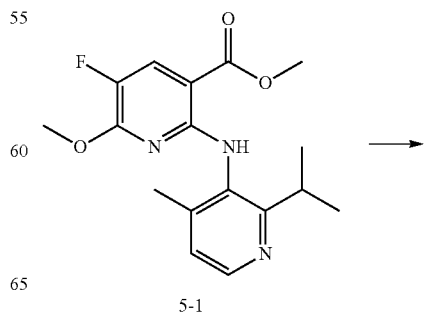

5-1

-continued

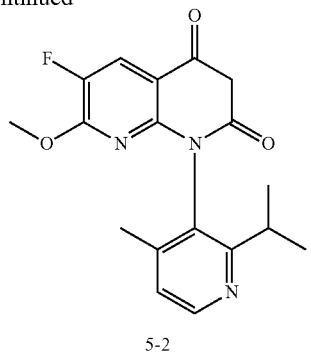
5-2

Compound 5-1 (13.32 g, 40 mmol, 1.0 eq) was dissolved in N,N-dimethylformamide (150 mL), and sodium hydride (4.8 g, 120 mmol, 3.0 eq) was added in batches at room temperature (20° C.), after the addition was completed, the system was stirred at room temperature (20° C.) for 10 min, acetyl chloride (7.02 g, 120 mmol, 3.0 eq) was added dropwise thereto. After the dropwise addition was completed, the system was heated to 100° C. and stirred for 2 hours. The system was cooled to room temperature, saturated ammonium chloride aqueous solution (50 mL) was added to quench the reaction, diluted with 1000 mL of water, extracted with ethyl acetate (3×500 mL); the organic phases were combined, and the organic phase was dried over anhydrous sodium sulfate, filtered; the filtrate was concentrated to obtain a crude product, the crude product was purified by reverse-phase medium pressure column chromatography (acetonitrile/water (v/v)=30-45%) to obtain compound 5-2.

MS (ESI) m/z (M+H)⁺=344.1.

Step 3: Preparation of Compound 5-3

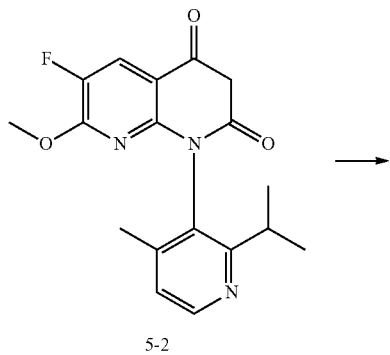
5-2

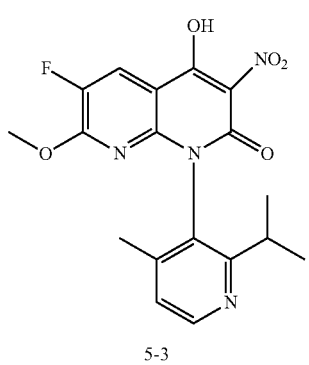
5-3

Compound 5-2 (688 mg, 2 mmol) was dissolved in acetic acid (10 mL), and concentrated nitric acid (2 mL) was added dropwise thereto at room temperature; after the dropwise addition was completed, the system was heated to 50° C. and stirred for 1 hour. The system was cooled to room temperature and poured into ice water (100 mL), the pH was adjusted to neutral with 10 N sodium hydroxide, extracted with ethyl acetate (4×100 mL), the organic phases were combined, and the organic phase was dried over anhydrous sodium sulfate, filtered, and the filtrate was concentrated to obtain compound 5-3, which was used directly in the next reaction without further purification.

MS (ESI) m/z (M+H)⁺=389.40.

Step 4: Preparation of Compound 5-4

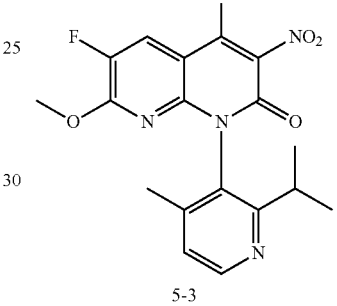
5-3

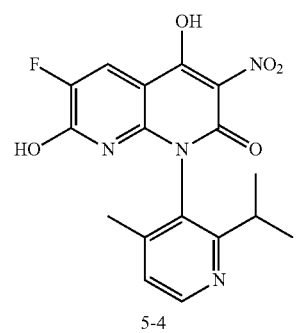
5-4

Compound 5-3 (300 mg, 0.77 mmol) was dissolved in acetic acid (3 mL), and hydrobromic acid (48%, 1.5 mL) was added thereto at room temperature. After the addition was completed, the system was heated to 100° C. and stirred for 16 hours. The reaction mixture was cooled to room temperature and concentrated to obtain crude compound 5-4, which was directly used in the next reaction without further purification.

MS (ESI) m/z (M+H)⁺=375.00.

Step 5: Preparation of Compound 5-5

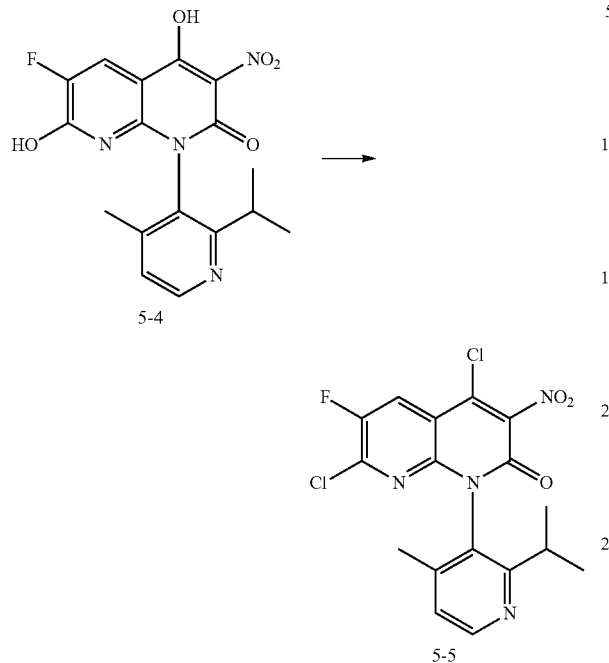

Compound 5-4 (290 mg, 0.77 mmol) and N,N-diisopropylethylamine (0.77 mL, 4.64 mmol) were dissolved in acetonitrile (10 mL), and phosphorus oxychloride (0.44 mL) was added thereto at room temperature, and the reaction system turned black. The system was heated to 80° C. and stirred for 1 hour. The system was concentrated, and the crude product was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-15%) to obtain compound 5-5.

MS (ESI) m/z (M+H)$^+$=411.00.

Step 6: Preparation of Compound 5-6

Compound 5-5 (120 mg, 0.3 mmol), compound 1-11 (73 mg, 0.315 mmol), cuprous iodide (57.3 mg, 0.3 mmol), and cesium carbonate (197 mg, 0.6 mmol) were dissolved in dioxane (4 mL), under nitrogen atmosphere, the system was heated to 100° C. and stirred for 2 hours. The system was filtered by diatomite, and the filtrate was concentrated to obtain a crude product. The crude product was purified by medium pressure column chromatography (ethyl acetate/petroleum ether (v/v)=0-40%) to obtain compound 5-6.

MS (ESI) m/z (M+H)$^+$=605.20.

Step 7: Preparation of Compound 5-7

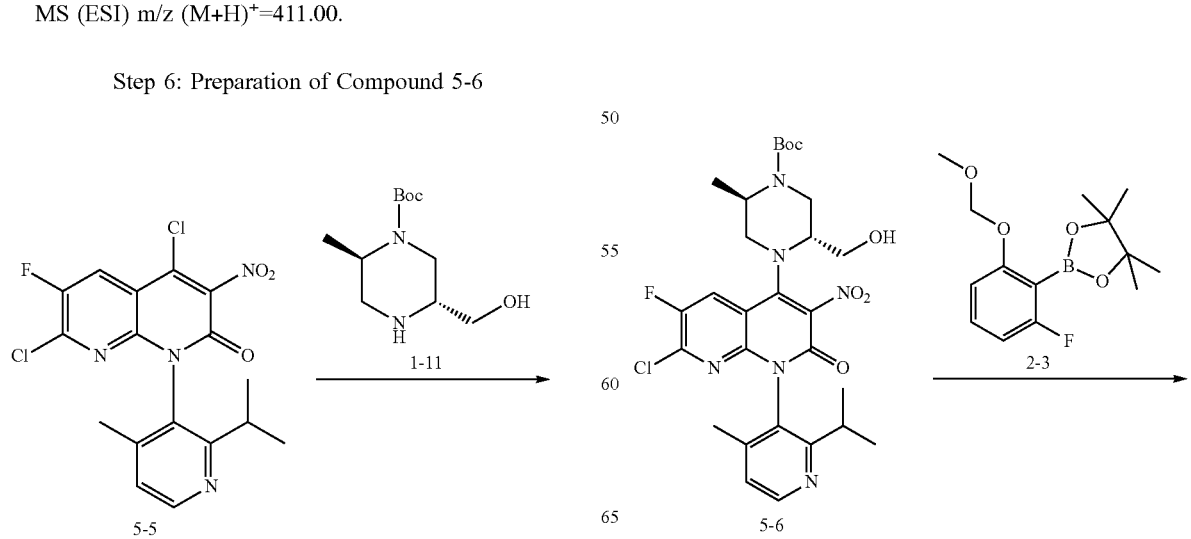

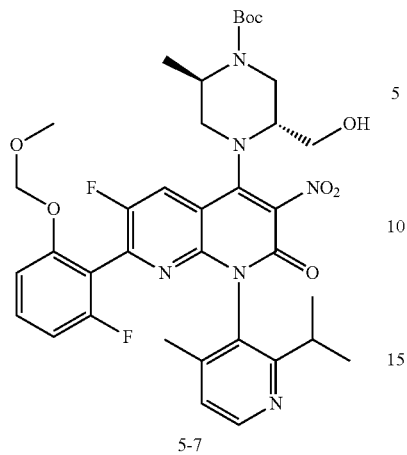

5-7

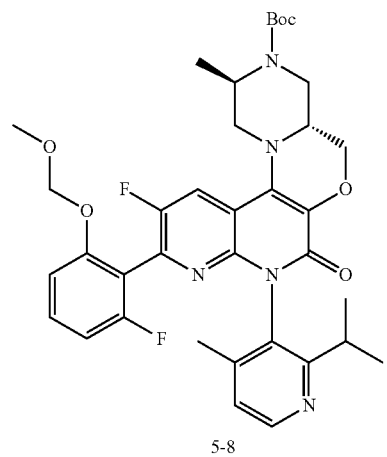

5-8

Compound 5-6 (100 mg, 0.165 mmol), compound 2-13 (94 mg, 0.332 mmol), 1,1-bis(diphenylphosphino)ferrocene palladium dichloride (12.3 mg, 0.0169 mmol), potassium carbonate (46.6 mg, 0.338 mmol) were dissolved in a mixed solution of tetrahydrofuran (3 mL) and water (0.3 mL), under nitrogen atmosphere, the system was heated to 80° C. and stirred for 1 hour. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 5-7.

MS (ESI) m/z (M+H)$^+$=725.40.

Step 8: Preparation of Compound 5-8

Compound 5-7 (25 mg, 0.034 mmol) was dissolved in N,N-dimethylacetamide (2 mL), and tetrahydrofuran solution of lithium bis(trimethylsilyl)amide (24%, 0.5 mL) was added thereto at room temperature, under nitrogen atmosphere, the system was heated to 160° C. and stirred for 10 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 5-8.

MS (ESI) m/z (M+H)$^+$=678.40.

Step 9: Preparation of Compound 5-9

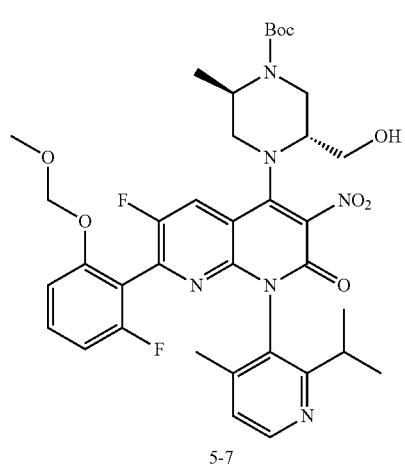

5-7

→

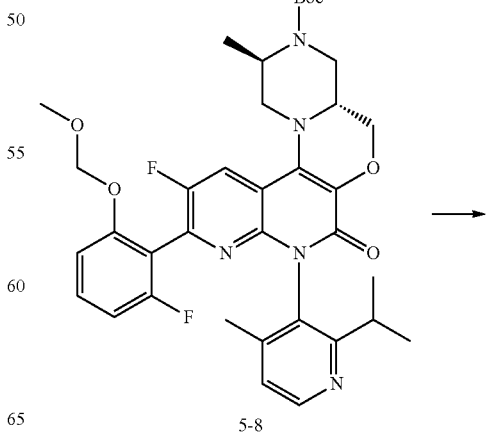

5-8

→

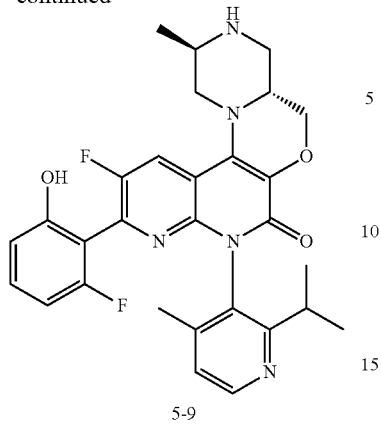

5-9

Compound 5-8 (13 mg, 0.0192 mmol), hydrochloric acid (6N, 1 mL) were added to a mixed solution of methanol (0.9 mL) and tetrahydrofuran (0.1 mL). The system was heated to 55° C. and stirred for 15 min. The system was concentrated to obtain crude product compound 5-9, which was directly used in the next reaction without further purification.

MS (ESI) m/z (M+H)$^+$=534.20.

Step 10: Preparation of Compounds 5A and 5B

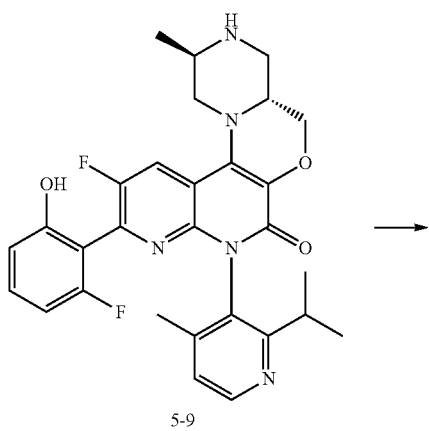

5-9

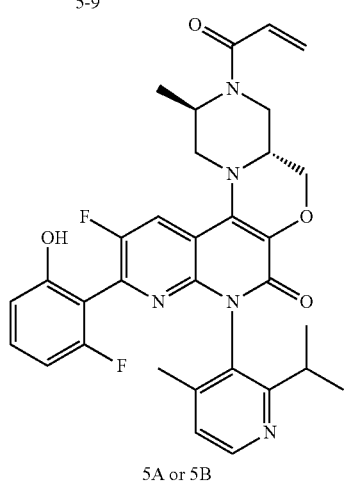

5A or 5B

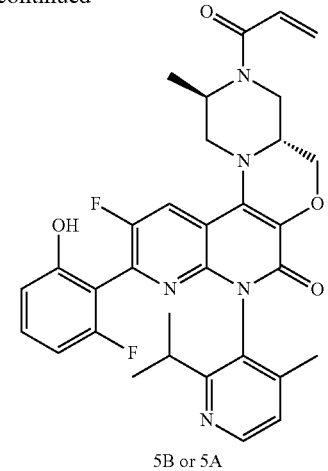

5B or 5A

Compound 5-9 (12 mg, 0.0192 mmol) was dissolved in dichloromethane (1 mL), and triethylamine (2.52 mg, 0.0252 mmol) and acryloyl chloride (2.27 mg, 0.0252 mmol) were added dropwise thereto at 0° C. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column Welch Xtimate C18 10*250 mm, 5 μm; column temperature 25° C.; mobile phase: water (10 mM/L ammonium bicarbonate aqueous solution)-acetonitrile; acetonitrile 32%-47% 16 min; flow rate 8 mL/min) to obtain compound 5A and compound 5B.

Compound 5A:

$^1$H NMR (400 MHz, DMSO-d$_6$) δ 10.00 (s, 1H), 8.36 (d, J=4.9 Hz, 1H), 7.79 (d, J=8.9 Hz, 1H), 7.24-7.06 (m, 2H), 6.87-6.71 (m, 1H), 6.68-6.51 (m, 2H), 6.10 (d, J=16.7 Hz, 1H), 5.69 (d, J=10.5 Hz, 1H), 4.51-4.07 (m, 3H), 3.67-3.42 (m, 4H), 2.65-2.48 (m, 2H), 1.73 (s, 3H), 1.55-1.48 (m, 3H), 0.98 (d, J=6.7 Hz, 3H), 0.84 (d, J=6.8 Hz, 3H).

MS (ESI) m/z (M+H)$^+$=588.20.

HPLC 100% purity; retention time was 4.917 min.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min.

Compound 5B:

$^1$H NMR (400 MHz, DMSO-d$_6$) δ 10.38 (brs, 1H), 8.44 (d, J=4.9 Hz, 1H), 7.92 (d, J=8.5 Hz, 1H), 7.37-7.18 (m, 2H), 6.97-6.80 (m, 1H), 6.79-6.62 (m, 2H), 6.21 (dd, J=16.7, 2.1 Hz, 1H), 5.82 (d, J=10.6 Hz, 1H), 4.51-4.07 (m, 3H), 3.67-3.42 (m, 4H), 2.65-2.48 (m, 1H), 2.48-2.42 (m, 1H), 1.91 (s, 3H), 1.72-1.53 (m, 3H), 1.05 (d, J=6.7 Hz, 3H), 0.90 (d, J=6.7 Hz, 3H).

MS (ESI) m/z (M+H)$^+$=588.20.

HPLC 100% purity; retention time was 4.975 min.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min.

Embodiment 6: Preparation of Compound 6

Step 1: Preparation of Compound 6-1

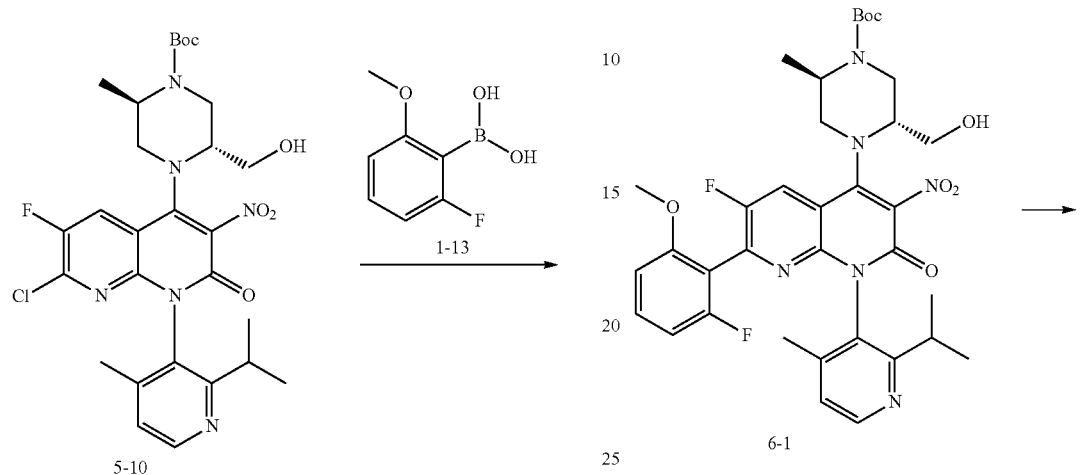

Step 2: Preparation of Compound 6-2

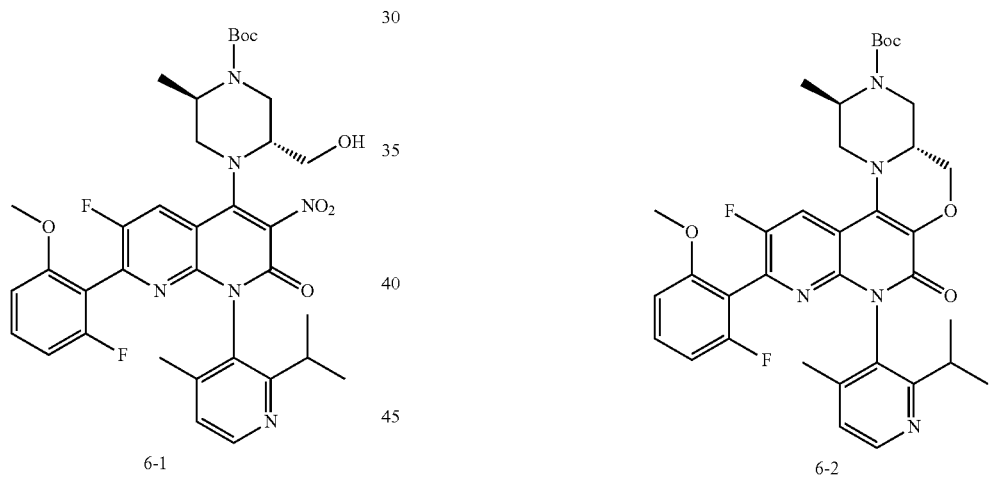

Compound 5-10 (90 mg, 0.15 mmol), compound 1-13 (51 mg, 0.30 mmol), 1,1-bis(diphenylphosphino)ferrocene palladium dichloride (11 mg, 0.015 mmol), potassium carbonate (41 mg, 0.3 mmol) were dissolved in a mixed solution of tetrahydrofuran (3 mL) and water (0.3 mL), under nitrogen atmosphere, the system was heated to 80° C. and stirred for 1 hour. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 6-1.

MS (ESI) m/z $(M+H)^+$=695.40.

Compound 6-1 (40 mg, 0.058 mmol) was dissolved in N,N-dimethylacetamide (2 mL), and tetrahydrofuran solution of lithium bis(trimethylsilyl)amide (24%, 0.5 mL) was added thereto at room temperature, under nitrogen atmosphere, the system was heated to 160° C. and stirred for 10 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 6-2.

MS (ESI) m/z $(M+H)^+$=648.40.

Step 3: Preparation of Compounds 6A and 6B

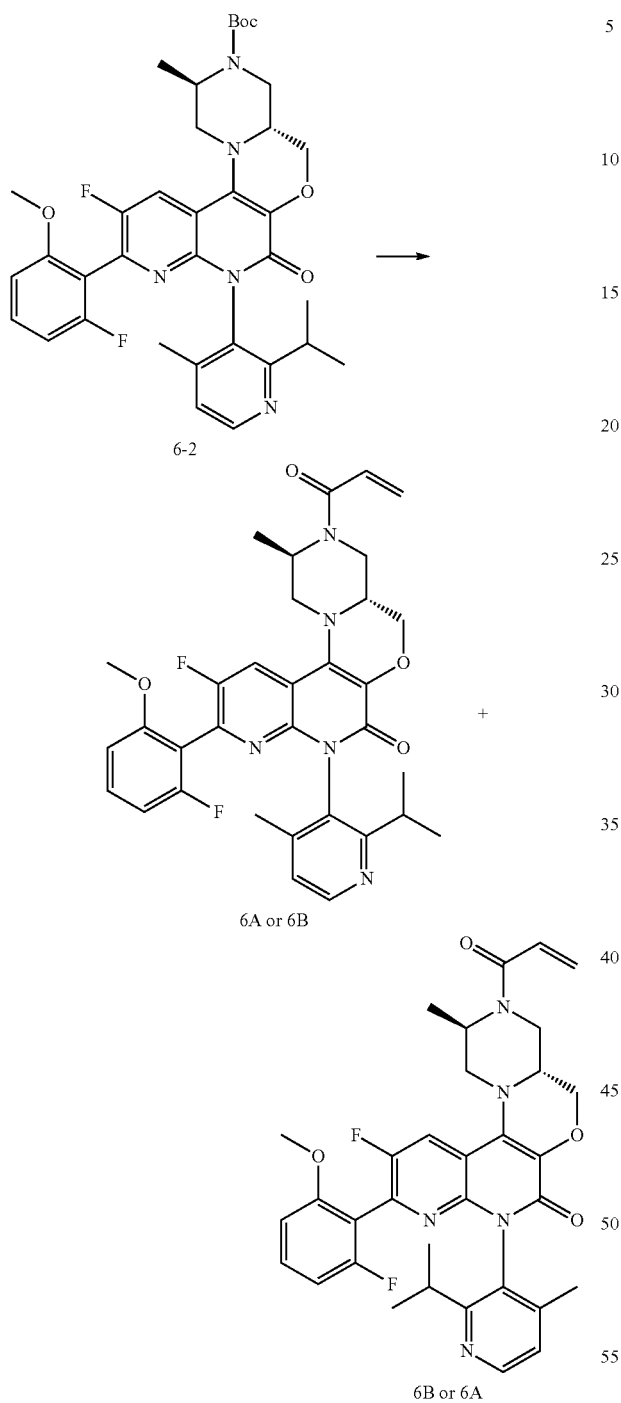

6-2

6A or 6B 6B or 6A

Compound 6-2 (14 mg, 0.022 mmol) was dissolved in dichloromethane (1 mL), trifluoroacetic acid (1 mL) was added thereto at room temperature, and the mixture was stirred at room temperature (20° C.) for 1 hour. The system was concentrated and the residue was dissolved in dichloromethane (2 mL); and the system was cooled to 0° C., then triethylamine (0.014 mL, 0.1 mmol) and acryloyl chloride (4 mg, 0.04 mmol) were added dropwise thereto. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column Welch Xtimate C18 10*250 mm, 5 μm; column temperature 25° C.; mobile phase: water (10 mM ammonium bicarbonate aqueous solution)-acetonitrile; acetonitrile 28%-50% 19 min; flow rate 8 mL/min) to obtain compound 6A and compound 6B.

Compound 6A:

$^1$H NMR (400 MHz, DMSO-$d_6$) δ 8.44-8.24 (m, 1H), 7.80 (d, J=9.0 Hz, 1H), 7.51-7.31 (m, 1H), 7.15 (dd, J=4.9, 0.8 Hz, 1H), 6.97-6.64 (m, 3H), 6.10 (d, J=16.6 Hz, 1H), 5.70 (d, J=15.0 Hz, 1H), 4.87-4.09 (m, 2H), 3.59 (d, J=3.5 Hz, 3H), 3.55-3.45 (m, 5H), 2.56-2.50 (m, 2H), 1.72 (d, J=8.1 Hz, 3H), 1.62-1.39 (m, 3H), 1.09-0.94 (m, 3H), 0.92-0.72 (m, 3H).

MS (ESI) m/z (M+H)$^+$=602.20.

HPLC 100% purity; retention time was 5.388 min.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min.

Compound 6B:

$^1$H NMR (400 MHz, Chloroform-d) δ 8.67 (s, 1H), 7.81 (d, J=8.4 Hz, 1H), 7.35 (q, J=7.9 Hz, 1H), 7.27-7.14 (m, 1H), 6.72 (d, J=8.5 Hz, 2H), 6.66-6.50 (m, 1H), 6.40 (d, J=16.4 Hz, 1H), 5.83 (d, J=10.3 Hz, 1H), 4.52-4.27 (m, 2H), 3.78-3.58 (m, 5H), 3.58-3.37 (m, 2H), 3.10 (d, J=12.6 Hz, 1H), 2.82-2.59 (m, 1H), 2.13-1.98 (m, 1H), 1.74 (s, 3H), 1.31-0.96 (m, 9H).

MS (ESI) m/z (M+H)$^+$=602.20.

HPLC 100% purity; retention time was 5.455 min.

Separation conditions: chromatographic column: Waters Xbridge C18 3.5 μm, 100*4.6 mm; column temperature: 40° C.; mobile phase: water (10 mM ammonium bicarbonate aqueous solution)-acetonitrile; acetonitrile: 5%-95% 7 min, 95% 8 min; flow rate: 1.2 mL/min.

Embodiment 7: Preparation of Compound 7

Step 1: Preparation of Compound 7-2

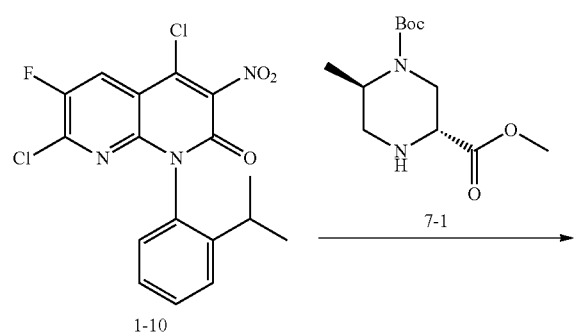

1-10                    7-1

-continued

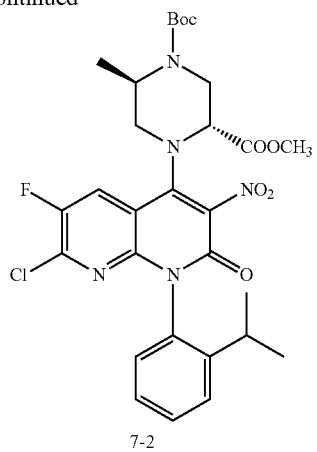

7-2

Compound 1-10 (2000 mg, 5.063 mmol), compound 7-1 (2000 mg, 7.751 mmol), cuprous iodide (470.0 mg, 2.46 mmol), and cesium carbonate (3280 mg, 10 mmol) were dissolved in dioxane (30 mL), under nitrogen atmosphere, the system was heated to 100° C. and stirred for 1 hour. The system was filtered by diatomite, and the filtrate was concentrated to obtain a crude product. The crude product was purified by medium pressure column chromatography (ethyl acetate/petroleum ether (v/v)=0-30%) to obtain compound 7-2.

MS (ESI) m/z (M+H)$^+$=618.2.

Step 2: Preparation of Compound 7-3

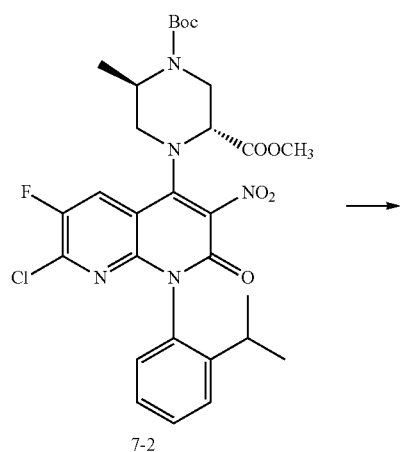

7-2

-continued

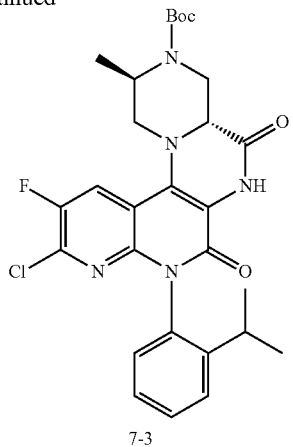

7-3

Compound 7-2 (320 mg, 0.517 mmol) and iron powder (115 mg, 2.068 mmol) were dissolved in acetic acid (10 mL), and the system was heated to 80° C. and stirred for 1 hour under nitrogen atmosphere. The system was filtered by diatomite, and the filtrate was concentrated to obtain a crude product of compound 7-3. Which was directly used in the next reaction without further purification.

MS (ESI) m/z (M+H)$^+$=556.2.

Step 3: Preparation of Compound 7-4

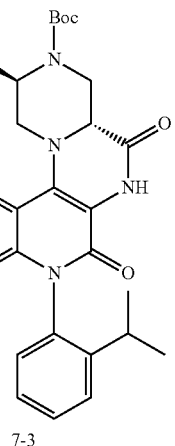

7-3

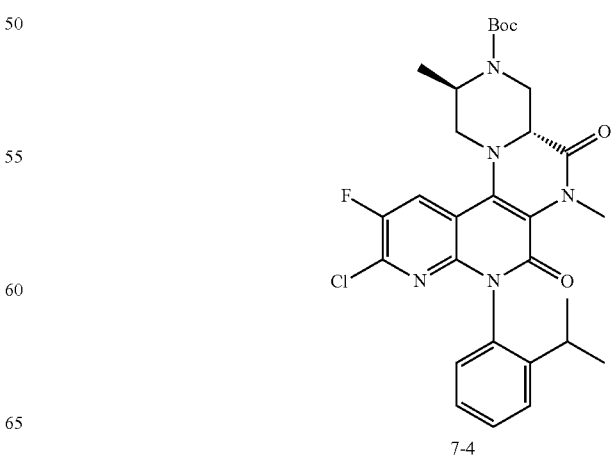

7-4

Compound 7-3 (287 mg, 0.517 mmol) and potassium carbonate (276 mg, 2 mmol) were dissolved in acetone (20 mL), and methyl iodide (284 mg, 2 mmol) was added thereto at room temperature (20° C.). After the addition was completed, under nitrogen atmosphere, the system was heated to 45° C. and stirred for 3 hours. The system was cooled to room temperature and concentrated to obtain a crude product. The crude product was purified by medium pressure column chromatography (ethyl acetate/petroleum ether (v/v)=0-30%) to obtain compound 7-4.

MS (ESI) m/z (M+H)$^+$=570.2.

Step 4: Preparation of Compound 7-5

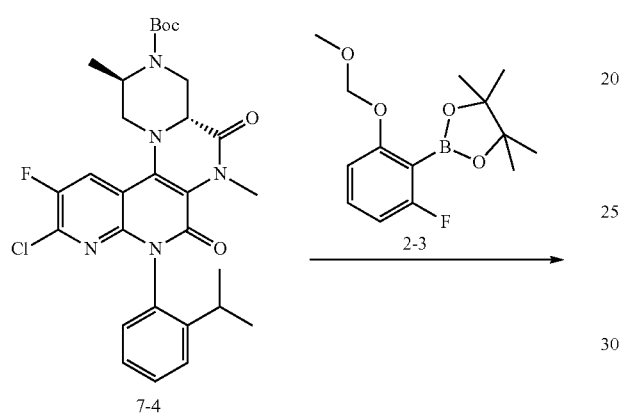

7-4

Compound 7-4 (120 mg, 0.210 mmol), compound 2-3 (177 mg, 0.627 mmol), tetrakis(triphenylphosphine)palladium (240 mg, 0.207 mmol) and sodium carbonate (90 mg, 0.849 mmol) were dissolved in dioxane (5 mL) and water (0.5 mL). Under nitrogen atmosphere, the system was heated to 100° C. and stirred for 1 hour. The system was concentrated to obtain a crude product, the crude product was purified by medium pressure column chromatography (ethyl acetate/petroleum ether (v/v)=0-50%) to obtain compound 7-5.

MS (ESI) m/z (M+H)$^+$=690.3.

Step 5: Preparation of Compound 7-6

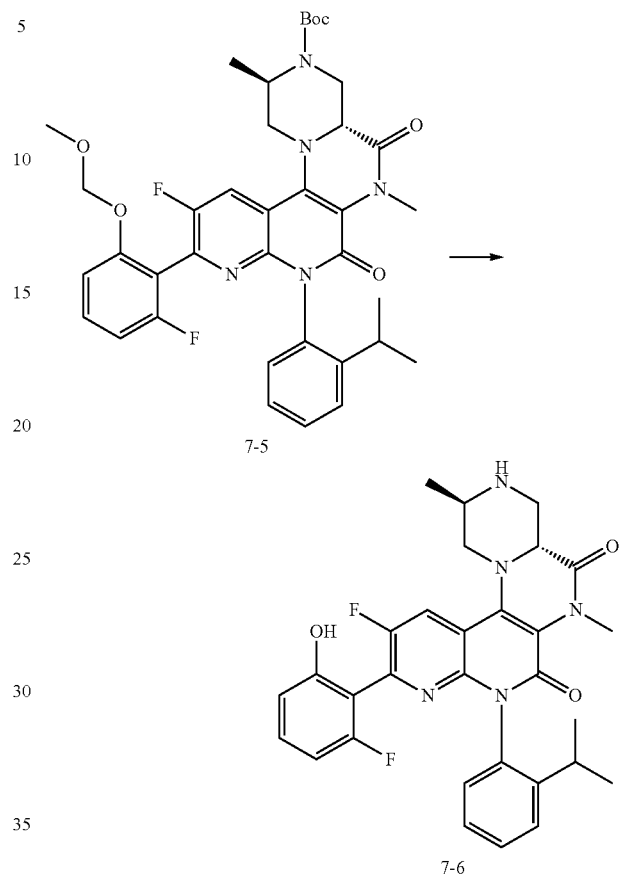

7-5

Compound 7-5 (180 mg, 0.261 mmol), hydrochloric acid (6N, 2 mL) were added to a mixed solution of methanol (10 mL) and tetrahydrofuran (1 mL). The system was heated to 55° C. and stirred for 1 hour. The system was concentrated to obtain crude product compound 7-6, which was directly used in the next reaction without further purification.

MS (ESI) m/z (M+H)$^+$=546.2.

Step 6: Preparation of Compound 7

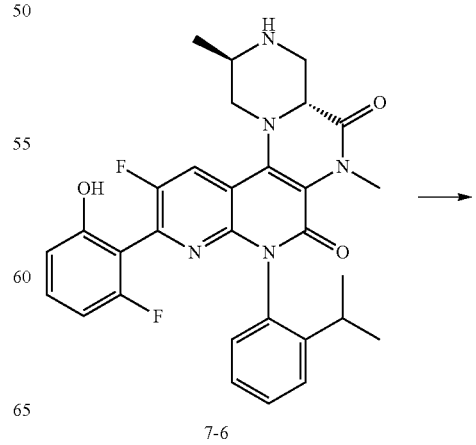

7-6

-continued

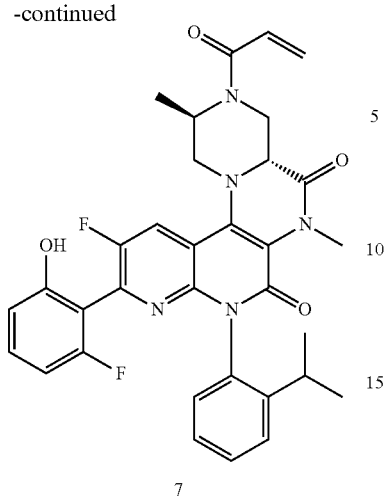

7

Compound 7-6 (140 mg, 0.256 mmol) was dissolved in dichloromethane (5 mL), and the system was cooled to 0° C., triethylamine (78 mg, 0.771 mmol) and acryloyl chloride (46 mg, 0.514 mmol) were added dropwise thereto, the reaction was carried out at 0° C. for 0.5 hours. The system was separated and extracted with water (5 mL) and dichloromethane (3 mL), and the organic phase was concentrated to obtain a crude product. The crude product was dissolved in a mixed solvent of tetrahydrofuran (5 mL) and water (10 mL), lithium hydroxide (40 mg) was added thereto, after the addition was completed, the system was stirred at room temperature (20° C.) for 30 min. The system was extracted with ethyl acetate (50 mL), the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: Water (10 mM ammonium bicarbonate aqueous solution)-acetonitrile; acetonitrile 51%-81% 9.5 min; flow rate 30 mL/min) to obtain compound 7.

Step 7: Preparation of Compounds 7A and 7B

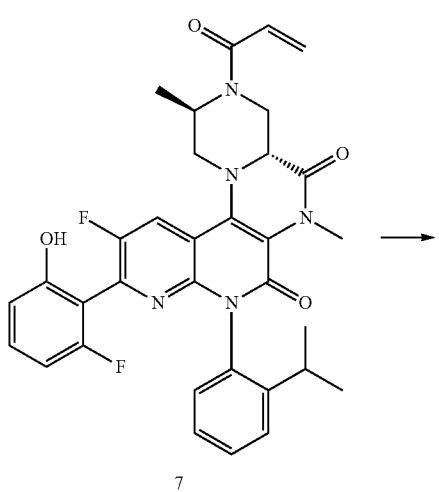

7

-continued

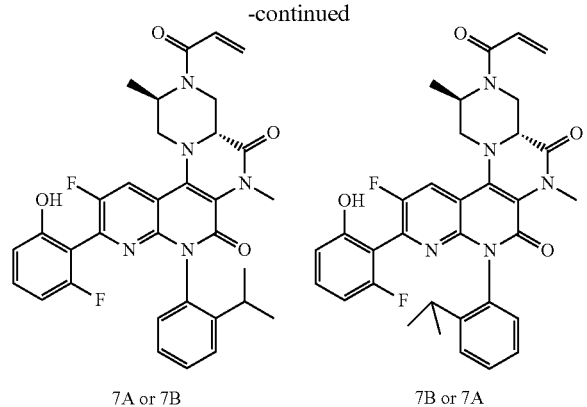

7A or 7B          7B or 7A

Diastereoisomeric compound 7 was purified by SFC (separation conditions: chromatographic column: DAICEL CHIRALCEL OD (250 mm*30 mm, 10 μm); mobile phase: [0.1% ammonia solution-ethanol]; ethanol %: 40%-40%; flow rate: 70 mL/min). After concentration, compound 7A and compound 7B were obtained.

Compound 7A $^1$H NMR (400 MHz, Methanol-$d_4$) δ 8.20-7.90 (m, 1H), 7.54-7.41 (m, 2H), 7.34 (t, J=7.4 Hz, 1H), 7.20 (p, J=8.1 Hz, 1H), 7.16-7.07 (m, 1H), 6.71-6.48 (m, 2H), 6.24 (d, J=17.1 Hz, 1H), 5.82 (d, J=11.1 Hz, 1H), 4.75 (d, J=14.3 Hz, 1H), 4.65-4.46 (m, 1H), 4.01-3.82 (m, 2H), 3.48 (s, 3H), 3.00-2.84 (m, 1H), 2.45-2.32 (m, 1H), 1.67 (d, J=6.8 Hz, 3H), 1.12 (d, J=6.8 Hz, 3H), 0.96 (d, J=6.8 Hz, 3H).

MS (ESI) m/z $(M+H)^+$=600.0.

HPLC 100% purity; retention time was 5.05 min.

Separation conditions: chromatographic column: Ultimate C18 3.0*50 mm, 3 μm; column temperature: 40° C.; mobile phase: water (0.0688% trifluoroacetic acid aqueous solution)-acetonitrile (0.0625% trifluoroacetic acid solution); acetonitrile: 10%-80% 6 min, 80% 2 min; flow rate: 1.2 mL/min.

SFC 100% ee. Retention time was 3.939 min.

Separation conditions: chromatographic column Chiralcel OD-3 3 μm, 100*4.6 mm; column temperature: 35° C.; mobile phase: $CO_2$-ethanol (0.05% DEA); ethanol: 5%-40% 4 min, 40% 2.5 min, 5% 1.5 min; flow rate: 2.8 mL/min.

Compound 7B $^1$H NMR (400 MHz, Methanol-$d_4$) δ 8.06 (d, J=8.9 Hz, 1H), 7.58-7.40 (m, 2H), 7.36-7.26 (m, 1H), 7.25-7.16 (m, 1H), 7.11 (dd, J=16.9, 10.7 Hz, 1H), 7.06-6.95 (m, 1H), 6.67-6.44 (m, 2H), 6.22 (dd, J=16.9, 1.9 Hz, 1H), 5.80 (dd, J=10.7, 2.0 Hz, 1H), 4.74 (d, J=13.9 Hz, 1H), 4.67-4.52 (m, 1H), 3.99-3.81 (m, 2H), 3.45 (s, 3H), 2.93 (dd, J=12.4, 3.8 Hz, 1H), 2.68 (p, J=7.0 Hz, 1H), 1.65 (d, J=6.9 Hz, 3H), 1.17 (d, J=6.9 Hz, 3H), 1.05 (d, J=6.9 Hz, 3H).

MS (ESI) m/z $(M+H)^+$=600.0.

HPLC 100% purity; retention time was 5.00 min.

Separation conditions: chromatographic column: Ultimate C18 3.0*50 mm, 3 μm; column temperature: 40° C.; mobile phase: water (0.0688% trifluoroacetic acid aqueous solution)-acetonitrile (0.0625% trifluoroacetic acid solution); acetonitrile: 10%-80% 6 min, 80% 2 min; flow rate: 1.2 mL/min.

SFC 100% ee. Retention time was 4.329 min

Separation conditions: chromatographic column Chiralcel OD-3 3 μm, 100*4.6 mm; column temperature: 35° C.; mobile phase: $CO_2$-ethanol (0.05% DEA); ethanol: 5%-40% 4 min, 40% 2.5 min, 5% 1.5 min; flow rate: 2.8 mL/min.

Embodiment 8: Preparation of Compound 8

Step 1: Preparation of Compound 8-2

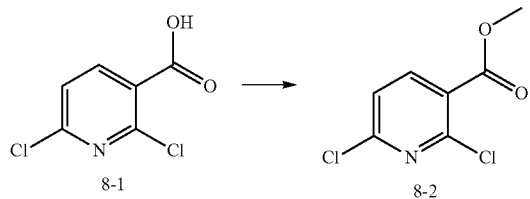

Raw material 8-1 (10 g, 52.351 mmol) was dissolved in thionyl chloride (30 mL), and the system was heated to 85° C. to react for 16 hours. The system was concentrated and the residue was dissolved in 1,4-dioxane (30 mL); the solution was slowly added to stirred methanol at 0° C., and the system was heated to 70° C. for 2 hours. The system was concentrated to obtain compound 8-2.

Step 2: Preparation of Compound 8-3

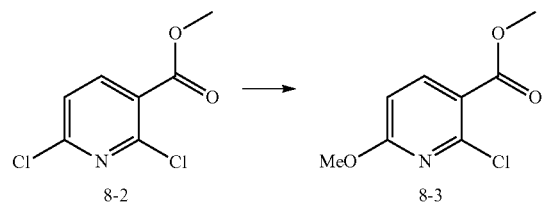

Compound 8-2 (4 g, 19.4 mmol) was dissolved in methanol (50 mL), and methanol solution of sodium methoxide (4 mL, 21.3 mmol) was added dropwise thereto, the reaction was carried out at room temperature (20° C.) for 3 hours. The system was concentrated, poured into water (50 mL), extracted with ethyl acetate (50 mL×3), the combined organic phases were dried over anhydrous sodium sulfate, filtered, and the filtrate was concentrated to obtain crude product 8-3.

MS (ESI) m/z (M+H)$^+$=202.0.

Step 3: Preparation of Compound 8-4

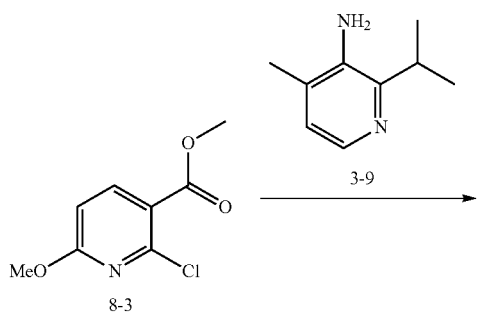

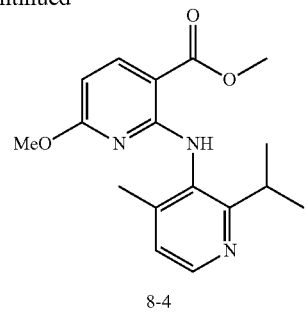

At room temperature (20° C.), compound 8-3 (1.48 g, 7.36 mmol), compound 3-9 (1.11 g, 7.36 mmol), palladium acetate (165 mg, 0.736 mmol), 4,5-bisdiphenylphosphino-9,9-dimethylxanthene (425 mg, 0.735 mmol), cesium carbonate (4.8 g, 14.73 mmol) were dissolved in dioxane (15 mL), under nitrogen atmosphere, the system was heated to 110° C. and stirred for 4 hours. The system was cooled to room temperature and concentrated to obtain a crude product. The crude product was purified by medium pressure column chromatography (ethyl acetate/petroleum ether (v/v)=0-20%) to obtain compound 8-4.

MS (ESI) m/z (M+H)$^+$=316.0.

Step 4: Preparation of Compound 8-5

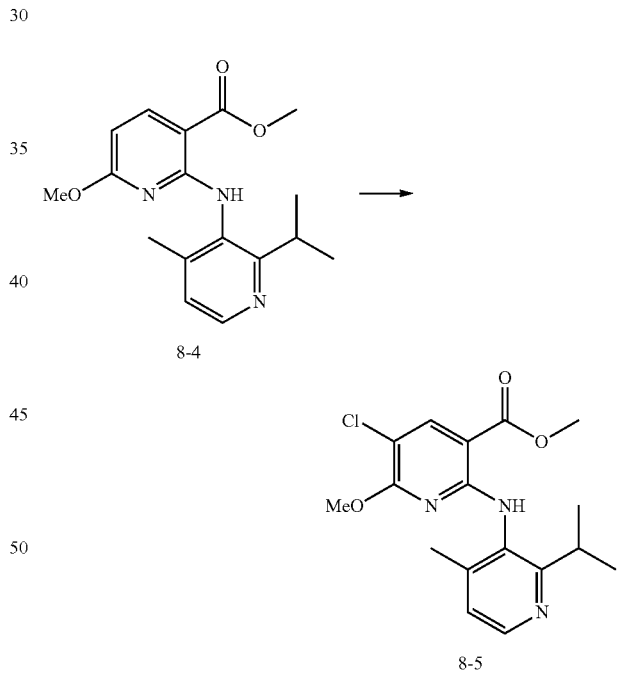

Compound 8-4 (1.58 g, 4.80 mmol) was dissolved in N,N-dimethylformamide (15 mL), and N-chlorosuccinimide (0.706 g, 5.28 mmol) was added thereto, and the system was heated to 80° C. for 5 hours. The system cooled to room temperature, poured into water (50 mL), extracted with ethyl acetate (50 mL×3), the organic phases were combined, and the organic phase was dried over anhydrous sodium sulfate, filtered and the filtrate was concentrated to obtain a crude product, the crude product was purified by medium pressure column chromatography (ethyl acetate/petroleum ether (v/v) =0-5%) to obtain compound 8-5.

MS (ESI) m/z (M+H)⁺=350.0

Step 5: Preparation of Compound 8-6

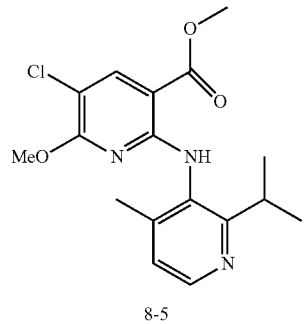

8-5

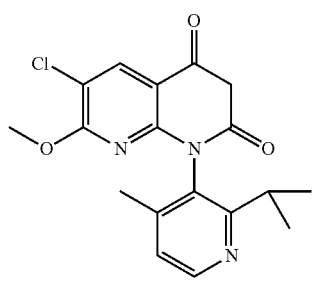

8-6

Compound 8-5 (6.3 g, 7.82 mmol) was dissolved in N,N-dimethylformamide (30 mL) at room temperature (20° C.), and sodium hydride (2.17 g, 54.15 mmol) was added thereto in batches at 0° C., after the addition was completed, the reaction was carried out at 0° C. for 30 min, and acetyl chloride (3.85 g, 54.15 mmol) was added thereto dropwise. Water (30 mL) and saturated potassium carbonate aqueous solution were added to the system successively, the reaction was carried out at room temperature (20° C.) for 3 hours. After the mixture was extracted with EA (100 mL×2), the water phase was adjusted to pH 4-5 with hydrochloric acid (4 N), and then extracted with ethyl acetate (100 mL×4), the combined organic phase was dried over anhydrous sodium sulfate, filtered, and the filtrate was concentrated to obtain a crude product, the crude product was purified by medium pressure column chromatography (methanol/dichloromethane (v/v)=0-5%) to obtain compound 8-6.

MS (ESI) m/z (M+H)⁺=360.0.

Step 6: Preparation of Compound 8-7

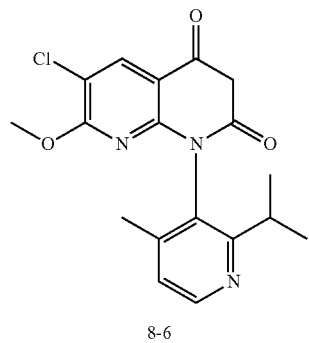

8-6

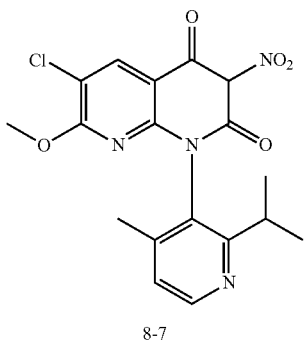

8-7

Compound 8-6 (1.86 g, 5.18 mmol) was dissolved in glacial acetic acid (30 mL), and nitric acid (15 mL) was added dropwise to the system at room temperature (20° C.). After the addition was completed, the system was stirred at room temperature (20° C.) for 2 hours. The system was concentrated to remove most of the glacial acetic acid, and the remainder was poured into ice water (25 mL), the pH was adjusted to 5-6; then the mixture was filtered, and the filter cake was washed with water and dried to obtain compound 8-7.

MS (ESI) m/z (M+H)⁺=405.0.

Step 7: Preparation of Compound 8-8

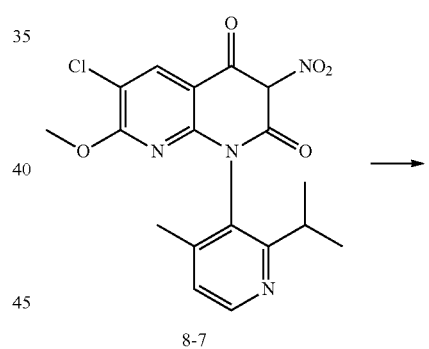

8-7

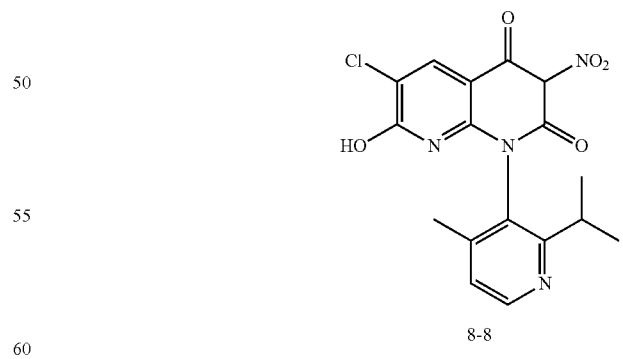

8-8

Compound 8-7 (1 g, 2.47 mmol) was dissolved in a mixed solution of acetic acid (6 mL) and hydrobromic acid (8 mL). The system was heated to 100° C. and stirred for 16 hours. The system was spin-dried to obtain compound 8-8.

MS (ESI) m/z (M+H)⁺=391.0.

Step 8: Preparation of Compound 8-9

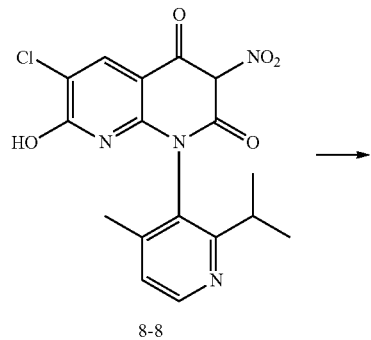

8-8

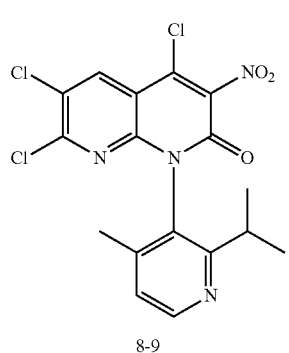

8-9

Compound 8-8 (2.0 g, 5.13 mmol) and N,N-diisopropylethylamine (5 mL, 30.7 mmol) were dissolved in acetonitrile (6 mL), and phosphorus oxychloride (7 mL, 77 mmol) was added thereto at room temperature (20° C.). After the addition was completed, the system was heated to 80° C. and stirred for 2 hours. The system was concentrated to obtain a crude product. The crude product was purified by medium pressure column chromatography (ethyl acetate/petroleum ether (v/v)=0-50%) to obtain compound 8-9.

MS (ESI) m/z (M+H)⁺=427.0.

Step 9: Preparation of Compound 8-10

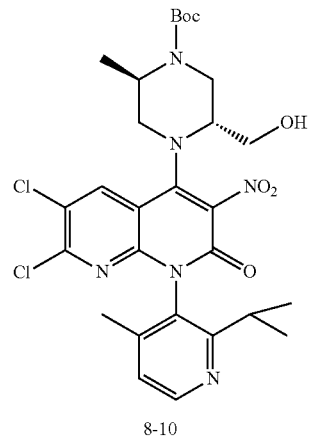

8-10

Compound 8-9 (754 mg, 1.77 mmol), compound 1-11 (447 mg, 1.955 mmol), cesium carbonate (1.15 g, 3.54 mmol) and cuprous iodide (67 mg, 0.354 mmol) were dissolved in dioxane (5 mL). Under nitrogen atmosphere, the system was heated to 100° C. and stirred for 3 hours. The system was concentrated to obtain a crude product. The crude product was purified by medium pressure column chromatography (ethyl acetate/petroleum ether (v/v)=0-30%) to obtain compound 8-10.

MS (ESI) m/z (M+H)⁺=621.2.

Step 10: Preparation of Compound 8-11

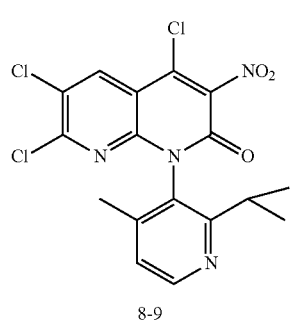

8-9

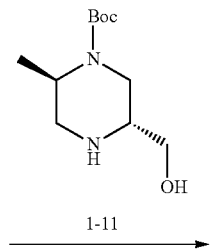

1-11

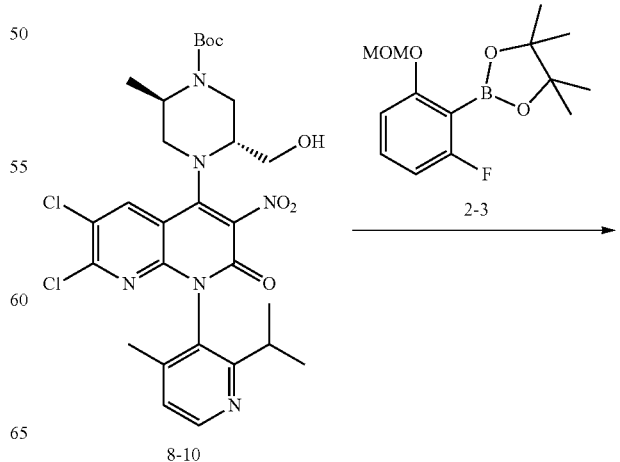

8-10

-continued

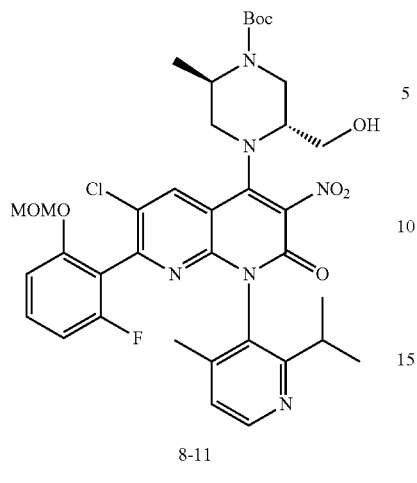

8-11

-continued

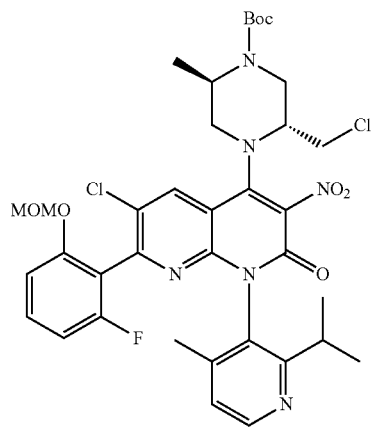

8-12

Compound 8-10 (345 mg, 0.556 mmol), compound 2-3 (470 mg, 1.669 mmol), 1,1-bis(diphenylphosphino)ferrocene palladium dichloride (23.4 mg, 0.032 mmol), potassium carbonate (44 mg, 0.321 mmol) was dissolved in a mixed solution of dioxane (4 mL) and water (1 mL), under nitrogen atmosphere, the system was heated to 100° C. and stirred for 6 hours. The system was concentrated, and the residue was dissolved in ethyl acetate (20 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-70%) to obtain compound 8-11.

MS (ESI) m/z (M+H)$^+$=741.2.

Step 11: Preparation of Compound 8-12

Compound 8-11 (230 mg, 0.311 mmol) was dissolved in anhydrous 1,2-dichloroethane (10 mL), and triphenylphosphine (244 mg, 0.932 mmol), imidazole (42 mg, 0.622 mmol) and carbon tetrachloride (143 mg, 0.932 mmol) were added thereto at room temperature (20° C.). After the addition was completed, under nitrogen atmosphere, the system was heated to 80° C. and stirred for 2 hours. The system was concentrated to obtain a crude product. The crude product was purified by medium pressure column chromatography (ethyl acetate/petroleum ether (v/v)=0-50%) to obtain compound 8-12.

Step 12: Preparation of Compound 8-13

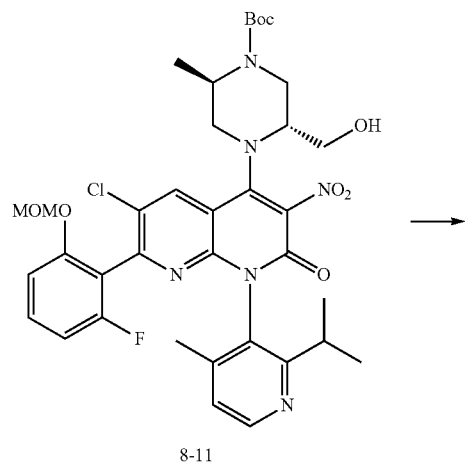

8-11

→

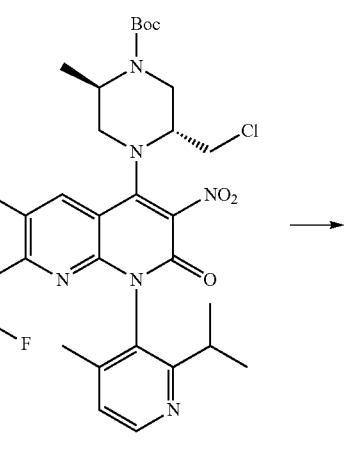

8-12

→

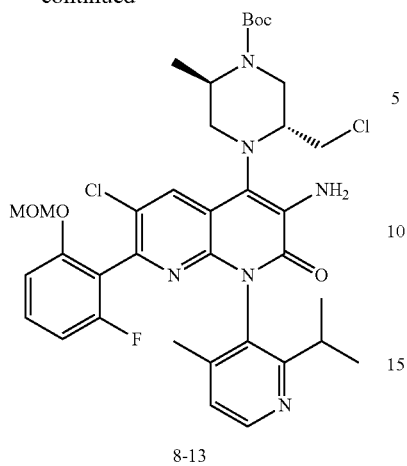

8-13

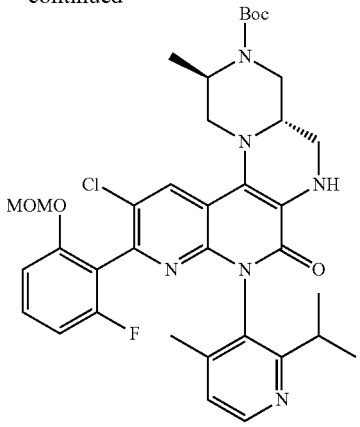

8-14

Compound 8-12 (150 mg, 0.198 mmol) was dissolved in glacial acetic acid (4 mL), and iron powder (112 mg, 1.98 mmol) was added thereto, the reaction was carried out at room temperature (20° C.) for 1 hour. The system was concentrated, the residue was dissolved in ethyl acetate, the organic phase was washed with saturated sodium bicarbonate aqueous solution, dried over anhydrous sodium sulfate, filtered, and the filtrate was concentrated to obtain compound 8-13.

Step 13: Preparation of Compound 8-14

Compound 8-13 (90 mg, 0.124 mmol) and N,N-diisopropylethylamine (48 mg, 0.371 mmol) were dissolved in N,N-dimethylformamide (2 mL), and the system was heated to 120° C. for 4 hours. The system was cooled to room temperature, added with water (50 mL), and then extracted with ethyl acetate (15 mL×3); the combined organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 8-14.

Step 14: Preparation of Compound 8-15

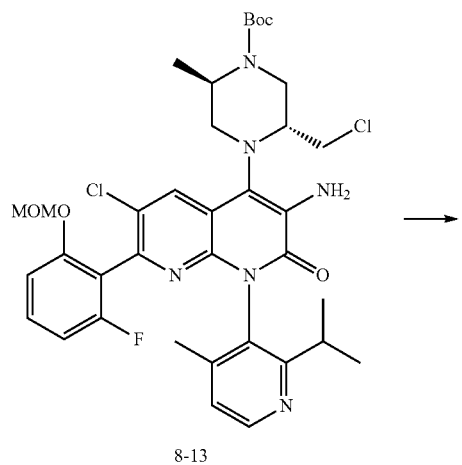

8-13 →

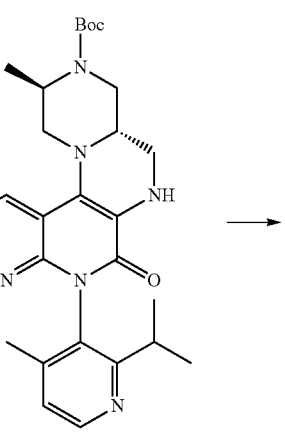

8-14 →

-continued

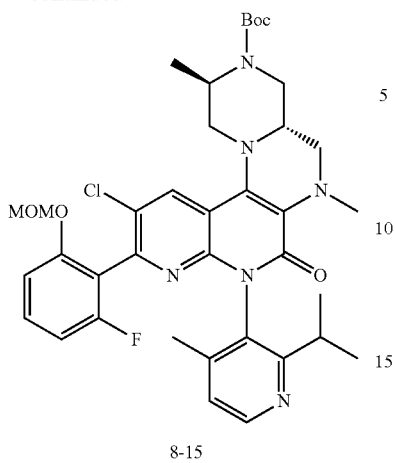

8-15

Compound 8-14 (40 mg, 0.0578 mmol) was dissolved in tetrahydrofuran (2 mL), and sodium hydride (5 mg, 0.1156 mmol) was added thereto at 0° C. After the addition was completed, the system was heated to room temperature and stirred for 30 min. Iodomethane (12.3 mg, 0.086 mmol) was added to the system, after the addition was completed, the system was stirred at room temperature (20° C.) for 2 hours. Water (5 mL) was added to the system to quench the reaction, the mixture was extracted with ethyl acetate (15 mL×4), the combined organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 8-15.

Step 15: Preparation of Compound 8-16

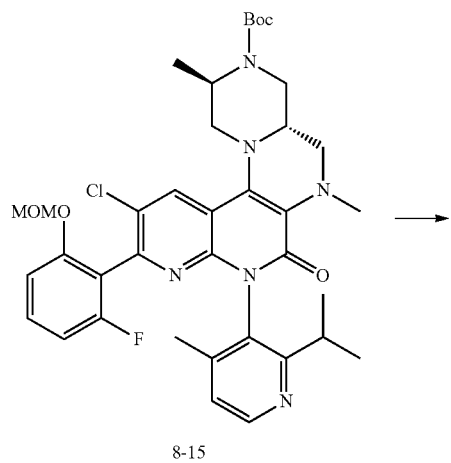

8-15

-continued

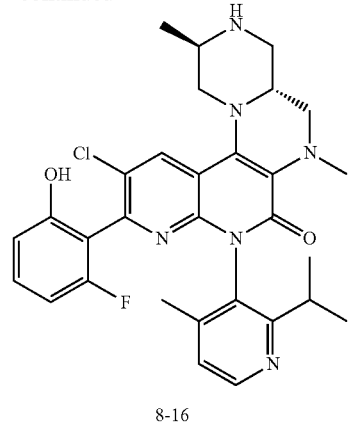

8-16

Compound 8-15 (16 mg, 0.02266 mmol), hydrochloric acid (6N, 1 mL) were added to a mixed solution of methanol (0.9 mL) and tetrahydrofuran (0.1 mL). The system was heated to 55° C. and stirred for 15 min. The system was concentrated to obtain crude product 8-16.

Step 16: Preparation of Compound 8

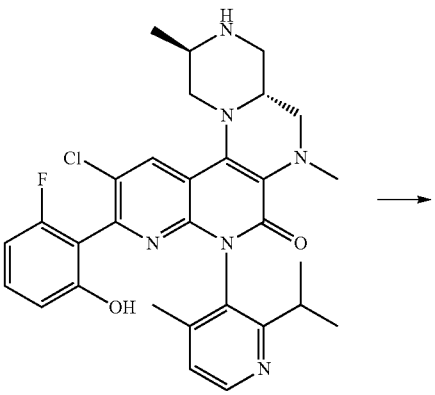

8-16

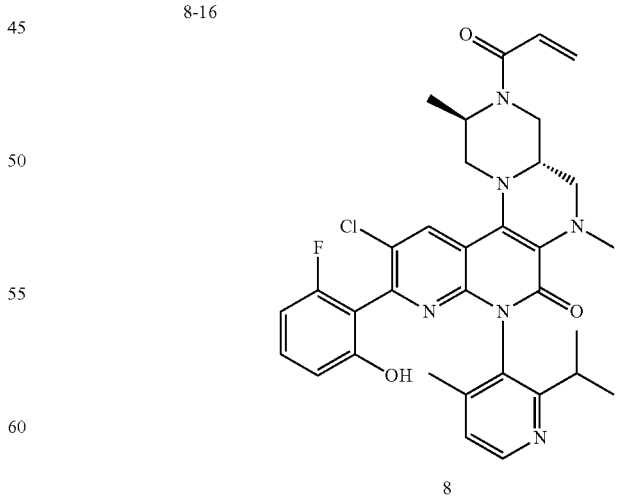

8

Compound 8-16 (13 mg) was dissolved in dichloromethane (2 mL), and triethylamine (11 mg, 0.112 mmol) and acryloyl chloride (7 mg, 0.084 mmol) were added dropwise thereto at room temperature (20° C.). After the addition was completed, the system was stirred at room temperature (20° C.) for 2 hours. Tetrahydrofuran (4 mL), water (1 mL) and lithium hydroxide aqueous solution (31.74 mg, 756.47 μmol) were added to the system, and the mixture was stirred at room temperature (20° C.) for 2 hours. The pH of the system was adjusted to neutral with 1 N hydrochloric acid; and the mixture was extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Agilent 10 Prep-C8 250×21.2 mm; column temperature: 25° C.; mobile phase: water (0.1% FA)-acetonitrile; acetonitrile ratio in mobile phase was 30%-50% in 16 min; flow rate 30 mL/min) to obtain compound 8.

Compound 8:

$^1$H NMR (400 MHz, CDCl3) δ$^1$H NMR (400 MHz, CDCl$_3$) 8.56 (s, 1H), 8.08 (s, 1H), 7.15 (s, 1H), 6.57 (s, 3H), 6.34 (s, 1H), 5.73 (s, 1H), 5.06 (s, 1H), 4.67 (s, 0.5H), 4.30 (s, 0.5H), 3.53 (s, 2H), 3.37-2.84 (m, 7H), 2.67 (s, 1H), 1.93 (s, 3H), 1.19 (s, 6H), 1.05 (s, 3H).

MS (ESI) m/z (M+H)$^+$=617.3.

HPLC 99% purity; retention time was 5.46 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Embodiment 9: Preparation of Compound 9

Step 1: Preparation of Compound 9-1

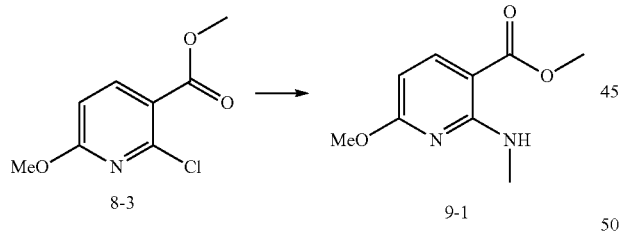

Compound 8-3 (6 g, 29.8 mmol) and ethanol solution of methylamine (15 mL) were dissolved in ethanol (30 mL), then acetyl chloride (2.5 g, 2.36 mL, 31 mmol) was added dropwise thereto, and after the dropwise addition was completed, the system was heated to 100° C. for 2 hours. The system was concentrated, and the residue was dissolved in ethyl acetate (200 mL), washed with saturated saline (80 mL), the organic phase was dried over anhydrous sodium sulfate, filtered and the filtrate was concentrated to obtain a crude product, the crude product was purified by medium pressure column chromatography (ethyl acetate/petroleum ether (v/v)=0-20%) to obtain compound 9-1.

Step 2: Preparation of Compound 9-2

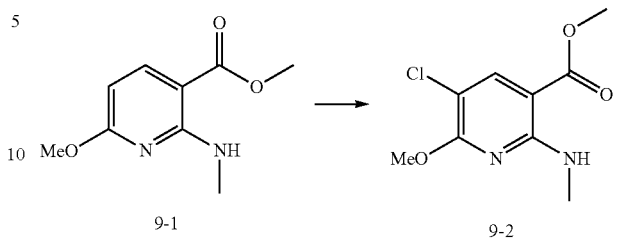

Compound 9-1 (2.02 g, 10.3 mmol) was dissolved in N,N-dimethylformamide (10 mL), and N-chlorosuccinimide (1.5 g, 11.3 mmol) was added thereto, and the system was heated to 80° C. for 2 hours. The system cooled to room temperature, poured into water (50 mL), extracted with ethyl acetate (50 mL×3), the organic phases were combined, and the organic phase was dried over anhydrous sodium sulfate, filtered and the filtrate was concentrated to obtain a crude product, the crude product was purified by medium pressure column chromatography (ethyl acetate/petroleum ether (v/v) =0-5%) to obtain compound 9-2.

MS (ESI) m/z (M+H)$^+$=231.0.

Step 3: Preparation of Compound 9-3

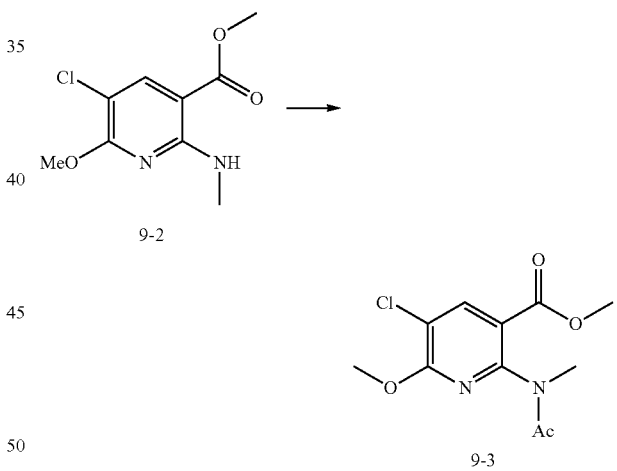

Compound 9-2 (1.8 g, 7.82 mmol) and triethylamine (4.8 g, 6.6 mL, 47 mmol) were dissolved in dichloromethane (30 mL), acetyl chloride (2.5 g, 2.36 mL, 31 mmol) was added dropwise thereto. After the dropwise addition was completed, the system was heated to 50° C. and the reaction was carried out for 16 hours. The system was concentrated, and the residue was dissolved in ethyl acetate (100 mL), washed with saturated saline (80 mL), the organic phase was dried over anhydrous sodium sulfate, filtered and the filtrate was concentrated to obtain a crude product, the crude product was purified by medium pressure column chromatography (ethyl acetate/petroleum ether (v/v)=0-10%) to obtain compound 9-3.

MS (ESI) m/z (M+H)$^+$=273.2.

Step 4: Preparation of Compound 9-4

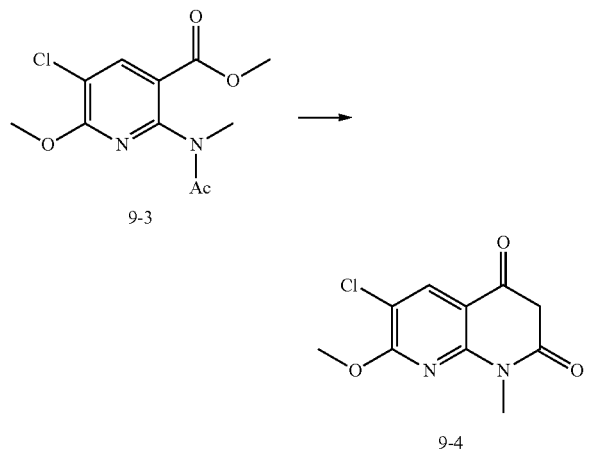

At room temperature (20° C.), compound 9-3 (1.3 g, 1.91 mmol) was dissolved in toluene (20 mL), and potassium tert-butoxide (1.28 g, 11.46 mmol) was added thereto. After the addition was completed, under nitrogen atmosphere, the reaction was carried out at room temperature (20° C.) for 4 hours. The reaction was quenched by adding 1 M hydrochloric acid to the system, diluted with water (40 mL), extracted with ethyl acetate (50 mL×3), the organic phase was dried over anhydrous sodium sulfate, filtered, and the filtrate was concentrated to obtain a crude product, the crude product was slurried with methanol to obtain compound 9-4.

MS (ESI) m/z (M+H)$^+$=241.0.

Step 5: Preparation of Compound 9-5

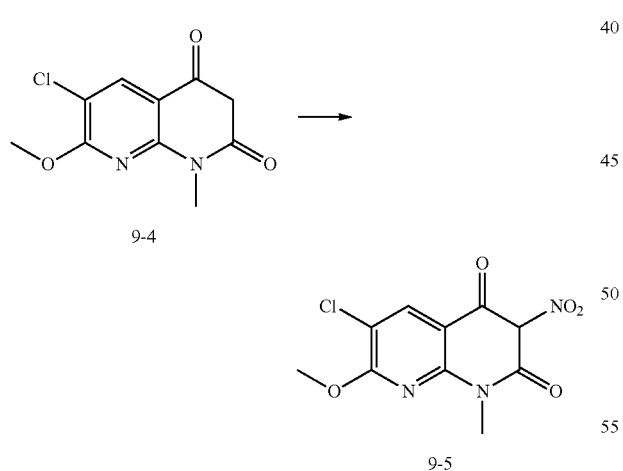

Compound 9-4 (1 g, 2.84 mmol) was dissolved in glacial acetic acid (20 mL), and nitric acid (2.80 g, 44.44 mmol, 2 mL) was added dropwise to the system at room temperature (20° C.). After the dropwise addition was completed, the system was heated to 80° C. and stirred for 1 hour. The system was cooled to room temperature, concentrated to remove most of the glacial acetic acid; the residue was poured into ice water (25 mL) and extracted with ethyl acetate (20 mL×2); the organic phase was dried over anhydrous sodium sulfate, filtered, and the filtrate was concentrated to obtain compound 9-5.

MS (ESI) m/z (M+H)$^+$=286.0.

Step 6: Preparation of Compound 9-6

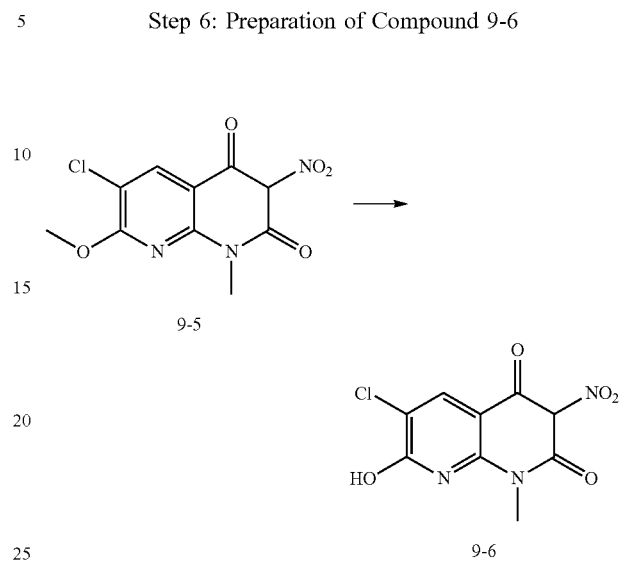

Compound 9-5 (320 mg, 1.12 mmol) was dissolved in a mixed solution of glacial acetic acid (10 mL) and hydrobromic acid (5 mL), and the system was heated to 100° C. to react for 8 hours. The system was spin-dried to obtain compound 9-6.

MS (ESI) m/z (M+H)$^+$=272.0.

Step 7: Preparation of Compound 9-7

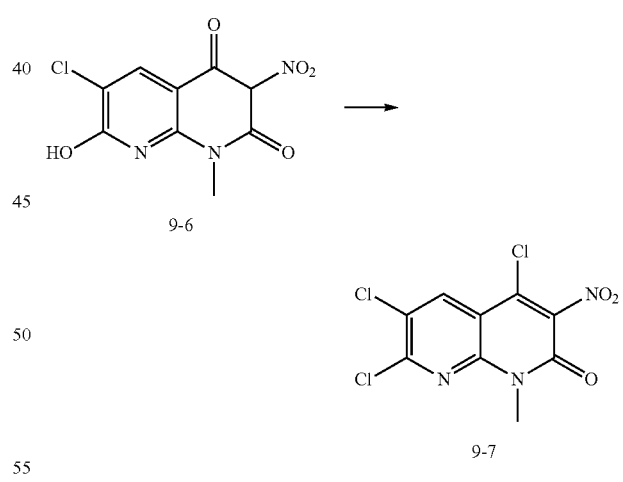

Compound 9-6 (300 g, 1.05 mmol) and N,N-diisopropylethylamine (781 mg, 6.06 mmol) were dissolved in acetonitrile (2 mL), and at room temperature, phosphorus oxychloride (2.46 g, 16.12 mmol) was added thereto. After the addition was completed, the system was heated to 80° C. and stirred for 1 hour. The system was cooled to room temperature and concentrated to obtain a crude product. The crude product was purified by medium pressure column chromatography (ethyl acetate/petroleum ether (v/v)=0-20%) to obtain 150 mg of yellow solid compound 9-7.

MS (ESI) m/z (M+H)$^+$=308.3.

Step 8: Preparation of Compound 9-8

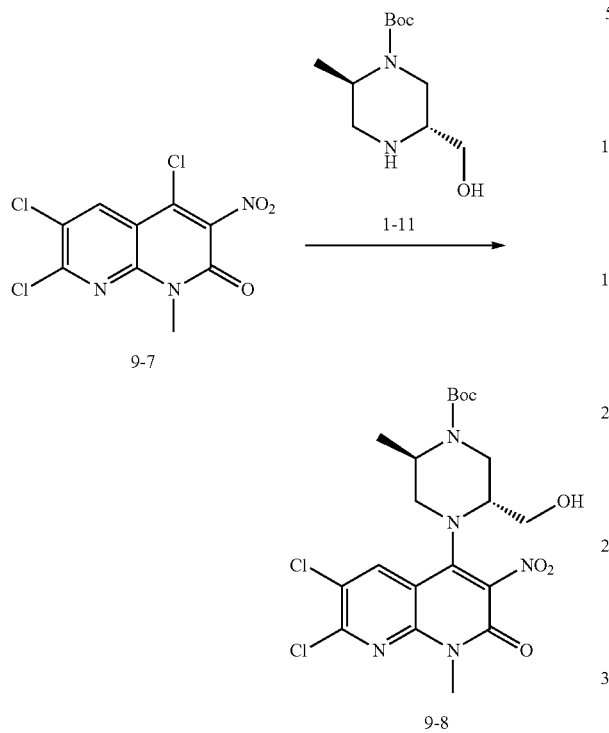

Compound 9-7 (130 mg, 0.423 mmol), compound 1-11 (107 mg, 0.465 mmol), cesium carbonate (275 mg, 0.846 mmol) and cuprous iodide (16 mg, 0.0846 mmol) were dissolved in 1,4-dioxane (3 mL). Under nitrogen atmosphere, the system was heated to 100° C. and stirred for 3 hours. The system was concentrated to obtain a crude product. The crude product was purified by medium pressure column chromatography (ethyl acetate/petroleum ether (v/v)=0-30%) to obtain compound 9-8.

MS (ESI) m/z (M+H)$^+$=502.2.

Step 9: Preparation of Compound 9-9

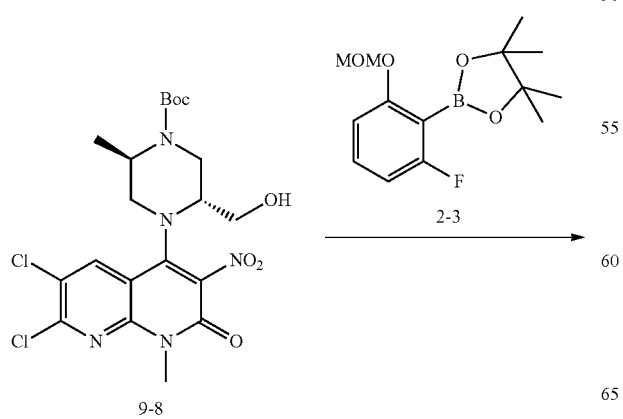

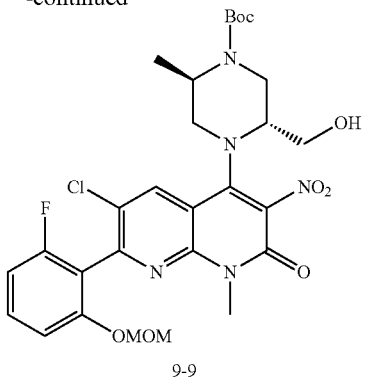

Compound 9-8 (80 mg, 0.16 mmol), compound 2-3 (58.5 mg, 0.207 mmol), 1,1-bis(diphenylphosphino)ferrocene palladium dichloride (23.4 mg, 0.032 mmol), potassium carbonate (44 mg, 0.321 mmol) were dissolved in a mixed solution of tetrahydrofuran (4 mL) and water (1 mL). Under nitrogen atmosphere, the system was heated to 100° C. and the reaction was carried out for 6 hours. The system was concentrated, then separated and extracted with ethyl acetate (20 mL×2) and water (10 mL), the organic phase was dried over anhydrous sodium sulfate, filtered and the filtrate was concentrated to obtain a crude product, the crude product was purified by medium pressure column chromatography (ethyl acetate/petroleum ether (v/v)=0-70%) to obtain compound 9-9.

MS (ESI) m/z (M+H)$^+$=622.2.

Step 10: Preparation of Compound 9-10

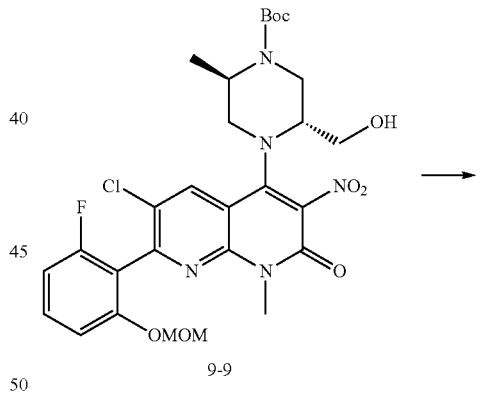

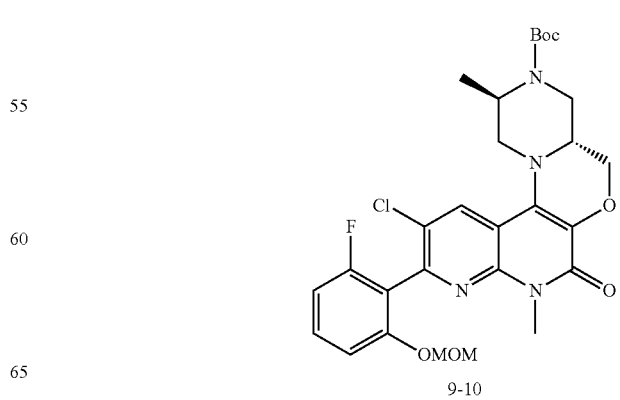

Compound 9-9 (86 mg, 0.138 mmol) was dissolved in N-dimethylacetamide (3 mL), and tetrahydrofuran solution of lithium bis(trimethylsilyl)amide (1 M, 0.8 mL) was added thereto at room temperature. After the addition was completed, under nitrogen atmosphere, the system was heated to 160° C. and stirred for 5 hours. The system was cooled to room temperature and filtered, the filtrate was diluted with ethyl acetate (20 mL) and washed with water (10 mL×2) and saturated saline (10 mL) successively. The organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 9-10.

MS (ESI) m/z (M+H)$^+$=575.2.

Step 11: Preparation of Compound 9-11

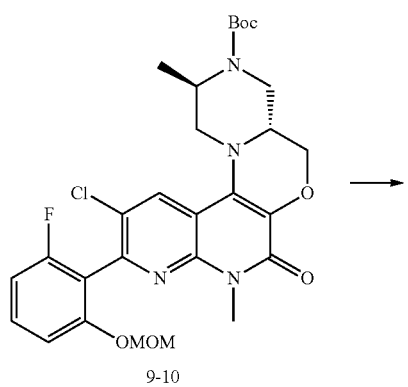

9-10

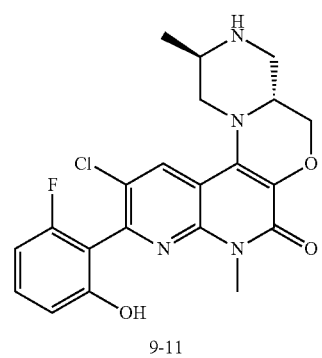

9-11

Compound 9-10 (32 mg, 0.0577 mmol), hydrochloric acid (6 N, 1 mL) were added to a mixed solution of methanol (0.9 mL) and tetrahydrofuran (0.1 mL). The system was heated to 55° C. and stirred for 15 min. The system was concentrated to obtain crude product 9-11.

Step 12: Preparation of Compound 9

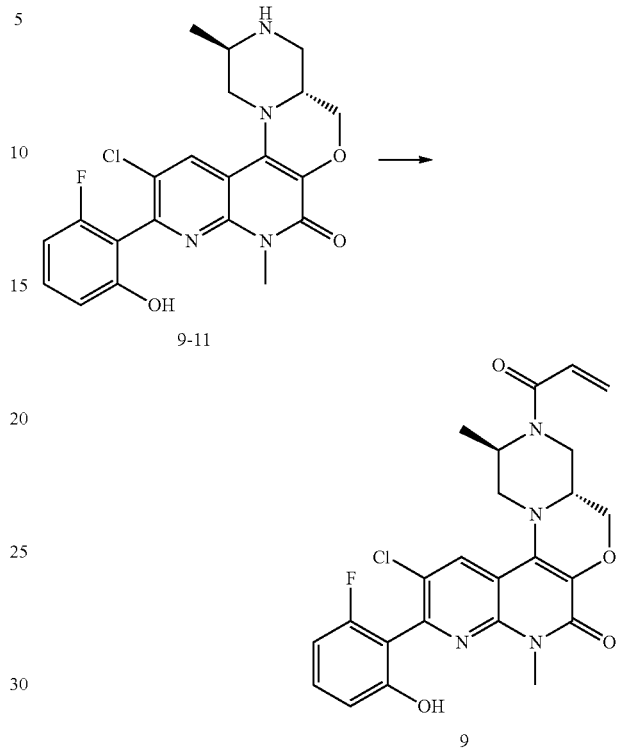

Compound 9-11 (24 mg, 0.056 mmol) was dissolved in dichloromethane (2 mL), and triethylamine (11 mg, 0.112 mmol) and acryloyl chloride (7 mg, 0.084 mmol) were added dropwise thereto at room temperature (20° C.). After the addition was completed, the system was stirred at room temperature (20° C.) for 2 hours. Tetrahydrofuran (4 mL), water (1 mL) and lithium hydroxide aqueous solution (31.74 mg, 756.47 μmol) were added to the system, and the mixture was stirred at room temperature (20° C.) for 2 hours. The pH of the system was adjusted to neutral with 1 N hydrochloric acid; and the mixture was extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Agilent 10 Prep-C8 250×21.2 mm; mobile phase: [water (0.1% FA)-acetonitrile]; acetonitrile %: 30%-50% 9 min, flow rate 30 mL/min) to obtain compound 9.

Compound 9:

$^1$H NMR (400 MHz, CDCl3) δ$^1$H NMR (400 MHz, CDCl$_3$) δ 8.11 (s, 1H), 7.35 (td, J=8.3, 6.5 Hz, 1H), 6.90 (d, J=8.3 Hz, 1H), 6.78 (t, J=9.1 Hz, 1H), 6.57 (s, 1H), 6.38 (d, J=17.0 Hz, 1H), 5.80 (d, J=11.3 Hz, 1H), 4.39 (s, 2H), 3.82 (s, 3H), 3.64 (s, 1H), 3.38 (d, J=13.4 Hz, 2H), 2.99 (d, J=13.0 Hz, 1H), 1.72 (s, 3H).

MS (ESI) m/z (M+H)$^+$=485.2.

HPLC 99% purity; retention time was 5.27 min.

Separation conditions: chromatographic column: Waters XSelect CSH C18, 4.6*100 mm, 3.5 μm; mobile phase: [water (0.01% trifluoroacetic acid)-acetonitrile (0.01% trifluoroacetic acid)]; acetonitrile: 5%-95% 7 min; flow rate: 1.2 mL/min.

Embodiment 10: Preparation of Compound 10

Step 1: Preparation of Compound 10-1

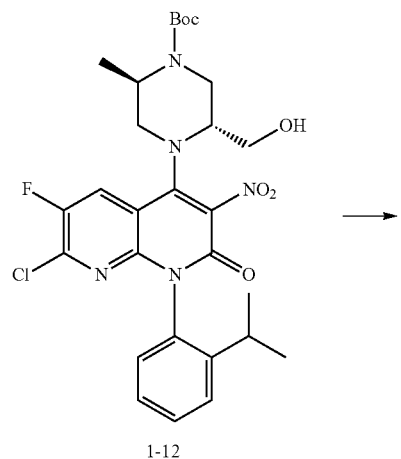

1-12

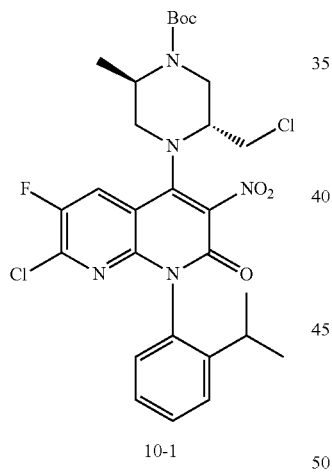

10-1

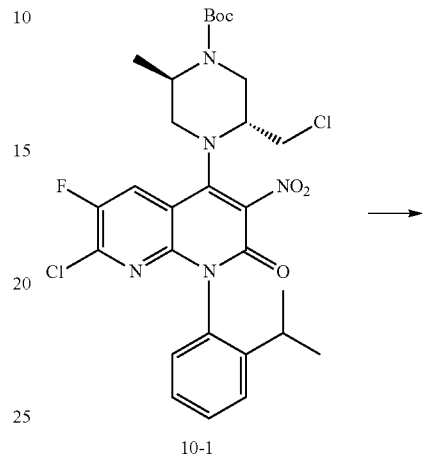

10-1

Step 2: Preparation of Compound 10-2

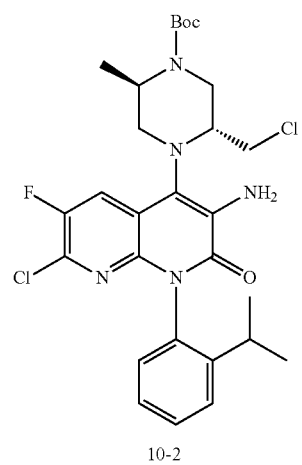

10-2

Compound 1-12 (470 mg, 0.798 mmol), triphenylphosphine (630 mg, 2.4 mmol) were added to 1,2-dichloroethane (20 mL), under nitrogen atmosphere, carbon tetrachloride (370 mg, 2.4 mmol) was added thereto. After the addition was completed, the system was heated to 80° C. and the reaction was carried out for 1 hour. The system was concentrated to obtain a crude product, the crude product was purified by medium pressure column chromatography (ethyl acetate/petroleum ether (v/v)=0-30%) to obtain compound 10-1.

MS (ESI) m/z (M+H)$^+$=608.2.

Compound 10-1 (330 mg, 0.54 mmol) was dissolved in glacial acetic acid (10 mL), iron powder (300 mg, 5.4 mmol) was added thereto, and the system was heated to 80° C. for 1 hour. The system was concentrated, the residue was dissolved in ethyl acetate, filtered with diatomite, the filtered filtrate was concentrated under vacuum, and purified by column chromatography (ethyl acetate/petroleum ether (v/v)=0-40%) to obtain compound 10-2.

MS (ESI) m/z (M+H)$^+$=578.2

Step 3: Preparation of Compound 10-3

Step 4: Preparation of Compound 10-4

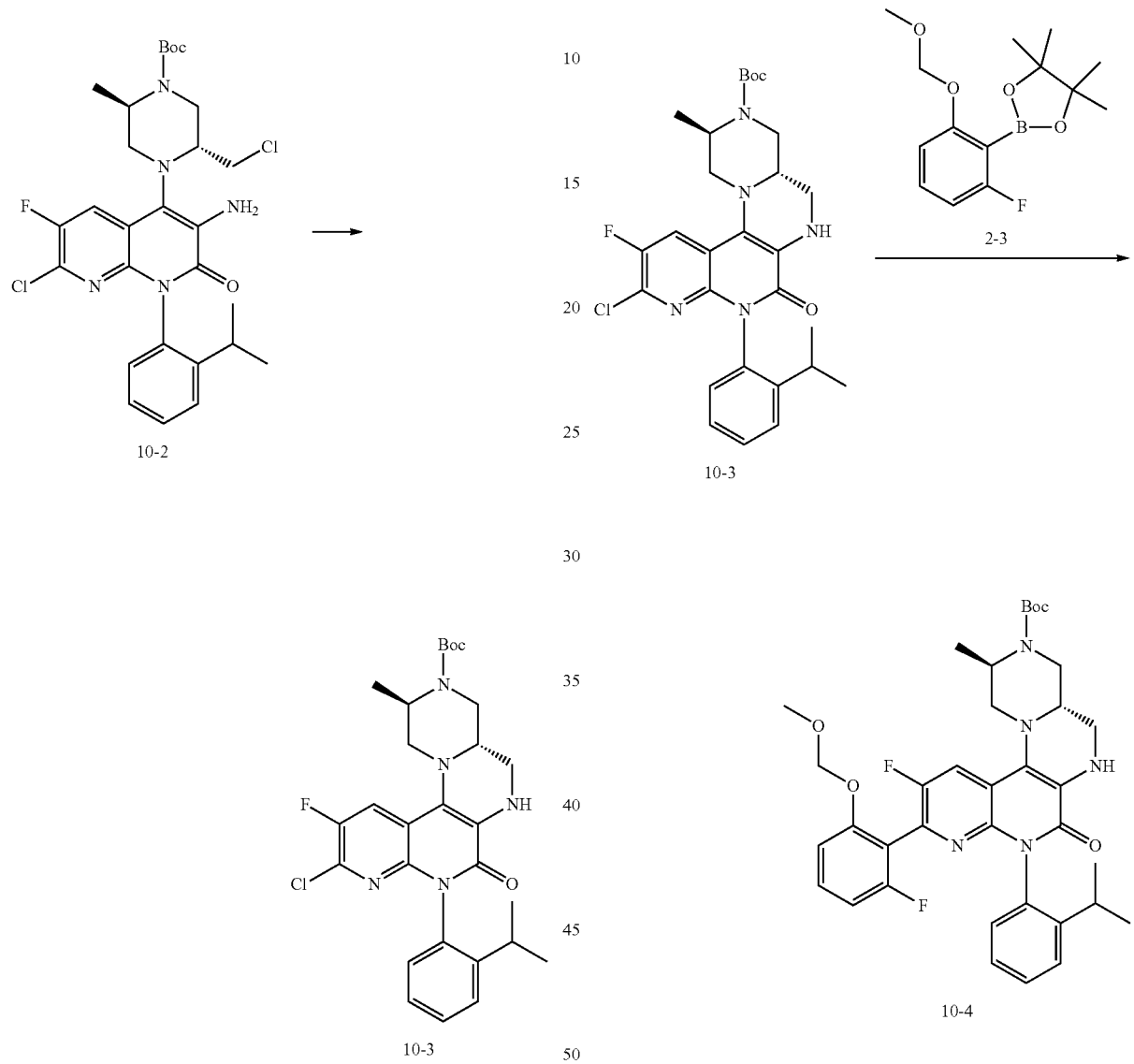

Compound 10-2 (200 mg, 0.347 mmol) and N,N-diisopropylethylamine (400 mg, 3.47 mmol) were dissolved in N,N-dimethylformamide (5 mL), the system was heated to 150° C. for 3 hours. The system was cooled to room temperature, added with water (50 mL), and then extracted with ethyl acetate (15 mL×3); the combined organic phase was dried over anhydrous sodium sulfate, filtered, and the filtrate was concentrated to obtain a crude product. The crude product was purified by medium pressure column chromatography (ethyl acetate/petroleum ether (v/v)=0-30%) to obtain compound 10-3.

MS (ESI) m/z (M+H)$^+$=542.2.

Compound 10-3 (130 mg, 0.24 mmol), compound 2-3 (135 mg, 0.48 mmol), tetrakis (triphenylphosphine) palladium (138 mg, 0.12 mmol), sodium carbonate (234 mg, 0.72 mmol) were dissolved in a mixed solution of dioxane (5 mL) and water (0.5 mL), under nitrogen atmosphere, the system was heated to 100° C. and stirred for 1 hour. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 10-4.

MS (ESI) m/z (M+H)$^+$=662.2.

Step 5: Preparation of Compound 10-5

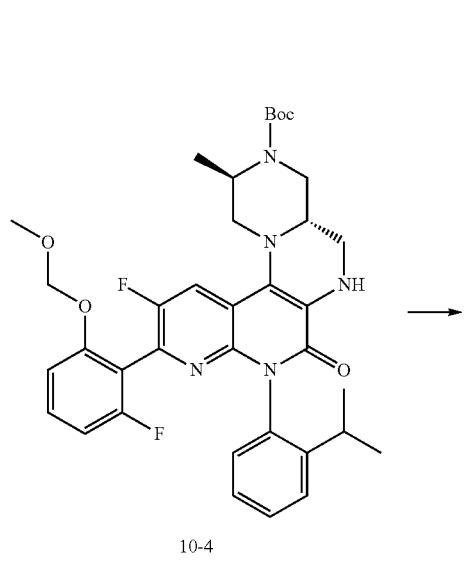

10-4

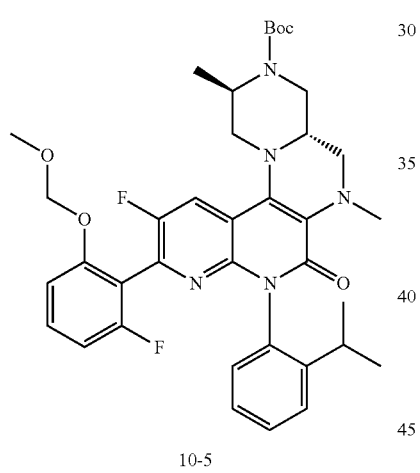

10-5

Compound 10-4 (40 mg, 0.06 mmol) was dissolved in tetrahydrofuran (2 mL), and sodium hydride (7.2 mg, 0.18 mmol) was added thereto at 0° C. After the addition was completed, the system was heated to room temperature and stirred for 30 min. Iodomethane (17 mg, 0.12 mmol) was added to the system, after the addition was completed, the system was stirred at room temperature (20° C.) for 1 hour. Water (5 mL) was added to the system to quench the reaction, the mixture was extracted with ethyl acetate (15 mL×4), the combined organic phase was dried over anhydrous sodium sulfate, filtered, and the filtrate was concentrated to obtain a crude product. The crude product was purified by medium pressure column chromatography (ethyl acetate/petroleum ether (v/v)=0-30%) to obtain compound 10-5.

MS (ESI) m/z (M+H)$^+$=676.2.

Step 6: Preparation of Compound 10-6

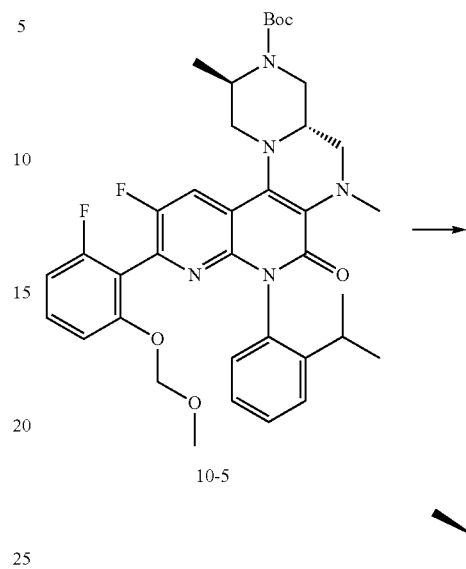

10-5

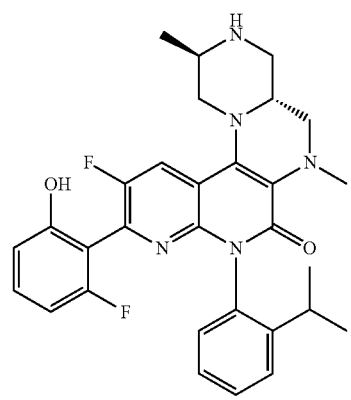

10-6

Compound 10-5 (30 mg, 0.044 mmol, hydrochloric acid (6N, 2 mL) were added to a mixed solution of methanol (10 mL) and tetrahydrofuran (1 mL). The system was heated to 55° C. and stirred for 15 min. The system was concentrated to obtain crude product 10-6.

MS (ESI) m/z (M+H)$^+$=532.4.

Step 7: Preparation of Compound 10

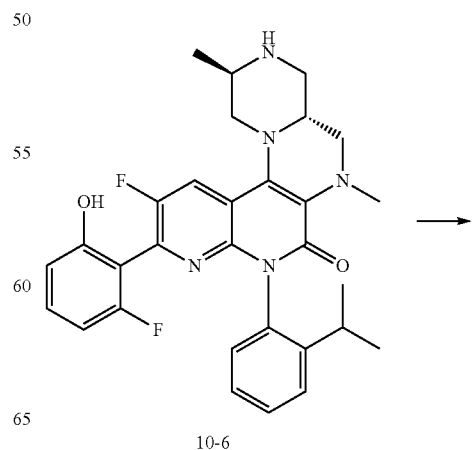

10-6

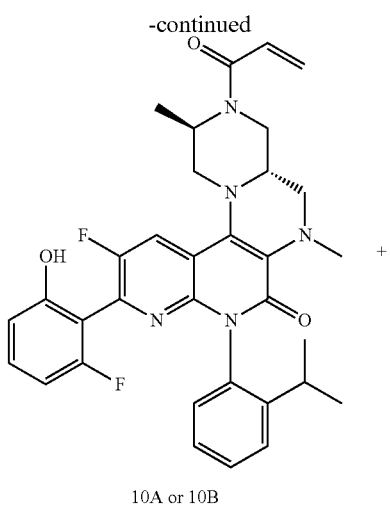

10A or 10B

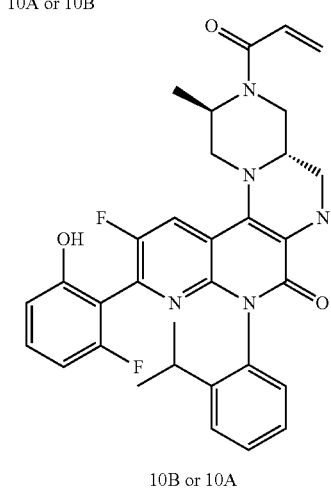

10B or 10A

Compound 10-6 (15 mg, 0.060 mmol) was dissolved in dichloromethane (5 mL), and the system was cooled to 0° C., triethylamine (10 mg, 0.100 mmol) and acryloyl chloride (5 mg, 0.055 mmol) were added dropwise thereto. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column: Welch Ultimate XB-C18 10×250 mm 5 μm; mobile phase: [water (0.1% FA)-acetonitrile]; acetonitrile %: 50%-60% 10 min, 60% 20 min; flow rate 8 mL/min). After concentration, compound 10A and compound 10B were obtained.

MS (ESI) m/z (M+H)$^+$=586.2.
Compound 10A:
$^1$H NMR (400 MHz, Methanol-d$_4$) δ 7.83 (d, J=9.8 Hz, 1H), 7.47-7.30 (m, 2H), 7.23 (td, J=7.5, 1.7 Hz, 1H), 7.10 (td, J=8.3, 6.5 Hz, 1H), 6.96 (dd, J=7.9, 1.3 Hz, 1H), 6.74 (dd, J=16.7, 10.7 Hz, 1H), 6.58-6.43 (m, 2H), 6.18 (dd, J=16.8, 2.0 Hz, 1H), 5.72 (d, J=10.6 Hz, 1H), 5.24 (td, J=4.5, 2.2 Hz, 1H), 4.41 (m, 2H), 4.06 (d, J=20.7 Hz, 1H), 3.69-3.57 (m, 1H), 3.48-3.35 (m, 2H), 3.07 (m, 3H), 3.073 (m, 1H), 2.92 (d, J=12.3 Hz, 1H), 2.51-2.34 (m, 1H), 1.63 (m, 3H), 1.04 (m, 3H), 0.89 (m, 3H).

HPLC 93% purity; retention time was 6.397 min.
Separation conditions: chromatographic column: Waters X-bridge C18, 4.6*100 mm, 3.5 μm; mobile phase: water (10 mM ammonium bicarbonate aqueous solution)-acetonitrile; acetonitrile: 5%-95% 7 min; flow rate: 1.2 mL/min.
Compound 10B:
$^1$H NMR (400 MHz, Methanol-d$_4$) δ 7.83 (d, J=9.8 Hz, 1H), 7.48-7.30 (m, 2H), 7.22 (td, J=7.5, 1.7 Hz, 1H), 7.09 (td, J=8.3, 6.5 Hz, 1H), 7.01 (dd, J=7.9, 1.3 Hz, 1H), 6.74 (dd, J=16.8, 10.6 Hz, 1H), 6.62-6.38 (m, 2H), 6.18 (dd, J=16.8, 2.0 Hz, 1H), 5.72 (d, J=10.7 Hz, 1H), 5.24 (td, J=4.5, 2.2 Hz, 1H), 4.52 (m, 2H), 4.06 (d, J=19.0 Hz, 1H), 3.72-3.57 (m, 1H), 3.47-3.33 (m, 2H), 3.07 (s, 3H), 3.05-3.00 (m, 1H), 2.51-2.34 (m, 1H), 1.63 (d, J=26.2 Hz, 3H), 1.04 (d, J=6.9 Hz, 3H), 0.89 (d, J=6.9 Hz, 3H).

HPLC 95% purity; retention time was 6.580 min.
Separation conditions: chromatographic column: Waters X-bridge C18, 4.6*100 mm, 3.5 μm; mobile phase: water (10 mM ammonium bicarbonate aqueous solution)-acetonitrile; acetonitrile: 5%-95% 7 min; flow rate: 1.2 mL/min.

Embodiment 11: Preparation of Compound 11

Step 1: Preparation of Compound 11-1

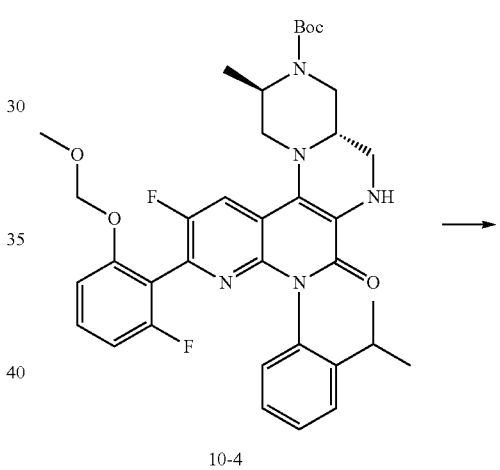

10-4

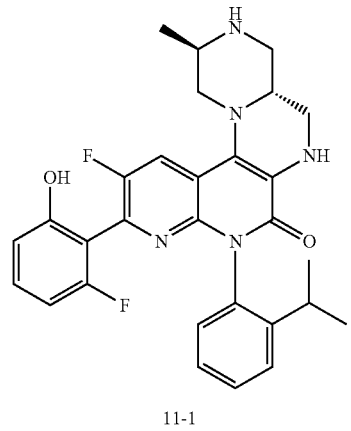

11-1

Compound 10-4 (40 mg, 0.06 mmol), hydrochloric acid (6N, 1 mL) were added to a mixed solution of methanol (3 mL) and tetrahydrofuran (0.5 mL). The system was heated to 55° C. and stirred for 15 min. The system was concentrated to obtain crude product 11-1.

MS (ESI) m/z (M+H)$^+$=518.2.

Step 2: Preparation of Compound 11

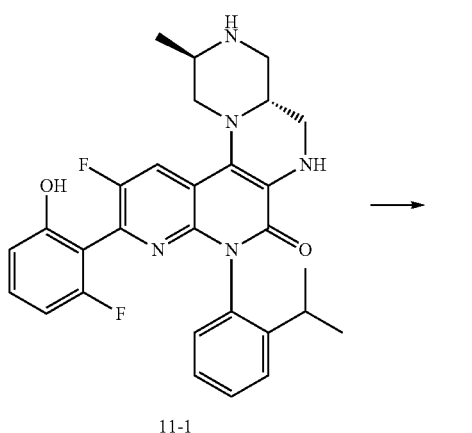

11-1

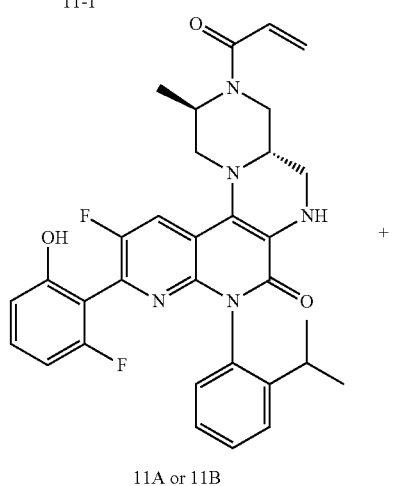

11A or 11B

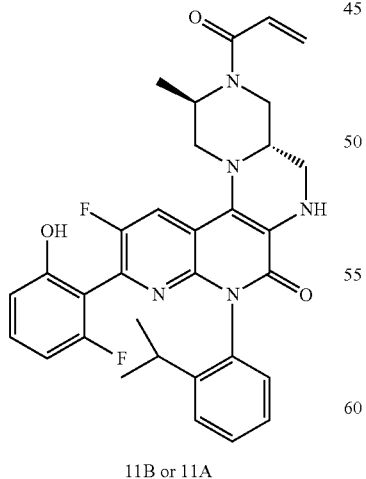

11B or 11A

Compound 11-1 (15 mg, 0.060 mmol) was dissolved in dichloromethane (5 mL), and the system was cooled to 0° C., triethylamine (10 mg, 0.100 mmol) and acryloyl chloride (5 mg, 0.055 mmol) were added dropwise thereto. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column: Welch Ultimate XB-C18 10×250 mm 5 μm; mobile phase: [water (0.1% FA)-acetonitrile]; acetonitrile %: 50%-60% 10 min, 60% 20 min; flow rate 8 mL/min) to obtain compound 11A and compound 11B.

Compound 11A:

$^1$H NMR (400 MHz, Methanol-d$_4$) δ 7.85 (dd, J=10.0, 6.7 Hz, 1H), 7.54-7.40 (m, 2H), 7.33 (td, J=7.5, 1.8 Hz, 1H), 7.17 (td, J=8.3, 6.5 Hz, 1H), 7.11-7.04 (m, 1H), 6.83 (dd, J=16.8, 10.7 Hz, 2H), 6.59 (td, J=8.5, 1.3 Hz, 2H), 6.26 (dd, J=16.8, 2.0 Hz, 1H), 5.80 (ddd, J=10.7, 6.5, 2.0 Hz, 1H), 5.33 (td, J=4.4, 2.2 Hz, 1H), 4.70-4.55 (m, 2H), 4.24-4.05 (m, 1H), 3.84-3.61 (m, 2H), 3.53-3.31 (m, 2H), 3.04 (ddd, J=16.8, 12.4, 3.7 Hz, 1H), 2.47 (td, J=6.9, 2.6 Hz, 1H), 1.73 (dd, J=31.0, 6.8 Hz, 3H), 1.11 (d, J=6.9 Hz, 3H), 0.96 (d, J=6.8 Hz, 3H).

MS (ESI) m/z (M+H)$^+$=572.2.

HPLC 95% purity; retention time was 6.180 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Compound 11B:

$^1$H NMR (400 MHz, Methanol-d$_4$) δ 7.75 (dd, J=9.9, 6.5 Hz, 1H), 7.47-7.30 (m, 2H), 7.23 (td, J=7.5, 1.7 Hz, 1H), 7.16-6.95 (m, 1H), 6.74 (ddd, J=16.8, 10.6, 2.6 Hz, 1H), 6.55-6.41 (m, 2H), 6.17 (dd, J=16.8, 1.9 Hz, 1H), 5.71 (ddd, J=10.7, 6.5, 2.0 Hz, 1H), 5.24 (td, J=4.5, 2.2 Hz, 1H), 4.59-4.48 (m, 1H), 4.41 (s, 1H), 4.14-3.92 (m, 1H), 3.72-3.54 (m, 2H), 3.46-3.28 (m, 2H), 2.93 (ddd, J=16.6, 12.5, 3.7 Hz, 1H), 2.30 (q, J=6.9 Hz, 1H), 1.64 (dd, J=30.9, 6.8 Hz, 3H), 1.02 (d, J=6.9 Hz, 3H), 0.89 (d, J=6.9 Hz, 3H).

MS (ESI) m/z (M+H)$^+$=572.2.

HPLC 95% purity; retention time was 6.328 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Embodiment 12: Preparation of Compound 12

Step 1: Preparation of Compound 12-2

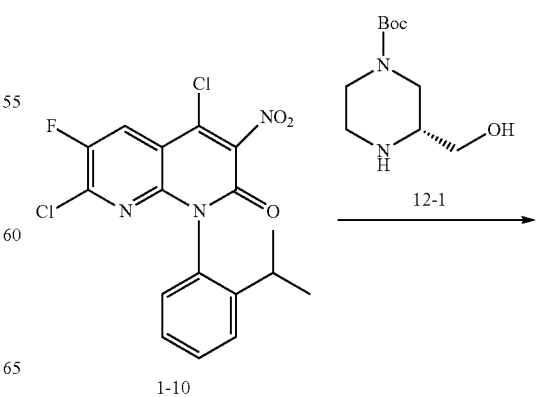

1-10

-continued

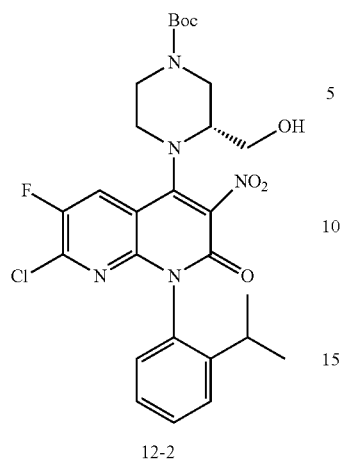

12-2

Compound 1-10 (1.37 g, 3.46 mmol), compound 12-1 (900 mg, 4.16 mmol), cuprous iodide (395 mg, 0.5 mmol), and cesium carbonate (2.26 g, 6.92 mmol) were dissolved in dioxane (20.0 mL), under nitrogen atmosphere, the system was heated to 100° C. and stirred for 1 hour. The system was filtered by diatomite, and the filtrate was concentrated to obtain a crude product. The crude product was purified by medium pressure column chromatography (ethyl acetate/petroleum ether (v/v)=0-33%) to obtain compound 12-2.

MS (ESI) m/z (M+H)$^+$=576.20.

Step 2: Preparation of Compound 12-3

-continued

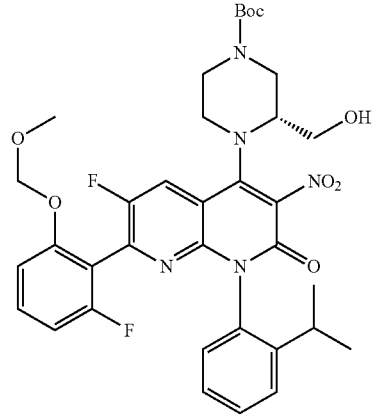

12-3

Compound 12-2 (700 mg, 1.2 mmol), compound 2-3 (508 mg, 1.8 mmol), 1,1-bis(diphenylphosphino)ferrocene palladium dichloride (176 mg, 0.24 mmol), potassium carbonate (323 mg, 2.4 mmol) were dissolved in a mixed solution of dioxane (20 mL) and water (2 mL), under nitrogen atmosphere, the system was heated to 100° C. and stirred for 2 hours. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 12-3.

MS (ESI) m/z (M+H)$^+$=696.40.

Step 3: Preparation of Compound 12-4

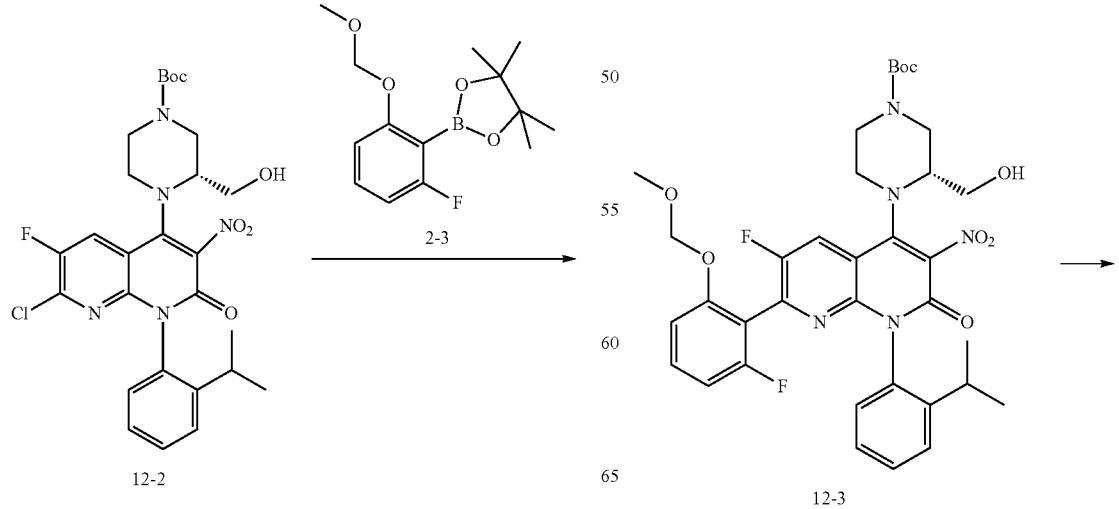

-continued

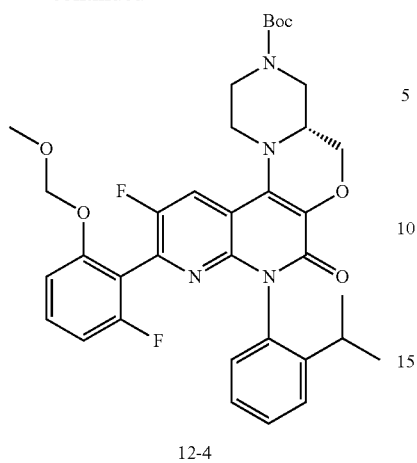

12-4

Compound 12-3 (50 mg) was dissolved in N, N-dimethylacetamide (1 mL), and tetrahydrofuran solution of lithium bis(trimethylsilyl)amide (24%, 0.5 mL) was added thereto at room temperature, under nitrogen atmosphere, the system was heated to 150° C. and stirred for 4 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 12-4.

MS (ESI) m/z (M+H)$^+$=649.40.

Step 4: Preparation of Compound 12-5

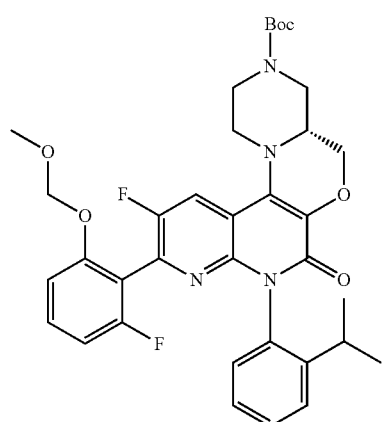

12-4

-continued

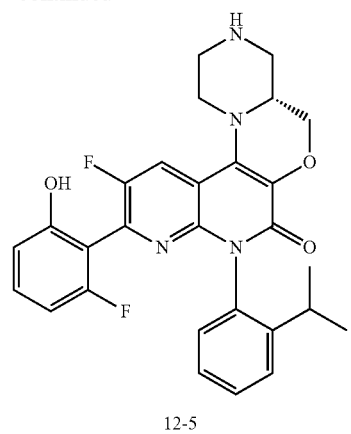

12-5

Compound 12-4 (60.0 mg), hydrochloric acid (6 N, 1 mL) were added to a mixed solution of methanol (0.9 mL) and tetrahydrofuran (0.1 mL). The system was heated to 55° C. and stirred for 15 min. The system was concentrated to obtain crude product 12-5.

MS (ESI) m/z (M+H)$^+$=505.20.

Step 5: Preparation of Compounds 12A and 12B

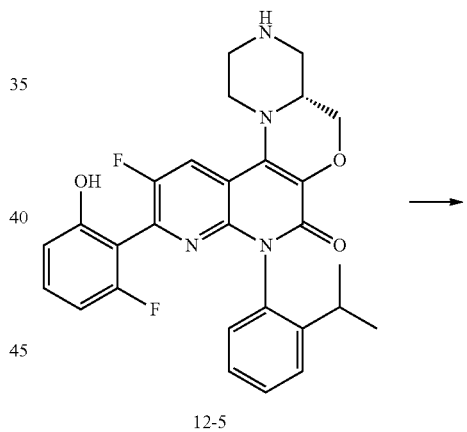

12-5

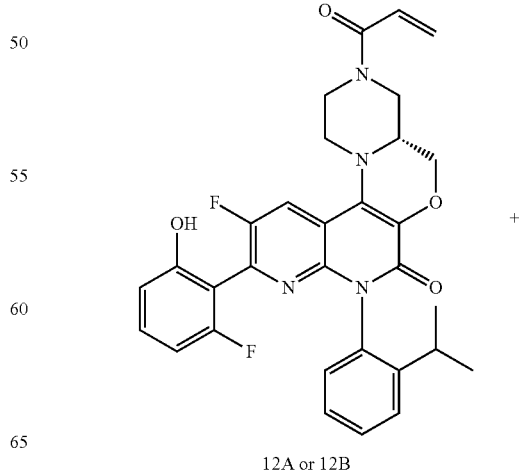

12A or 12B

-continued

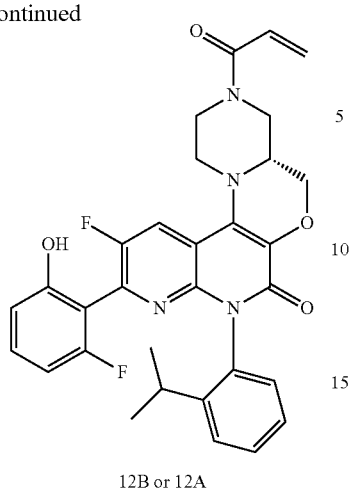

12B or 12A

Compound 12-5 (45 mg, 0.09 mmol) was dissolved in dichloromethane (1 mL), and triethylamine (22 μL, 0.27 mmol) and acryloyl chloride (39 μL, 0.27 mmol) were added dropwise thereto at 0° C. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain an intermediate. Then the intermediate was dissolved in tetrahydrofuran (2.0 mL) and water (1.0 mL), lithium hydroxide (18.9 mg, 0.45 mmol) was added, and the mixture was stirred at room temperature for 30 min. The pH of the reaction mixture was adjusted to 5-6 with dilute hydrochloric acid (3.0 N), and then the crude product was obtained by extraction with ethyl acetate and concentration. The crude product was purified by preparative high performance liquid chromatography (separation conditions: chromatographic column: Agilent 10 Prep-C8 250×21.2 mm; column temperature: 25° C.; mobile phase: water (0.1% FA)-acetonitrile; acetonitrile ratio in mobile phase was 40%-52% in 12 min, 52%-52% 16 min; flow rate 30 mL/min) to obtain compound 12B.

Compound 12A:

$^1$H NMR (400 MHz, Chloroform-d) δ 7.94 (d, J=9.9 Hz, 1H), 7.61-7.50 (m, 2H), 7.47-7.34 (m, 1H), 7.22 (td, J=8.3, 6.4 Hz, 1H), 7.05 (d, J=7.5 Hz, 1H), 6.73-6.57 (m, 3H), 6.41 (dd, J=16.8, 1.7 Hz, 1H), 5.85 (d, J=10.1 Hz, 1H), 4.68-4.30 (m, 4H), 3.81-3.35 (m, 4H), 3.16 (s, 1H), 2.57 (q, J=6.8 Hz, 1H), 1.19 (d, J=6.8 Hz, 3H), 0.99 (d, J=6.8 Hz, 3H).

MS (ESI) m/z (M+H)$^+$=559.20.

HPLC 100% purity; retention time was 5.483 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Compound 12B:

$^1$H NMR (400 MHz, Chloroform-d) δ 7.93 (d, J=9.9 Hz, 1H), 7.63-7.48 (m, 2H), 7.44-7.33 (m, 1H), 7.25-7.17 (m, 1H), 7.13 (d, J=7.8 Hz, 1H), 6.70-6.56 (m, 3H), 6.41 (dd, J=16.7, 1.7 Hz, 1H), 5.84 (d, J=10.4 Hz, 1H), 4.62-4.23 (m, 3H), 4.07-4.00 (m, 1H), 3.79-3.47 (m, 4H), 3.21-3.03 (m, 1H), 2.47 (q, J=6.8 Hz, 1H), 1.18 (d, J=6.8 Hz, 3H), 0.98 (d, J=6.8 Hz, 3H).

MS (ESI) m/z (M+H)$^+$=559.20.

HPLC 100% purity; retention time was 5.555 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Embodiment 13: Preparation of Compound 13

Step 1: Preparation of Compound 13-2

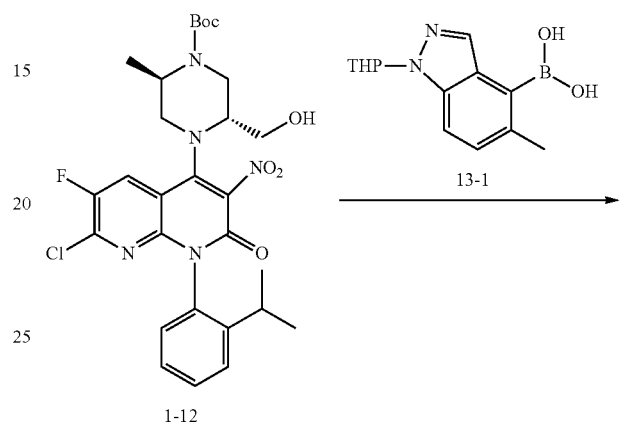

1-12

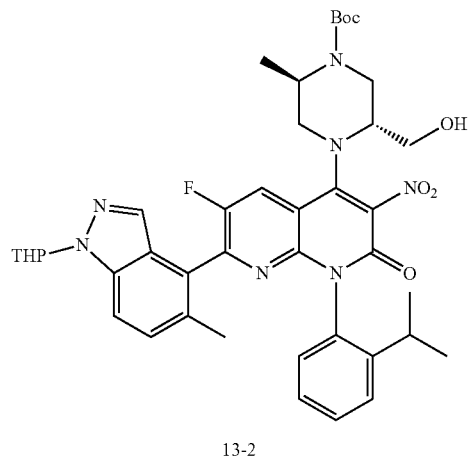

13-2

Compound 1-12 (766 mg, 1.3 mmol), compound 13-1 (534 mg, 1.56 mmol), 1,1-bis(diphenylphosphino)ferrocene palladium dichloride (96 mg, 0.13 mmol), potassium carbonate (359 mg, 2.6 mmol) was dissolved in a mixed solution of tetrahydrofuran (20 mL) and water (2 mL), under nitrogen atmosphere, the system was heated to 80° C. and stirred for 2 hours. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-33%) to obtain compound 13-2.

MS (ESI) m/z (M+H)$^+$=770.20.

Step 2: Preparation of Compound 13-3

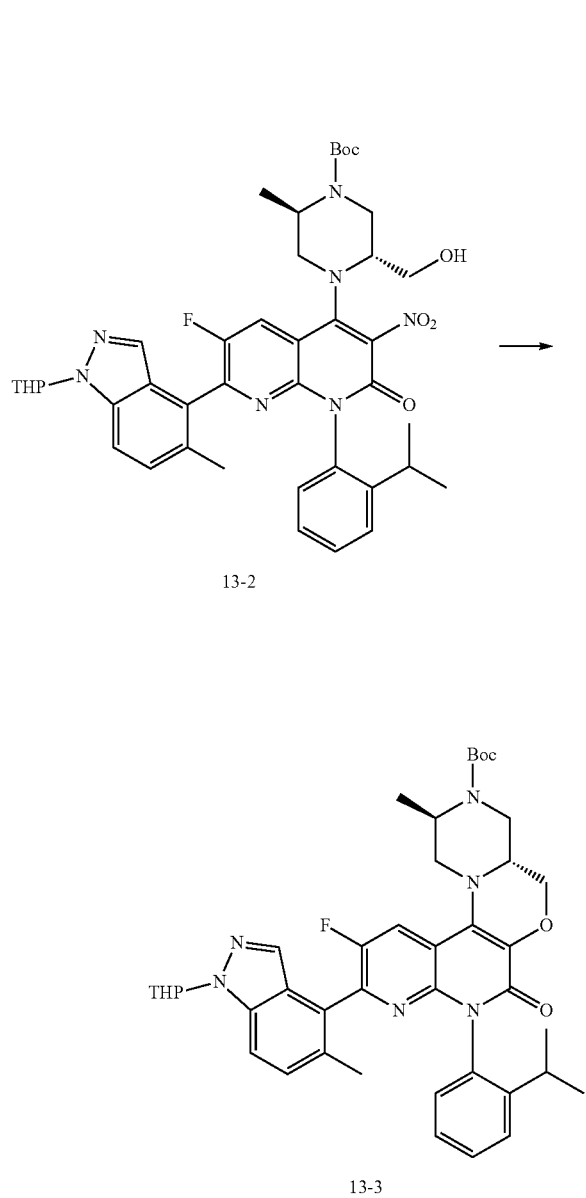

13-2

13-3

Compound 13-2 (300 mg) was dissolved in N, N-dimethylformamide (6 mL), and tetrahydrofuran solution of lithium bis(trimethylsilyl)amide (24%, 3.0 mL) was added thereto at room temperature, the system was heated to 150° C. and stirred for 16 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 13-3.

MS (ESI) m/z (M+H)$^+$=723.30.

Step 3: Preparation of Compound 13-4

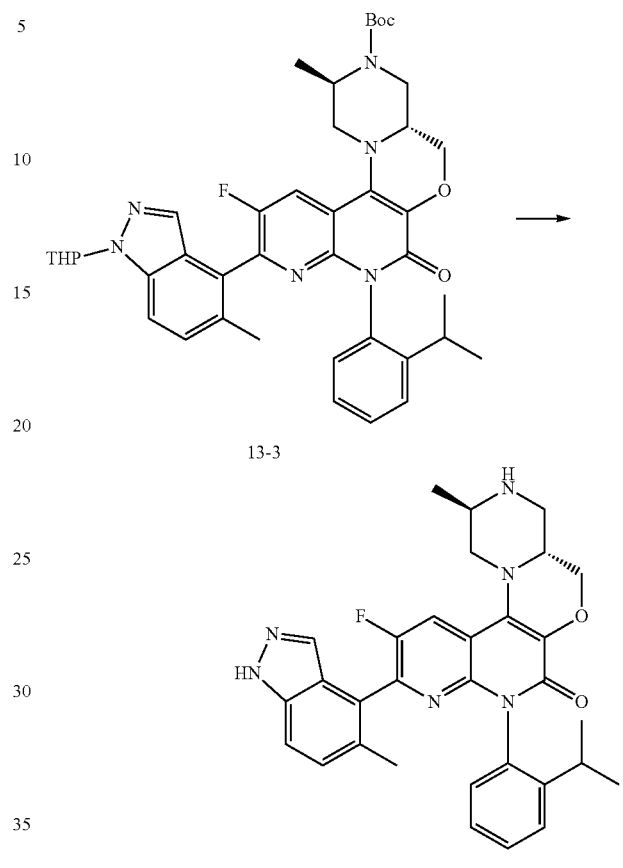

13-3

13-4

Compound 13-3 (214.0 mg), hydrochloric acid (6 N, 4.0 mL) were added to a mixed solution of methanol (3.6 mL) and tetrahydrofuran (0.4 mL). The system was heated to 55° C. and stirred for 15 min. The system was concentrated to obtain crude product 13-4.

MS (ESI) m/z (M+H)$^+$=539.20

Step 4: Preparation of Compounds 13A and 13B

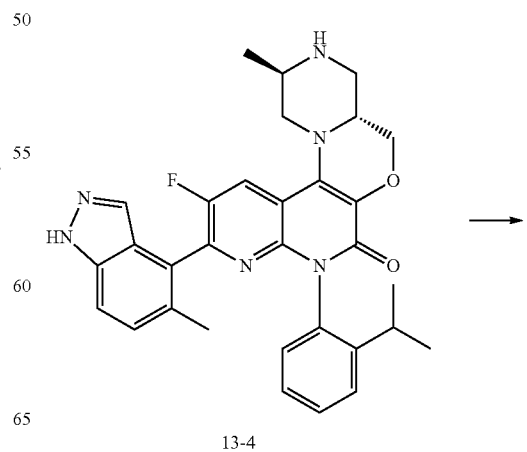

13-4

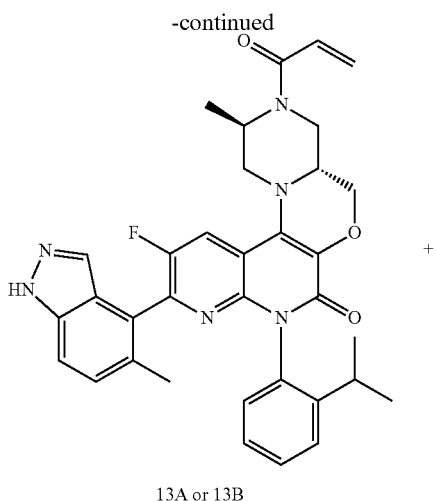

13A or 13B

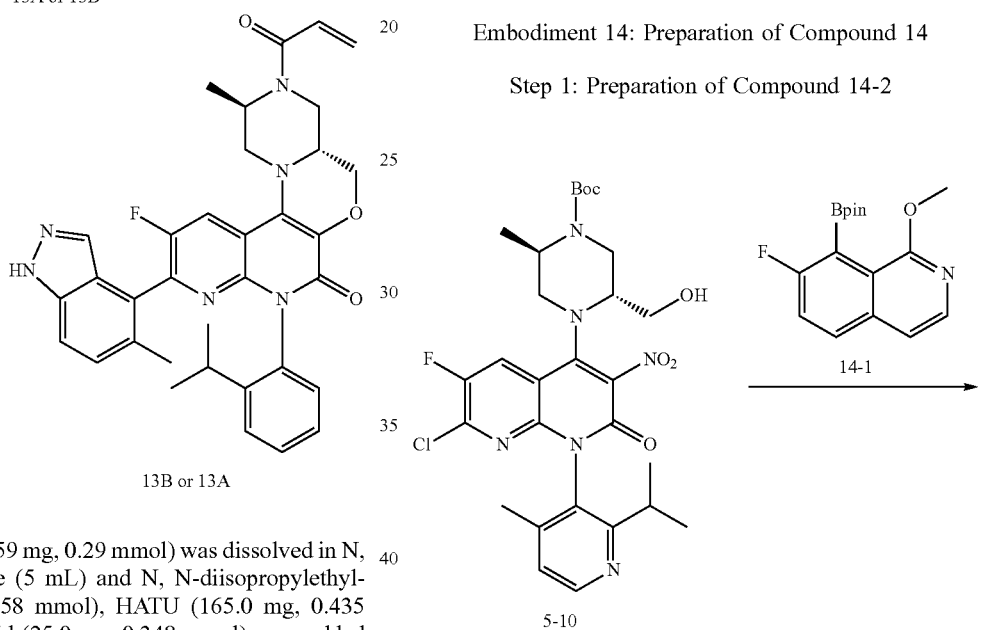

13B or 13A

Compound 13-4 (159 mg, 0.29 mmol) was dissolved in N, N-dimethylformamide (5 mL) and N, N-diisopropylethylamine (0.072 mL, 0.58 mmol), HATU (165.0 mg, 0.435 mmol) and acrylic acid (25.0 mg, 0.348 mmol) were added dropwise thereto at room temperature. After the dropwise addition was completed, the system was raised to room temperature (20° C.) and the reaction was carried out for 30 min. The reaction mixture was washed with water (30 mL), extracted with ethyl acetate (30 mL); the organic phase was dried over anhydrous sodium sulfate, filtered, and the filtrate was concentrated to obtain a crude product. The crude product was purified by preparative high performance liquid chromatography (chromatographic column: Agilent 10 Prep-C8 250×21.2 mm; column temperature: 25° C.; mobile phase: water (0.1% FA)-acetonitrile; acetonitrile ratio in mobile phase was 25%-40% in 9 min, 40%-45% in 12 min; flow rate 30 mL/min) to obtain compound 13A and compound 13B.

Compound 13A:
$^1$H NMR (400 MHz, Chloroform-d) δ 7.84 (d, J=9.1 Hz, 1H), 7.60 (s, 1H), 7.45 (d, J=8.6 Hz, 1H), 7.40-7.33 (m, 2H), 7.33-7.26 (m, 2H), 7.07 (d, J=7.8 Hz, 1H), 6.70-6.53 (m, 1H), 6.40 (d, J=16.3 Hz, 1H), 5.87-5.76 (m, 1H), 5.19-4.70 (m, 1H), 4.53-4.29 (m, 2H), 4.19-3.91 (m, 1H), 3.76-3.34 (m, 3H), 3.16 (d, J=12.2 Hz, 1H), 2.59 (p, J=6.9 Hz, 1H), 2.19 (s, 3H), 1.89-1.63 (m, 3H), 1.15 (d, J=6.8 Hz, 3H), 0.86 (d, J=6.8 Hz, 3H).

HPLC 100% purity; retention time was 5.069 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Compound 13B:
$^1$H NMR (400 MHz, Chloroform-d) δ 7.84 (d, J=9.1 Hz, 1H), 7.57 (s, 1H), 7.43-7.32 (m, 3H), 7.26-7.16 (m, 2H), 7.11 (d, J=7.7 Hz, 1H), 6.73-6.55 (m, 1H), 6.40 (d, J=16.5 Hz, 1H), 5.82 (dd, J=10.5, 1.7 Hz, 1H), 5.15-4.68 (m, 1H), 4.42 (d, J=26.9 Hz, 2H), 4.23-3.93 (m, 1H), 3.77-3.42 (m, 3H), 3.12 (d, J=12.2 Hz, 1H), 2.49 (p, J=6.8 Hz, 1H), 2.15 (s, 3H), 1.75 (d, J=23.3 Hz, 3H), 1.15 (d, J=6.8 Hz, 3H), 0.84 (d, J=6.8 Hz, 3H).

HPLC 100% purity; retention time was 5.279 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Embodiment 14: Preparation of Compound 14

Step 1: Preparation of Compound 14-2

Compound 5-10 (504 mg, 0.84 mmol), compound 14-1 (500 mg, 1.67 mmol), 1,1-bis(diphenylphosphino)ferrocene palladium dichloride (62 mg, 0.084 mmol), potassium carbonate (232 mg, 1.68 mmol) was dissolved in a mixed solution of tetrahydrofuran (20 mL) and water (2 mL), under nitrogen atmosphere, the system was heated to 80° C. and stirred for 6 hours. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-60%) to obtain compound 14-2.

MS (ESI) m/z (M+H)$^+$=746.20.

Step 2: Preparation of Compound 14-3

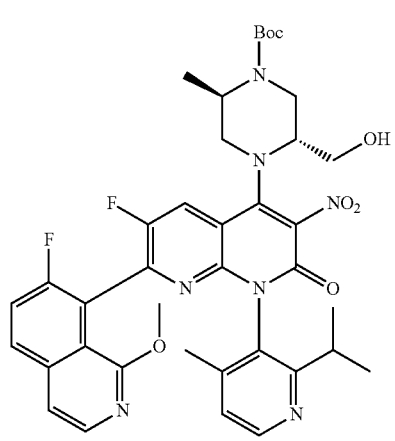

14-2

Step 3: Preparation of Compound 14-4

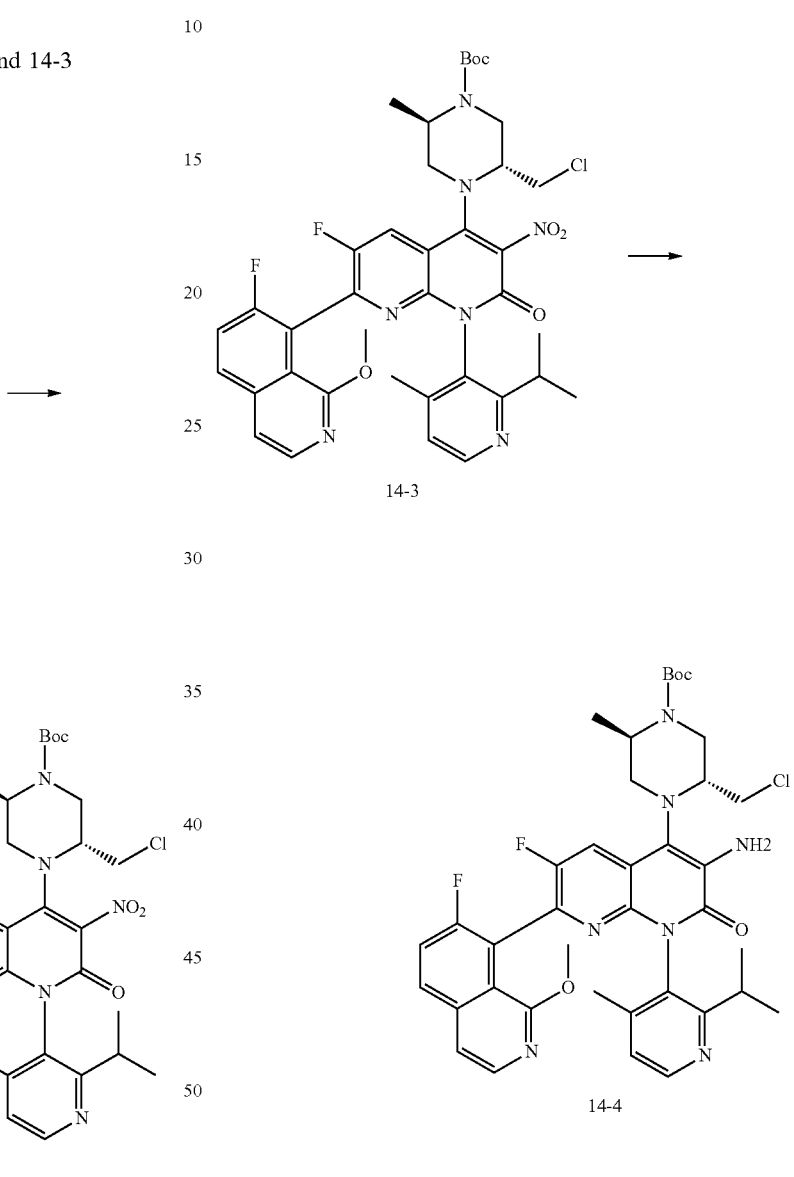

Compound 14-2 (200 mg, 0.268 mmol), triphenylphosphine (213 mg, 0.8 mmol) were added to 1,2-dichloroethane (4 mL), under nitrogen atmosphere, carbon tetrachloride (130 mg, 0.8 mmol) was added thereto. After the addition was completed, the system was heated to 80° C. and the reaction was carried out for 1 hour. The system was concentrated to obtain a crude product, the crude product was purified by medium pressure column chromatography (ethyl acetate/petroleum ether (v/v)=0-50%) to obtain compound 14-3.

MS (ESI) m/z (M+H)$^+$=764.20.

Compound 14-3 (40 mg, 0.05 mmol) was dissolved in glacial acetic acid (3 mL), iron powder (30.0 mg, 0.054 mmol) was added thereto, and the system was heated to 80° C. for 1 hour. The system was concentrated, the residue was dissolved in ethyl acetate, filtered with diatomite, the filtered filtrate was concentrated under vacuum, and purified by column chromatography (ethyl acetate/petroleum ether (v/v)=0-50%) to obtain compound 14-4.

MS (ESI) m/z (M+H)$^+$=734.20.

Step 4: Preparation of Compound 14-5

Step 5: Preparation of Compound 14-6

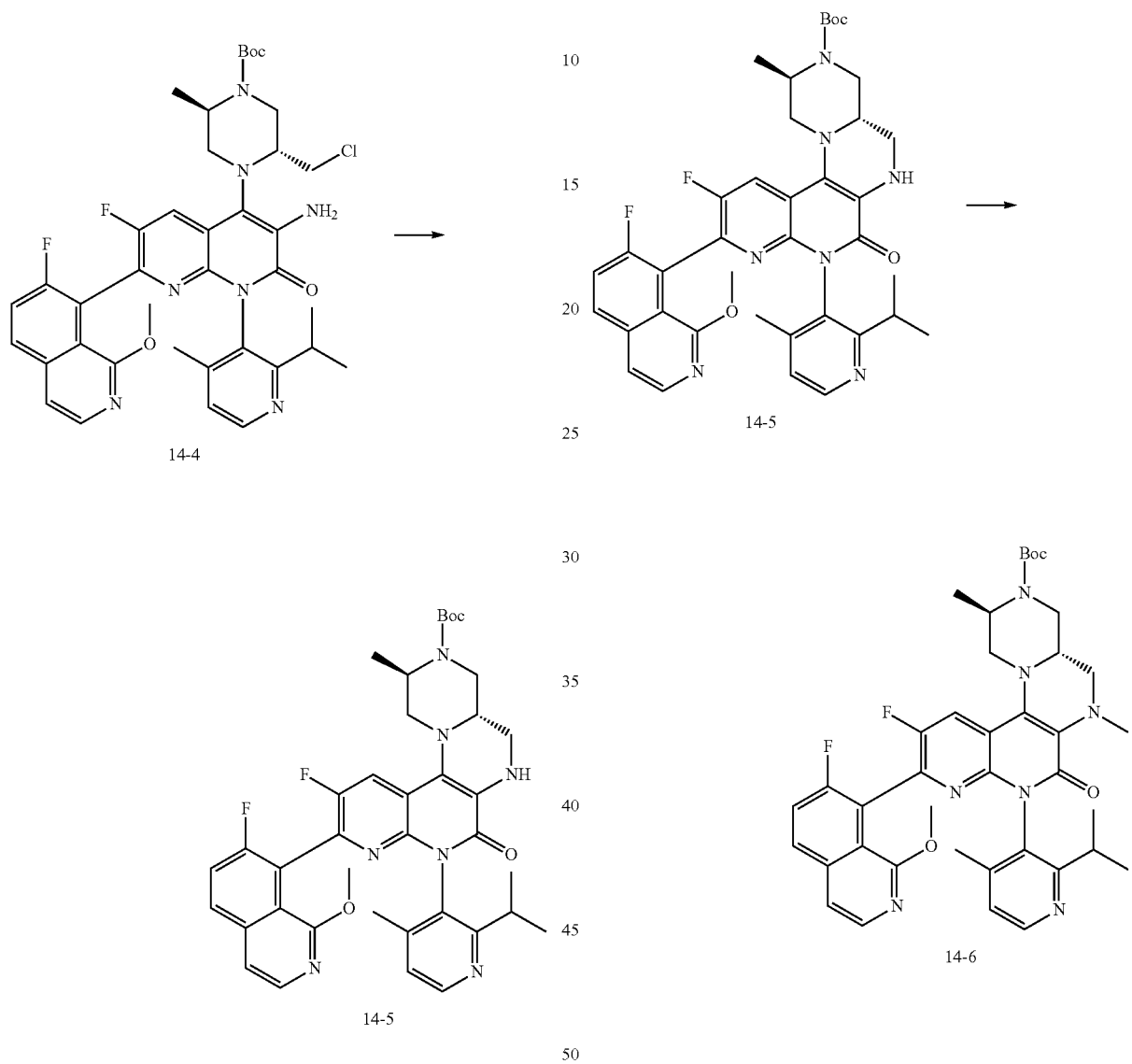

Compound 14-4 (60 mg, 0.082 mmol) and N,N-diisopropylethylamine (0.4 mL) and potassium iodide (14 mg, 0.082 mmol) were dissolved in N,N-dimethylformamide (4 mL), the system was heated to 120° C. for 7 hours. The system was cooled to room temperature, added with water (50 mL), and then extracted with ethyl acetate (15 mL×3); the combined organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 14-5.

MS (ESI) m/z (M+H)$^+$=698.40.

Compound 14-5 (33 mg, 0.047 mmol) was dissolved in tetrahydrofuran (2 mL), and sodium hydride (7.2 mg, 0.18 mmol) was added thereto at 0° C. After the addition was completed, the system was heated to room temperature and stirred for 30 min. Iodomethane (17 mg, 0.12 mmol) was added to the system, after the addition was completed, the system was stirred at room temperature (20° C.) for 1 hour. Water (5 mL) was added to the system to quench the reaction, the mixture was extracted with ethyl acetate (15 mL×4), the combined organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 14-6.

MS (ESI) m/z (M+H)$^+$=712.50.

Step 6: Preparation of Compound 14-7

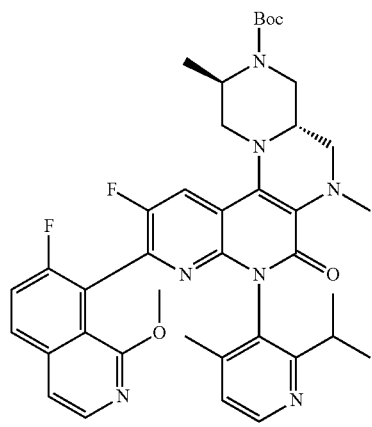

14-6

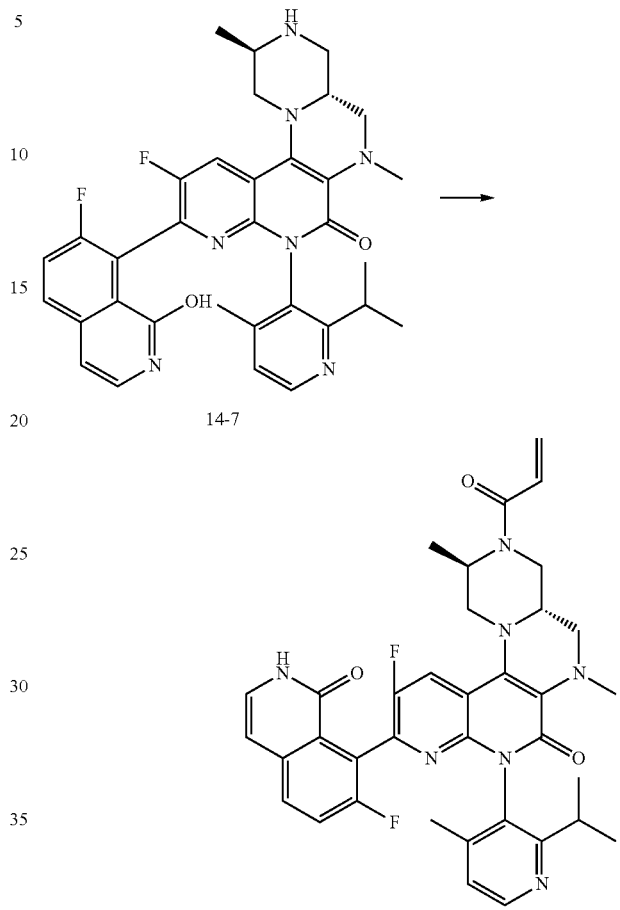

14-7

Compound 14-6 (40 mg, 0.056 mmol), lithium chloride (10 mg, 0.25 mmol), p-toluenesulfonic acid (45 mg, 0.25 mmol) were dissolved in N,N-dimethylformamide (1.5 mL). The system was heated to 120° C. for microwave reaction for 30 min. The system was concentrated and the residue was dissolved in dichloromethane (4 mL), trifluoroacetic acid (0.4 mL) was added thereto, the reaction was carried out for 1 hour at room temperature (20° C.). The system was concentrated to obtain crude product 14-7.

MS (ESI) m/z (M+H)$^+$=598.30.

Step 7: Preparation of Compound 14

14-7

14

Compound 14-7 (30 mg, 0.05 mmol) was dissolved in dichloromethane (5 mL), and triethylamine (25.2 mg, 0.0252 mmol) and acryloyl chloride (10 mg, 0.1 mmol) were added dropwise thereto at 0° C. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column: Kinetex® 5 µm F5 100 Å LC Column 150×21.2 mm; column temperature: 25° C.; mobile phase: water (0.1% FA)-acetonitrile; acetonitrile: 20%-35% in 10 min; flow rate 30 mL/min) to obtain compound 14.

$^1$H NMR (400 MHz, DMSO-d$_6$) δ 11.37 (s, 1H), 8.37 (d, J=4.9 Hz, 1H), 8.33 (s, 1H), 7.82 (d, J=10.4 Hz, 1H), 7.78 (d, J=9.9 Hz, 1H), 7.46 (d, J=6.7 Hz, 1H), 7.18 (d, J=4.9 Hz, 1H), 7.11 (t, J=6.2 Hz, 1H), 6.90-6.75 (m, 1H), 6.40 (d, J=7.2 Hz, 1H), 6.11 (d, J=16.7 Hz, 1H), 5.78-5.64 (m, 1H), 4.52-4.04 (m, 1H), 3.29-4.00 (m, 6H), 3.08 (s, 3H), 1.97-1.89 (m, 1H), 1.76 (s, 3H), 1.53 (d, J=26.4 Hz, 3H), 1.00 (d, J=6.8 Hz, 3H), 0.88 (d, J=6.6 Hz, 3H).

MS (ESI) m/z (M+H)$^+$=652.40.

Embodiment 15: Preparation of Compound 15

Step 1: Preparation of Compound 15-1

Step 2: Preparation of Compound 15-2

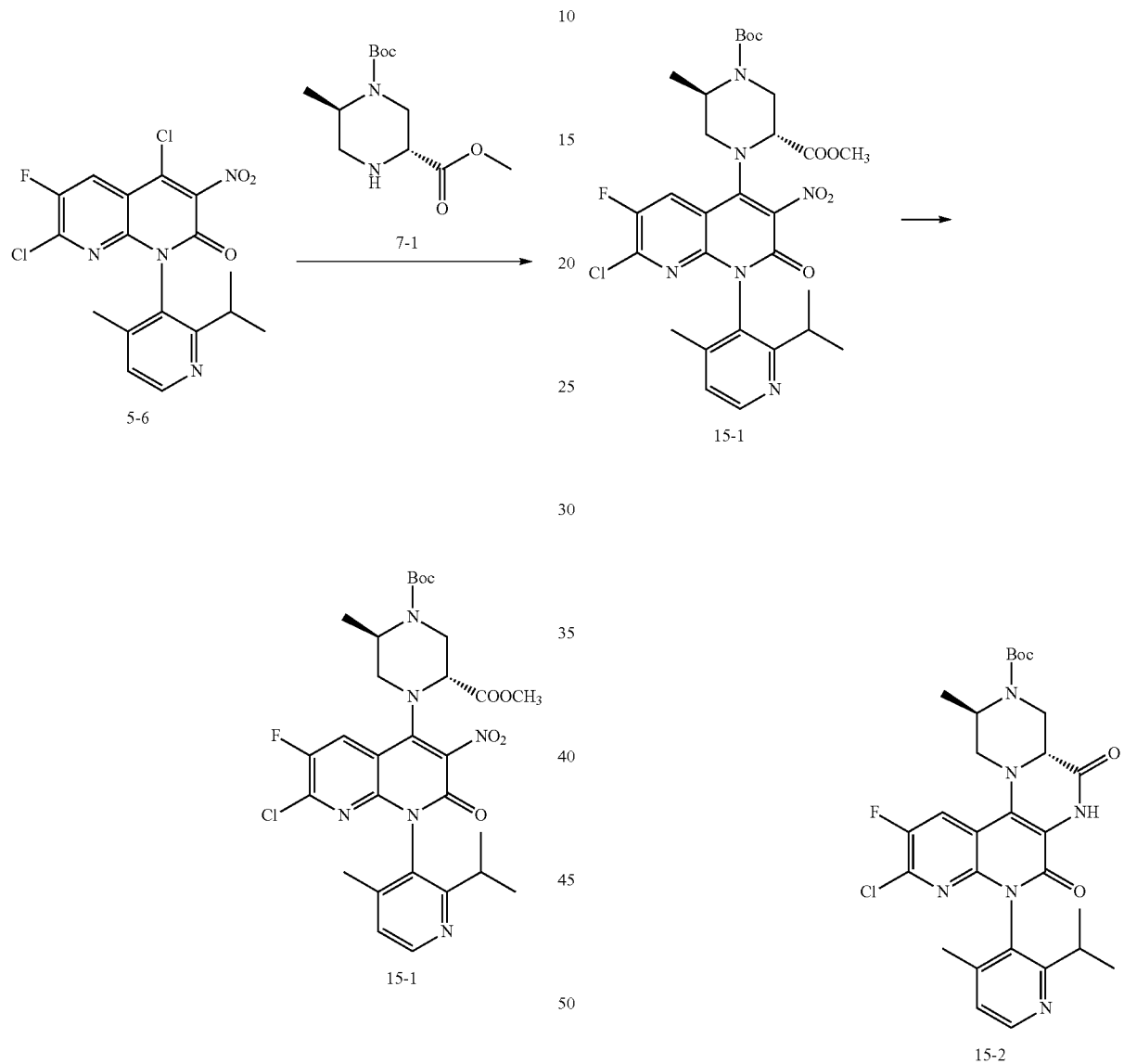

Compound 5-6 (2000 mg, 5.063 mmol), compound 7-1 (2000 mg, 7.751 mmol), cuprous iodide (470.0 mg, 2.46 mmol), and cesium carbonate (3280 mg, 10 mmol) were dissolved in dioxane (30 mL), under nitrogen atmosphere, the system was heated to 100° C. and stirred for 1 hour. The system was filtered by diatomite, and the filtrate was concentrated to obtain a crude product. The crude product was purified by medium pressure column chromatography (ethyl acetate/petroleum ether (v/v)=0-30%) to obtain compound 15-1.

MS (ESI) m/z (M+H)$^+$=633.2.

Compound 15-1 (320 mg, 0.517 mmol) and iron powder (115 mg, 2.068 mmol) were dissolved in acetic acid (10 mL), and the system was heated to 80° C. and stirred for 1 hour under nitrogen atmosphere. The system was filtered by diatomite, and the filtrate was concentrated to obtain crude product 15-2.

MS (ESI) m/z (M+H)$^+$=571.2.

Step 3: Preparation of Compound 15-3

Step 4: Preparation of Compound 15-4

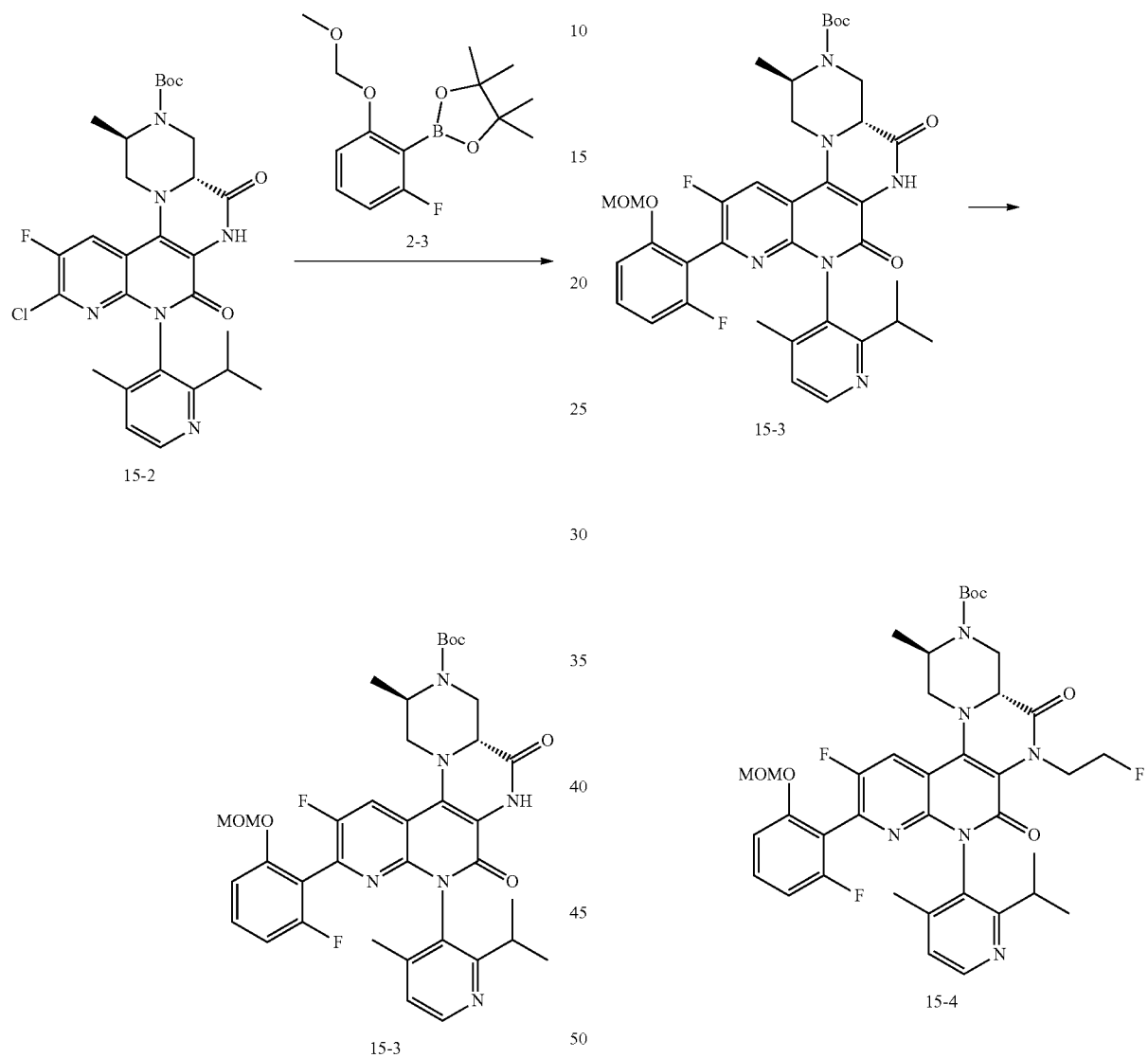

Compound 15-2 (100 mg, 0.17 mmol), compound 2-3 (100 mg, 0.34 mmol), tetrakis(triphenylphosphine)palladium (50 mg, 0.04 mmol) and potassium carbonate (50 mg, 0.34 mmol) were dissolved in dioxane (5 mL) and water (0.5 mL). Under nitrogen atmosphere, the system was heated to 100° C. and stirred for 2 hours. The system was concentrated to obtain a crude product, the crude product was purified by medium pressure column chromatography (ethyl acetate/petroleum ether (v/v)=0-50%) to obtain compound 15-3.

MS (ESI) m/z (M+H)$^+$=691.40.

Compound 15-3 (57 mg, 0.07 mmol) and potassium carbonate (30 mg, 0.2 mmol) were dissolved in N,N-dimethylformamide (2 mL), and 1-fluoro-2-bromoethane (30 mg, 0.2 mmol) was added thereto at room temperature (20° C.). After the addition was completed, under nitrogen atmosphere, the system was heated to 100° C. and stirred for 1 hour. The system was cooled to room temperature and concentrated to obtain a crude product. The crude product was purified by medium pressure column chromatography (ethyl acetate/petroleum ether (v/v)=0-50%) to obtain compound 15-4.

MS (ESI) m/z (M+H)$^+$=737.5.

Step 5: Preparation of Compound 15-5

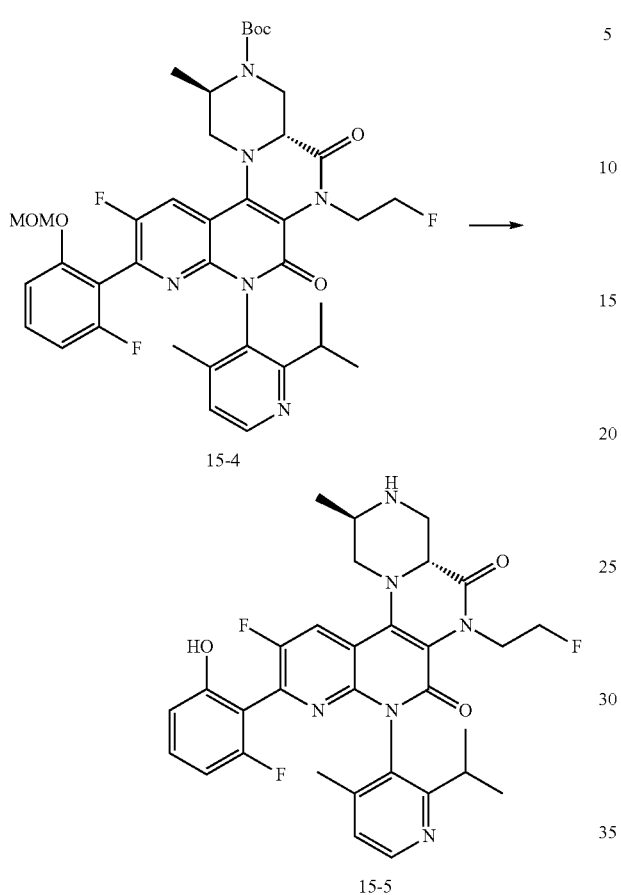

15-4

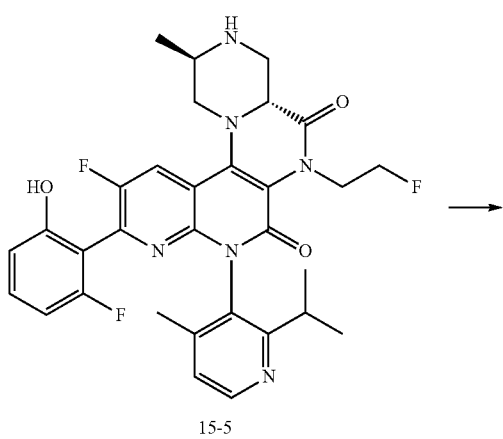

15-5

Compound 15-4 (25 mg, 0.035 mmol), hydrochloric acid (6N, 2 mL) were added to a mixed solution of methanol (2 mL) and tetrahydrofuran (0.2 mL). The system was heated to 55° C. and stirred for 1 hour. The system was concentrated to obtain crude compound 15-5.

MS (ESI) m/z (M+H)$^+$=593.40.

Step 6: Preparation of Compound 15

15-5

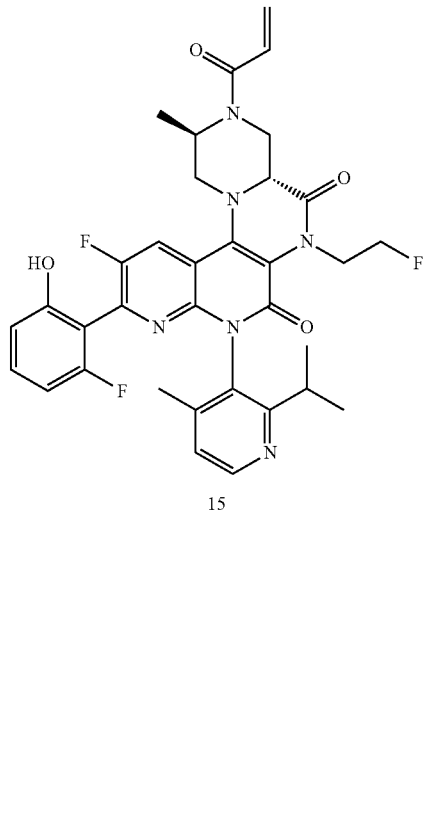

15

Compound 15-5 (25 mg, 0.04 mmol) was dissolved in dichloromethane (3 mL), and the system was cooled to 0° C., triethylamine (0.1 mL) and acryloyl chloride (4.6 mg, 0.0514 mmol) were added dropwise thereto, the reaction was carried out at 0° C. for 0.5 hours. The system was separated and extracted with water (5 mL) and dichloromethane (3 mL), and the organic phase was concentrated to obtain a crude product. The crude product was purified by preparative high performance liquid chromatography (separation conditions: chromatographic column: Kinetex® 5 μm F5 100 Å LC Column 150×21.2 mm; column temperature: 25° C.; mobile phase: water (0.1% FA)-acetonitrile; acetonitrile: 15%-35% in 10 min, 35%-35% in 16 min; flow rate 30 mL/min) to obtain compound 15.

$^1$H NMR (400 MHz, DMSO-d$_6$) δ 8.38 (d, J=4.8 Hz, 1H), 7.95 (d, J=8.5 Hz, 1H), 7.30-7.12 (m, 2H), 6.95 (dd, J=16.8, 10.6 Hz, 1H), 6.82-6.53 (m, 2H), 6.08 (dd, J=16.8, 2.4 Hz, 1H), 5.69 (dd, J=10.5, 2.5 Hz, 1H), 4.58-4.43 (m, 3H), 3.96 (dd, J=23.4, 4.0 Hz, 1H), 3.69 (dd, J=14.2, 4.3 Hz, 1H), 3.50-3.32 (m, 3H), 2.83-2.71 (m, 1H), 2.71-2.54 (m, 1H), 1.81 (d, J=55.9 Hz, 3H), 1.48 (dd, J=6.8, 2.1 Hz, 3H), 1.08-0.63 (m, 6H).

MS (ESI) m/z (M+H)$^+$=647.4.

HPLC 90% purity; retention time was 5.224 min.

Separation conditions: chromatographic column: Waters Xbridge C18 3.5 μm, 100*4.6 mm; chromatographic column temperature: 40° C.; mobile phase: water (10 mM ammonium bicarbonate aqueous solution)-acetonitrile; acetonitrile: 5%-95% 7 min, 95% 8 min; flow rate: 1.2 mL/min.

Embodiment 16: Preparation of Compound 16

Step 1: Preparation of Compound 16-1

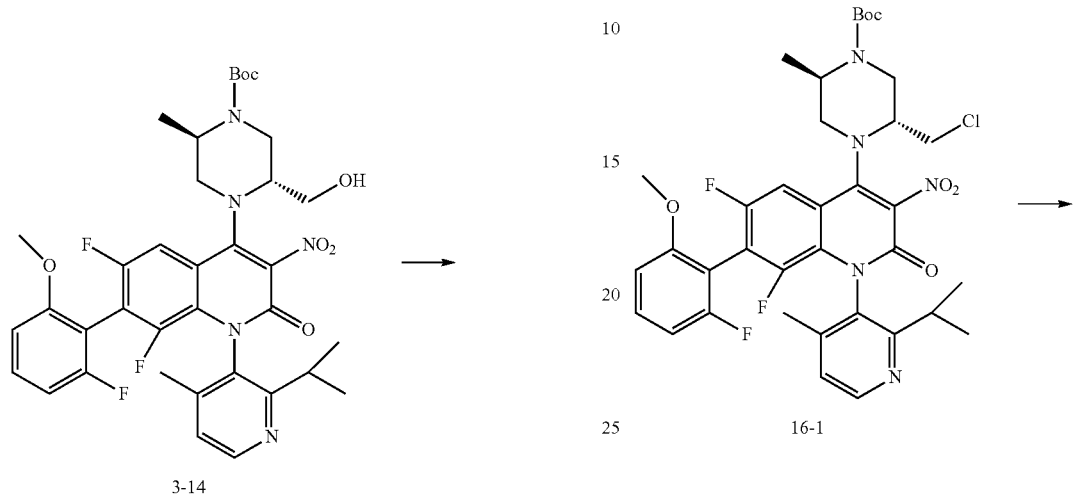

3-14

Step 2: Preparation of Compound 16-2

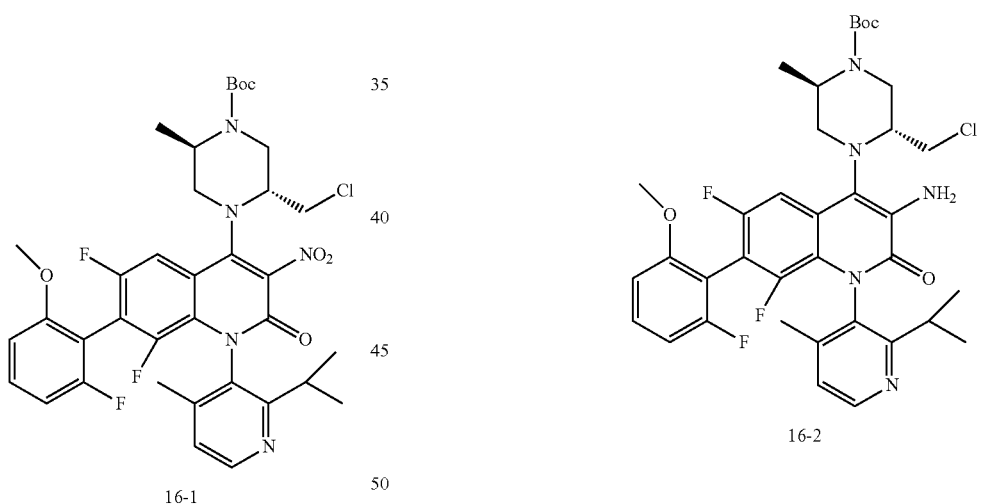

16-1

16-2

Under the protection of nitrogen, compound 3-14 (100 mg, 140.50 μmol) was dissolved in 1, 2-dichloroethane (3 mL), and triphenylphosphine (112 mg, 427.01 μmol) and carbon tetrachloride (80 mg, 520.08 μmol, 0.05 mL) were added sequentially, and the mixture was heated to 80° C. and the reaction was carried out for 16 hours. The reaction mixture was concentrated under reduced pressure, and the crude product was purified by preparative silica gel plate chromatography (ethyl acetate/petroleum ether (v/v)=100%) to obtain compound 16-1.

MS (ESI) m/z (M+H)$^+$=730.3.

Compound 16-1 (80 mg, 109.56 μmol) was dissolved in acetic acid (1 mL), iron powder (31 mg, 555.11 μmol) was added and the reaction was stirred for 1 hour at 80° C. The reaction mixture was diluted with ethyl acetate (10 mL) and filtered; the filtrate was concentrated under reduced pressure; the crude product was dissolved in ethyl acetate (10 mL), washed with saturated sodium bicarbonate solution (10 mL), dried over anhydrous sodium sulfate, and filtered; the filtrate was concentrated under reduced pressure, and the crude product was purified by preparative silica gel plate chromatography (ethyl acetate/petroleum ether (v/v)=100%) to obtain compound 16-2.

MS (ESI) m/z (M+H)$^+$=700.2.

Step 3: Preparation of Compound 16-3

Step 4: Preparation of Compound 16-4

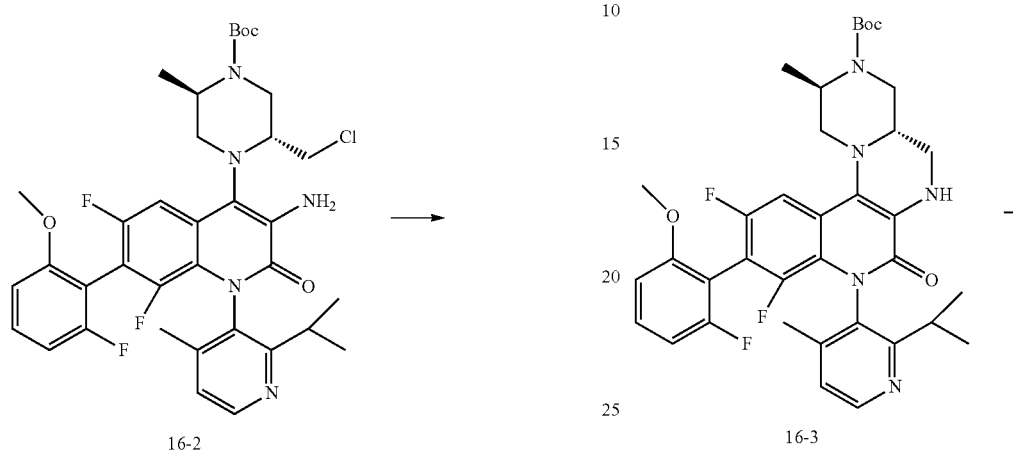

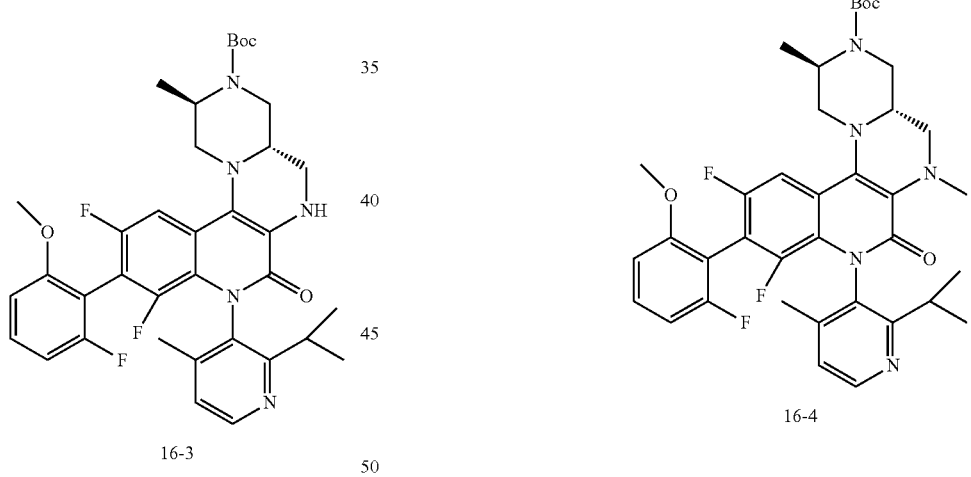

Compound 16-2 (60 mg, 85.69 μmol) was dissolved in N,N-dimethylformamide (1 mL), and diisopropylethylamine (37.10 mg, 287.06 μmol, 0.05 mL) was added, and the reaction was stirred at 120° C. for 6 hours in a sealed tube. The reaction mixture was concentrated under reduced pressure, and the crude product was purified by preparative silica gel plate chromatography (methanol/dichloromethane (v/v) =1/15) to obtain compound 16-3.

MS (ESI) m/z (M+H)$^+$=664.1.

Compound 16-3 (40 mg, 60.27 μmol) was dissolved in tetrahydrofuran (1 mL), and sodium hydride (5 mg, 125.01 μmol, 60%) and iodomethane (10 mg, 70.45 μmol) were added sequentially, and the reaction was stirred at 25° C. for 1 hour. The reaction mixture was quenched with 2 drops of saturated ammonium chloride solution, diluted with ethyl acetate (20 mL), washed with water (20 mL) and saturated sodium chloride solution (20 mL) successively, and the organic phase was dried with anhydrous sodium sulfate and filtered; the filtrate was concentrated under reduced pressure to obtain crude product 16-4.

MS (ESI) m/z (M+H)$^+$=678.4.

Step 5: Preparation of Compound 16-5

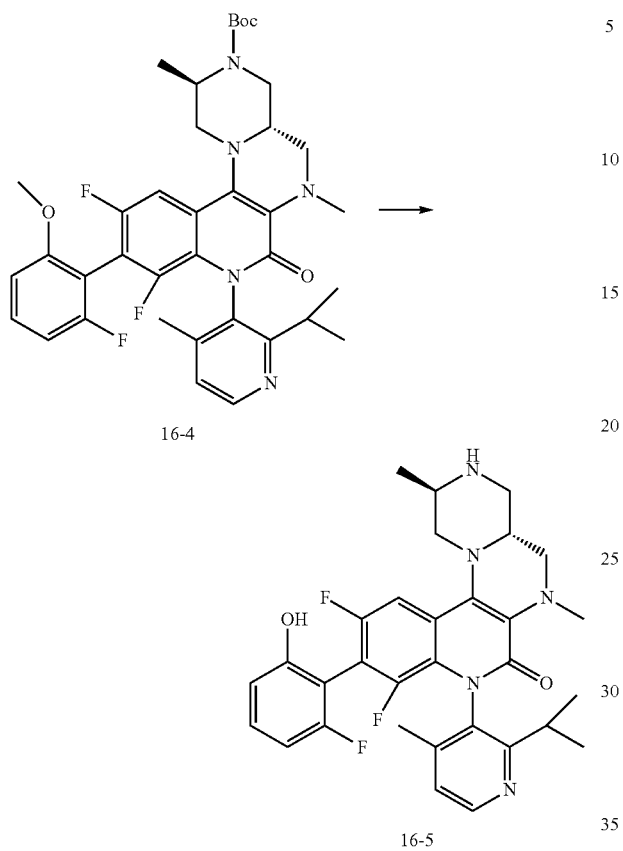

16-4

Compound 16-4 (40 mg, 59.02 μmol) was dissolved in dichloromethane (1 mL) and boron tribromide (73.93 mg, 295.09 μmol, 28.43 μL) was added, and the reaction was stirred at 20° C. for 3 hours. The reaction mixture was quenched with methanol (10 mL), stirred for 10 min, and concentrated under reduced pressure to obtain crude product 16-5.

MS (ESI) m/z (M+H)$^+$=564.0.

Step 6: Preparation of Compound 16

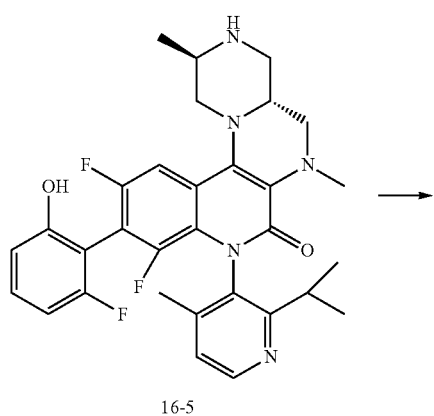

16-5

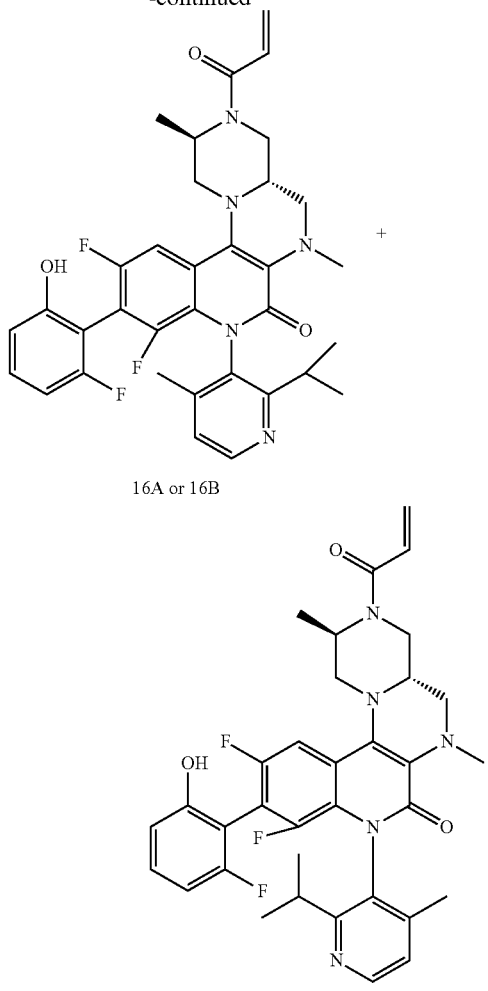

16A or 16B 16B or 16A

Compound 16-5 (50 mg, 77.58 μmol) was dissolved in tetrahydrofuran (1 mL), then saturated sodium bicarbonate solution (2.16 g, 25.71 mmol, 1 mL) and acrylic anhydride (11 mg, 87.23 μmol) were added successively, and the reaction was stirred at 20° C. for 1 hour. Methanol (1 mL) and potassium carbonate aqueous solution (2 M, 1 mL) were added and stirred for 1.5 hours. The reaction mixture was diluted with water (10 mL), extracted with ethyl acetate (20 mL×2); the organic phases were combined, dried over anhydrous sodium sulfate, filtered, and the filtrate was concentrated under reduced pressure; then the crude product was separated by preparative high performance liquid chromatography (separation conditions: chromatographic column: Phenomenex Gemini-NX 80*30 mm*3 μm; mobile phase: [water (10 mM ammonium bicarbonate)-acetonitrile]; acetonitrile %: 36%-66%, 9.5 min) to obtain compound 16A (peak 1) and compound 16B (peak B).

Compound 16A:

$^1$H NMR (400 MHz, MeOD) δ 8.41 (d, J=5.1 Hz, 1H), 7.55 (br d, J=9.7 Hz, 1H), 7.28-7.16 (m, 2H), 6.84 (dd, J=10.7, 16.6 Hz, 1H), 6.71-6.57 (m, 2H), 6.28 (dd, J=1.9, 16.6 Hz, 1H), 5.82 (br d, J=10.8 Hz, 1H), 5.04-4.91 (m, 2H), 4.60-4.53 (m, 1H), 4.13 (br s, 1H), 3.74 (br s, 1H), 3.59-3.43 (m, 2H), 3.15 (s, 3H), 3.02 (br s, 1H), 2.81-2.57 (m, 1H), 2.05 (d, J=15.7 Hz, 3H), 1.83-1.65 (m, 3H), 1.18-1.06 (m, 6H).

MS (ESI) m/z (M+H)$^+$=618.2.

HPLC 97% of purity; retention time was: 4.00 min+4.051 min.

Separation conditions: chromatographic column Xbridge Shield RP-18, 5 μm, 2.1*50 mm; column temperature: 50° C.; mobile phase: [water (0.02% ammonia solution)-acetonitrile]; acetonitrile: 10%-80% 6 min, 80% 2 min; flow rate: 0.8 mL/min.

Compound 16B:

$^1$H NMR (400 MHz, MeOD) δ 8.41 (d, J=5.1 Hz, 1H), 7.54 (br d, J=9.0 Hz, 1H), 7.30-7.14 (m, 2H), 6.84 (dd, J=10.9, 16.6 Hz, 1H), 6.71-6.55 (m, 2H), 6.35-6.21 (m, 1H), 5.81 (br d, J=9.5 Hz, 1H), 5.01-4.90 (m, 2H), 4.66-4.50 (m, 1H), 4.15 (br d, J=15.4 Hz, 1H), 3.71 (br s, 1H), 3.62-3.42 (m, 2H), 3.14 (s, 3H), 3.01 (br s, 1H), 2.81-2.56 (m, 1H), 2.12-1.95 (m, 3H), 1.83-1.61 (m, 3H), 1.19-1.02 (m, 6H).

MS (ESI) m/z (M+H)$^+$=618.3.

HPLC 94% of purity; retention time was: 4.082 min.

Separation conditions: chromatographic column Xbridge Shield RP-18, 5 μm, 2.1*50 mm; column temperature: 50° C.; mobile phase: [water (0.02% ammonia solution)-acetonitrile]; acetonitrile: 10%-80% 6 min, 80% 2 min; flow rate: 0.8 mL/min.

Step 7: Preparation of Compounds 16A-1 and 16A-2

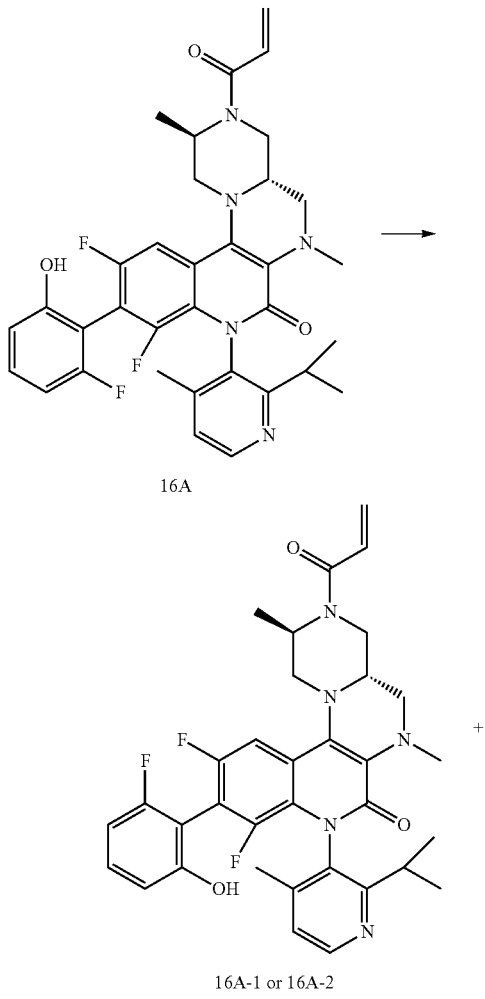

16A 16A-1 or 16A-2

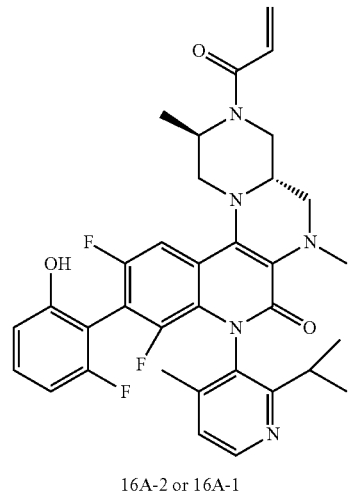

16A-2 or 16A-1

Diastereoisomeric compound 16A was purified by SFC (separation conditions: chromatographic column: DAICEL CHIRALPAK AD-H (250 mm*30 mm, 5 μm); mobile phase: [CO$_2$-isopropanol (0.1% ammonia)]; isopropanol %: 35%). After concentration, compound 16A-1 and compound 16A-2 were obtained.

Compound 16A-1:

$^1$H NMR (400 MHz, DMSO-d$_6$) δ 8.42 (br d, J=4.9 Hz, 1H), 7.40 (br s, 1H), 7.29-7.07 (m, 2H), 6.85 (br d, J=10.3 Hz, 1H), 6.75-6.53 (m, 2H), 6.16 (br d, J=9.0 Hz, 1H), 5.74 (br d, J=10.0 Hz, 1H), 4.79 (br s, 1H), 4.46 (br d, J=14.4 Hz, 1H), 4.16 (br d, J=14.2 Hz, 1H), 3.89 (br d, J=14.7 Hz, 1H), 3.51-3.36 (m, 2H), 3.23-3.15 (m, 2H), 3.08 (s, 2H), 2.98-2.85 (m, 2H), 2.66 (br d, J=1.7 Hz, 1H), 1.90 (s, 3H), 1.72-1.47 (m, 3H), 1.26-0.88 (m, 6H).

MS (ESI) m/z (M+H)$^+$=618.3.

SFC retention time was 1.516 min.

Separation conditions: chromatographic column: Chiralpak AD-3 50×4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Compound 16A-2:

$^1$H NMR (400 MHz, METHANOL-d$_4$) δ 8.41 (br d, J=4.9 Hz, 1H), 7.55 (br d, J=11.0 Hz, 1H), 7.30-7.10 (m, 2H), 6.84 (br dd, J=10.5, 16.6 Hz, 1H), 6.71-6.51 (m, 2H), 6.27 (br dd, J=1.8, 16.8 Hz, 1H), 5.82 (br d, J=10.6 Hz, 1H), 4.96-4.92 (m, 1H), 4.61 (br s, 2H), 4.26-4.13 (m, 1H), 3.72 (br s, 1H), 3.52-3.38 (m, 2H), 3.14 (s, 3H), 2.99 (br s, 1H), 2.62 (td, J=6.8, 13.7 Hz, 1H), 2.06 (s, 3H), 1.85-1.59 (m, 3H), 1.39-1.03 (m, 6H).

MS (ESI) m/z (M+H)$^+$=618.3.

SFC retention time was 1.644 min.

Separation conditions: chromatographic column: Chiralpak AD-3 50×4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Step 8: Preparation of Compounds 16B-1 and 16B-2

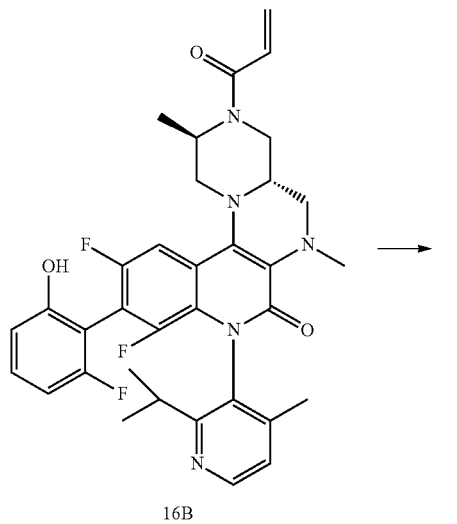

16B

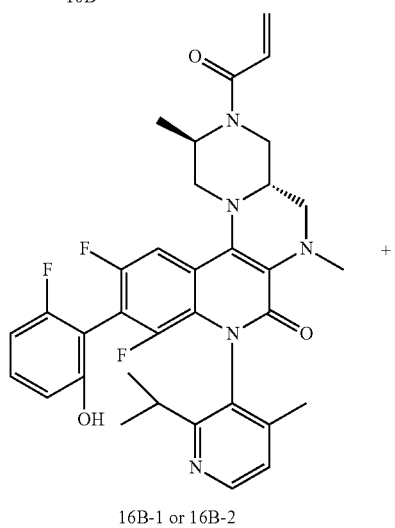

16B-1 or 16B-2

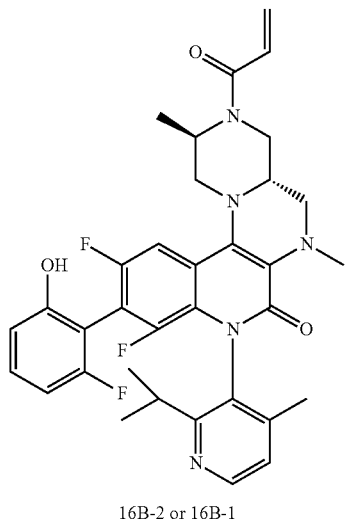

16B-2 or 16B-1

Diastereoisomeric compound 16B was purified by SFC (separation conditions: chromatographic column: DAICEL CHIRALPAK AD-H (250 mm*30 mm, 5 μm); mobile phase: [CO$_2$-isopropanol (0.1% ammonia)]; isopropanol %: 35%). After concentration, compound 16B-1 and compound 16B-2 were obtained.

Compound 16B-1:

$^1$H NMR (400 MHz, DMSO-d$_6$) δ 8.43 (br d, J=4.9 Hz, 1H), 7.41 (br s, 1H), 7.29-7.14 (m, 2H), 6.86 (br d, J=11.0 Hz, 1H), 6.75-6.59 (m, 2H), 6.19 (br s, 1H), 5.75 (br d, J=10.8 Hz, 1H), 4.80 (br s, 1H), 4.47 (br d, J=14.4 Hz, 1H), 4.15 (br s, 1H), 3.90 (br d, J=17.1 Hz, 1H), 3.55-3.40 (m, 2H), 3.21 (br d, J=11.2 Hz, 2H), 3.09 (s, 3H), 2.97-2.81 (m, 2H), 1.89 (s, 3H), 1.68-1.51 (m, 3H), 1.19-0.90 (m, 6H).

MS (ESI) m/z (M+H)$^+$=618.3.

SFC retention time was 1.521 min.

Separation conditions: chromatographic column: column: Chiralpak AD-3 50×4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Compound 16B-2:

$^1$H NMR (400 MHz, METHANOL-d$_4$) δ 8.41 (br d, J=5.1 Hz, 1H), 7.55 (br d, J=10.4 Hz, 1H), 7.34-7.13 (m, 2H), 6.84 (br dd, J=10.7, 16.6 Hz, 1H), 6.73-6.53 (m, 2H), 6.28 (br dd, J=1.8, 16.8 Hz, 1H), 5.81 (br s, 1H), 4.98-4.93 (m, 1H), 4.61 (br s, 2H), 4.15 (br s, 1H), 3.72 (br s, 1H), 3.47 (br d, J=13.9 Hz, 2H), 3.15 (s, 3H), 3.06-2.94 (m, 1H), 2.68-2.57 (m, 1H), 2.08 (s, 3H), 1.87-1.63 (m, 3H), 1.36-1.01 (m, 6H).

MS (ESI) m/z (M+H)$^+$=618.3.

SFC retention time was 1.652 min.

Separation conditions: chromatographic column: column: Chiralpak AD-3 50×4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Embodiment 17: Preparation of Compound 17

Step 1: Preparation of Compound 17-2

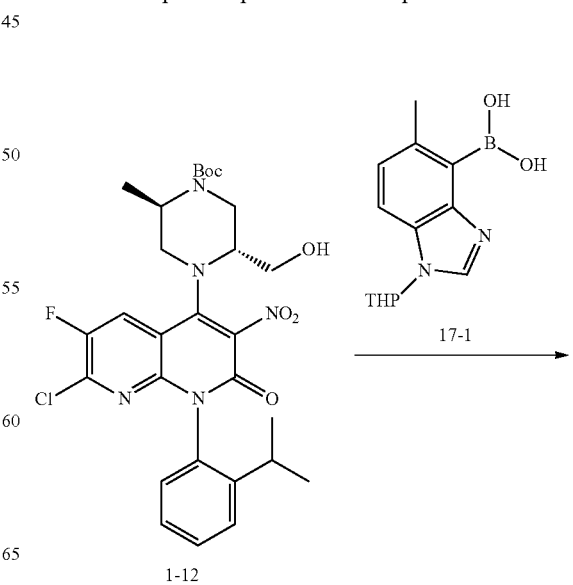

1-12

-continued

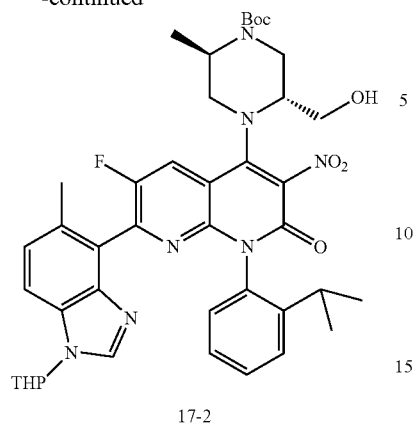

17-2

-continued

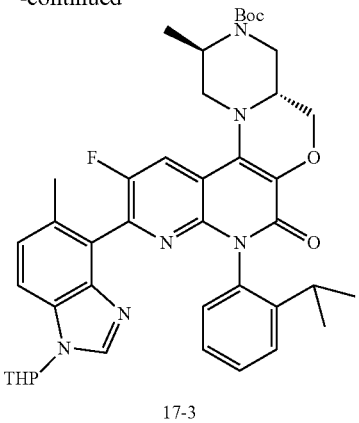

17-3

Compound 1-12 (450 mg, 0.76 mmol), compound 17-1 (240 mg, 0.92 mmol), 1,1-bis(diphenylphosphino)ferrocene palladium dichloride (65 mg, 0.076 mmol), potassium carbonate (210 mg, 1.5 mmol) was dissolved in a mixed solution of dioxane (20 mL) and water (2 mL), under nitrogen atmosphere, the system was heated to 90° C. and stirred for 3 hours. The system was concentrated, and the residue was dissolved in ethyl acetate (10 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-30%) to obtain compound 17-2.

MS (ESI) m/z: (M+H)$^+$=770.1.

Step 2: Preparation of Compound 17-3

Compound 17-2 (50 mg, 0.065 mmol) was dissolved in N,N-dimethylacetamide (5 mL), and tetrahydrofuran solution of lithium bis(trimethylsilyl)amide (24%, 0.65 mL) was added thereto at room temperature, under nitrogen atmosphere, the system was heated to 160° C. and stirred for 8 hours. The system was cooled to room temperature, concentrated, and the residue was dissolved in ethyl acetate (3 mL), then washed with water, left to stratify; and the organic phase was dried over anhydrous sodium sulfate, filtered, and the filtrate was concentrated to obtain a crude product. The crude product was purified by medium pressure column chromatography (ethyl acetate/petroleum ether (v/v)=0-40%) to obtain compound 17-3.

MS(ESI) m/z: (M+H)$^+$=723.3.

Step 3: Preparation of Compound 17-4

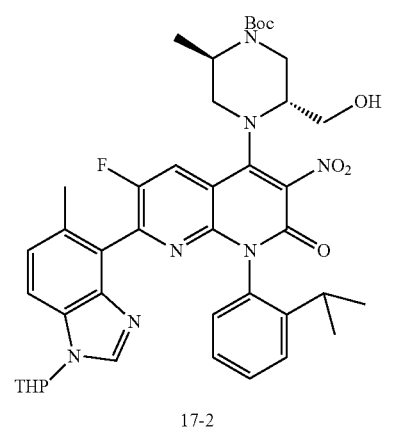

17-2

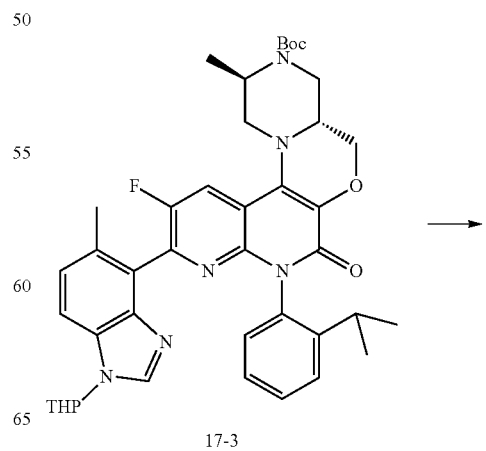

17-3

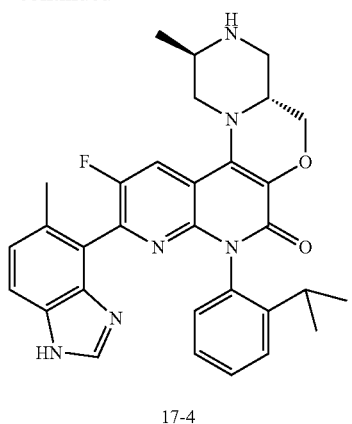

17-4

Compound 17-3 (30 mg, 0.041 mmol) was dissolved in methanol (3 mL), and concentrated hydrochloric acid (12 N, 2 mL) was added thereto. After the addition was completed, the system was heated to 70° C. and the reaction was carried out for 3 hours. The system was concentrated to obtain yellow oil 17-4, which was directly used in the next reaction without further purification.

MS (ESI) m/z (M+H)$^+$=539.2.

Step 4: Preparation of Compound 17-6

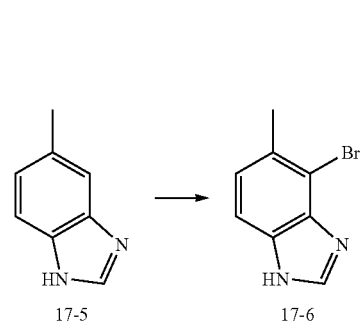

Compound 17-5 (2 g, 15.2 mmol) was dissolved in trifluoroacetic acid (10 mL), N-bromosuccinimide (3 g, 16.7 mmol) was added thereto. After the addition was completed, under airtight conditions, the system was heated to 80° C. and stirred for 1 hour. The system was concentrated, and saturated sodium bicarbonate aqueous solution was added to adjust the pH>7; then the mixture was extracted with ethyl acetate; the organic phase was dried over anhydrous sodium sulfate and filtered, the filtrate was concentrated to obtain a crude product, the crude product was purified by medium pressure column chromatography (methanol/dichloromethane (v/v)=0-10%) to obtain compound 17-6.

MS(ESI) m/z: (M+H)$^+$=212.8.

Step 5: Preparation of Compound 17-7

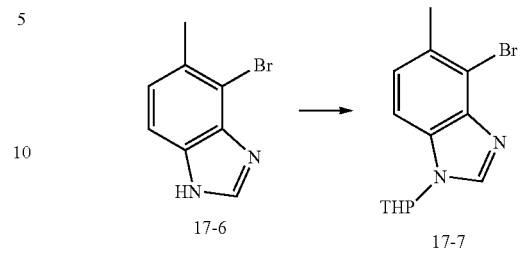

Compound 17-6 (350 mg, 1.66 mmol) was dissolved in tetrahydrofuran (20 mL), and tetrahydropyran (420 mg, 5.0 mmol) and p-toluenesulfonic acid (65 mg, 0.33 mmol) were added thereto. After the addition was completed, the system was heated to 80° C. and refluxed for 24 hours. The system was concentrated to obtain a crude product, the crude product was purified by medium pressure column chromatography (methanol/dichloromethane (v/v)=0-1%) to obtain compound 17-7.

MS(ESI) m/z: (M+H)$^+$=297.0.

Step 6: Preparation of Compound 17-1

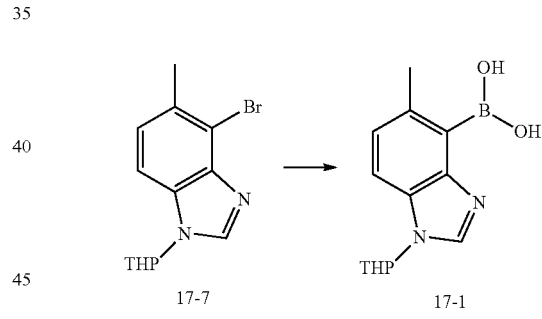

Compound 17-7 (300 mg, 1.0 mmol), bis(pinacolato)diboron (500 mg, 2.0 mmol), potassium acetate (300 mg, 3.0 mmol) and dichlorobis(tricyclohexylphosphine)palladium (II) (74 mg, 0.1 mmol) were dissolved in a mixed solution of N,N-dimethylacetamide (10 mL) and water (1 mL). Under nitrogen atmosphere, the system was heated to 155° C. and stirred for 2 hours. The system was cooled to room temperature, poured into water, extracted with ethyl acetate; the organic phase was washed with saturated saline, dried over anhydrous sodium sulfate, filtered, and the filtrate was concentrated to obtain compound 17-1, which was directly used in the next reaction without further purification.

MS(ESI) m/z: (M+H)$^+$=261.0.

Step 7: Preparation of Compound 17

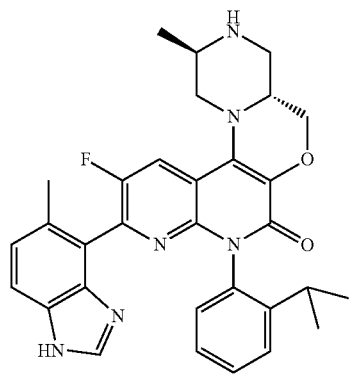

17-4

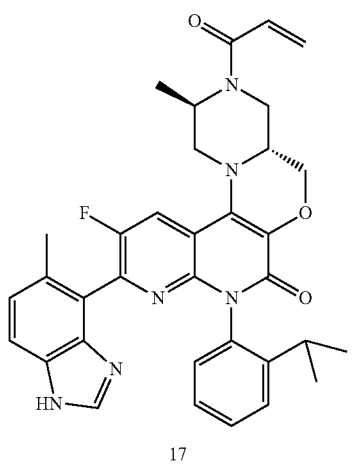

17

Compound 17-4 (20 mg, 0.037 mmol) was dissolved in dichloromethane (1 mL) at room temperature, and the system was cooled to 0° C., triethylamine (10 mg, 0.1 mmol) and acryloyl chloride (5 mg, 0.05 mmol) were added dropwise thereto. After the dropwise addition was completed, the system was raised to room temperature (20° C.) and the reaction was carried out for 30 min. The reaction mixture was washed with water (5 mL), extracted with dichloromethane (3 mL); the organic phase was dried over anhydrous sodium sulfate, filtered, and the filtrate was concentrated to obtain a crude product. The crude product was purified by preparative high performance liquid chromatography (separation conditions: chromatographic column: Agilent 10 Prep-C8 250×21.2 mm; column temperature: 25° C.; mobile phase: water (0.1% FA FA)-acetonitrile; acetonitrile: 20%-40% in 12 min; flow rate 30 mL/min) to obtain compound 17.

MS (ESI) m/z (M+H)$^+$=593.3.

HPLC: 95%, 4.875 min+5.087 min.

Separation conditions: chromatographic column: Waters X-bridge C18, 4.6*100 mm, 3.5 μm; mobile phase: [water (10 mM ammonium bicarbonate aqueous solution)-acetonitrile]; acetonitrile: 5%-95% 7 min; flow rate: 1.2 mL/min.

Embodiment 18: Preparation of Compounds 18A-1/18A-2/18B-1 and 18B-2

Step 1: Preparation of Compound 18-1

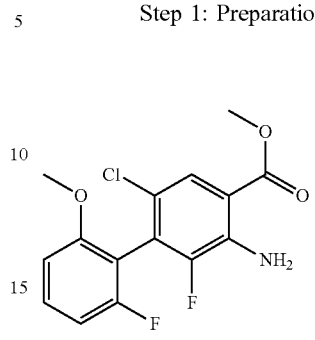

4-8

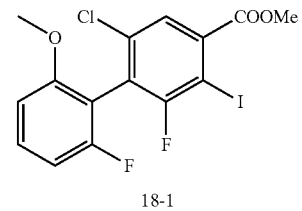

18-1

At 0° C. and under the protection of nitrogen, compound 4-8 (8.6 g, 26.24 mmol) was dissolved in acetonitrile (40 mL), and cuprous iodide (5.05 g, 26.51 mmol) and potassium iodide (8.84 g, 53.27 mmol) and tert-butyl nitrite (5.66 g, 54.85 mmol, 6.52 mL) were added successively, then the reaction was heated to 80° C. and stirred for 2 hours. The reaction mixture was cooled to room temperature, filtered, the filtrate was concentrated under reduced pressure; the residue was dissolved in ethyl acetate (80 mL), washed with saturated sodium thiosulfate solution (80 mL×2); the organic phases were combined, dried over anhydrous sodium sulfate, filtered, the filtrate was concentrated under reduced pressure, and the crude product was purified by silica gel column chromatography (petroleum ether/ethyl acetate (v/v) =1/0-2/3) to obtain compound 18-1.

$^1$H NMR (400 MHz, CDCl$_3$) δ 7.77 (d, J=1.5 Hz, 1H), 7.46-7.38 (m, 1H), 6.87-6.77 (m, 2H), 3.98 (s, 3H), 3.80 (s, 3H).

Step 2: Preparation of Compound 18-2

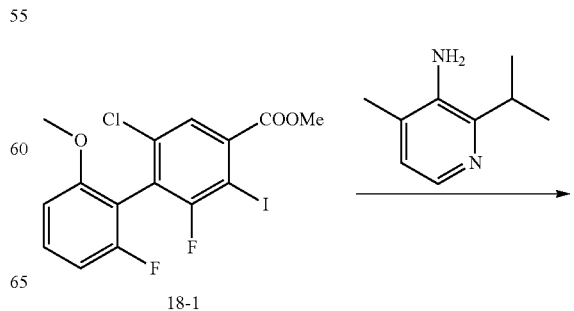

18-1

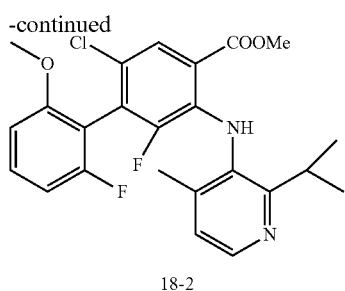

18-2

Under the protection of nitrogen, compound 18-1 (6.5 g, 14.82 mmol) and 2-isopropyl-4-methyl-pyridin-3-amine (2.60 g, 17.31 mmol) were dissolved in toluene (10 mL), and 4,5-bis(diphenylphosphino)-9,9-dimethylxanthene (950 mg, 1.64 mmol), tris(dibenzylideneacetone)dipalladium (1.5 g, 1.64 mmol) and cesium carbonate (14.49 g, 44.46 mmol) were added successively, and the reaction was heated to 100° C. and stirred for 16 hours. The reaction mixture was diluted with ethyl acetate (100 mL), filtered, the filtrate was concentrated under reduced pressure, and the crude product was purified by silica gel column chromatography (petroleum ether/ethyl acetate (v/v)=1/0-2/3) to obtain compound 18-2.

MS (ESI) m/z (M+H)$^+$=460.

$^1$H NMR (400 MHz, CDCl$_3$) δ 9.08 (br s, 1H), 8.29 (d, J=4.9 Hz, 1H), 8.04-7.92 (m, 1H), 7.36-7.28 (m, 1H), 6.94 (t, J=5.4 Hz, 1H), 6.78-6.68 (m, 2H), 3.98 (s, 3H), 3.74 (d, J=17.4 Hz, 3H), 3.52-3.41 (m, 1H), 2.20 (s, 3H), 1.27-1.24 (m, 3H), 1.21 (d, J=6.6 Hz, 3H).

Step 9: Preparation of Compound 18-3

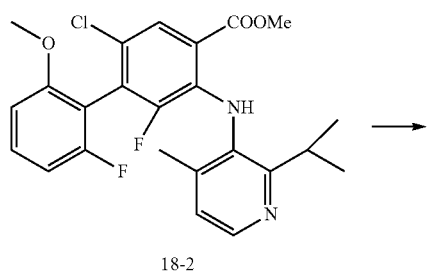

18-2

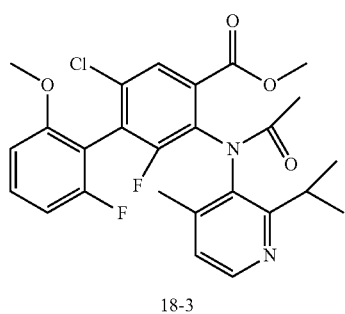

18-3

At 0° C., compound 18-2 (3.2 g, 6.94 mmol) was dissolved in N, N-dimethylformamide (30 mL), sodium hydride (1.39 g, 34.71 mmol, 60%) was added and stirred for 20 min, then acetyl chloride (2.73 g, 34.71 mmol, 2.48 mL) was added and the reaction was raised to 25° C. and stirred for 16 hours. The reaction mixture was quenched with water (100 mL), saturated potassium carbonate solution (100 mL) was added and stirred for 1 hour; and the mixture was extracted with ethyl acetate (100 mL×2); the organic phases were combined, dried over anhydrous sodium sulfate, filtered, and the filtrate was concentrated, then the crude product was purified by silica gel column chromatography (petroleum ether/ethyl acetate (v/v)=1/0-0/1) to obtain compound 18-3.

MS (ESI) m/z (M+H)$^+$=503.1.

$^1$H NMR (400 MHz, CDCl$_3$) δ 8.49-8.43 (m, 1H), 7.85 (s, 1H), 7.37-7.30 (m, 1H), 7.07-7.01 (m, 1H), 6.80-6.64 (m, 2H), 4.04-3.89 (m, 3H), 3.80-3.74 (m, 1H), 3.74-3.42 (m, 4H), 2.33 (br d, J=3.1 Hz, 3H), 1.97 (br d, J=4.9 Hz, 3H), 1.29 (br d, J=6.4 Hz, 3H), 0.88-0.71 (m, 3H).

Step 10: Preparation of Compound 18-4

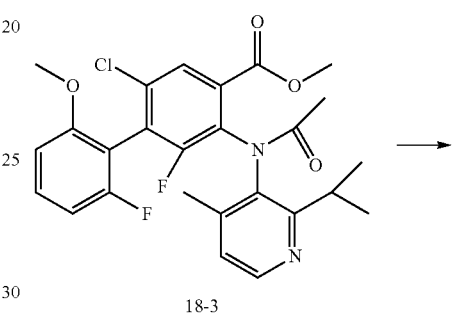

18-3

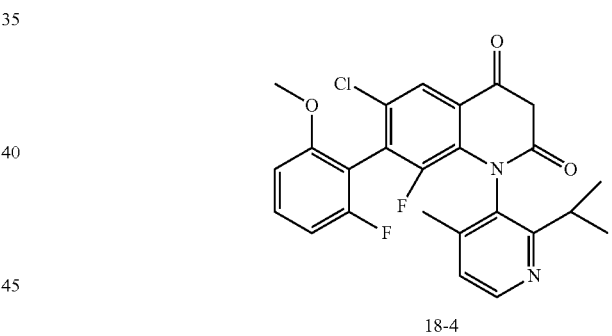

18-4

Under the protection of nitrogen, compound 18-3 (580 mg, 1.15 mmol) was dissolved in toluene (10 mL), and potassium tert-butoxide (1.0 M tetrahydrofuran solution, 3.74 mL) was added to react at 25° C. and stirred for 30 min. The reaction mixture was quenched with water (20 mL), the pH was adjusted to 7.0 by adding 1.0 M hydrochloric acid; and the mixture was extracted by ethyl acetate (30 mL×3); the organic phases were combined, dried over anhydrous sodium sulfate, filtered, and the filtrate was concentrated under reduced pressure to obtain the crude product 18-4, which was directly used in the next reaction without further purification.

MS (ESI) m/z (M+H)$^+$=471.2.

$^1$H NMR (400 MHz, Chloroform-d) δ 8.64-8.51 (m, 1H), 8.01 (s, 1H), 7.39-7.31 (m, 1H), 7.13 (t, J=4.1 Hz, 1H), 6.79-6.70 (m, 2H), 6.43 (s, 3H), 3.75-3.66 (m, 3H), 2.85-2.71 (m, 1H), 2.12-2.07 (m, 3H), 1.26-1.22 (m, 3H), 1.17-1.11 (m, 3H).

Step 11: Preparation of Compound 18-5

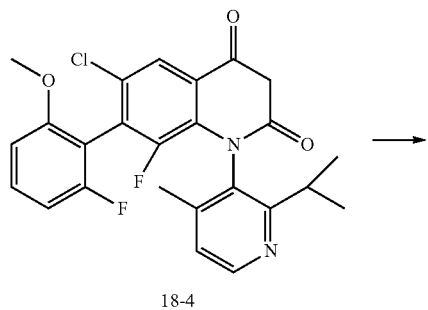

18-4

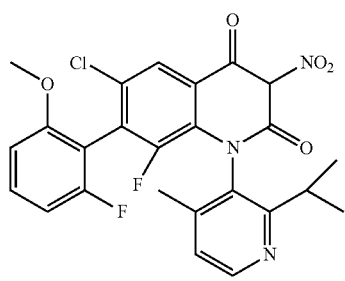

18-5

Under the protection of nitrogen, compound 18-4 (500 mg, 1.06 mmol) was dissolved in acetic acid (10 mL), then concentrated nitric acid (1.23 g, 19.51 mmol, 878.20 μL) was added, and the reaction was heated to 80° C. and stirred for 2 hours. The reaction mixture was concentrated under reduced pressure to remove most of the acetic acid, cooled to 0° C., added with water (50 mL), filtered, and the filter cake was dried under vacuum to obtain crude product 18-5, which was directly used in the next reaction without further purification.

MS (ESI) m/z (M+H)$^+$=516.2.

$^1$H NMR (400 MHz, DMSO-d$_6$) δ 8.57-8.55 (m, 1H), 8.06 (s, 1H), 7.67-7.38 (m, 2H), 7.03-6.77 (m, 2H), 3.74-3.61 (m, 1H), 3.58-3.50 (m, 3H), 2.53-2.51 (m, 3H), 2.15 (br d, J=6.0 Hz, 1H), 1.33-0.94 (m, 6H).

Step 12: Preparation of Compound 18-6

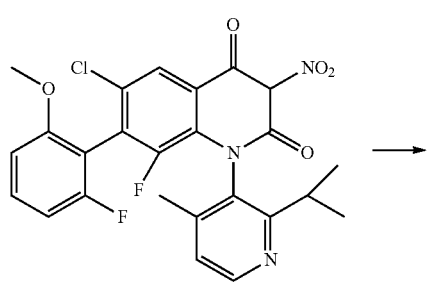

18-5

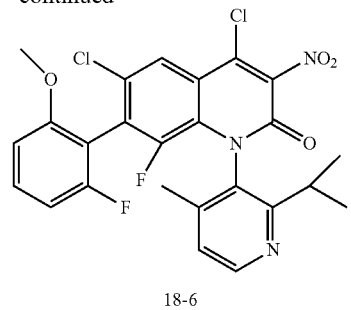

18-6

Under the protection of nitrogen, compound 18-5 (600 mg, 1.16 mmol) was dissolved in acetonitrile (10 mL), diisopropylethylamine (901.86 mg, 6.98 mmol, 1.22 mL) and phosphorus oxychloride (534.98 mg, 3.49 mmol, 324.23 μL) were added thereto successively, and the reaction was heated to 80° C. and stirred for 2 hours. The reaction was cooled to room temperature, concentrated under reduced pressure, and the crude product was purified by silica gel column chromatography (petroleum ether/ethyl acetate (v/v)=1/0-1/1) to obtain compound 18-6.

MS (ESI) m/z (M+H)$^+$=534.

$^1$H NMR (400 MHz, Chloroform-d) δ 8.57-8.51 (m, 1H), 8.17 (t, J=1.7 Hz, 1H), 7.43-7.34 (m, 1H), 7.09 (t, J=4.2 Hz, 1H), 6.81-6.71 (m, 2H), 3.81-3.65 (m, 4H), 2.77-2.67 (m, 1H), 2.13 (d, J=6.0 Hz, 3H), 1.35-1.17 (m, 6H).

Step 13: Preparation of Compound 18-7

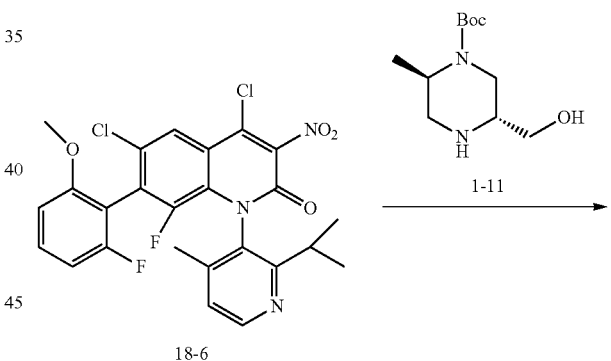

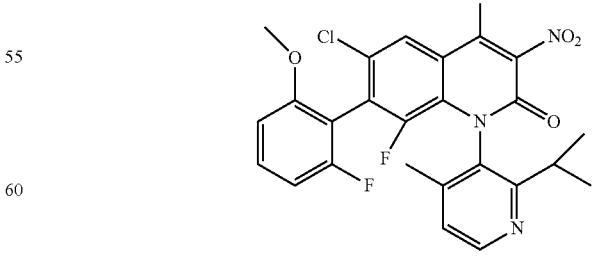

18-7

Under the protection of nitrogen, compound 18-6 (320 mg, 598.87 μmol) was dissolved in acetonitrile (8 mL), diisopropylethylamine (387.76 mg, 3.00 mmol, 522.59 μL) and compound 1-11 (206.88 mg, 898.31 μmol) were added thereto successively, and the reaction temperature was heated to 80° C. and stirred for 1 hour. The reaction was concentrated under reduced pressure, and the crude product was purified by silica gel column chromatography (petroleum ether/ethyl acetate (v/v)=1/0-2/3) to obtain compound 18-7.

MS (ESI) m/z (M+H)$^+$=728.2.

Step 14: Preparation of Compound 18-8

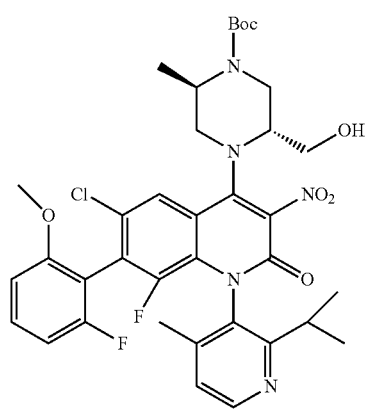

18-7

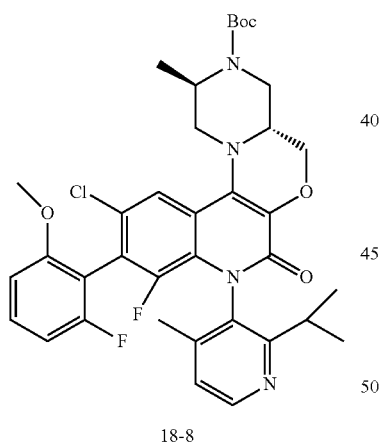

18-8

Under the protection of nitrogen, compound 18-7 (350 mg, 480.65 μmol) was dissolved in N-methylpyrrolidone (10 mL), and 4A molecular sieve (500 mg) and lithium bis(trimethylsilyl)amine (1 M tetrahydrofuran solution, 1.44 mL) were added thereto successively, and the reaction was heated to 130° C. and stirred for 16 hours. The reaction mixture was concentrated under reduced pressure to remove the solvent, diluted with ethyl acetate (50 mL), filtered and the filtrate was concentrated under reduced pressure, and the crude product was purified by preparative thin layer chromatography (dichloromethane/methanol (v/v)=10/1) to obtain compound 18-8.

MS (ESI) m/z (M+H)$^+$=681.3.

Step 15: Preparation of Compound 18-9

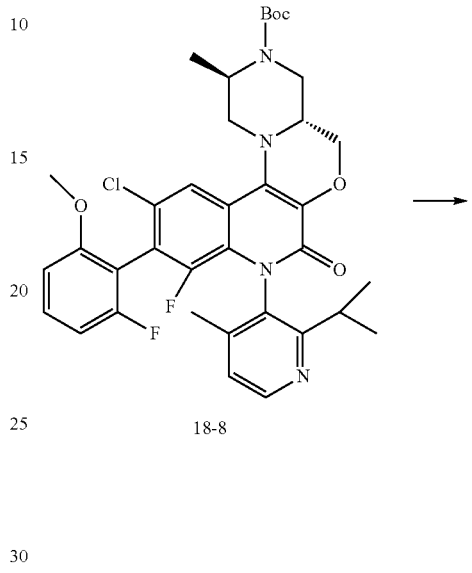

18-8

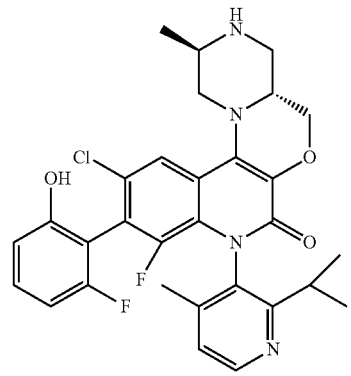

18-9

Under the protection of nitrogen, compound 18-8 (150 mg, 220.21 μmol) was dissolved in dichloromethane (3 mL) and boron tribromide (275.84 mg, 1.10 mmol, 106.09 μL) was added, and the reaction was stirred at 25° C. for 2 hours. The reaction mixture was quenched by adding methanol (10 mL), stirred for 10 min, and concentrated under reduced pressure to obtain the crude product 18-9, which was directly used in the next reaction without further purification.

MS (ESI) m/z (M+H)$^+$=567.1.

Step 16: Preparation of Compounds 18A and 18B

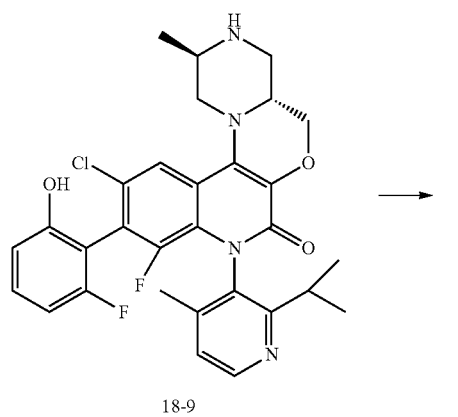

18-9

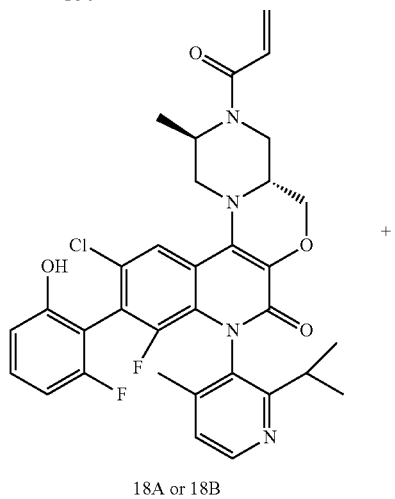

18A or 18B

+

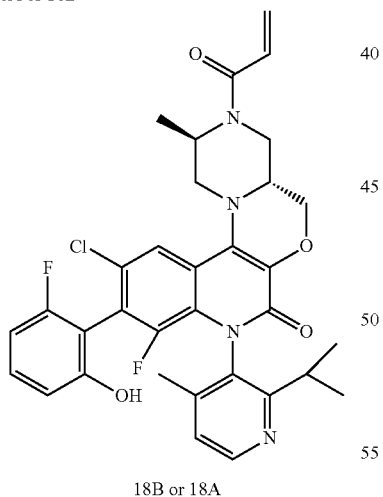

18B or 18A

Compound 18-9 (128.49 mg, 226.60 μmol) was dissolved in tetrahydrofuran (5 mL), sodium bicarbonate (3.79 g, 45.14 mmol, 1.76 mL) and acrylic anhydride (28.58 mg, 226.60 μmol) were added thereto sequentially, and the reaction was stirred at 25° C. for 30 min, then methanol (2 mL) and saturated potassium carbonate aqueous solution (2 mL) were added and stirred for 1 hour. The reaction mixture was diluted with water (10 mL), extracted with ethyl acetate (10 mL×2); the organic phases were combined, dried over anhydrous sodium sulfate, filtered, and the filtrate was concentrated under reduced pressure; then the crude product was separated and purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 50%-80%, 9 min, to obtain:

Compound 18A (HPLC retention time was 3.747, 3.871 min).

Compound 18B (HPLC retention time was 3.835, 3.916 min).

HPLC analysis conditions: chromatographic column: Xbridge Shield RP-18, 5 μm, 2.1*50 mm; mobile phase: [water (0.02% ammonia solution v/v)-acetonitrile]; acetonitrile %: 10%-80%, column temperature: 50° C.

Compound 18A:

MS (ESI) m/z (M+H)$^+$=621.2.

$^1$H NMR (400 MHz, Methanol-$d_4$) δ 8.42 (d, J=4.9 Hz, 1H), 7.89 (br s, 1H), 7.26-7.17 (m, 2H), 6.83 (dd, J=10.6, 16.8 Hz, 1H), 6.69-6.58 (m, 2H), 6.27 (br d, J=16.8 Hz, 1H), 5.82 (br d, J=10.1 Hz, 1H), 5.04-4.93 (m, 1H), 4.72-4.10 (m, 4H), 3.74 (br s, 1H), 3.65-3.44 (m, 2H), 3.14 (br s, 1H), 2.66 (td, J=6.6, 13.8 Hz, 1H), 2.12-2.01 (m, 3H), 1.84-1.64 (m, 3H), 1.19-1.03 (m, 6H).

Compound 18B:

MS (ESI) m/z (M+H)$^+$=621.2.

$^1$H NMR (400 MHz, Methanol-$d_4$) δ 8.42 (d, J=4.9 Hz, 1H), 7.89 (br s, 1H), 7.27-7.16 (m, 2H), 6.83 (dd, J=10.8, 16.8 Hz, 1H), 6.71-6.58 (m, 2H), 6.27 (dd, J=1.7, 16.9 Hz, 1H), 5.82 (br d, J=10.6 Hz, 1H), 5.04-4.92 (m, 1H), 4.73-4.10 (m, 4H), 3.74 (br s, 1H), 3.66-3.47 (m, 2H), 3.15 (br d, J=10.4 Hz, 1H), 2.77-2.58 (m, 1H), 2.05 (d, J=2.9 Hz, 3H), 1.84-1.62 (m, 3H), 1.17-1.02 (m, 6H).

Step 17: Separation of Compounds 18A-1 and 18A-2

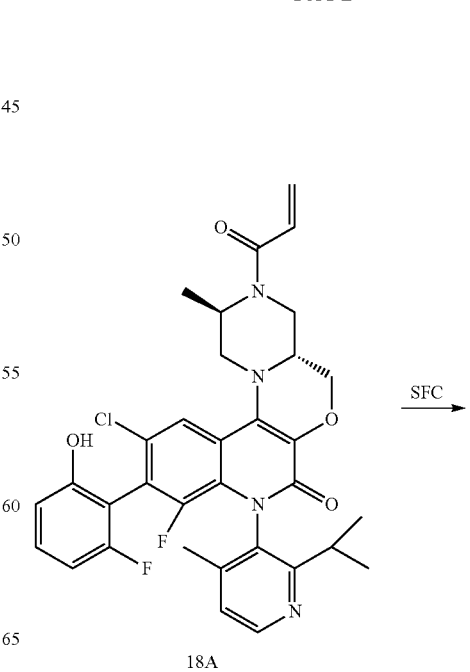

18A

SFC →

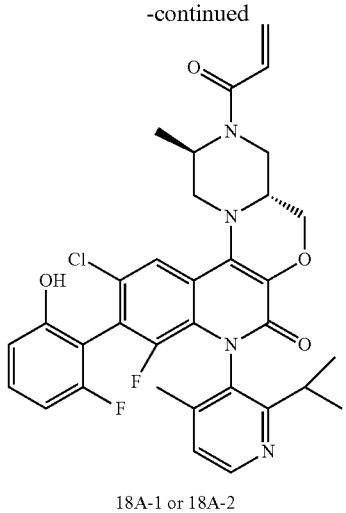

18A-1 or 18A-2

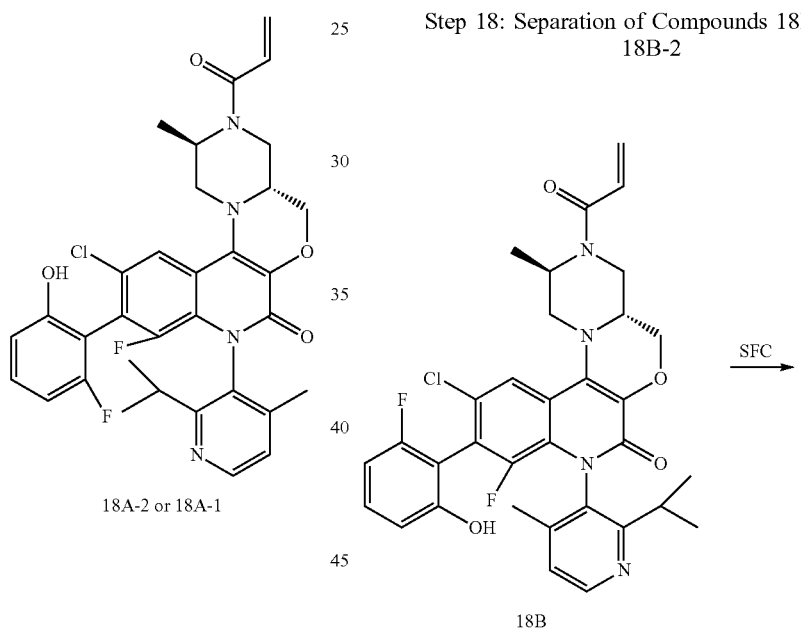

18A-2 or 18A-1

Compound 18A was separated and purified by SFC (separation conditions: chromatographic column: REGIS (s, s) WHELK-O1 (250 mm*30 mm, 5 μm); mobile phase: [supercritical carbon dioxide-ethanol]; ethanol %: 50%-50%), to obtain:

Compound 18A-1 (HPLC retention time was 8.29 min; ee: 99.24%).

Compound 18A-2 (HPLC retention time was 8.37 min; ee: 99.38%).

HPLC analysis conditions: chromatographic column: WELCH Ultimate LP-C18 150*4.6 mm, 5 μm; mobile phase: [water (0.06875 trifluoroacetic acid solution v/v)-acetonitrile (0.0625% trifluoroacetic acid solution v/v)]; acetonitrile %: 10%-80%, column temperature: 40° C.

SFC chiral analysis conditions: chromatographic column: (S,S)-Whelk-01 100*4.6 mm, 3 μm; mobile phase: [supercritical carbon dioxide-ethanol (0.05% diethylamine solution v/v)]; ethanol %: 40%-40%, column temperature: 35° C.

Compound 18A-1:

MS (ESI) m/z (M+H)$^+$=621.3.

$^1$H NMR (400 MHz, Methanol-d$_4$) δ 8.42 (d, J=5.1 Hz, 1H), 7.89 (br s, 1H), 7.27-7.15 (m, 2H), 6.83 (dd, J=10.7, 16.6 Hz, 1H), 6.72-6.56 (m, 2H), 6.28 (dd, J=1.8, 16.8 Hz, 1H), 5.82 (br d, J=10.1 Hz, 1H), 5.05-4.94 (m, 1H), 4.70-4.35 (m, 3H), 3.83-3.68 (m, 1H), 3.65-3.51 (m, 2H), 3.20-3.13 (m, 1H), 2.79-2.66 (m, 1H), 2.13-2.02 (m, 3H), 1.83-1.65 (m, 3H), 1.16 (br d, J=6.6 Hz, 3H), 1.11-1.00 (m, 3H).

Compound 18A-2:

MS (ESI) m/z (M+H)$^+$=621.2.

$^1$H NMR (400 MHz, Methanol-d$_4$) δ 8.42 (d, J=4.9 Hz, 1H), 7.89 (br s, 1H), 7.28-7.17 (m, 2H), 6.83 (dd, J=10.6, 16.8 Hz, 1H), 6.69-6.58 (m, 2H), 6.27 (dd, J=1.8, 16.8 Hz, 1H), 5.82 (br d, J=11.0 Hz, 1H), 5.03-4.94 (m, 1H), 4.70-4.34 (m, 3H), 3.76 (br d, J=11.5 Hz, 1H), 3.64-3.48 (m, 2H), 3.14 (br d, J=9.3 Hz, 1H), 2.66 (td, J=6.8, 13.6 Hz, 1H), 2.06 (s, 3H), 1.80-1.67 (m, 3H), 1.14 (d, J=6.8 Hz, 3H), 1.11 (d, J=6.8 Hz, 3H).

Step 18: Separation of Compounds 18B-1 and 18B-2

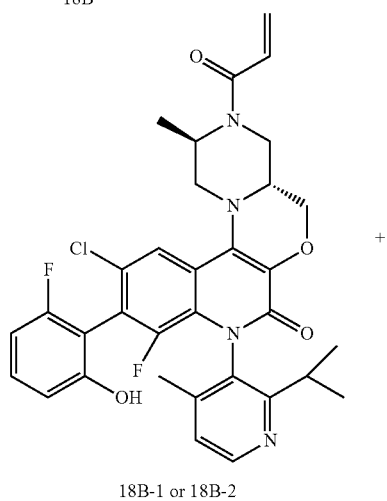

18B-1 or 18B-2

449
-continued

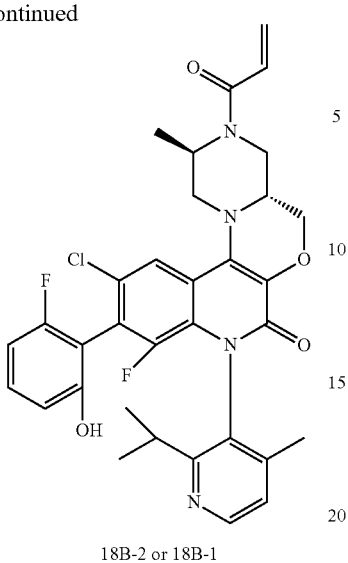

18B-2 or 18B-1

Compound 18B was separated and purified by SFC (separation conditions: chromatographic column: REGIS (s, s) WHELK-O1 (250 mm*30 mm, 5 μm); mobile phase: [supercritical carbon dioxide-ethanol]; ethanol %: 50%-50%), to obtain:

Compound 18B-1 (HPLC retention time was 8.59 min; ee: 100%).

Compound 18B-2 (HPLC retention time was 8.53 min; ee: 100%).

HPLC analysis conditions: chromatographic column: WELCH Ultimate LP-C18 150*4.6 mm, 5 μm; mobile phase: [water (0.06875 trifluoroacetic acid solution v/v)-acetonitrile (0.0625% trifluoroacetic acid solution v/v)]; acetonitrile %: 10%-80%, column temperature: 40° C.

SFC chiral analysis conditions: chromatographic column: (S,S)-Whelk-01 100*4.6 mm, 3 μm; mobile phase: [supercritical carbon dioxide-ethanol (0.05% diethylamine solution v/v)]; ethanol %: 40%-40%, column temperature: 35° C.

18B-1:

MS (ESI) m/z (M+H)$^+$=621.2.

$^1$H NMR (400 MHz, Methanol-$d_4$) δ 8.42 (d, J=5.1 Hz, 1H), 7.88 (br s, 1H), 7.27-7.15 (m, 2H), 6.83 (dd, J=10.8, 16.8 Hz, 1H), 6.70-6.55 (m, 2H), 6.27 (dd, J=1.7, 16.9 Hz, 1H), 5.82 (br d, J=9.9 Hz, 1H), 5.04-4.93 (m, 1H), 4.70-4.34 (m, 3H), 3.75 (br d, J=10.8 Hz, 1H), 3.65-3.45 (m, 2H), 3.17 (br d, J=8.6 Hz, 1H), 2.75-2.63 (m, 1H), 2.09-1.99 (m, 3H), 1.81-1.65 (m, 3H), 1.14 (br d, J=6.6 Hz, 3H), 1.11-1.04 (m, 3H).

18B-2:

MS (ESI) m/z (M+H)$^+$=621.2.

$^1$H NMR (400 MHz, Methanol-$d_4$) δ 8.42 (br d, J=5.1 Hz, 1H), 7.89 (br s, 1H), 7.29-7.17 (m, 2H), 6.83 (br dd, J=10.9, 16.6 Hz, 1H), 6.71-6.55 (m, 2H), 6.27 (br d, J=16.8 Hz, 1H), 5.82 (br d, J=9.5 Hz, 1H), 5.03-4.92 (m, 1H), 4.68-4.35 (m, 3H), 3.75 (br d, J=11.2 Hz, 1H), 3.64-3.44 (m, 2H), 3.14 (br d, J=8.4 Hz, 1H), 2.65 (td, J=6.4, 13.1 Hz, 1H), 2.06 (s, 3H), 1.84-1.66 (m, 3H), 1.19-1.12 (m, 3H), 1.11-0.97 (m, 3H).

450

Embodiment 19: Preparation of Compound 19

Step 1: Preparation of Compound 19-3

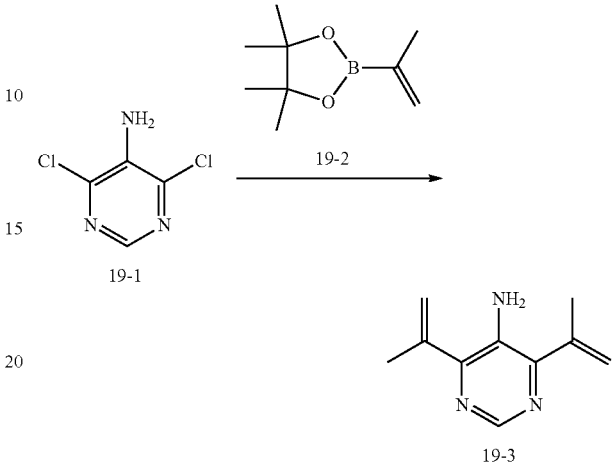

At room temperature (20° C.), compound 19-1 (9.5 g, 57.93 mmol), compound 19-2 (29.20 g, 173.79 mmol), 1,1-bis(diphenylphosphino)ferrocene palladium dichloride (3.39 g, 4.63 mmol) and potassium carbonate (24.02 g, 173.79 mmol) were dissolved in 1,4-dioxane (150 mL) and water (30 mL), under nitrogen atmosphere, the system was stirred at 100° C. for 12 hours. The system was cooled to room temperature, concentrated to remove most of the solvent, water (100 mL) was added thereto, and the mixture was extracted with ethyl acetate (80 mL×2); and the organic phase was combined, then the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 19-3.

$^1$H NMR (400 MHz, DMSO-$d_6$) 8.39 (s, 1H), 5.57-5.51 (m, 2H), 5.42 (s, 2H), 4.89 (s, 2H), 2.06 (s, 6H).

MS (ESI) m/z (M+H)$^+$=175.9.

Step 2: Preparation of Compound 19-4

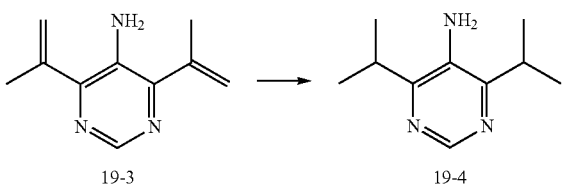

Compound 19-3 (10.37 g, 59.18 mmol) was dissolved in methanol (50 mL), and 10% palladium carbon (1 g) was added thereto under nitrogen atmosphere. After the addition was completed, the system was replaced with hydrogen. Under hydrogen atmosphere (15 psi), the system was heated to 25° C. and stirred for 12 hours. The system was filtered, and the filtrate was concentrated. The residue was dissolved in dichloromethane (100 mL), washed with 2 M hydrochloric acid aqueous solution (50 mL), the pH of the aqueous phase was adjusted to 9-10 with sodium hydroxide, then the aqueous phase was extracted with dichloromethane (100 mL); and the organic phase was dried over anhydrous sodium sulfate, filtered, and the filtrate was concentrated to obtain compound 19-4, which was used directly in the next reaction without further purification.

$^1$H NMR (400 MHz, DMSO-$d_6$) 8.31 (s, 1H), 5.04 (s, 2H), 3.25-3.16 (m, 2H), 1.13 (d, J=6.5 Hz, 12H).

MS (ESI) m/z (M+H)$^+$=180.0.

Step 3: Preparation of Compound 19-5

Step 4: Preparation of Compound 19-6

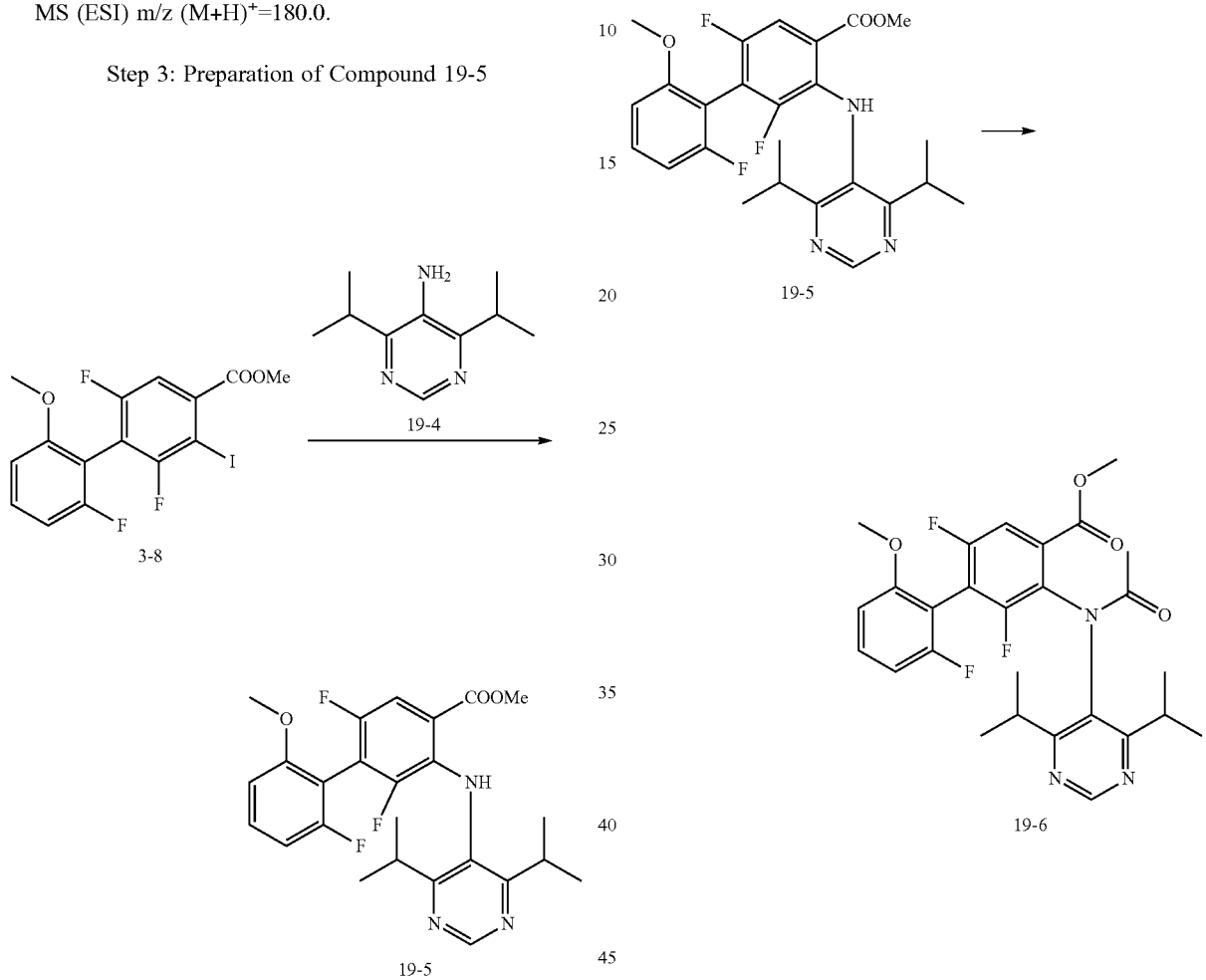

At room temperature (20° C.), compound 3-8 (4.8 g, 11.37 mmol), compound 19-4 (2.65 g, 14.78 mmol), tris(dibenzylacetone)diparadium (1.2 g, 1.31 mmol), 4,5-diphenylphosphino-9,9-dimethoxyanthracene (750 mg, 1.30 mmol) and cesium carbonate (11.11 g, 34.11 mmol) were dissolved in toluene (40 mL). Under nitrogen atmosphere, the system was heated to 100° C. and stirred for 16 hours. The system was cooled to room temperature, filtered, and concentrated to obtain a crude product. The crude product was purified by medium pressure column chromatography (ethyl acetate/petroleum ether (v/v)=0-50%) to obtain compound 19-5.

$^1$H NMR (400 MHz, Chloroform-d) δ8.97 (s, 1H), 8.90 (br d, J=3.7 Hz, 1H), 7.67 (br dd, J=2.0, 9.5 Hz, 1H), 7.39-7.30 (m, 1H), 6.84-6.65 (m, 2H), 3.99 (s, 3H), 3.72 (s, 3H), 3.45-3.31 (m, 2H), 1.37-0.89 (m, 12H).

MS (ESI) m/z (M+H)$^+$=474.4.

Compound 19-5 (3.75 g, 7.92 mmol) was dissolved in N,N-dimethylformamide (40 mL), and sodium hydride (1.90 g, 47.52 mmol, 60% purity) was added in batches at 0° C., after the reaction was carried out at 0° C. for 20 min, acetyl chloride (3.73 g) was added dropwise thereto. After the addition was completed, under nitrogen atmosphere, the reaction was carried out at room temperature (25° C.) for 16 hours. The reaction was quenched by adding water (20 mL) to the system, and saturated potassium carbonate aqueous solution was added thereto; and the mixture was stirred at room temperature (25° C.) for 1 hour, extracted with ethyl acetate (100 mL×2); the organic phase was dried over anhydrous sodium sulfate, filtered and the filtrate was concentrated to obtain a crude product, the crude product was purified by medium pressure column chromatography (ethyl acetate/petroleum ether (v/v)=0-100%) to obtain compound 19-6.

MS (ESI) m/z (M+H)$^+$=516.3.

Step 5: Preparation of Compound 19-7

Step 6: Preparation of Compound 19-8

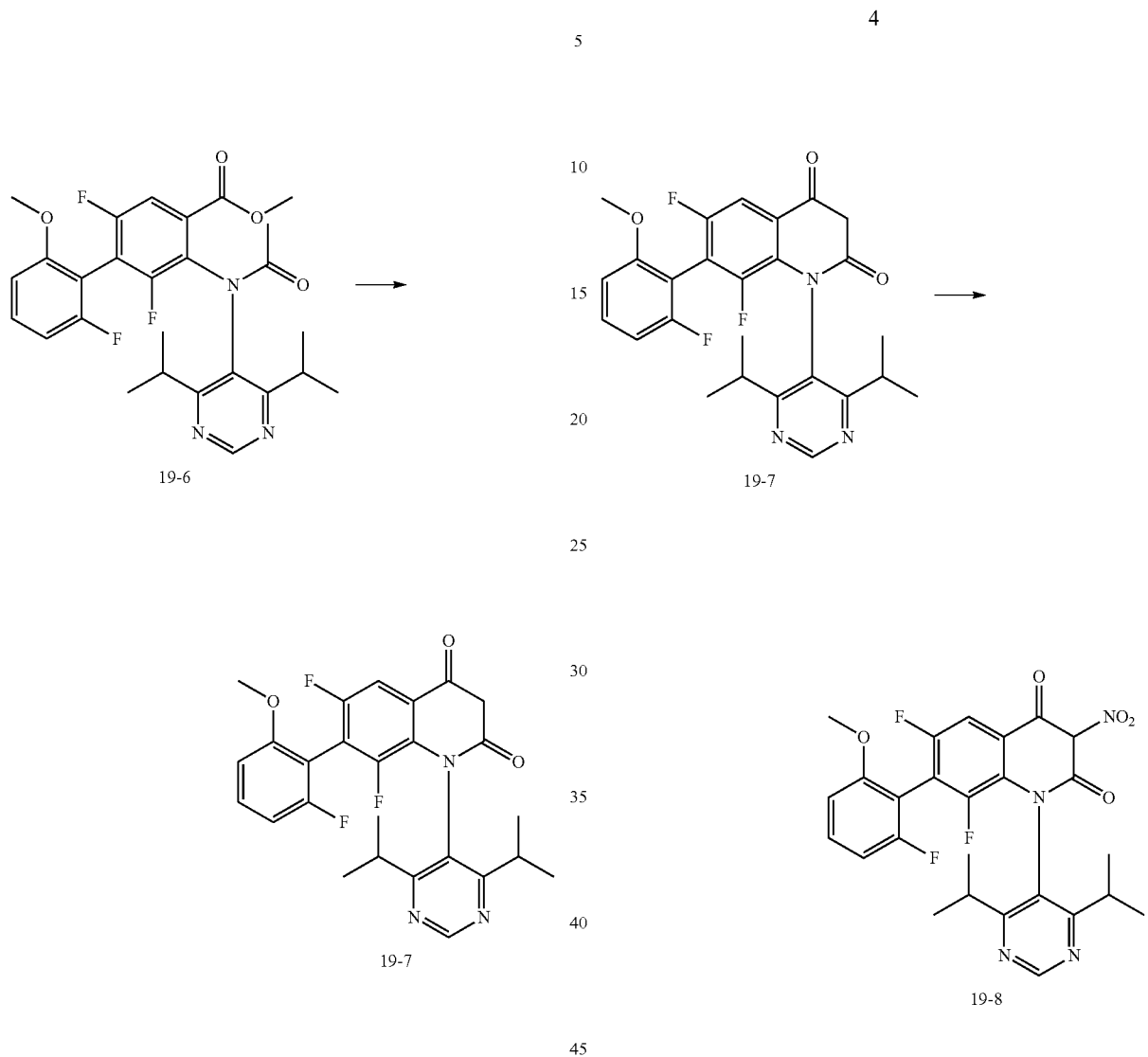

At room temperature (20° C.), compound 19-6 (1 g, 1.94 mmol) was dissolved in toluene (10 mL), and potassium tert-butoxide (1 M, 6.28 mL) was added thereto. After the addition was completed, under nitrogen atmosphere, the reaction was carried out at room temperature (25° C.) for 0.5 hours. The reaction was quenched by adding water (20 mL) to the system, the pH was adjusted to neutral with 1 N hydrochloric acid; and the mixture was extracted with ethyl acetate (30 mL×3), the organic phase was dried over anhydrous sodium sulfate, filtered, and the filtrate was concentrated to obtain compound 19-7, which were used directly in the next reaction without further purification.

$^1$H NMR (400 MHz, Chloroform-d) δ 11.25 (br s, 1H), 9.48-9.16 (m, 1H), 7.53 (dd, J=1.4, 8.5 Hz, 1H), 7.36 (dt, J=6.7, 8.4 Hz, 1H), 6.80-6.72 (m, 2H), 6.53 (s, 1H), 3.72 (s, 3H), 2.88-2.74 (m, 2H), 1.23 (dd, J=6.7, 10.9 Hz, 6H), 1.14 (dd, J=6.7, 11.6 Hz, 6H).

MS (ESI) m/z (M+H)$^+$=484.0.

Compound 19-7 (1.3 g, 2.69 mmol) was dissolved in glacial acetic acid (15 mL), and nitric acid (3.11 g, 49.42 mmol, 2.22 mL) was added dropwise to the system at room temperature (20° C.). After the dropwise addition was completed, the system was heated to 80° C. and stirred for 2 hours. The system was cooled to room temperature, concentrated to remove most of the glacial acetic acid, and the remainder was poured into ice water (50 mL), precipitated, filtered, and the filter cake was washed with water and dried to obtain compound 19-8, which was used directly in the next step without further purification.

$^1$H NMR (400 MHz, DMSO-d$_6$) δ 9.02 (s, 1H), 7.80 (br d, J=9.0 Hz, 1H), 7.51-7.40 (m, 1H), 6.99-6.85 (m, 2H), 3.73-3.63 (m, 3H), 3.17 (s, 1H), 2.91-2.75 (m, 2H), 1.33-0.90 (m, 12H).

MS (ESI) m/z (M+H)$^+$=529.0.

Step 7: Preparation of Compound 19-9

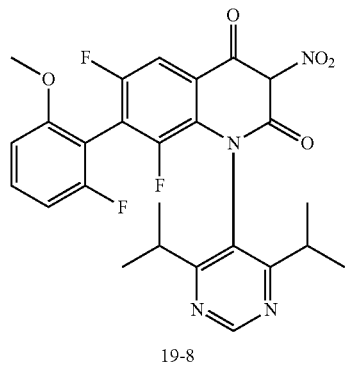

19-8

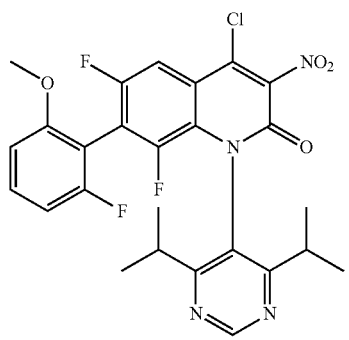

19-9

Compound 19-8 (800 mg, 1.51 mmol) and N,N-diisopropylethylamine (1.17 g, 9.08 mmol, 1.58 mL) were dissolved in acetonitrile (10 mL), and at room temperature, phosphorus oxychloride (696.32 mg, 4.54 mmol, 422.01 µL) was added thereto. After the addition was completed, the system was heated to 80° C. and stirred for 2 hours. The system was concentrated to obtain a crude product. The crude product was purified by medium pressure column chromatography (ethyl acetate/petroleum ether (v/v)=0-100%) to obtain compound 19-9.

$^1$H NMR (400 MHz, Chloroform-d) δ 9.18 (s, 1H), 7.88 (br d, J=8.6 Hz, 1H), 7.48-7.34 (m, 1H), 6.87-6.68 (m, 2H), 3.82-3.66 (m, 3H), 2.89-2.61 (m, 2H), 1.39-1.07 (m, 12H).

MS (ESI) m/z (M+H)$^+$=547.0.

Step 8: Preparation of Compound 19-10

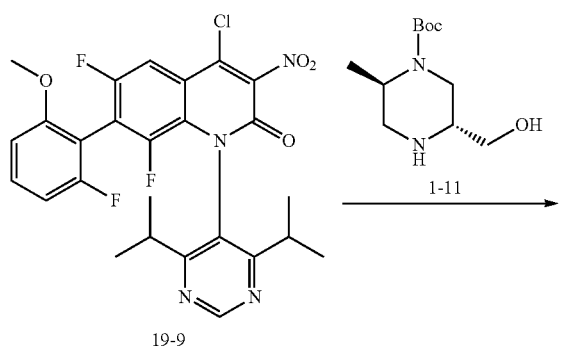

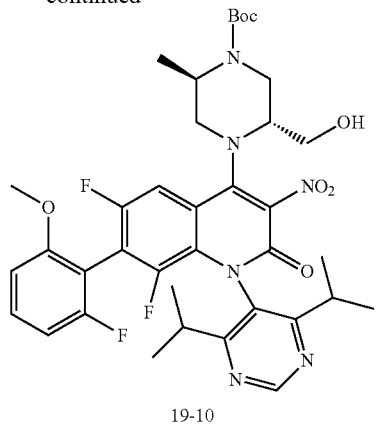

19-10

Compound 19-9 (400 mg, 731.36 µmol), compound 1-11 (252.65 mg, 1.10 mmol) and N,N-diisopropylethylamine (473.56 mg, 3.66 mmol, 638.22 µL) were dissolved in acetonitrile (10 mL). Under nitrogen atmosphere, the system was heated to 80° C. and stirred for 1 hour. The system was concentrated to obtain a crude product. The crude product was purified by medium pressure column chromatography (ethyl acetate/petroleum ether (v/v)=0-100%) to obtain compound 19-10.

MS (ESI) m/z (M+H)$^+$=741.1.

Step 9: Preparation of Compound 19-11

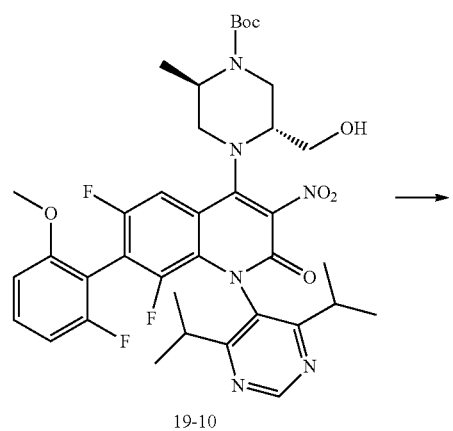

19-10

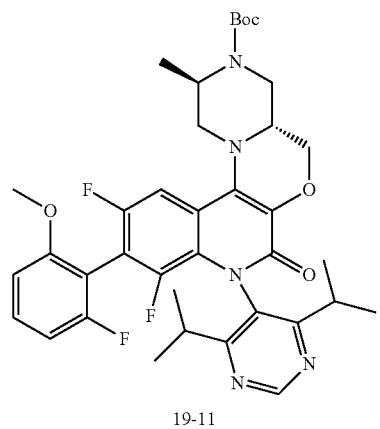

19-11

Compound 19-10 (270 mg, 364.49 µmol) and 4 Å molecular sieve (1 g) were dissolved in N-methylpyrrolidone (8 mL), and tetrahydrofuran solution of lithium bis(trimethylsilyl)amide (1 M, 1.09 mL) was added thereto at room temperature. After the addition was completed, under nitrogen atmosphere, the system was heated to 130° C. and stirred for 16 hours. The system was cooled to room temperature, added with water (20 mL), and then extracted with ethyl acetate (20 mL×2); the organic phase was washed with saturated saline (20 mL), dried over anhydrous sodium sulfate, filtered, and the filtrate was concentrated to obtain a crude product. The crude product was purified by medium pressure column chromatography (ethyl acetate/petroleum ether (v/v)=0-100%) to obtain compound 19-11.

MS (ESI) m/z (M+H)$^+$=694.1.

Step 10: Preparation of Compound 19-12

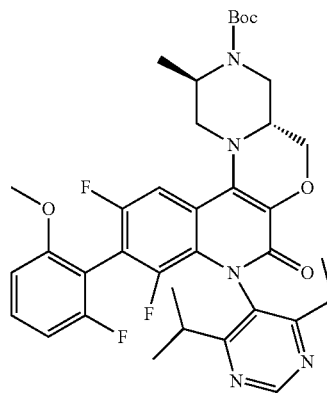

19-11

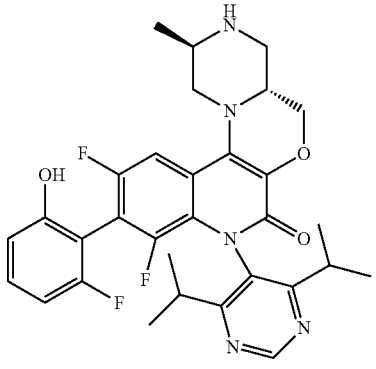

19-12

Compound 19-11 (60 mg, 86.49 µmol) was dissolved in anhydrous dichloromethane (2 mL), and boron tribromide (108.33 mg, 432.43 µmol, 41.67 µL) was added thereto at 0° C. After the addition was completed, under nitrogen atmosphere, the system was raised to room temperature (25° C.) and stirred for 2 hours. Methanol (5 mL) was added to the system and stirred for 10 min. The system was concentrated and lyophilized to obtain compound 19-12 (hydrobromide), which was directly used in the next reaction without further purification.

MS (ESI) m/z (M+H)$^+$=580.1.

Step 11: Preparation of Compounds 19A and 19B

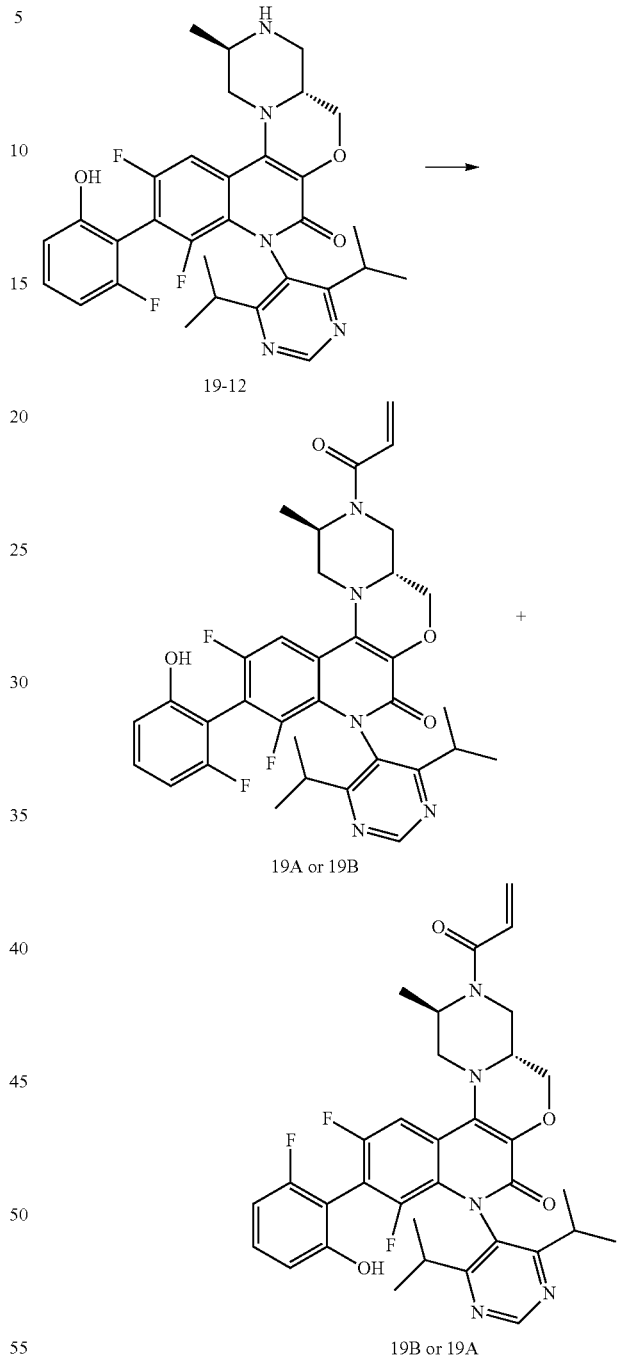

Compound 19-12 (70 mg, 120.77 µmol, hydrobromide) was dissolved in tetrahydrofuran (2 mL) and saturated sodium bicarbonate aqueous solution (6.05 g, 71.99 mmol, 2.80 mL), and acrylic anhydride (15.23 mg, 120.77 µmol) was added thereto at room temperature (25° C.). After the addition was completed, the system was stirred at room temperature (25° C.) for 30 min. Methanol (2 mL) and saturated potassium carbonate aqueous solution (2 mL) were added to the system, and the mixture was stirred at room temperature (25° C.) for 1 hour. The system was diluted with water (10 mL) and extracted with ethyl acetate (10 mL×2), the organic phase was dried over anhydrous sodium sulfate, filtered, and the filtrate was concentrated to obtain a crude product. The crude product was purified by medium pressure column chromatography (methanol/dichloromethane (v/v)= 0-10%) and preparative high performance liquid chromatography (separation conditions: chromatographic column: Phenomenex Gemini-NX 150*30 mm*5 μm; mobile phase: [water (0.05% ammonia solution)-acetonitrile]; acetonitrile %: 42%-72% 7 min) to obtain compounds 19A and 19B.

Compound 19A:

$^1$H NMR (400 MHz, Methanol-$d_4$) δ 9.06 (s, 1H), 7.55 (br d, J=8.4 Hz, 1H), 7.29-7.15 (m, 1H), 6.82 (dd, J=10.4, 16.8 Hz, 1H), 6.72-6.58 (m, 2H), 6.27 (dd, J=2.0, 16.8 Hz, 1H), 5.81 (br d, J=11.7 Hz, 1H), 4.64-4.09 (m, 4H), 3.83-3.41 (m, 3H), 3.12 (br s, 1H), 2.81-2.63 (m, 2H), 1.84-1.63 (m, 3H), 1.18-1.06 (m, 12H).

MS (ESI) m/z (M+H)$^+$=634.3.

HPLC 91% purity; retention time was 3.84 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

Compound 19B:

$^1$H NMR (400 MHz, Methanol-$d_4$) δ 9.07 (s, 1H), 7.56 (br d, J=8.8 Hz, 1H), 7.30-7.16 (m, 1H), 6.82 (br dd, J=10.6, 17.0 Hz, 1H), 6.72-6.59 (m, 2H), 6.27 (dd, J=1.8, 16.5 Hz, 1H), 5.82 (br d, J=10.1 Hz, 1H), 4.67-4.09 (m, 4H), 3.82-3.42 (m, 3H), 3.13 (br s, 1H), 2.82-2.63 (m, 2H), 1.82-1.62 (m, 3H), 1.17-1.04 (m, 12H).

MS (ESI) m/z (M+H)$^+$=634.3.

HPLC 91% purity; retention time was 3.88 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

Embodiment 20: Preparation of Compound 20

Step 1: Preparation of Compound 20-1

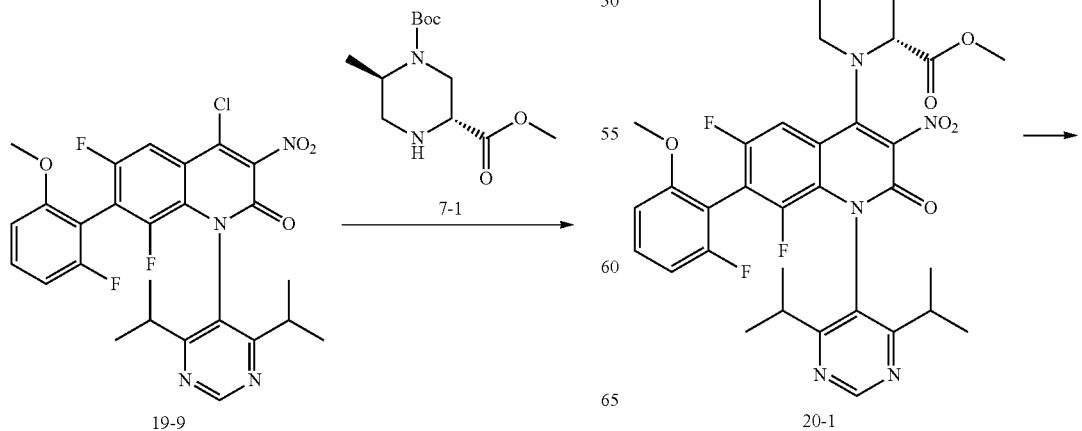

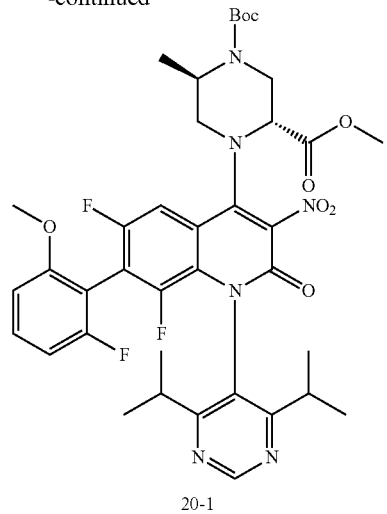

Compound 19-9 (390 mg, 713.08 μmol), compound 7-1 (276.30 mg, 1.07 mmol) and N,N-diisopropylethylamine (461.72 mg, 3.57 mmol, 622.27 μL) were dissolved in acetonitrile (10 mL). Under nitrogen atmosphere, the system was heated to 80° C. and stirred for 12 hour. The system was concentrated to obtain a crude product, the crude product was purified by medium pressure column chromatography (ethyl acetate/petroleum ether (v/v)=0-100%) to obtain compound 20-1.

MS (ESI) m/z (M+H)$^+$=769.1.

Step 2: Preparation of Compound 20-2

-continued

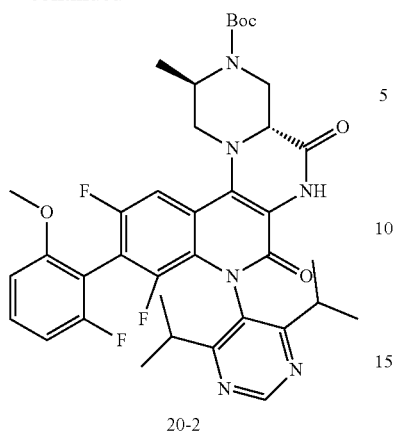

20-2

-continued

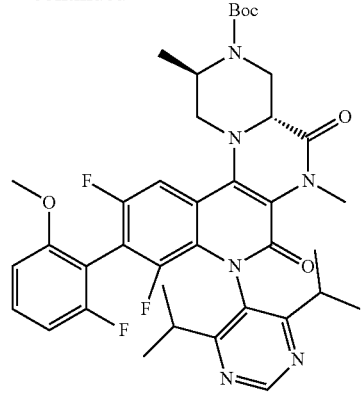

20-3

Compound 20-1 (400 mg, 520.31 μmol) and iron powder (116.52 mg, 2.09 mmol) were dissolved in acetic acid (7 mL), under nitrogen atmosphere, the system was heated to 80° C. and stirred for 45 min. The system was concentrated, diluted with dichloromethane (20 mL), filtered, the filtrate was washed with saturated sodium bicarbonate aqueous solution, dried over anhydrous sodium sulfate, filtered, and the filtrate was concentrated to obtain compound 20-2, which was directly used for the next reaction without further purification.

MS (ESI) m/z (M+H)$^+$=707.2.

Step 3: Preparation of Compound 20-3

Compound 20-2 (100 mg, 141.49 μmol) and potassium carbonate (52.99 mg, 383.44 μmol) were dissolved in acetone (2 mL), and methyl iodide (271.12 mg, 1.91 mmol, 118.91 μL) was added at room temperature (25° C.). After the addition was completed, under nitrogen atmosphere, the system was heated to 40° C. and stirred for 16 hours. The system was concentrated, dichloromethane (10 mL) and water (10 mL) were added for separation and extraction, the organic phase was dried over anhydrous sodium sulfate, filtered, and the filtrate was concentrated to obtain compound 20-3, which was directly used in the next reaction without further purification.

MS (ESI) m/z (M+H)$^+$=721.3.

Step 4: Preparation of Compound 20-4

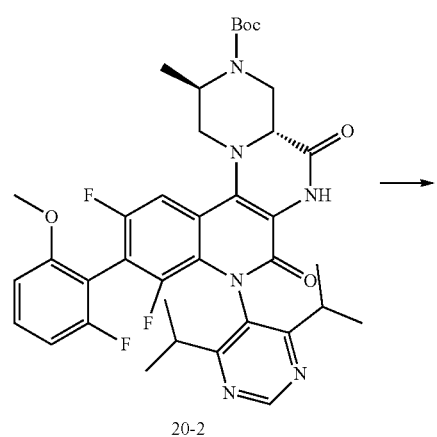

20-2

→

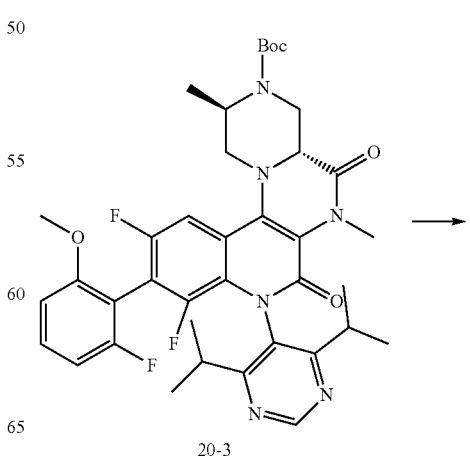

20-3

→

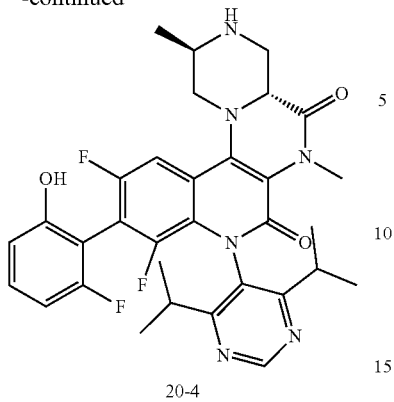

20-4

Compound 20-3 (100 mg, 138.74 μmol) was dissolved in dichloromethane (2 mL), and boron tribromide (1 M, 1 mL) was added thereto, and the reaction was stirred at 20° C. for 16 hours. The reaction mixture was quenched with methanol (10 mL), stirred for 10 min, and concentrated under reduced pressure to obtain compound 20-4 (hydrobromide), which was directly used in the next reaction without further purification.

MS (ESI) m/z (M+H)$^+$=607.1.

Step 5: Preparation of Compound 20

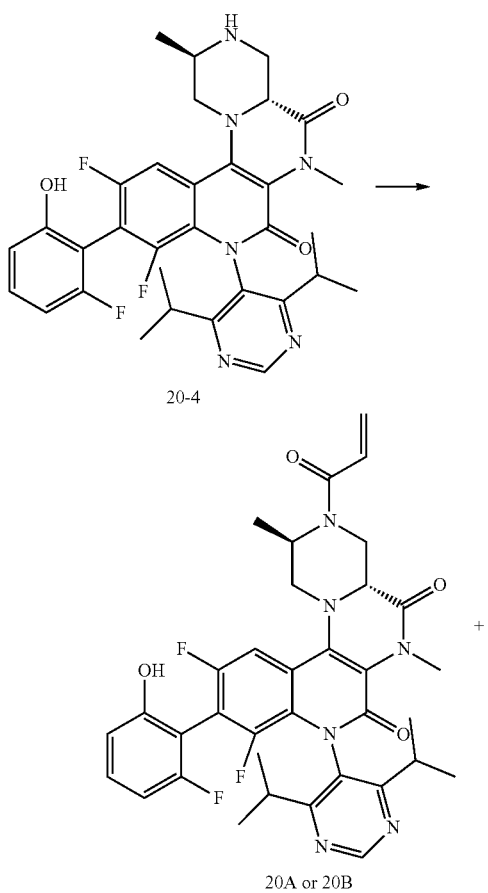

20-4

20A or 20B

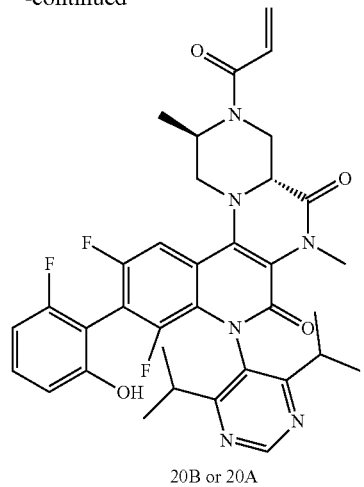

20B or 20A

Compound 20-4 (100 mg, 164.84 μmol, hydrobromide) was dissolved in tetrahydrofuran (2 mL) and saturated sodium bicarbonate aqueous solution (13.85 mg, 164.84 μmol, 6.41 μL), and acrylic anhydride (20.79 mg, 164.84 μmol) was added thereto at room temperature (25° C.). After the addition was completed, the system was stirred at room temperature (25° C.) for 30 min. Methanol (2 mL) and saturated potassium carbonate aqueous solution (2 mL) were added to the system, and the mixture was stirred at room temperature (25° C.) for 1 hour. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 150*30 mm*5 μm; mobile phase: [water (10 mM ammonium bicarbonate aqueous solution)-acetonitrile]; acetonitrile %: 50%-80% 9 min) to obtain compounds 20A and 20B.

Compound 20A:
$^1$H NMR (400 MHz, Methanol-d$_4$) δ 9.08 (s, 1H), 7.68 (br d, J=9.1 Hz, 1H), 7.29-7.20 (m, 1H), 7.12 (dd, J=11.0, 16.8 Hz, 1H), 6.71-6.57 (m, 2H), 6.32-6.17 (m, 1H), 5.86-5.74 (m, 1H), 4.79-4.42 (m, 3H), 4.02-3.86 (m, 2H), 3.42 (s, 3H), 3.04-2.85 (m, 2H), 2.68-2.52 (m, 1H), 1.74-1.62 (m, 3H), 1.21 (d, J=6.8 Hz, 3H), 1.17-1.07 (m, 9H).

MS (ESI) m/z (M+H)$^+$=661.1.

HPLC 95% purity; retention time was 10.49 min.

Separation conditions: chromatographic column WELCH MLtimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 20B:
$^1$H NMR (400 MHz, Methanol-d$_4$) δ 9.08 (s, 1H), 7.68 (br d, J=8.8 Hz, 1H), 7.29-7.20 (m, 1H), 7.12 (dd, J=10.7, 16.9 Hz, 1H), 6.72-6.59 (m, 2H), 6.32-6.17 (m, 1H), 5.87-5.74 (m, 1H), 4.86-4.44 (m, 2H), 4.04-3.86 (m, 2H), 3.52-3.34 (m, 4H), 3.05-2.85 (m, 2H), 2.67-2.54 (m, 1H), 1.76-1.63 (m, 3H), 1.23-1.03 (m, 12H).

MS (ESI) m/z (M+H)$^+$=661.1.

HPLC 94% purity; retention time was 10.82 min.

Separation conditions: chromatographic column WELCH MLtimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Embodiment 21: Preparation of Compound 21

Step 1: Preparation of Compound 21-1

Step 2: Preparation of Compound 21-2

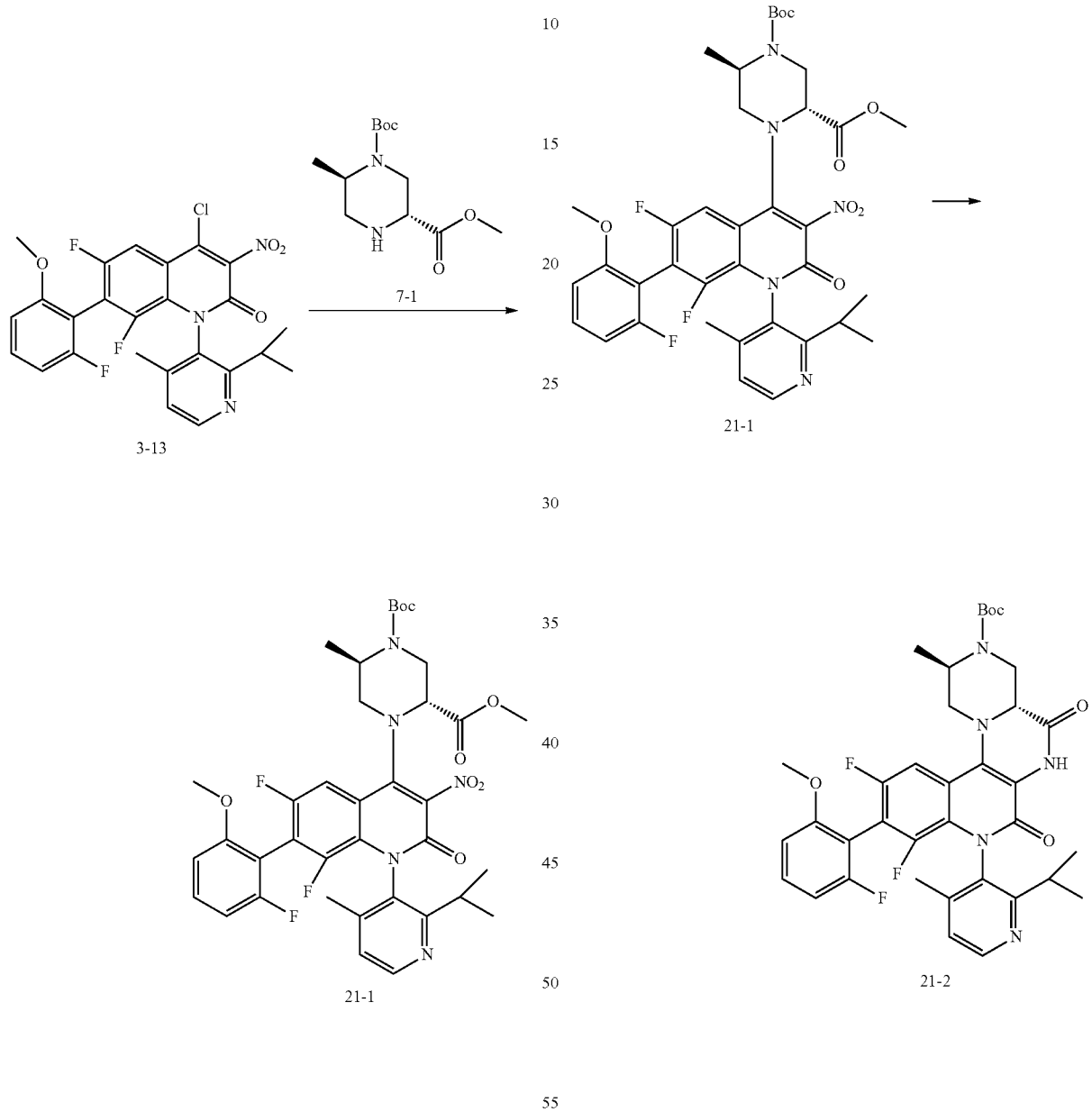

Compound 3-13 (500 mg, 965.47 μmol), compound 7-1 (374.09 mg, 1.45 mmol) and N,N-diisopropylethylamine (625.15 mg, 4.84 mmol, 842.52 μL) were dissolved in acetonitrile (10 mL). Under nitrogen atmosphere, the system was heated to 80° C. and stirred for 12 hours. The system was concentrated to obtain a crude product, the crude product was purified by medium pressure column chromatography (ethyl acetate/petroleum ether (v/v)=0-100%) to obtain compound 21-1.

MS (ESI) m/z (M+H)$^+$=740.2.

Compound 21-1 (500 mg, 675.92 μmol) and iron powder (151.36 mg, 2.71 mmol) were dissolved in acetic acid (8 mL), under nitrogen atmosphere, the system was heated to 80° C. and stirred for 45 min. The system was concentrated, diluted with dichloromethane (20 mL), filtered, the filtrate was washed with saturated sodium bicarbonate aqueous solution, dried over anhydrous sodium sulfate, filtered, and the filtrate was concentrated to obtain compound 21-2, which was directly used for the next reaction without further purification.

MS (ESI) m/z (M+H)$^+$=678.1.

Step 3: Preparation of Compound 21-3

Step 4: Preparation of Compound 21-4

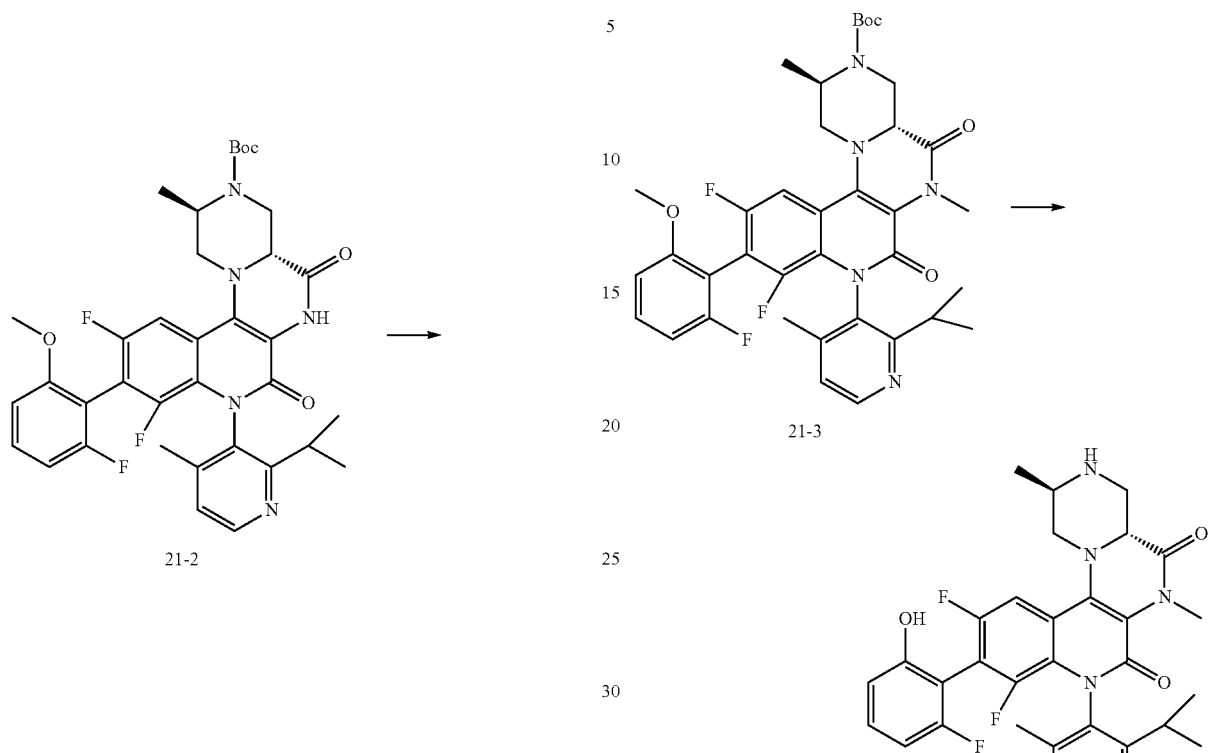

21-2

21-3

21-3

Compound 21-3 (100 mg, 144.56 μmol) was dissolved in dichloromethane (2 mL) and boron tribromide (181.08 mg, 722.82 μmol, 69.65 μL) was added thereto, and the reaction was stirred at 25° C. for 2 hours. The reaction mixture was quenched with methanol (10 mL), stirred for 10 min, and concentrated under reduced pressure to obtain compound 21-4 (hydrobromide), which was directly used in the next reaction without further purification.

MS (ESI) m/z (M+H)$^+$=578.1.

Step 5: Preparation of Compounds 21A and 21B

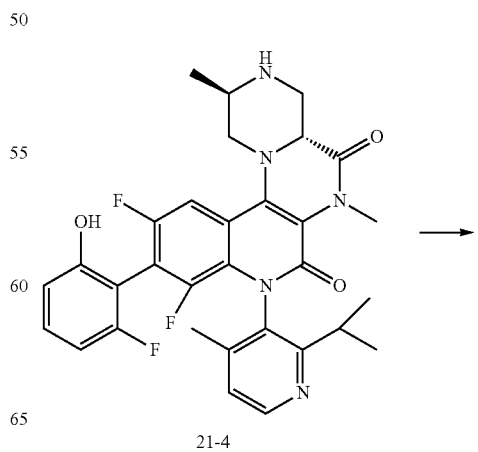

21-4

Compound 21-2 (120 mg, 177.07 μmol) and potassium carbonate (66.31 mg, 479.77 μmol) were dissolved in acetone (2 mL), and methyl iodide (339.29 mg, 2.39 mmol, 148.81 μL) was added at room temperature (25° C.). After the addition was completed, under nitrogen atmosphere, the system was heated to 40° C. and stirred for 16 hours. The system was concentrated, dichloromethane (10 mL) and water (10 mL) were added for separation and extraction, the organic phase was dried over anhydrous sodium sulfate, filtered, and the filtrate was concentrated to obtain compound 21-3, which was directly used in the next reaction without further purification.

MS (ESI) m/z (M+H)$^+$=692.2.

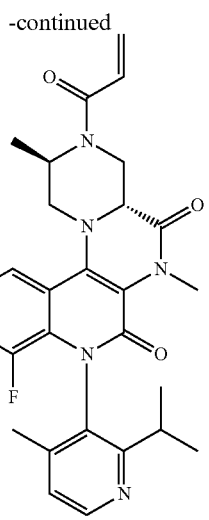

21A or 21B

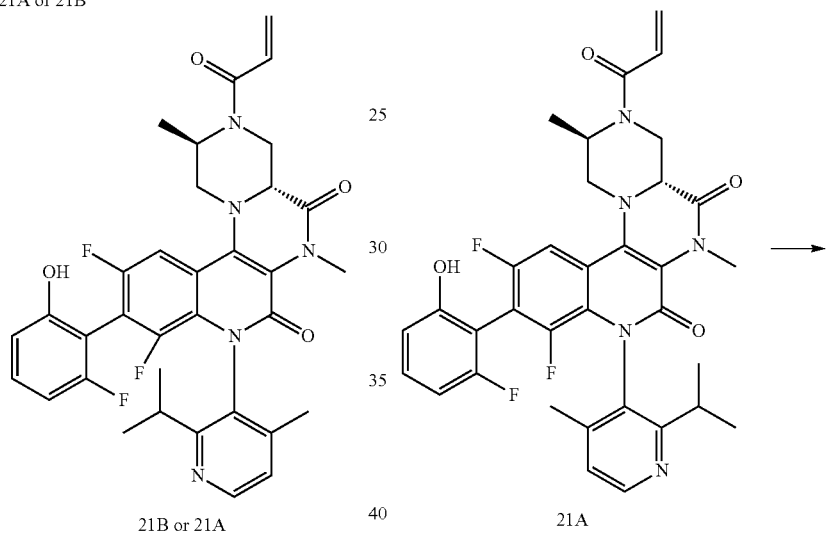

21B or 21A                    21A

Compound 21-4 (100 mg, 151.86 μmol, hydrobromide) was dissolved in tetrahydrofuran (2 mL) and saturated sodium bicarbonate aqueous solution (4.62 g, 55.01 mmol, 2.14 mL), and acrylic anhydride (19.15 mg, 151.86 μmol) was added thereto at room temperature (25° C.). After the addition was completed, the system was stirred at room temperature (25° C.) for 30 min. Methanol (2 mL) and saturated potassium carbonate aqueous solution (2 mL) were added to the system, and the mixture was stirred at room temperature (25° C.) for 1 hour. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 38%-68% 9 min) to obtain compounds 21A and 21B.

Compound 21A:

$^1$H NMR (400 MHz, Methanol-d$_4$) δ 8.45 (d, J=4.9 Hz, 1H), 7.68 (br d, J=8.2 Hz, 1H), 7.31-7.20 (m, 2H), 7.12 (dd, J=10.7, 16.9 Hz, 1H), 6.72-6.60 (m, 2H), 6.30-6.21 (m, 1H), 5.84-5.74 (m, 1H), 4.96-4.92 (m, 1H), 4.75 (br d, J=13.0 Hz, 1H), 4.67-4.48 (m, 1H), 3.91 (br d, J=12.1 Hz, 2H), 3.44 (d, J=3.7 Hz, 3H), 3.03-2.47 (m, 2H), 2.29-1.90 (m, 3H), 1.75-1.62 (m, 3H), 1.26-1.06 (m, 6H).

MS (ESI) m/z (M+H)$^+$=632.2.

Compound 21B:

$^1$H NMR (400 MHz, Methanol-d$_4$) δ 8.45 (d, J=4.9 Hz, 1H), 7.67 (br d, J=8.8 Hz, 1H), 7.30-7.20 (m, 2H), 7.12 (dd, J=10.8, 17.0 Hz, 1H), 6.72-6.59 (m, 2H), 6.31-6.20 (m, 1H), 5.85-5.75 (m, 1H), 4.96-4.92 (m, 1H), 4.75 (br d, J=13.0 Hz, 1H), 4.66-4.44 (m, 1H), 3.91 (br d, J=11.9 Hz, 2H), 3.44 (d, J=4.0 Hz, 3H), 3.03-2.49 (m, 2H), 2.24-1.94 (m, 3H), 1.75-1.63 (m, 3H), 1.23-1.01 (m, 6H).

MS (ESI) m/z (M+H)$^+$=632.3.

Step 6: Separation of Isomer of Compound 21A

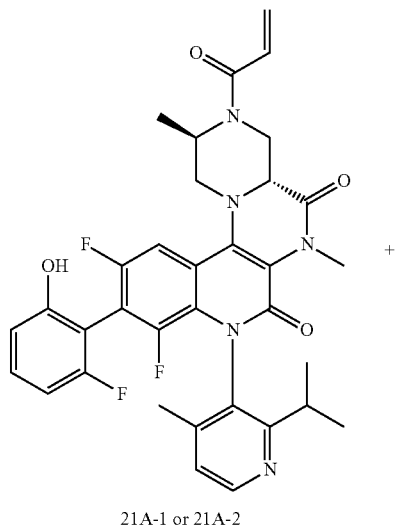

21A-1 or 21A-2

-continued

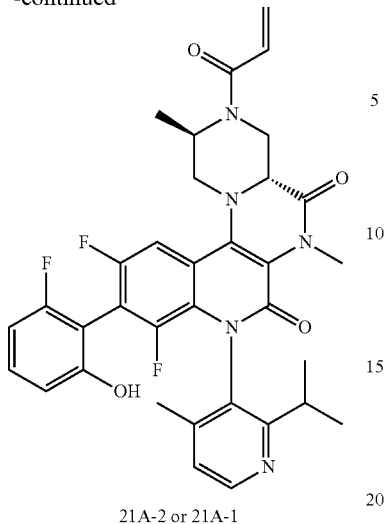

21A-2 or 21A-1

Diastereoisomeric compound 21A was purified by SFC (separation conditions: chromatographic column: Phenomenex-CellµLose-2 (250 mm*30 mm, 10 µm); mobile phase: [0.1% ammonia in methanol]; methanol %: 40%-40%). After concentration, compound 21A-1 and compound 21A-2 were obtained.

Compound 21A-1:

$^1$H NMR (400 MHz, Methanol-$d_4$) δ 8.45 (d, J=5.0 Hz, 1H), 7.71-7.63 (m, 1H), 7.31-7.19 (m, 2H), 7.12 (dd, J=10.7, 16.9 Hz, 1H), 6.72-6.57 (m, 2H), 6.31-6.18 (m, 1H), 5.86-5.74 (m, 1H), 4.98-4.92 (m, 1H), 4.80-4.45 (m, 2H), 4.02-3.86 (m, 2H), 3.53-3.41 (m, 3H), 3.03-2.85 (m, 1H), 2.64-2.48 (m, 1H), 2.20 (s, 3H), 1.74-1.65 (m, 3H), 1.10 (dd, J=6.8, 12.3 Hz, 6H).

MS (ESI) m/z (M+H)$^+$=632.2.

HPLC 92% purity; retention time was 8.18 min.

Separation conditions: chromatographic column WELCH Ultimate LP-C18 150*4.6 mm 5 µm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 90% ee. Retention time was 4.707 min.

Separation conditions: chromatographic column: Cellulose 2 100*4.6 mm I.D., 3 µm; column temperature: 35° C.; mobile phase: $CO_2$-methanol (0.05% DEA); methanol: 5%-40% 4 min, 40% 2.5 min, 5% 1.5 min; flow rate: 2.8 mL/min.

Compound 21A-2:

$^1$H NMR (400 MHz, Methanol-$d_4$) δ 8.44 (d, J=5.0 Hz, 1H), 7.68 (br d, J=8.9 Hz, 1H), 7.29-7.19 (m, 2H), 7.12 (dd, J=10.7, 17.0 Hz, 1H), 6.72-6.60 (m, 2H), 6.31-6.19 (m, 1H), 5.87-5.75 (m, 1H), 4.99-4.94 (m, 1H), 4.80-4.30 (m, 2H), 4.01-3.84 (m, 2H), 3.44 (s, 3H), 3.04-2.88 (m, 2H), 1.99 (s, 3H), 1.72-1.65 (m, 3H), 1.23 (d, J=6.8 Hz, 3H), 1.14 (d, J=6.8 Hz, 3H).

MS (ESI) m/z (M+H)$^+$=632.2.

HPLC 98% purity; retention time was 8.17 min.

Separation conditions: chromatographic column WELCH Ultimate LP-C18 150*4.6 mm 5 µm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 100% ee. Retention time was 5.145 min.

Separation conditions: chromatographic column: Cellulose 2 100*4.6 mm I.D., 3 µm; column temperature: 35° C.; mobile phase: $CO_2$-methanol (0.05% DEA); methanol: 5%-40% 4 min, 40% 2.5 min, 5% 1.5 min; flow rate: 2.8 mL/min.

Step 7: Separation of Isomer of Compound 21B

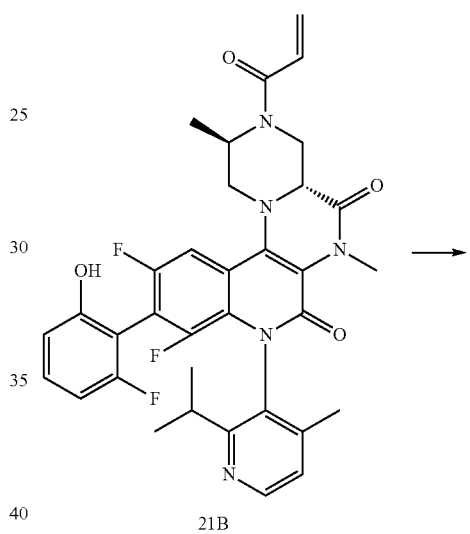

21B

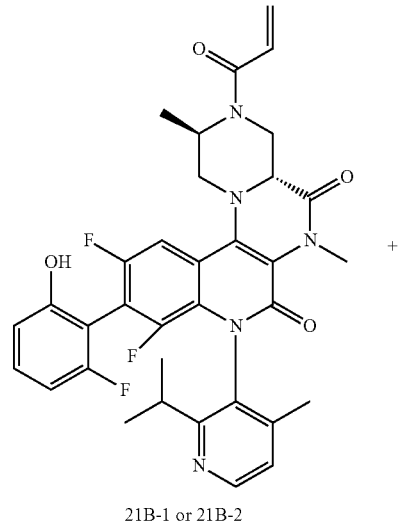

21B-1 or 21B-2

-continued

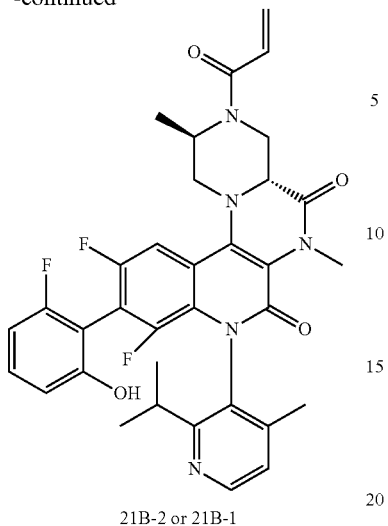

21B-2 or 21B-1

Diastereoisomeric compound 21B was purified by SFC (separation conditions: chromatographic column: DAICEL CHIRALPAK AD-H (250 mm*30 mm, 5 μm); mobile phase: [0.1% ammonia in ethanol]; ethanol %: 35%-35%). After concentration, compound 21B-1 and compound 21B-2 were obtained.

Compound 21B-1:

$^1$H NMR (400 MHz, Methanol-$d_4$) δ 8.44 (d, J=5.0 Hz, 1H), 7.73-7.59 (m, 1H), 7.29-7.19 (m, 2H), 7.12 (dd, J=10.7, 16.8 Hz, 1H), 6.72-6.56 (m, 2H), 6.32-6.17 (m, 1H), 5.87-5.73 (m, 1H), 4.98-4.93 (m, 1H), 4.80-4.38 (m, 2H), 4.00-3.85 (m, 2H), 3.52-3.40 (m, 3H), 3.03-2.87 (m, 2H), 1.98 (s, 3H), 1.75-1.63 (m, 3H), 1.19 (dd, J=6.7, 20.0 Hz, 6H).

MS (ESI) m/z (M+H)$^+$=632.1.

HPLC 99% purity; retention time was 8.38 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 100% ee. Retention time was 4.041 min.

separation conditions: chromatographic column: Chiralpak AD-3 150×4.6 mm I.D., 3 μm; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Compound 21B-2:

$^1$H NMR (400 MHz, Methanol-$d_4$) δ 8.45 (d, J=5.0 Hz, 1H), 7.71-7.63 (m, 1H), 7.31-7.20 (m, 2H), 7.12 (dd, J=10.7, 16.9 Hz, 1H), 6.73-6.59 (m, 2H), 6.30-6.19 (m, 1H), 5.86-5.72 (m, 1H), 4.98-4.92 (m, 1H), 4.80-4.36 (m, 2H), 4.02-3.85 (m, 2H), 3.54-3.41 (m, 3H), 3.02-2.85 (m, 1H), 2.54 (td, J=6.6, 13.4 Hz, 1H), 2.20 (s, 3H), 1.75-1.64 (m, 3H), 1.16-1.00 (m, 6H).

MS (ESI) m/z (M+H)$^+$=632.1.

HPLC 99% purity; retention time was 8.30 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 100% ee. Retention time was 4.707 min separation conditions: chromatographic column: Chiralpak AD-3 150×4.6 mm I.D., 3 μm; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Embodiment 22: Preparation of Compound 22

Step 1: Preparation of Compound 22-1

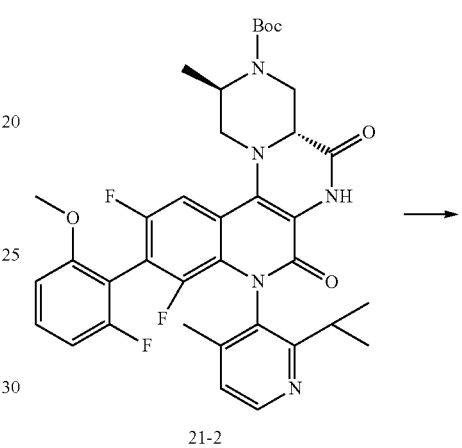

21-2

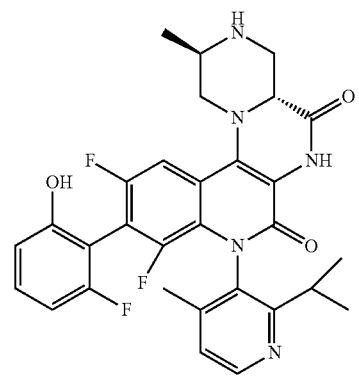

22-1

Compound 21-2 (80 mg, 118.04 μmol) was dissolved in dichloromethane (2 mL) and boron tribromide (147.86 mg, 590.22 μmol, 56.87 μL) was added thereto, and the reaction was stirred at 25° C. for 2 hours. The reaction mixture was quenched with methanol (10 mL), stirred for 10 min, and concentrated under reduced pressure to obtain compound 22-1 (hydrobromide), which was directly used in the next reaction without further purification.

MS (ESI) m/z (M+H)$^+$=564.1.

Step 2: Preparation of Compounds 22A and 22B

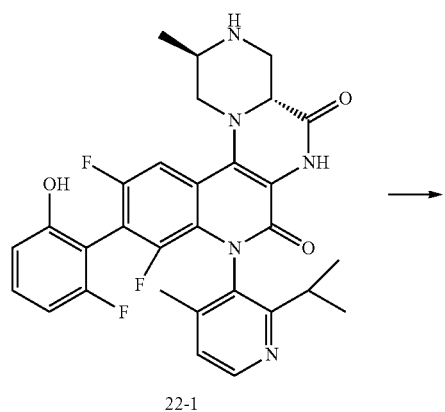

22-1

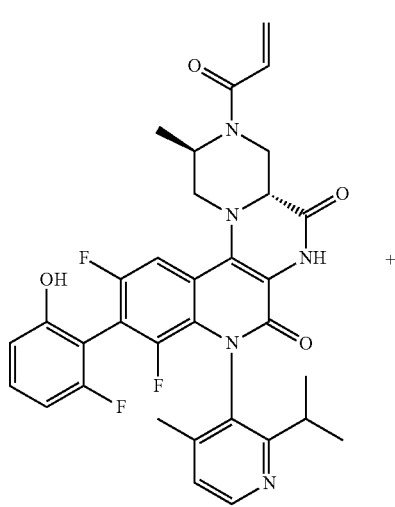

22A or 22B

Compound 22-1 (80 mg, 124.13 μmol, hydrobromide) was dissolved in tetrahydrofuran (2 mL) and saturated sodium bicarbonate aqueous solution (3.78 g, 44.97 mmol, 1.75 mL), and acrylic anhydride (15.65 mg, 124.13 μmol) was added thereto at room temperature (25° C.). After the addition was completed, the system was stirred at room temperature (25° C.) for 30 min. Methanol (2 mL) and saturated potassium carbonate aqueous solution (2 mL) were added to the system, and the mixture was stirred at room temperature (25° C.) for 1 hour. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 37%-67% 9 min) to obtain compounds 22A and 22B.

Compound 22A:

$^1$H NMR (400 MHz, Methanol-$d_4$) δ 8.44 (d, J=5.1 Hz, 1H), 7.63 (br d, J=9.0 Hz, 1H), 7.32-7.17 (m, 2H), 7.09 (br dd, J=10.7, 17.1 Hz, 1H), 6.74-6.57 (m, 2H), 6.29-6.18 (m, 1H), 5.84-5.75 (m, 1H), 4.82-4.46 (m, 3H), 4.13-3.72 (m, 2H), 3.17-2.97 (m, 1H), 2.80-2.67 (m, 1H), 2.09-2.02 (m, 3H), 1.76-1.58 (m, 3H), 1.20-1.05 (m, 6H).

MS (ESI) m/z (M+H)$^+$=618.2.

Compound 22B:

$^1$H NMR (400 MHz, Methanol-$d_4$) δ 8.44 (d, J=5.1 Hz, 1H), 7.63 (br d, J=9.0 Hz, 1H), 7.31-7.21 (m, 2H), 7.10 (dd, J=10.8, 16.8 Hz, 1H), 6.73-6.59 (m, 2H), 6.31-6.18 (m, 1H), 5.88-5.72 (m, 1H), 5.01-4.93 (m, 1H), 4.80 (br d, J=13.9 Hz, 1H), 4.71-4.39 (m, 1H), 4.11-3.77 (m, 2H), 3.03 (br t, J=9.0 Hz, 1H), 2.73 (td, J=6.9, 10.1 Hz, 1H), 2.07 (d, J=13.0 Hz, 3H), 1.74-1.60 (m, 3H), 1.19-1.05 (m, 6H).

MS (ESI) m/z (M+H)$^+$=618.2 & 618.1.

Step 3: Separation of Isomer of Compound 22A

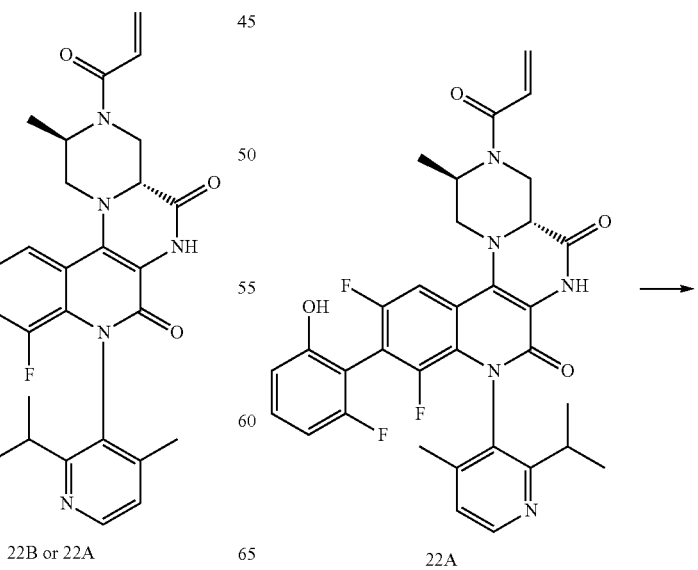

22B or 22A            22A

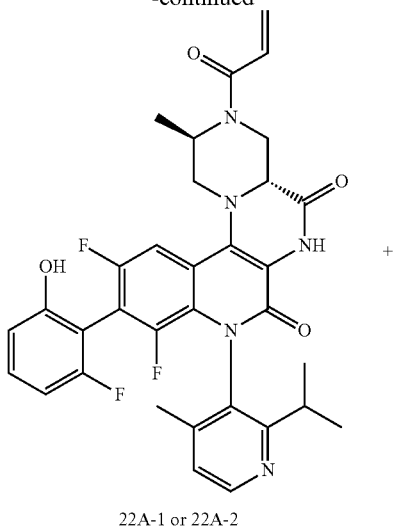

22A-1 or 22A-2

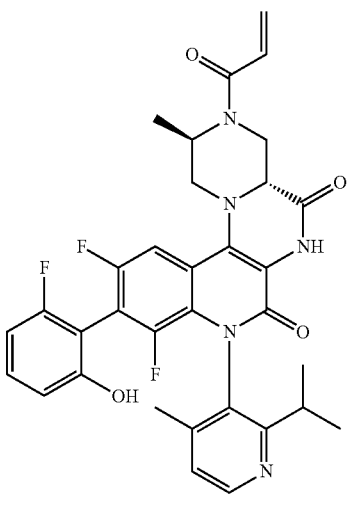

22A-2 or 22A-1

Diastereoisomeric compound 21A was purified by SFC (separation conditions: chromatographic column: DAICEL CHIRALCEL OD-H (250 mm*30 mm, 5 μm); mobile phase: [Neu-ethanol]; ethanol %: 50%-50%). After concentration, compound 22A-1 and compound 22A-2 were obtained.

Compound 22A-1:

$^1$H NMR (400 MHz, Methanol-$d_4$) δ 8.44 (d, J=5.1 Hz, 1H), 7.63 (br d, J=9.0 Hz, 1H), 7.30-7.20 (m, 2H), 7.09 (dd, J=10.8, 17.0 Hz, 1H), 6.73-6.60 (m, 2H), 6.31-6.18 (m, 1H), 5.87-5.72 (m, 1H), 4.93 (br s, 1H), 4.83-4.75 (m, 1H), 4.66-4.46 (m, 1H), 4.08-3.83 (m, 2H), 3.17-3.00 (m, 1H), 2.83-2.68 (m, 1H), 2.07 (s, 3H), 1.74-1.63 (m, 3H), 1.18 (d, J=6.8 Hz, 3H), 1.09 (d, J=6.8 Hz, 3H).

MS (ESI) m/z (M+H)$^+$=618.1.

HPLC 100% purity; retention time was 7.85 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC 100% ee. Retention time was 4.917 min.

separation conditions: chromatographic column: Chiralcel OD-3 100*4.6 mm I.D., 3 μm; column temperature: 35° C.; mobile phase: CO$_2$-ethanol (0.05% DEA); ethanol: 5%-40% 4 min, 40% 2.5 min, 5% 1.5 min; flow rate: 2.8 mL/min.

Compound 22A-2:

$^1$H NMR (400 MHz, Methanol-$d_4$) δ 8.44 (d, J=5.1 Hz, 1H), 7.73-7.57 (m, 1H), 7.33-7.19 (m, 2H), 7.10 (dd, J=10.7, 17.1 Hz, 1H), 6.71-6.57 (m, 2H), 6.32-6.17 (m, 1H), 5.88-5.73 (m, 1H), 4.99 (br s, 1H), 4.83-4.50 (m, 2H), 4.10-3.84 (m, 2H), 3.14-2.98 (m, 1H), 2.78-2.67 (m, 1H), 2.09 (s, 3H), 1.76-1.63 (m, 3H), 1.14 (dd, J=6.8, 9.9 Hz, 6H).

MS (ESI) m/z (M+H)$^+$=618.1.

HPLC 99.3% purity; retention time was 7.91 min.

Separation conditions: chromatographic column WELCH MLtimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 98.5% ee. Retention time was 5.310 min.

separation conditions: chromatographic column: Chiralcel OD-3 100*4.6 mm I.D., 3 μm; column temperature: 35° C.; mobile phase: CO$_2$-ethanol (0.05% DEA); ethanol: 5%-40% 4 min, 40% 2.5 min, 5% 1.5 min; flow rate: 2.8 mL/min.

Step 4: Separation of Isomer of Compound 22B

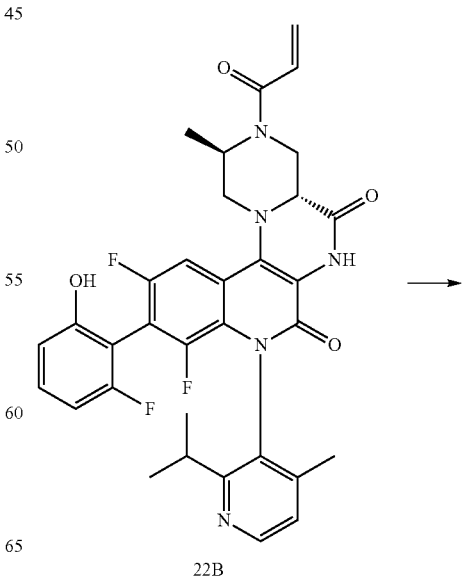

22B

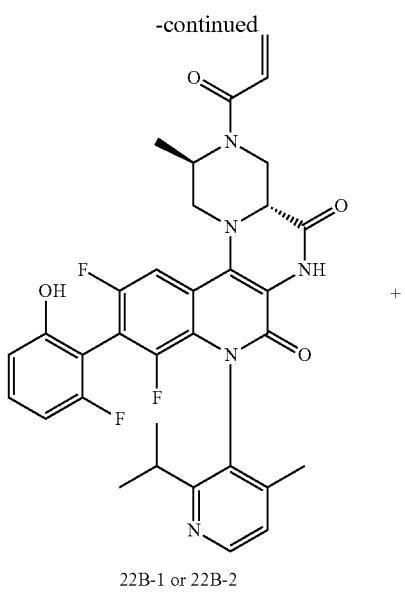

22B-1 or 22B-2

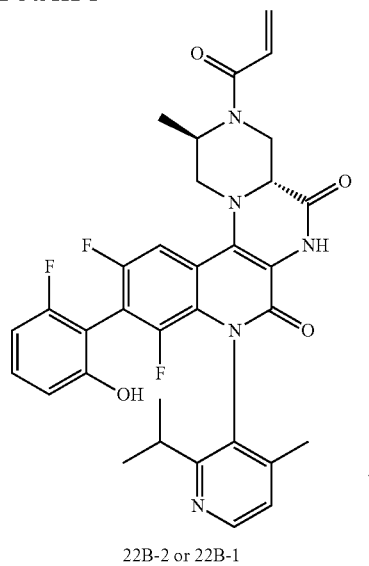

22B-2 or 22B-1

Diastereoisomeric compound 21A was purified by SFC (separation conditions: chromatographic column: DAICEL CHIRALCEL OD-H (250 mm*30 mm, 5 μm); mobile phase: [Neu-methanol]; methanol %: 40%-40%). After concentration, compound 22B-1 and compound 22B-2 were obtained.

Compound 22B-1:

$^1$H NMR (400 MHz, Methanol-d$_4$) δ 8.44 (d, J=5.1 Hz, 1H), 7.63 (br d, J=9.0 Hz, 1H), 7.28-7.18 (m, 2H), 7.09 (dd, J=10.7, 17.1 Hz, 1H), 6.70-6.61 (m, 2H), 6.29-6.17 (m, 1H), 5.83-5.74 (m, 1H), 4.97-4.92 (m, 1H), 4.78 (br s, 1H), 4.64-4.48 (m, 1H), 4.06-3.85 (m, 2H), 3.14-2.98 (m, 1H), 2.81-2.64 (m, 1H), 2.06 (s, 3H), 1.74-1.65 (m, 3H), 1.15 (dd, J=6.8, 18.3 Hz, 6H).

MS (ESI) m/z (M+H)$^+$=618.1.

HPLC 93.6% purity; retention time was 8.14 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC 100% ee. Retention time was 3.589 min.

separation conditions: chromatographic column: Chiralcel OD-3 100*4.6 mm I.D., 3 μm; column temperature: 35° C.; mobile phase: CO$_2$-methanol (0.05% DEA); methanol: 40%-40%; flow rate: 2.8 mL/min.

Compound 22B-2:

$^1$H NMR (400 MHz, Methanol-d$_4$) δ 8.44 (d, J=5.1 Hz, 1H), 7.63 (br d, J=8.8 Hz, 1H), 7.28-7.19 (m, 2H), 7.09 (dd, J=10.7, 17.1 Hz, 1H), 6.72-6.58 (m, 2H), 6.29-6.18 (m, 1H), 5.83-5.73 (m, 1H), 4.99-4.91 (m, 1H), 4.78 (br s, 1H), 4.67-4.42 (m, 1H), 4.09-3.86 (m, 2H), 3.14-2.97 (m, 1H), 2.80-2.62 (m, 1H), 2.19-2.05 (m, 3H), 1.75-1.64 (m, 3H), 1.16 (br d, J=6.8 Hz, 3H), 1.08 (d, J=6.8 Hz, 3H).

MS (ESI) m/z (M+H)$^+$=618.1.

HPLC 99.3% purity; retention time was 8.12 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC 97.8% ee. Retention time was 4.079 min.

separation conditions: chromatographic column: Chiralcel OD-3 100*4.6 mm I.D., 3 μm; column temperature: 35° C.; mobile phase: CO$_2$-methanol (0.05% DEA); methanol: 40%-40%; flow rate: 2.8 mL/min.

Embodiment 23: Preparation of Compound 23

Step 1: Preparation of Compound 23-1

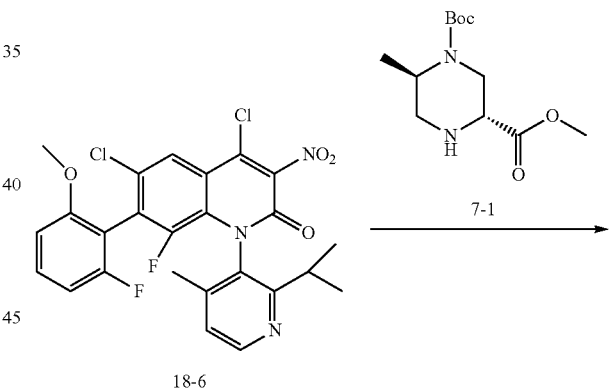

18-6

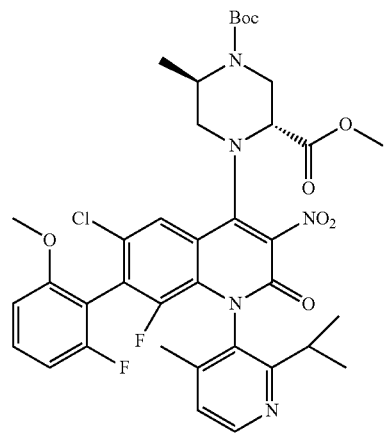

23-1

Under the protection of nitrogen, compound 18-6 (450 mg, 842.16 μmol) was dissolved in acetonitrile (8 mL), diisopropylethylamine (545.29 mg, 4.22 mmol, 734.90 μL) and compound JMKX-1805-Inter 5A (326.31 mg, 1.26 mmol) were added thereto successively, and the reaction was heated to 80° C. and stirred for 12 hours. The reaction was concentrated under reduced pressure, and the crude product was purified by silica gel column chromatography (petroleum ether/ethyl acetate (v/v)=1/0-0/1) to obtain compound 23-1.

MS (ESI) m/z (M+H)$^+$=756.2.

Step 2: Preparation of Compound 23-2

Step 3: Preparation of Compound 23-3

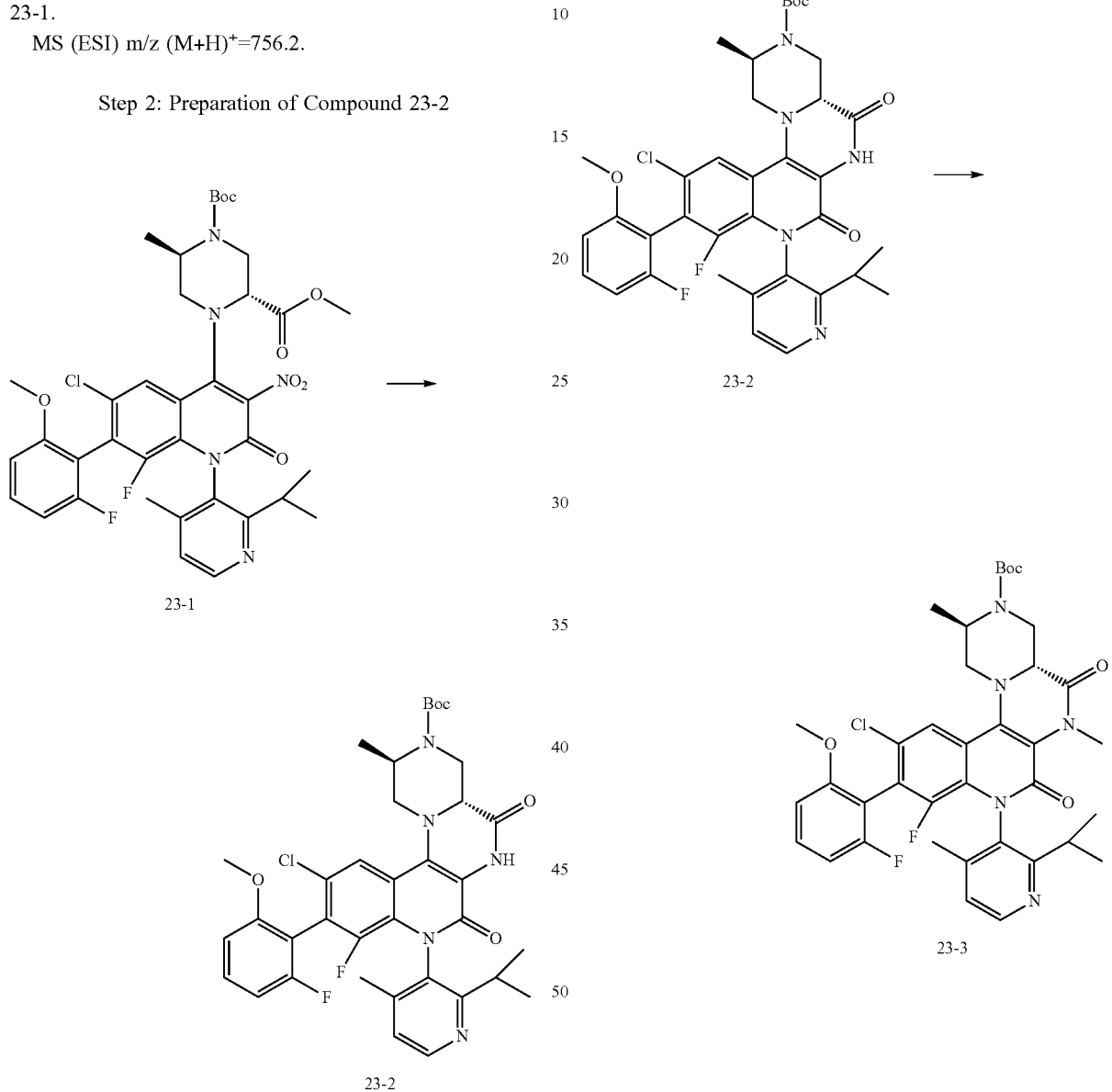

Compound 23-1 (200 mg, 264.48 μmol) and iron powder (59.23 mg, 1.06 mmol) were dissolved in acetic acid (5 mL), under nitrogen atmosphere, the system was heated to 80° C. and stirred for 45 min. The system was concentrated, diluted with dichloromethane (20 mL), filtered, the filtrate was washed with saturated sodium bicarbonate aqueous solution, dried over anhydrous sodium sulfate, filtered, and the filtrate was concentrated to obtain compound 23-2, which was directly used for the next reaction without further purification.

MS (ESI) m/z (M+H)$^+$=694.1.

Compound 23-2 (150 mg, 216.09 μmol) and potassium carbonate (80.94 mg, 585.60 μmol) were dissolved in acetone (2 mL), and methyl iodide (414.06 mg, 2.92 mmol, 181.61 μL) was added at room temperature (25° C.). After the addition was completed, under nitrogen atmosphere, the system was heated to 40° C. and stirred for 16 hours. The system was concentrated, dichloromethane (10 mL) and water (10 mL) were added for separation and extraction, the organic phase was dried over anhydrous sodium sulfate, filtered, and the filtrate was concentrated to obtain compound 23-3, which was directly used in the next reaction without further purification.

MS (ESI) m/z (M+H)$^+$=708.1.

Step 4: Preparation of Compound 23-4

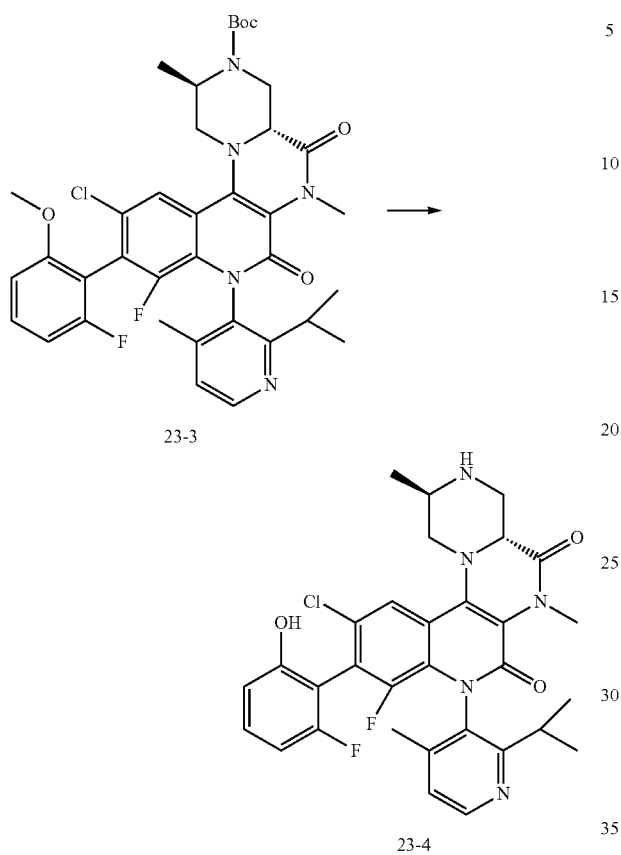

Compound 23-3 (110 mg, 155.33 μmol) was dissolved in dichloromethane (2 mL), and boron tribromide (1 M, 776.63 μL) was added thereto, and the reaction was stirred at 20° C. for 2 hours. The reaction mixture was quenched with methanol (5 mL), stirred for 10 min, and concentrated under reduced pressure to obtain compound 23-4 (hydrobromide), which was directly used in the next reaction without further purification.

MS (ESI) m/z (M+H)$^+$=594.1.

Step 5: Preparation of Compounds 23A and 23B

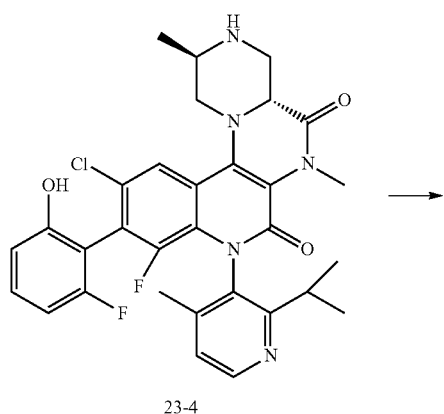

Compound 23-4 (130 mg, 153.92 μmol, hydrobromide) was dissolved in tetrahydrofuran (5 mL) and saturated sodium bicarbonate aqueous solution (4.32 g, 51.42 mmol, 2 mL), and acrylic anhydride (19.41 mg, 153.92 μmol) was added thereto at room temperature (25° C.). After the addition was completed, the system was stirred at room temperature (25° C.) for 30 min. Methanol (2 mL) and saturated potassium carbonate aqueous solution (2 mL) were added to the system, and the mixture was stirred at room temperature (25° C.) for 1 hour. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate aqueous solution)-acetonitrile]; acetonitrile %: 44%-74% 9 min) to obtain compounds 23A and 23B.

Compound 23A:

$^1$H NMR (400 MHz, Methanol-d$_4$) δ 8.44 (d, J=4.8 Hz, 1H), 8.02 (s, 1H), 7.30-7.07 (m, 3H), 6.72-6.57 (m, 2H), 6.32-6.19 (m, 1H), 5.86-5.75 (m, 1H), 4.98-4.94 (m, 1H), 4.80-4.48 (m, 2H), 4.01-3.84 (m, 2H), 3.44 (d, J=3.8 Hz, 3H), 3.02-2.89 (m, 1H), 2.62-2.47 (m, 1H), 2.22-1.97 (m, 3H), 1.77-1.62 (m, 3H), 1.25-1.04 (m, 6H). MS (ESI) m/z (M+H)$^+$=648.1.

Compound 23B:

¹H NMR (400 MHz, Methanol-d₄) δ 8.44 (d, J=5.0 Hz, 1H), 8.02 (s, 1H), 7.31-7.06 (m, 3H), 6.74-6.57 (m, 2H), 6.30-6.20 (m, 1H), 5.86-5.76 (m, 1H), 4.98-4.94 (m, 1H), 4.76 (br d, J=13.3 Hz, 2H), 4.03-3.87 (m, 2H), 3.44 (d, J=3.8 Hz, 3H), 3.00-2.88 (m, 1H), 2.59-2.49 (m, 1H), 2.25-1.93 (m, 3H), 1.75-1.64 (m, 3H), 1.24-1.00 (m, 6H). MS (ESI) m/z (M+H)⁺=648.1.

Step 6: Separation of Isomer of Compound 23A

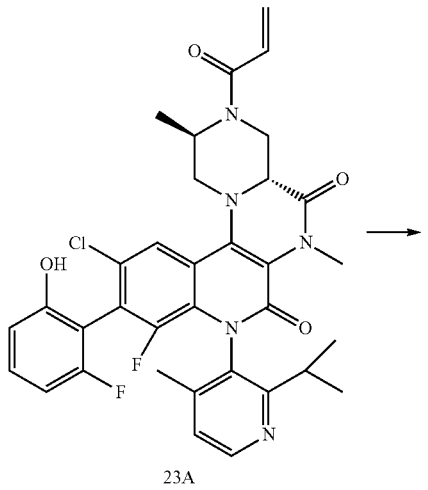

23A

→

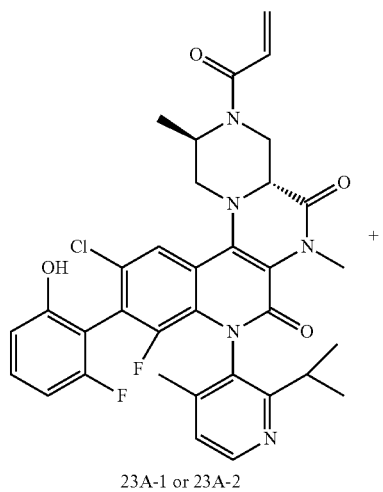

23A-1 or 23A-2

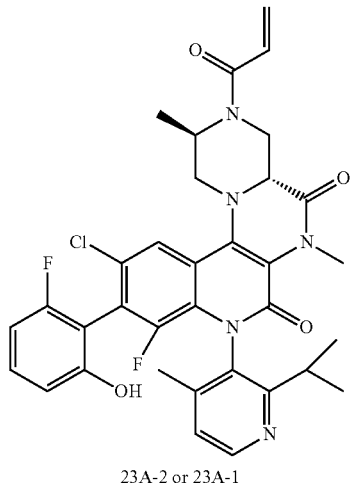

23A-2 or 23A-1

Diastereoisomeric compound 23A was purified by SFC (separation conditions: chromatographic column: DAICEL CHIRALCEL OJ H (250 mm*30 mm, 5 μm); mobile phase: [0.1% ammonia in isopropanol]; isopropanol %: 35%-35%). After concentration, compounds 23A-1 (2.46 mg, yield 12.30%) and 23A-2 (4.07 mg, yield 20.35%) were obtained.

Compound 23A-1:

¹H NMR (400 MHz, Acetonitrile-d₃) δ 8.45 (d, J=4.9 Hz, 1H), 8.01-7.96 (m, 1H), 7.28 (dt, J=6.9, 8.3 Hz, 1H), 7.18 (d, J=4.9 Hz, 1H), 7.02 (dd, J=10.6, 16.9 Hz, 1H), 6.77-6.69 (m, 2H), 6.26-6.15 (m, 1H), 5.79-5.67 (m, 1H), 4.89 (br s, 1H), 4.69-4.31 (m, 1H), 3.90-3.74 (m, 2H), 3.39 (s, 3H), 3.20 (br d, J=12.3 Hz, 1H), 3.01-2.80 (m, 1H), 2.59 (td, J=6.6, 13.3 Hz, 1H), 2.14 (s, 3H), 1.67-1.58 (m, 3H), 1.06 (d, J=6.7 Hz, 3H), 1.01 (d, J=6.8 Hz, 3H).

MS (ESI) m/z (M+H)⁺=648.2.

SFC retention time was 2.544 min separation conditions: chromatographic column: Chiralcel OJ-3 100 mm×4.6 mm I.D., 3 μm; column temperature: 35° C.; mobile phase: CO₂-ethanol (0.05% DEA); ethanol: 5%-40% 4 min, 40% 2.5 min, 5% 1.5 min; flow rate: 2.8 mL/min.

Compound 23A-2:

¹H NMR (400 MHz, Methanol-d₄) δ 8.48 (d, J=5.2 Hz, 1H), 8.02 (d, J=1.4 Hz, 1H), 7.37 (br d, J=5.1 Hz, 1H), 7.23 (dt, J=6.8, 8.3 Hz, 1H), 7.11 (dd, J=10.8, 17.0 Hz, 1H), 6.73-6.59 (m, 2H), 6.31-6.18 (m, 1H), 5.86-5.73 (m, 1H), 4.99-4.93 (m, 1H), 4.75 (br d, J=13.0 Hz, 2H), 3.98-3.84 (m, 2H), 3.43 (s, 3H), 3.14-2.86 (m, 2H), 2.04 (s, 3H), 1.76-1.63 (m, 3H), 1.25 (d, J=6.8 Hz, 3H), 1.15 (d, J=6.8 Hz, 3H).

MS (ESI) m/z (M+H)⁺=648.2.

SFC retention time was 2.670 min.

separation conditions: chromatographic column: Chiralcel OJ-3 100 mm×4.6 mm I.D., 3 μm; column temperature: 35° C.; mobile phase: CO₂-ethanol (0.05% DEA); ethanol: 5%-40% 4 min, 40% 2.5 min, 5% 1.5 min; flow rate: 2.8 mL/min.

Step 7: Separation of Isomer of Compound 23B

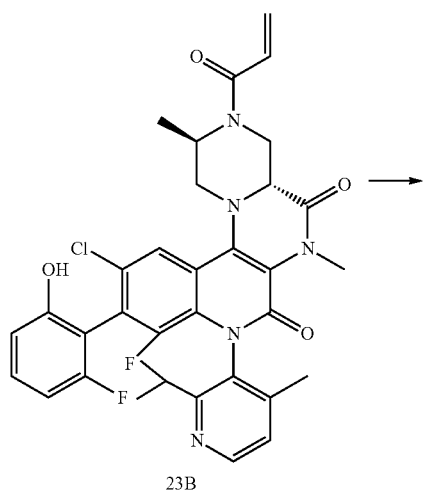

23B

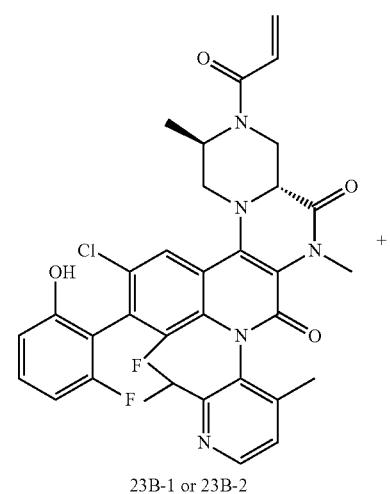

23B-1 or 23B-2

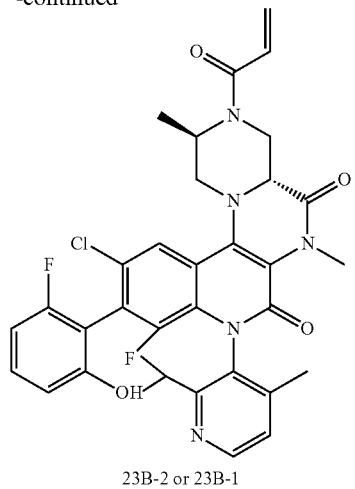

23B-2 or 23B-1

Diastereoisomeric compound 23B was purified by SFC (separation conditions: chromatographic column: REGIS (s,s) WHELK-O1 (250 mm*30 mm, 5 μm); mobile phase: [0.1% ammonia in ethanol]; ethanol %: 40%-40%). After concentration, compound 23B-1 and compound 23B-2 were obtained.

Compound 23B-1:

$^1$H NMR (400 MHz, Acetonitrile-$d_3$) δ 8.43 (d, J=4.9 Hz, 1H), 8.00-7.93 (m, 1H), 7.31-7.22 (m, 1H), 7.12 (d, J=4.9 Hz, 1H), 7.01 (dd, J=10.6, 16.9 Hz, 1H), 6.77-6.66 (m, 2H), 6.25-6.13 (m, 1H), 5.78-5.65 (m, 1H), 4.87 (br s, 1H), 4.67-4.31 (m, 1H), 3.83-3.66 (m, 2H), 3.40-3.32 (m, 3H), 3.21 (d, J=11.2 Hz, 1H), 3.01-2.81 (m, 2H), 2.10 (br s, 3H), 1.66-1.54 (m, 3H), 1.12 (d, J=6.7 Hz, 3H), 1.07 (d, J=6.7 Hz, 3H).

MS (ESI) m/z (M+H)$^+$=648.2.

SFC retention time was 5.051 min separation conditions: chromatographic column: (S,S)-Whelk-O1 100 mm×4.6 mm I.D., 3 μm; column temperature: 35° C.; mobile phase: $CO_2$-ethanol (0.05% DEA); ethanol: 5%-40% 4 min, 40% 2.5 min, 5% 1.5 min; flow rate: 2.8 mL/min.

Compound 23B-2:

$^1$H NMR (400 MHz, Acetonitrile-$d_3$) δ 8.46 (d, J=4.9 Hz, 1H), 8.02-7.95 (m, 1H), 7.34-7.24 (m, 1H), 7.20 (d, J=4.9 Hz, 1H), 7.02 (dd, J=10.6, 16.8 Hz, 1H), 6.78 (d, J=8.3 Hz, 1H), 6.75-6.66 (m, 1H), 6.27-6.14 (m, 1H), 5.79-5.67 (m, 1H), 4.89 (br s, 1H), 4.65 (d, J=13.6 Hz, 1H), 3.90-3.74 (m, 2H), 3.44-3.34 (m, 3H), 3.20 (br d, J=12.2 Hz, 1H), 3.04-2.80 (m, 1H), 2.57 (td, J=6.6, 13.3 Hz, 1H), 2.16 (s, 3H), 1.68-1.58 (m, 3H), 1.06 (d, J=6.7 Hz, 3H), 0.97 (d, J=6.7 Hz, 3H).

MS (ESI) m/z (M+H)$^+$=648.2.

SFC retention time was 5.618 min separation conditions: chromatographic column: (S,S)-Whelk-O1 100 mm×4.6 mm I.D., 3 μm; column temperature: 35° C.; mobile phase: $CO_2$-ethanol (0.05% DEA); ethanol: 5%-40% 4 min, 40% 2.5 min, 5% 1.5 min; flow rate: 2.8 mL/min.

Embodiment 24: Preparation of Compound 24

Step 1: Preparation of Compound 24-1

Step 2: Preparation of Compound 24-2

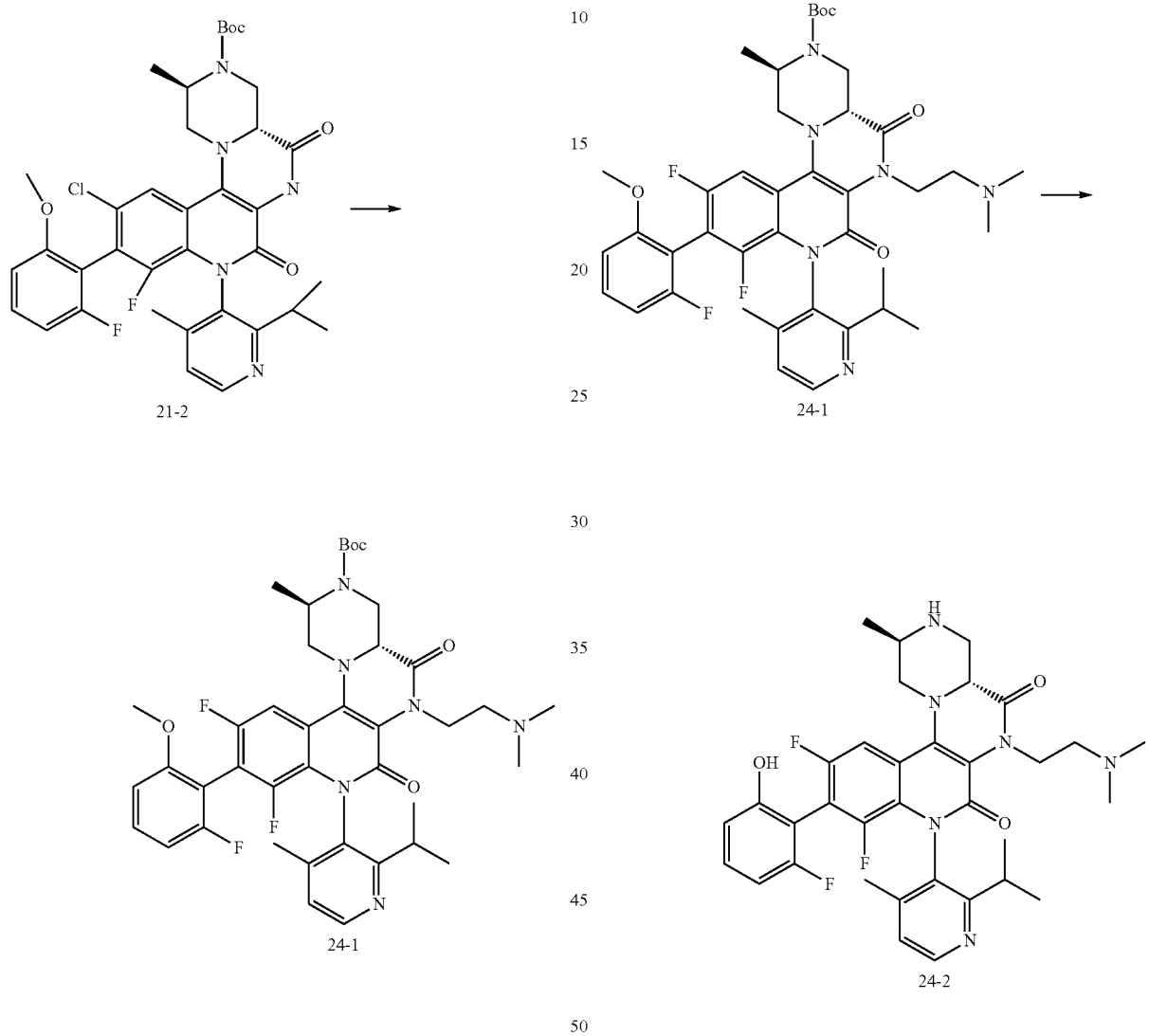

Compound 21-2 (100 mg, 147.56 μmol) and potassium carbonate (123 mg, 889.98 μmol) were dissolved in N,N-dimethylformamide (3 mL), and 2-bromo-N,N-dimethylamine (100 mg, 429 μmol, HBr) and potassium iodide (25 mg, 150.60 μmol) were added thereto at room temperature (25° C.). After the addition was completed, the system was heated to 100° C. and stirred for 16 hours. The system was diluted with ethyl acetate (30 mL), washed with water (20 mL) and saturated saline (20 mL) successively, the organic phase was dried over anhydrous sodium sulfate, filtered, and the filtrate was concentrated to obtain a crude product, the crude product was purified by silica gel column chromatography (dichloromethane/methanol (v/v)=1/15) to obtain compound 24-1.

MS (ESI) m/z (M+H)$^+$=749.4.

Compound 24-1 (45 mg, 60.09 μmol) was dissolved in dichloromethane (2 mL), and boron tribromide (1 M, 1 μL) was added thereto, under nitrogen atmosphere, the reaction was stirred at room temperature (20° C.) for 8 hours. The reaction mixture was quenched with methanol (5 mL), stirred for 10 min, and concentrated under reduced pressure to obtain compound 24-2 (hydrobromide), which was directly used in the next reaction without further purification.

MS (ESI) m/z (M+H)$^+$=635.2.

Step 3: Preparation of Compounds 24A, 24B, 24C and 24D

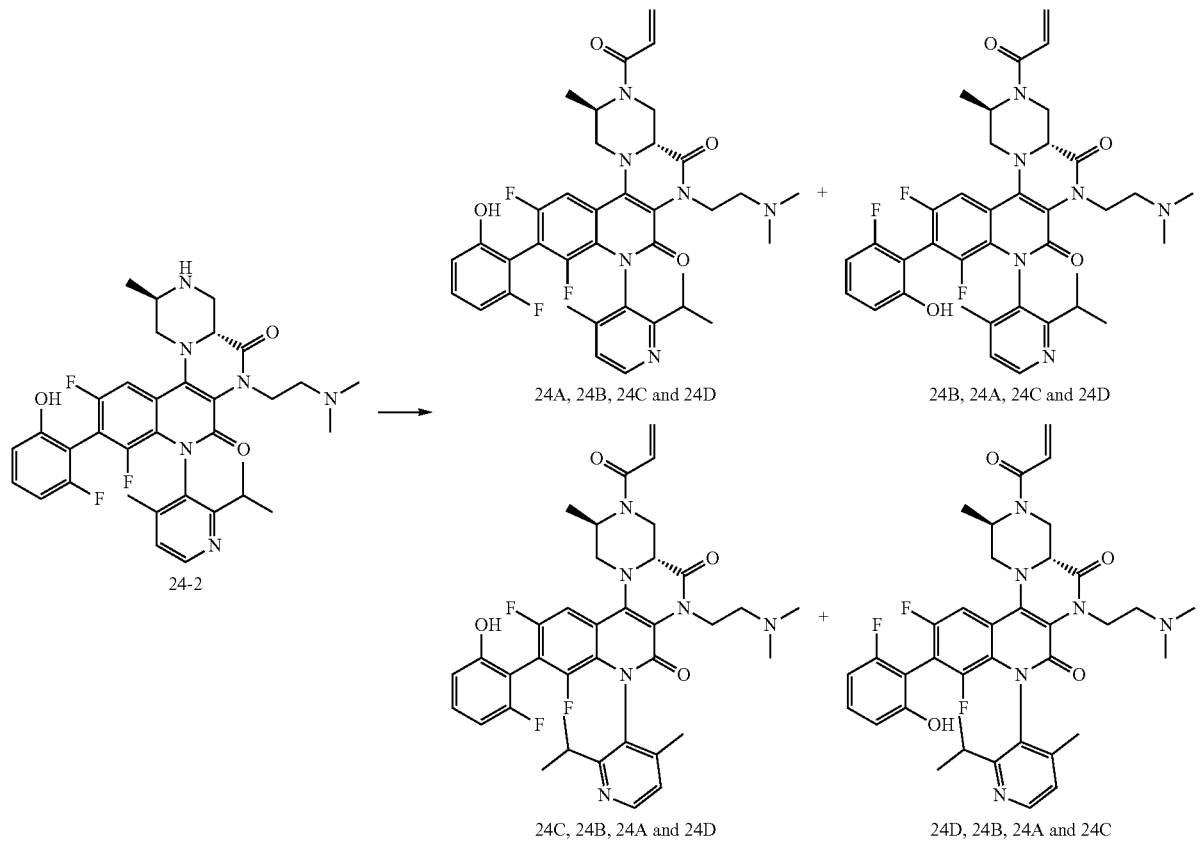

24A, 24B, 24C and 24D 24B, 24A, 24C and 24D 24C, 24B, 24A and 24D 24D, 24B, 24A and 24C Compound 24-2 (45 mg, 62.88 μmol, hydrobromide) was dissolved in tetrahydrofuran (2 mL) and saturated sodium bicarbonate aqueous solution (2.16 g, 25.71 mmol, 1 mL), and tetrahydrofuran (0.5 mL) solution of acrylic anhydride (15 mg, 118.94 μmol) was added thereto at room temperature (25° C.). After the addition was completed, the system was stirred at room temperature (25° C.) for 2 hours. Methanol (1 mL) and saturated potassium carbonate aqueous solution (2 M, 1 mL) were added to the system, and the mixture was stirred at room temperature (25° C.) for 1.5 hours. The system was diluted with water (10 mL), the pH was adjusted to 7 with 1 N HCl; and the mixture was extracted with ethyl acetate (20 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate aqueous solution)-acetonitrile]; acetonitrile %: 40%-70% 9 min) and then purified by SFC (separation conditions: chromatographic column: DAICEL CHIRALCEL OD (250 mm*30 mm, 10 μm); mobile phase: [0.1% ammonia in isopropanol]; isopropanol %: 25%-25% and DAICEL CHIRALPAK AD-H (250 mm*30 mm, 5 μm); mobile phase: [0.1% ammonia in ethanol]; ethanol %: 25%-25%). After concentration, compound 24A, 24B, 24C and 24D were obtained.

Compound 24A:

$^1$H NMR (400 MHz, Methanol-$d_4$) δ 8.46 (d, J=5.0 Hz, 1H), 7.74-7.63 (m, 1H), 7.32-7.21 (m, 2H), 7.11 (dd, J=10.8, 16.8 Hz, 1H), 6.74-6.59 (m, 2H), 6.24 (d, J=15.1 Hz, 1H), 5.81 (br d, J=10.8 Hz, 1H), 5.01-4.94 (m, 1H), 4.75 (d, J=12.5 Hz, 1H), 4.64-4.46 (m, 1H), 4.40-4.24 (m, 1H), 4.13 (br s, 1H), 4.05-3.88 (m, 2H), 3.37 (s, 2H), 3.03 (br d, J=14.6 Hz, 1H), 2.83-2.49 (m, 7H), 2.21 (s, 3H), 1.78-1.67 (m, 3H), 1.13 (d, J=6.8 Hz, 3H), 1.03 (d, J=6.5 Hz, 3H).

MS (ESI) m/z (M+H)$^+$=689.2.

SFC retention time was 3.949 min.

Separation conditions: chromatographic column: Chiralpak AD-3 150 mm×4.6 mm 4.6 mm I.D., 3 μm; column temperature: 35° C.; mobile phase: $CO_2$-isopropanol (0.05% DEA); ethanol: 5%-40% 5 min, 40%-5% 0.5 min, 5% 1.5 min; flow rate: 2.5 mL/min.

Compound 24B:

$^1$H NMR (400 MHz, Methanol-$d_4$) δ 8.35 (d, J=5.1 Hz, 1H), 7.59 (br d, J=9.3 Hz, 1H), 7.21-7.10 (m, 2H), 7.03 (dd, J=10.8, 17.0 Hz, 1H), 6.60-6.47 (m, 2H), 6.21-6.06 (m, 1H), 5.71 (br d, J=11.0 Hz, 1H), 4.88-4.85 (m, 1H), 4.65 (br d, J=13.9 Hz, 1H), 4.51 (s, 1H), 4.22 (br dd, J=7.8, 15.8 Hz, 2H), 3.90-3.75 (m, 2H), 3.04 (br d, J=8.8 Hz, 1H), 2.63-2.35 (m, 3H), 2.20-2.06 (m, 9H), 1.65-1.56 (m, 3H), 1.00 (dd, J=6.8, 15.0 Hz, 6H).

MS (ESI) m/z (M+H)$^+$=689.4.

SFC retention time was 3.389 min.

Separation conditions: chromatographic column: Chiralpak AD-3 150 mm×4.6 mm 4.6 mm I.D., 3 μm; column Compound 24C:

¹H NMR (400 MHz, Methanol-d₄) δ 8.45 (d, J=5.0 Hz, 1H), 7.70 (br d, J=9.3 Hz, 1H), 7.30-7.21 (m, 2H), 7.13 (dd, J=10.7, 16.9 Hz, 1H), 6.75-6.60 (m, 2H), 6.23 (d, J=15.1 Hz, 1H), 5.81 (br d, J=12.3 Hz, 1H), 4.95 (br s, 1H), 4.74 (br d, J=12.5 Hz, 1H), 4.61 (s, 1H), 4.30 (br d, J=6.8 Hz, 2H), 4.00-3.85 (m, 2H), 3.24-3.12 (m, 1H), 3.01-2.89 (m, 1H), 2.71 (br s, 1H), 2.60 (br s, 1H), 2.40-2.24 (m, 6H), 1.99 (s, 3H), 1.74-1.66 (m, 3H), 1.24 (d, J=6.8 Hz, 3H), 1.13 (d, J=6.5 Hz, 3H).

MS (ESI) m/z (M+H)⁺=689.4.

SFC retention time was 3.917 min.

Separation conditions: chromatographic column: Chiralpak AD-3 150 mm×4.6 mm 4.6 mm I.D., 3 μm; column temperature: 35° C.; mobile phase: CO₂-isopropanol (0.05% DEA); ethanol: 5%-40% 5 min, 40%-5% 0.5 min, 5% 1.5 min; flow rate: 2.5 mL/min.

Compound 24D:

¹H NMR (400 MHz, Methanol-d₄) δ 8.43 (d, J=4.9 Hz, 1H), 7.68 (br d, J=7.7 Hz, 1H), 7.29-7.17 (m, 2H), 7.11 (br dd, J=10.5, 16.9 Hz, 1H), 6.71-6.58 (m, 2H), 6.28-6.14 (m, 1H), 5.79 (br d, J=10.8 Hz, 1H), 4.97-4.93 (m, 1H), 4.72 (br d, J=12.3 Hz, 1H), 4.59 (s, 1H), 4.28 (br t, J=6.5 Hz, 2H), 4.01-3.84 (m, 2H), 3.21-3.08 (m, 1H), 2.98-2.87 (m, 1H), 2.64 (br s, 1H), 2.52 (br s, 1H), 2.35-2.14 (m, 6H), 1.96 (s, 3H), 1.72-1.62 (m, 3H), 1.21 (br d, J=6.8 Hz, 3H), 1.14 (br d, J=6.6 Hz, 3H).

MS (ESI) m/z (M+H)⁺=689.4.

SFC retention time was 4.278 min.

Separation conditions: chromatographic column: Chiralpak AD-3 150 mm×4.6 mm 4.6 mm I.D., 3 μm; column temperature: 35° C.; mobile phase: CO₂-isopropanol (0.05% DEA); ethanol: 5%-40% 5 min, 40%-5% 0.5 min, 5% 1.5 min; flow rate: 2.5 mL/min.

Embodiment 25: Preparation of Compounds 25A and 25B

Step 1: Preparation of Compound 25-1

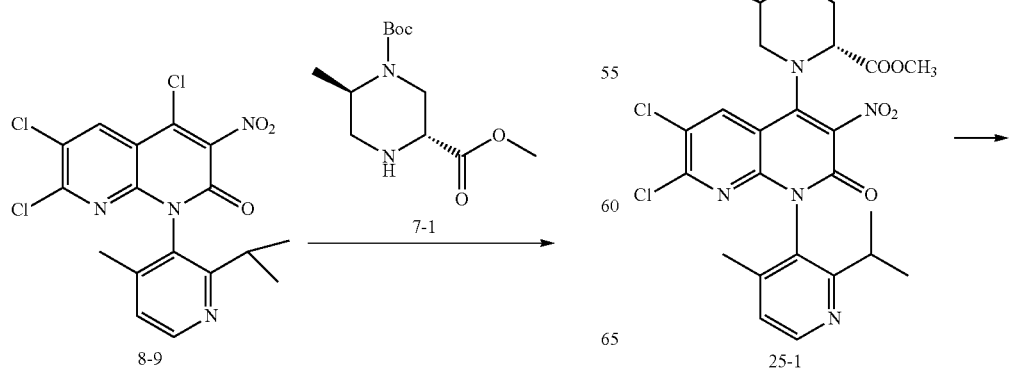

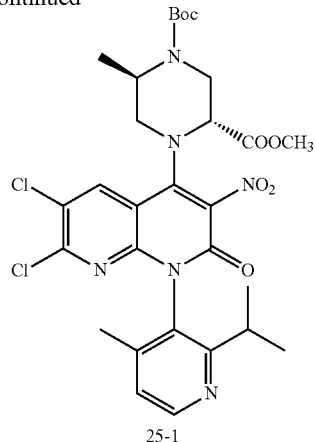

Compound 8-9 (426 mg, 1.0 mmol), compound 7-1 (286 mg, 1.1 mmol), N,N-diisopropylethylamine (0.2 mL) were dissolved in acetonitrile (10 mL), and the system was heated to 100° C. and stirred for 4 hours. The system was concentrated to obtain a crude product. The crude product was purified by medium pressure column chromatography (ethyl acetate/petroleum ether (v/v)=0-35%) to obtain compound 25-1.

MS (ESI) m/z (M+H)⁺=649.0.

Step 2: Preparation of Compound 25-2

-continued

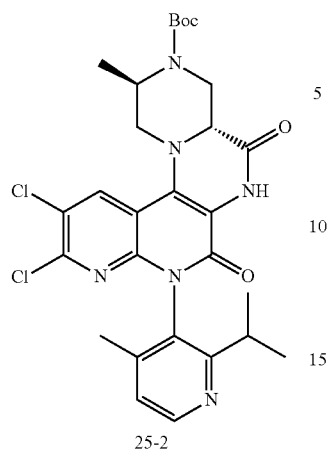

25-2

-continued

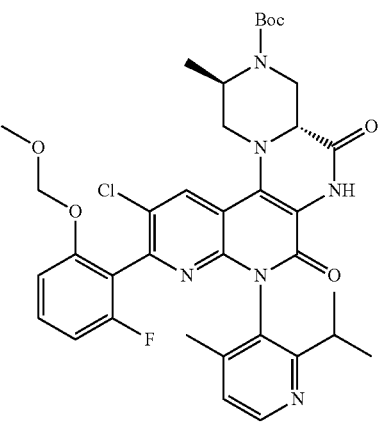

25-3

Compound 25-1 (326 mg, 0.502 mmol) and iron powder (200 mg, 3.6 mmol) were dissolved in acetic acid (15 mL), and the system was heated to 85° C. and stirred for 1 hour under nitrogen atmosphere. The system was filtered with diatomite, the filtrate was concentrated, the residue was dissolved in ethyl acetate, washed with saturated sodium bicarbonate, the organic phase was dried with anhydrous sodium sulfate, filtered and the filtrate was concentrated to obtain compound 25-2. Which was directly used in the next reaction without further purification.

MS (ESI) m/z (M+H)$^+$=587.0.

Step 3: Preparation of Compound 25-3

Compound 25-2 (277 mg, 0.5 mmol), compound 2-3 (282 mg, 1 mmol), tetrakis(triphenylphosphine)palladium (150 mg, 0.125 mmol) and potassium carbonate (138 mg, 1 mmol) were dissolved in dioxane (18 mL) and water (1.8 mL). Under nitrogen atmosphere, the system was heated to 100° C. and stirred for 2 hours. The system was concentrated to obtain a crude product, the crude product was purified by medium pressure column chromatography (ethyl acetate/petroleum ether (v/v)=0-50%) to obtain compound 25-3.

MS (ESI) m/z (M+H)$^+$=707.2.

Step 4: Preparation of Compound 25-4

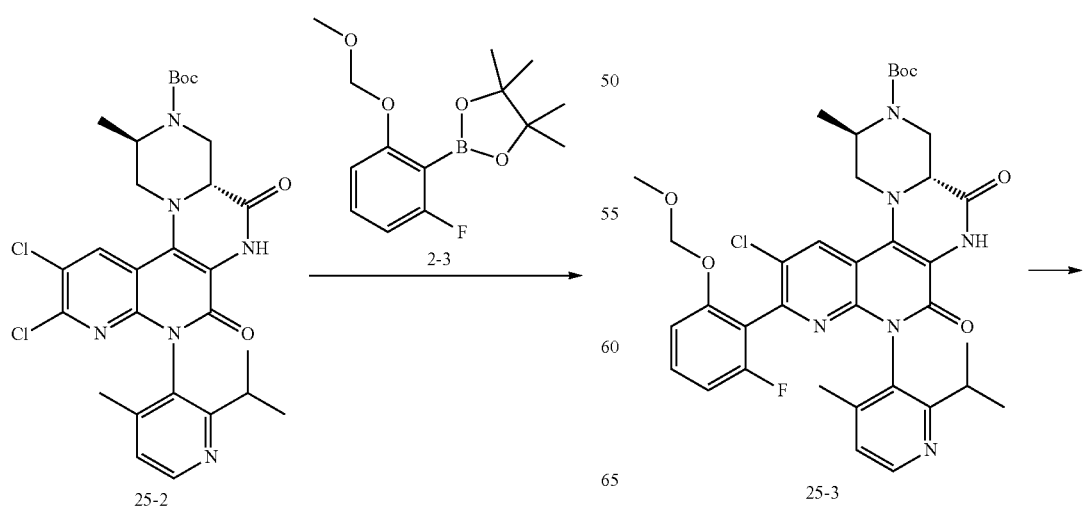

-continued

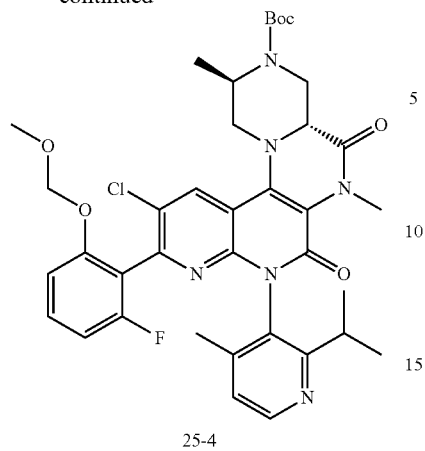

25-4

Compound 25-3 (40 mg, 0.057 mmol) and potassium carbonate (21 mg, 0.15 mmol) were dissolved in acetone (3 mL), and methyl iodide (21 mg, 0.15 mmol) was added thereto at room temperature (20° C.). After the addition was completed, under nitrogen atmosphere, the system was heated to 60° C. and stirred for 3 hours. The system was cooled to room temperature and concentrated to obtain a crude product. The crude product was purified by medium pressure column chromatography (ethyl acetate/petroleum ether (v/v)=0-50%) to obtain compound 25-4.

MS (ESI) m/z (M+H)$^+$=721.2.

Step 5: Preparation of Compound 25-5

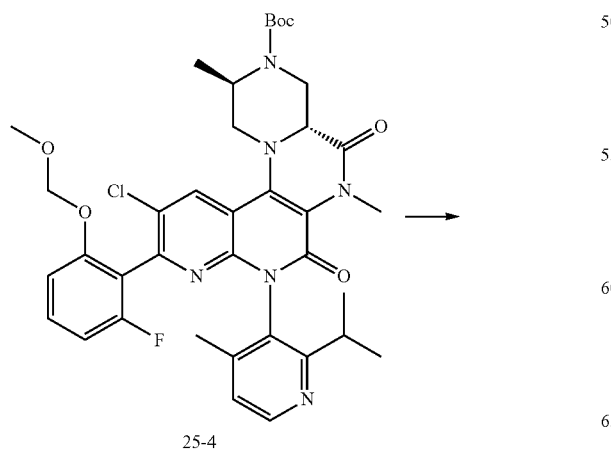

25-4

-continued

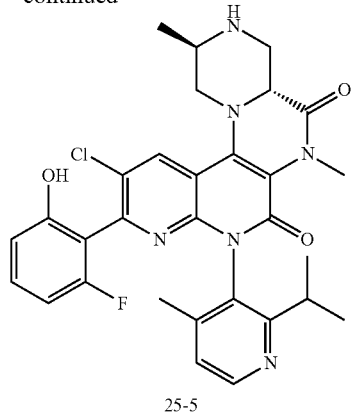

25-5

Compound 25-4 (50 mg, 0.069 mmol), hydrochloric acid (6N, 2 mL) were added to a mixed solution of methanol (2 mL) and tetrahydrofuran (0.2 mL). The system was heated to 55° C. and stirred for 10 min. The system was concentrated to obtain crude product compound 25-5, which was directly used in the next reaction without further purification.

MS (ESI) m/z (M+H)$^+$=577.2.

Step 6: Preparation of Compound 25

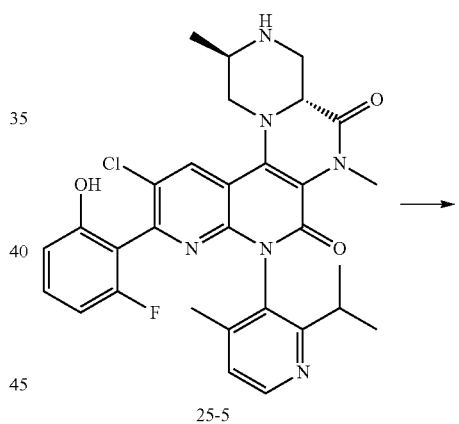

25-5

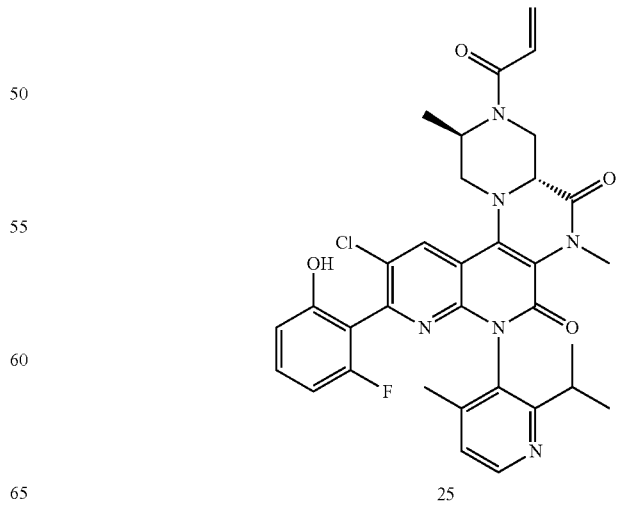

25

Compound 25-5 (40 mg, 0.069 mmol) was dissolved in dichloromethane (5 mL), and the system was cooled to 0° C., triethylamine (39 mg, 0.39 mmol) and acryloyl chloride (23 mg, 0.26 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (10 mL) and water (10 mL); and the organic phase was dried over anhydrous sodium sulfate, filtered, and the filtrate was concentrated to obtain a crude product, the crude product was purified by high performance liquid chromatography (separation conditions: chromatographic column Kinetex® 5 μm F5 100 Å LC Column 150×21.2 mm, mobile phase: water (0.1% FA)-acetonitrile; acetonitrile %: 22%-42% 9 min, flow rate 30 mL/min) to obtain compound 25.

MS (ESI) m/z (M+H)$^+$=631.2.

Step 7: Preparation of Compounds 25A and 25B

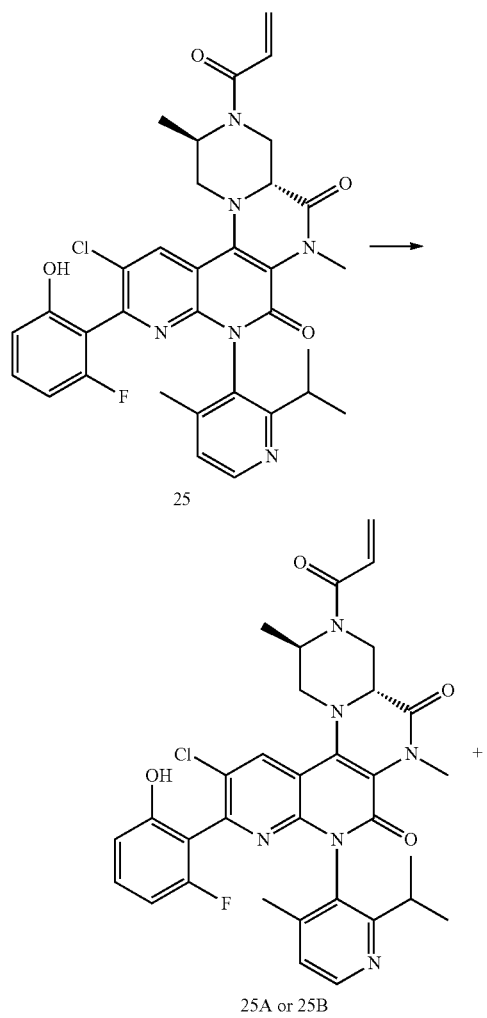

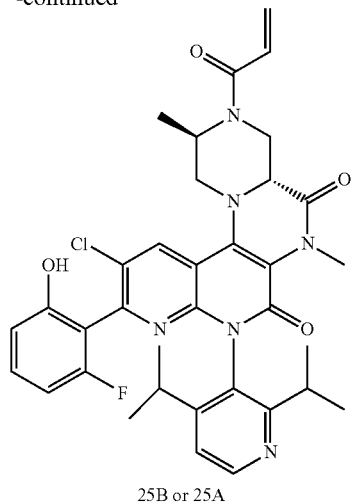

25B or 25A

Diastereoisomeric compound 25 was purified by SFC («Column_3»; mobile phase: [CO$_2$-ethanol (0.1% ammonia)]; ethanol %: 35%; flow rate 80 mL/min; column temperature: 38° C.). After concentration, compound 25A and compound 25B were obtained.

Compound 25A $^1$H NMR (400 MHz, DMSO-d$_6$) δ 10.07 (s, 1H), 8.44 (d, J=4.9 Hz, 1H), 8.24 (s, 1H), 7.30-7.17 (m, 2H), 7.03 (dd, J=16.8, 10.6 Hz, 1H), 6.76-6.63 (m, 2H), 6.15 (dd, J=16.8, 2.5 Hz, 1H), 5.77 (dd, J=10.6, 2.5 Hz, 1H), 4.85-4.72 (m, 1H), 4.62 (d, J=14.0 Hz, 1H), 3.99-3.91 (m, 1H), 3.76 (dd, J=14.1, 4.3 Hz, 1H), 3.51-3.39 (m, 1H), 2.91-2.83 (m, 1H), 2.76 (p, J=6.8 Hz, 1H), 1.81 (d, J=9.0 Hz, 3H), 1.53 (d, J=6.8 Hz, 3H), 1.24 (s, 3H), 1.11 (d, J=6.6 Hz, 3H), 0.96 (d, J=6.6 Hz, 3H).

MS (ESI) m/z (M+H)$^+$=631.2.

SFC 100% ee. Retention time was 4.102 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Compound 25B $^1$H NMR (400 MHz, DMSO-d$_6$) δ 9.98 (d, J=14.4 Hz, 1H), 8.36 (d, J=4.8 Hz, 1H), 8.17 (s, 1H), 7.16 (d, J=8.5 Hz, 2H), 6.96 (dd, J=16.9, 10.6 Hz, 1H), 6.69-6.54 (m, 2H), 6.08 (dd, J=16.8, 2.4 Hz, 1H), 5.69 (dd, J=10.5, 2.4 Hz, 1H), 4.74-4.63 (m, 1H), 4.54 (d, J=14.1 Hz, 1H), 4.05-3.87 (m, 1H), 3.68 (dd, J=14.1, 4.3 Hz, 1H), 3.37-3.26 (m, 1H), 2.93-2.79 (m, 1H), 2.80-2.68 (m, 1H), 1.92 (d, J=3.2 Hz, 3H), 1.46 (d, J=6.8 Hz, 3H), 1.17 (s, 3H), 0.96 (d, J=6.6 Hz, 3H), 0.85-0.73 (m, 3H).

MS (ESI) m/z (M+H)$^+$=631.2.

SFC 100% ee. Retention time was 5.424 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Embodiment 26: Preparation of Compound 26

Step 1: Preparation of Compound 26-2

Step 2: Preparation of Compound 26-3

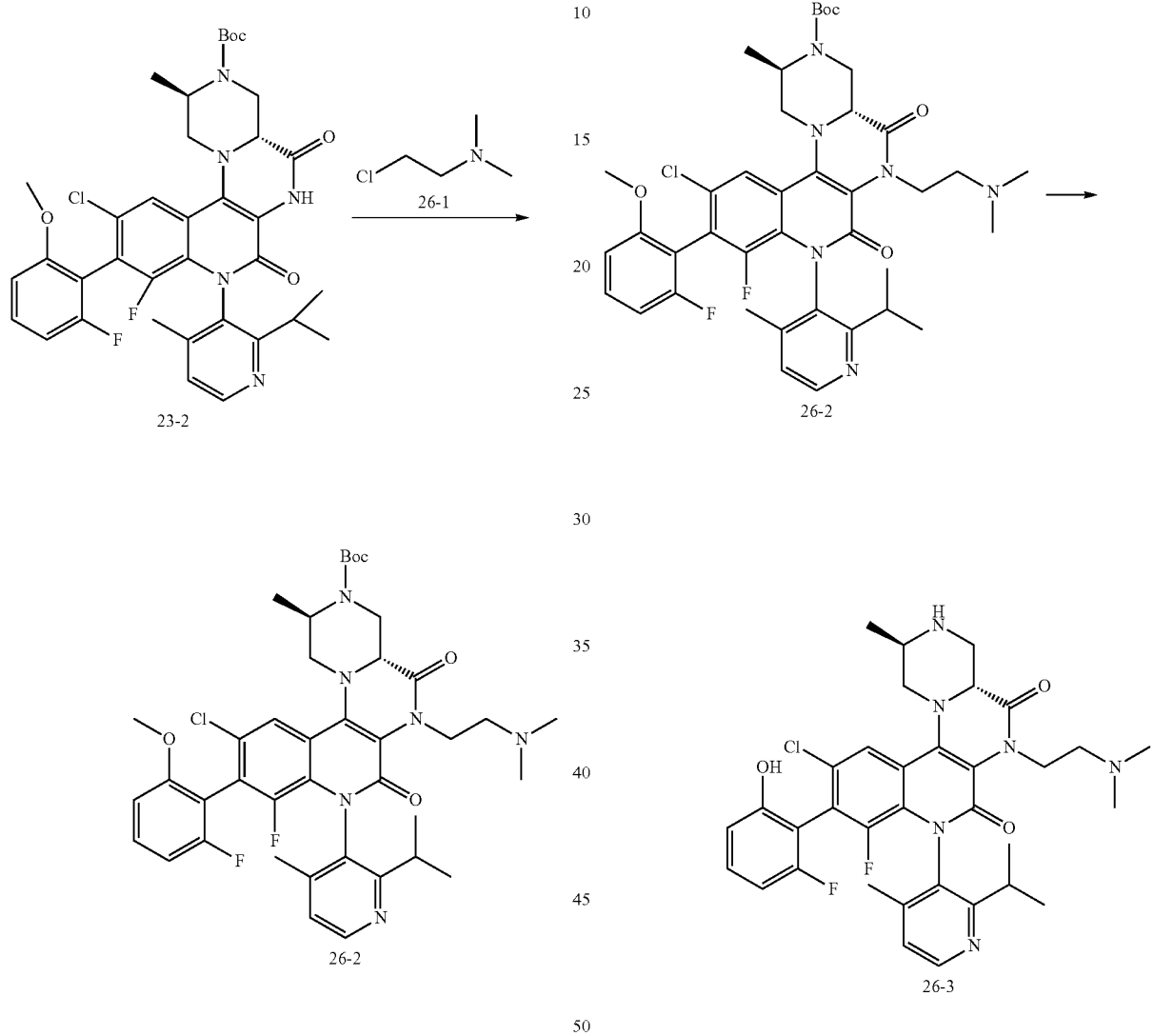

Compound 23-2 (400 mg, 576.23 μmol) and cesium carbonate (563.24 mg, 1.73 mmol) were dissolved in N,N-dimethylformamide (5 mL), and compound 26-1 (185.98 mg, 1.73 mmol) was added thereto at room temperature (25° C.). After the addition was completed, under nitrogen atmosphere, the system was heated to 120° C. and stirred for 3 hours. The system was concentrated, diluted with ethyl acetate (20 mL) and filtered, the filtrate was washed with saturated saline, the organic phase was dried over anhydrous sodium sulfate, filtered, and the filtrate was concentrated to obtain a crude product, the crude product was purified by silica gel column chromatography (dichloromethane/methanol (v/v)=1/10) to obtain compound 26-2.

MS (ESI) m/z (M+H)$^+$=765.5.

Compound 26-2 (230 mg, 345.78 μmol) was dissolved in dichloromethane (1 mL), and boron tribromide (1 M, 407.10 μL) was added thereto, and the reaction was stirred at 20° C. for 16 hours. The reaction mixture was quenched with methanol (5 mL), stirred for 10 min. The reaction was added with saturated sodium bicarbonate (30 mL), extracted with ethyl acetate (30 mL×2); and the organic phase was dried over anhydrous sodium sulfate, filtered, and the filtrate was concentrated to obtain compound 26-3, which was directly used in the next reaction without further purification.

MS (ESI) m/z (M+H)$^+$=651.3.

Step 3: Preparation of Compounds 26A and 26B

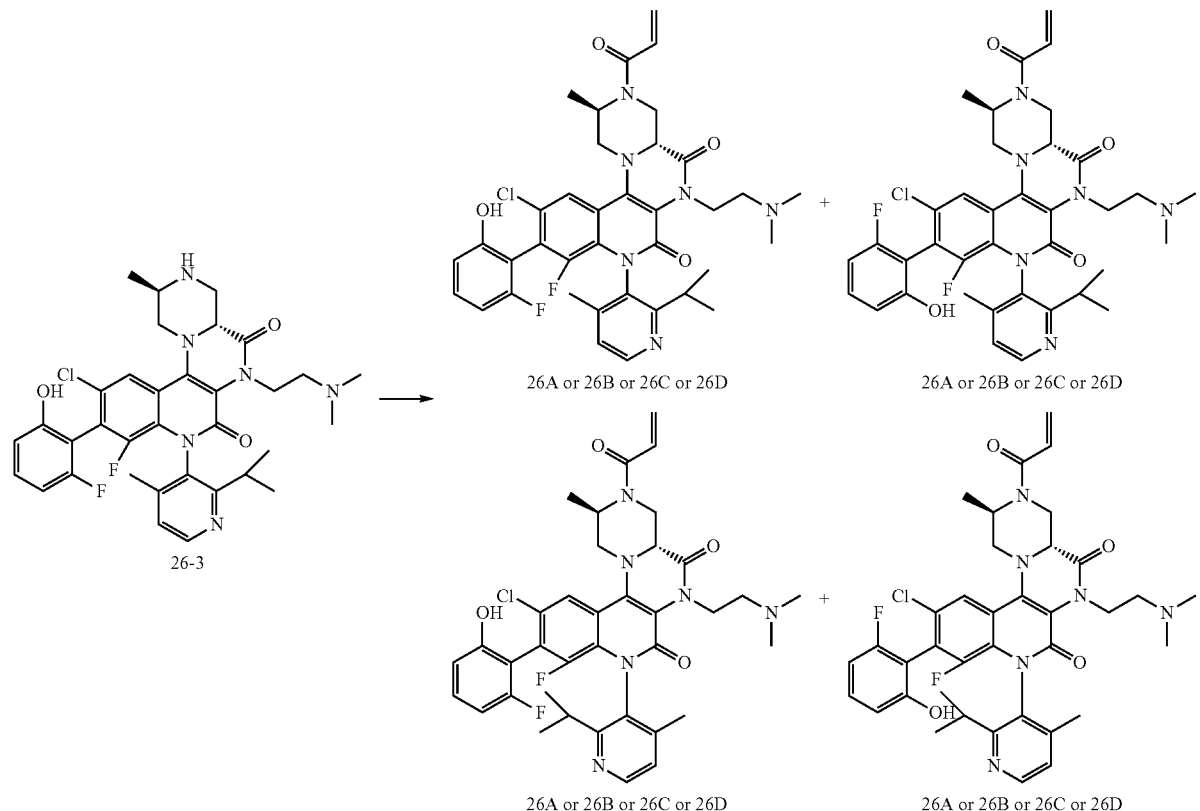

Compound 26-3 (280 mg, 430.01 μmol) was dissolved in tetrahydrofuran (3 mL) and saturated sodium bicarbonate aqueous solution (4.32 g, 51.42 mmol, 2 mL), and acrylic anhydride (108.46 mg, 860.02 μmol) was added thereto at room temperature (25° C.). After the addition was completed, the system was stirred at room temperature (25° C.) for 30 min. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [–water (10 mM ammonium bicarbonate aqueous solution)-acetonitrile]; acetonitrile %: 55%-85% 9 min) and then purified by SFC (separation conditions: chromatographic column: DAICEL CHIRALPAK AD-H (250 mm*30 mm, 5 μm); mobile phase: [$CO_2$-(0.1% ammonia) isopropanol]; isopropanol %: 35%-35%). After concentration, compound 26A, 26B, 26C and 26D were obtained.

Compound 26A:
$^1$H NMR (400 MHz, Methanol-$d_4$) δ 8.44 (d, J=5.0 Hz, 1H), 8.04 (s, 1H), 7.31-7.20 (m, 2H), 7.13 (dd, J=10.7, 16.9 Hz, 1H), 6.69 (d, J=8.3 Hz, 1H), 6.63 (t, J=8.8 Hz, 1H), 6.30-6.19 (m, 1H), 5.86-5.75 (m, 1H), 4.99-4.94 (m, 1H), 4.75 (br d, J=13.8 Hz, 1H), 4.67-4.44 (m, 1H), 4.39-4.23 (m, 2H), 4.03-3.85 (m, 2H), 3.22-3.07 (m, 1H), 2.66 (br d, J=11.8 Hz, 1H), 2.60-2.47 (m, 2H), 2.32-2.09 (m, 9H), 1.76-1.64 (m, 3H), 1.12 (d, J=6.8 Hz, 3H), 1.02 (d, J=6.8 Hz, 3H).

MS (ESI) m/z (M+H)$^+$=705.3.

HPLC retention time was 6.9 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC retention time was 4.077 min separation conditions: chromatographic column: Chiralpak AD-3 150×4.6 mm I.D., 3 μm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 26B:
$^1$H NMR (400 MHz, Methanol-$d_4$) δ 8.52-8.34 (m, 1H), 8.03 (s, 1H), 7.31-7.19 (m, 2H), 7.13 (dd, J=10.8, 16.8 Hz, 1H), 6.72-6.56 (m, 2H), 6.32-6.16 (m, 1H), 5.89-5.73 (m, 1H), 4.95 (br s, 1H), 4.81-4.68 (m, 1H), 4.67-4.44 (m, 1H), 4.39-4.20 (m, 2H), 4.04-3.84 (m, 2H), 3.14 (dd, J=3.5, 12.0 Hz, 1H), 2.72-2.42 (m, 3H), 2.31-2.18 (m, 9H), 1.76-1.64 (m, 3H), 1.10 (dd, J=6.8, 15.1 Hz, 6H).

MS (ESI) m/z (M+H)$^+$=705.3.

HPLC retention time was 6.67 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 4.515 min separation conditions: chromatographic column: Chiralpak AD-3 150×4.6 mm I.D., 3 μm; column temperature: 35° C.; mobile phase: CO$_2$-isopropanol (0.05% DEA); isopropanol: 5%-40% 5 min, 40% 2.5 min, 5% 2.5 min; flow rate: 2.5 mL/min.

Compound 26C:

$^1$H NMR (400 MHz, Methanol-d$_4$) δ 8.44 (d, J=5.0 Hz, 1H), 8.04 (s, 1H), 7.30-7.20 (m, 2H), 7.13 (dd, J=10.7, 16.9 Hz, 1H), 6.73-6.58 (m, 2H), 6.32-6.16 (m, 1H), 5.87-5.73 (m, 1H), 4.95 (br s, 1H), 4.74 (br d, J=13.6 Hz, 1H), 4.66-4.45 (m, 1H), 4.37-4.20 (m, 2H), 3.99-3.82 (m, 2H), 3.20 (br dd, J=3.4, 12.4 Hz, 1H), 2.94 (td, J=6.7, 13.5 Hz, 1H), 2.67 (br d, J=12.0 Hz, 1H), 2.55 (br d, J=5.3 Hz, 1H), 2.34-2.15 (m, 6H), 2.10-1.93 (m, 3H), 1.77-1.61 (m, 3H), 1.23 (d, J=6.8 Hz, 3H), 1.11 (d, J=6.8 Hz, 3H).

MS (ESI) m/z (M+H)$^+$=705.3.

HPLC retention time was 6.67 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 4.826 min separation conditions: chromatographic column: Chiralpak AD-3 150×4.6 mm I.D., 3 μm; column temperature: 35° C.; mobile phase: CO$_2$-isopropanol (0.05% DEA); isopropanol: 5%-40% 5 min, 40% 2.5 min, 5% 2.5 min; flow rate: 2.5 mL/min.

Compound 26D:

$^1$H NMR (400 MHz, Methanol-d$_4$) δ 8.44 (d, J=4.8 Hz, 1H), 8.04 (s, 1H), 7.34-7.20 (m, 2H), 7.13 (dd, J=10.7, 16.9 Hz, 1H), 6.72-6.53 (m, 2H), 6.33-6.15 (m, 1H), 5.92-5.65 (m, 1H), 4.95 (br s, 1H), 4.75 (d, J=12.8 Hz, 1H), 4.66-4.42 (m, 1H), 4.30 (br t, J=6.9 Hz, 2H), 4.02-3.83 (m, 2H), 3.26-3.13 (m, 1H), 2.93 (quin, J=6.8 Hz, 1H), 2.74-2.59 (m, 1H), 2.58-2.45 (m, 1H), 2.34-2.18 (m, 6H), 1.99 (s, 3H), 1.78-1.63 (m, 3H), 1.22 (d, J=6.8 Hz, 3H), 1.15 (d, J=6.8 Hz, 3H).

MS (ESI) m/z (M+H)$^+$=705.3.

HPLC retention time was 6.88 min.

Separation conditions: chromatographic column WELCH Ultimate LP-C18 150*4.6 mm 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 5.114 min separation conditions: chromatographic column: Chiralpak AD-3 150×4.6 mm I.D., 3 μm; column temperature: 35° C.; mobile phase: CO$_2$-isopropanol (0.05% DEA); isopropanol: 5%-40% 5 min, 40% 2.5 min, 5% 2.5 min; flow rate: 2.5 mL/min.

Embodiment 27: Preparation of Compound 27

Step 1: Preparation of Compound 27-1

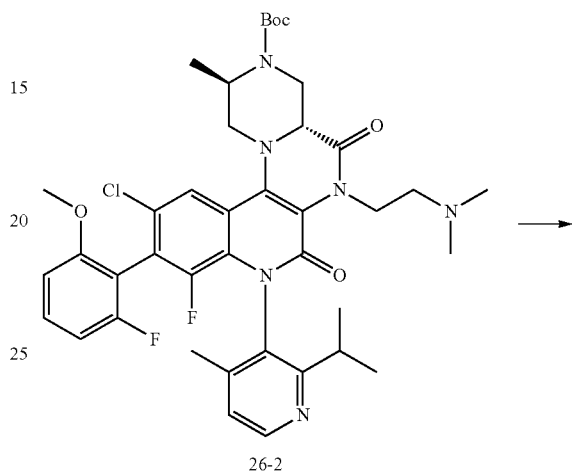

26-2

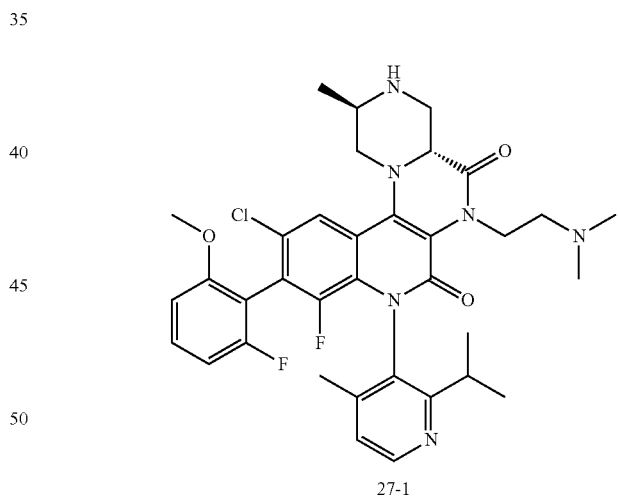

27-1

Compound 26-2 (600 mg, 784.02 μmol) was dissolved in dichloromethane (6 mL), and trifluoroacetic acid (1.83 g, 16.06 mmol, 1.19 mL) was added thereto, and the reaction was stirred at 25° C. for 16 hours. The reaction mixture was concentrated to obtain compound 27-1, which was directly used in the next reaction without further purification.

MS (ESI) m/z (M+H)$^+$=665.3.

Step 2: Preparation of Compound 27

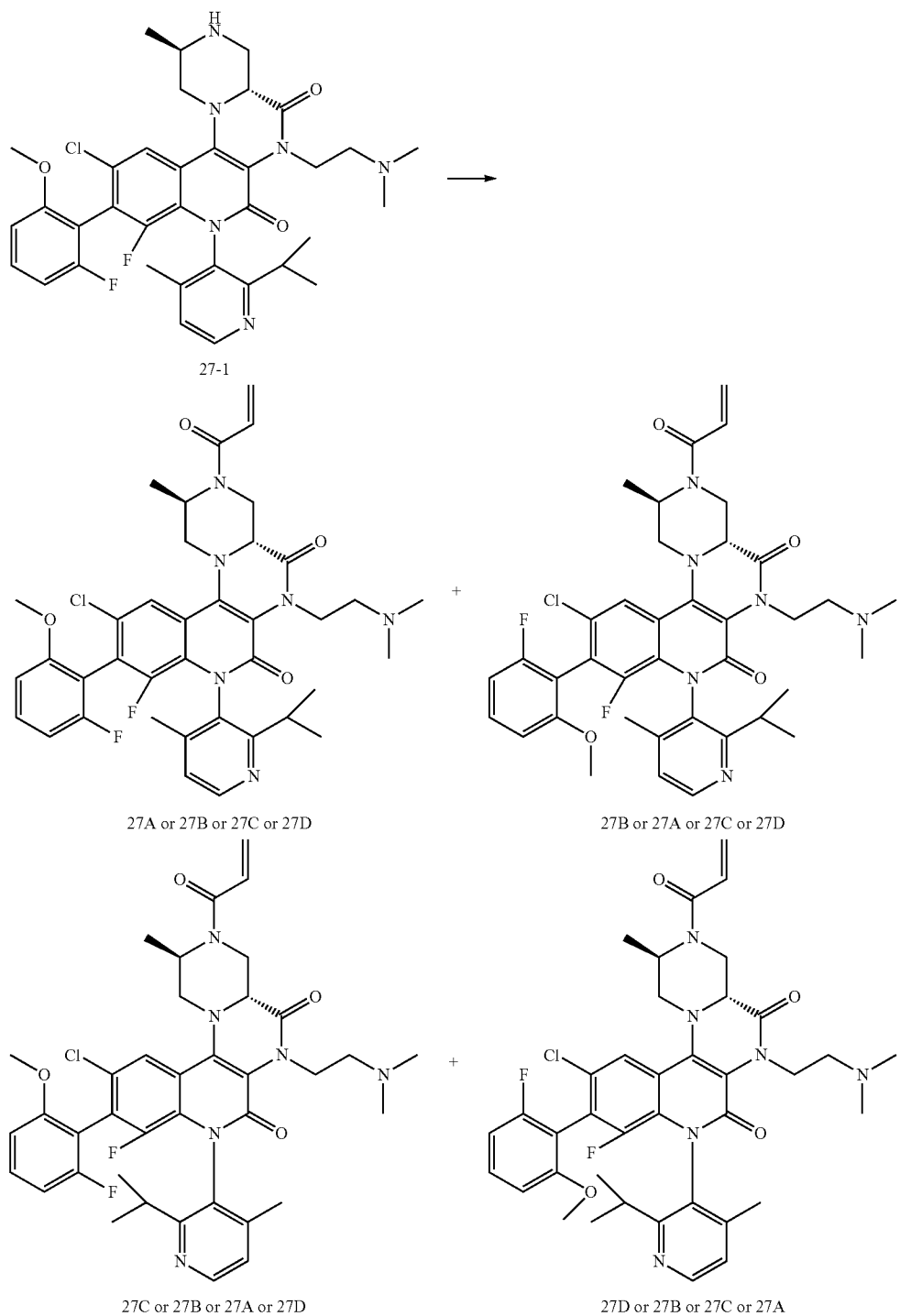

Compound 27-1 (200 mg, 300.67 µmol) was dissolved in tetrahydrofuran (2 mL) and saturated sodium bicarbonate aqueous solution (4.32 g, 51.42 mmol, 2 mL), and acrylic anhydride (75.84 mg, 601.35 µmol) was added thereto at room temperature (25° C.). After the addition was completed, the system was stirred at room temperature (25° C.) for 30 min. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 µm; mobile phase: [−water (10 mM ammonium bicarbonate aqueous solution)-acetonitrile]; acetonitrile %: 49%-79% 9 min) and then purified by SFC (separation conditions: chromatographic column: DAICEL CHIRALPAK AD-H (250 mm*30 mm, 5 μm); mobile phase: [$CO_2$-(0.1% ammonia) ethanol]; ethanol %: 25%-25%). After concentration, compound 27A, 27B, 27C and 27D were obtained.

Compound 27A:

$^1$H NMR (400 MHz, Methanol-$d_4$) δ 8.44 (d, J=5.0 Hz, 1H), 8.03 (d, J=1.3 Hz, 1H), 7.46-7.38 (m, 1H), 7.27 (d, J=5.0 Hz, 1H), 7.13 (dd, J=10.8, 16.8 Hz, 1H), 6.89 (d, J=8.5 Hz, 1H), 6.79 (t, J=8.8 Hz, 1H), 6.31-6.18 (m, 1H), 5.87-5.75 (m, 1H), 4.95 (br s, 1H), 4.80-4.70 (m, 1H), 4.68-4.42 (m, 1H), 4.39-4.26 (m, 2H), 4.02-3.87 (m, 2H), 3.68 (s, 3H), 3.25-3.12 (m, 1H), 2.65-2.37 (m, 3H), 2.23-2.14 (m, 9H), 1.76-1.64 (m, 3H), 1.13 (d, J=6.8 Hz, 3H), 1.05 (d, J=6.8 Hz, 3H).

MS (ESI) m/z (M+H)$^+$=719.3.

HPLC retention time was 4.761 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

SFC retention time was 4.329 min.

separation conditions: chromatographic column: Chiralpak IG-3 100×4.6 mm I.D., 3 μm; column temperature: 35° C.; mobile phase: $CO_2$-isopropanol (0.05% DEA); isopropanol: 5%-40% 4 min, 40% 2.5 min, 5% 1.5 min; flow rate: 2.8 mL/min.

Compound 27B:

$^1$H NMR (400 MHz, Methanol-$d_4$) δ 8.45 (d, J=5.0 Hz, 1H), 8.04 (s, 1H), 7.48-7.37 (m, 1H), 7.27 (d, J=5.0 Hz, 1H), 7.13 (dd, J=10.7, 16.9 Hz, 1H), 6.91 (d, J=8.5 Hz, 1H), 6.79 (t, J=8.5 Hz, 1H), 6.31-6.17 (m, 1H), 5.87-5.75 (m, 1H), 4.95 (br s, 1H), 4.83-4.69 (m, 1H), 4.67-4.49 (m, 1H), 4.39-4.29 (m, 2H), 4.05-3.85 (m, 2H), 3.76 (s, 3H), 3.27-3.13 (m, 1H), 2.65-2.39 (m, 3H), 2.24-2.13 (m, 9H), 1.77-1.63 (m, 3H), 1.12 (d, J=6.8 Hz, 3H), 1.02 (d, J=6.8 Hz, 3H).

MS (ESI) m/z (M+H)$^+$=719.3.

HPLC retention time was 4.775 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

SFC retention time was 4.523 min.

separation conditions: chromatographic column: Chiralpak IG-3 100×4.6 mm I.D., 3 μm; column temperature: 35° C.; mobile phase: $CO_2$-isopropanol (0.05% DEA); isopropanol: 5%-40% 4 min, 40% 2.5 min, 5% 1.5 min; flow rate: 2.8 mL/min.

Compound 27C:

$^1$H NMR (400 MHz, Methanol-$d_4$) δ 8.44 (d, J=5.0 Hz, 1H), 8.04 (s, 1H), 7.50-7.37 (m, 1H), 7.26 (d, J=5.0 Hz, 1H), 7.18-7.11 (m, 1H), 6.91 (d, J=8.3 Hz, 1H), 6.80 (t, J=8.7 Hz, 1H), 6.31-6.17 (m, 1H), 5.86-5.75 (m, 1H), 4.99-4.93 (m, 1H), 4.75 (br d, J=12.8 Hz, 1H), 4.65-4.40 (m, 1H), 4.36-4.18 (m, 2H), 4.02-3.85 (m, 2H), 3.74 (s, 3H), 3.16 (br dd, J=3.5, 12.3 Hz, 1H), 2.96 (td, J=6.9, 13.6 Hz, 1H), 2.86-2.67 (m, 2H), 2.45-2.33 (m, 6H), 1.99 (s, 3H), 1.77-1.64 (m, 3H), 1.23 (d, J=6.8 Hz, 3H), 1.14-1.09 (m, 3H).

MS (ESI) m/z (M+H)$^+$=719.3.

HPLC retention time was 4.732 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

SFC retention time was 8.150 min.

separation conditions: chromatographic column: ChiralPak IC-3 150×4.6 mm I.D., 3 μm; column temperature: 40° C.; mobile phase: $CO_2$-ethanol (0.05% DEA); isopropanol: 5%-40% 5.5 min, 40% 3 min, 5% 1.5 min; flow rate: 2.5 mL/min.

Compound 27D:

$^1$H NMR (400 MHz, Methanol-$d_4$) δ 8.45 (d, J=4.8 Hz, 1H), 8.05 (s, 1H), 7.48-7.38 (m, 1H), 7.25 (d, J=5.3 Hz, 1H), 7.13 (dd, J=10.8, 17.1 Hz, 1H), 6.90 (d, J=8.5 Hz, 1H), 6.80 (t, J=8.5 Hz, 1H), 6.32-6.16 (m, 1H), 5.85-5.76 (m, 1H), 4.96 (br s, 1H), 4.75 (br d, J=12.3 Hz, 1H), 4.67-4.45 (m, 1H), 4.36-4.20 (m, 2H), 4.01-3.86 (m, 2H), 3.71 (s, 3H), 3.27-3.14 (m, 1H), 2.94 (td, J=6.8, 13.6 Hz, 1H), 2.85-2.56 (m, 2H), 2.39-2.24 (m, 6H), 1.99 (s, 3H), 1.76-1.65 (m, 3H), 1.24 (d, J=6.8 Hz, 3H), 1.14 (d, J=6.8 Hz, 3H).

MS (ESI) m/z (M+H)$^+$=719.3.

HPLC retention time was 4.716 min.

Separation conditions: chromatographic column Xbridge Shield RP-18, 5 μm, 2.1*50 mm; column temperature: 50° C.; mobile phase: water (0.2 mL/L ammonia solution)-acetonitrile; acetonitrile: 10%-80% 6 min, 80% 2 min; flow rate: 0.8 mL/min.

SFC retention time was 6.545 min.

separation conditions: chromatographic column: ChiralPak IC-3 150×4.6 mm I.D., 3 μm; column temperature: 40° C.; mobile phase: $CO_2$-ethanol (0.05% DEA); isopropanol: 5%-40% 5.5 min, 40% 3 min, 5% 1.5 min; flow rate: 2.5 mL/min.

Embodiment 28: Preparation of Compound 28

Step 1: Preparation of Compound 28-2

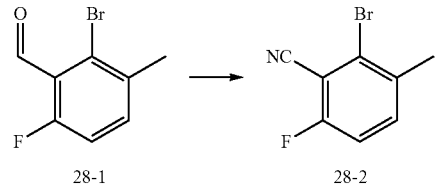

Compound 28-1 (1 g, 4.61 mmol), ammonium acetate (2.13 g, 27.65 mmol), diacetoxyiodobenzene (2.97 g, 9.22 mmol) and sodium lauryl sulfate (265.74 mg, 921.51 μmol, 263.11 μL) were suspended in water (10 mL), and the system was heated to 70° C. and the reaction was carried out for 30 min. The system was cooled to room temperature (25° C.), saturated sodium thiosulfate (5 mL) was added thereto, and the system was stirred at room temperature (25° C.) for 15 min, then extracted with ethyl acetate (20 mL×3); the organic phases were combined, then the organic phase was dried over anhydrous sodium sulfate, filtered and the filtrate was concentrated to obtain a crude product, the crude product was purified by medium pressure column chromatography (ethyl acetate/petroleum ether (v/v)=0-5%) to obtain compound 28-2.

$^1$H NMR (400 MHz, CHLOROFORM-d) δ 7.46 (dd, J=6.0, 8.6 Hz, 1H), 7.11 (t, J=8.4 Hz, 1H), 2.44 (s, 3H).

Step 2: Preparation of Compound 28-3

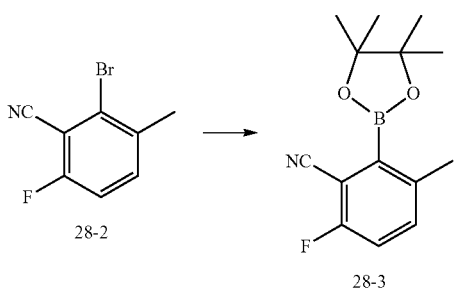 [SMILES: Cc1ccc(F)c(C#N)c1Br ; Cc1ccc(F)c(C#N)c1B1OC(C)(C)C(C)(C)O1]

At room temperature (20° C.), compound 28-2 (760 mg, 3.55 mmol), bis(pinacolato)diboron (1.35 g, 5.33 mmol), 1,1-bis(diphenylphosphino)ferrocene palladium dichloride (289.97 mg, 355.08 μmol) and potassium acetate (1.05 g, 10.65 mmol) were dissolved in 1,4-dioxane (5 mL). Under nitrogen atmosphere, the system was heated to 100° C. and stirred for 16 hours. The system was cooled to room temperature and concentrated to obtain a crude product. The crude product was purified by medium pressure column chromatography (ethyl acetate/petroleum ether (v/v)=0-5%) to obtain compound 28-3.

Step 3: Preparation of Compound 28-5

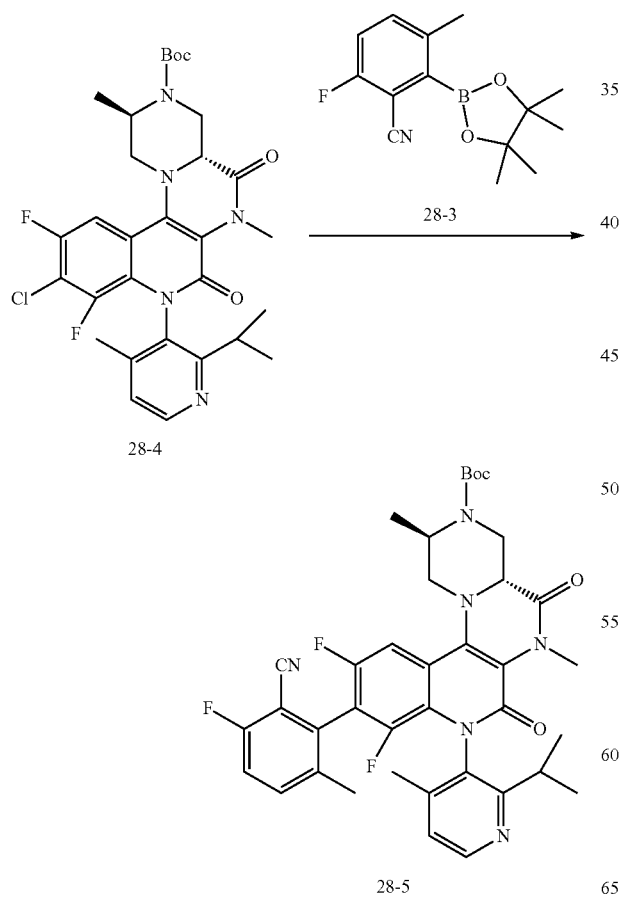

Compound 28-4 (210 mg, 348.80 μmol), compound 28-3 (136.61 mg, 523.19 μmol), methanesulfonato (2-dicyclohexylphosphino-2',6'-di-i-propoxy-1,1'-biphenyl)(2'-amino-1,1'-biphenyl-2-yl) palladium(II) (29.17 mg, 34.88 μmol), 2-dicyclohexylphosphino-2',6'-di-i-propoxy-1,1'-biphenyl (16.28 mg, 34.88 μmol) and potassium carbonate (96.41 mg, 697.59 μmol) were dissolved in a mixed solution of dioxane (3 mL) and water (0.3 mL), under nitrogen atmosphere, the system was stirred at 100° C. for 5 hours. The system was filtered, and the filtrate was concentrated to obtain a crude product. The crude product was purified by medium pressure column chromatography (ethyl acetate/petroleum ether (v/v) =0-50%) to obtain compound 28-5.

MS (ESI) m/z (M+H)$^+$=701.1.

Step 4: Preparation of Compound 28-6

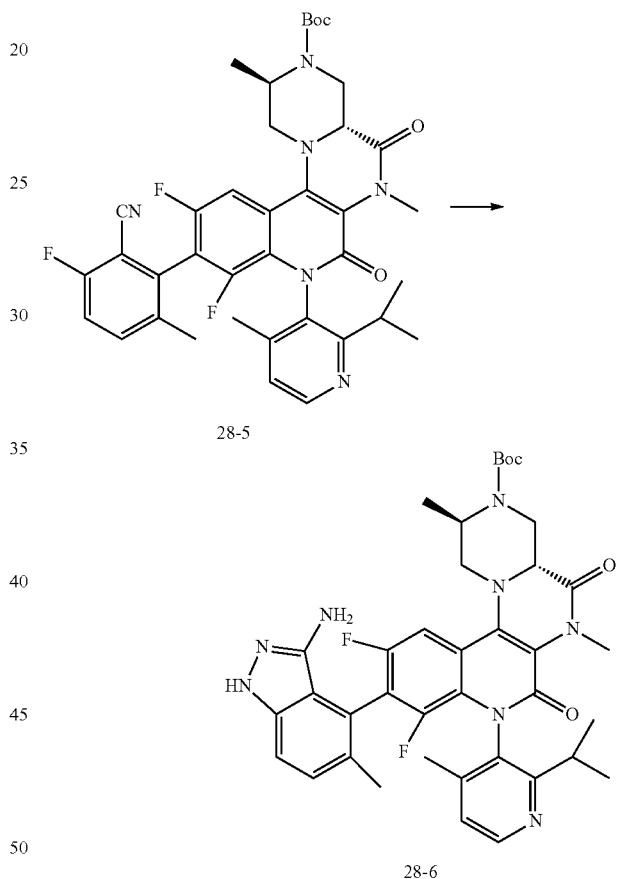

Compound 28-5 (150 mg, 214.06 μmol) was dissolved in ethanol (5 mL), hydrazine hydrate (214.31 mg, 4.28 mmol, 208.07 μL) was added thereto, and the system was heated to 80° C. and the reaction was carried out for 4 hours. The system was cooled to room temperature (25° C.) and then concentrated; the residue was dissolved in ethyl acetate (10 mL) and extracted with 1 N hydrochloric acid (20 mL×3); the aqueous phases were combined, and the pH was adjusted to 8 with 1 M sodium hydroxide; then the mixture was extracted with ethyl acetate (10 mL×3), and the organic phases were combined; and the organic phase was washed with water (50 mL×2), dried over anhydrous sodium sulfate, filtered, and the filtrate was concentrated to obtain compound 28-6, which was used directly in the next reaction without further purification.

MS (ESI) m/z (M+H)$^+$=713.4.

Step 5: Preparation of Compound 28-7

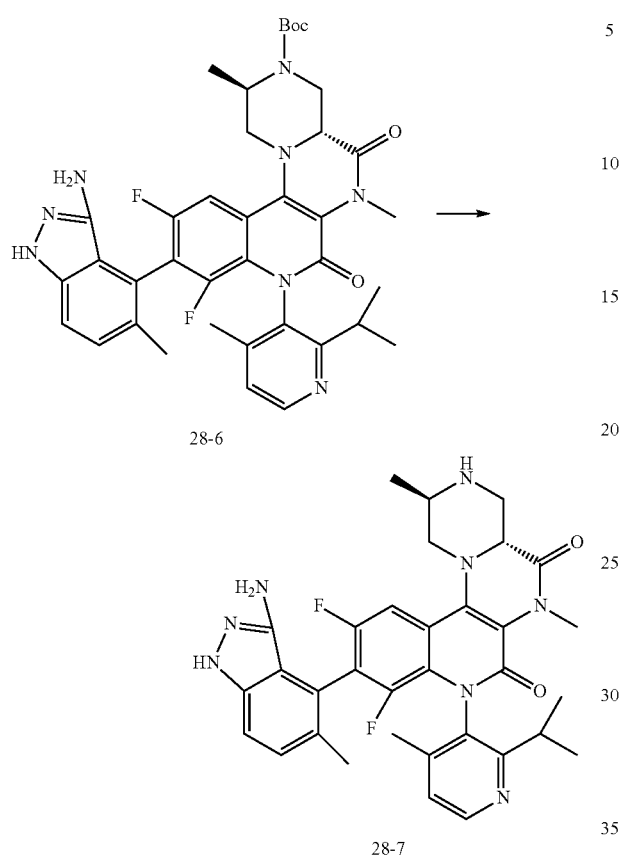

28-6

28-7

Compound 28-6 (60 mg, 84.18 μmol) was dissolved in dichloromethane (10 mL), and trifluoroacetic acid (1.54 g, 13.51 mmol, 1 mL) was added thereto, and the reaction was stirred at 25° C. for 1 hour. The reaction mixture was concentrated to obtain compound 28-7, which was directly used in the next reaction without further purification.

MS (ESI) m/z (M+H)$^+$=613.3.

Step 6: Preparation of Compound 28

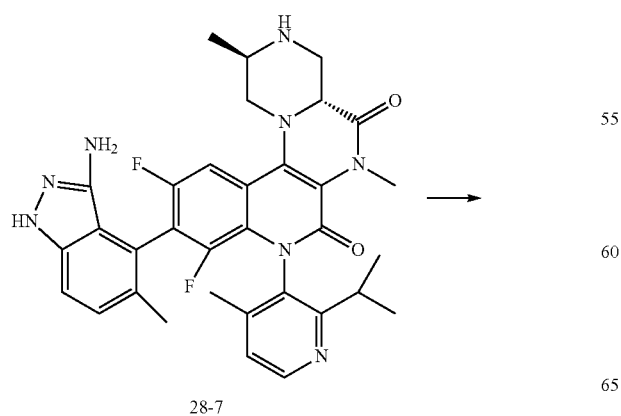

28-7

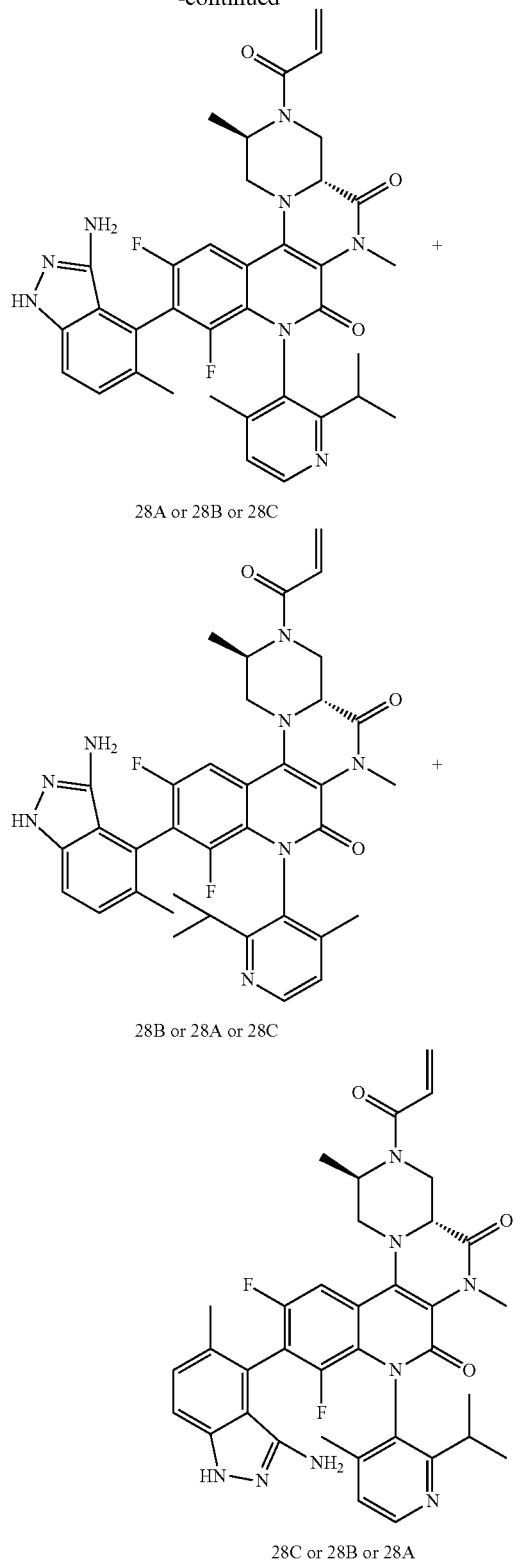

28A or 28B or 28C 28B or 28A or 28C 28C or 28B or 28A

Compound 28-7 (50 mg, 81.61 μmol) was dissolved in tetrahydrofuran (3 mL) and saturated sodium bicarbonate aqueous solution (3 mL), and acrylic anhydride (11.32 mg, 89.77 μmol) was added thereto at room temperature (25° C.). After the addition was completed, the system was stirred at room temperature (25° C.) for 2 hours. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [–water (10 mM ammonium bicarbonate aqueous solution)-acetonitrile]; acetonitrile %: 36%-66% 9 min) and then purified by SFC (separation conditions: chromatographic column: DAICEL CHIRALPAK IG (250 mm*30 mm, 10 μm); mobile phase: [CO$_2$-(0.1% ammonia) methanol]; methanol %: 55%-55%). After concentration, compounds 28A, 28B and 28C were obtained.

Compound 28A:

$^1$H NMR (400 MHz, Methanol-d$_4$) δ 8.40 (d, J=5.0 Hz, 1H), 7.80 (br d, J=8.8 Hz, 1H), 7.34-7.24 (m, 2H), 7.23-7.19 (m, 1H), 7.13 (dd, J=10.7, 16.9 Hz, 1H), 6.25 (dd, J=1.8, 16.8 Hz, 1H), 5.87-5.76 (m, 1H), 4.95 (br s, 1H), 4.77 (br d, J=12.5 Hz, 1H), 3.99-3.87 (m, 2H), 3.46 (s, 3H), 3.40 (br d, J=12.3 Hz, 1H), 3.03-2.92 (m, 2H), 2.07 (d, J=5.8 Hz, 6H), 1.69 (d, J=7.0 Hz, 3H), 1.22 (d, J=6.8 Hz, 3H), 1.13 (d, J=6.8 Hz, 3H).

MS (ESI) m/z (M+H)$^+$=667.3.

HPLC retention time was 6.49 min.

Separation conditions: chromatographic column WELCH Ultimate C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC retention time was 1.661 min.

separation conditions: chromatographic column: Chiralpak IG-3 50*4.6 mm I.D., 3 μm; column temperature: 35° C.; mobile phase: CO$_2$-methanol (0.05% DEA); methanol: 40%-40%; flow rate: 4 mL/min.

Compound 28B:

$^1$H NMR (400 MHz, Methanol-d$_4$) δ 8.41 (d, J=5.0 Hz, 1H), 7.78 (br d, J=8.8 Hz, 1H), 7.32-7.21 (m, 3H), 7.14 (dd, J=10.7, 16.9 Hz, 1H), 6.25 (dd, J=1.8, 16.8 Hz, 1H), 5.88-5.76 (m, 1H), 5.00-4.96 (m, 1H), 4.77 (br d, J=11.8 Hz, 1H), 4.02-3.87 (m, 2H), 3.49 (br d, J=3.3 Hz, 1H), 3.46 (s, 3H), 3.12-2.93 (m, 2H), 2.07 (s, 3H), 1.97 (s, 3H), 1.75 (s, 1H), 1.69 (d, J=6.8 Hz, 2H), 1.23 (d, J=6.8 Hz, 3H), 1.17 (d, J=6.8 Hz, 3H).

MS (ESI) m/z (M+H)$^+$=667.3.

HPLC retention time was 6.66 min.

Separation conditions: chromatographic column WELCH Ultimate C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC retention time was 4.234 min.

separation conditions: chromatographic column: Chiralpak IG-3 50*4.6 mm I.D., 3 μm; column temperature: 35° C.; mobile phase: CO$_2$-methanol (0.05% DEA); methanol: 40%-40%; flow rate: 4 mL/min.

Compound 28C:

$^1$H NMR (400 MHz, Methanol-d$_4$) δ 8.40 (d, J=5.0 Hz, 1H), 7.77 (br d, J=9.0 Hz, 1H), 7.32-7.22 (m, 3H), 7.13 (dd, J=10.7, 16.9 Hz, 1H), 6.31-6.20 (m, 1H), 5.86-5.76 (m, 1H), 4.94 (br s, 1H), 4.77 (br d, J=12.5 Hz, 1H), 4.06-3.88 (m, 2H), 3.46 (s, 4H), 2.93 (m, J=3.5, 12.3 Hz, 1H), 2.64-2.54 (m, 1H), 2.25 (s, 3H), 2.09 (s, 3H), 1.69 (d, J=6.8 Hz, 3H), 1.13 (d, J=6.8 Hz, 3H), 1.01 (d, J=6.8 Hz, 3H).

MS (ESI) m/z (M+H)$^+$=667.3.

HPLC retention time was 6.77 min.

Separation conditions: chromatographic column WELCH Ultimate C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 2.725 min.

separation conditions: chromatographic column: Chiralpak IG-3 50*4.6 mm I.D., 3 μm; column temperature: 35° C.; mobile phase: CO$_2$-methanol (0.05% DEA); methanol: 40%-40%; flow rate: 4 mL/min.

Embodiment 29: Preparation of Compound 29

Step 1: Preparation of Compound 29-1

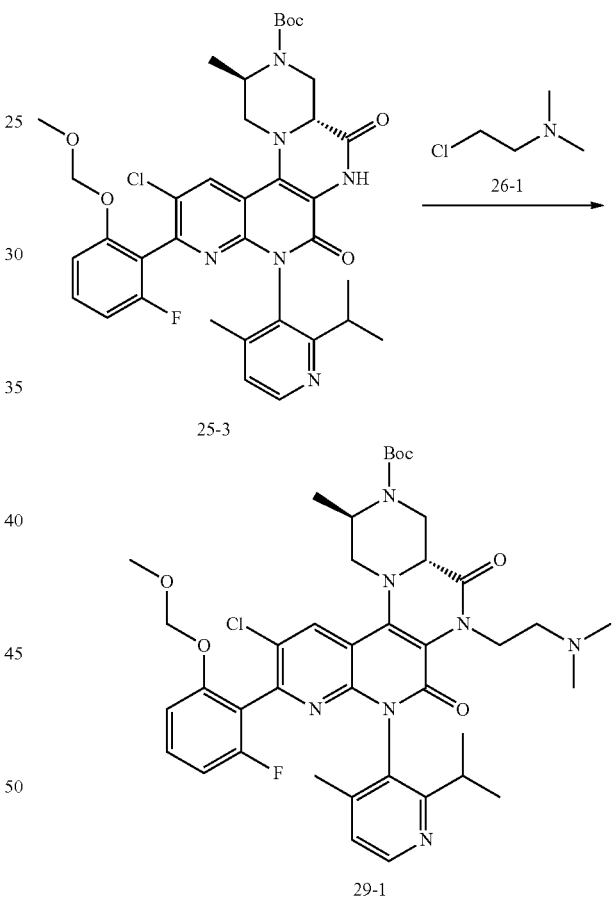

Compound 25-3 (700 mg, 1 mmol) and cesium carbonate (977 mg, 3 mmol) were dissolved in N,N-dimethylformamide (20 mL), and compound 26-1 (432 mg, 3 mmol) was added thereto at room temperature (25° C.). After the addition was completed, under nitrogen atmosphere, the system was heated to 120° C. and stirred for 2 hours. The system was filtered and concentrated to obtain a crude product, the crude product was purified by silica gel column chromatography (dichloromethane/methanol (v/v)=1/10) to obtain compound 29-1.

MS (ESI) m/z (M+H)$^+$=778.2.

Step 2: Preparation of Compound 29-2

Step 3: Preparation of Compound 29

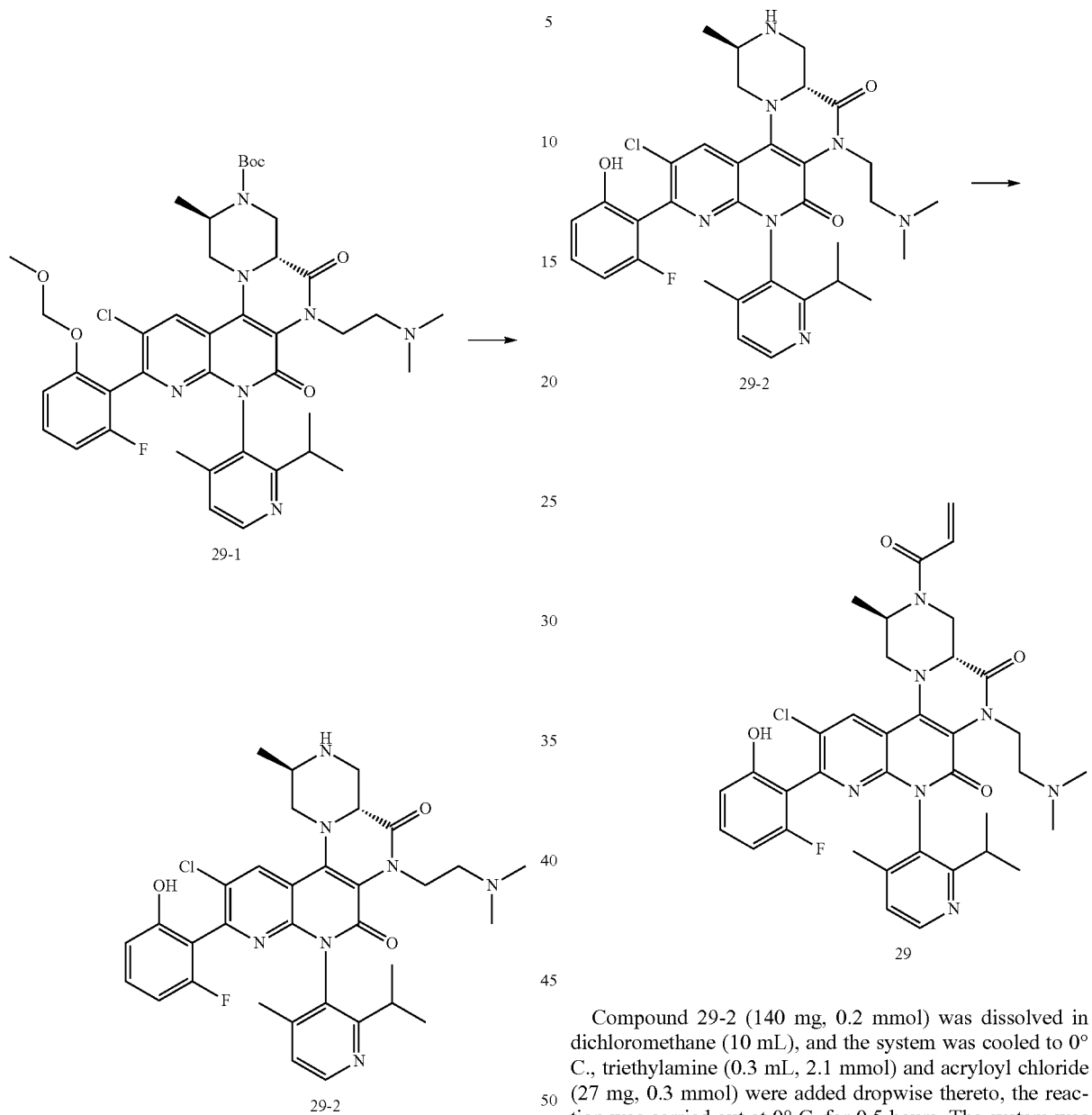

Compound 29-1 (150 mg, 0.2 mmol), hydrochloric acid (6N, 7 mL) were added to a mixed solution of methanol (0.6 mL) and tetrahydrofuran (6 mL). The system was heated to 55° C. and stirred for 10 min. The system was concentrated to obtain crude product compound 29-2, which was directly used in the next reaction without further purification.

MS (ESI) m/z (M+H)$^+$=634.2.

Compound 29-2 (140 mg, 0.2 mmol) was dissolved in dichloromethane (10 mL), and the system was cooled to 0° C., triethylamine (0.3 mL, 2.1 mmol) and acryloyl chloride (27 mg, 0.3 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (20 mL) and water (20 mL); and the organic phase was dried over anhydrous sodium sulfate, filtered, and the filtrate was concentrated to obtain a crude product, the crude product was purified by high performance liquid chromatography (separation conditions: chromatographic column Welch Xtimate® C18 21.2×250 mm, 10 µm; column temperature: 25° C., mobile phase: water (10 mM/L NH$_4$HCO$_3$)-acetonitrile; acetonitrile 40%-60% 9 min; flow rate 30 mL/min) to obtain compound 29.

MS (ESI) m/z (M+H)$^+$=688.2.

Step 4: Preparation of Compounds 29A and 29B

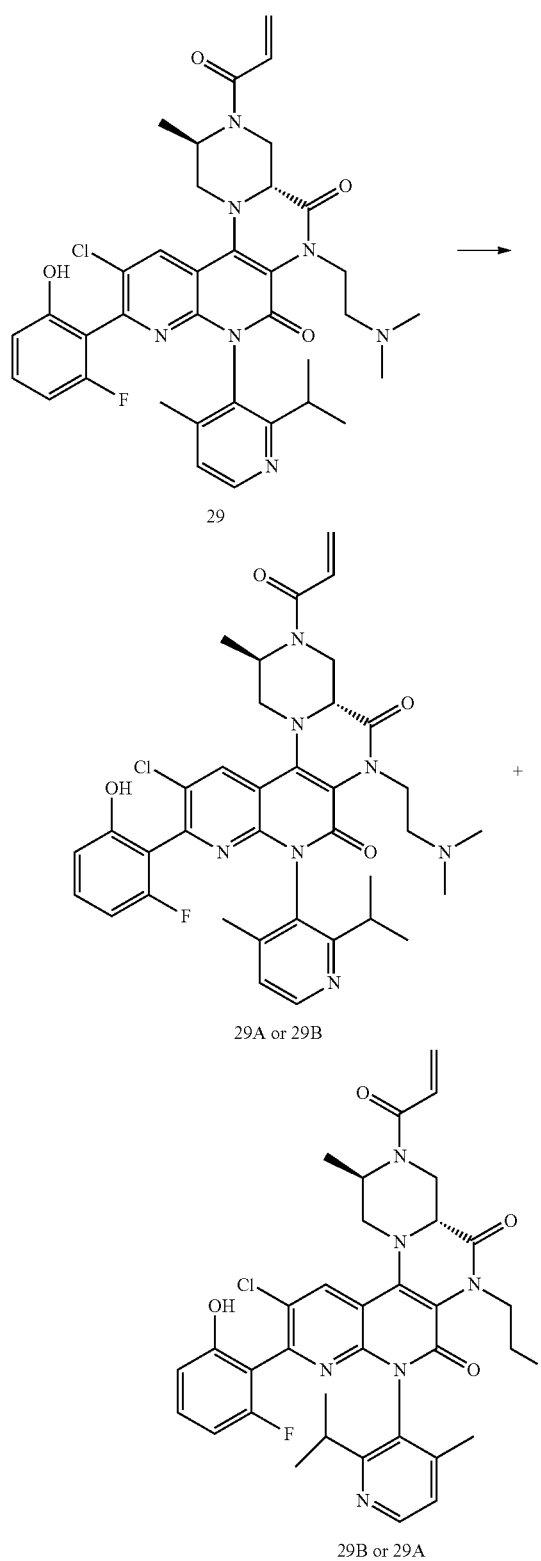

29

29A or 29B 29B or 29A

Diastereoisomeric compound 29 was purified by SFC («Column_3»; mobile phase: [CO$_2$-ethanol (0.1% ammonia)]; ethanol %: 25%; flow rate: 60 mL/min; column temperature: 38° C.). After concentration, compound 29A and compound 29B were obtained.

Compound 29A:
$^1$H NMR (400 MHz, DMSO-d$_6$) δ 10.06 (brs, 1H), 8.37 (d, J=4.9 Hz, 1H), 8.18 (s, 1H), 7.29-7.05 (m, 2H), 6.97 (dd, J=16.8, 10.6 Hz, 0.75H), 6.79 (dd, J=16.7, 10.7 Hz, 0.25H), 6.69-6.46 (m, 2H), 6.07 (dd, J=16.8, 2.5 Hz, 1H), 5.68 (dd, J=10.5, 2.4 Hz, 1H), 4.95 (d, J=13.9 Hz, 0.25H), 4.82-4.66 (m, 0.75H), 4.54 (d, J=14.0 Hz, 1H), 4.40-4.12 (m, 2H), 3.94 (dd, J=20.5, 4.4 Hz, 1H), 3.68 (dd, J=14.2, 4.4 Hz, 1H), 3.14-2.90 (m, 1H), 2.43-2.34 (m, 2H), 2.27-2.08 (m, 2H), 1.97-1.82 (m, 9H), 1.56-1.45 (m, 3H), 0.97 (dd, J=6.6, 2.2 Hz, 3H), 0.78 (t, J=6.0 Hz, 3H).

MS (ESI) m/z (M+H)$^+$=688.3.

SFC 100% ee. Retention time was 3.559 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Compound 29B:
$^1$H NMR (400 MHz, DMSO-d$_6$) δ 10.18 (brs, 1H), 8.45 (d, J=4.9 Hz, 1H), 8.26 (s, 1H), 7.29-7.20 (m, 2H), 7.04 (dd, J=16.8, 10.4 Hz, 0.75H), 6.86 (dd, J=17.6, 10.4 Hz, 0.25H), 6.72-6.60 (m, 2H), 6.14 (d, J=16.4 Hz, 1H), 5.75 (d, J=10.7 Hz, 1H), 5.03 (d, J=13.8 Hz, 0.25H), 4.80 (d, J=7.8 Hz, 0.75H), 4.61 (d, J=14.1 Hz, 1H), 4.43-4.30 (m, 1H), 4.28-4.15 (m, 1H), 4.04-3.89 (m, 1H), 3.75 (dd, J=14.5, 4.4 Hz, 1H), 3.28-3.10 (m, 2H), 2.75-2.65 (m, 1H), 2.39-2.28 (m, 1H), 2.28-2.17 (m, 1H), 2.06-1.96 (m, 6H), 1.81 (d, J=9.5 Hz, 3H), 1.53 (d, J=6.8 Hz, 3H), 1.11 (d, J=6.9 Hz, 3H), 0.95 (d, J=6.6 Hz, 3H).

MS (ESI) m/z (M+H)$^+$=688.3.

HPLC retention time was 5.269 min.

Separation conditions: chromatographic column: Waters XBridge 4.6*100 mm, 3.5 μm; column temperature: 40° C.; mobile phase: water (10 mM ammonium bicarbonate)-acetonitrile; acetonitrile: 5%-95% 7 min; flow rate: 1.2 mL/min. SFC 100% ee. Retention time was 4.349 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Embodiment 30: Preparation of Compound 30

Step 1: Preparation of Compound 30-1

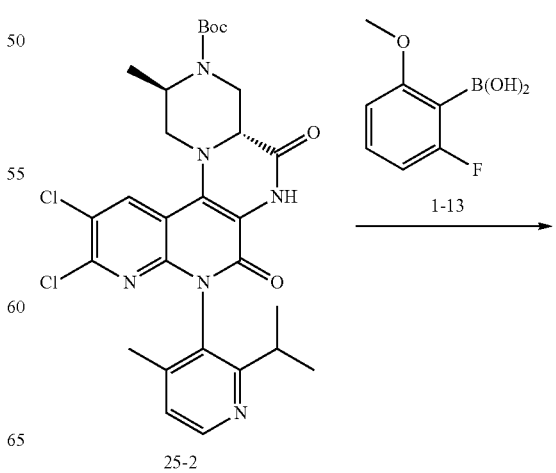

25-2

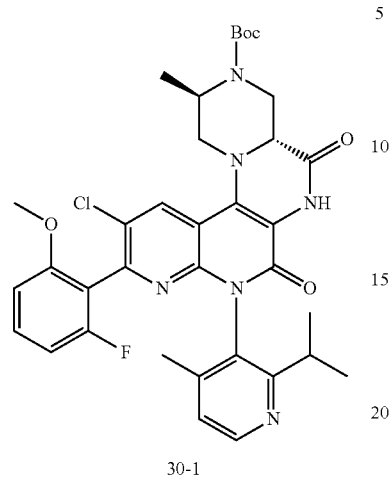

30-1

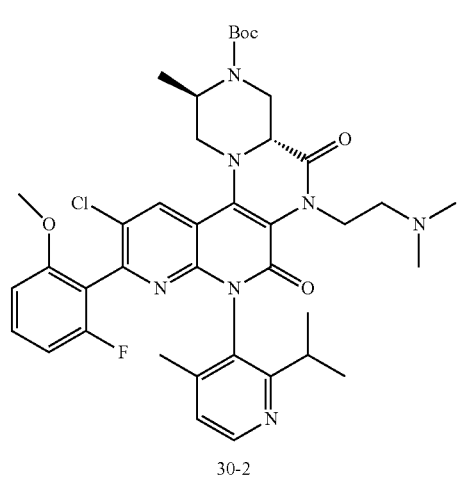

30-2

Compound 25-2 (286 mg, 0.5 mmol), compound 1-13 (170 mg, 1 mmol), tetrakis(triphenylphosphine)palladium (150 mg, 0.125 mmol) and potassium carbonate (138 mg, 1 mmol) were dissolved in a mixed solution of dioxane (18 mL) and water (1.8 mL). Under nitrogen atmosphere, the system was heated to 100° C. and stirred for 2 hours. The system was concentrated to obtain a crude product, the crude product was purified by medium pressure column chromatography (ethyl acetate/petroleum ether (v/v)=0-50%) to obtain compound 30-1.

MS (ESI) m/z (M+H)$^+$=677.2.

Compound 30-1 (700 mg, 1 mmol) and cesium carbonate (977 mg, 3 mmol) were dissolved in N,N-dimethylformamide (20 mL), and compound 26-1 (432 mg, 3 mmol) was added thereto at room temperature (25° C.). After the addition was completed, under nitrogen atmosphere, the system was heated to 120° C. and stirred for 2 hours. The system was filtered and concentrated to obtain a crude product, the crude product was purified by silica gel column chromatography (dichloromethane/methanol (v/v)=1/10) to obtain compound 30-2.

MS (ESI) m/z (M+H)$^+$=748.2.

Step 2: Preparation of Compound 30-2

Step 3: Preparation of Compound 30-3

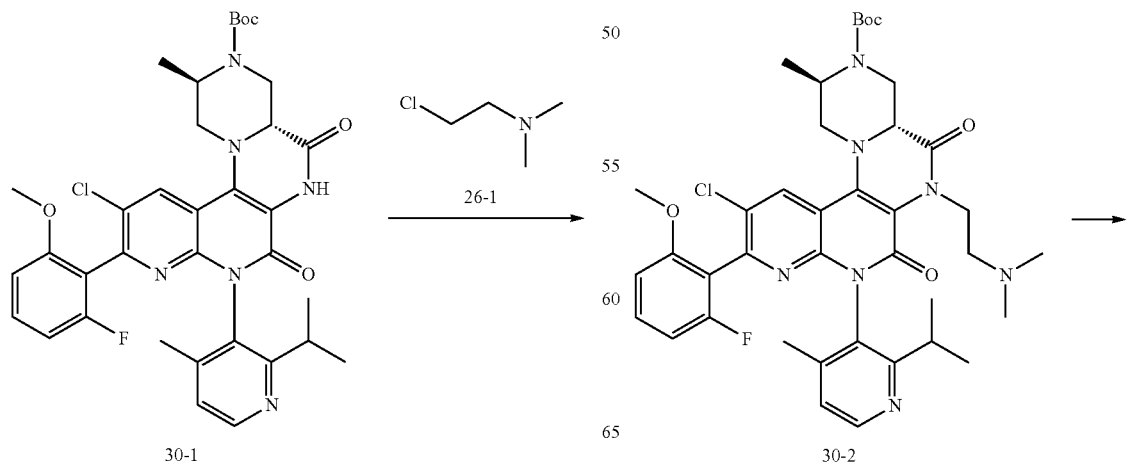

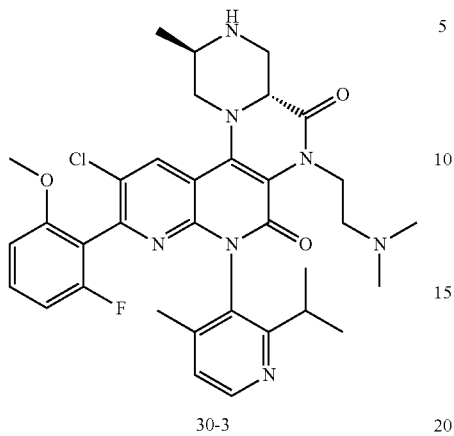

30-3

Compound 30-2 (80 mg, 0.107 μmol) was dissolved in dichloromethane (10 mL), and trifluoroacetic acid (1 mL) was added thereto, and the reaction was stirred at 25° C. for 1 hour. The reaction mixture was concentrated to obtain compound 30-3, which was directly used in the next reaction without further purification.

MS (ESI) m/z (M+H)$^+$=648.4.

Step 4: Preparation of Compound 30

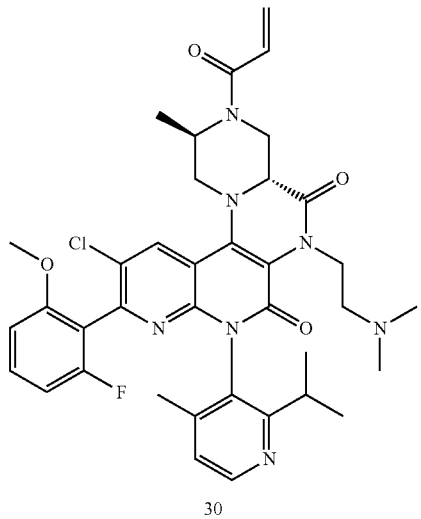

30

Compound 30-3 (70 mg, 0.107 mmol) was dissolved in dichloromethane (10 mL), and the system was cooled to 0° C., triethylamine (0.1 mL, 0.7 mmol) and acryloyl chloride (14 mg, 0.2 mmol) were added dropwise thereto, the reaction was carried out at 0° C. for 0.5 hours. The system was quenched with water, the mixture was extracted with dichloromethane (10 mL) and water (10 mL); and the organic phase was dried over anhydrous sodium sulfate, filtered, and the filtrate was concentrated to obtain a crude product, the crude product was purified by high performance liquid chromatography (separation conditions: chromatographic column Welch Xtimate® C18 21.2×250 mm, 10 μm; column temperature: 25° C., mobile phase: water (10 mM/L NH$_4$HCO$_3$)-acetonitrile; acetonitrile 45%-75% 9 min; flow rate 30 mL/min) to obtain compound 30.

MS (ESI) m/z (M+H)$^+$=702.2.

Step 5: Preparation of Compounds 30A and 30B

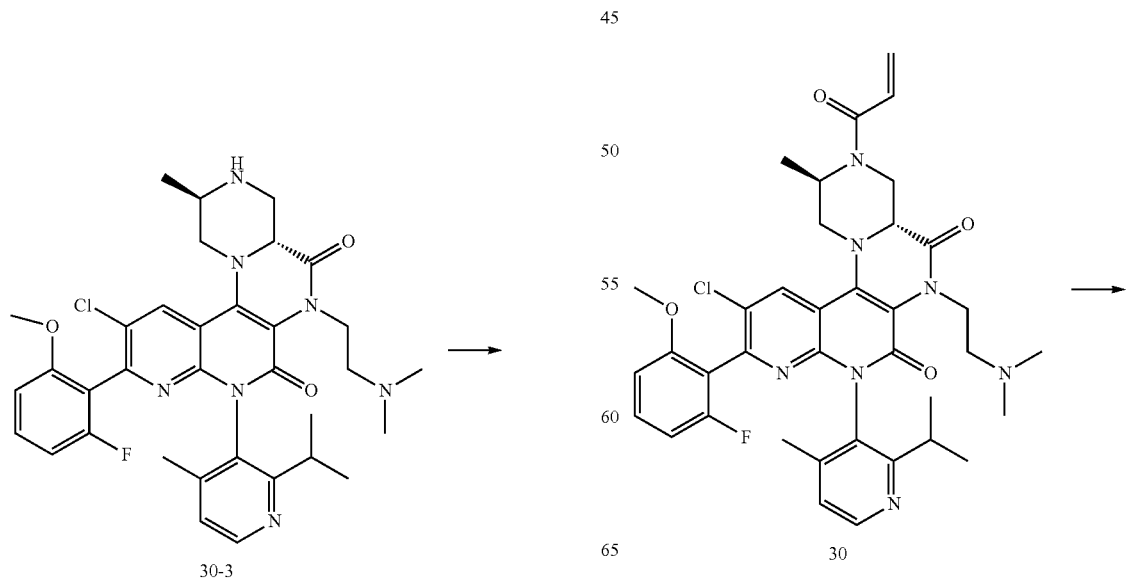

30-3

30

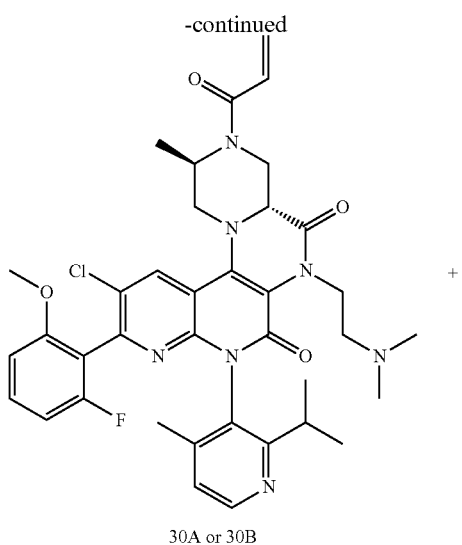

30A or 30B

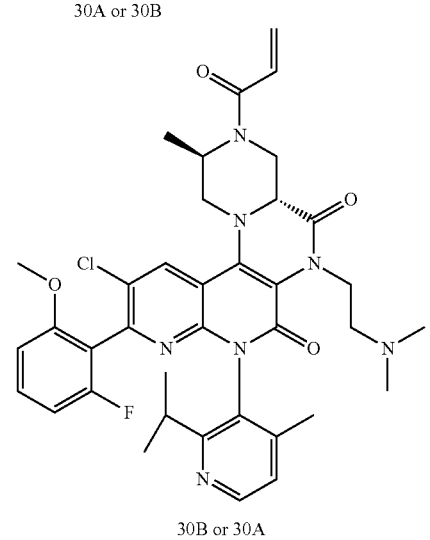

30B or 30A

Diastereoisomeric compound 30 was purified by SFC («Column_3»; mobile phase: [CO$_2$-ethanol (0.1% ammonia)]; ethanol %: 35%; flow rate: 80 mL/min; column temperature: 38° C.). After concentration, compound 30A and compound 30B were obtained.

Compound 30A:

$^1$H NMR (400 MHz, Chloroform-d) δ 8.51 (t, J=4.5 Hz, 1H), 8.25 (s, 1H), 7.45-7.27 (m, 1H), 7.18-6.98 (m, 2H), 6.88-6.61 (m, 2H), 6.34 (dd, J=16.9, 1.9 Hz, 1H), 5.79 (dt, J=10.7, 1.7 Hz, 1H), 5.07 (d, J=7.3 Hz, 1H), 4.77 (d, J=13.9 Hz, 1H), 4.64-4.37 (m, 1H), 3.80 (dt, J=14.1, 4.7 Hz, 1H), 3.68 (d, J=26.8 Hz, 3H), 3.34-3.02 (m, 2H), 2.48 (dt, J=13.7, 7.1 Hz, 1H), 2.30-2.16 (m, 4H), 2.02 (d, J=1.7 Hz, 3H), 1.75-1.46 (m, 9H), 1.19 (t, J=6.5 Hz, 3H), 0.95 (dd, J=12.9, 6.7 Hz, 3H).

MS (ESI) m/z (M+H)$^+$=702.3.

SFC 100% ee. Retention time was 3.619 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Compound 30B:

$^1$H NMR (400 MHz, Chloroform-d) δ 8.51 (dd, J=4.9, 1.9 Hz, 1H), 8.26 (s, 1H), 7.32 (td, J=8.4, 6.6 Hz, 1H), 7.15-6.98 (m, 2H), 6.83-6.66 (m, 2H), 6.34 (dd, J=16.9, 2.0 Hz, 1H), 5.79 (dt, J=10.8, 1.5 Hz, 1H), 5.13-5.01 (m, 1H), 4.77 (d, J=14.0 Hz, 1H), 4.53-4.35 (m, 1H), 3.79 (dt, J=14.1, 4.3 Hz, 1H), 3.69 (d, J=10.7 Hz, 3H), 3.43-3.17 (m, 2H), 2.70 (h, J=6.7 Hz, 1H), 2.48-2.02 (m, 4H), 1.97-1.83 (m, 3H), 1.73-1.52 (m, 9H), 1.21 (dd, J=6.8, 5.0 Hz, 3H), 1.05 (dd, J=8.0, 6.7 Hz, 3H).

MS (ESI) m/z (M+H)$^+$=702.3.

SFC 100% ee. Retention time was 4.635 min.

Separation conditions: chromatographic column: «Column_2»; mobile phase: [CO$_2$-ethanol (0.05% DEA)]; ethanol %: 5%-40% 5 min, 40% 2.5 min, 5% 2.5 min; flow rate: 2.5 mL/min; column temperature: 35° C.

Embodiment 31: Preparation of Compound 31

Step 1: Preparation of Compound 31-2

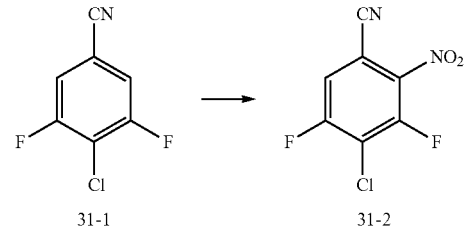 [SMILES: N#Cc1cc(F)c(Cl)c(F)c1 ; N#Cc1cc(F)c(Cl)c(F)c1[N+](=O)[O-]]

31-1    31-2

Potassium nitrate (10.49 g, 103.72 mmol) was dissolved in concentrated sulfuric acid (80 mL), and the system was stirred at room temperature (20° C.) for 1 hour, then compound 31-1 (10 g, 57.62 mmol) was added thereto in batches, after the addition was completed, and the system was heated to 80° C. and stirred for 2 hours. The system was quenched by adding ice water (200 mL) and filtered, and the filter cake was washed with water (20 mL×2) and dried to obtain compound 31-2.

Step 2: Preparation of Compound 31-3

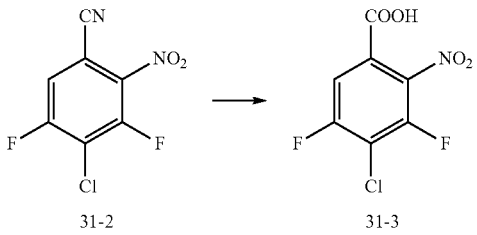 [SMILES: N#Cc1cc(F)c(Cl)c(F)c1[N+](=O)[O-] ; O=C(O)c1cc(F)c(Cl)c(F)c1[N+](=O)[O-]]

31-2    31-3

Compound 31-2 (12.6 g, 57.65 mmol) was dissolved in 20% sulfuric acid aqueous solution (200 mL), and the system was heated to 85° C. and stirred for 16 hours. The system was cooled to room temperature (20° C.), diluted with water (1 L), extracted with ethyl acetate (2×500 mL); the organic phases were combined, dried over anhydrous sodium sulfate, filtered, and the filtrate was concentrated to obtain compound 31-3.

$^1$H NMR (400 MHz, DMSO-d$_6$) δ=7.77 (d, J=7.8 Hz, 1H).

Step 3: Preparation of Compound 31-4

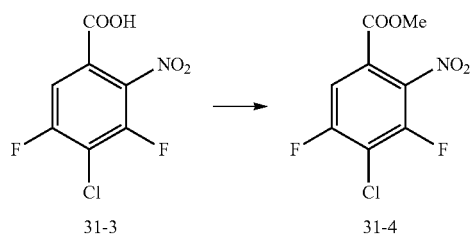 [SMILES: O=C(O)c1cc(F)c(Cl)c(F)c1[N+](=O)[O-] ; COC(=O)c1cc(F)c(Cl)c(F)c1[N+](=O)[O-]]

Compound 31-3 (13 g, 54.73 mmol) was dissolved in methanol (120 mL), thionyl chloride (26.04 g, 218.91 mmol, 15.88 mL) was added thereto. After the addition was completed, the system was heated to 70° C. and stirred for 16 hours. The system was cooled to room temperature (20° C.) and concentrated to obtain a crude product. The crude product was purified by medium pressure column chromatography (ethyl acetate/petroleum ether (v/v)=0-10%) to obtain compound 31-4.

Step 4: Preparation of Compound 31-5

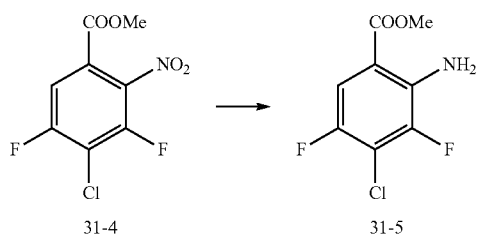 [SMILES: COC(=O)c1cc(F)c(Cl)c(F)c1[N+](=O)[O-] ; COC(=O)c1cc(F)c(Cl)c(F)c1N]

Compound 31-4 (6 g, 23.85 mmol) was dissolved in a mixed solvent of ethyl acetate (50 mL) and dichloromethane (50 mL), and stannous chloride dihydrate (26.91 g, 119.25 mmol) was added thereto. After the addition was completed, the system was stirred at room temperature (20° C.) for 16 hours. The system was filtered, and the filtrate was concentrated to obtain compound 31-5.

$^1$H NMR (400 MHz, CHLOROFORM-d) δ=7.50 (dd, J=2.3, 9.8 Hz, 1H), 5.74 (br s, 2H), 3.92 (s, 3H).

Step 5: Preparation of Compound 31-6

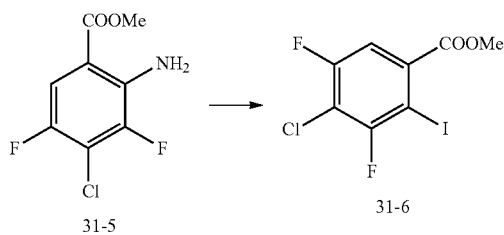 [SMILES: COC(=O)c1cc(F)c(Cl)c(F)c1N ; COC(=O)c1cc(F)c(Cl)c(F)c1I]

Compound 31-5 (8 g, 36.10 mmol), cuprous iodide (6.88 g, 36.10 mmol), and potassium iodide (11.99 g, 72.21 mmol) were dissolved in acetonitrile (100 mL), and tert-butyl nitrite (11.17 g, 108.31 mmol, 12.88 mL) was added thereto at 0° C. Under nitrogen atmosphere, the system was heated to 80° C. and stirred for 2 hours. The system was cooled to room temperature (20° C.), quenched by adding sodium thiosulfate aqueous solution (100 mL), diluted with water (100 mL), and extracted with ethyl acetate (100 mL×3); the organic phases were combined, and the organic phase was dried over anhydrous sodium sulfate, filtered and the filtrate was concentrated to obtain a crude product, which was purified by medium pressure column chromatography (ethyl acetate/petroleum ether (v/v)=0-7%) to obtain compound 31-6.

$^1$H NMR (400 MHz, DMSO-d6) δ=7.82-7.74 (m, 1H), 3.89 (s, 3H).

Step 6: Preparation of Compound 31-7

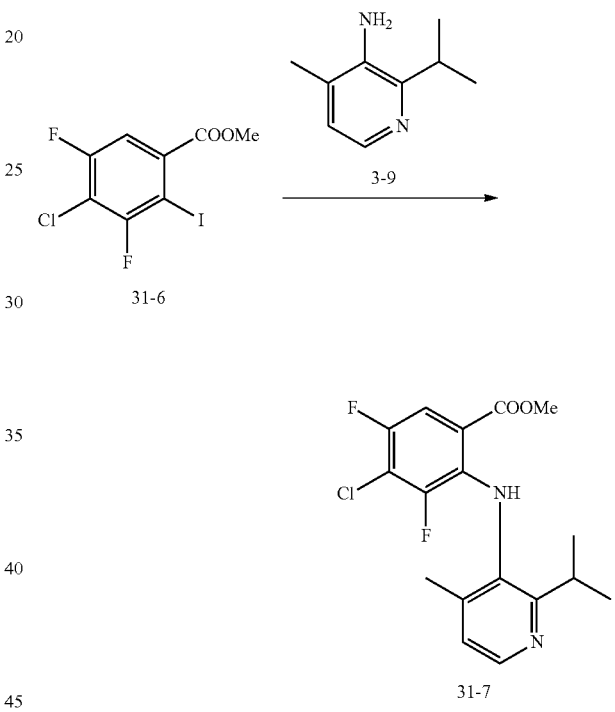

At room temperature (20° C.), compound 31-6 (7 g, 21.05 mmol), compound 3-9 (3.51 g, 23.37 mmol), Pd$_2$(dba)$_3$ (1.93 g, 2.11 mmol), Xantphos (1.22 g), 2.11 mmol), cesium carbonate (13.72 g, 42.11 mmol) were dissolved in toluene (100 mL), and under nitrogen atmosphere, the system was heated to 100° C. and stirred for 16 hours. The system was cooled to room temperature and concentrated, the residue was separated and extracted with water (50 mL) and ethyl acetate (30 mL×3), the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-7%) to obtain compound 31-7.

$^1$H NMR (400 MHz, DMSO-d6) δ=8.74-8.72 (m, 1H), 8.28-8.26 (m, 1H), 7.72-7.68 (m, 1H), 7.11-7.08 (m, 1H), 3.84 (s, 3H), 3.26-3.21 (m, 1H), 2.08 (s, 3H), 1.12-1.04 (m, 6H).

Step 7: Preparation of Compound 31-8

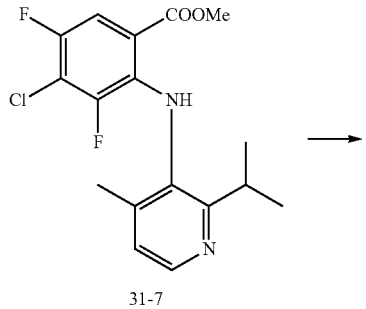

31-7

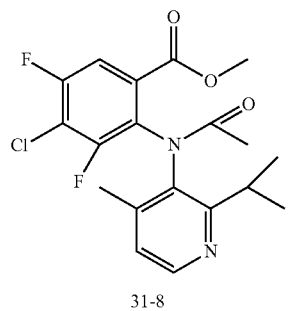

31-8

At 0° C., compound 31-7 (3 g, 8.46 mmol) was dissolved in N,N-dimethylformamide (30 mL), and sodium hydride (2.03 g, 50.74 mmol, 60% purity) was added thereto in batches, after the addition was completed, the reaction was carried out at 0° C. for 30 min. Acetyl chloride (3.98 g, 50.74 mmol, 3.62 mL) was added dropwise to the system at 0° C. After the addition was completed, under nitrogen atmosphere, the system was heated to room temperature (20° C.) and the reaction was carried out for 16 hours. The reaction was quenched by adding water (300 mL) to the system, and extracted with ethyl acetate (50 mL×2); the organic phases were combined, dried over anhydrous sodium sulfate, filtered and the filtrate was concentrated to obtain a crude product, the crude product was purified by medium pressure column chromatography (ethyl acetate/petroleum ether (v/v) =0-100%) to obtain compound 31-8.

MS (ESI) m/z (M+H)$^+$=397.0.

Step 8: Preparation of Compound 31-9

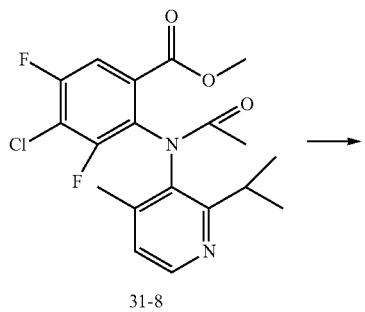

31-8

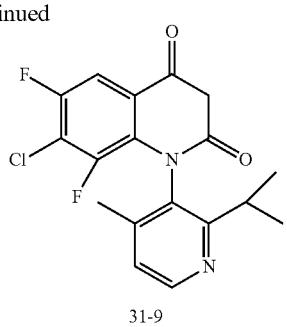

31-9

At room temperature (20° C.), compound 31-8 (1.5 g, 3.78 mmol) was dissolved in toluene (40 mL), and potassium tert-butoxide (1 M, 11.34 mL) was added thereto. After the addition was completed, under nitrogen atmosphere, the reaction was carried out at room temperature (20° C.) for 20 min. The reaction was quenched by adding water (10 mL) to the system, the pH was adjusted to neutral with 1 N hydrochloric acid; and the mixture was extracted with ethyl acetate (10 mL×3), the organic phase was dried over anhydrous sodium sulfate, filtered, and the filtrate was concentrated to obtain compound 31-9, which were used directly in the next reaction without further purification.

MS (ESI) m/z (M+H)$^+$=364.9.

Step 9: Preparation of Compound 31-10

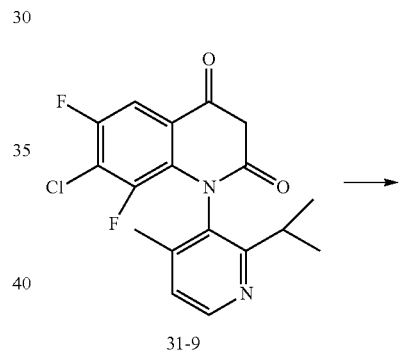

31-9

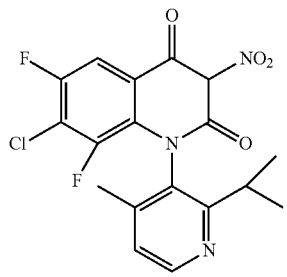

31-10

Compound 31-9 (1.2 g, 3.29 mmol) was dissolved in glacial acetic acid (15 mL), and nitric acid (2.49 g, 39.48 mmol, 1.78 mL) was added dropwise to the system at room temperature (20° C.). After the dropwise addition was completed, the system was heated to 80° C. and stirred for 2 hours. The system was cooled to room temperature, concentrated to remove most of the glacial acetic acid, and the remainder was poured into ice water (10 mL), precipitated, filtered, and the filter cake was washed with water and dried to obtain compound 31-10, which was used directly in the next step without further purification.

MS (ESI) m/z (M+H)$^+$=409.9.

Step 10: Preparation of Compound 31-11

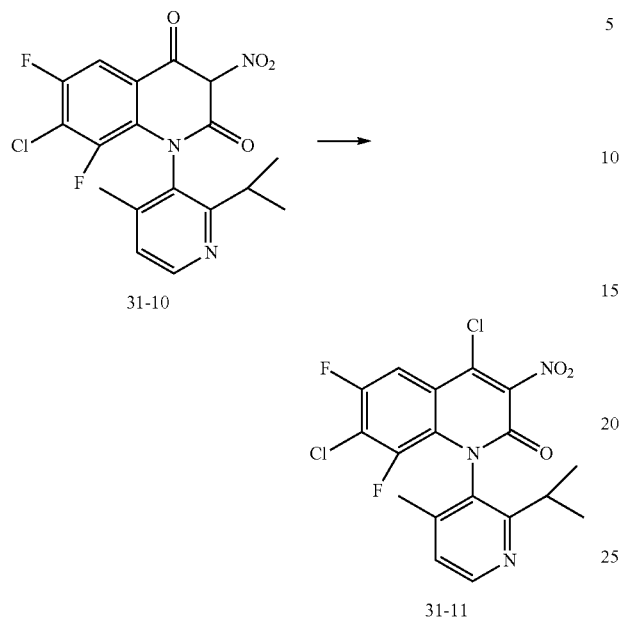

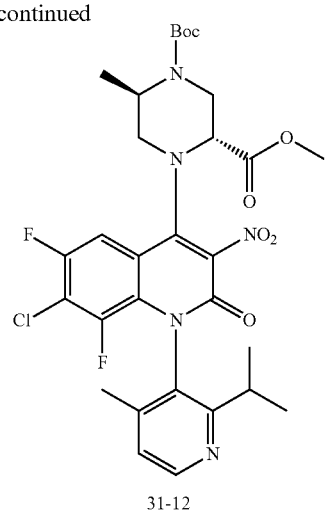

Compound 31-10 (0.9 g, 2.20 mmol) and N,N-diisopropylethylamine (851.59 mg, 6.59 mmol, 1.15 mL) were dissolved in acetonitrile (10 mL), and at room temperature (20° C.), phosphorus oxychloride (1.01 g, 6.59 mmol, 612.31 µL) was added thereto. After the addition was completed, the system was heated to 80° C. and stirred for 2 hours. The system was cooled to room temperature (20° C.), poured into water (20 mL) and extracted with ethyl acetate (3×10 mL). The organic phases were combined, dried over anhydrous sodium sulfate, filtered, and the filtrate was concentrated to obtain compound 31-11, which was directly used in the next reaction without further purification.

$^1$H NMR (400 MHz, CHLOROFORM-d) δ=8.64 (d, J=5.0 Hz, 1H), 7.89 (dd, J=2.0, 8.5 Hz, 1H), 7.18 (d, J=4.8 Hz, 1H), 2.69-2.58 (m, 1H), 2.12 (s, 3H), 1.26-1.12 (m, 6H).

Step 11: Preparation of Compound 31-12

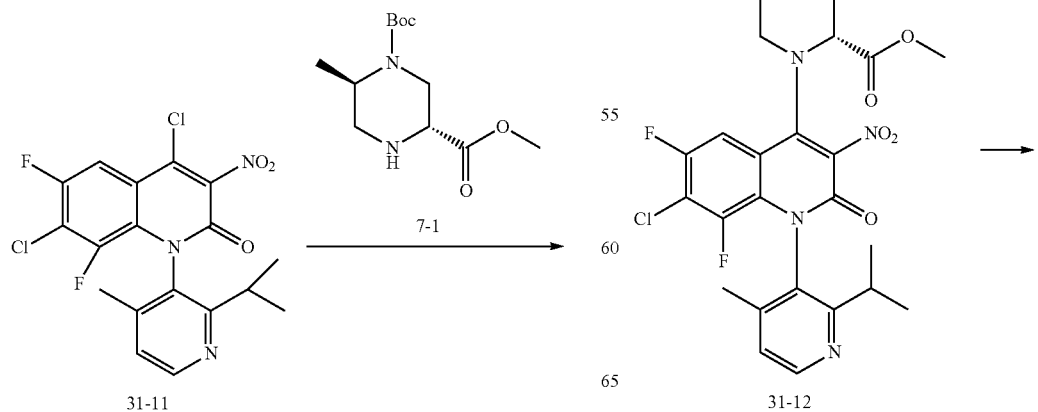

Compound 31-11 (0.8 g, 1.87 mmol), compound 7-1 (579.10 mg, 2.24 mmol), N,N-diisopropylethylamine (362.17 mg, 2.80 mmol, 488.10 µL) were dissolved in tetrahydrofuran (10 mL), and the system was heated to 70° C. and stirred for 20 hours. The system was concentrated to obtain a crude product. The crude product was purified by medium pressure column chromatography (ethyl acetate/petroleum ether (v/v)=0-40%) to obtain compound 31-12.

MS (ESI) m/z (M+H)$^+$=650.1.

$^1$H NMR (400 MHz, CHLOROFORM-d) δ=8.60 (dd, J=2.1, 4.9 Hz, 1H), 8.15-7.76 (m, 1H), 7.15 (dd, J=5.1, 6.7 Hz, 1H), 4.60-4.41 (m, 2H), 4.31 (br s, 1H), 4.00 (br s, 1H), 3.81 (d, J=1.0 Hz, 3H), 3.63-3.48 (m, 1H), 3.24-3.07 (m, 1H), 2.77-2.55 (m, 1H), 2.10-2.02 (m, 3H), 1.51 (d, J=1.3 Hz, 9H), 1.35 (t, J=6.0 Hz, 3H), 1.25-1.13 (m, 6H)

Step 12: Preparation of Compound 31-13

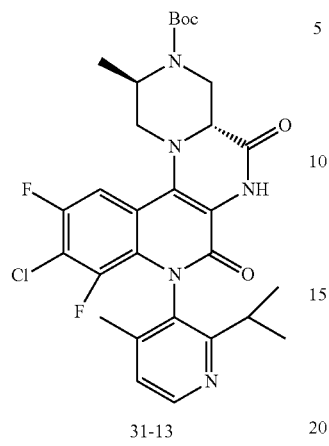

31-13

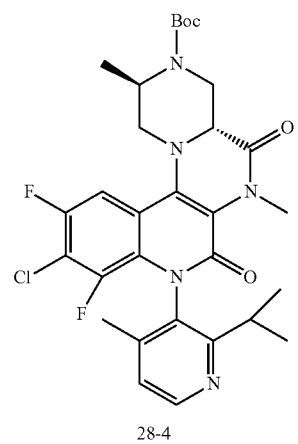

28-4

Compound 31-12 (0.9 g, 1.38 mmol) and iron powder (231.95 mg, 4.15 mmol) were dissolved in acetic acid (15 mL), and the system was heated to 85° C. and stirred for 1 hour under nitrogen atmosphere. The system was filtered with diatomite, the filtrate was concentrated, the residue was dissolved in ethyl acetate, washed with saturated sodium bicarbonate, the organic phase was dried with anhydrous sodium sulfate, filtered and the filtrate was concentrated to obtain compound 31-13. Which was directly used in the next reaction without further purification.

MS (ESI) m/z (M+H)$^+$=588.1.

Step 13: Preparation of Compound 28-4

Compound 31-13 (800 mg, 1.36 mmol) and potassium carbonate (376.04 mg, 2.72 mmol) were dissolved in acetone (10 mL), and methyl iodide (1.93 g, 13.60 mmol, 846.92 μL) was added thereto at room temperature (20° C.). After the addition was completed, under nitrogen atmosphere, the system was heated to 40° C. and stirred for 16 hours. The system was cooled to room temperature, filtered, and concentrated to obtain a crude product. The crude product was purified by medium pressure column chromatography (ethyl acetate/petroleum ether (v/v)=0-50%) to obtain compound 28-4.

$^1$H NMR (400 MHz, CHLOROFORM-d) δ=8.62 (d, J=5.0 Hz, 1H), 7.59 (br d, J=9.0 Hz, 1H), 7.17 (dd, J=4.8, 15.8 Hz, 1H), 4.90 (br d, J=12.3 Hz, 1H), 4.64-4.29 (m, 1H), 3.55-3.38 (m, 4H), 3.14-2.92 (m, 2H), 2.88-2.35 (m, 1H), 2.21-2.00 (m, 3H), 1.45-1.59 (m, 12H), 1.26-1.01 (m, 6H).

Step 14: Preparation of Compound 31-14

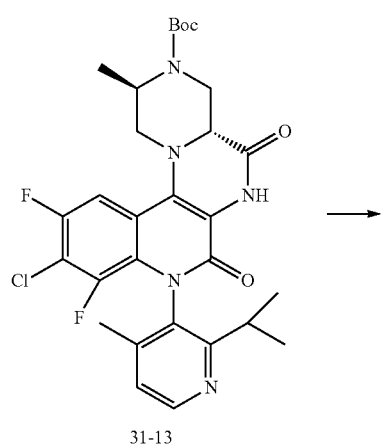

31-13

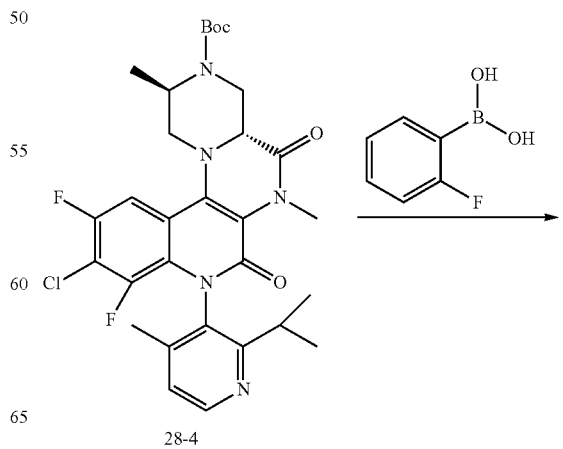

28-4

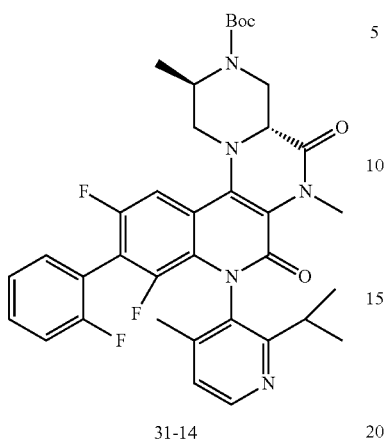

31-14

Compound 28-4 (100 mg, 166.09 μmol), o-fluorophenyl-boronic acid (46.48 mg, 332.19 μmol), methanesulfonato (2-dicyclohexylphosphino-2',6'-di-i-propoxy-1,1'-biphenyl)(2-amino-1,1'-biphenyl-2-yl) palladium(II) (13.89 mg, 16.61 μmol), 2-dicyclohexylphosphino-2',6'-di-i-propoxy-1,1'-biphenyl (7.75 mg, 16.61 μmol) and potassium carbonate (45.91 mg, 332.19 μmol) were dissolved in a mixed solution of dioxane (1 mL) and water (0.1 mL). Under nitrogen atmosphere, the system was heated to 100° C. and stirred for 5 hours. The system was concentrated to obtain a crude product, the crude product was purified by medium pressure column chromatography (ethyl acetate/petroleum ether (v/v)=0-40%) to obtain compound 31-14.

MS (ESI) m/z (M+H)$^+$=662.6.

Step 15: Preparation of Compound 31-15

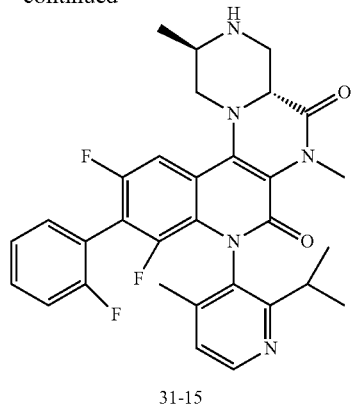

31-15

Compound 31-14 (100 mg, 151.12 μmol) was dissolved in dichloromethane (1 mL), dioxane solution of hydrochloride (5 M, 5 mL) was added thereto, after the addition was completed, and the system was stirred at room temperature (25° C.) for 2 hours. The system was concentrated to obtain compound 31-15, which was directly used in the next reaction without further purification.

MS (ESI) m/z (M+H)$^+$=562.1.

Step 16: Preparation of Compound 31

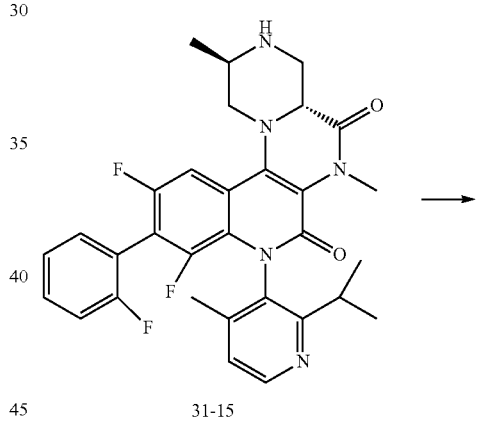

31-15

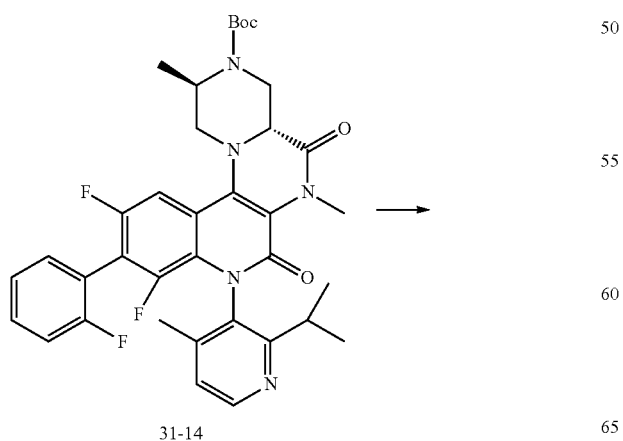

31-14

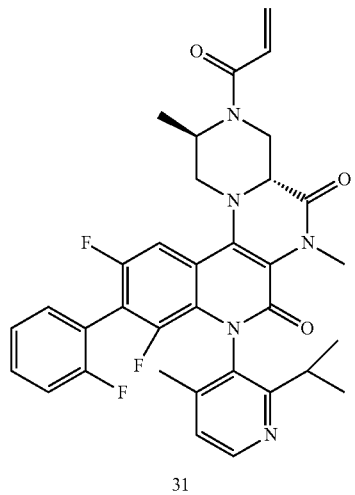

31

Compound 31-15 (90 mg, 150.49 μmol, hydrochloride) was dissolved in tetrahydrofuran (5 mL) and sodium bicarbonate (63.21 mg, 752.44 μmol) aqueous solution (5 mL), and tetrahydrofuran solution of acrylic anhydride (0.5 M, 361.17 μL) was added dropwise thereto. After the addition was completed, the reaction was carried out at room temperature (20° C.) for 1 hour. The system was quenched with methanol (0.1 mL) and extracted with ethyl acetate (5 mL), the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 46%-76% 9 min) to obtain compounds 31.

MS (ESI) m/z (M+H)$^+$=616.4.

Step 17: Preparation of Compounds 31A and 31B

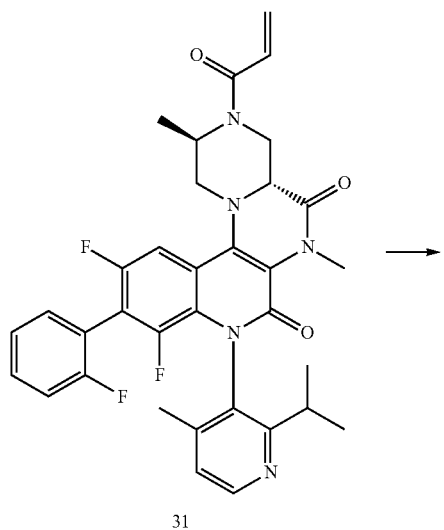

31

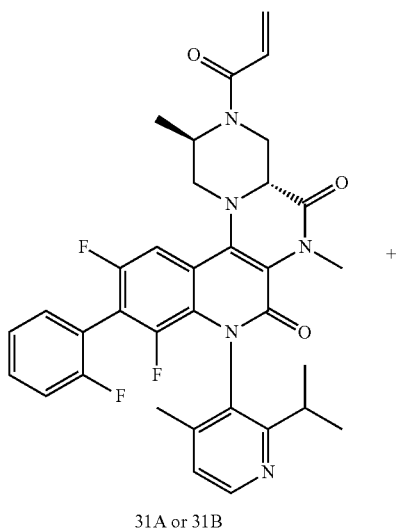

31A or 31B

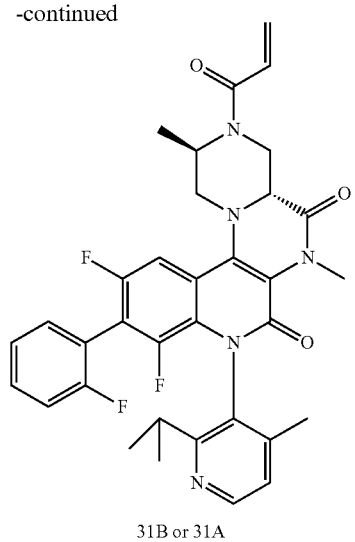

31B or 31A

Diastereoisomeric compound 31 was purified by SFC (Phenomenex-Cellulose-2 (250 mm*30 mm, 10 μm); mobile phase: [CO$_2$-methanol (0.1% ammonia)]; methanol %: 50%). After concentration, compound 31A and compound 31B were obtained.

Compound 31A:
$^1$H NMR (400 MHz, METHANOL-d$_4$) δ=8.48 (d, J=4.8 Hz, 1H), 7.74 (d, J=8.5 Hz, 1H), 7.49 (s, 1H), 7.41-7.12 (m, 5H), 6.33-6.18 (m, 1H), 5.90-5.74 (m, 1H), 4.78 (m, 2H), 4.04-3.85 (m, 2H), 3.52-3.45 (m, 4H), 3.04-2.87 (m, 1H), 2.58-2.52 (m, 1H), 2.23 (s, 3H), 1.77-1.63 (m, 3H), 1.20-1.03 (m, 6H).

MS (ESI) m/z (M+H)$^+$=616.2

HPLC retention time was 4.12 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 5.115 min.

Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Compound 31B:
$^1$H NMR (400 MHz, METHANOL-d$_4$) δ=8.47 (d, J=4.8 Hz, 1H), 7.75 (d, J=9.5 Hz, 1H), 7.56-7.47 (m, 1H), 7.42-7.03 (m, 5H), 6.33-6.22 (m, 1H), 5.88-5.77 (m, 1H), 4.82-4.50 (m, 2H), 4.01-3.85 (m, 2H), 3.53-4.35 (m, 4H), 3.09-2.89 (m, 2H), 2.00 (d, J=6.0 Hz, 3H), 1.76-1.64 (m, 3H), 1.29-1.13 (m, 6H).

MS (ESI) m/z (M+H)$^+$=616.2.

HPLC retention time was 4.11 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 7.223 min Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Embodiment 32: Preparation of Compound 32

Step 1: Preparation of Compound 32-2

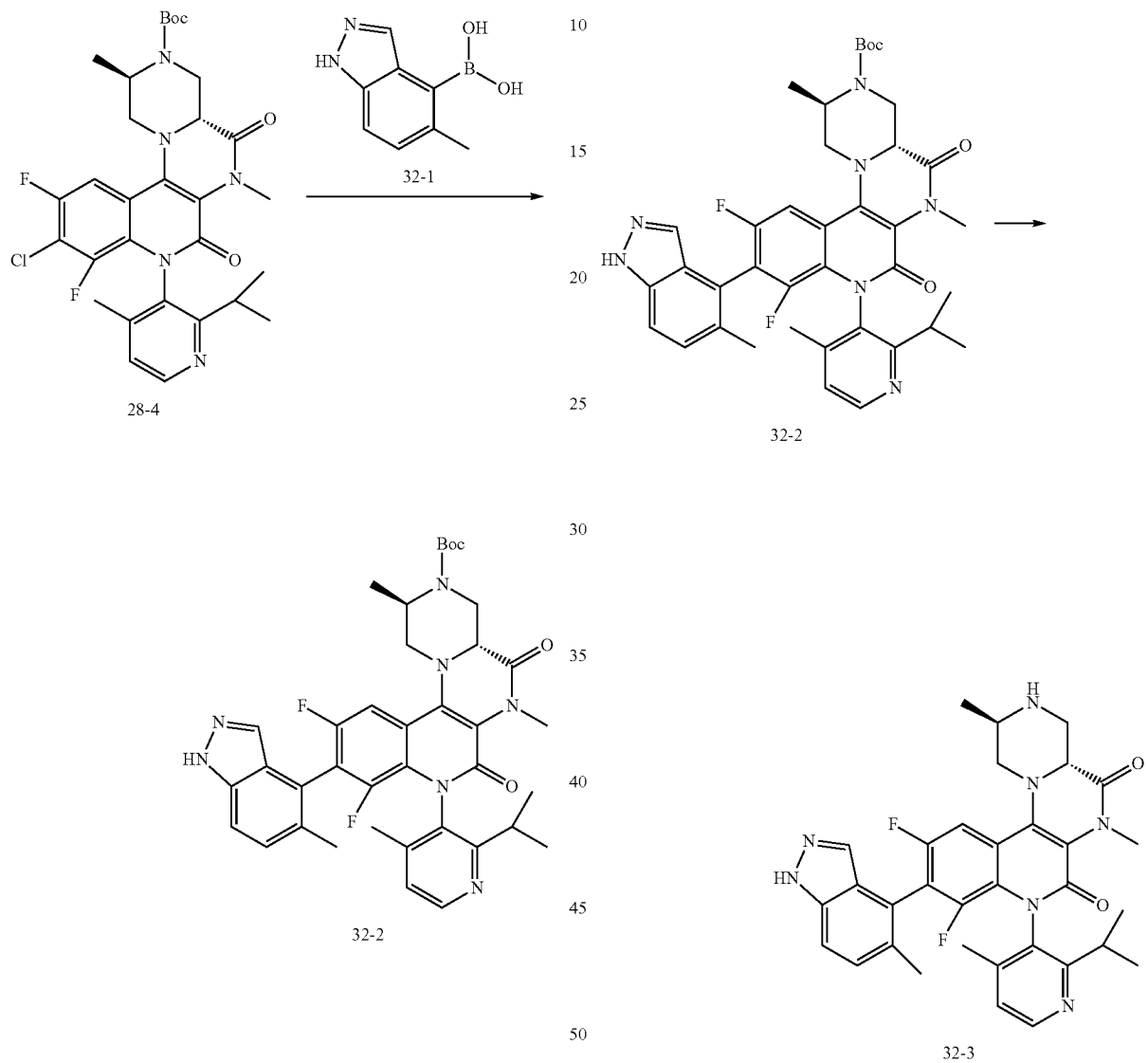

Compound 28-4 (120 mg, 199.31 μmol), compound 32-1 (70.15 mg, 398.62 μmol), methanesulfonato (2-dicyclohexylphosphino-2',6'-di-i-propoxy-1,1'-biphenyl)(2-amino-1,1'-biphenyl yl) palladium(II) (16.67 mg, 19.93 μmol), 2-dicyclohexylphosphino-2',6'-di-i-propoxy-1,1'-biphenyl (9.30 mg, 19.93 μmol) and potassium carbonate (55.09 mg, 398.62 μmol) were dissolved in a mixed solution of dioxane (1 mL) and water (0.1 mL). Under nitrogen atmosphere, the system was heated to 100° C. and stirred for 5 hours. The system was concentrated to obtain a crude product, the crude product was purified by medium pressure column chromatography (ethyl acetate/petroleum ether (v/v)=0-60%) to obtain compound 32-2.

MS (ESI) m/z (M+H)$^+$=698.3.

Step 2: Preparation of Compound 32-3

Compound 32-2 (102 mg, 146.18 μmol) was dissolved in dichloromethane (1 mL), dioxane solution of hydrochloride (5 M, 5 mL) was added thereto, after the addition was completed, and the system was stirred at room temperature (25° C.) for 2 hours. The system was concentrated to obtain compound 32-3, which was directly used in the next reaction without further purification.

MS (ESI) m/z (M+H)$^+$=598.1.

Step 3: Preparation of Compound 32

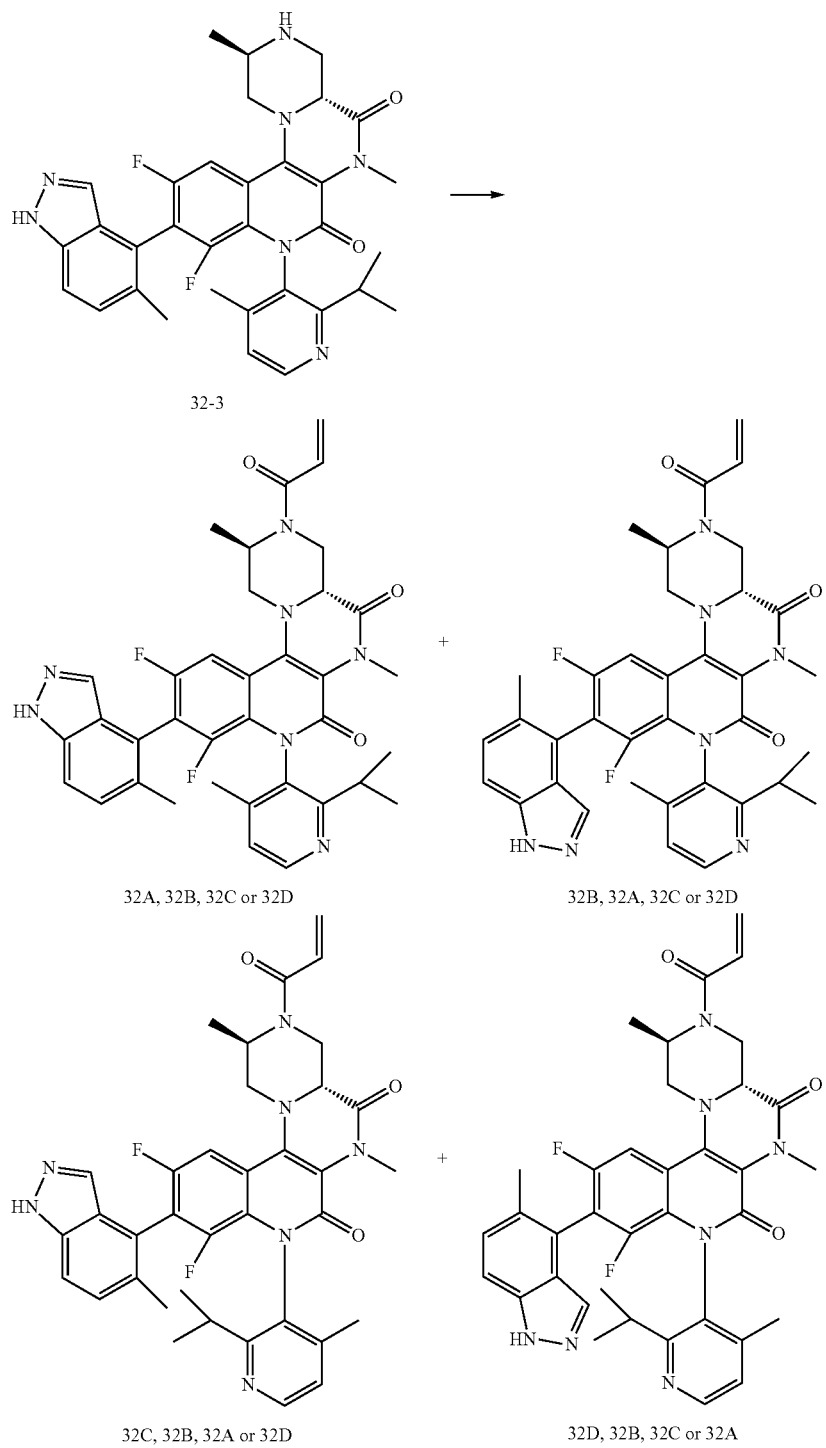

32-3

32A, 32B, 32C or 32D 32B, 32A, 32C or 32D 32C, 32B, 32A or 32D 32D, 32B, 32C or 32A

Compound 32-3 (92 mg, 145.08 μmol, hydrochloride) was dissolved in tetrahydrofuran (5 mL) and sodium bicarbonate (121.88 mg, 1.45 mmol) aqueous solution (5 mL), and tetrahydrofuran solution of acrylic anhydride (0.5 M, 377.21 μL) was added dropwise thereto. After the addition was completed, the reaction was carried out at room temperature (20° C.) for 2 hours. The system was quenched with methanol (0.1 mL) and extracted with ethyl acetate (5 mL×2), the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 39%-69% 9 min) to obtain compounds 32A, 32B, 32C and 32D.

Compound 32A:

$^1$H NMR (400 MHz, METHANOL-$d_4$) δ=8.41 (d, J=5.0 Hz, 1H), 7.82 (d, J=8.0 Hz, 1H), 7.55 (d, J=9.0 Hz, 1H), 7.46 (s, 1H), 7.37 (d, J=8.5 Hz, 1H), 7.28 (d, J=5.3 Hz, 1H), 7.20-6.74 (m, 1H), 6.27 (d, J=18.8 Hz, 1H), 5.90-5.74 (m, 1H), 4.82-4.50 (m, 2H), 4.07-3.91 (m, 2H), 3.52-3.45 (m, 4H), 2.99-2.60 (m, 2H), 2.23 (s, 1H), 2.18 (s, 3H), 1.78-1.65 (m, 3H), 1.20-0.97 (m, 6H).

MS (ESI) m/z (M+H)$^+$=652.2.

HPLC retention time was 3.49 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min Compound 32B:

$^1$H NMR (400 MHz, METHANOL-$d_4$) δ=8.42 (d, J=4.8 Hz, 1H), 7.82 (d, J=8.0 Hz, 1H), 7.55 (d, J=8.8 Hz, 1H), 7.48 (s, 1H), 7.37 (d, J=8.5 Hz, 1H), 7.23 (d, J=4.8 Hz, 1H), 7.20-6.80 (m, 1H), 6.33-6.24 (m, 1H), 5.88-5.79 (m, 1H), 4.82-4.50 (m, 2H), 4.04-3.85 (m, 2H), 3.54-3.37 (m, 4H), 3.10-2.90 (m, 2H), 2.19 (s, 3H), 2.05 (s, 3H), 1.77-1.66 (m, 3H), 1.27-1.12 (m, 6H).

MS (ESI) m/z (M+H)$^+$=652.2.

HPLC retention time was 3.53 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 32C:

$^1$H NMR (400 MHz, METHANOL-$d_4$) δ=8.43 (d, J=5.0 Hz, 1H), 7.80 (d, J=9.5 Hz, 1H), 7.59-7.48 (m, 2H), 7.38 (d, J=8.5 Hz, 1H), 7.25 (d, J=5.3 Hz, 1H), 7.21-6.83 (m, 1H), 6.29-6.25 (m, 1H), 5.88-5.78 (m, 1H), 4.82-4.50 (m, 2H), 4.03-3.86 (m, 2H), 3.54-3.39 (m, 4H), 3.15-2.90 (m, 2H), 2.18 (s, 3H), 2.01 (s, 3H), 1.77-1.66 (m, 3H), 1.30-1.07 (m, 6H).

MS (ESI) m/z (M+H)$^+$=652.2.

HPLC retention time was 3.66 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 32D:

$^1$H NMR (400 MHz, METHANOL-$d_4$) δ=8.42 (d, J=5.0 Hz, 1H), 7.80 (d, J=10.0 Hz, 1H), 7.58-7.50 (m, 2H), 7.37 (d, J=8.5 Hz, 1H), 7.26 (d, J=4.8 Hz, 1H), 7.18-7.12 (m, 1H), 6.35-6.21 (m, 1H), 5.91-5.75 (m, 1H), 4.82-4.50 (m, 2H), 4.07-3.87 (m, 2H), 3.50-3.38 (m, 4H), 2.99-2.87 (m, 1H), 2.72-2.51 (m, 1H), 2.26 (s, 3H), 2.18 (s, 3H), 1.79-1.65 (m, 3H), 1.19-0.96 (m, 6H).

MS (ESI) m/z (M+H)$^+$=652.2.

HPLC retention time was 3.70 min

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Embodiment 33: Preparation of Compound 33

Step 1: Preparation of Compound 33-2

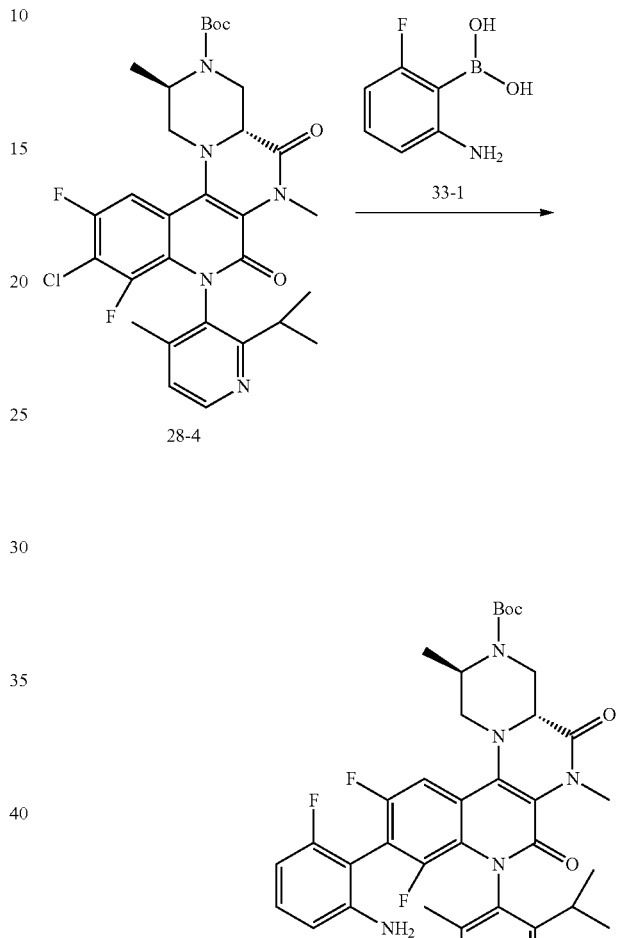

Compound 28-4 (100 mg, 166.09 μmol), compound 33-1 (68.15 mg, 249.14 μmol), methanesulfonato (2-dicyclohexylphosphino-2',6'-di-i-propoxy-1,1'-biphenyl)(2-amino-1,1'-biphenyl-2-yl) palladium(II) (13.89 mg, 16.61 μmol), 2-dicyclohexylphosphino-2',6'-di-i-propoxy-1,1'-biphenyl (7.75 mg, 16.61 μmol) and potassium carbonate (68.86 mg, 498.27 μmol) were dissolved in a mixed solution of dioxane (2 mL) and water (0.2 mL). Under nitrogen atmosphere, the system was heated to 100° C. and stirred for 5 hours. The system was concentrated to obtain a crude product, the crude product was purified by medium pressure column chromatography (ethyl acetate/petroleum ether (v/v)=0-30%) to obtain compound 33-2.

MS (ESI) m/z (M+H)$^+$=677.3.

Step 2: Preparation of Compound 33-3

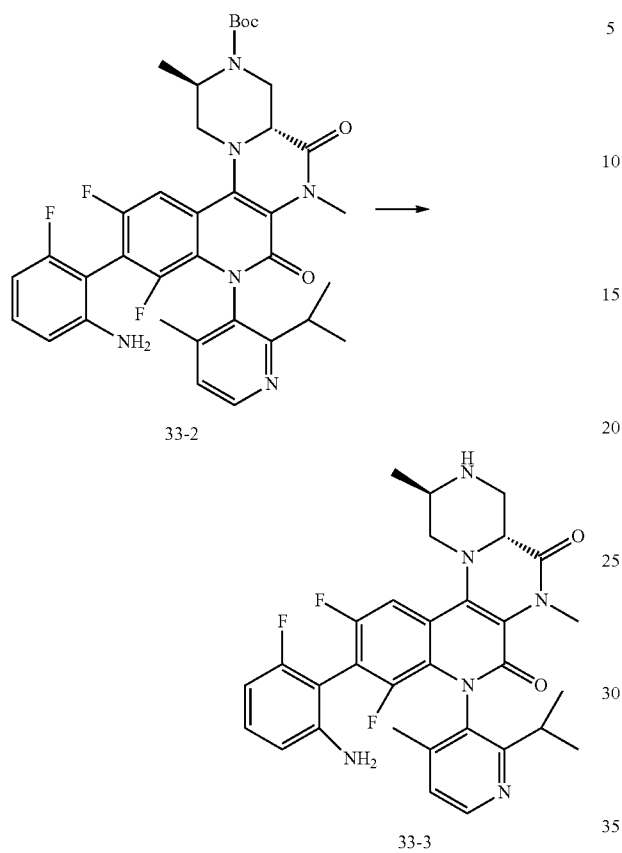

Compound 33-2 (95 mg, 140.38 μmol) was dissolved in dichloromethane (1 mL), dioxane solution of hydrochloride (5 M, 5 mL) was added thereto, after the addition was completed, and the system was stirred at room temperature (25° C.) for 2 hours. The system was concentrated to obtain compound 33-3, which was directly used in the next reaction without further purification.

MS (ESI) m/z (M+H)$^+$=577.2.

Step 3: Preparation of Compound 33

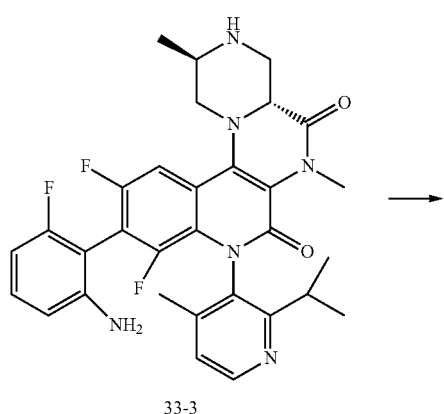

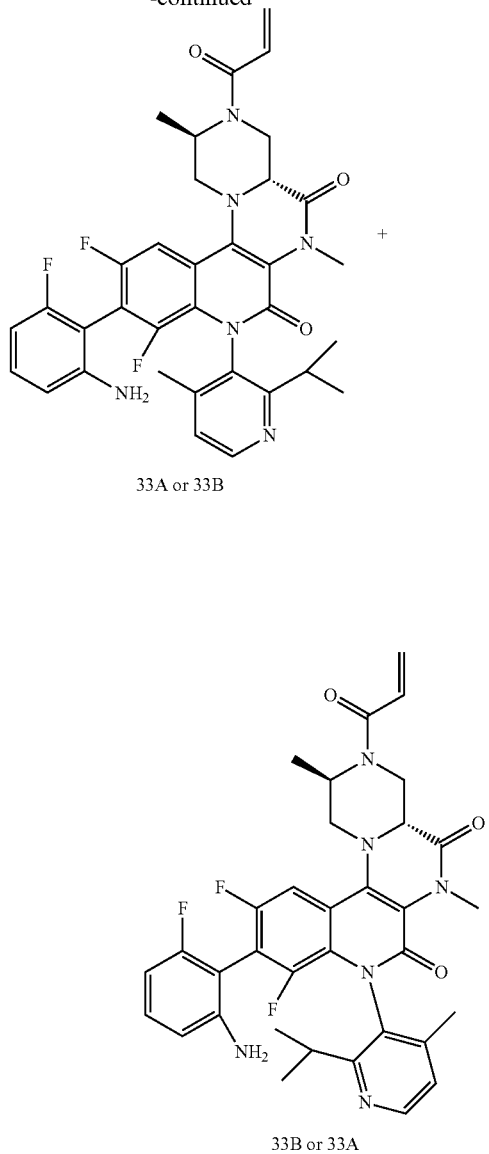

Compound 33-3 (90 mg, 146.80 μmol, hydrochloride) was dissolved in tetrahydrofuran (5 mL) and sodium bicarbonate (12.33 mg, 146.80 μmol) aqueous solution (5 mL), and tetrahydrofuran solution of acrylic anhydride (0.5 M, 352.32 μL) was added dropwise thereto. After the addition was completed, the reaction was carried out at room temperature (20° C.) for 2 hours. The system was quenched with methanol (0.1 mL) and extracted with ethyl acetate (5 mL×2), the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 42%-72% 9 min) to obtain compounds 33A and 33B.

Step 4: Preparation of Compounds 33A-1 and 33A-2

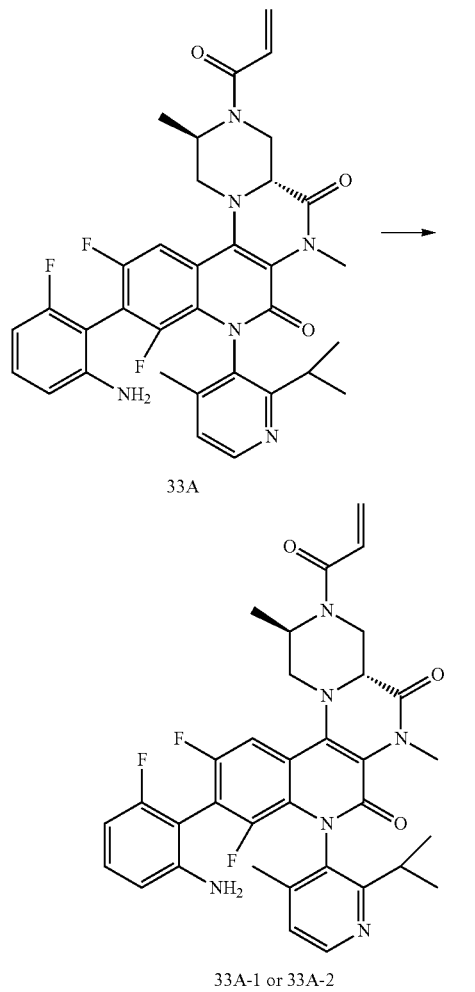

Diastereoisomeric compound 33A was purified by SFC (Phenomenex-Cellulose-2 (250 mm*30 mm, 10 μm); mobile phase: [CO$_2$-methanol (0.1% ammonia)]; methanol %: 45%). After concentration, compound 33A-1 and compound 33A-2 were obtained.

Compound 33A-1:

$^1$H NMR (400 MHz, DMSO-d$_6$) δ=8.46 (d, J=4.8 Hz, 1H), 7.57 (d, J=8.3 Hz, 1H), 7.26 (d, J=5.0 Hz, 1H), 7.15-6.83 (m, 2H), 6.50 (d, J=8.3 Hz, 1H), 6.35 (t, J=8.8 Hz, 1H), 6.21-6.09 (m, 1H), 5.82-5.64 (m, 1H), 5.21 (br s, 2H), 4.85-4.78 (m, 1H), 4.64-4.37 (m, 1H), 3.99-3.88 (m, 1H), 3.79-3.71 (m, 1H), 3.45-3.35 (m, 4H), 2.94-2.73 (m, 1H), 2.71-2.58 (m, 1H), 2.06 (s, 3H), 1.63-1.48 (m, 3H), 1.10-0.91 (m, 6H).

MS (ESI) m/z (M+H)$^+$=631.2.

HPLC retention time was 3.70 min

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 5.22 min.

Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Compound 33A-2:

$^1$H NMR (400 MHz, METHANOL-d$_4$) δ=8.46 (d, J=4.8 Hz, 1H), 7.74 (d, J=7.8 Hz, 1H), 7.27 (d, J=5.0 Hz, 1H), 7.23-6.83 (m, 2H), 6.61 (d, J=8.5 Hz, 1H), 6.41 (t, J=8.9 Hz, 1H), 6.31-6.21 (m, 1H), 5.91-5.74 (m, 1H), 4.82-4.50 (m, 2H), 3.99-3.84 (m, 2H), 3.51-3.43 (m, 4H), 2.98-2.92 (m, 2H), 2.04 (s, 3H), 1.76-1.64 (m, 3H), 1.27-1.09 (m, 6H).

MS (ESI) m/z (M+H)$^+$=631.1.

HPLC retention time was 3.67 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

SFC retention time was 6.417 min.

Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Step 5: Preparation of Compounds 33B-1 and 33B-2

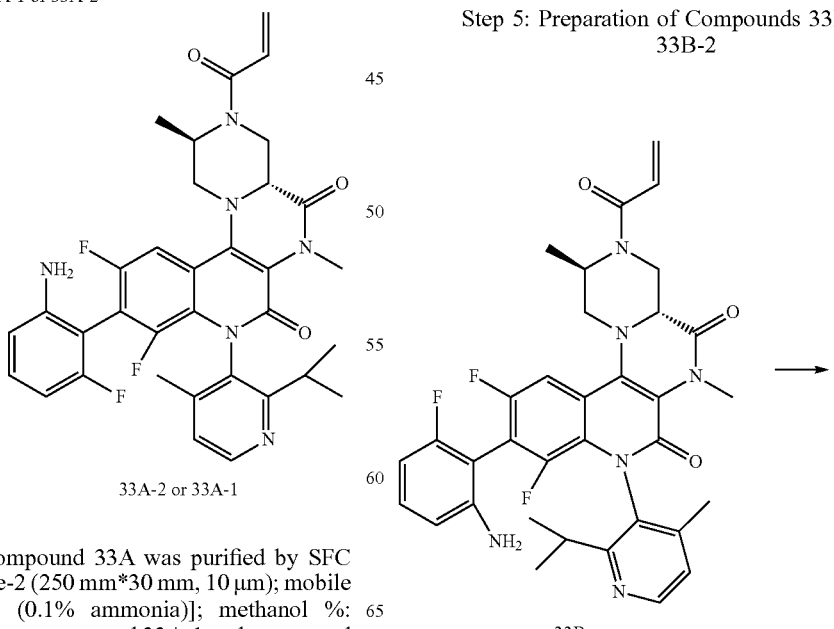

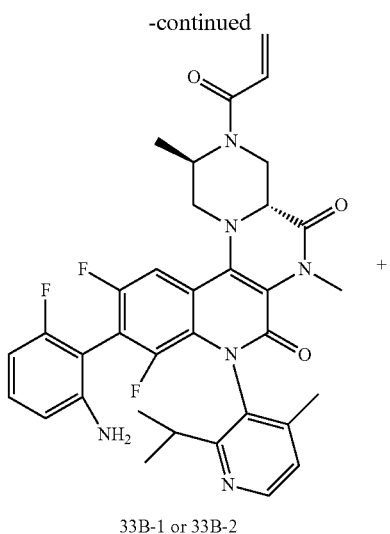

33B-1 or 33B-2

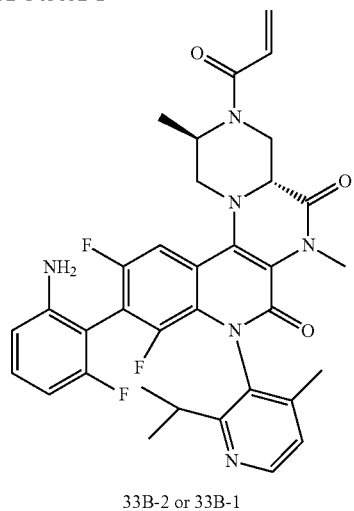

33B-2 or 33B-1

Diastereoisomeric compound 33B was purified by SFC (Phenomenex-Cellulose-2 (250 mm*30 mm, 10 μm); mobile phase: [CO$_2$-methanol (0.1% ammonia)]; methanol %: 45%). After concentration, compound 33B-1 and compound 33B-2 were obtained.

Compound 33B-1:

$^1$H NMR (400 MHz, METHANOL-d$_4$) δ=8.47 (d, J=5.0 Hz, 1H), 7.72 (d, J=9.8 Hz, 1H), 7.30 (d, J=4.8 Hz, 1H), 7.19-7.08 (m, 2H), 6.60 (d, J=8.0 Hz, 1H), 6.40 (t, J=8.8 Hz, 1H), 6.28-6.22 (m, 1H), 5.88-5.81 (m, 1H), 4.82-4.50 (m, 2H), 4.07-3.89 (m, 2H), 3.55-3.36 (m, 4H), 3.00-2.85 (m, 1H), 2.62-2.46 (m, 1H), 2.25 (s, 3H), 1.77-1.63 (m, 3H), 1.15-0.98 (m, 6H).

MS (ESI) m/z (M+H)$^+$=631.1.

HPLC retention time was 3.82 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 4.576 min.

Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Compound 33B-2:

$^1$H NMR (400 MHz, METHANOL-d$_4$) δ=8.47 (d, J=5.0 Hz, 1H), 7.73 (d, J=8.8 Hz, 1H), 7.28 (d, J=5.0 Hz, 1H), 7.21-7.10 (m, 2H), 6.59 (d, J=8.3 Hz, 1H), 6.40 (t, J=8.7 Hz, 1H), 6.31-6.23 (m, 1H), 5.88-5.76 (m, 1H), 4.81-4.50 (m, 2H), 4.02-3.84 (m, 2H), 3.53-3.38 (m, 4H), 3.09-2.93 (m, 2H), 1.97 (s, 3H), 1.76-1.65 (m, 3H), 1.27-1.11 (m, 6H).

MS (ESI) m/z (M+H)$^+$=631.1.

HPLC retention time was 3.87 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 6.411 min.

Separation conditions: chromatographic column: Cellulose 2 150*4.6 mm I.D., 5 μm; column temperature: 35° C.; mobile phase: CO$_2$-methanol (0.05% DEA); methanol: 40%-40%; flow rate: 2.5 mL/min.

Embodiment 34: Preparation of Compound 34

Step 1: Preparation of Compound 34-2

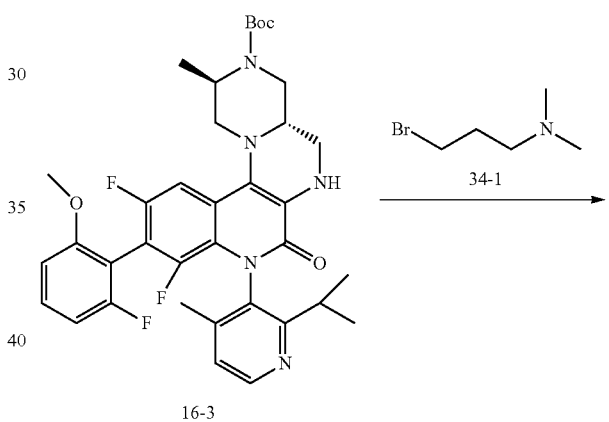

16-3

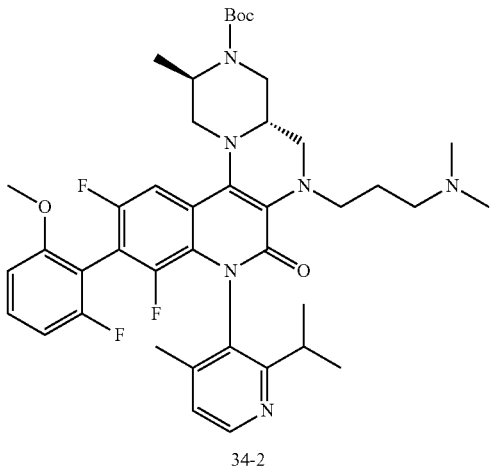

34-2

Compound 16-3 (120 mg, 180.80 μmol) was dissolved in N,N-dimethylformamide (2 mL), and sodium hydride (60 mg, 1.50 mmol, 60%) was added thereto, after the addition was completed, and the reaction was stirred at room temperature (25° C.) for 0.5 hours; then compound 34-1 (178.47 mg, 722.66 µmol, HBr salt) was added thereto and the reaction was stirred at room temperature (25° C.) for 2 hours. The reaction mixture was quenched with 10 drops of saturated ammonium chloride solution, diluted with ethyl acetate (30 mL), washed with water (10 mL) and saturated sodium chloride solution (10 mL) successively, and the organic phase was dried over anhydrous sodium sulfate and filtered; the filtrate was concentrated under reduced pressure to obtain crude product 34-2, which was directly used in the next reaction without further purification.

MS (ESI) m/z (M+H)⁺=749.3.

Step 2: Preparation of Compound 34-3

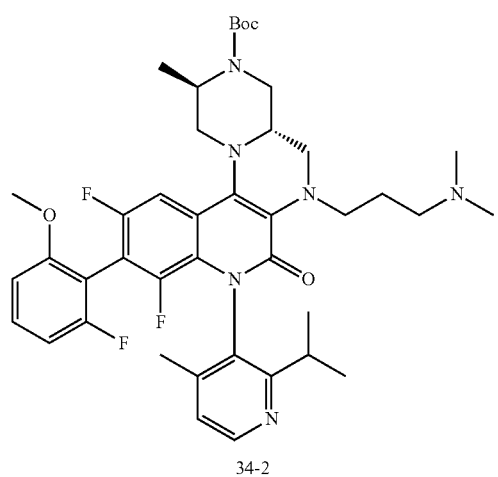

34-2

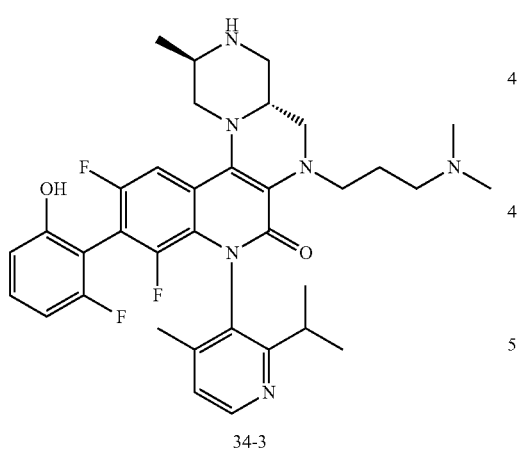

34-3

Compound 34-2 (150 mg, 200.30 µmol) was dissolved in dichloromethane (2 mL), and boron tribromide (390 mg, 1.56 mmol, 0.15 mL) was added thereto, and the reaction was stirred at room temperature (20° C.) for 5 hours. The reaction mixture was quenched by adding methanol (5 mL), stirred for 10 min, and concentrated under reduced pressure to obtain the crude product 34-3, which was directly used in the next reaction without further purification.

MS (ESI) m/z (M+H)⁺=635.2.

Step 3: Preparation of Compound 34

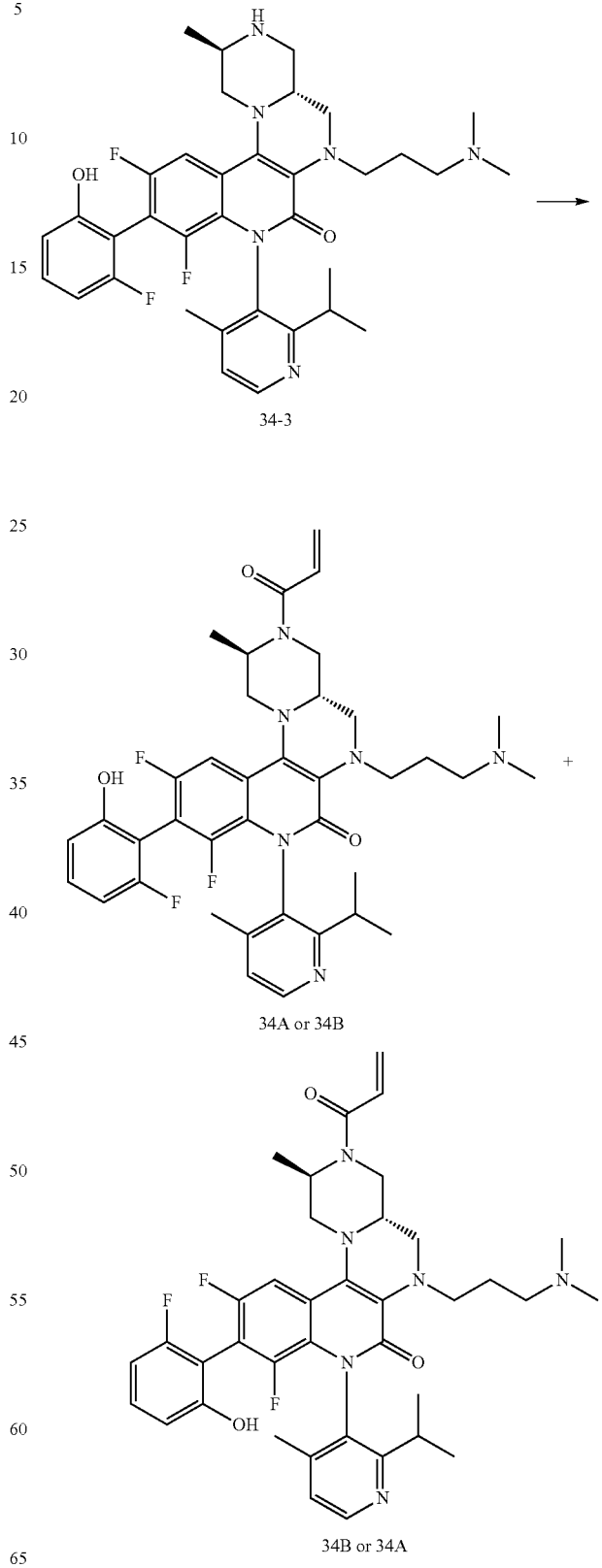

Compound 34-3 (150 mg, 209.60 μmol, HBr salt) was dissolved in tetrahydrofuran (2.5 mL) and sodium bicarbonate (5.40 g, 64.28 mmol) aqueous solution (2.5 mL), and tetrahydrofuran solution (0.5 mL) of acrylic anhydride (29.87 mg, 236.85 μmol) was added dropwise thereto. After the addition was completed, the system was stirred at room temperature (20° C.) for 2 hours. Methanol (1 mL) and saturated potassium carbonate aqueous solution (2 M, 1.50 mL) were added to the system, and the system was stirred at room temperature (20° C.) for 1.5 hours. The system was diluted by adding water (10 mL), the pH was adjusted to 6 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Xtimate C18 100*30 mm*3 μm, mobile phase: water (0.225% formic acid)-acetonitrile; acetonitrile 25%-35% 8 min) and then purified by SFC (separation conditions: chromatographic column: DAICEL CHIRALPAK IC (250 mm*30 mm 5 μm); mobile phase: [CO$_2$-ethanol (0.1% ammonia)]; ethanol %: 35%) to obtain compounds 34A and 34B.

Compound 34A:

$^1$H NMR (400 MHz, Methanol-d$_4$) δ 8.42 (d, J=5.1 Hz, 1H), 7.59 (br d, J=9.7 Hz, 1H), 7.29-7.16 (m, 2H), 6.91-6.79 (m, 1H), 6.73-6.56 (m, 2H), 6.28 (dd, J=1.8, 16.8 Hz, 1H), 5.82 (br d, J=10.6 Hz, 1H), 4.95-4.91 (m, 1H), 4.63 (br d, J=13.2 Hz, 1H), 4.53 (br s, 1H), 4.19 (br s, 1H), 3.79 (br s, 1H), 3.57 (br dd, J=7.7, 11.7 Hz, 2H), 3.24 (br s, 3H), 3.10-2.90 (m, 3H), 2.83-2.40 (m, 7H), 2.11 (br s, 2H), 2.05 (s, 3H), 1.77 (br s, 3H), 1.20-1.03 (m, 6H).

MS (ESI) m/z (M+H)$^+$=689.3.

LCMS retention time was 2.483 min.

Separation conditions: chromatographic column: Xtimate C18 2.1*30 mm, 3 μm; column temperature: 50° C.; mobile phase: water (1.5 mL/4 L trifluoroacetic acid solution)-acetonitrile (0.75 mL/4 L trifluoroacetic acid solution); acetonitrile: 10%-80% 6 min, 80% 0.5 min; flow rate: 0.8 mL/min.

Compound 34B:

$^1$H NMR (400 MHz, Methanol-d$_4$) δ 8.43 (d, J=4.0 Hz, 1H), 7.59 (br d, J=9.7 Hz, 1H), 7.32-7.15 (m, 2H), 6.85 (br s, 1H), 6.72-6.55 (m, 2H), 6.28 (dd, J=1.7, 16.6 Hz, 1H), 5.82 (br d, J=10.1 Hz, 1H), 5.04-4.95 (m, 1H), 4.79-4.38 (m, 2H), 4.22 (br s, 1H), 3.76 (br s, 1H), 3.64-3.48 (m, 2H), 3.28-3.11 (m, 3H), 3.09-2.91 (m, 3H), 2.86-2.45 (m, 7H), 2.11 (br d, J=7.9 Hz, 1H), 2.05 (d, J=5.7 Hz, 3H), 1.77 (br s, 3H), 1.24-1.05 (m, 6H). MS (ESI) m/z (M+H)$^+$=689.2.

MS (ESI) m/z (M+H)$^+$=689.2.

LCMS retention time was 2.676 & 2.730 min.

Separation conditions: chromatographic column: Xtimate C18 2.1*30 mm, 3 μm; column temperature: 50° C.; mobile phase: water (1.5 mL/4 L trifluoroacetic acid solution)-acetonitrile (0.75 mL/4 L trifluoroacetic acid solution); acetonitrile: 10%-80% 6 min, 80% 0.5 min; flow rate: 0.8 mL/min.

Embodiment 35: Preparation of Compound 35

Step 1: Preparation of Compound 35-2

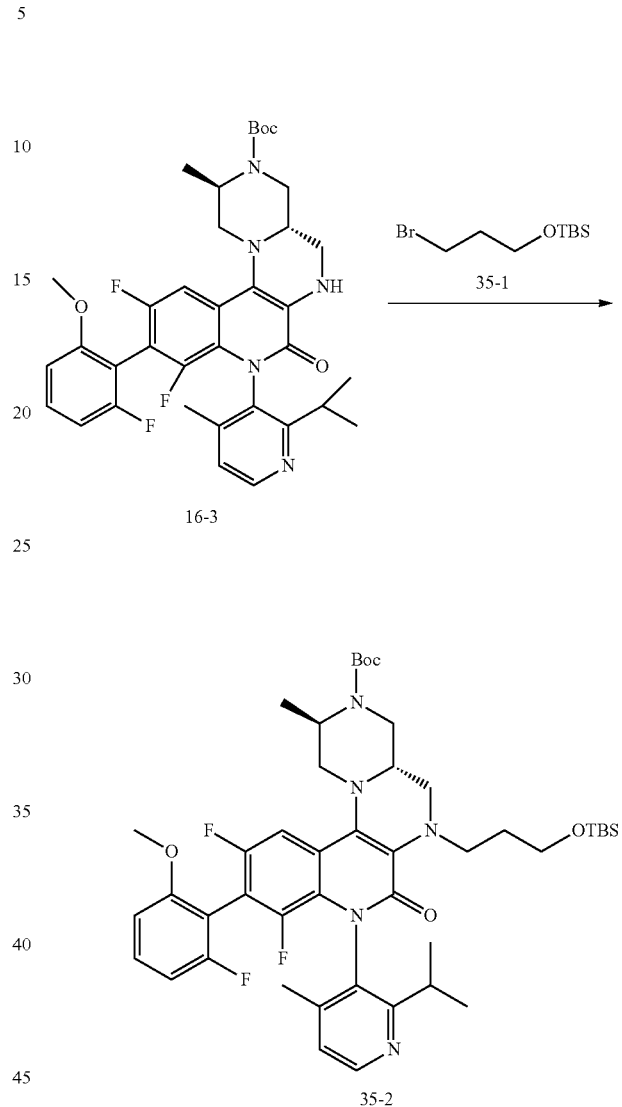

Compound 16-3 (150 mg, 226.00 μmol) was dissolved in N,N-dimethylformamide (3 mL), and sodium hydride (50 mg, 1.25 mmol, 60%) was added thereto, after the addition was completed, and the reaction was stirred at room temperature (25° C.) for 0.5 hours; then compound 35-1 (170 mg, 671.27 μmol) was added thereto and the reaction was stirred at room temperature (25° C.) for 1 hour. The reaction mixture was quenched with 3 drops of saturated ammonium chloride solution, diluted with ethyl acetate (30 mL), washed with water (10 mL) and saturated sodium chloride solution (10 mL) successively, and the organic phase was dried over anhydrous sodium sulfate and filtered; the filtrate was concentrated under reduced pressure to obtain a crude product, the crude product was purified by medium pressure column chromatography (ethyl acetate/petroleum ether (v/v)=0-7%) to obtain compound 35-2.

MS (ESI) m/z (M+H)$^+$=836.1.

Step 2: Preparation of Compound 35-3

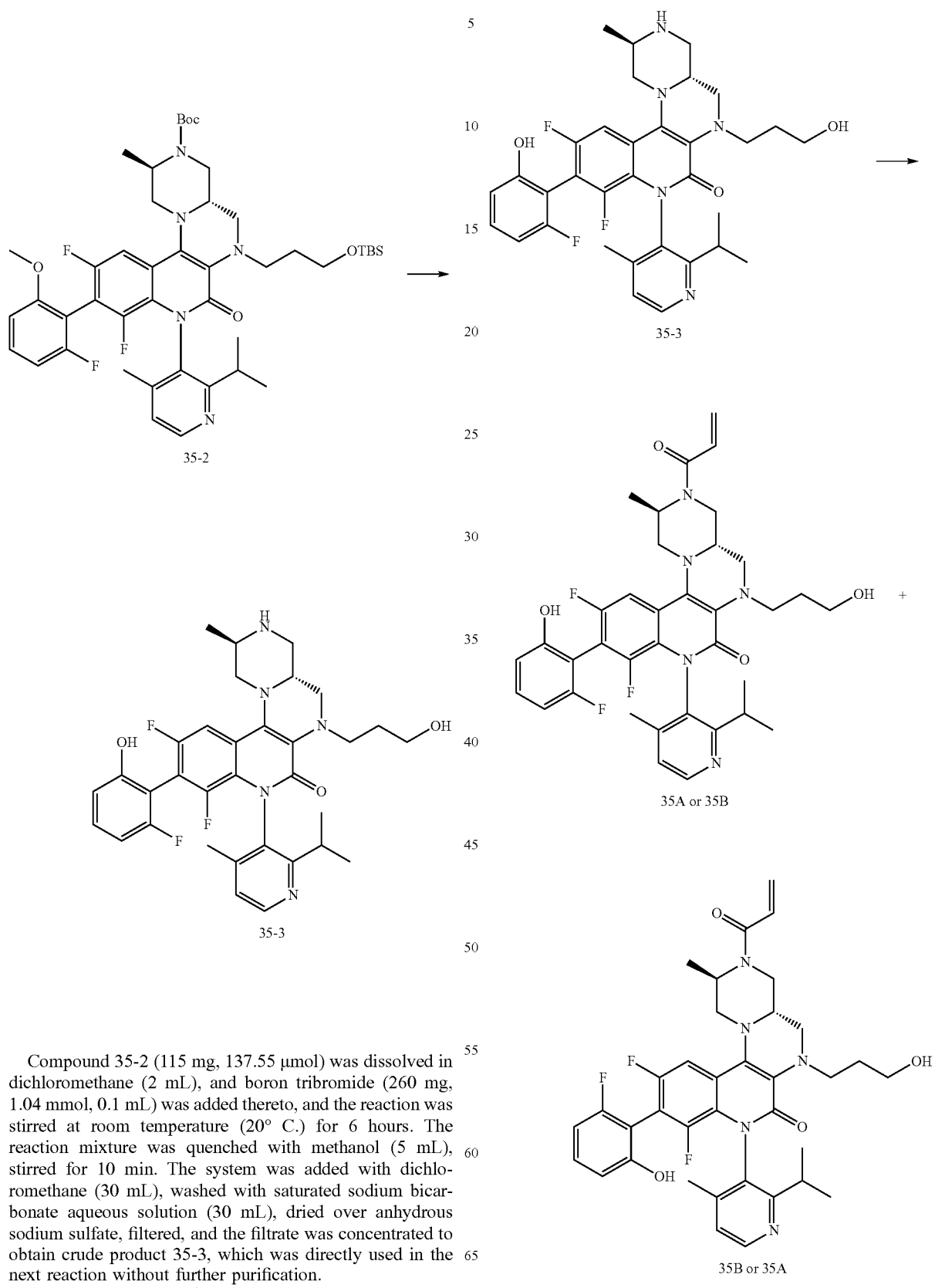

Compound 35-2 (115 mg, 137.55 μmol) was dissolved in dichloromethane (2 mL), and boron tribromide (260 mg, 1.04 mmol, 0.1 mL) was added thereto, and the reaction was stirred at room temperature (20° C.) for 6 hours. The reaction mixture was quenched with methanol (5 mL), stirred for 10 min. The system was added with dichloromethane (30 mL), washed with saturated sodium bicarbonate aqueous solution (30 mL), dried over anhydrous sodium sulfate, filtered, and the filtrate was concentrated to obtain crude product 35-3, which was directly used in the next reaction without further purification.

MS (ESI) m/z (M+H)$^+$=608.3.

Step 3: Preparation of Compounds 35A and 35B

Compound 35-3 (93.8 mg, 139.88 µmol) was dissolved in tetrahydrofuran (2 mL) and sodium bicarbonate (4.32 g, 51.42 mmol) aqueous solution (2 mL), and tetrahydrofuran solution (0.5 mL) of acrylic anhydride (29.87 mg, 236.85 µmol) was added dropwise thereto. After the addition was completed, the system was stirred at room temperature (20° C.) for 2 hours. Methanol (1 mL) and saturated potassium carbonate aqueous solution (2 M, 1 mL) were added to the system, and the system was stirred at room temperature (20° C.) for 1.5 hours. The system was diluted by adding water (10 mL), the pH was adjusted to 6 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 µm, mobile phase: water (10 mM ammonium bicarbonate)-acetonitrile; acetonitrile 43%-73% 9 min) to obtain compounds 35A and 35B.

Compound 35A:

$^1$H NMR (400 MHz, Methanol-$d_4$) δ 8.40 (d, J=4.9 Hz, 1H), 7.56 (br d, J=9.4 Hz, 1H), 7.25-7.15 (m, 2H), 6.91-6.79 (m, 1H), 6.71-6.56 (m, 2H), 6.28 (dd, J=1.7, 16.7 Hz, 1H), 5.81 (br d, J=10.6 Hz, 1H), 5.02-4.89 (m, 1H), 4.69-4.45 (m, 1H), 4.35-3.99 (m, 1H), 3.84-3.58 (m, 4H), 3.56-3.43 (m, 2H), 3.38-3.33 (m, 1H), 3.25 (br s, 1H), 2.99 (br d, J=9.8 Hz, 1H), 2.68 (tt, J=6.7, 13.2 Hz, 1H), 2.04 (d, J=2.7 Hz, 3H), 1.90-1.80 (m, 2H), 1.79-1.63 (m, 3H), 1.18-1.03 (m, 6H).

MS (ESI) m/z (M+H)$^+$=662.2.

LCMS retention time was 2.835 min.

Separation conditions: chromatographic column: Xtimate C18 2.1*30 mm, 3 µm; column temperature: 50° C.; mobile phase: water (1.5 mL/4 L trifluoroacetic acid solution)-acetonitrile (0.75 mL/4 L trifluoroacetic acid solution); acetonitrile: 10%-80% 6 min, 80% 0.5 min; flow rate: 0.8 mL/min.

Compound 35B:

$^1$H NMR (400 MHz, Methanol-$d_4$) δ 8.40 (d, J=4.9 Hz, 1H), 7.55 (br d, J=9.2 Hz, 1H), 7.27-7.15 (m, 2H), 6.84 (br s, 1H), 6.71-6.55 (m, 2H), 6.28 (br d, J=16.5 Hz, 1H), 5.82 (br s, 1H), 5.02-4.91 (m, 1H), 4.60 (br s, 1H), 4.27-3.95 (m, 1H), 3.93-3.54 (m, 4H), 3.48 (br d, J=12.5 Hz, 2H), 3.35 (br s, 1H), 3.25 (br s, 1H), 3.00 (br s, 1H), 2.67 (tt, J=6.6, 12.9 Hz, 1H), 2.04 (d, J=10.7 Hz, 3H), 1.91-1.80 (m, 2H), 1.79-1.60 (m, 3H), 1.20-1.04 (m, 6H).

MS (ESI) m/z (M+H)$^+$=662.3.

LCMS retention time was 2.994 min.

Separation conditions: chromatographic column: Xtimate C18 2.1*30 mm, 3 µm; column temperature: 50° C.; mobile phase: water (1.5 mL/4 L trifluoroacetic acid solution)-acetonitrile (0.75 mL/4 L trifluoroacetic acid solution); acetonitrile: 10%-80% 6 min, 80% 0.5 min; flow rate: 0.8 mL/min.

Step 4: Preparation of Compounds 35A-1 and 35A-2

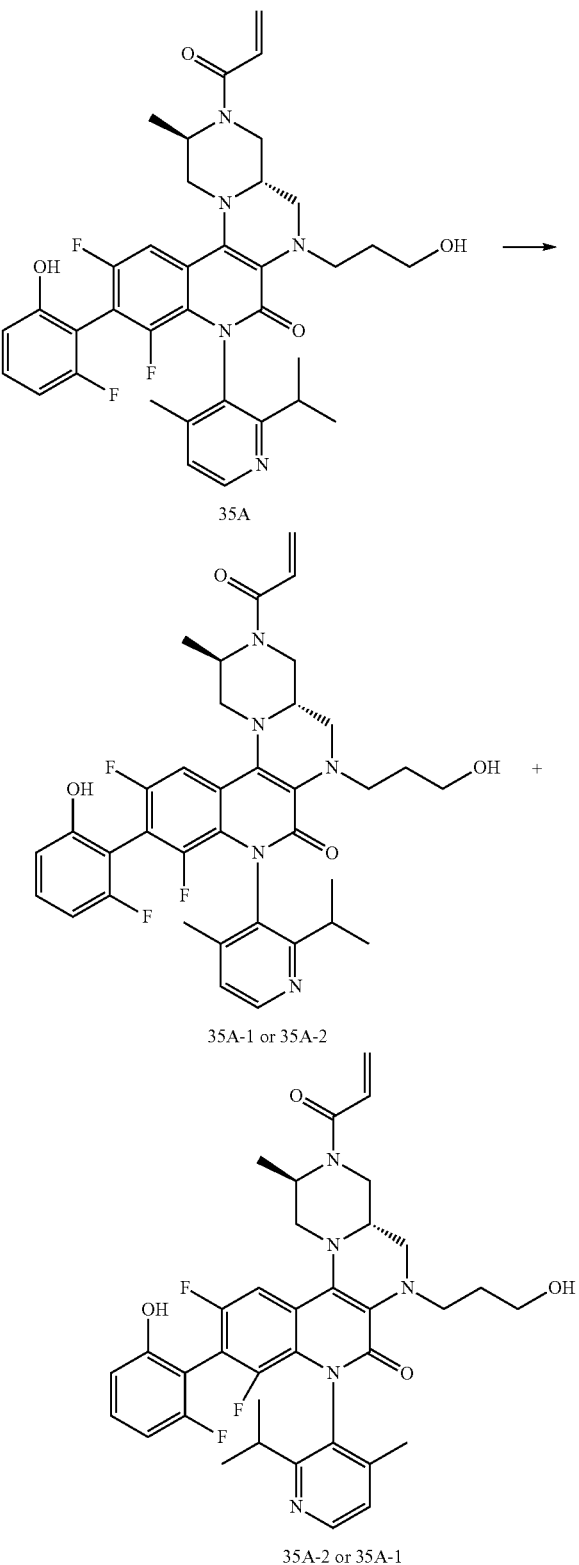

Diastereoisomeric compound 35A was purified by SFC (separation conditions: chromatographic column: DAICEL CHIRALPAK IC (250 mm*30 mm, 10 μm); mobile phase: [CO$_2$-methanol (0.1% ammonia)]; methanol %: 40%). After concentration, compound 35A-1 and compound 35A-2 were obtained.

Compound 35A-1:

$^1$H NMR (400 MHz, Methanol-d$_4$) δ 8.41 (d, J=4.9 Hz, 1H), 7.56 (br d, J=9.9 Hz, 1H), 7.28-7.11 (m, 2H), 6.89-6.76 (m, 1H), 6.71-6.55 (m, 2H), 6.28 (br dd, J=1.8, 16.8 Hz, 1H), 5.82 (br d, J=9.9 Hz, 1H), 4.99-4.90 (m, 1H), 4.72-4.38 (m, 2H), 4.27-4.10 (m, 1H), 3.75-3.58 (m, 3H), 3.47 (br d, J=11.9 Hz, 2H), 3.25 (br s, 2H), 2.99 (br s, 1H), 2.67 (td, J=6.7, 13.5 Hz, 1H), 2.05 (s, 3H), 1.92-1.64 (m, 5H), 1.14 (dd, J=6.8, 15.9 Hz, 6H).

MS (ESI) m/z (M+H)$^+$=662.4.

SFC retention time was 2.242 min separation conditions: chromatographic column: Chiralpak IC-3 150×4.6 mm I.D., 3 μm; column temperature: 35° C.; mobile phase: CO$_2$-isopropanol (0.05% DEA); isopropanol: 50%-50%; flow rate: 2.5 mL/min.

Compound 35A-2:

$^1$H NMR (400 MHz, Methanol-d$_4$) δ 8.40 (d, J=4.9 Hz, 1H), 7.55 (br d, J=9.3 Hz, 1H), 7.26-7.12 (m, 2H), 6.83 (br dd, J=10.4, 16.1 Hz, 1H), 6.71-6.56 (m, 2H), 6.27 (br dd, J=1.8, 16.8 Hz, 1H), 5.81 (br d, J=10.4 Hz, 1H), 5.00-4.90 (m, 1H), 4.71-4.42 (m, 2H), 4.25-4.10 (m, 1H), 3.82-3.62 (m, 3H), 3.54-3.40 (m, 2H), 3.29-3.14 (m, 2H), 3.00 (br s, 1H), 2.76-2.66 (m, 1H), 2.03 (s, 3H), 1.92-1.68 (m, 5H), 1.25-0.96 (m, 6H).

MS (ESI) m/z (M+H)$^+$=662.4.

SFC retention time was 2.800 min.

separation conditions: chromatographic column: Chiralpak IC-3 150×4.6 mm I.D., 3 μm; column temperature: 35° C.; mobile phase: CO$_2$-isopropanol (0.05% DEA); isopropanol: 50%-50%; flow rate: 2.5 mL/min.

Step 5: Preparation of Compounds 35B-1 and 35B-2

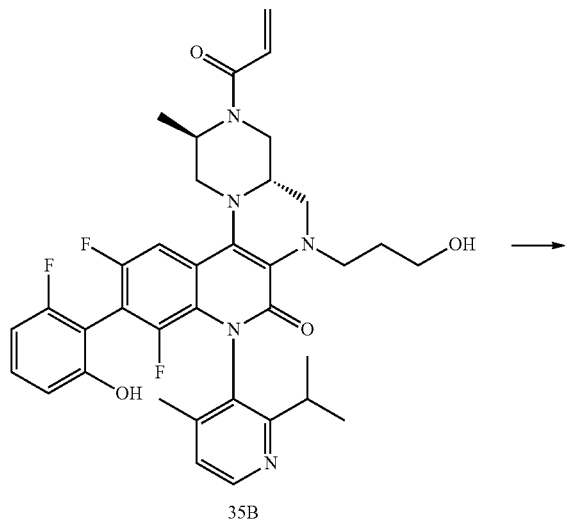

35B

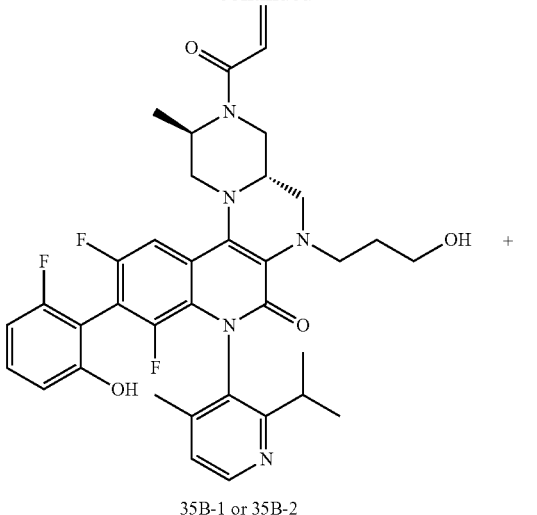

35B-1 or 35B-2

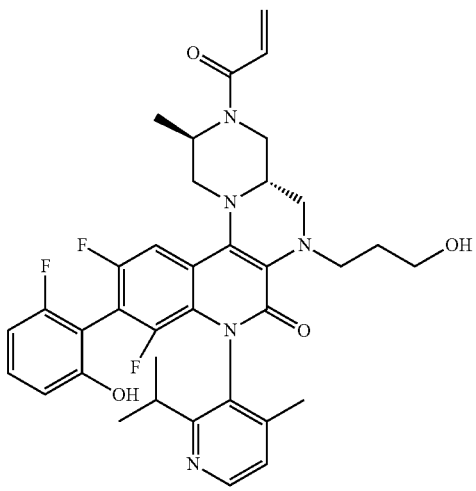

35B-2 or 35B-1

Diastereoisomeric compound 35B was purified by SFC (separation conditions: chromatographic column: DAICEL CHIRALPAK IC (250 mm*30 mm, 10 μm); mobile phase: [CO$_2$-methanol (0.1% ammonia)]; methanol %: 40%). After concentration, compound 35B-1 and compound 35B-2 were obtained.

Compound 35B-1:

$^1$H NMR (400 MHz, Methanol-d$_4$) δ 8.41 (d, J=4.9 Hz, 1H), 7.55 (br d, J=9.3 Hz, 1H), 7.34-7.12 (m, 2H), 6.82 (br d, J=13.7 Hz, 1H), 6.69-6.55 (m, 2H), 6.28 (dd, J=1.8, 16.8 Hz, 1H), 5.81 (br d, J=9.9 Hz, 1H), 4.96 (br s, 1H), 4.71-4.43 (m, 2H), 4.27-4.08 (m, 1H), 3.82-3.57 (m, 3H), 3.48 (br d, J=12.6 Hz, 2H), 3.27-3.30 (m, 2H), 3.02 (br d, J=10.4 Hz, 1H), 2.81-2.62 (m, 1H), 2.03 (s, 3H), 1.85-1.67 (m, 5H), 1.13 (dd, J=6.8, 15.7 Hz, 6H).

MS (ESI) m/z (M+H)$^+$=662.4.

SFC retention time was 1.850 min.

separation conditions: chromatographic column: Chiralpak IC-3 150×4.6 mm I.D., 3 μm; column temperature: 35° C.; mobile phase: CO$_2$-methanol (0.05% DEA); methanol: 40%-40%; flow rate: 2.8 mL/min.

Compound 35B-2:

$^1$H NMR (400 MHz, Methanol-d$_4$) δ 8.30 (d, J=4.9 Hz, 1H), 7.45 (br d, J=9.3 Hz, 1H), 7.16-7.01 (m, 2H), 6.74 (br s, 1H), 6.61-6.46 (m, 2H), 6.17 (br dd, J=1.5, 16.8 Hz, 1H), 5.72 (br s, 1H), 4.88-4.81 (m, 1H), 4.59-4.30 (m, 2H), 4.16-4.00 (m, 1H), 3.63-3.46 (m, 3H), 3.38 (br d, J=11.9 Hz, 2H), 3.15 (br s, 2H), 2.88 (br s, 1H), 2.56 (td, J=6.6, 13.5 Hz, 1H), 1.95 (s, 3H), 1.81-1.55 (m, 5H), 1.11-0.89 (m, 6H).

MS (ESI) m/z $(M+H)^+$=662.4.

SFC retention time was 2.290 min.

separation conditions: chromatographic column: Chiralpak IC-3 150×4.6 mm I.D., 3 μm; column temperature: 35° C.; mobile phase: $CO_2$-methanol (0.05% DEA); isopropanol: 40%-40%; flow rate: 2.8 mL/min.

Embodiment 36: Preparation of Compound 36

Step 1: Preparation of Compound 36-2 was completed, and the reaction was stirred at room temperature (25° C.) for 0.5 hours; then compound 36-1 (100 mg, 418.02 μmol) was added thereto and the reaction was stirred at room temperature (25° C.) for 1 hour. The reaction mixture was quenched with 3 drops of saturated ammonium chloride solution, diluted with ethyl acetate (30 mL), washed with water (10 mL) and saturated sodium chloride solution (10 mL) successively, and the organic phase was dried over anhydrous sodium sulfate and filtered; the filtrate was concentrated under reduced pressure to obtain a crude product, the crude product was purified by medium pressure column chromatography (ethyl acetate/petroleum ether (v/v)=0-7%) to obtain compound 36-2.

MS (ESI) m/z $(M+H)^+$=822.4.

Step 2: Preparation of Compound 36-3

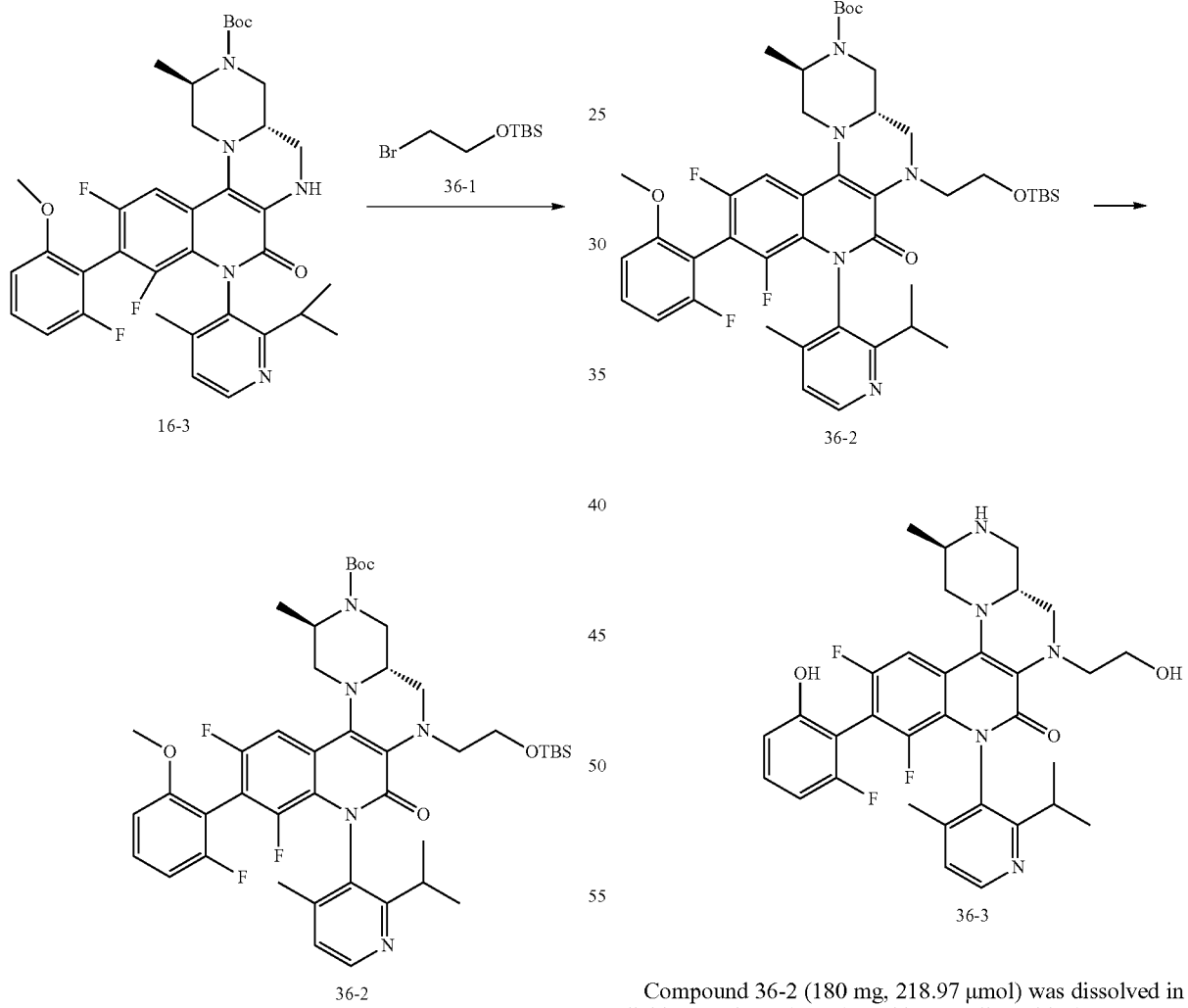

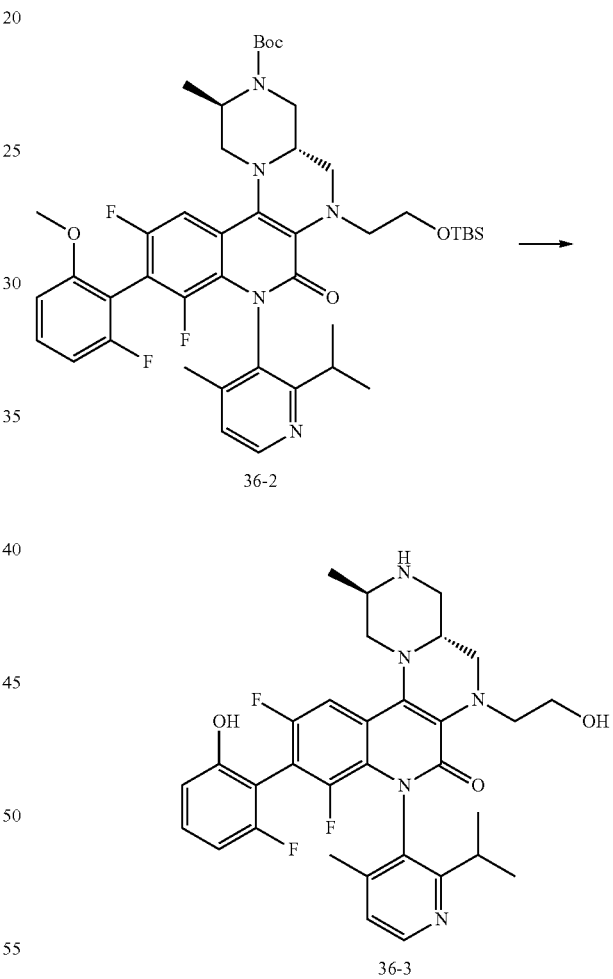

Compound 16-3 (100 mg, 150.66 μmol) was dissolved in N,N-dimethylformamide (2 mL), and sodium hydride (40 mg, 1.00 mmol, 60%) was added thereto, after the addition Compound 36-2 (180 mg, 218.97 μmol) was dissolved in dichloromethane (2 mL), and boron tribromide (274.28 mg, 1.09 mmol, 105.49 μL) was added thereto, and the reaction was stirred at room temperature (20° C.) for 5 hours. The reaction mixture was quenched with methanol (10 mL), stirred for 10 min. The system was concentrated to obtain compound 36-3, which was directly used in the next reaction without further purification.

MS (ESI) m/z $(M+H)^+$=594.4.

Step 3: Preparation of Compounds 36A and 36B

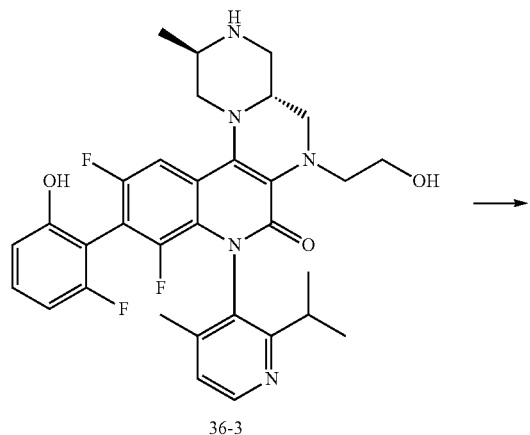

36-3

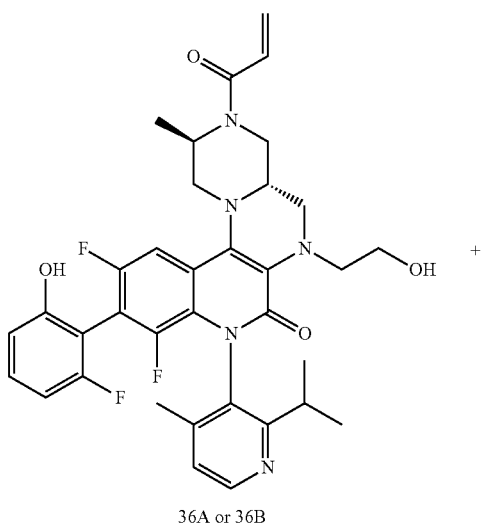

36A or 36B

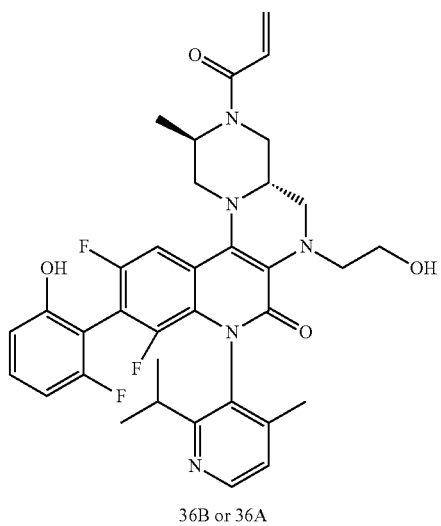

36B or 36A

Compound 36-3 (150 mg, 222.37 μmol, HBr salt) was dissolved in tetrahydrofuran (2 mL) and sodium bicarbonate (5.40 g, 64.28 mmol) aqueous solution (2.5 mL), and tetrahydrofuran solution (0.5 mL) of acrylic anhydride (28.04 mg, 222.37 μmol) was added dropwise thereto. After the addition was completed, the system was stirred at room temperature (20° C.) for 2 hours. Methanol (1 mL) and saturated potassium carbonate aqueous solution (2 M, 1 mL) were added to the system, and the system was stirred at room temperature (20° C.) for 1.5 hours. The system was diluted by adding water (10 mL), the pH was adjusted to 6 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 43%-73% 9 min) to obtain compounds 36A and 36B.

Compound 36A:

$^1$H NMR (400 MHz, Methanol-$d_4$) δ 8.40 (d, J=4.9 Hz, 1H), 7.55 (br d, J=7.9 Hz, 1H), 7.27-7.14 (m, 2H), 6.83 (dd, J=10.6, 16.8 Hz, 1H), 6.71-6.55 (m, 2H), 6.27 (dd, J=1.8, 16.8 Hz, 1H), 5.81 (br d, J=12.1 Hz, 1H), 5.00-4.92 (m, 1H), 4.68-4.45 (m, 2H), 4.25-4.06 (m, 1H), 3.86 (br dd, J=5.1, 14.3 Hz, 1H), 3.74 (dt, J=6.2, 11.6 Hz, 4H), 3.57-3.40 (m, 2H), 3.15-2.99 (m, 1H), 2.80-2.60 (m, 1H), 2.05 (d, J=7.5 Hz, 3H), 1.81-1.65 (m, 3H), 1.21-1.05 (m, 6H).

MS (ESI) m/z (M+H)$^+$=648.4.

LCMS retention time was 1.579 & 1.635 min.

Separation conditions: chromatographic column XBridge C18, 3.5 μm, 2.1*30 mm; column temperature: 50° C.; mobile phase: water (0.8 mL/4 L NH$_3$·H$_2$O)-acetonitrile; acetonitrile: 10%-80% 2 min, 80% 0.48 min; flow rate: 1 mL/min.

Compound 36B:

$^1$H NMR (400 MHz, Methanol-$d_4$) δ 8.41 (d, J=5.1 Hz, 1H), 7.55 (br d, J=7.3 Hz, 1H), 7.31-7.13 (m, 2H), 6.84 (br dd, J=10.7, 16.9 Hz, 1H), 6.71-6.53 (m, 2H), 6.33-6.21 (m, 1H), 5.82 (br s, 1H), 5.01-4.93 (m, 1H), 4.68-4.45 (m, 2H), 4.16 (br d, J=13.7 Hz, 1H), 3.85 (br d, J=14.3 Hz, 1H), 3.80-3.64 (m, 4H), 3.55-3.40 (m, 2H), 3.19-2.99 (m, 1H), 2.78-2.56 (m, 1H), 2.05 (d, J=15.7 Hz, 3H), 1.81-1.64 (m, 3H), 1.22-1.05 (m, 6H).

MS (ESI) m/z (M+H)$^+$=648.4.

LCMS retention time was 1.613 & 1.653 min.

Separation conditions: chromatographic column XBridge C18, 3.5 μm, 2.1*30 mm; column temperature: 50° C.; mobile phase: water (0.8 mL/4 L NH$_3$·H$_2$O)-acetonitrile; acetonitrile: 10%-80% 2 min, 80% 0.48 min; flow rate: 1 mL/min.

Step 4: Preparation of Compounds 36A-1 and 36A-2

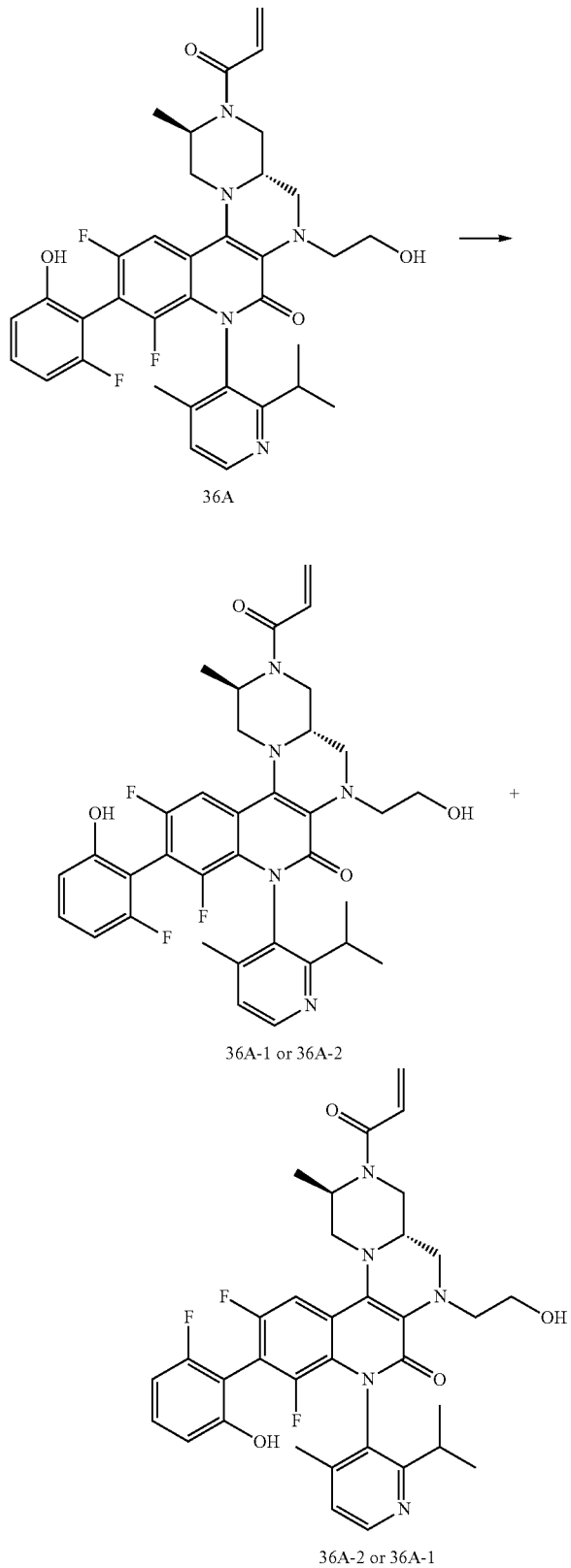

36A 36A-1 or 36A-2

36A-2 or 36A-1

Diastereoisomeric compound 36A was purified by SFC (separation conditions: chromatographic column: DAICEL CHIRALPAK AD-H (250 mm*30 mm, 5 μm); mobile phase: [$CO_2$-isopropanol (0.1% ammonia)]; isopropanol %: 30%). After concentration, compound 36A-1 and compound 36A-2 were obtained.

Compound 36A-1:

$^1$H NMR (400 MHz, Methanol-$d_4$) δ=8.41 (d, J=5.0 Hz, 1H), 7.55 (br d, J=8.3 Hz, 1H), 7.27-7.16 (m, 2H), 6.84 (dd, J=10.7, 16.7 Hz, 1H), 6.71-6.56 (m, 2H), 6.27 (dd, J=1.8, 16.7 Hz, 1H), 5.81 (br d, J=9.7 Hz, 1H), 5.00-4.92 (m, 1H), 4.68-4.47 (m, 2H), 4.33-4.06 (m, 1H), 3.91-3.64 (m, 5H), 3.55-3.38 (m, 2H), 3.14-2.99 (m, 1H), 2.79-2.68 (m, 1H), 2.04 (s, 3H), 1.82-1.66 (m, 3H), 1.21-1.04 (m, 6H).

MS (ESI) m/z (M+H)$^+$=648.2.

HPLC retention time was 7.86 min

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 1.604 min separation conditions: chromatographic column: Chiralpak AD-3 50*4.6 mm I.D., 3 μm; column temperature: 35° C.; mobile phase: $CO_2$-isopropanol (0.05% DEA); isopropanol: 5%-40% 2 min, 40% 1.2 min, 5% 0.8 min; flow rate: 4 mL/min.

Compound 36A-2:

$^1$H NMR (400 MHz, Methanol-$d_4$) δ=8.40 (d, J=5.0 Hz, 1H), 7.55 (br d, J=9.9 Hz, 1H), 7.26-7.17 (m, 1H), 7.16 (s, 1H), 6.83 (dd, J=10.7, 16.7 Hz, 1H), 6.68-6.57 (m, 2H), 6.27 (dd, J=1.7, 16.7 Hz, 1H), 5.81 (br d, J=11.1 Hz, 1H), 5.00-4.91 (m, 1H), 4.75-4.40 (m, 2H), 4.24-4.06 (m, 1H), 3.93-3.74 (m, 4H), 3.52-3.39 (m, 2H), 3.05 (br d, J=12.0 Hz, 1H), 2.65 (td, J=6.8, 13.6 Hz, 1H), 2.10-2.01 (m, 3H), 1.81-1.68 (m, 3H), 1.13 (dd, J=6.8, 17.0 Hz, 6H).

MS (ESI) m/z (M+H)$^+$=648.2.

HPLC retention time was 7.96 min

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 1.705 min separation conditions: chromatographic column: Chiralpak AD-3 50*4.6 mm I.D., 3 μm; column temperature: 35° C.; mobile phase: $CO_2$-isopropanol (0.05% DEA); isopropanol: 5%-40% 2 min, 40% 1.2 min, 5% 0.8 min; flow rate: 4 mL/min.

Step 5: Preparation of Compounds 36B-1 and 36B-2

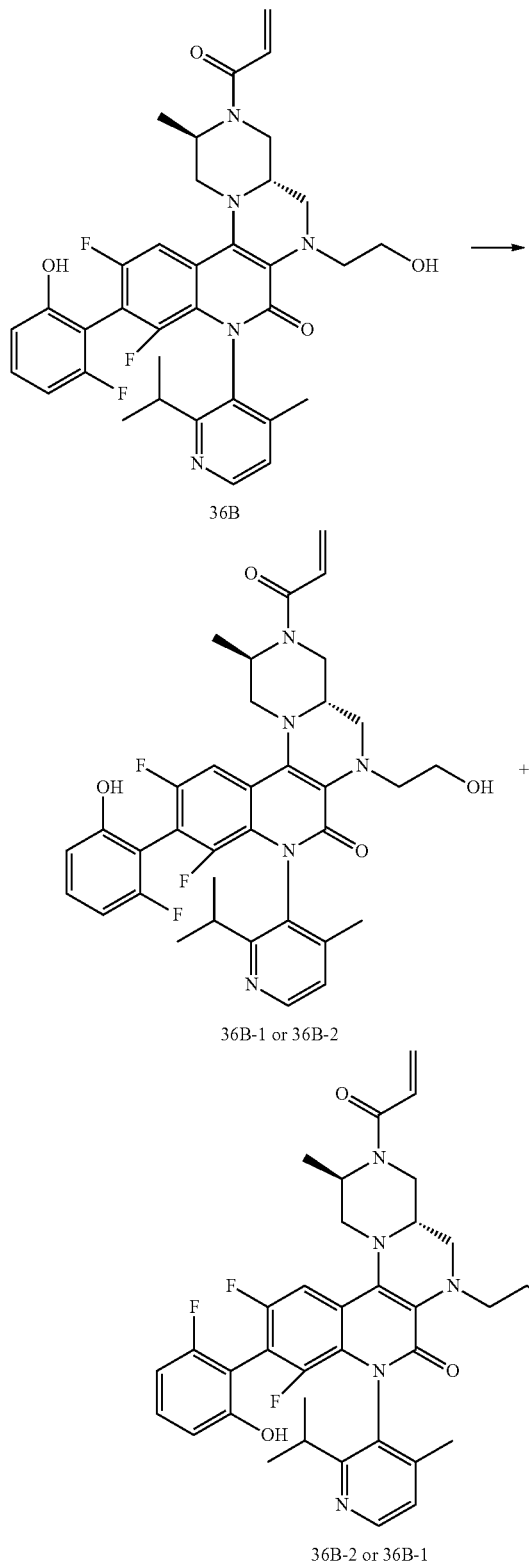

Diastereoisomeric compound 36B was purified by SFC (separation conditions: chromatographic column: DAICEL CHIRALPAK AD-H (250 mm*30 mm, 10 μm); mobile phase: [CO$_2$-isopropanol (0.1% ammonia)]; isopropanol %: 30%). After concentration, compound 36B-1 and compound 36B-2 were obtained.

Compound 36B-1:
$^1$H NMR (400 MHz, Methanol-d$_4$) δ=8.41 (d, J=5.0 Hz, 1H), 7.55 (br d, J=9.3 Hz, 1H), 7.27-7.15 (m, 2H), 6.83 (br dd, J=10.8, 16.5 Hz, 1H), 6.68-6.55 (m, 2H), 6.27 (dd, J=1.5, 16.8 Hz, 1H), 5.80 (br d, J=9.1 Hz, 1H), 5.00-4.92 (m, 1H), 4.67-4.49 (m, 2H), 4.25-4.06 (m, 1H), 3.90-3.65 (m, 5H), 3.55-3.39 (m, 2H), 3.16-2.99 (m, 1H), 2.79-2.67 (m, 1H), 2.03 (s, 3H), 1.80-1.66 (m, 3H), 1.13 (dd, J=6.7, 18.3 Hz, 6H).

MS (ESI) m/z (M+H)$^+$=648.1.

HPLC retention time was 8.16 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 1.603 min separation conditions: chromatographic column: Chiralpak AD-3 50*4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Compound 36B-2:
$^1$H NMR (400 MHz, Methanol-d$_4$) δ=8.40 (d, J=4.9 Hz, 1H), 7.55 (br d, J=10.3 Hz, 1H), 7.26-7.15 (m, 2H), 6.83 (dd, J=10.7, 16.7 Hz, 1H), 6.71-6.56 (m, 2H), 6.27 (dd, J=1.8, 16.7 Hz, 1H), 5.81 (br d, J=10.1 Hz, 1H), 4.95 (br s, 1H), 4.74-4.45 (m, 2H), 4.32-4.04 (m, 1H), 3.92-3.62 (m, 5H), 3.56-3.40 (m, 2H), 3.03 (br s, 1H), 2.71-2.58 (m, 1H), 2.07 (s, 3H), 1.82-1.66 (m, 3H), 1.19-1.02 (m, 6H).

MS (ESI) m/z (M+H)$^+$=648.1.

HPLC retention time was 8.11 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 1.730 min.

separation conditions: chromatographic column: Chiralpak AD-3 50*4.6 mm I.D., 3 μm; column temperature: 35° C.; mobile phase: CO$_2$-isopropanol (0.05% DEA); isopropanol: 5%-40% 2 min, 40% 1.2 min, 5% 0.8 min; flow rate: 4 mL/min.

Embodiment 37: Preparation of Compound 37

Step 1: Preparation of Compound 37-2

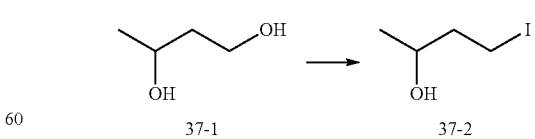

Triphenylphosphine (2.18 g, 8.32 mmol) was dissolved in anhydrous dichloromethane (20 mL), iodine (2.11 g, 8.32 mmol) and 4-dimethylaminopyridine (271.12 mg, 2.22 mmol) were added thereto, and the reaction was stirred at room temperature (25° C.) for 5 min; compound 37-1 (0.5 g, 5.55 mmol) was added thereto, and the reaction was stirred at room temperature (25° C.) for 12 hours. The reaction mixture was quenched with saturated sodium thiosulfate solution and extracted with dichloromethane (20 mL×2), the organic phase was dried over anhydrous sodium sulfate, filtered, and the filtrate was concentrated under reduced pressure to obtain a crude product, the crude product was purified by medium pressure column chromatography (methanol/dichloromethane (v/v)=0-10%) to obtain compound 37-2.

$^1$H NMR (400 MHz, DMSO-$d_6$) 4.63 (d, J=4.8 Hz, 1H), 3.69-3.57 (m, 1H), 3.32-3.23 (m, 2H), 1.87-1.76 (m, 2H), 1.07 (d, J=6.0 Hz, 3H).

Step 2: Preparation of Compound 37-3

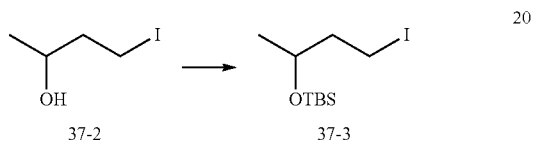

Compound 37-2 (1 g, 5.00 mmol) was dissolved in anhydrous dichloromethane (20 mL), and imidazole (408.46 mg, 6.00 mmol) and tert-butyldimethylchlorosilane (904.33 mg, 6.00, 735.23 uL) were added sequentially at 0° C., after the addition was completed, the reaction was heated to room temperature (25° C.) and stirred for 12 hours. The reaction mixture was diluted with water (30 mL) and extracted with dichloromethane (30 mL×2); the organic phase was washed with saturated saline (20 mL), dried over anhydrous sodium sulfate, filtered and the filtrate was concentrated to obtain a crude product, the crude product was purified by medium pressure column chromatography (ethyl acetate/petroleum ether (v/v)=0-10%) to obtain compound 37-3.

$^1$H NMR (400 MHz, DMSO-$d_6$) 3.91-3.81 (m, 1H), 3.32-3.17 (m, 2H), 1.89-1.81 (m, 2H), 1.12 (d, J=6.3 Hz, 3H), 0.87 (s, 9H), 0.08 (d, J=6.3 Hz, 6H).

Step 3: Preparation of Compound 37-4

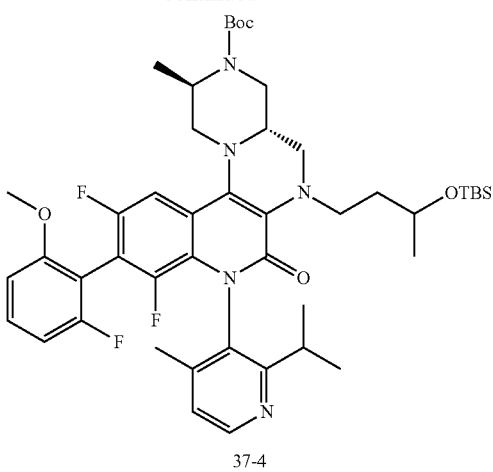

Compound 16-3 (100 mg, 150.66 μmol) was dissolved in N,N-dimethylformamide (2 mL), and sodium hydride (31 mg, 775.07 μmol, 60%) was added thereto, after the addition was completed, and the reaction was stirred at room temperature (25° C.) for 0.5 hours; then compound 37-3 (140 mg, 445.47 μmol) was added thereto and the reaction was stirred at room temperature (25° C.) for 1 hour. The reaction mixture was quenched with 3 drops of saturated ammonium chloride solution, diluted with ethyl acetate (30 mL), washed with water (10 mL) and saturated sodium chloride solution (10 mL) successively, and the organic phase was dried over anhydrous sodium sulfate and filtered; the filtrate was concentrated under reduced pressure to obtain a crude product, the crude product was purified by medium pressure column chromatography (ethyl acetate/petroleum ether (v/v)=0-7%) to obtain compound 37-4.

MS (ESI) m/z (M+H)$^+$=850.2.

Step 4: Preparation of Compound 37-5

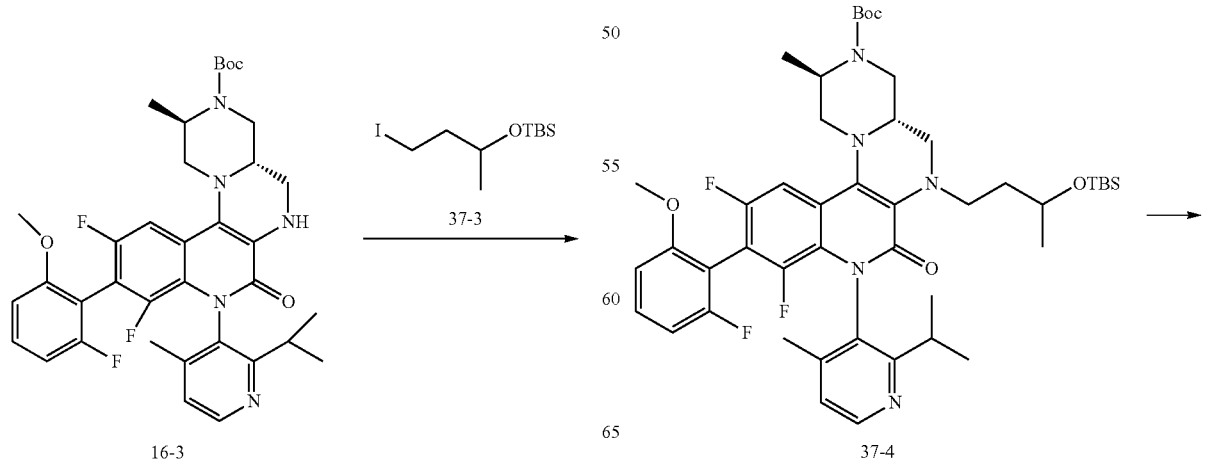

571
-continued

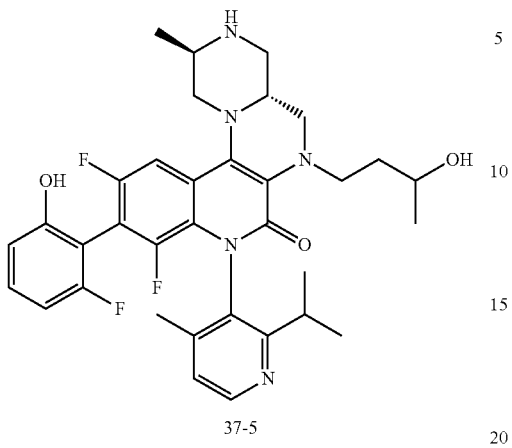

37-5

Compound 37-4 (85 mg, 99.99 μmol) was dissolved in dichloromethane (2 mL), and boron tribromide (260 mg, 1.04 mmol, 0.1 mL) was added thereto, and the reaction was stirred at room temperature (20° C.) for 6 hours. The reaction mixture was quenched with methanol (5 mL), stirred for 10 min. The system was diluted with dichloromethane (30 mL), washed with saturated sodium bicarbonate aqueous solution (30 mL), dried over anhydrous sodium sulfate, filtered, and the filtrate was concentrated to obtain compound 37-5, which was directly used in the next reaction without further purification.

MS (ESI) m/z (M+H)$^+$=622.1.

Step 5: Preparation of Compounds 37A and 37B

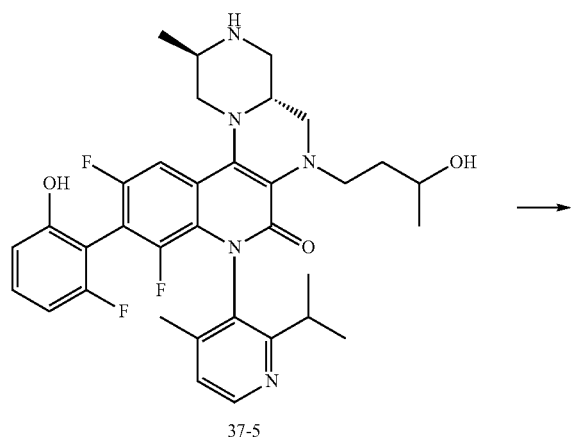

37-5

572
-continued 37A or 37B 37B or 37A

Compound 37-5 (70 mg, 112.60 μmol) was dissolved in tetrahydrofuran (1.5 mL) and sodium bicarbonate (3.49 g, 41.53 mmol) aqueous solution (1.62 mL), and tetrahydrofuran solution (0.5 mL) of acrylic anhydride (28.04 mg, 222.37 μmol) was added dropwise thereto. After the addition was completed, the system was stirred at room temperature (20° C.) for 2 hours. Methanol (1 mL) and saturated potassium carbonate aqueous solution (2 M, 1 mL) were added to the system, and the system was stirred at room temperature (20° C.) for 1.5 hours. The system was diluted by adding water (10 mL), the pH was adjusted to 6 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 43%-73% 9 min) to obtain compounds 37A and 37B.

Compound 37A:
$^1$H NMR (400 MHz, Methanol-d$_4$) δ 8.41 (d, J=5.0 Hz, 1H), 7.56 (br d, J=8.5 Hz, 1H), 7.28-7.14 (m, 2H), 6.84 (br dd, J=10.7, 16.6 Hz, 1H), 6.71-6.56 (m, 2H), 6.28 (br d, J=17.3 Hz, 1H), 5.82 (br d, J=10.0 Hz, 1H), 5.00-4.60 (m, 4H), 4.27-4.04 (m, 1H), 3.98-3.66 (m, 2H), 3.60-3.43 (m, 2H), 3.27-2.90 (m, 2H), 2.83-2.59 (m, 1H), 2.11-1.99 (m, 3H), 1.89-1.58 (m, 5H), 1.24-1.05 (m, 9H).

MS (ESI) m/z (M+H)$^+$=676.3.

The LCMS retention time was 2.927 min.

Separation conditions: chromatographic column: Xtimate C18 2.1*30 mm, 3 μm; column temperature: 50° C.; mobile phase: water (1.5 mL/4 L trifluoroacetic acid)-acetonitrile (0.75 mL/4 L trifluoroacetic acid solution); acetonitrile: 10%-80% 6 min, 80% 0.5 min; flow rate: 0.8 mL/min.

Compound 37B:

$^1$H NMR (400 MHz, Methanol-d$_4$) δ 8.41 (d, J=4.8 Hz, 1H), 7.56 (br d, J=9.7 Hz, 1H), 7.27-7.16 (m, 2H), 6.84 (br dd, J=10.8, 16.6 Hz, 1H), 6.70-6.57 (m, 2H), 6.28 (br d, J=16.6 Hz, 1H), 5.82 (br s, 1H), 4.60 (br s, 3H), 4.30-4.06 (m, 1H), 3.98-3.65 (m, 2H), 3.57-3.40 (m, 2H), 3.25-2.92 (m, 3H), 2.78-2.59 (m, 1H), 2.10-1.99 (m, 3H), 1.90-1.52 (m, 5H), 1.23-1.01 (m, 9H).

MS (ESI) m/z (M+H)$^+$=676.3.

LCMS retention time was 3.109 min.

Separation conditions: chromatographic column: Xtimate C18 2.1*30 mm, 3 μm; column temperature: 50° C.; mobile phase: water (1.5 mL/4 L trifluoroacetic acid)-acetonitrile (0.75 mL/4 L trifluoroacetic acid solution); acetonitrile: 10%-80% 6 min, 80% 0.5 min; flow rate: 0.8 mL/min.

Embodiment 38: Preparation of Compound 38

Step 1: Preparation of Compound 38-1

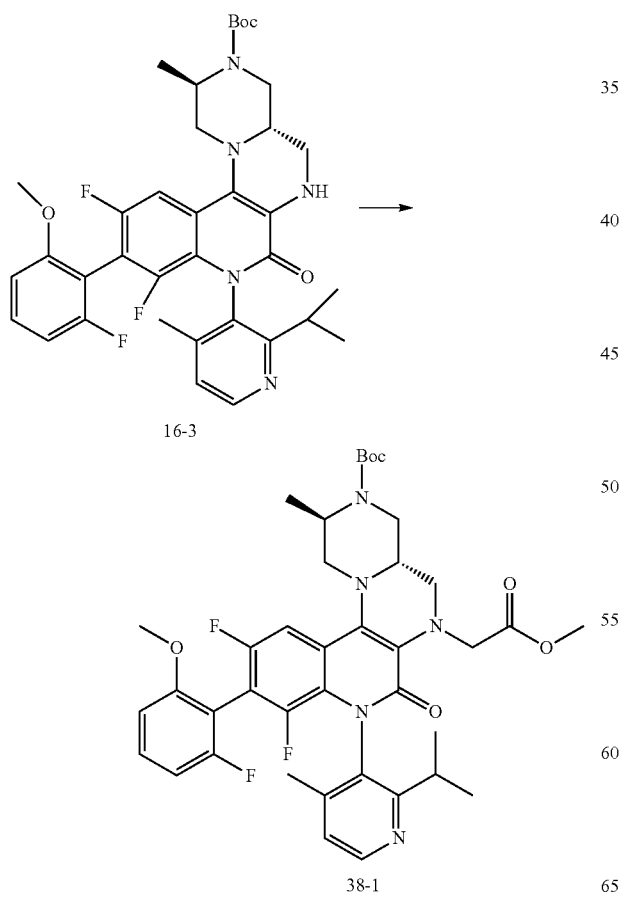

Compound 16-3 (150 mg, 226.00 μmol) was dissolved in N,N-dimethylformamide (2 mL), and sodium hydride (50 mg, 1.25 mmol, 60%) was added thereto, after the addition was completed, the reaction was stirred at room temperature (25° C.) for 0.5 hour; then methyl bromoacetate (100 mg, 653.70 μmol, 61.73 μL) was added thereto and the reaction was stirred at room temperature (25° C.) for 1 hour. The reaction mixture was quenched with 3 drops of saturated ammonium chloride solution, then poured into ice water, precipitated, filtered to obtain a filter cake, the filter cake was dried to obtain compound 38-1, which was directly used in the next reaction without further purification.

MS (ESI) m/z (M+Na)$^+$=758.3.

Step 2: Preparation of Compound 38-2

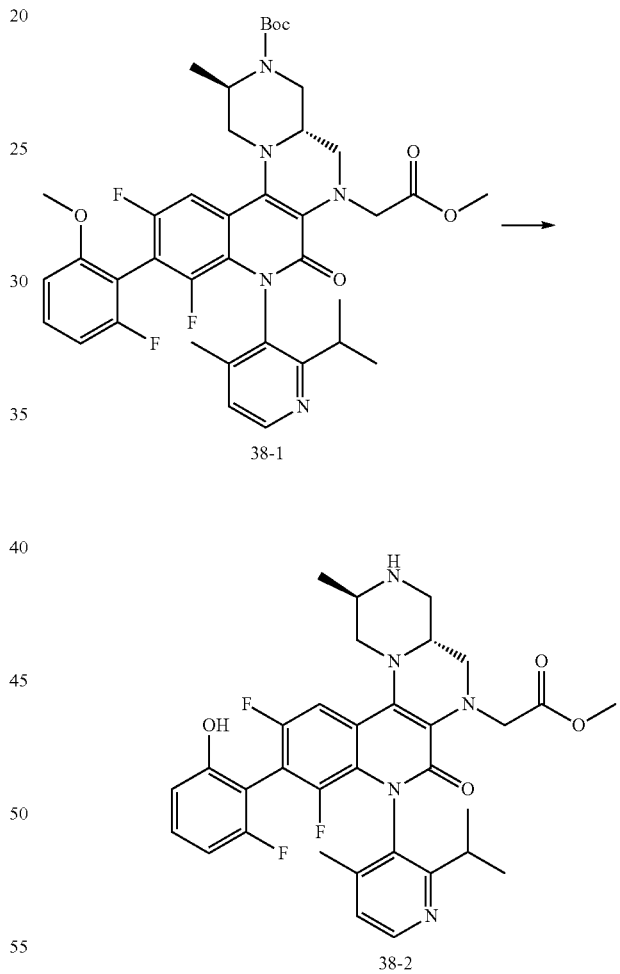

Compound 38-1 (160 mg, 217.45 μmol) was dissolved in dichloromethane (2 mL), and boron tribromide (160 mg, 217.45 μmol) was added thereto, and the reaction was stirred at room temperature (20° C.) for 6 hours. The reaction mixture was quenched with methanol (5 mL), stirred for 10 min. The system was concentrated to obtain compound 38-2, which was directly used in the next reaction without further purification.

MS (ESI) m/z (M+H)$^+$=622.1.

Step 3: Preparation of Compounds 38A and 38B

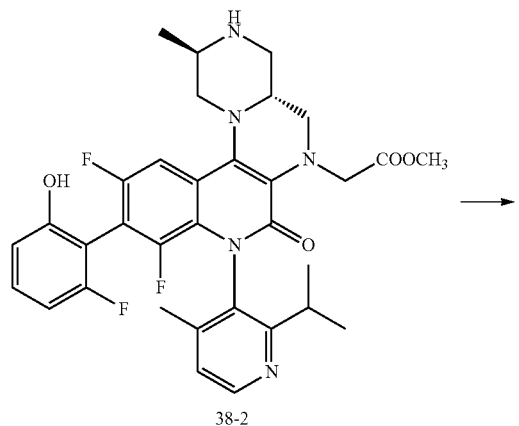

38-2

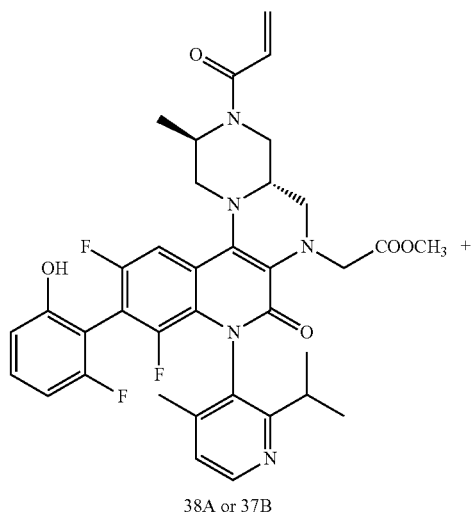

38A or 37B

Compound 38-2 (200 mg, 284.67 μmol, hydrobromide) was dissolved in tetrahydrofuran (2 mL) and sodium bicarbonate (4.32 g, 51.42 mmol) aqueous solution (2 mL), and tetrahydrofuran solution (1 mL) of acrylic anhydride (70 mg, 555.11 μmol) was added dropwise thereto. After the addition was completed, the system was stirred at room temperature (20° C.) for 1 hour. Methanol (1 mL) and saturated potassium carbonate aqueous solution (2 M, 1 mL) were added to the system, and the system was stirred at room temperature (20° C.) for 1.5 hours. The system was diluted by adding water (10 mL), the pH was adjusted to 6 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 50%-80% 9 min) to obtain compounds 38A and 38B.

Compound 38A:

$^1$H NMR (400 MHz, Methanol-$d_4$) δ 8.40 (d, J=4.9 Hz, 1H), 7.58 (br d, J=8.6 Hz, 1H), 7.27-7.14 (m, 2H), 6.89-6.75 (m, 1H), 6.72-6.58 (m, 2H), 6.27 (br dd, J=1.2, 16.9 Hz, 1H), 5.81 (br d, J=10.8 Hz, 1H), 5.00 (br d, J=16.8 Hz, 1H), 4.67-4.50 (m, 2H), 4.27-4.04 (m, 2H), 3.92-3.58 (m, 5H), 3.55-3.45 (m, 1H), 3.38 (br dd, J=4.5, 12.5 Hz, 1H), 3.28-3.09 (m, 2H), 2.71-2.58 (m, 1H), 2.01 (br d, J=12.6 Hz, 3H), 1.84-1.63 (m, 3H), 1.23-0.93 (m, 6H).

MS (ESI) m/z (M+H)$^+$=676.2.

Compound 38B:

$^1$H NMR (400 MHz, Methanol-$d_4$) δ 8.40 (d, J=4.9 Hz, 1H), 7.58 (br d, J=8.6 Hz, 1H), 7.27-7.14 (m, 2H), 6.89-6.75 (m, 1H), 6.72-6.58 (m, 2H), 6.27 (br dd, J=1.2, 16.9 Hz, 1H), 5.81 (br d, J=10.8 Hz, 1H), 5.00 (br d, J=16.8 Hz, 1H), 4.67-4.50 (m, 2H), 4.27-4.04 (m, 2H), 3.92-3.58 (m, 5H), 3.55-3.45 (m, 1H), 3.38 (br dd, J=4.5, 12.5 Hz, 1H), 3.28-3.09 (m, 2H), 2.71-2.58 (m, 1H), 2.01 (br d, J=12.6 Hz, 3H), 1.84-1.63 (m, 3H), 1.23-0.93 (m, 6H).

MS (ESI) m/z (M+H)$^+$=676.2.

Step 4: Preparation of Compounds 38A-1 and 38A-2

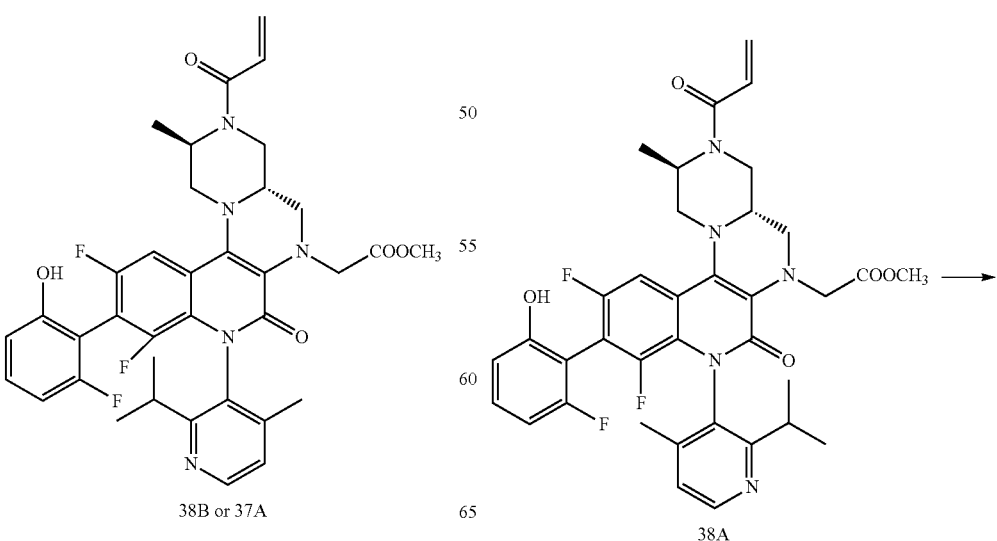

38B or 37A

38A

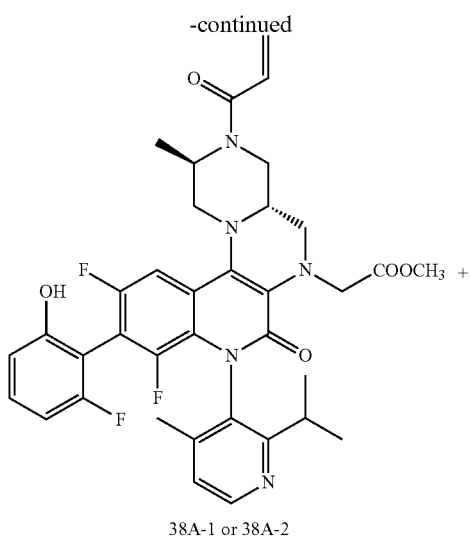

38A-1 or 38A-2

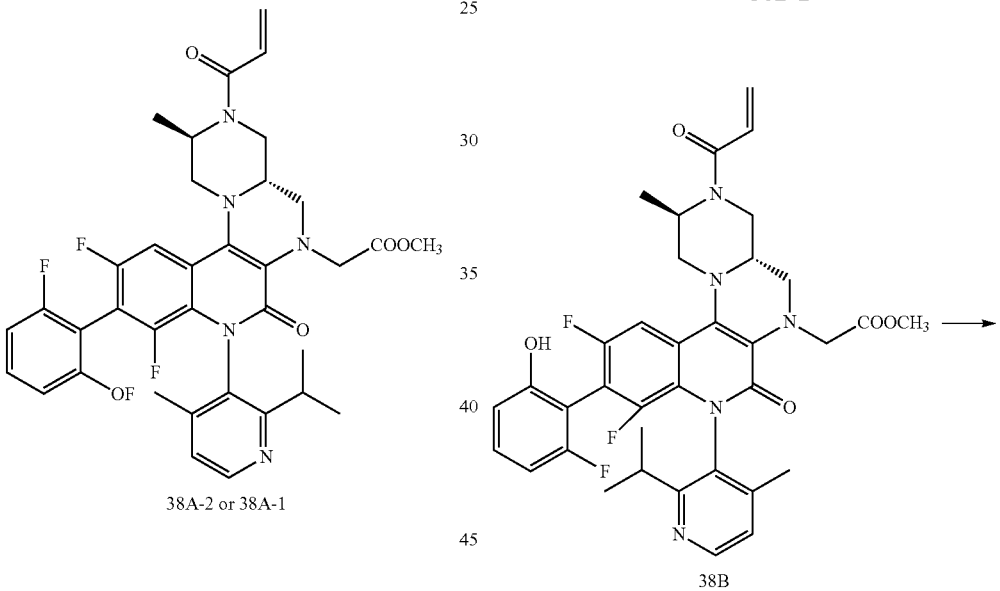

38A-2 or 38A-1

Diastereoisomeric compound 38A was purified by SFC (separation conditions: chromatographic column: DAICEL CHIRALPAK IG (250 mm*30 mm, 10 μm); mobile phase: [CO₂-isopropanol (0.1% ammonia)]; isopropanol %: 35%). After concentration, compound 38A-1 and compound 38A-2 were obtained.

Compound 38A-1:

$^1$H NMR (400 MHz, Methanol-$d_4$) δ 8.39 (d, J=5.1 Hz, 1H), 7.57 (br d, J=8.8 Hz, 1H), 7.27-7.14 (m, 2H), 6.89-6.77 (m, 1H), 6.70-6.56 (m, 2H), 6.26 (br dd, J=1.8, 16.8 Hz, 1H), 5.81 (br d, J=10.4 Hz, 1H), 5.08-4.96 (m, 1H), 4.61 (br d, J=13.7 Hz, 1H), 4.52 (br s, 1H), 4.29-4.07 (m, 2H), 3.86-3.76 (m, 1H), 3.73-3.58 (m, 3H), 3.50 (br d, J=17.2 Hz, 1H), 3.37 (br d, J=12.8 Hz, 1H), 3.27-3.12 (m, 2H), 2.66-2.56 (m, 1H), 2.01 (s, 3H), 1.85-1.65 (m, 3H), 1.12 (br t, J=7.1 Hz, 6H).

MS (ESI) m/z (M+H)$^+$=676.2.

SFC retention time was 5.434 min.

separation conditions: chromatographic column: ChiralPak IC-3 150×4.6 mm I.D., 3 μm; column temperature: 40° C.; mobile phase: CO₂-ethanol (0.05% DEA); ethanol: 5%-40% 5.5 min, 40% 3 min, 5% 1.5 min; flow rate: 2.5 mL/min.

Compound 38A-2:

$^1$H NMR (400 MHz, Methanol-$d_4$) δ 8.41 (d, J=5.1 Hz, 1H), 7.58 (br d, J=8.2 Hz, 1H), 7.32-7.14 (m, 2H), 6.91-6.76 (m, 1H), 6.70-6.55 (m, 2H), 6.27 (br d, J=17.0 Hz, 1H), 5.81 (dd, J=1.9, 10.7 Hz, 1H), 5.30-5.16 (m, 1H), 4.70-4.40 (m, 2H), 4.20-4.02 (m, 2H), 3.90-3.69 (m, 2H), 3.65 (s, 3H), 3.56-3.44 (m, 1H), 3.38 (br d, J=13.0 Hz, 1H), 3.23 (br d, J=13.5 Hz, 1H), 2.73 (br s, 1H), 2.02 (s, 3H), 1.79-1.66 (m, 3H), 1.18-1.02 (m, 6H).

MS (ESI) m/z (M+H)$^+$=676.2.

SFC retention time was 5.906 min.

separation conditions: chromatographic column: ChiralPak IC-3 150×4.6 mm I.D., 3 μm; column temperature: 40° C.; mobile phase: CO₂-ethanol (0.05% DEA); ethanol: 5%-40% 5.5 min, 40% 3 min, 5% 1.5 min; flow rate: 2.5 mL/min.

Step 5: Preparation of Compounds 38B-1 and 38B-2

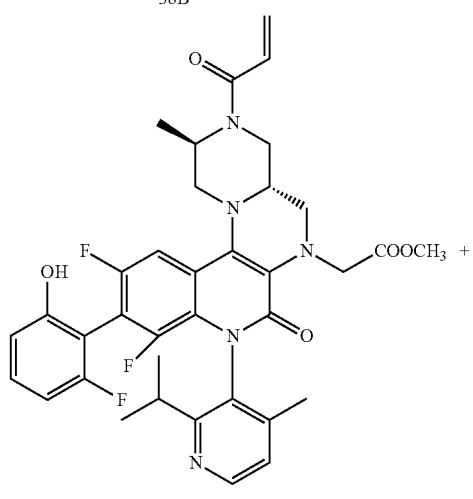

38B-1 or 38B-2

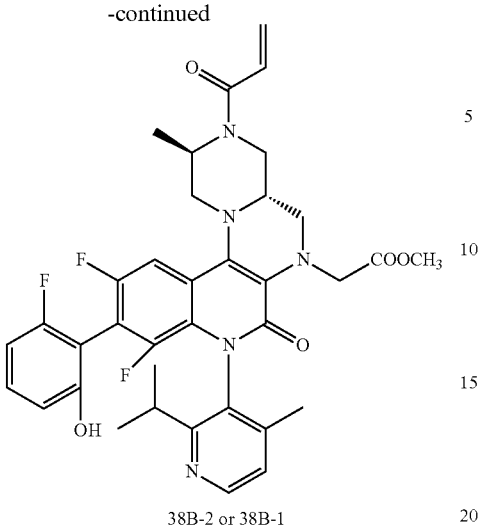

38B-2 or 38B-1

Diastereoisomeric compound 38B was purified by SFC (separation conditions: chromatographic column: DAICEL CHIRALPAK IC (250 mm*30 mm, 5 μm); mobile phase: [$CO_2$-ethanol (0.1% ammonia)]; isopropanol %: 35%). After concentration, compound 38B-1 and compound 38B-2 were obtained.

Compound 38B-1:

$^1$H NMR (400 MHz, Methanol-$d_4$) δ 8.40 (d, J=4.9 Hz, 1H), 7.58 (br d, J=9.5 Hz, 1H), 7.27-7.17 (m, 2H), 6.88-6.77 (m, 1H), 6.67-6.58 (m, 2H), 6.27 (br d, J=15.2 Hz, 1H), 5.81 (br d, J=10.8 Hz, 1H), 5.29-5.15 (m, 1H), 4.64-4.52 (m, 2H), 4.20-4.03 (m, 2H), 3.90-3.78 (m, 1H), 3.65 (s, 3H), 3.58-3.47 (m, 1H), 3.40 (br d, J=12.3 Hz, 1H), 3.24 (br d, J=13.2 Hz, 2H), 2.71 (br s, 1H), 2.00 (s, 3H), 1.82-1.67 (m, 3H), 1.10 (br dd, J=3.1, 6.6 Hz, 6H).

MS (ESI) m/z (M+H)$^+$=676.2.

SFC retention time was 5.362 min.

separation conditions: chromatographic column: ChiralPak IG-3 100×4.6 mm I.D., 3 μm; column temperature: 40° C.; mobile phase: $CO_2$-isopropanol (0.05% DEA); isopropanol: 5%-40% 5.5 min, 40% 3 min, 5% 1.5 min; flow rate: 2.5 mL/min.

Compound 38B-2:

$^1$H NMR (400 MHz, Methanol-$d_4$) δ 8.39 (d, J=5.1 Hz, 1H), 7.57 (br d, J=9.5 Hz, 1H), 7.24-7.15 (m, 2H), 6.88-6.77 (m, 1H), 6.70-6.57 (m, 2H), 6.26 (dd, J=1.8, 16.8 Hz, 1H), 5.81 (br d, J=10.8 Hz, 1H), 5.00 (br d, J=16.5 Hz, 1H), 4.65-4.48 (m, 2H), 4.31-4.06 (m, 2H), 3.86-3.67 (m, 2H), 3.64 (s, 3H), 3.56-3.44 (m, 1H), 3.38 (br d, J=12.8 Hz, 1H), 3.26-3.09 (m, 1H), 2.61 (td, J=6.8, 13.5 Hz, 1H), 2.07-1.99 (m, 3H), 1.79-1.67 (m, 3H), 1.17-1.10 (m, 3H), 1.09-1.01 (m, 3H).

MS (ESI) m/z (M+H)$^+$=676.2.

SFC retention time was 5.897 min.

separation conditions: chromatographic column: ChiralPak IG-3 100×4.6 mm I.D., 3 μm; column temperature: 40° C.; mobile phase: $CO_2$-isopropanol (0.05% DEA); isopropanol: 5%-40% 5.5 min, 40% 3 min, 5% 1.5 min; flow rate: 2.5 mL/min.

Embodiment 39: Preparation of Compound 39

Step 1: Preparation of Compounds 39A and 39B

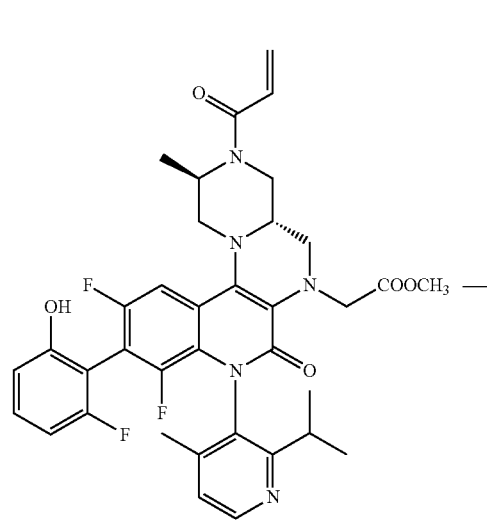

38A and 38B

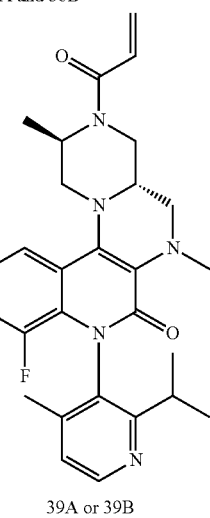

39A or 39B

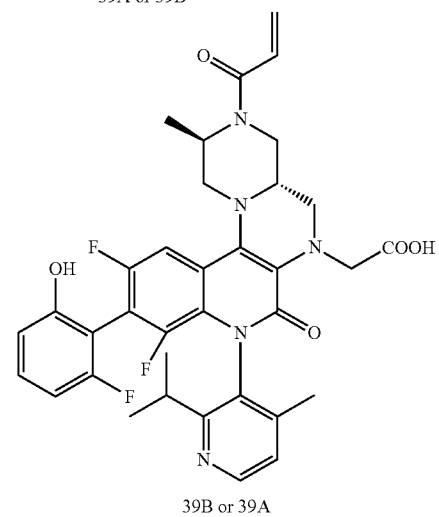

39B or 39A

A mixture of compounds 38A and 38B (50 mg, 74.00 μmol) was dissolved in a mixed solvent of methanol (1 mL)

and water (1 mL), and lithium hydroxide (20 mg, 476.60 µmol) was added thereto. After the addition was completed, the system was stirred at room temperature (20° C.) for 2 hours. The system was diluted by adding water (5 mL), the pH was adjusted to 5 with 1 N HCl, then the mixture was extracted with ethyl acetate (10 mL×3); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 µm, mobile phase: water (10 mM ammonium bicarbonate)-acetonitrile; acetonitrile 10%-80% 9 min) to obtain compounds 39A and 39B.

Compound 39A:

$^1$H NMR (400 MHz, Methanol-$d_4$) δ 8.39 (br d, J=4.4 Hz, 1H), 7.56 (br d, J=8.2 Hz, 1H), 7.21 (br d, J=4.2 Hz, 2H), 6.82 (br d, J=8.8 Hz, 1H), 6.72-6.51 (m, 1H), 6.27 (br d, J=16.8 Hz, 1H), 5.80 (br d, J=10.1 Hz, 1H), 5.01-4.96 (m, 1H), 4.70-4.37 (m, 2H), 4.26-3.97 (m, 2H), 3.93-3.66 (m, 2H), 3.48 (br s, 1H), 3.22 (br d, J=13.9 Hz, 2H), 2.81-2.47 (m, 2H), 2.02 (br d, J=9.5 Hz, 3H), 1.87-1.49 (m, 3H), 1.39-0.78 (m, 6H).

MS (ESI) m/z (M+H)$^+$=662.2.

Compound 39B:

$^1$H NMR (400 MHz, Methanol-$d_4$) δ 8.39 (d, J=5.1 Hz, 1H), 7.56 (br d, J=9.0 Hz, 1H), 7.27-7.14 (m, 2H), 6.81 (br d, J=10.4 Hz, 1H), 6.69-6.52 (m, 2H), 6.27 (br d, J=16.8 Hz, 1H), 5.80 (br d, J=10.6 Hz, 1H), 5.30-5.06 (m, 1H), 4.66-4.48 (m, 1H), 4.25-3.86 (m, 2H), 3.84-3.56 (m, 2H), 3.55-3.43 (m, 1H), 3.37-3.34 (m, 1H), 3.29-3.14 (m, 2H), 2.76-2.59 (m, 1H), 2.02 (br d, J=19.6 Hz, 3H), 1.90-1.58 (m, 3H), 1.19-1.02 (m, 6H).

MS (ESI) m/z (M+H)$^+$=662.2.

Step 2: Preparation of Compounds 39A-1 and 39A-2

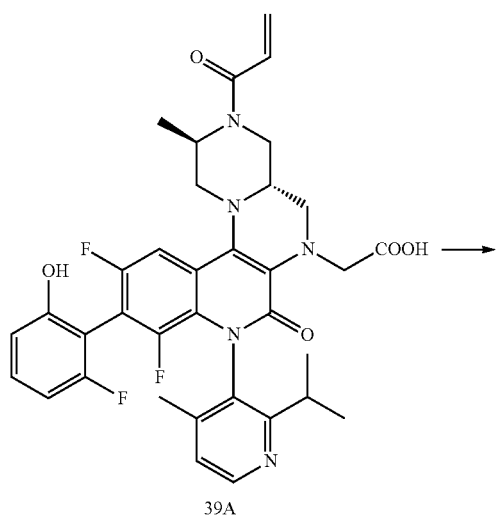

39A

-continued

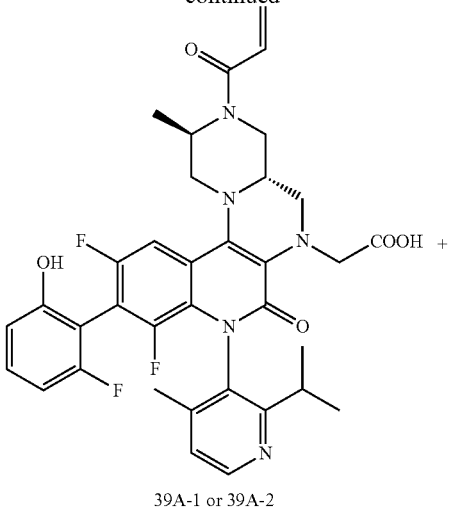

39A-1 or 39A-2

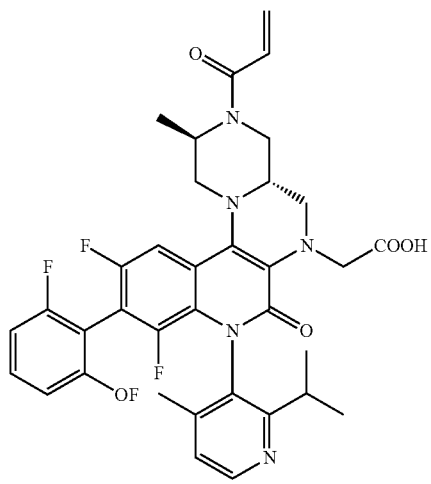

39A-2 or 39A-1

Diastereoisomeric compound 39A was purified by SFC (separation conditions: chromatographic column: DAICEL CHIRALPAK IC (250 mm*30 mm, 5 µm); mobile phase: [CO$_2$-methanol (0.1% ammonia)]; methanol %: 35%). After concentration, compound 39A-1 and compound 39A-2 were obtained.

Compound 39A-1:

$^1$H NMR (400 MHz, Methanol-$d_4$) δ 8.38 (d, J=4.9 Hz, 1H), 7.57 (br s, 1H), 7.25-7.15 (m, 2H), 6.83 (br s, 1H), 6.67-6.54 (m, 2H), 6.26 (br d, J=17.4 Hz, 1H), 5.80 (br d, J=11.0 Hz, 1H), 5.01-4.93 (m, 1H), 4.69-4.39 (m, 2H), 4.21-3.94 (m, 2H), 3.89-3.66 (m, 2H), 3.49 (br s, 1H), 3.15 (br s, 2H), 2.62 (br s, 1H), 2.04 (s, 3H), 1.81-1.67 (m, 3H), 1.15-1.09 (m, 6H).

MS (ESI) m/z (M+H)$^+$=662.2.

SFC retention time was 5.408 min.

separation conditions: chromatographic column: ChiralPak IC-3 150×4.6 mm I.D., 3 µm; column temperature: 40° C.; mobile phase: CO$_2$-methanol (0.05% DEA); methanol: 5%-40% 5.5 min, 40% 3 min, 5% 1.5 min; flow rate: 2.5 mL/min.

Compound 39A-2:

$^1$H NMR (400 MHz, Methanol-$d_4$) δ 8.39 (br d, J=4.9 Hz, 1H), 7.58 (br s, 1H), 7.20 (br d, J=8.4 Hz, 2H), 6.83 (br s, 1H), 6.71-6.56 (m, 2H), 6.27 (br d, J=16.8 Hz, 1H), 5.81 (br d, J=10.1 Hz, 1H), 5.14 (br s, 1H), 4.69-4.46 (m, 2H), 4.05

(br s, 2H), 3.82 (br s, 1H), 3.69 (br d, J=5.3 Hz, 1H), 3.48 (br s, 1H), 3.14 (br s, 2H), 2.74 (br s, 1H), 2.01 (s, 3H), 1.84-1.67 (m, 3H), 1.25-1.03 (m, 6H).

MS (ESI) m/z (M+H)$^+$=662.2.

SFC retention time was 5.896 min.

separation conditions: chromatographic column: ChiralPak IC-3 150×4.6 mm I.D., 3 μm; column temperature: 40° C.; mobile phase: CO$_2$-methanol (0.05% DEA); methanol: 5%-40% 5.5 min, 40% 3 min, 5% 1.5 min; flow rate: 2.5 mL/min.

Embodiment 40: Preparation of Compound 40

Step 1: Preparation of Compound 40-1

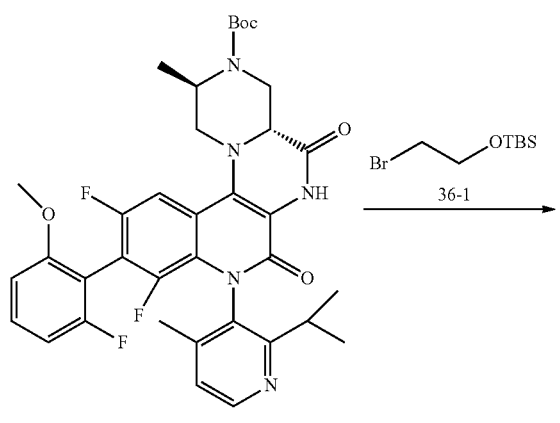

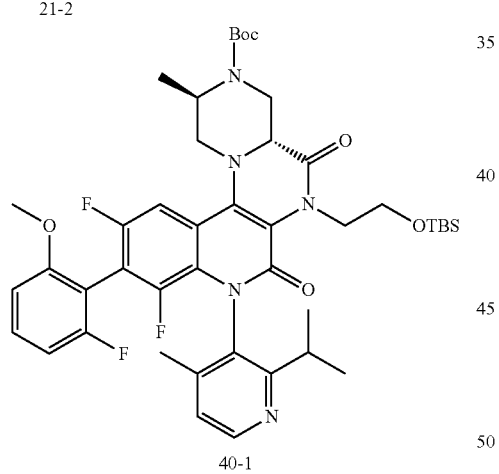

Compound 21-2 (110 mg, 162.31 μmol) was dissolved in N,N-dimethylformamide (2 mL); potassium carbonate (89.73 mg, 649.24 μmol), compound 36-1 (116.49 mg, 486.93 μmol) and potassium iodide (26.94 mg, 162.31 μmol) were added thereto; after the addition was completed, the system was heated to 100° C. and stirred for 16 hours. After the reaction was cooled to room temperature (25° C.), water (10 mL) and ethyl acetate (10 mL×2) were added thereto for separation and extraction; the organic phase was dried over anhydrous sodium sulfate, filtered, and the filtrate was concentrated under reduced pressure to obtain compound 40-1, which was directly used in the next reaction without further purification.

MS (ESI) m/z (M+H)$^+$=836.3.

Step 2: Preparation of Compound 40-2

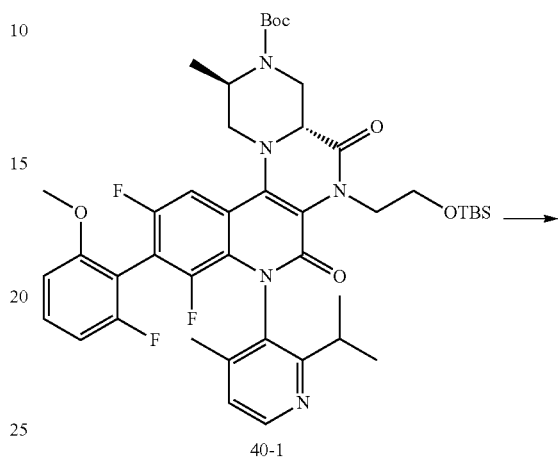

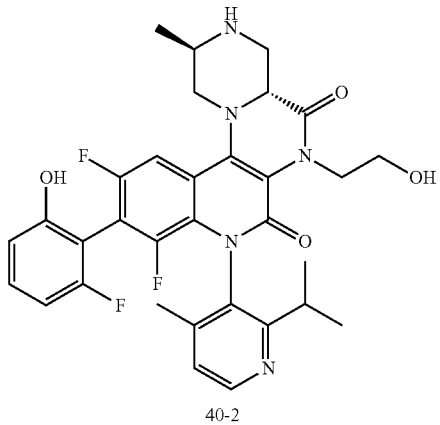

Compound 40-1 (170 mg, 203.34 μmol) was dissolved in dichloromethane (2 mL), and boron tribromide (260 mg, 1.04 mmol, 0.1 mL) was added thereto, and the reaction was stirred at room temperature (20° C.) for 2 hours. The reaction mixture was quenched with methanol (2 mL), stirred for 10 min. The system was added with dichloromethane (30 mL), washed with saturated sodium bicarbonate aqueous solution (30 mL), dried over anhydrous sodium sulfate, filtered, and the filtrate was concentrated to obtain crude product 40-2, which was directly used in the next reaction without further purification.

MS (ESI) m/z (M+H)$^+$=608.1.

Step 3: Preparation of Compounds 40A and 40B

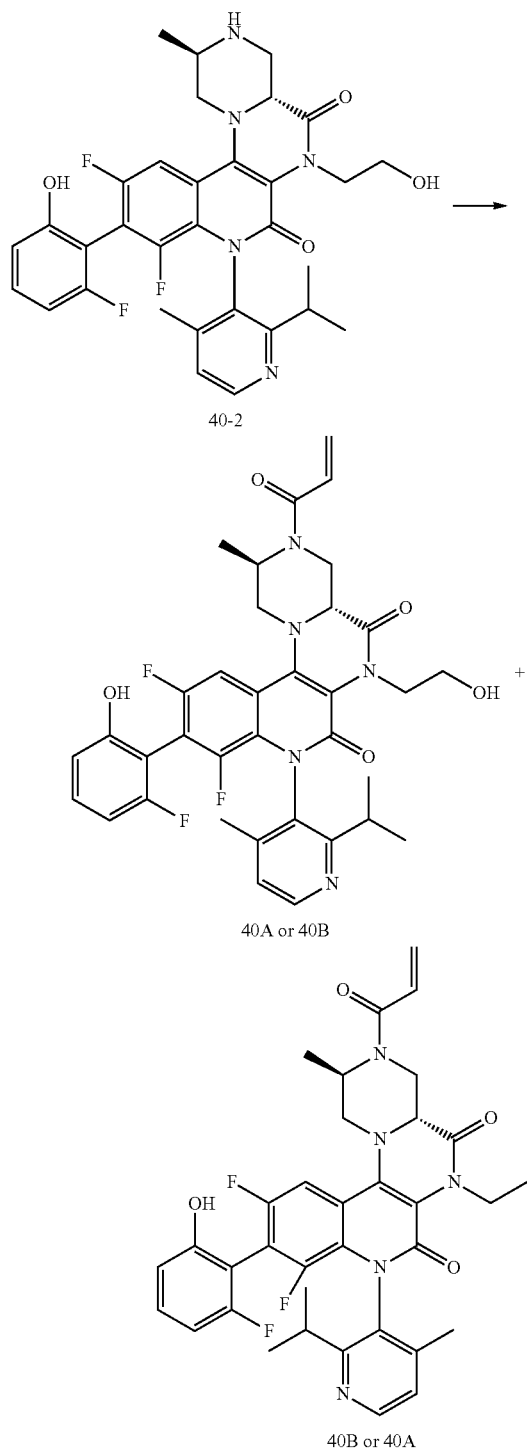

40-2

40A or 40B 40B or 40A

Compound 40-2 (120.00 mg, 197.49 μmol) was dissolved in tetrahydrofuran (2 mL) and sodium bicarbonate (4.32 g, 51.42 mmol) aqueous solution (2 mL), and acrylic anhydride (24.91 mg, 197.49 μmol) was added dropwise thereto. After the addition was completed, the system was stirred at room temperature (25° C.) for 0.5 hours. Methanol (2 mL) and saturated potassium carbonate aqueous solution (2 mL) were added to the system, and the system was stirred at room temperature (20° C.) for 1 hour. The system was diluted by adding water (10 mL), extracted with ethyl acetate (10 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 32%-62% 9 min) to obtain compounds 40A and 40B.

Compound 40A:

$^1$H NMR (400 MHz, Methanol-$d_4$) δ 8.44 (d, J=5.1 Hz, 1H), 7.69 (br d, J=9.0 Hz, 1H), 7.34-7.04 (m, 3H), 6.66 (td, J=9.4, 18.7 Hz, 2H), 6.23 (br d, J=16.1 Hz, 1H), 5.81 (br d, J=10.4 Hz, 1H), 4.97-4.94 (m, 1H), 4.68-4.33 (m, 3H), 3.91 (br d, J=11.0 Hz, 1H), 3.64 (br d, J=5.5 Hz, 2H), 3.48 (br s, 1H), 3.23-2.95 (m, 2H), 2.55 (s, 1H), 2.21-1.97 (m, 3H), 1.76-1.65 (m, 3H), 1.10 (br dd, J=6.6, 17.2 Hz, 6H).

MS (ESI) m/z (M+H)$^+$=662.3.

SFC retention time was 5.835 min.

Separation conditions: chromatographic column: Cellulose 2 150×4.6 mm I.D., 5 μm; column temperature: 35° C.; mobile phase: $CO_2$-methanol (0.05% DEA)-methanol %: 5%-40% 5 min, 40% 2.5 min, 5% 2.5 min; flow rate: 2.5 mL/min.

Compound 40B:

$^1$H NMR (400 MHz, Methanol-$d_4$) δ 8.44 (d, J=5.1 Hz, 1H), 7.68 (br d, J=9.3 Hz, 1H), 7.33-7.03 (m, 3H), 6.75-6.53 (m, 2H), 6.32-6.14 (m, 1H), 5.87-5.71 (m, 1H), 5.00-4.91 (m, 1H), 4.80-4.30 (m, 2H), 4.00-3.51 (m, 4H), 3.26-2.89 (m, 3H), 2.61-2.44 (m, 1H), 2.26-1.90 (m, 3H), 1.79-1.56 (m, 3H), 1.26-0.85 (m, 6H).

MS (ESI) m/z (M+H)$^+$=662.3.

SFC retention time was 6.379 min.

Separation conditions: chromatographic column: Cellulose 2 150×4.6 mm I.D., 5 μm; column temperature: 35° C.; mobile phase: $CO_2$-methanol (0.05% DEA)-methanol %: 5%-40% 5 min, 40% 2.5 min, 5% 2.5 min; flow rate: 2.5 mL/min.

Step 4: Preparation of Compounds 40A-1 and 40A-2

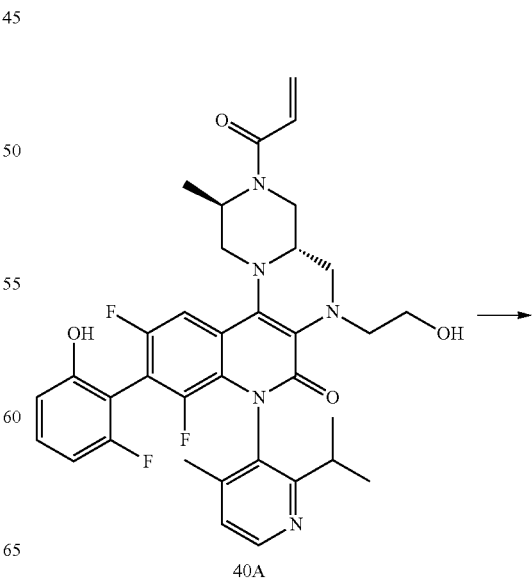

40A

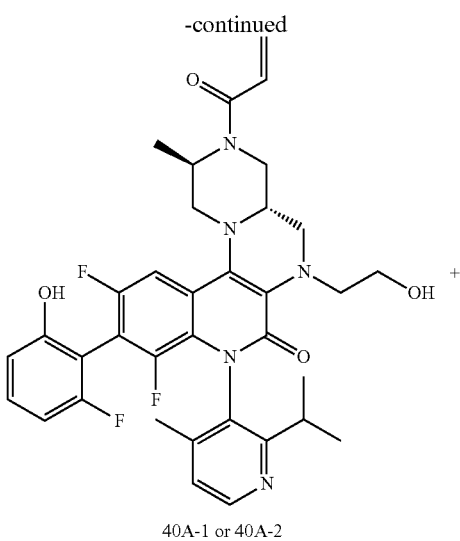

40A-1 or 40A-2

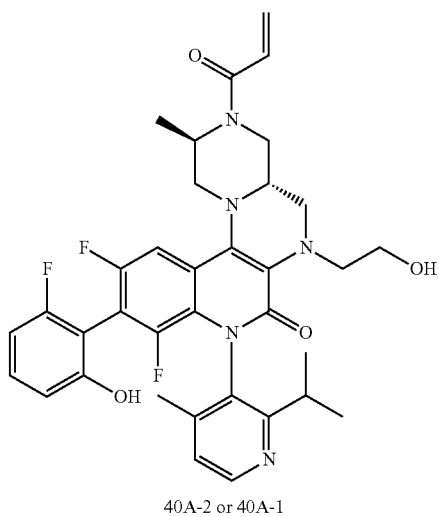

40A-2 or 40A-1

Diastereoisomeric compound 40A was purified by SFC (separation conditions: chromatographic column: Phenomenex-Cellulose-2 (250 mm*30 mm, 10 μm); mobile phase: [CO$_2$-methanol (0.1% ammonia)]; methanol %: 40%). After concentration, compound 40A-1 and compound 40A-2 were obtained.

Compound 40A-1:

$^1$H NMR (400 MHz, Methanol-d$_4$) δ 8.44 (d, J=5.0 Hz, 1H), 7.69 (br d, J=9.2 Hz, 1H), 7.29-7.20 (m, 2H), 7.13 (dd, J=10.7, 16.9 Hz, 1H), 6.73-6.59 (m, 2H), 6.31-6.18 (m, 1H), 5.84-5.74 (m, 1H), 4.97-4.94 (m, 1H), 4.79-4.59 (m, 2H), 4.53-4.27 (m, 2H), 4.01-3.86 (m, 2H), 3.73-3.55 (m, 2H), 3.21-3.12 (m, 1H), 3.00 (quin, J=6.7 Hz, 1H), 1.98 (s, 3H), 1.75-1.65 (m, 3H), 1.23 (d, J=6.7 Hz, 3H), 1.12 (d, J=6.8 Hz, 3H).

MS (ESI) m/z (M+H)$^+$=662.2.

HPLC retention time was 7.66 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 4.617 min.

separation conditions: chromatographic column: ChiralPak IG-3 100×4.6 mm I.D., 3 μm; column temperature: 40° C.; mobile phase: CO$_2$-ethanol (0.05% DEA)-ethanol: 5%-40% 5.5 min, 40% 3 min, 5% 1.5 min; flow rate: 2.5 mL/min.

Compound 40A-2:

$^1$H NMR (400 MHz, Methanol-d$_4$) δ=8.44 (d, J=5.0 Hz, 1H), 7.76-7.63 (m, 1H), 7.28-7.19 (m, 2H), 7.12 (dd, J=10.7, 16.9 Hz, 1H), 6.70-6.59 (m, 2H), 6.28-6.18 (m, 1H), 5.84-5.73 (m, 1H), 4.94 (br s, 1H), 4.78-4.71 (m, 1H), 4.55 (br s, 1H), 4.47-4.39 (m, 2H), 4.01-3.86 (m, 2H), 3.69-3.59 (m, 2H), 3.23-3.06 (m, 1H), 2.55 (td, J=6.7, 13.4 Hz, 1H), 2.18 (s, 3H), 1.75-1.65 (m, 3H), 1.12 (d, J=6.7 Hz, 3H), 1.08 (d, J=6.8 Hz, 3H).

MS (ESI) m/z (M+H)$^+$=662.2.

HPLC retention time was 7.68 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 4.826 min.

separation conditions: chromatographic column: ChiralPak IG-3 100×4.6 mm I.D., 3 μm; column temperature: 40° C.; mobile phase: CO$_2$-ethanol (0.05% DEA)-ethanol: 5%-40% 5.5 min, 40% 3 min, 5% 1.5 min; flow rate: 2.5 mL/min.

Step 5: Preparation of Compounds 40B-1 and 40B-2

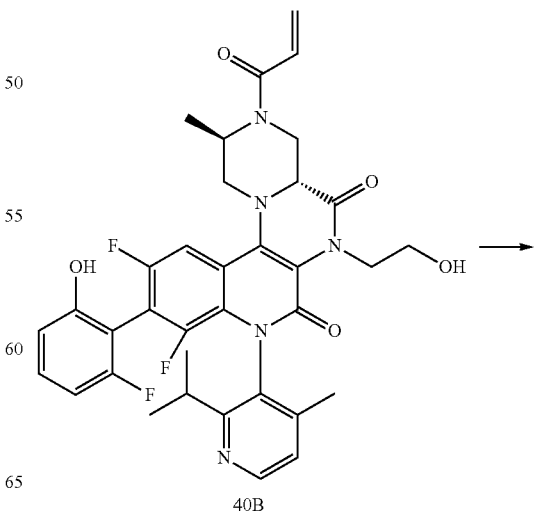

40B

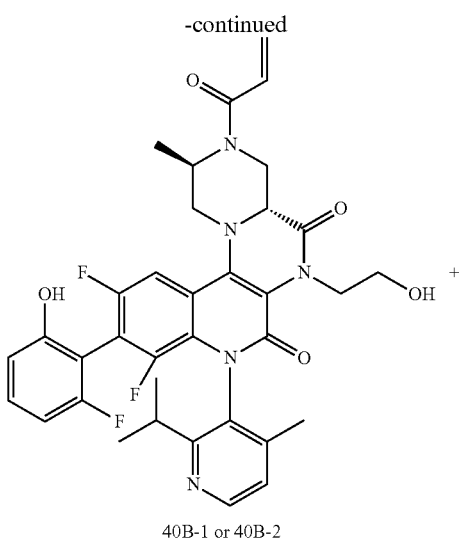

40B-1 or 40B-2

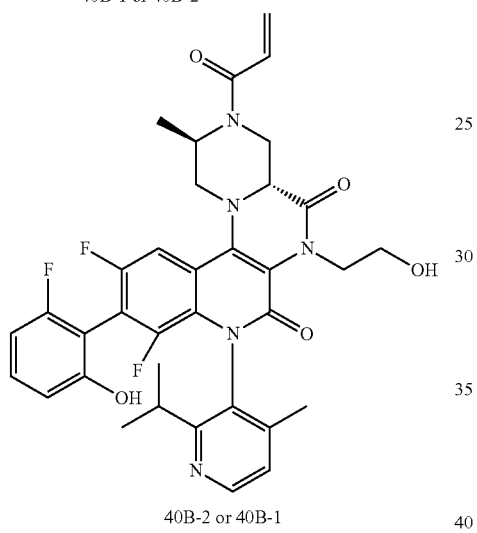

40B-2 or 40B-1

Diastereoisomeric compound 40B was purified by SFC (separation conditions: chromatographic column: Phenomenex-Cellulose-2 (250 mm*30 mm, 10 μm); mobile phase: [CO$_2$-methanol (0.1% ammonia)]; methanol %: 40%). After concentration, compound 40B-1 and compound 40B-2 were obtained.

Compound 40B-1:

$^1$H NMR (400 MHz, Methanol-d$_4$) δ 8.44 (d, J=5.0 Hz, 1H), 7.68 (br d, J=9.2 Hz, 1H), 7.29-7.20 (m, 2H), 7.12 (dd, J=10.7, 16.9 Hz, 1H), 6.72-6.57 (m, 2H), 6.30-6.17 (m, 1H), 5.85-5.74 (m, 1H), 4.92 (br s, 1H), 4.74 (br d, J=13.1 Hz, 1H), 4.58 (br s, 1H), 4.43 (t, J=5.5 Hz, 2H), 4.04-3.85 (m, 2H), 3.71-3.58 (m, 2H), 3.23-3.06 (m, 1H), 2.59-2.49 (m, 1H), 2.19 (s, 3H), 1.76-1.66 (m, 3H), 1.12 (d, J=6.7 Hz, 3H), 1.02 (d, J=6.8 Hz, 3H).

MS (ESI) m/z (M+H)$^+$=662.2.

HPLC retention time was 8.02 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 5.835 min.

Separation conditions: chromatographic column: Cellulose 2 150×4.6 mm I.D., 5 μm; column temperature: 35° C.; mobile phase: CO$_2$-methanol (0.05% DEA)-methanol %: 5%-40% 5 min, 40% 2.5 min, 5% 2.5 min; flow rate: 2.5 mL/min.

Compound 40B-2:

$^1$H NMR (400 MHz, Methanol-d$_4$) δ 8.45 (d, J=5.0 Hz, 1H), 7.68 (br d, J=9.2 Hz, 1H), 7.30-7.18 (m, 2H), 7.11 (dd, J=10.7, 16.9 Hz, 1H), 6.71-6.58 (m, 2H), 6.29-6.17 (m, 1H), 5.84-5.73 (m, 1H), 4.92 (br s, 1H), 4.74 (br d, J=12.8 Hz, 1H), 4.52-4.32 (m, 2H), 4.00-3.85 (m, 2H), 3.77-3.42 (m, 3H), 3.20-3.11 (m, 1H), 3.00 (td, J=6.6, 13.6 Hz, 1H), 1.98 (s, 3H), 1.75-1.64 (m, 3H), 1.23 (d, J=6.8 Hz, 3H), 1.16 (d, J=6.7 Hz, 3H).

MS (ESI) m/z (M+H)$^+$=662.1.

HPLC retention time was 8.08 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min SFC retention time was 6.379 min.

Separation conditions: chromatographic column: Cellulose 2 150×4.6 mm I.D., 5 μm; column temperature: 35° C.; mobile phase: CO$_2$-methanol (0.05% DEA)-methanol %: 5%-40% 5 min, 40% 2.5 min, 5% 2.5 min; flow rate: 2.5 mL/min.

Embodiment 41: Preparation of Compound 41

Step 1: Preparation of Compound 41-2

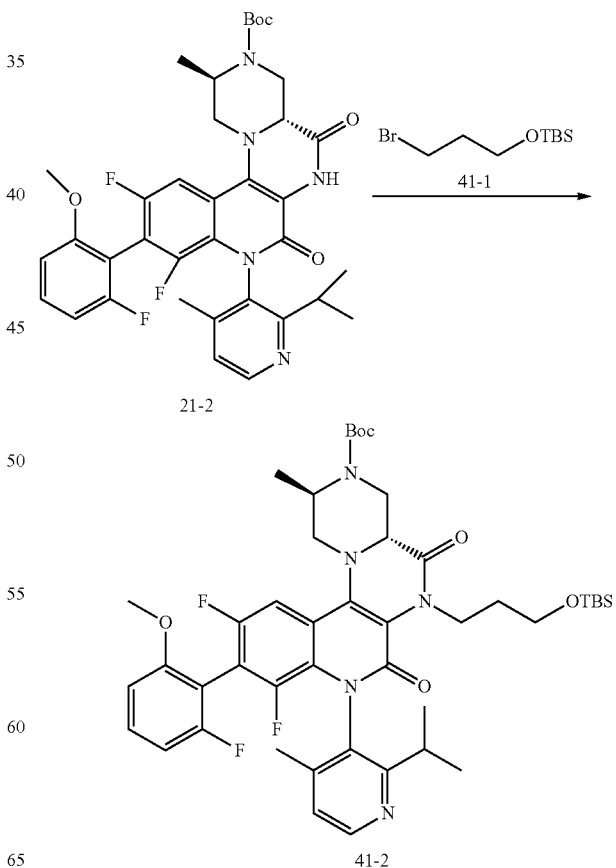

Compound 21-2 (90 mg, 132.80 μmol) was dissolved in N,N-dimethylformamide (2 mL); potassium carbonate (73.42 mg, 531.20 μmol), compound 41-1 (100.90 mg, 398.40 μmol) and potassium iodide (22.04 mg, 132.80 μmol) were added thereto; after the addition was completed, the system was heated to 100° C. and stirred for 16 hours. After the reaction was cooled to room temperature (25° C.), water (10 mL) and ethyl acetate (10 mL×2) were added thereto for separation and extraction; the organic phase was dried over anhydrous sodium sulfate, filtered, and the filtrate was concentrated under reduced pressure to obtain compound 41-2, which was directly used in the next reaction without further purification.

MS (ESI) m/z (M+H)⁺=850.3.

Step 2: Preparation of Compound 41-3

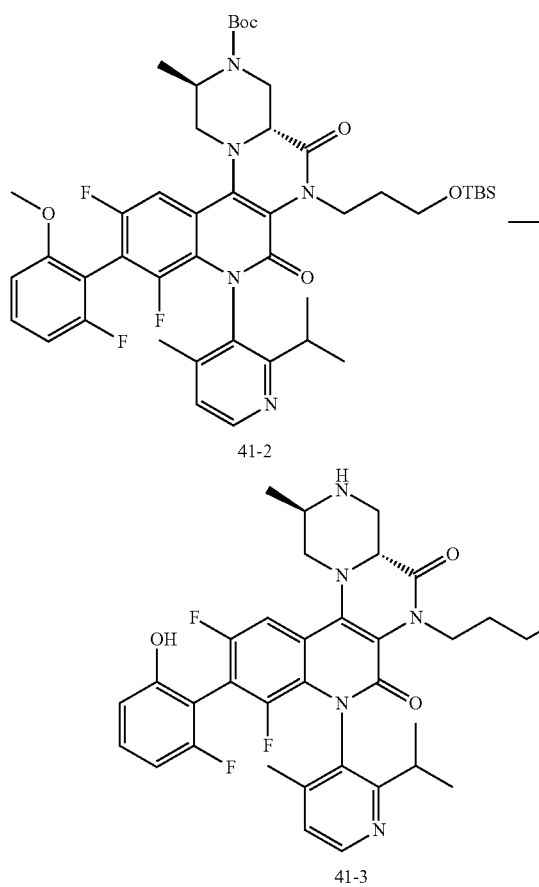

Compound 41-2 (120 mg, 141.17 μmol) was dissolved in dichloromethane (2 mL), and boron tribromide (176.83 mg, 705.84 μma 68.01 μL) was added thereto, and the reaction was stirred at room temperature (25° C.) for 2 hours. The reaction mixture was quenched with methanol (2 mL), stirred for 10 min. The system was added with dichloromethane (20 mL), washed with saturated sodium bicarbonate aqueous solution (10 mL), dried over anhydrous sodium sulfate, filtered, and the filtrate was concentrated to obtain crude product 41-3, which was directly used in the next reaction without further purification.

MS (ESI) m/z (M+H)⁺=622.4.

Step 3: Preparation of Compounds 41A and 41B

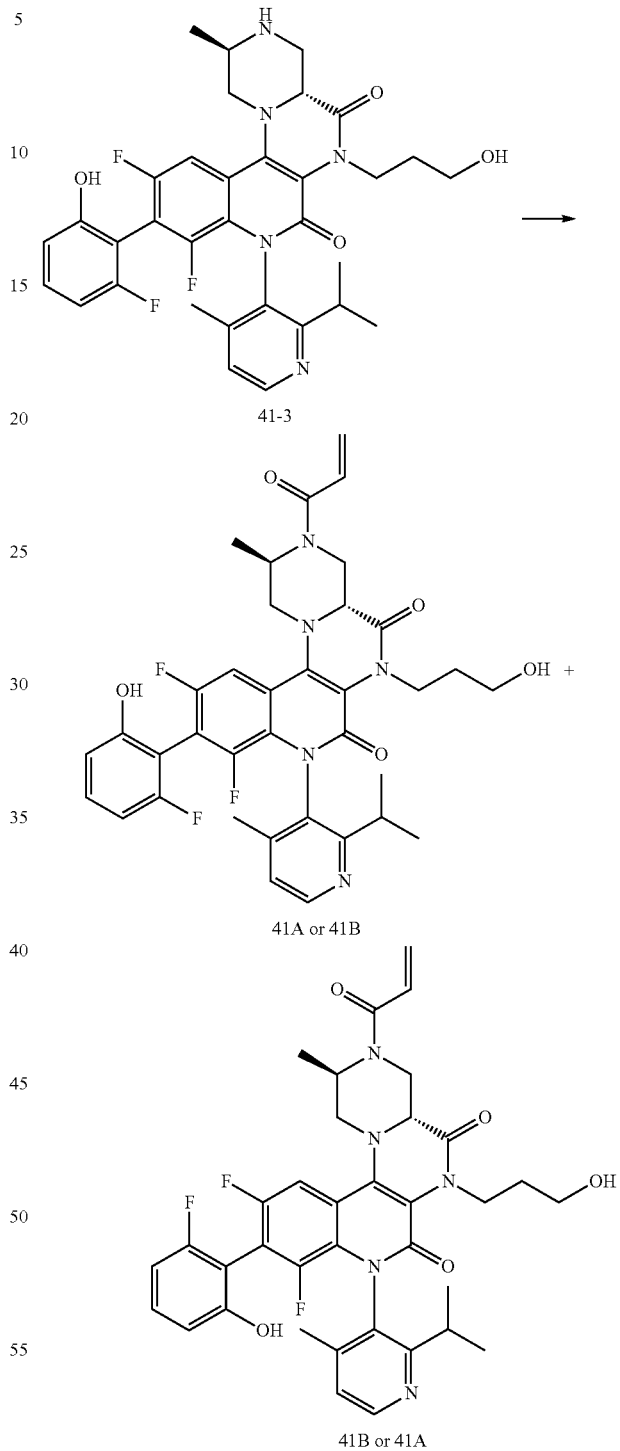

Compound 41-3 (90 mg, 131.47 μmol) was dissolved in tetrahydrofuran (5 mL) and sodium bicarbonate aqueous solution (3.61 g, 42.98 mmol, 1.67 mL), and acrylic anhydride (16.58 mg, 131.47 μmol) was added dropwise thereto. After the addition was completed, the system was stirred at room temperature (25° C.) for 0.5 hours. Methanol (2 mL) and saturated potassium carbonate aqueous solution (2 mL)

were added to the system, and the system was stirred at room temperature (20° C.) for 1 hour. The system was diluted by adding water (10 mL), extracted with ethyl acetate (10 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 46%-76% 9 min) to obtain compounds 41A and 41B.

Compound 41A:

$^1$H NMR (400 MHz, Methanol-$d_4$) 8.45 (d, J=5.1 Hz, 1H), 7.68 (br d, J=9.7 Hz, 1H), 7.32-7.04 (m, 3H), 6.73-6.59 (m, 2H), 6.29-6.20 (m, 1H), 5.88-5.77 (m, 1H), 4.99-4.95 (m, 1H), 4.75 (br d, J=12.4 Hz, 1H), 4.62 (s, 2H), 4.32 (br dd, J=7.3, 13.8 Hz, 1H), 4.26-4.15 (m, 1H), 3.93-3.89 (m, 1H), 3.57-3.49 (m, 2H), 3.40-3.36 (m, 1H), 2.61-2.48 (m, 1H), 2.20 (s, 3H), 1.82 (br s, 2H), 1.75-1.65 (m, 3H), 1.10 (dd, J=6.8, 12.8 Hz, 6H).

MS (ESI) m/z (M+H)$^+$=676.3.

HPLC retention time was 3.033 min.

Separation conditions: chromatographic column: Ultimate C18 3*50 mm 3 μm; column temperature: 50° C.; mobile phase: water (1.5 mL/4 L trifluoroacetic acid solution)-acetonitrile; acetonitrile: 10%-80% 6 min, 80% 2 min; flow rate: 1.2 mL/min.

Compound 41B:

$^1$H NMR (400 MHz, Methanol-$d_4$) δ 8.45 (br d, J=4.6 Hz, 1H), 7.68 (br d, J=8.7 Hz, 1H), 7.31-7.20 (m, 2H), 7.12 (br dd, J=10.7, 16.9 Hz, 1H), 6.73-6.59 (m, 2H), 6.32-6.19 (m, 1H), 5.88-5.75 (m, 1H), 4.99-4.93 (m, 1H), 4.80-4.45 (m, 2H), 4.41-4.04 (m, 2H), 4.02-3.86 (m, 2H), 3.57-3.34 (m, 3H), 3.05-2.87 (m, 2H), 2.60-2.48 (m, 1H), 2.20 (br s, 3H), 1.76-1.63 (m, 3H), 1.31-1.06 (m, 6H).

MS (ESI) m/z (M+H)$^+$=676.2.

HPLC retention time was 3.277 min.

Separation conditions: chromatographic column: Ultimate C18 3*50 mm 3 μm; column temperature: 50° C.; mobile phase: water (1.5 mL/4 L trifluoroacetic acid solution)-acetonitrile; acetonitrile: 10%-80% 6 min, 80% 2 min; flow rate: 1.2 mL/min.

Embodiment 42: Preparation of Compound 42

Step 1: Preparation of Compound 42-1

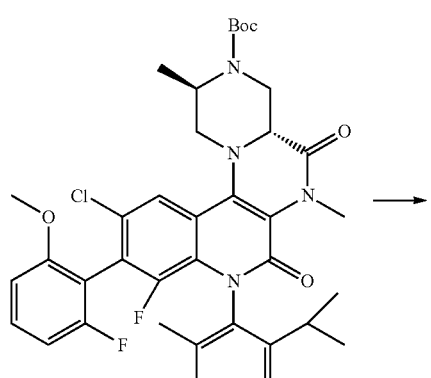

23-3

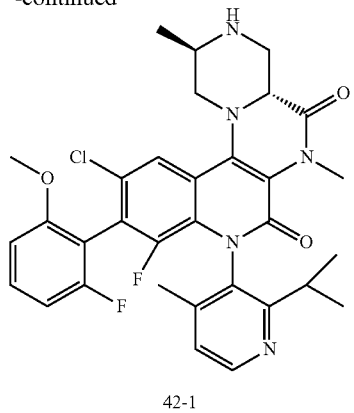

42-1

Compound 23-3 (80 mg, 112.96 μmol) was dissolved in dichloromethane (2 mL), trifluoroacetic acid (211.11 mg, 1.85 mmol, 137.08 μL) was added thereto, after the addition was completed, and the system was stirred at room temperature (25° C.) for 3 hours. The system was concentrated to obtain compound 42-1, which was directly used in the next reaction without further purification.

MS (ESI) m/z (M+H)$^+$=608.1.

Step 2: Preparation of Compound 42

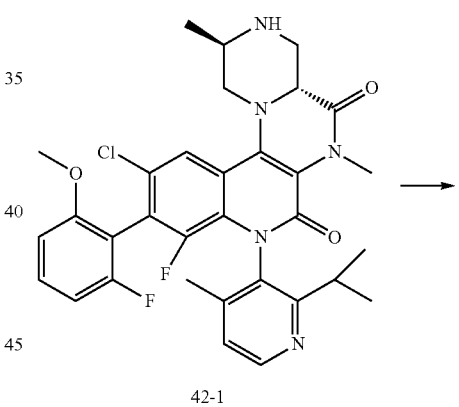

42-1

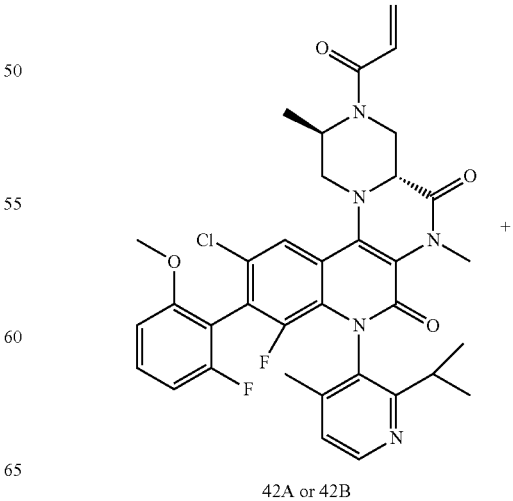

42A or 42B

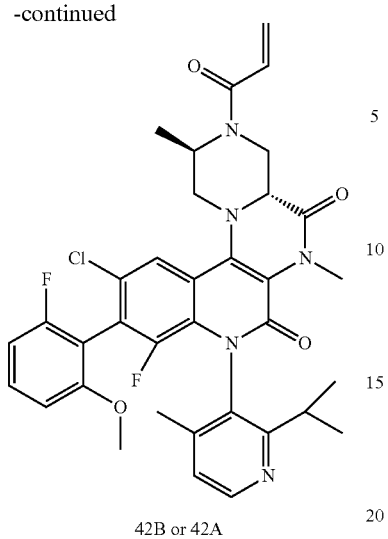

42B or 42A

Compound 42-1 (80 mg, 110.79 μmol, trifluoroacetate) was dissolved in tetrahydrofuran (5 mL) and sodium bicarbonate aqueous solution (4.32 g, 51.42 mmol, 2.00 mL), and acrylic anhydride (13.97 mg, 110.79 μmol) was added dropwise thereto. After the addition was completed, the reaction was carried out at room temperature (25° C.) for 0.5 hours. The system was quenched with methanol (2 mL), added with water (10 mL), and extracted with ethyl acetate (10 mL×2), the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 55%-85% 9 min) and then purified by SFC (separation conditions: chromatographic column Phenomenex-Cellulose-2 (250 mm*30 mm, 10 μm), mobile phase: $CO_2$-methanol (0.1% ammonia); methanol 45%) to obtain compounds 42A and 42B.

Compound 42A:

$^1$H NMR (400 MHz, Methanol-$d_4$) δ 8.43 (d, J=5.0 Hz, 1H), 8.02 (s, 1H), 7.49-7.37 (m, 1H), 7.24 (dd, J=2.7, 4.8 Hz, 1H), 7.12 (dd, J=10.7, 17.0 Hz, 1H), 6.89 (dd, J=4.1, 8.5 Hz, 1H), 6.79 (t, J=8.6 Hz, 1H), 6.31-6.18 (m, 1H), 5.87-5.75 (m, 1H), 4.93 (br s, 1H), 4.78-4.46 (m, 2H), 4.01-3.84 (m, 2H), 3.72 (d, J=16.2 Hz, 3H), 3.43 (s, 3H), 3.04-2.88 (m, 2H), 1.98 (d, J=3.5 Hz, 3H), 1.76-1.62 (m, 3H), 1.22 (d, J=6.8 Hz, 3H), 1.13 (dd, J=6.8, 10.0 Hz, 3H).

MS (ESI) m/z (M+H)$^+$=662.2.

HPLC retention time was 8.63 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 42B:

$^1$H NMR (400 MHz, Methanol-$d_4$) δ 8.44 (d, J=4.9 Hz, 1H), 8.02 (s, 1H), 7.47-7.39 (m, 1H), 7.27 (d, J=4.9 Hz, 1H), 7.12 (dd, J=10.7, 17.0 Hz, 1H), 6.89 (t, J=8.4 Hz, 1H), 6.79 (dt, J=3.2, 8.6 Hz, 1H), 6.32-6.17 (m, 1H), 5.88-5.75 (m, 1H), 4.93 (br s, 1H), 4.80-4.51 (m, 2H), 4.03-3.87 (m, 2H), 3.77-3.66 (m, 3H), 3.45 (s, 3H), 3.03-2.87 (m, 1H), 2.62- 2.51 (m, 1H), 2.25-2.16 (m, 3H), 1.75-1.63 (m, 3H), 1.12 (t, J=6.3 Hz, 3H), 1.04 (dd, J=6.8, 12.8 Hz, 3H).

MS (ESI) m/z (M+H)$^+$=662.2.

HPLC retention time was 8.57 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Embodiment 43: Preparation of Compound 43

Step 1: Preparation of Compound 43-2

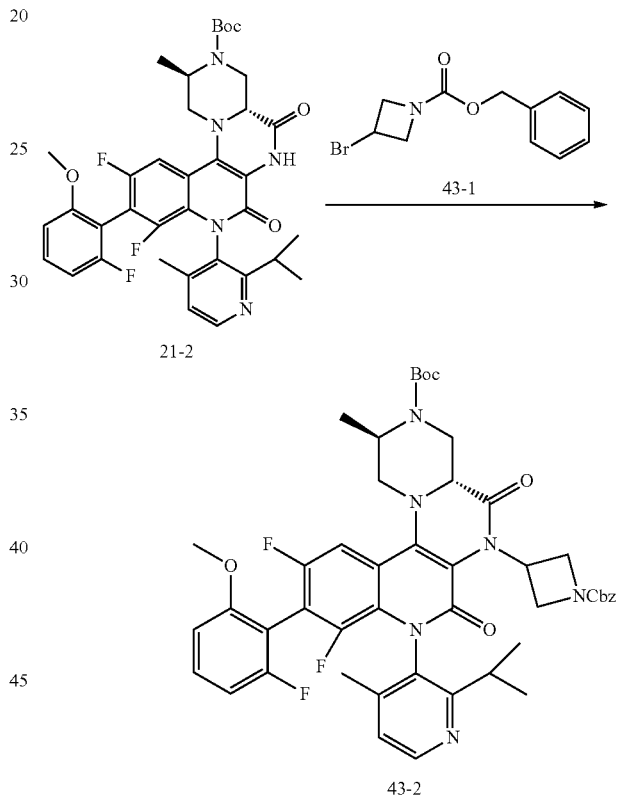

Compound 21-2 (200 mg, 295.11 μmol) was dissolved in N,N-dimethylformamide (2 mL); potassium carbonate (163.14 mg, 1.18 mmol), compound 43-1 (239.15 mg, 885.33 μmol) and potassium iodide (48.99 mg, 295.11 μmol) were added thereto; after the addition was completed, the system was heated to 100° C. and stirred for 16 hours. After the reaction was cooled to room temperature (25° C.), water (10 mL) and ethyl acetate (10 mL×2) were added thereto for separation and extraction; the organic phase was dried over anhydrous sodium sulfate, filtered, and the filtrate was concentrated under reduced pressure to obtain a crude product, the crude product was purified by medium pressure column chromatography (methanol/dichloromethane (v/v)=0-5%) to obtain compound 43-2.

MS (ESI) m/z (M+H)$^+$=867.4.

Step 2: Preparation of Compound 43-3

Step 3: Preparation of Compound 43-4

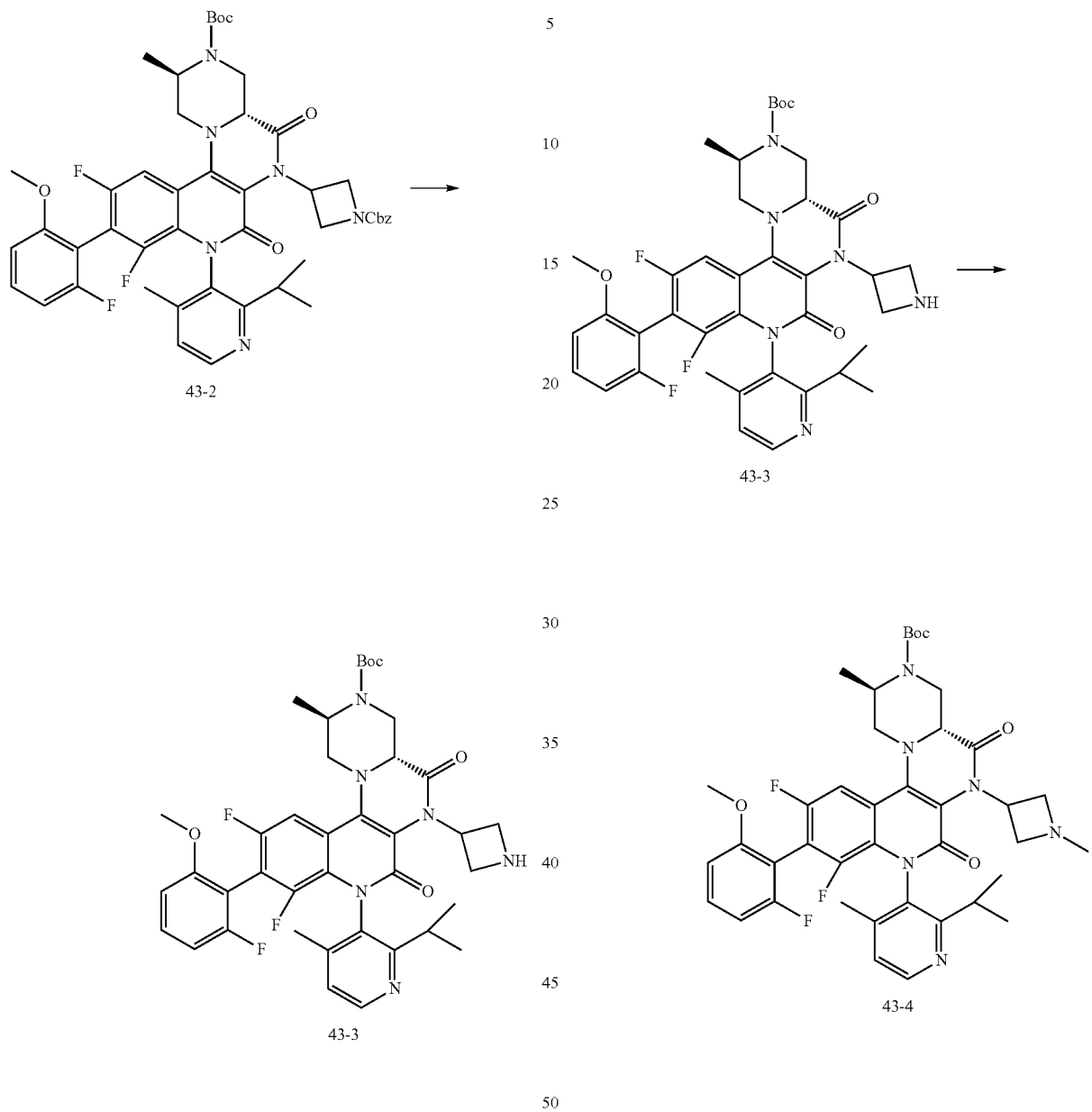

Compound 43-2 (140 mg, 161.49 μmol) was dissolved in methanol (2 mL), and palladium/carbon (40 mg, 10%) was added thereto, and under hydrogen atmosphere, the reaction was stirred at room temperature (20° C.) for 12 hours. The system was filtered, and the filtrate was concentrated to obtain a crude product, the crude product was purified by medium pressure column chromatography (methanol/dichloromethane (v/v)=0-5%) to obtain compound 43-3.

MS (ESI) m/z (M+H)$^+$=733.1.

Compound 43-3 (60 mg, 81.88 μmol) and sodium acetate (70 mg, 853.31 μmol) were dissolved in methanol (2 mL), and formaldehyde (654.00 mg, 8.06 mmol, 0.6 mL, 37% purity) was added thereto, and then tetrahydrofuran solution (1 mL) of sodium cyanoborohydride (60 mg, 954.78 μmol) was added thereto. After the addition was completed, the reaction was stirred at room temperature (25° C.) for 16 hours. The system was added with water (10 mL) and ethyl acetate (20 mL) for separation and extraction; the organic phase was dried over anhydrous sodium sulfate, filtered, and the filtrate was concentrated to obtain a crude product, the crude product was purified by medium pressure column chromatography (methanol/dichloromethane (v/v)=0-7%) to obtain compound 43-4.

MS (ESI) m/z (M+H)$^+$=747.3.

Step 4: Preparation of Compound 43-5

Step 5: Preparation of Compound 43

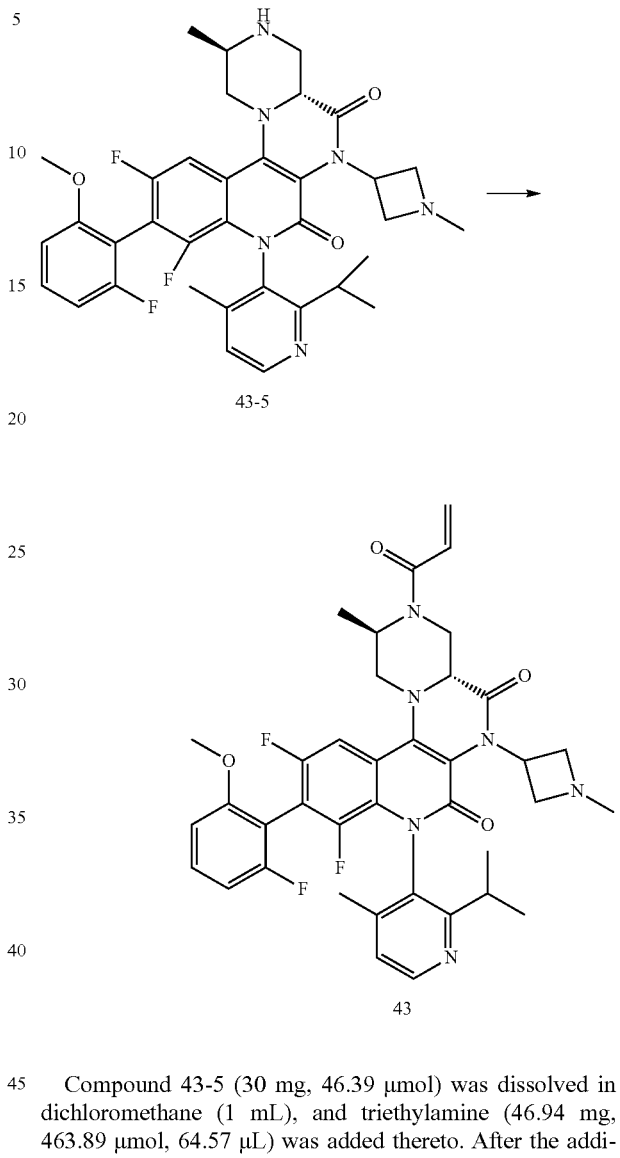

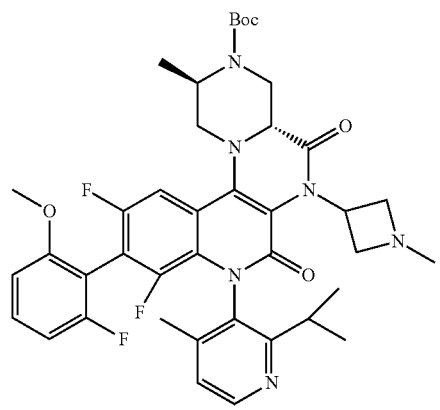

Compound 43-4 (60 mg, 80.34 μmol) was dissolved in dichloromethane (2 mL), trifluoroacetic acid (187.61 mg, 1.65 mmol, 121.82 μL) was added thereto, after the addition was completed, and the system was stirred at room temperature (25° C.) for 3 hours. The system was concentrated, and ethyl acetate (20 mL) was added thereto, then the mixture was extracted with water (20 mL×2) and washed with saturated sodium bicarbonate aqueous solution, the organic phase was dried over anhydrous sodium sulfate, filtered, and the filtrate was concentrated to obtain compound 43-5, which was directly used in the next reaction without further purification.

MS (ESI) m/z (M+H)$^+$=647.1.

Compound 43-5 (30 mg, 46.39 μmol) was dissolved in dichloromethane (1 mL), and triethylamine (46.94 mg, 463.89 μmol, 64.57 μL) was added thereto. After the addition was completed, the system was cooled to −40° C., and dichloromethane solution (1 mL) of acryloyl chloride (8.40 mg, 92.78 μmol, 7.57 μL) was added dropwise thereto. After the addition was completed, the system was stirred at −40° C. for 0.5 hours. The system was diluted by adding water (10 mL), extracted with ethyl acetate (10 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 49%-79% 9 min) to obtain compounds 43.

Compound 43:

$^1$H NMR (400 MHz, Methanol-$d_4$) δ 8.45 (d, J=5.4 Hz, 1H), 7.67 (br s, 1H), 7.52-7.40 (m, 1H), 7.32-7.21 (m, 1H), 7.08 (dd, J=11.1, 17.5 Hz, 1H), 6.91 (br s, 1H), 6.84-6.78 (m, 1H), 6.24 (br d, J=15.7 Hz, 1H), 5.81 (br d, J=10.8 Hz, 1H), 5.03-4.94 (m, 1H), 4.73 (br d, J=13.9 Hz, 1H), 4.57 (br s, 1H), 4.08 (br s, 1H), 3.89 (br d, J=12.7 Hz, 2H), 3.79-3.66 (m, 5H), 3.48 (br s, 1H), 3.21-3.03 (m, 2H), 2.47 (s, 1H), 2.35 (br s, 3H), 2.24-1.91 (m, 3H), 1.74-1.66 (m, 3H), 1.20-0.96 (m, 6H).

MS (ESI) m/z (M+H)$^+$=701.3.

HPLC retention time was 4.305 min.

Separation conditions: chromatographic column Xbridge Shield RP-18, 5 μm, 2.1*50 mm; column temperature: 50° C.; mobile phase: water (0.2 mL/1 L ammonia)-acetonitrile; acetonitrile: 10%-80% 6 min, 80% 2 min; flow rate: 0.8 mL/min Embodiment 44: Preparation of Compound 44

Step 1: Preparation of Compound 44-1

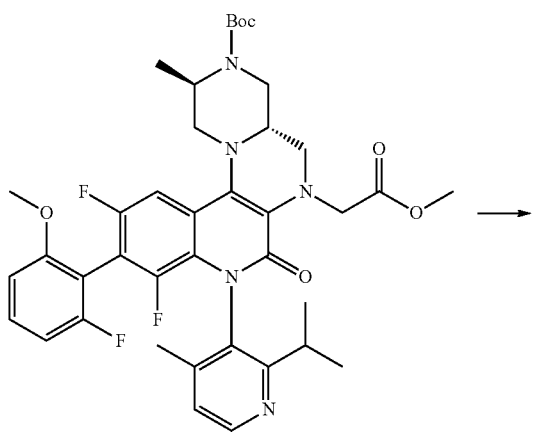

38-1

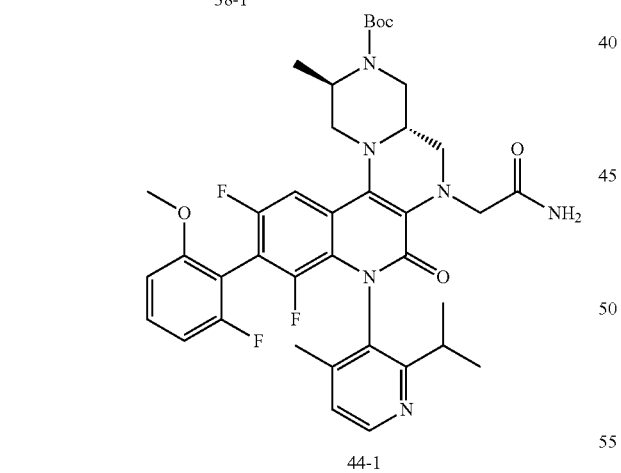

44-1

Compound 38-1 (70 mg, 95.14 μmol) was dissolved in ammonia methanol solution (7 M, 7.00 mL), under airtight conditions, the system was heated to 100° C. and stirred for 6 hours. The system was cooled to room temperature and concentrated to obtain a crude product. The crude product was purified by medium pressure column chromatography (methanol/dichloromethane (v/v)=0-5%) to obtain compound 44-1.

MS (ESI) m/z (M+H)$^+$=721.3.

Step 2: Preparation of Compound 44-2

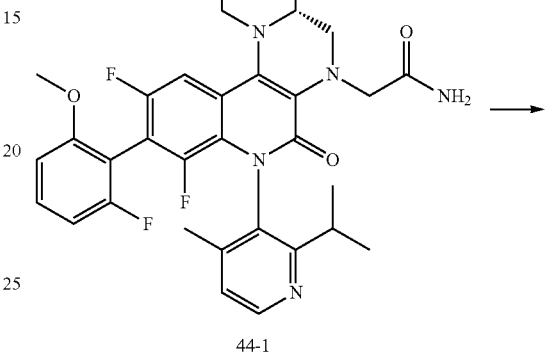

44-1

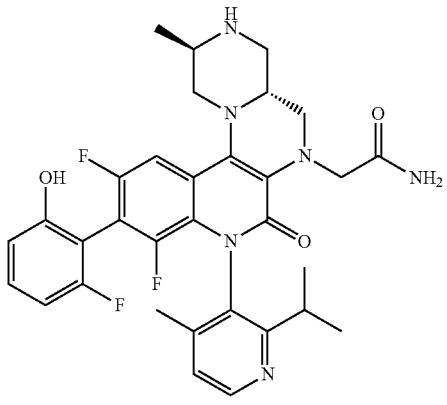

44-2

Compound 44-1 (20 mg, 32.22 μmol) was dissolved in dichloromethane solution of boron tribromide (1 M, 1 mL), and the reaction was stirred at room temperature (25° C.) for 2 hours. At 0° C., the reaction mixture was quenched with methanol (1 mL), and the system was concentrated to obtain compound 44-2, which was directly used in the next reaction without further purification.

MS (ESI) m/z (M+H)$^+$=607.4.

Step 3: Preparation of Compounds 44A and 44B

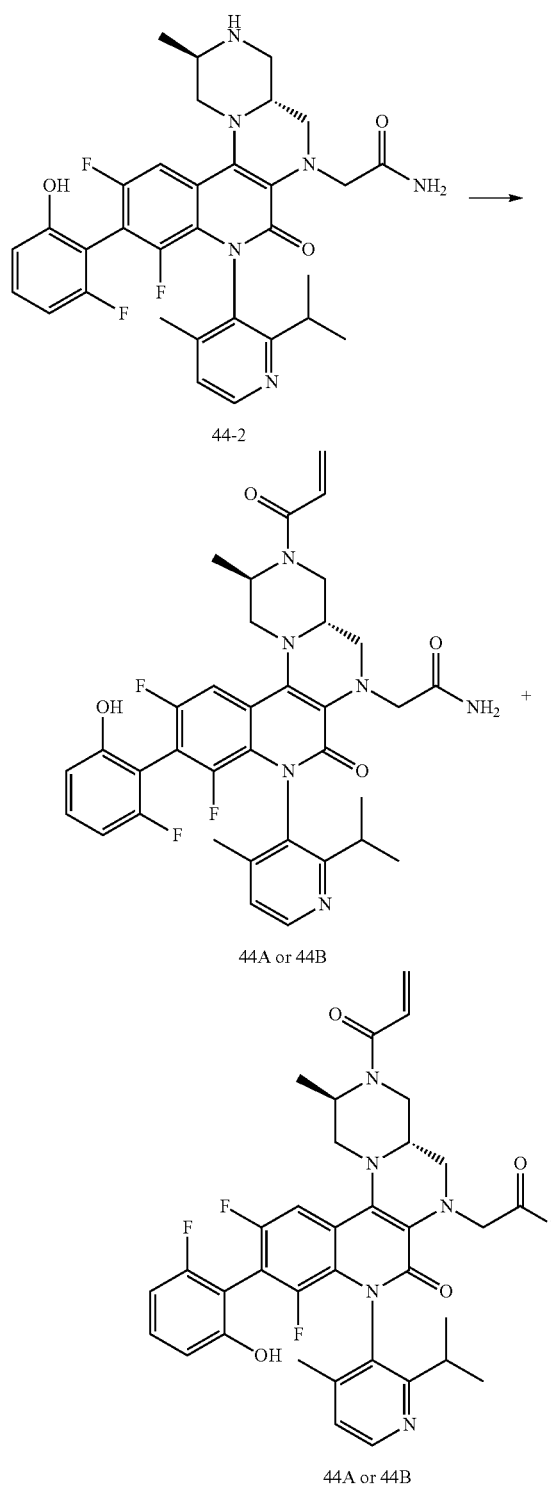

44-2

44A or 44B 44A or 44B

Compound 44-2 (22 mg, 32.00 μmol, HBr salt) was dissolved in tetrahydrofuran (1 mL) and saturated sodium bicarbonate aqueous solution (3.17 g, 37.71 mmol, 1.47 mL), and acrylic anhydride (4.44 mg, 35.20 μmol) was added dropwise thereto. After the addition was completed, the system was stirred at room temperature (25° C.) for 2 hours. The system was diluted by adding water (10 mL), extracted with ethyl acetate (10 mL×2); the organic phases were combined, washed with water (10 mL×3); then the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 33%-63% 9 min) to obtain compounds 44A and 44B.

Compound 44A:

$^1$H NMR (400 MHz, Methanol-$d_4$) δ 8.42 (br d, J=5.1 Hz, 1H), 7.58 (br s, 1H), 7.29-7.17 (m, 2H), 6.86-6.78 (m, 1H), 6.69-6.57 (m, 2H), 6.27 (br d, J=16.8 Hz, 1H), 5.81 (br d, J=10.6 Hz, 1H), 4.96-4.93 (m, 1H), 4.66-4.49 (m, 2H), 4.19-4.10 (m, 1H), 3.98 (br d, J=17.6 Hz, 1H), 3.72 (br s, 1H), 3.48 (br s, 1H), 3.44-3.34 (m, 2H), 3.18 (br s, 2H), 2.87-2.77 (m, 1H), 2.68 (br s, 1H), 2.05 (br d, J=11.5 Hz, 3H), 1.80-1.66 (m, 3H), 1.21-0.98 (m, 6H).

MS (ESI) m/z (M+H)$^+$=661.3.

HPLC retention time was 6.71 & 6.79 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Compound 44B:

$^1$H NMR (400 MHz, Methanol-$d_4$) δ 8.41 (br d, J=5.1 Hz, 1H), 7.56 (br s, 1H), 7.30-7.16 (m, 2H), 6.82 (br dd, J=10.3, 16.9 Hz, 1H), 6.71-6.56 (m, 2H), 6.26 (br d, J=18.5 Hz, 1H), 5.80 (br d, J=10.4 Hz, 1H), 4.96-4.92 (m, 1H), 4.64-4.47 (m, 2H), 4.14 (br d, J=17.2 Hz, 2H), 3.96 (br s, 1H), 3.71 (br s, 2H), 3.48-3.37 (m, 2H), 3.26-3.07 (m, 2H), 2.89-2.77 (m, 1H), 2.66 (br s, 1H), 2.15-1.95 (m, 3H), 1.84-1.65 (m, 3H), 1.32-0.99 (m, 6H).

MS (ESI) m/z (M+H)$^+$=661.3.

HPLC retention time was 6.90 & 6.97 min.

Separation conditions: chromatographic column WELCH Ultimate LP-C18 150*4.6 mm, 5 μm; column temperature: 40° C.; mobile phase: water (0.0688% trifluoroacetic acid solution)-acetonitrile (0.0625% trifluoroacetic acid solution); acetonitrile: 10%-80% 10 min, 80% 5 min; flow rate: 1.5 mL/min.

Embodiment 45: Preparation of Compound 45

Step 1: Preparation of Compound 45-1

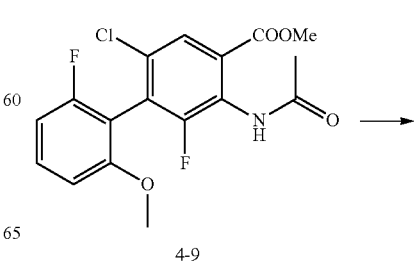

4-9

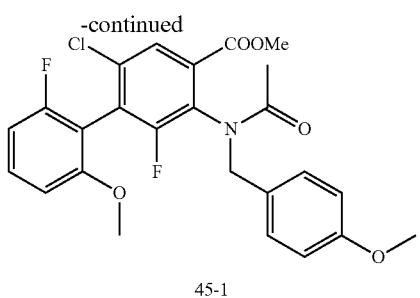

45-1

Compound 4-9 (3.5 g, 9.47 mmol), p-methoxybenzyl chloride (2.96 g, 18.93 mmol, 2.58 mL) and potassium carbonate (3.92 g, 28.40 mmol) were dissolved in N,N-dimethylformamide (30 mL), after the addition was completed, the system was heated to 70° C. and stirred for 6 hours. The system was diluted with ethyl acetate (50 mL), washed with saturated saline (50 mL×2), the organic phase was dried over anhydrous sodium sulfate, filtered, and the filtrate was concentrated to obtain a crude product. The crude product was purified by medium pressure column chromatography (ethyl acetate/petroleum ether (v/v)=0-50%) to obtain compound 45-1.

MS (ESI) m/z (M+Na)$^+$=512.2.

Step 2: Preparation of Compound 45-2

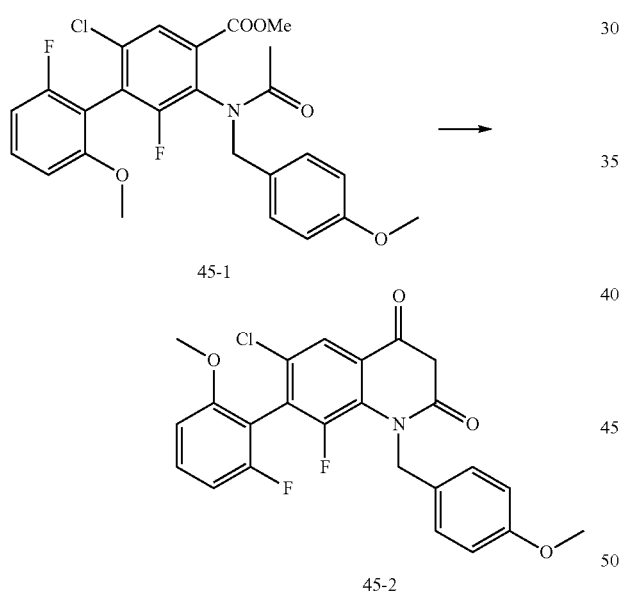

At room temperature (20° C.), compound 45-1 (4.4 g, 8.98 mmol) was dissolved in toluene (80 mL), and potassium tert-butoxide (1 M, 17.96 mL) was added thereto. After the addition was completed, under nitrogen atmosphere, the reaction was carried out at room temperature (20° C.) for 4 hours. The reaction was quenched by adding 1 M hydrochloric acid to the system, and the system was concentrated and lyophilized to obtain a crude product. The crude product was purified by medium pressure column chromatography (ethyl acetate/petroleum ether (v/v)=0-100%) to obtain compound 45-2.

$^1$H NMR (400 MHz, DMSO-d$_6$) 12.04 (br s, 1H), 7.88 (d, J=1.2 Hz, 1H), 7.55-7.45 (m, 1H), 7.03-6.79 (m, 6H), 6.07 (s, 1H), 5.38 (br s, 2H), 3.71-3.59 (m, 6H).

MS (ESI) m/z (M+Na)$^+$=480.1.

Step 3: Preparation of Compound 45-3

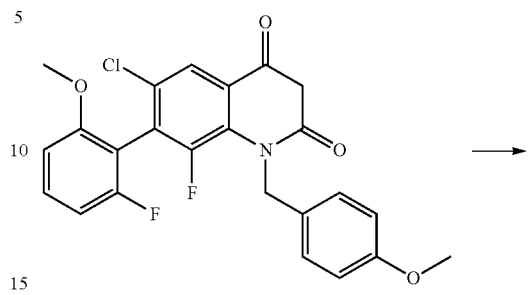

45-2

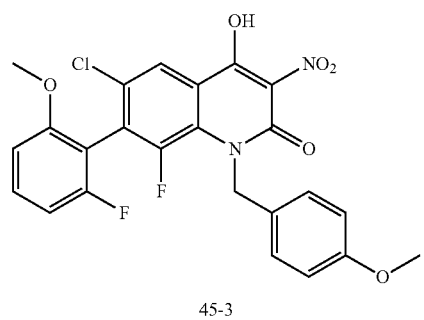

45-3

Compound 45-2 (3.6 g, 7.86 mmol) was dissolved in glacial acetic acid (30 mL), and nitric acid (4.20 g, 66.65 mmol, 3 mL) was added dropwise to the system at room temperature (20° C.). After the dropwise addition was completed, the system was heated to 40° C. and stirred for 1 hour. The system was cooled to room temperature, poured into water (50 mL) and extracted with ethyl acetate (50 mL×2). The pH of the aqueous phase was adjusted to 9, then the aqueous phase was extracted with ethyl acetate (50 mL); and the organic phase was dried over anhydrous sodium sulfate and filtered, and the filtrate was concentrated to obtain compound 45-3, which was used directly in the next step without further purification.

$^1$H NMR (400 MHz, DMSO-d$_6$) 11.98 (br s, 1H), 7.99 (d, J=1.5 Hz, 1H), 7.52-7.43 (m, 1H), 7.05-6.89 (m, 4H), 6.83 (d, J=8.5 Hz, 2H), 5.69-5.06 (m, 2H), 3.72-3.63 (m, 6H).

MS (ESI) m/z (M+Na)$^+$=524.9.

Step 4: Preparation of Compound 45-4

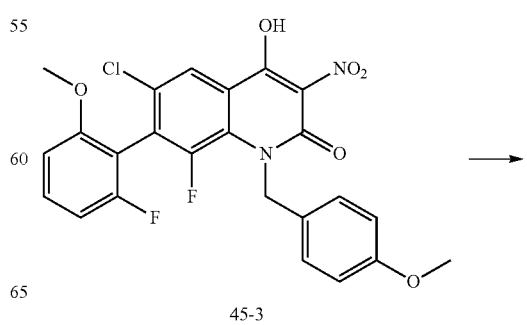

45-3

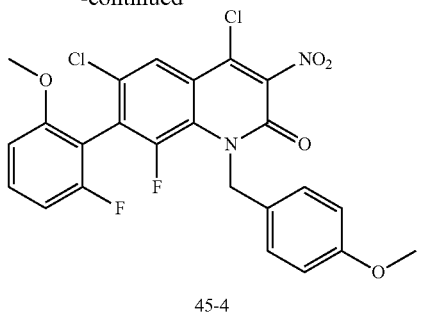

45-4

Compound 45-3 (2.94 g, 5.85 mmol) and N,N-diisopropylethylamine (3.78 g, 29.23 mmol, 5.09 mL) were dissolved in acetonitrile (30 mL), and at room temperature, phosphorus oxychloride (3.59 g, 23.39 mmol, 2.17 mL) was added thereto. After the addition was completed, the system was heated to 80° C. and stirred for 1 hour. The system was cooled to room temperature and concentrated to obtain a crude product. The crude product was purified by medium pressure column chromatography (ethyl acetate/petroleum ether (v/v)=0-50%) to obtain compound 45-4.

$^1$H NMR (400 MHz, DMSO-d$_6$) 8.18 (d, J=1.4 Hz, 1H), 7.58-7.53 (m, 1H), 7.12 (d, J=8.6 Hz, 2H), 7.07-6.95 (m, 2H), 6.90-6.84 (m, 2H), 5.61-5.40 (m, 2H), 3.72-3.66 (m, 6H).

MS (ESI) m/z (M+Na)$^+$=542.9.

Step 5: Preparation of Compound 45-5

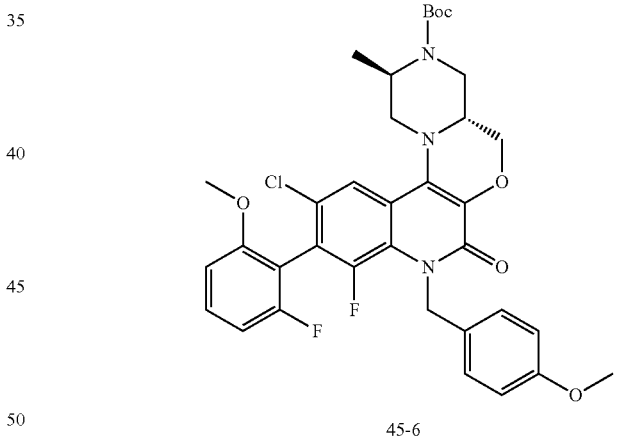

45-4    1-11    45-5

Compound 45-4 (1.6 g, 3.07 mmol), compound 1-11 (1.06 g, 4.60 mmol), N,N-diisopropylethylamine (1.19 g, 9.21 mmol, 1.60 mL) were dissolved in acetonitrile (30 mL), under nitrogen atmosphere, the system was heated to 80° C. and stirred for 3 hours. The system was concentrated to obtain a crude product. The crude product was purified by medium pressure column chromatography (ethyl acetate/petroleum ether (v/v)=0-50%) to obtain compound 45-5.

$^1$H NMR (400 MHz, DMSO-d$_6$) 7.87 (br s, 1H), 7.58-7.49 (m, 1H), 7.09-6.94 (m, 4H), 6.91-6.83 (m, 2H), 5.58-5.31 (m, 2H), 4.88-4.76 (m, 1H), 4.29 (br s, 1H), 4.09-3.96 (m, 1H), 3.75-3.68 (m, 6H), 3.64 (s, 2H), 3.61-3.50 (m, 2H), 3.41 (br s, 1H), 2.99 (br s, 1H), 1.46-1.42 (m, 9H), 1.25 (d, J=6.8 Hz, 3H).

MS (ESI) m/z (M+H)$^+$=715.2.

Step 6: Preparation of Compound 45-6

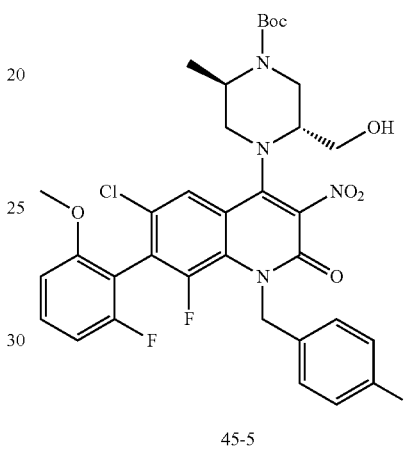

45-5   →   45-6

Compound 45-5 (1.56 g, 2.18 mmol) and 4 Å molecular sieve (0.6 g) were dissolved in N-methylpyrrolidone (15 mL), and tetrahydrofuran solution of LiHMDS (1 M, 4.36 mL) was added thereto at room temperature. After the addition was completed, under nitrogen atmosphere, the system was heated to 130° C. and stirred for 12 hours. The system was cooled to room temperature and filtered, the filtrate was diluted with ethyl acetate (40 mL), and washed with saturated saline (30 mL×2). The organic phase was dried over anhydrous sodium sulfate, filtered, and the filtrate was concentrated to obtain a crude product. The crude product was purified by medium pressure column chromatography (ethyl acetate/petroleum ether (v/v)=0-60%) to obtain compound 45-6.

MS (ESI) m/z (M+H)$^+$=668.1.

Step 7: Preparation of Compound 45-7

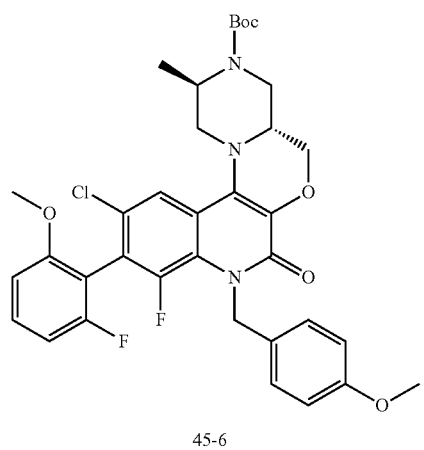

45-6

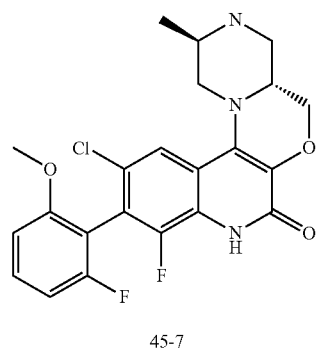

45-7

Compound 45-6 (0.56 g, 838.17 μmol) was dissolved in a mixed solvent of trifluoroacetic acid (7.70 g, 67.53 mmol, 5 mL) and anisole (2 mL); and trifluoromethanesulfonic acid (1.70 g, 11.33 mmol, 1 mL) was added thereto at room temperature (20° C.). After the addition was completed, under nitrogen atmosphere, the system was raised to room temperature (20° C.) and stirred for 12 hours. The system was concentrated, and the residue was poured into a mixture of ice water and saturated sodium bicarbonate solution (adjusted pH to 7), extracted with ethyl acetate; the organic phase was dried over anhydrous sodium sulfate, filtered and the filtrate was concentrated to obtain a crude product. The crude product was purified by medium pressure column chromatography (methanol/dichloromethane (v/v)=0-30%) to obtain compound 45-7.

MS (ESI) m/z (M+H)$^+$=448.0.

Step 8: Preparation of Compound 45-8

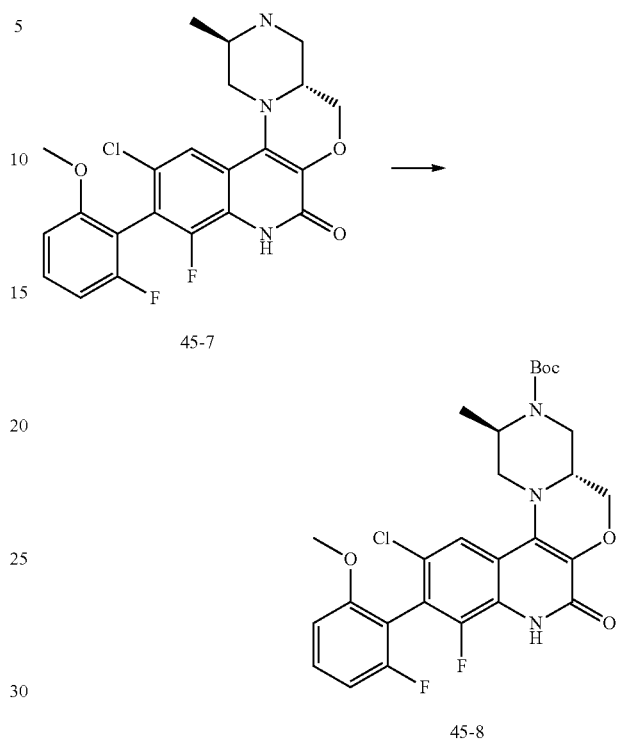

45-7

45-8

Compound 45-7 (0.35 g, 781.49 μmol) and triethylamine (158.16 mg, 1.56 mmol, 217.55 μL) were dissolved in dichloromethane (5 mL), and di-tert-butyl dicarbonate (341.12 mg, 1.56 mmol, 359.07 μL) was added thereto at 0° C. After the addition was completed, the system was heated to room temperature (20° C.) and stirred for 12 hours. The system was concentrated to obtain a crude product, the crude product was purified by medium pressure column chromatography (ethyl acetate/petroleum ether (v/v)=0-70%) to obtain compound 45-8.

$^1$H NMR (400 MHz, DMSO-d$_6$) 12.00 (s, 1H), 7.58-7.47 (m, 2H), 7.08-6.95 (m, 2H), 4.37-4.18 (m, 3H), 3.95 (br d, J=14.9 Hz, 1H), 3.77 (d, J=4.8 Hz, 3H), 3.61 (br s, 2H), 3.21 (br s, 1H), 2.93 (br d, J=12.8 Hz, 1H), 1.48 (br d, J=6.7 Hz, 3H), 1.46-1.43 (m, 1H), 1.44 (s, 8H).

MS (ESI) m/z (M+Na)$^+$=570.0.

Step 9: Preparation of Compound 45-10

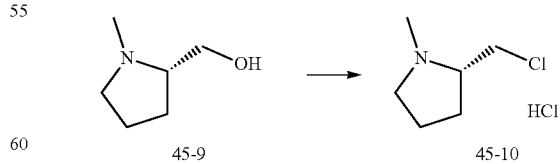

45-9       45-10

Compound 45-9 (6 g, 52.10 mmol, 6.19 mL) was dissolved in chloroform (60 mL), and thionyl chloride (32.80 g, 275.70 mmol, 20.00 mL) was added dropwise thereto at 0° C. After the addition was completed, under nitrogen atmosphere, the system was heated to 65° C. and stirred for 12

Step 8: Preparation of Compound 45-11

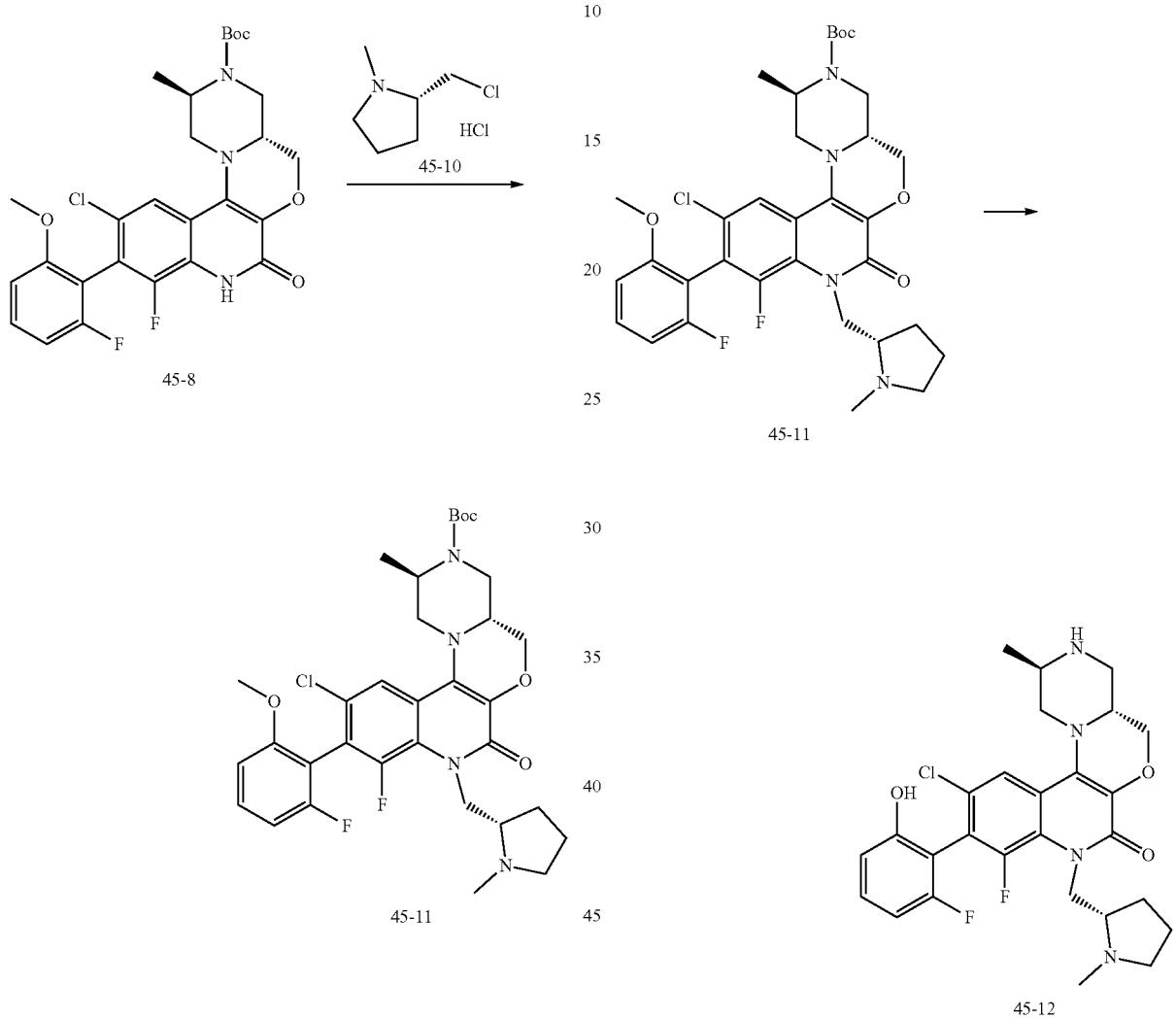

Step 9: Preparation of Compound 45-12

Compound 45-8 (120 mg, 218.99 μmol), compound 45-10 (74.49 mg, 437.97 μmol, HCl salt) and potassium carbonate (60.53 mg, 437.97 μmol) were dissolved in N,N-dimethylformamide (1 mL). After the addition was completed, the system was heated to 70° C. and stirred for 8 hours. The system was concentrated, the residue was diluted with water (30 mL) and extracted with ethyl acetate (25 mL×2); the organic phases were combined, dried over anhydrous sodium sulfate, filtered, and the filtrate was concentrated to obtain a crude product. The crude product was purified by medium pressure column chromatography (methanol/dichloromethane (v/v)=0-20%) and then purified by preparative high performance liquid chromatography (separation conditions: chromatographic column: Xtimate C18 100*30 mm*3 μm; mobile phase: [water (0.225% formic acid)-acetonitrile]; acetonitrile %: 34%-54% 8 min) to obtain compound 45-11.
MS (ESI) m/z (M+H)$^+$=645.4.

Compound 45-11 (30 mg, 46.50 μmol) was dissolved in dichloromethane (1 mL), and dichloromethane solution (0.3 mL) of boron tribromide (130 mg, 518.92 μmol, 0.05 mL) was added thereto. After the addition was completed, under nitrogen atmosphere, the reaction was stirred at room temperature (25° C.) for 4 hours. The reaction mixture was quenched with methanol (5 mL), and the system was concentrated to obtain compound 45-12, which was directly used in the next reaction without further purification.
MS (ESI) m/z (M+H)$^+$=531.3.

Step 10: Preparation of Compounds 45A and 45B

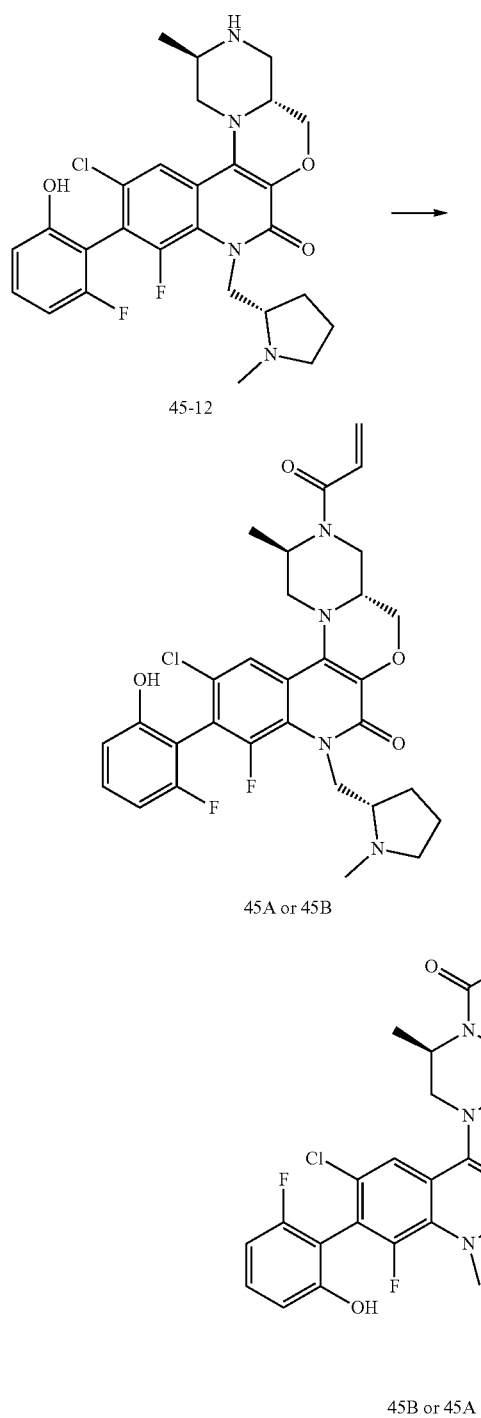

45-12

45A or 45B 45B or 45A

Compound 45-12 (30 mg, 56.50 μmol, hydrobromide) was dissolved in tetrahydrofuran (2 mL) and saturated sodium bicarbonate aqueous solution (2.16 g, 25.71 mmol, 1 mL), and tetrahydrofuran solution (0.3 mL) of acrylic anhydride (10 mg, 79.30 μmol) was added thereto at room temperature (20° C.). After the addition was completed, the system was stirred at room temperature (20° C.) for 2 hours. Methanol (1 mL) and potassium carbonate aqueous solution (2 M, 1 mL) were added to the system, and the mixture was stirred at room temperature (20° C.) for 1.5 hours. The system was diluted with water (10 mL), the pH of was adjusted to 6 with 1 N hydrochloric acid; and the mixture was extracted with ethyl acetate (20 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate solution)-acetonitrile]; acetonitrile %: 40%-70% 9 min) to obtain compounds 45A and 45B.

Compound 45A $^1$H NMR (400 MHz, Methanol-$d_4$) δ 7.82 (br s, 1H), 7.39-7.25 (m, 1H), 6.86-6.65 (m, 3H), 6.26 (br d, J=16.5 Hz, 1H), 5.80 (br d, J=9.0 Hz, 1H), 4.83-4.77 (m, 1H), 4.61 (br s, 2H), 4.54-4.07 (m, 3H), 3.72 (br s, 1H), 3.47 (br d, J=12.3 Hz, 1H), 3.38-3.35 (m, 1H), 3.16 (br s, 1H), 3.03 (br s, 1H), 2.92 (br s, 1H), 2.46 (s, 4H), 1.84-1.58 (m, 7H).

MS (ESI) m/z (M+H)$^+$=585.3.

HPLC retention time was 3.744 min.

Separation conditions: chromatographic column Xbridge Shield RP-18, 5 μm, 2.1*50 mm; column temperature: 50° C.; mobile phase: water (0.2 mL/1 L ammonia solution)-acetonitrile; acetonitrile: 10%-80% 6 min, 80% 2 min; flow rate: 0.8 mL/min.

Compound 45B $^1$H NMR (400 MHz, Methanol-$d_4$) δ 7.82 (br s, 1H), 7.37-7.24 (m, 1H), 6.94-6.59 (m, 3H), 6.26 (br dd, J=1.8, 16.8 Hz, 1H), 5.81 (br s, 1H), 4.82-4.57 (m, 3H), 4.56-4.34 (m, 2H), 4.23-4.06 (m, 1H), 3.70 (br d, J=16.1 Hz, 1H), 3.48 (br d, J=11.5 Hz, 1H), 3.44-3.35 (m, 1H), 3.17 (br s, 1H), 3.02 (br s, 1H), 2.91 (br s, 1H), 2.64-2.20 (m, 4H), 2.09-1.37 (m, 7H).

MS (ESI) m/z (M+H)$^+$=585.3.

HPLC retention time was 3.836 min.

Separation conditions: chromatographic column Xbridge Shield RP-18, 5 μm, 2.1*50 mm; column temperature: 50° C.; mobile phase: water (0.2 mL/1 L ammonia solution)-acetonitrile; acetonitrile: 10%-80% 6 min, 80% 2 min; flow rate: 0.8 mL/min.

Embodiment 46: Preparation of Compound 46

Step 1: Preparation of Compound 46-1

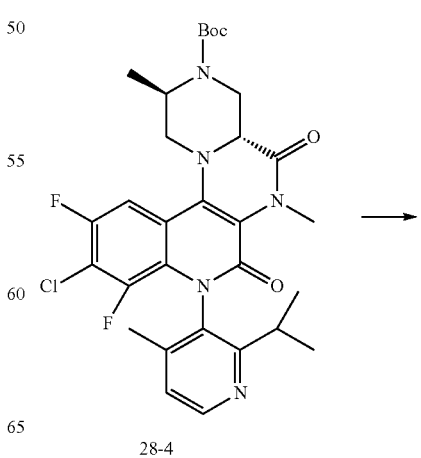

28-4

-continued

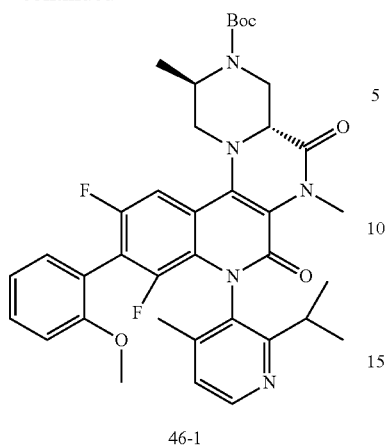

46-1

Compound 28-4 (100 mg, 166.09 μmol), o-methoxyphenylboronic acid (68.15 mg, 249.14 μmol), methanesulfonato (2-dicyclohexylphosphino-2',6'-di-i-propoxy-1,1'-biphenyl)(2-amino-1,1'-biphenyl-2-yl) palladium(II) (13.89 mg, 16.61 μmol), 2-dicyclohexylphosphino-2',6'-di-i-propoxy-1,1'-biphenyl (7.75 mg, 16.61 μmol) and potassium carbonate (68.86 mg, 498.27 μmol) were dissolved in a mixed solution of dioxane (2 mL) and water (0.2 mL). Under nitrogen atmosphere, the system was heated to 100° C. and stirred for 5 hours. The system was concentrated to obtain a crude product, the crude product was purified by medium pressure column chromatography (ethyl acetate/petroleum ether (v/v)=0-30%) to obtain compound 46-1.

MS (ESI) m/z (M+H)$^+$=694.7.

Step 2: Preparation of Compound 46-2

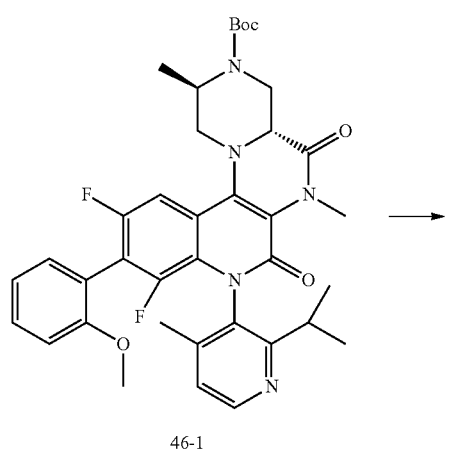

46-1

-continued

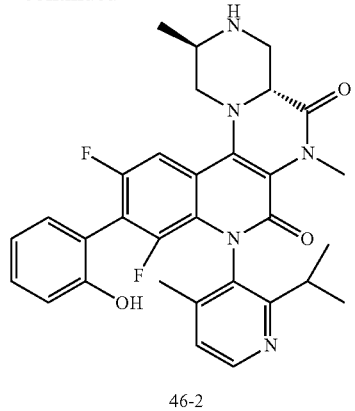

46-2

Compound 46-1 (0.1 g, 148.42 μmol) was dissolved in dichloromethane solution of boron tribromide (1 M, 3 mL), and the reaction was stirred at room temperature (20° C.) for 16 hours. The reaction mixture was quenched with methanol (1 mL), stirred for 10 min. The system was concentrated to obtain compound 46-2, which was directly used in the next reaction without further purification.

MS (ESI) m/z (M+H)$^+$=560.1.

Step 3: Preparation of Compounds 46A and 46B

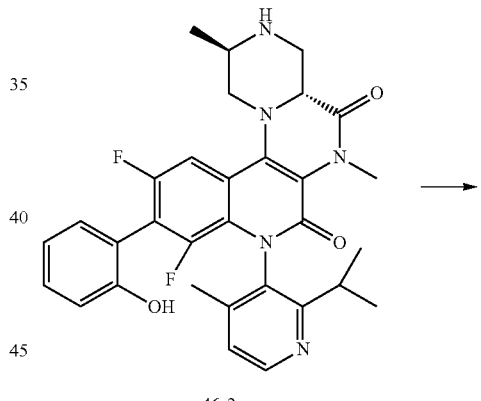

46-2

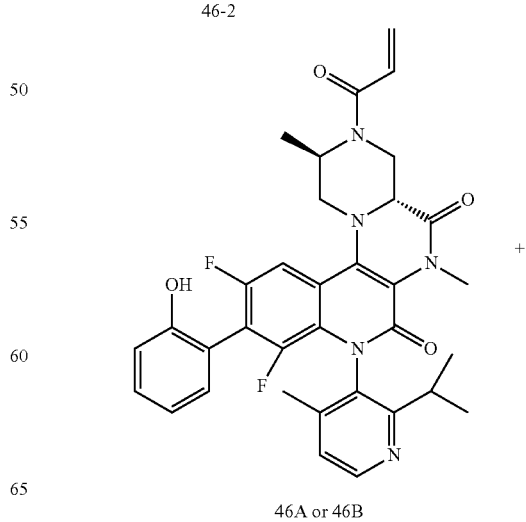

46A or 46B

-continued

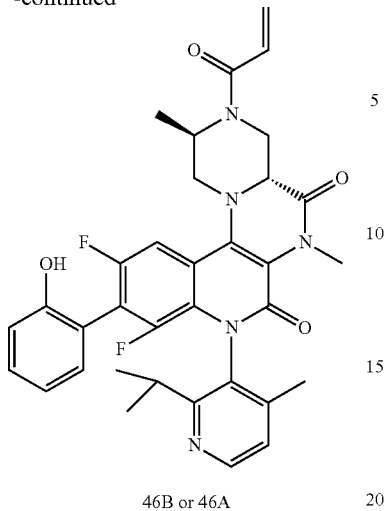

46B or 46A

Compound 46-2 (95 mg, 145.14 μmol) was dissolved in ethyl acetate (2 mL) and sodium bicarbonate aqueous solution (4.10 g, 48.79 mmol, 1.90 mL), and tetrahydrofuran solution of acrylic anhydride (1 M, 145.14 μL) was added dropwise thereto. After the addition was completed, the system was stirred at room temperature (20° C.) for 1 hour. After the system was extracted with ethyl acetate (10 mL×3); the organic phases were combined, washed with water (10 mL×3); then the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 36%-66% 9 min) and then purified by SFC (separation conditions: chromatographic column Phenomenex-Cellulose-2 (250 mm*30 mm, 10 μm), mobile phase: $CO_2$-methanol (0.1% ammonia); methanol 40%-40%) to obtain compounds 46A and 46B.

Compound 46A:
$^1$H NMR (400 MHz, Methanol-$d_4$) δ 8.49-8.38 (m, 1H), 7.65 (br d, J=8.4 Hz, 1H), 7.31-7.16 (m, 2H), 7.09 (br s, 2H), 6.90-6.76 (m, 2H), 6.23 (br d, J=17.0 Hz, 1H), 5.81 (br dd, J=1.9, 10.7 Hz, 1H), 4.82-4.68 (m, 2H), 4.48 (br s, 1H), 3.92 (br d, J=3.3 Hz, 2H), 3.44 (s, 4H), 2.89 (br dd, J=3.0, 12.5 Hz, 1H), 2.54 (br d, J=6.6 Hz, 1H), 2.20 (d, J=6.2 Hz, 3H), 1.67 (br d, J=6.6 Hz, 3H), 1.29-0.92 (m, 6H).
MS (ESI) m/z (M+H)$^+$=614.3.
SFC retention time was 5.221 min
Separation conditions: chromatographic column: Cellulose 2 100 mm×4.6 mm I.D., 3 μm; column temperature: 35° C.; mobile phase: $CO_2$-methanol (0.05% DEA); methanol: 5%-40% 4 min, 40% 2.5 min, 5% 1.5 min; flow rate: 2.8 mL/min.

Compound 46B:
$^1$H NMR (400 MHz, Methanol-$d_4$) δ 8.43 (br d, J=5.1 Hz, 1H), 7.66 (br d, J=6.6 Hz, 1H), 7.24 (br d, J=5.5 Hz, 2H), 7.17 (br d, J=8.8 Hz, 1H), 6.92-6.74 (m, 1H), 6.23 (br d, J=18.7 Hz, 1H), 5.81 (br d, J=12.6 Hz, 1H), 4.80-4.55 (m, 1H), 3.89-4.37 (m, 2H), 3.43-3.97 (m, 2H), 3.05-2.86 (m, 2H), 1.98 (br s, 1H), 1.67 (br d, J=6.8 Hz, 2H), 2.81-2.47 (m, 2H), 2.02 (br d, J=9.5 Hz, 3H), 1.43-0.99 (m, 3H), 1.39-0.78 (m, 6H).
MS (ESI) m/z (M+H)$^+$=614.3.

SFC retention time was 5.904 min
Separation conditions: chromatographic column: Cellulose 2 100 mm×4.6 mm I.D., 3 μm; column temperature: 35° C.; mobile phase: $CO_2$-methanol (0.05% DEA); methanol: 5%-40% 4 min, 40% 2.5 min, 5% 1.5 min; flow rate: 2.8 mL/min.

Embodiment 47: Preparation of Compound 47

Step 1: Preparation of Compound 47-1

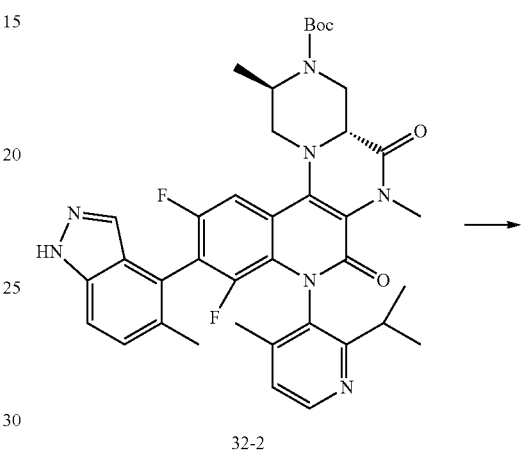

32-2

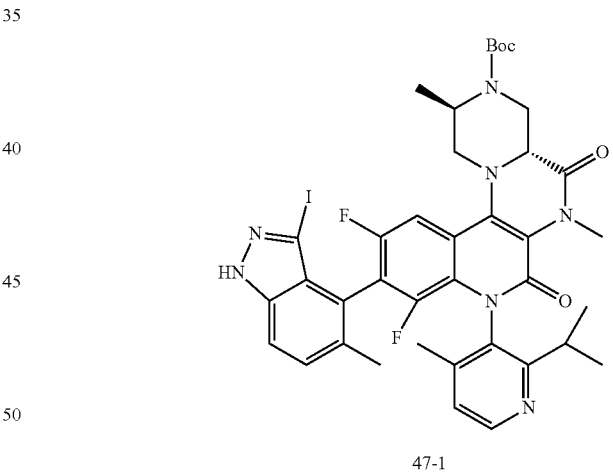

47-1

Compound 32-2 (120 mg, 171.98 μmol) was dissolved in N,N-dimethylformamide (2 mL), and iodine (66 mg, 260.04 μmol) and potassium hydroxide (15 mg, 267.35 μmol) were added thereto. After the addition was completed, the system was stirred at room temperature (20° C.) for 1 hour. The system was added with water (30 mL) and saturated sodium thiosulfate aqueous solution (1 mL), extracted with ethyl acetate (10 mL×3); the organic phases were combined, and the organic phase was dried over anhydrous sodium sulfate, filtered, and the filtrate was concentrated to obtain compound 47-1, which was directly used in the next reaction without further purification.
MS (ESI) m/z (M+H)$^+$=824.1.

Step 2: Preparation of Compound 47-2

Step 3: Preparation of Compound 47-3

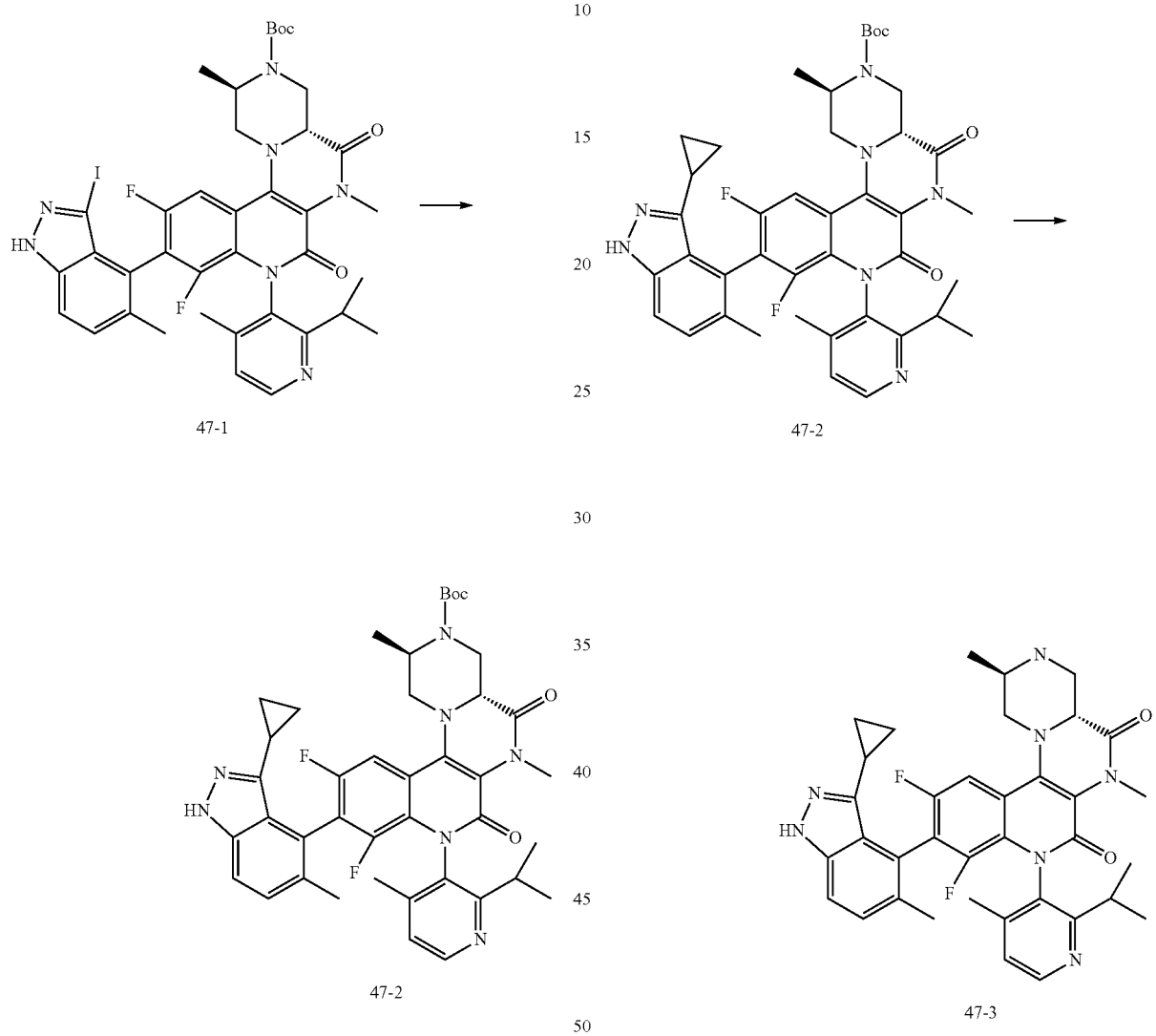

47-1

47-2

47-2

47-3

Compound 47-1 (120 mg, 145.69 μmol), cyclopropylboronic acid (40 mg, 465.67 μmol) were dissolved in a mixed solvent of toluene (5 mL) and water (0.5 mL), then tetrakis(triphenylphosphine)palladium (20 mg, 17.31 μmol) and potassium phosphate (93 mg, 438.13 μmol) were added thereto. After the addition was completed, under nitrogen atmosphere, the system was heated to 100° C. and stirred for 16 hours. The system was concentrated to obtain a crude product. The crude product was purified by medium pressure column chromatography (methanol/dichloromethane (v/v)=0-7%) to obtain compound 47-2.

MS (ESI) m/z (M+H)$^+$=738.1.

Compound 47-2 (120 mg, 162.64 μmol) was dissolved in dichloromethane (5 mL), and trifluoroacetic acid (770.00 mg, 6.75 mmol, 0.5 mL) was added thereto. After the addition was completed, the reaction was stirred at room temperature (20° C.) for 1 hour. The system was concentrated to obtain compound 47-3, which was directly used in the next reaction without further purification.

MS (ESI) m/z (M+H)$^+$=638.3.

Step 4: Preparation of Compounds 47A, 47B, 47C and 47D

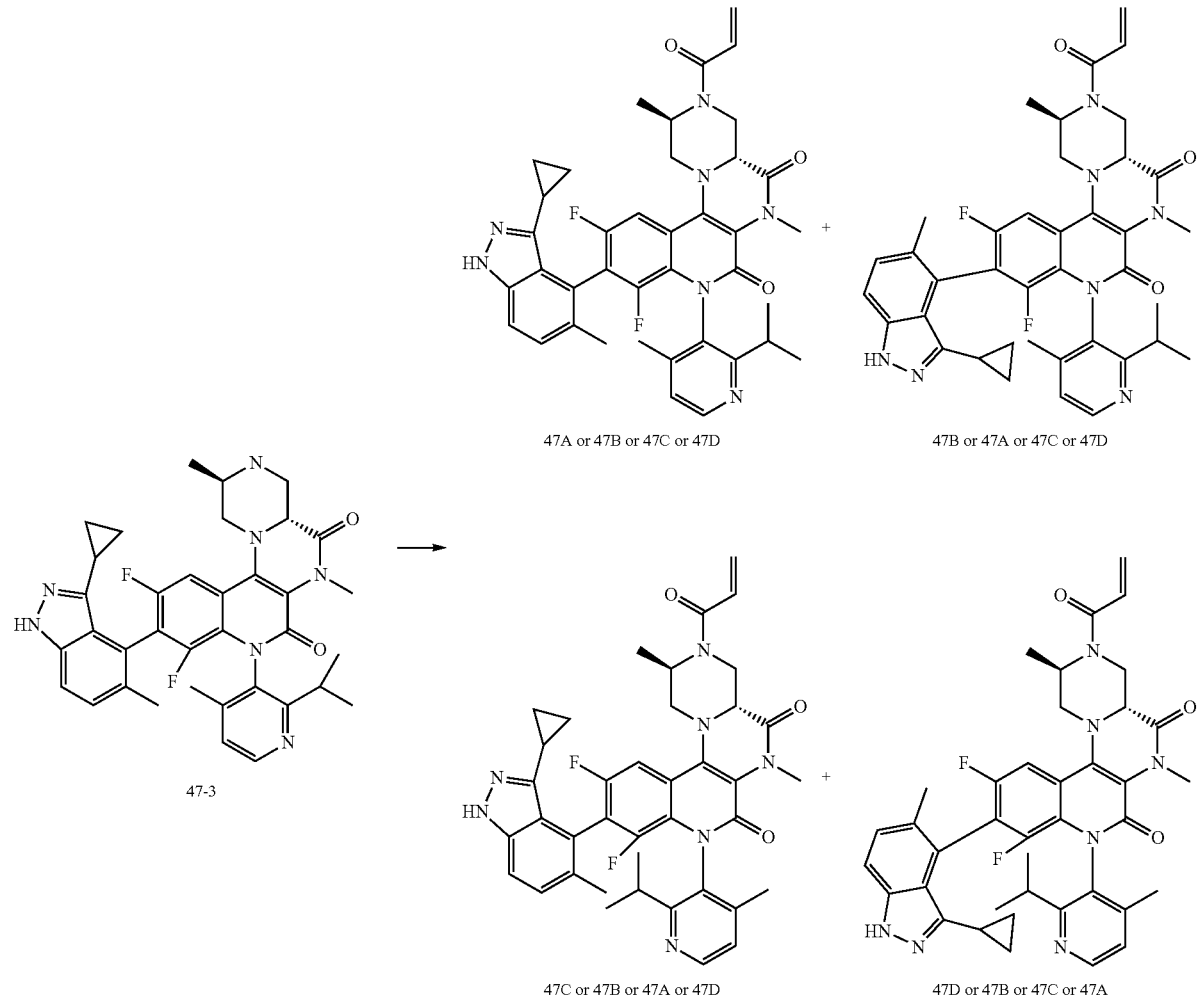

Compound 47-3 (120 mg, 159.63 μmol, trifluoroacetate) was dissolved in tetrahydrofuran (2 mL) and sodium bicarbonate aqueous solution (4.32 g, 51.42 mmol, 2.00 mL), and tetrahydrofuran solution (0.5 mL) of acrylic anhydride (25.00 mg, 198.24 μmol) was added dropwise thereto. After the addition was completed, the reaction was carried out at room temperature (20° C.) for 2 hours. The system was diluted by adding water (10 mL), the pH was adjusted to 7 with 1 N HCl, then the mixture was extracted with ethyl acetate (20 mL×2); the organic phase was dried over anhydrous sodium sulfate, filtered; and the filtrate was concentrated to obtain a crude product, the crude product was purified by preparative high performance liquid chromatography (separation condition: chromatographic column Phenomenex Gemini-NX 80*30 mm*3 μm, mobile phase: water (10 mM ammonium bicarbonate)-acetonitrile; acetonitrile 33%-63% 9 min) and then purified by SFC (separation conditions: chromatographic column: DAICEL CHIRALPAK IC (250 mm*30 mm, 10 μm), mobile phase: $CO_2$-ethanol (0.1% ammonia); ethanol 55%-55%) to obtain compounds 47A, 47B, 47C and 47D.

Compound 47A:
$^1$H NMR (400 MHz, METHANOL-$d_4$) δ 8.41 (d, J=5.1 Hz, 1H), 7.75 (br d, J=7.9 Hz, 1H), 7.43 (d, J=8.4 Hz, 1H), 7.36-7.25 (m, 2H), 7.13 (dd, J=11.0, 17.0 Hz, 1H), 6.25 (br d, J=16.8 Hz, 1H), 5.87-5.73 (m, 1H), 4.98-4.93 (m, 1H), 4.76 (br d, J=12.8 Hz, 1H), 4.65-4.44 (m, 1H), 4.05-3.88 (m, 2H), 3.46 (s, 3H), 2.94 (br d, J=12.8 Hz, 1H), 2.76-2.62 (m, 1H), 2.18 (s, 3H), 2.10 (s, 3H), 1.74-1.66 (m, 3H), 1.14 (br d, J=6.6 Hz, 3H), 1.00 (d, J=6.6 Hz, 3H), 0.89 (br d, J=7.3 Hz, 2H), 0.69-0.56 (m, 2H), 0.50-0.41 (m, 1H).
MS (ESI) m/z (M+H)$^+$=692.3.
SFC retention time was 5.462 min.
separation conditions: chromatographic column: Chiralpak IC-3 100×4.6 mm I.D., 3 μm; column temperature: 35° C.; mobile phase: $CO_2$-ethanol (0.05% DEA); ethanol: 40%-40%; flow rate: 2.8 mL/min.
Compound 47B:
$^1$H NMR (400 MHz, METHANOL-$d_4$) δ 8.41 (br d, J=5.1 Hz, 1H), 7.76 (br d, J=8.6 Hz, 1H), 7.44 (br d, J=8.2 Hz, 1H), 7.31 (br d, J=8.6 Hz, 1H), 7.22 (br d, J=4.9 Hz, 1H), 7.13 (br dd, J=10.7, 17.1 Hz, 1H), 6.29-6.20 (m, 1H), 5.86-5.77 (m, 1H), 5.00-4.94 (m, 1H), 4.76 (br d, J=12.6 Hz, 1H), 4.63-

4.47 (m, 1H), 4.02-3.87 (m, 2H), 3.45 (s, 3H), 3.05-2.91 (m, 2H), 2.21-2.06 (m, 3H), 2.00 (s, 3H), 1.78-1.64 (m, 3H), 1.19 (br dd, J=6.7, 14.0 Hz, 6H), 0.90 (br s, 1H), 0.69 (br d, J=2.6 Hz, 2H), 0.52 (br d, J=8.6 Hz, 1H), 0.42 (br s, 1H).

MS (ESI) m/z (M+H)$^+$=692.3.

SFC retention time was 4.669 min.

separation conditions: chromatographic column: Chiralpak IC-3 100×4.6 mm I.D., 3 μm; column temperature: 35° C.; mobile phase: CO$_2$-ethanol (0.05% DEA); ethanol: 40%-40%; flow rate: 2.8 mL/min.

Compound 47C:

$^1$H NMR (400 MHz, METHANOL-d$_4$) δ 8.42 (br d, J=4.9 Hz, 1H), 7.76 (br d, J=8.4 Hz, 1H), 7.44 (br d, J=8.8 Hz, 1H), 7.31 (br d, J=8.6 Hz, 1H), 7.25 (br d, J=4.9 Hz, 1H), 7.13 (br dd, J=10.9, 17.1 Hz, 1H), 6.31-6.19 (m, 1H), 5.82 (br d, J=12.6 Hz, 1H), 5.00-4.94 (m, 1H), 4.76 (br d, J=14.6 Hz, 1H), 4.63-4.49 (m, 1H), 4.04-3.87 (m, 2H), 3.45 (s, 3H), 3.09-2.93 (m, 2H), 2.19-2.03 (m, 3H), 1.98 (s, 3H), 1.77-1.60 (m, 3H), 1.29-1.04 (m, 6H), 0.90 (br s, 1H), 0.66 (br s, 2H), 0.54-0.35 (m, 2H).

MS (ESI) m/z (M+H)$^+$=692.3.

SFC retention time was 7.774 min.

separation conditions: chromatographic column: Chiralpak IC-3 100×4.6 mm I.D., 3 μm; column temperature: 35° C.; mobile phase: CO$_2$-ethanol (0.05% DEA); ethanol: 40%-40%; flow rate: 2.8 mL/min.

Compound 47D:

$^1$H NMR (400 MHz, METHANOL-d$_4$) δ 8.41 (d, J=4.9 Hz, 1H), 7.76 (br d, J=8.8 Hz, 1H), 7.44 (d, J=8.4 Hz, 1H), 7.31 (d, J=8.6 Hz, 1H), 7.25 (d, J=4.9 Hz, 1H), 7.13 (dd, J=10.9, 17.1 Hz, 1H), 6.34-6.18 (m, 1H), 5.88-5.76 (m, 1H), 5.01-4.95 (m, 1H), 4.76 (br d, J=12.6 Hz, 1H), 4.68-4.41 (m, 1H), 4.08-3.84 (m, 2H), 3.46 (s, 3H), 3.07-2.90 (m, 1H), 2.70-2.52 (m, 1H), 2.20 (s, 3H), 2.12 (s, 3H), 1.81-1.64 (m, 3H), 1.17-0.99 (m, 6H), 0.89 (br d, J=7.3 Hz, 1H), 0.66 (br s, 2H), 0.44 (br dd, J=3.1, 7.9 Hz, 2H).

MS (ESI) m/z (M+H)$^+$=692.3.

SFC retention time was 6.286 min.

separation conditions: chromatographic column: Chiralpak IC-3 100×4.6 mm I.D., 3 μm; column temperature: 35° C.; mobile phase: CO$_2$-ethanol (0.05% DEA); ethanol: 40%-40%; flow rate: 2.8 mL/min.

Embodiment 48: Preparation of Compound 48

Step 1: Preparation of Compound 48-1

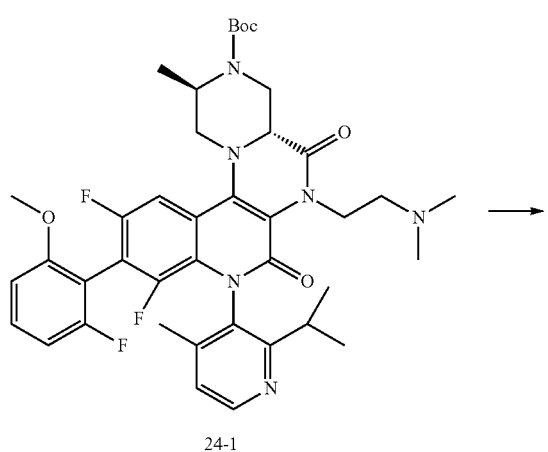

24-1

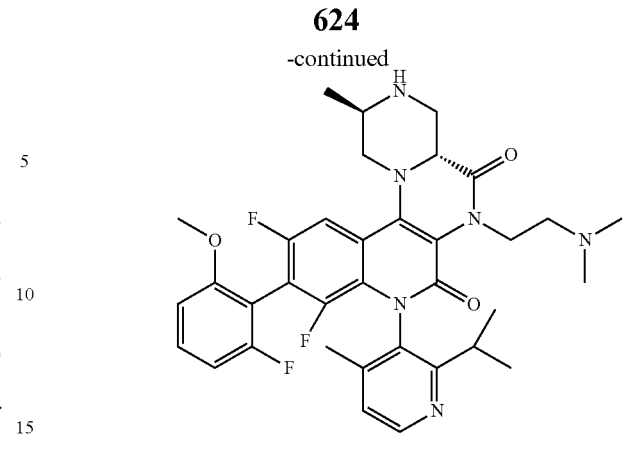

48-1

Compound 24-1 (550 mg, 734.48 μmol) was dissolved in dichloromethane (6 mL), and trifluoroacetic acid (1.72 g, 15.04 mmol, 1.11 mL) was added thereto, and the reaction was stirred at room temperature (20° C.) for 3 hours. The reaction mixture was concentrated to obtain compound 48-1, which was directly used in the next reaction without further purification.

MS (ESI) m/z (M+H)$^+$=649.3.

Step 2: Preparation of Compounds 48A and 48B

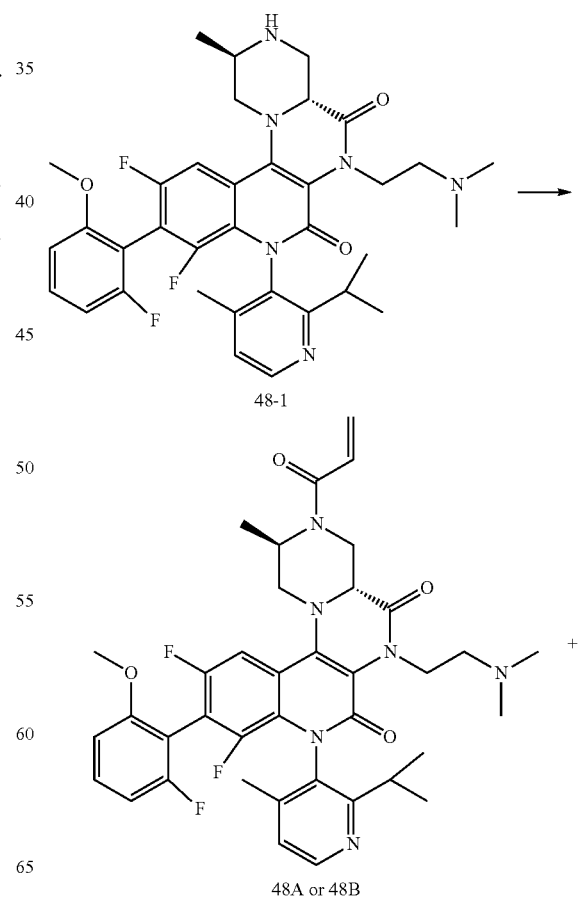

48-1

48A or 48B

Step 3: Preparation of Compounds 48A-1 and 48A-2

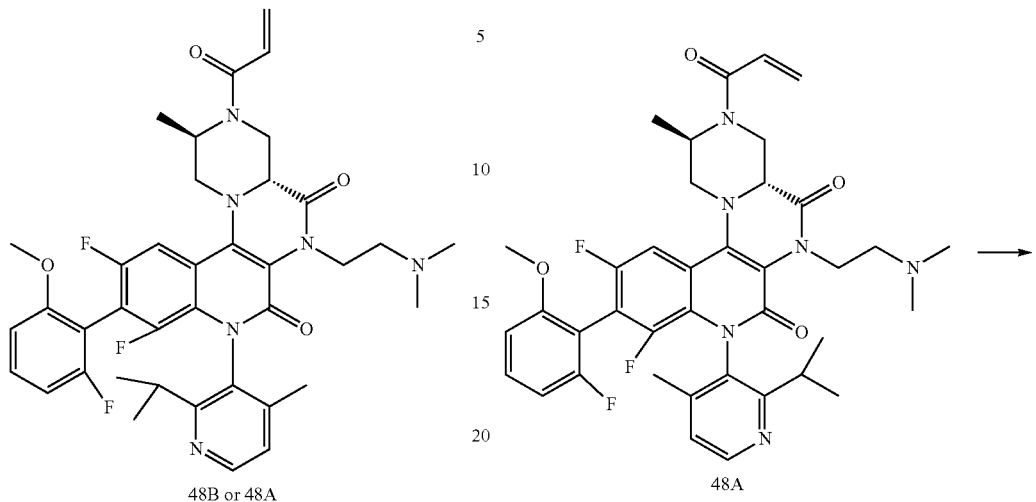

48B or 48A

48A

Compound 48-1 (200 mg, 308.30 μmol) was dissolved in tetrahydrofuran (2 mL) and saturated sodium bicarbonate aqueous solution (4.43 g, 52.73 mmol, 2.05 mL), and acrylic anhydride (77.76 mg, 616.60 μmol) was added thereto at room temperature (25° C.). After the addition was completed, the system was stirred at room temperature (25° C.) for 0.5 hours. The system was diluted with water (10 mL) and extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate aqueous solution)-acetonitrile]; acetonitrile %: 52%-82% 9 min) and then purified by SFC (separation conditions: chromatographic column: DAICEL CHIRALPAK IG (250 mm*30 mm μm); mobile phase: [0.1% ammonia isopropanol]; isopropanol %: 40%-40%) to obtain compounds 48A and 48B.

Compound 48A:

MS (ESI) m/z (M+H)$^+$=703.1.

SFC retention time was 4.816 & 5.020 min.

Separation conditions: chromatographic column: Chiralpak IG-3 100 mm×4.6 mm 4.6 mm I.D., 3 μm; column temperature: 40° C.; mobile phase: $CO_2$-ethanol (0.05% DEA); ethanol: 5%-40% 5.5 min, 5% 1.5 min; flow rate: 2.5 mL/min.

Compound 48B:

MS (ESI) m/z (M+H)$^+$=703.1.

SFC retention time was 3.769 & 4.831 min.

Separation conditions: chromatographic column: Chiralpak IC-3 100 mm×4.6 mm 4.6 mm I.D., 3 μm; column temperature: 35° C.; mobile phase: $CO_2$-ethanol (0.05% DEA); ethanol: 40%-40%; flow rate: 2.8 mL/min.

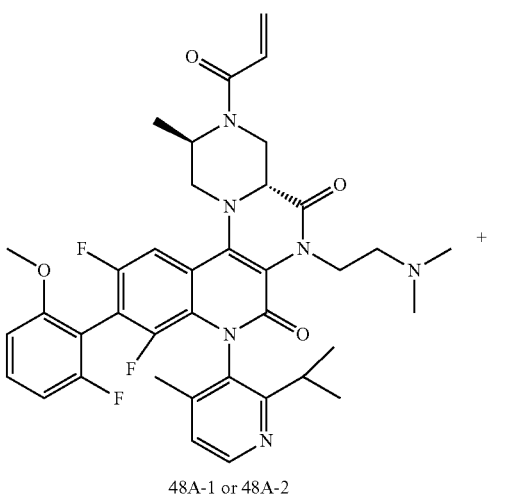

48A-1 or 48A-2

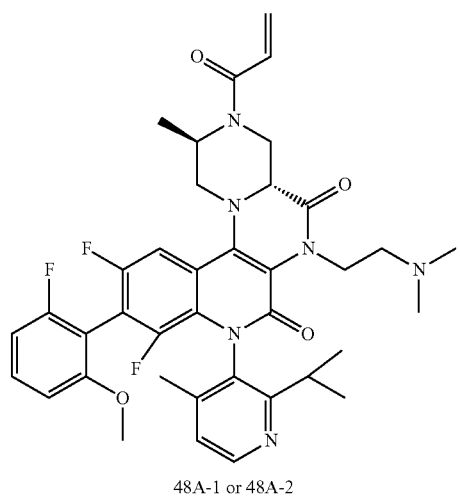

48A-1 or 48A-2

Diasteroisomeric compound 48A was purified by SFC (separation conditions: chromatographic column: DAICEL CHIRALPAK IG (250 mm*30 mm, 10 μm); mobile phase: [CO$_2$-ethanol (0.1% ammonia)]; ethanol %: 35%). After concentration, compound 48A-1 and compound 48A-2 were obtained.

Compound 48A-1:

$^1$H NMR (400 MHz, Methanol-d$_4$) δ 8.45 (d, J=4.8 Hz, 1H), 7.69 (br d, J=7.8 Hz, 1H), 7.48-7.39 (m, 1H), 7.28 (d, J=5.0 Hz, 1H), 7.13 (dd, J=10.8, 17.1 Hz, 1H), 6.90 (d, J=8.5 Hz, 1H), 6.85-6.75 (m, 1H), 6.31-6.18 (m, 1H), 5.86-5.75 (m, 1H), 4.94 (br s, 1H), 4.75 (br d, J=13.3 Hz, 1H), 4.61 (br s, 1H), 4.40-4.26 (m, 2H), 4.03-3.86 (m, 2H), 3.68 (s, 3H), 3.24-3.10 (m, 1H), 2.66-2.50 (m, 2H), 2.49-2.38 (m, 1H), 2.24-2.15 (m, 9H), 1.76-1.64 (m, 3H), 1.14 (d, J=6.8 Hz, 3H), 1.06 (d, J=6.8 Hz, 3H).

MS (ESI) m/z (M+H)$^+$=703.3.

HPLC retention time was 4.552 min.

Separation conditions: chromatographic column Xbridge Shield RP-18, 5 μm, 2.1*50 mm; column temperature: 50° C.; mobile phase: water (0.2 mL/1 L NH$_{32}$O)-acetonitrile; acetonitrile: 10%-80% 6 min, 80% 2 min; flow rate: 0.8 mL/min.

SFC retention time was 4.846 min separation conditions: chromatographic column: Chiral-Pak IG-3 100×4.6 mm I.D., 3 μm; column temperature: 40° C.; mobile phase: CO$_2$-ethanol (0.05% DEA); ethanol: 5%-40% 5.5 min, 5% 1.5 min; flow rate: 2.5 mL/min.

Compound 48A-2:

$^1$H NMR (400 MHz, Methanol-d$_4$) δ 8.45 (d, J=5.0 Hz, 1H), 7.69 (br d, J=8.8 Hz, 1H), 7.49-7.38 (m, 1H), 7.28 (d, J=5.0 Hz, 1H), 7.13 (dd, J=10.7, 16.9 Hz, 1H), 6.92 (d, J=8.5 Hz, 1H), 6.85-6.74 (m, 1H), 6.30-6.18 (m, 1H), 5.90-5.73 (m, 1H), 4.94 (br s, 1H), 4.75 (br d, J=13.3 Hz, 1H), 4.68-4.47 (m, 1H), 4.40-4.25 (m, 2H), 4.02-3.86 (m, 2H), 3.77 (s, 3H), 3.26-3.10 (m, 1H), 2.65-2.49 (m, 2H), 2.48-2.39 (m, 1H), 2.28-2.10 (m, 9H), 1.76-1.61 (m, 3H), 1.12 (d, J=6.5 Hz, 3H), 1.02 (d, J=6.8 Hz, 3H).

MS (ESI) m/z (M+H)$^+$=703.3.

HPLC retention time was 4.551 min.

Separation conditions: chromatographic column Xbridge Shield RP-18, 5 μm, 2.1*50 mm; column temperature: 50° C.; mobile phase: water (0.2 mL/1 L NH$_{32}$O)-acetonitrile; acetonitrile: 10%-80% 6 min, 80% 2 min; flow rate: 0.8 mL/min.

SFC retention time was 5.054 min separation conditions: chromatographic column: Chiral-Pak IG-3 100×4.6 mm I.D., 3 μm; column temperature: 40° C.; mobile phase: CO$_2$-ethanol (0.05% DEA); ethanol: 5%-40% 5.5 min, 5% 1.5 min; flow rate: 2.5 mL/min.

Step 4: Preparation of Compounds 48B-1 and 48B-2

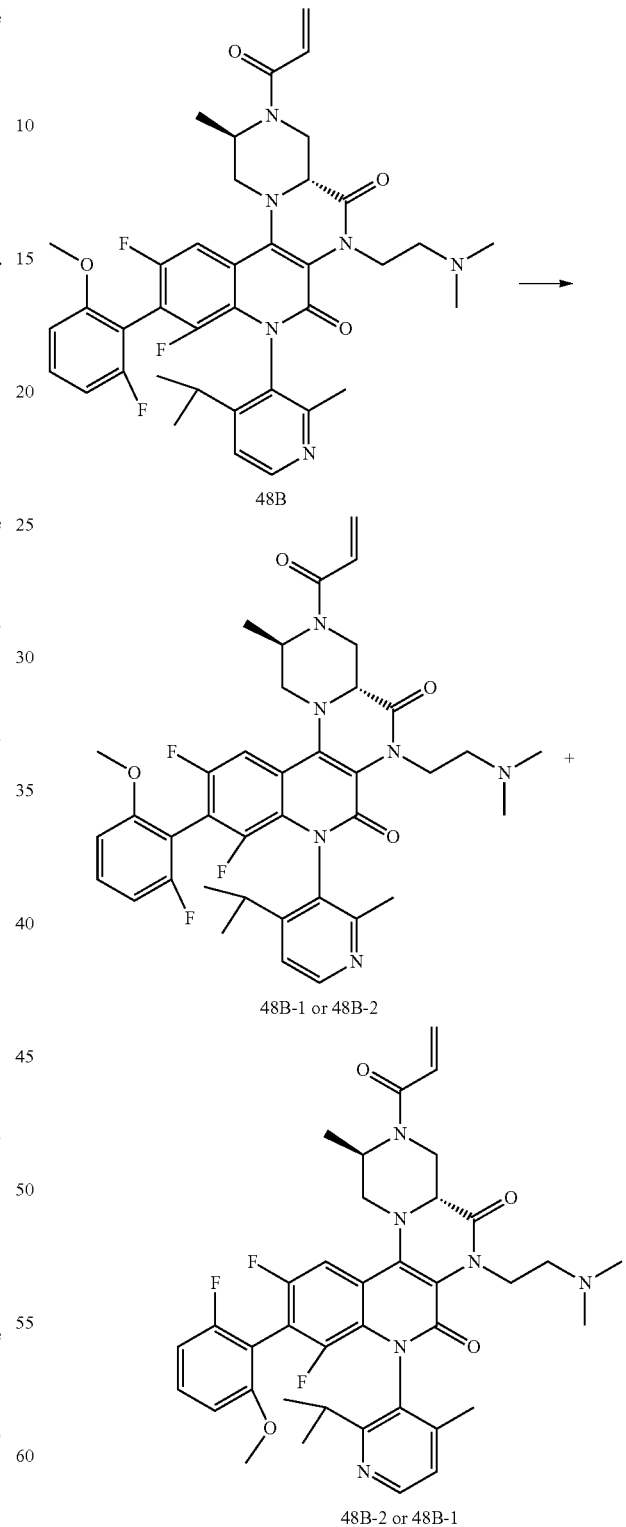

Diastereoisomeric compound 48B was purified by SFC (separation conditions: chromatographic column: DAICEL CHIRALPAK AD (250 mm*30 mm, 10 μm); mobile phase:

[CO₂-ethanol (0.1% ammonia)]; ethanol %: 45%). After concentration, compound 48B-1 and compound 48B-2 were obtained.

Compound 48B-1:

¹H NMR (400 MHz, Methanol-d₄) δ 8.45 (d, J=5.0 Hz, 1H), 7.70 (br d, J=9.3 Hz, 1H), 7.49-7.38 (m, 1H), 7.25 (d, J=5.0 Hz, 1H), 7.13 (dd, J=10.7, 16.9 Hz, 1H), 6.90 (d, J=8.5 Hz, 1H), 6.86-6.76 (m, 1H), 6.31-6.17 (m, 1H), 5.87-5.75 (m, 1H), 4.94 (br s, 1H), 4.74 (br d, J=12.5 Hz, 1H), 4.66-4.43 (m, 1H), 4.32 (br t, J=6.8 Hz, 2H), 4.02-3.84 (m, 2H), 3.72 (s, 3H), 3.27-3.15 (m, 1H), 2.95 (td, J=6.8, 13.4 Hz, 1H), 2.75-2.61 (m, 1H), 2.54 (br dd, J=6.3, 12.0 Hz, 1H), 2.30-2.18 (m, 6H), 1.97 (s, 3H), 1.75-1.65 (m, 3H), 1.24 (br d, J=6.8 Hz, 3H), 1.16 (br d, J=6.8 Hz, 3H).

MS (ESI) m/z (M+H)⁺=703.3.

HPLC retention time was 4.541 min.

Separation conditions: chromatographic column Xbridge Shield RP-18, 5 μm, 2.1*50 mm; column temperature: 50° C.; mobile phase: water (0.2 mL/1 L NH₃₂O)-acetonitrile; acetonitrile: 10%-80% 6 min, 80% 2 min; flow rate: 0.8 mL/min SFC retention time was 3.674 min separation conditions: chromatographic column: Chiralpak IC-3 100×4.6 mm I.D., 3 μm; column temperature: 35° C.; mobile phase: CO₂-ethanol (0.05% DEA); ethanol: 40%; flow rate: 2.8 mL/min.

Compound 48B-2:

¹H NMR (400 MHz, Methanol-d₄) δ 8.46 (d, J=5.0 Hz, 1H), 7.70 (br d, J=8.3 Hz, 1H), 7.50-7.39 (m, 1H), 7.27 (d, J=4.8 Hz, 1H), 7.14 (dd, J=10.8, 16.8 Hz, 1H), 6.92 (d, J=8.5 Hz, 1H), 6.86-6.78 (m, 1H), 6.32-6.17 (m, 1H), 5.86-5.73 (m, 1H), 5.00-4.94 (m, 1H), 4.75 (br d, J=13.1 Hz, 1H), 4.67-4.49 (m, 1H), 4.32 (br t, J=7.0 Hz, 2H), 3.99-3.85 (m, 2H), 3.75 (s, 3H), 3.25-3.15 (m, 1H), 2.97 (td, J=6.8, 13.6 Hz, 1H), 2.72-2.56 (m, 1H), 2.54-2.44 (m, 1H), 2.27-2.15 (m, 6H), 1.99 (s, 3H), 1.76-1.62 (m, 3H), 1.24 (d, J=6.8 Hz, 3H), 1.13 (d, J=6.8 Hz, 3H).

MS (ESI) m/z (M+H)⁺=703.3.

HPLC retention time was 4.542 min.

Separation conditions: chromatographic column Xbridge Shield RP-18, 5 μm, 2.1*50 mm; column temperature: 50° C.; mobile phase: water (0.2 mL/1 L NH₃₂O)-acetonitrile; acetonitrile: 10%-80% 6 min, 80% 2 min; flow rate: 0.8 mL/min SFC retention time was 4.668 min.

separation conditions: chromatographic column: Chiralpak IC-3 100×4.6 mm I.D., 3 μm; column temperature: 35° C.; mobile phase: CO₂-ethanol (0.05% DEA); ethanol: 40%; flow rate: 2.8 mL/min.

Embodiment 49: Preparation of Compound 49

Step 1: Preparation of Compound 49-2

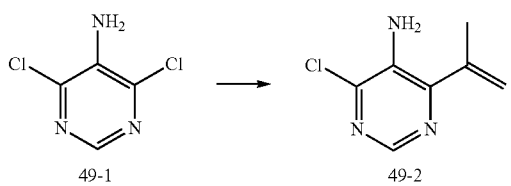

Compound 49-1 (16.4 g, 10 mmol), isopropenylboronic acid pinacol ester (20.2 g, 12 mmol) and sodium carbonate (31.8 g, 30 mmol) were dissolved in a mixed solvent of dioxane (200 mL) and water (50 mL), under the protection of nitrogen, [1,1'-bis(diphenylphosphino)ferrocene]palladium dichloride (7.3 g, 1 mmol) was added thereto. The reaction was heated to 95° C. and stirred for 16 hours. The reaction mixture was diluted with ethyl acetate (100 mL), filtered, the filtrate was concentrated under reduced pressure, and the crude product was purified by silica gel column chromatography (ethyl acetate/petroleum ether (v/v)=0-25%) to obtain compound 49-2.

¹H NMR (400 MHz, Chloroform-d) δ 8.40 (s, 1H), 5.70-5.58 (m, 1H), 5.56-5.18 (m, 1H), 4.52 (brs, 2H), 2.18 (s, 3H).

MS (ESI) m/z (M+H)⁺=169.80.

Step 2: Preparation of Compound 49-3

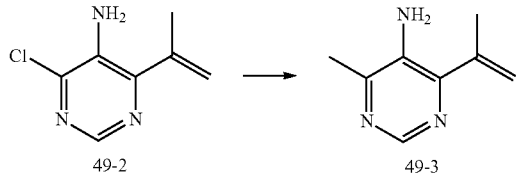

Compound 49-2 (8.4 g, 50 mmol), methylboronic acid (15 g, 250 mmol) and cesium carbonate (66.5 g, 150 mmol) were dissolved in a mixed solvent of dioxane (100 mL) and water (25 mL), under the protection of nitrogen, [1,1'-bis (diphenylphosphino)ferrocene]palladium dichloride (3.66 g, 5 mmol) was added thereto. The reaction was heated to 100° C. and stirred for 4 hours. The reaction mixture was diluted with ethyl acetate (100 mL), filtered, the filtrate was concentrated under reduced pressure, and the crude product was purified by silica gel column chromatography (ethyl acetate/petroleum ether (v/v)=0-25%) to obtain compound 49-3.

¹H NMR (400 MHz, Chloroform-d) δ 8.55 (s, 1H), 5.80-5.50 (m, 1H), 5.50-5.33 (m, 1H), 4.07 (brs, 2H), 2.49 (s, 3H), 2.17 (s, 3H).

MS (ESI) m/z (M+H)⁺=150.00.

Step 3: Preparation of Compound 49-4

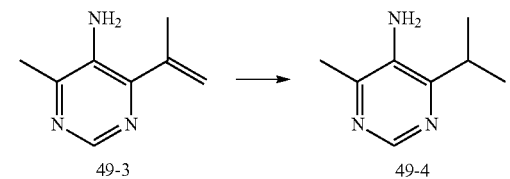

Compound 49-3 (2.4 g, 16 mmol) was dissolved in methanol (80 mL), and palladium/carbon (700 mg) was added thereto under the protection of nitrogen. After the addition was completed, under hydrogen atmosphere, the reaction was stirred at room temperature (20° C.) for 3 hours. The system was filtered, and the filtrate was concentrated under reduced pressure to obtain compound 49-4, which was directly used in the next reaction without further purification.

MS (ESI) m/z (M+H)⁺=151.80.

Step 4: Preparation of Compound 49-5

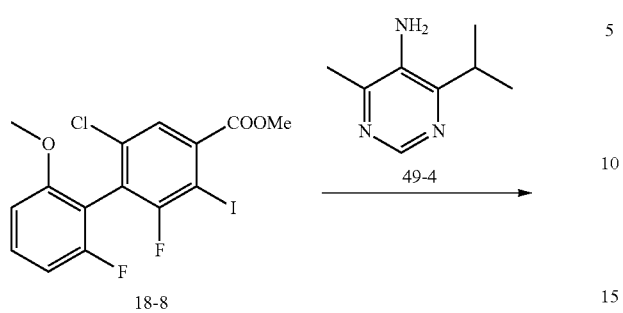

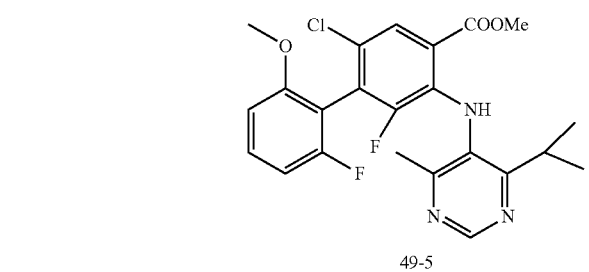

Under the protection of nitrogen, compound 18-8 (3.14 g, 7.2 mmol) and compound 49-4 (1.3 g, 8.6 mmol) were dissolved in toluene (20 mL), and 4,5-bis(diphenylphosphino)-9,9-dimethylxanthene (550 mg, 0.946 mmol), tris(dibenzylideneacetone)dipalladium (870 mg, 0.946 mmol) and cesium carbonate (7.04 g, 21.6 mmol) were added successively. After the addition was completed, the reaction was heated to 100° C. and stirred for 16 hours. The reaction mixture was diluted with ethyl acetate (100 mL), filtered, the filtrate was concentrated under reduced pressure, and the crude product was purified by silica gel column chromatography (ethyl acetate/petroleum ether (v/v)=0-50%) to obtain compound 49-5.

$^1$H NMR (400 MHz, Chloroform-d) δ 9.10 (s, 1H), 8.84 (d, J=2.4 Hz, 1H), 7.98 (dd, J=1.7, 0.9 Hz, 2H), 7.38-7.29 (m, 1H), 6.84-6.67 (m, 2H), 3.98 (s, 3H), 3.74 (d, J=18.8 Hz, 3H), 3.42 (h, J=6.8 Hz, 1H), 2.41 (d, J=3.7 Hz, 3H), 1.32-1.16 (m, 6H).

MS (ESI) m/z (M+H)$^+$=462.0.

Step 5: Preparation of Compound 49-6

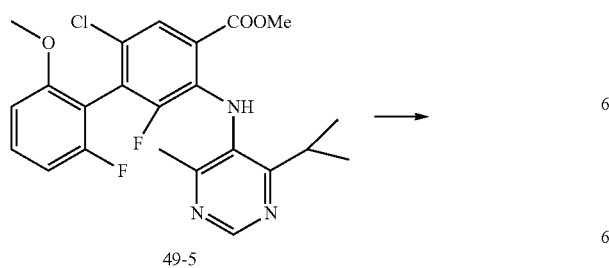

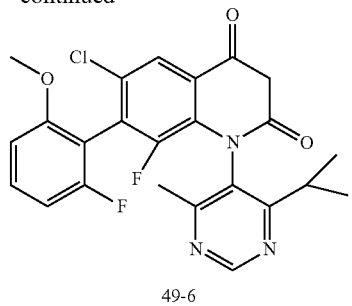

Compound 49-5 (2.1 g, 4.56 mmol) was dissolved in N,N-dimethylformamide (20 mL), and sodium hydride (910 mg, 22.8 mmol, 60%) was added thereto at 0° C. After the addition was completed, the system was stirred 0° C. for 20 min. The system was raised to room temperature (20° C.), and acetyl chloride (1.6 mL, 22.8 mmol) was added dropwise. After the addition was completed, the system was stirred at room temperature (20° C.) for 1 hour. The system was quenched with water (100 mL), extracted with ethyl acetate (100 mL×2); then the organic phases were combined, concentrated; methanol (50 mL) and potassium carbonate (5 g) were added thereto, and the mixture was stirred at room temperature (20° C.) for 1 hour. The system was concentrated, diluted with water (50 mL), the pH was adjusted to 7 with 1 N HCl; and the mixture was extracted with ethyl acetate (100 mL×2); then the organic phases were combined, dried over anhydrous sodium sulfate, filtered, and the filtrate was concentrated to obtain a crude product, the crude product was purified by reversed-phase silica gel column chromatography (acetonitrile/water (0.5% ammonium bicarbonate aqueous solution) (v/v)=5-95%) to obtain compound 49-6.

MS (ESI) m/z (M+H)$^+$=472.0.

Step 6: Preparation of Compound 49-7

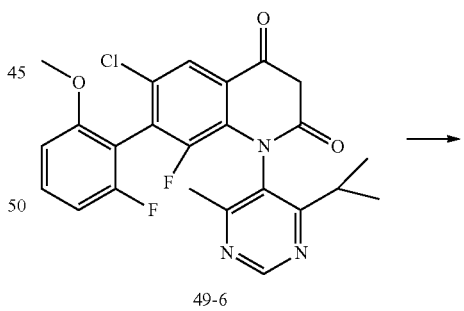

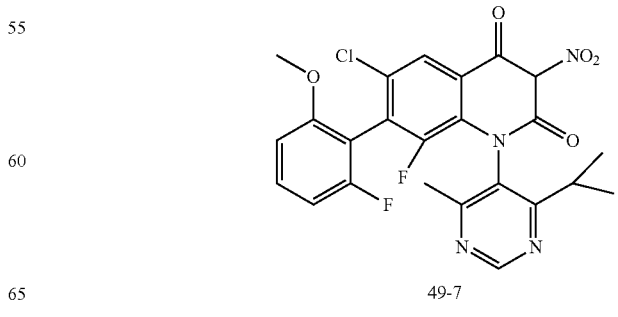

Under the protection of nitrogen, compound 49-6 (360 mg, 0.76 mmol) was dissolved in acetic acid (12 mL), and concentrated nitric acid (1.2 mL) was added thereto. After the addition was completed, the reaction was heated to 40° C. and stirred for 2 hours. The reaction mixture was concentrated under reduced pressure to remove most of the acetic acid, poured into ice water, the pH was adjusted to 6 with sodium hydroxide; and the mixture was extracted with ethyl acetate (100 mL×2); then the organic phases were combined, dried over anhydrous sodium sulfate, filtered, and the filtrate was concentrated to obtain a crude product, the crude product was purified by reversed-phase silica gel column chromatography (acetonitrile/water (0.5% ammonium bicarbonate aqueous solution) (v/v)=5-95%) to obtain compound 49-7.

MS (ESI) m/z (M+H)$^+$=517.0.

Step 7: Preparation of Compound 49-8

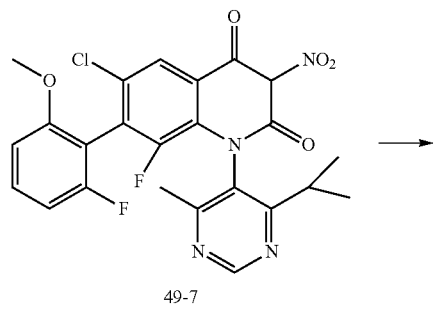

49-7

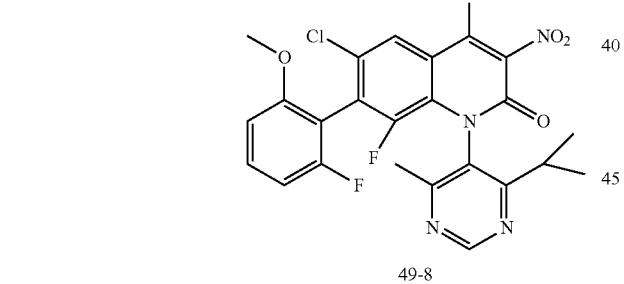

49-8

Under the protection of nitrogen, compound 49-7 (200 mg, 0.39 mmol) was dissolved in acetonitrile (6 mL), diisopropylethylamine (0.8 mL) and phosphorus oxychloride (0.5 mL) were added thereto sequentially. After the addition was completed, the reaction was heated to 80° C. and stirred for 2 hours. The reaction mixture was cooled to room temperature, concentrated under reduced pressure, the system was poured into ice water, the pH was adjusted to 8 with sodium hydroxide; and the mixture was extracted with ethyl acetate (100 mL×2); then the organic phases were combined, dried over anhydrous sodium sulfate, filtered, and the filtrate was concentrated to obtain a crude product, the crude product was purified by silica gel column chromatography (ethyl acetate/petroleum ether (v/v)=0-35%) to obtain compound 49-8.

MS (ESI) m/z (M+H)$^+$=535.0.

Step 8: Preparation of Compound 49-9

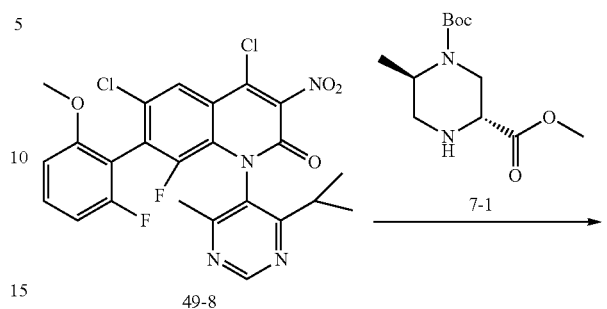

49-8

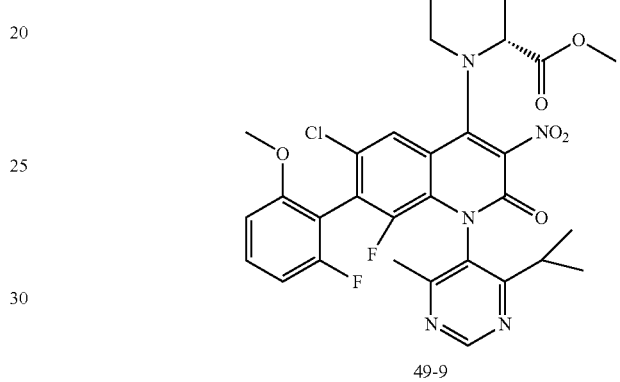

49-9

Compound 49-8 (112 mg, 0.2 mmol), compound 7-1 (57.2 mg, 0.22 mmol) and N,N-diisopropylethylamine (40 μL) were dissolved in acetonitrile (3 mL). Under airtight conditions, the system was heated to 100° C. and stirred for 4 hours. The system was concentrated to obtain a crude product, the crude product was purified by medium pressure column chromatography (ethyl acetate/petroleum ether (v/v)=0-35%) to obtain compound 49-9.

MS (ESI) m/z (M+H)$^+$=757.2.

Step 9: Preparation of Compound 49-10

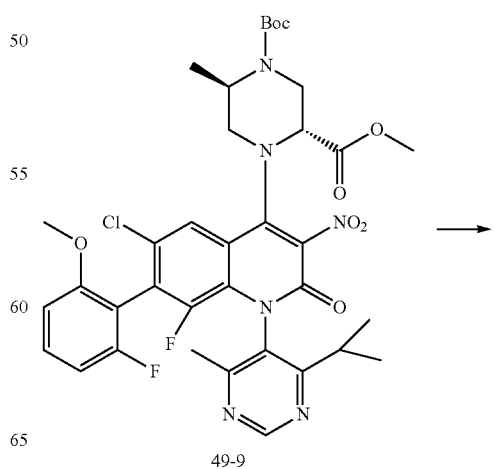

49-9

-continued

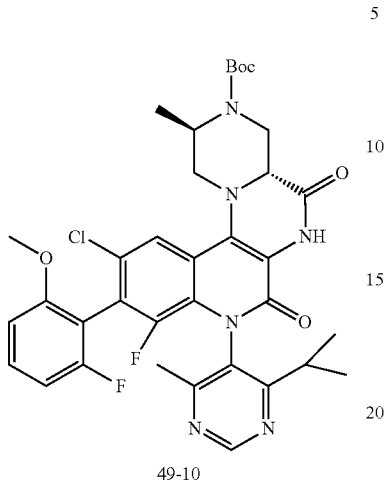

49-10

Compound 49-9 (282 mg, 0.37 mmol) and iron powder (280 mg, 5 mmol) were dissolved in acetic acid (15 mL), and the system was heated to 80° C. and stirred for 145 min under nitrogen atmosphere. The system was concentrated, diluted with dichloromethane (50 mL), filtered, the filtrate was washed with saturated sodium bicarbonate aqueous solution, dried over anhydrous sodium sulfate, filtered, and the filtrate was concentrated to obtain compound 49-10, which was directly used for the next reaction without further purification.

MS (ESI) m/z (M+H)$^+$=695.2.

Step 10: Preparation of Compound 49-11

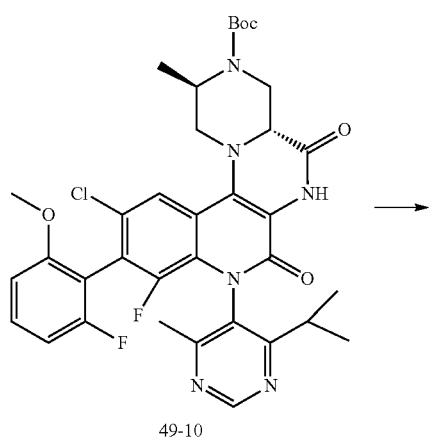

49-10

-continued

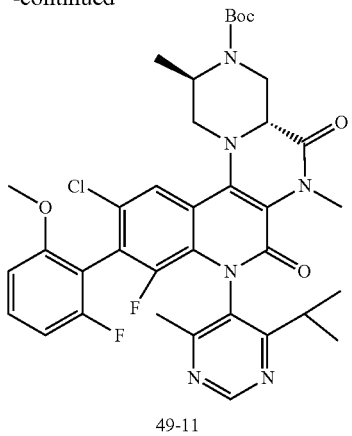

49-11

Compound 49-10 (220 mg, 317 μmol) and potassium carbonate (100 mg, 799.6 μmol) were dissolved in acetone (10 mL), and methyl iodide (200 μL) was added at room temperature (25° C.). After the addition was completed, under nitrogen atmosphere, the system was heated to 60° C. and stirred for 4 hours. The system was concentrated to obtain a crude product, the crude product was purified by medium pressure column chromatography (ethyl acetate/petroleum ether (v/v)=0-60%) to obtain compound 49-11.

MS (ESI) m/z (M+H)$^+$=709.2.

Step 11: Preparation of Compound 49-12 and 50-1

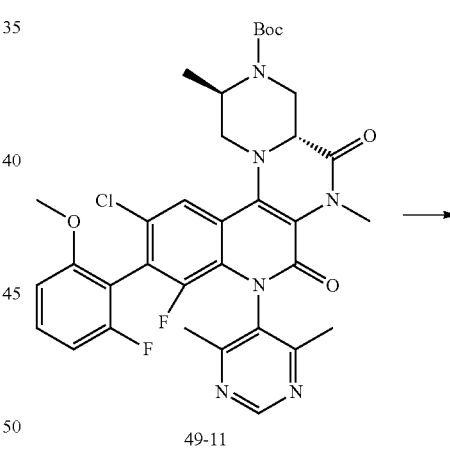

49-11

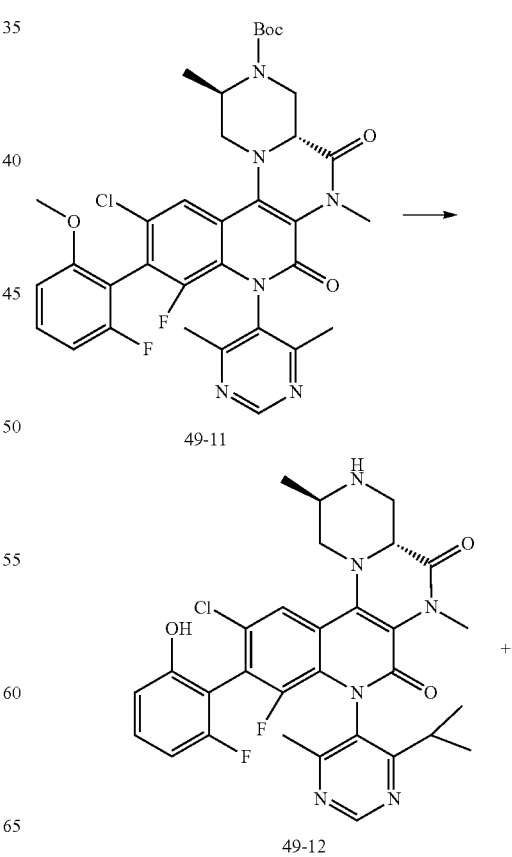

49-12

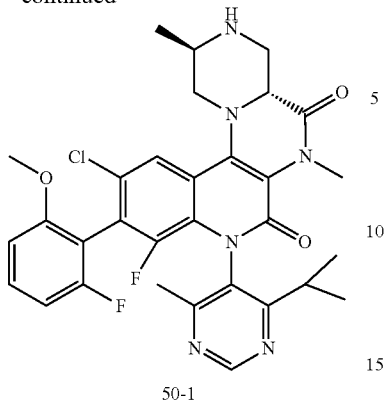

50-1

Compound 49-11 (100 mg, 141 µmol) was dissolved in dichloromethane (3 mL), and boron tribromide (1 mL) was added thereto, and the reaction was stirred at 25° C. for 2 hours. The reaction mixture was quenched with methanol (10 mL), stirred for 10 min, and concentrated under reduced pressure to obtain a mixture of compound 49-12 (hydrobromide) and 50-1 (hydrobromide), which was directly used in the next reaction without further purification.

Compound 49-12:
MS (ESI) m/z (M+H)$^+$=595.2.
Compound 50-1:
MS (ESI) m/z (M+H)$^+$=609.2.

Step 12: Preparation of Compound 49

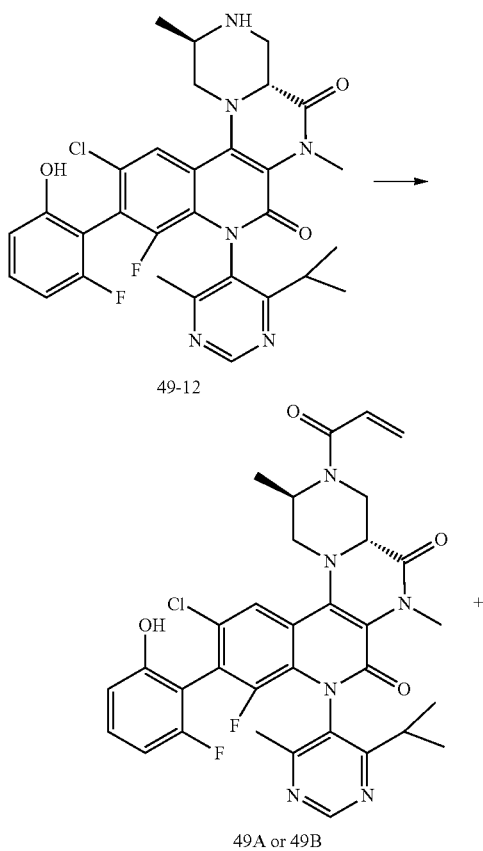

49-12

49A or 49B

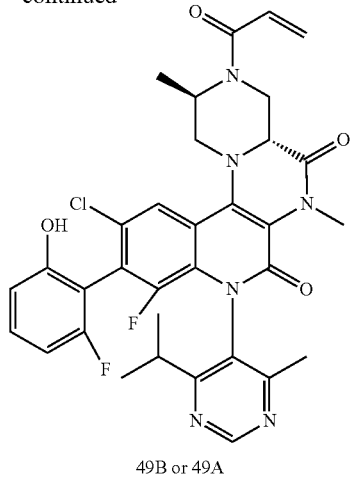

49B or 49A

Compound 49-12 (100 mg, 0.168 mmol) was dissolved in dichloromethane (10 mL), and the system was cooled to 0° C., triethylamine (0.3 mL, 2.1 mmol) and acryloyl chloride (27 mg, 0.3 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (20 mL) and water (20 mL); and the organic phase was dried over anhydrous sodium sulfate, filtered, and the filtrate was concentrated to obtain a crude product, the crude product was purified by high performance liquid chromatography (separation conditions: chromatographic column Welch Xtimate® C18 21.2×250 mm, 10 µm; column temperature: 25° C., mobile phase: water (10 mM/L NH$_4$HCO$_3$)-acetonitrile; acetonitrile 35%-75% 18 min; flow rate 30 mL/min) to obtain compound 49A and 49B.

MS (ESI) m/z (M+H)$^+$=649.2.

Compound 49A:
$^1$H NMR (400 MHz, DMSO-d$_6$) δ 10.20 (brs, 1H), 8.97 (s, 1H), 7.82 (d, J=1.5 Hz, 1H), 7.21 (q, J=7.9 Hz, 1H), 6.95 (dd, J=16.8, 10.6 Hz, 0.7H), 6.79 (dd, J=16.6, 10.6 Hz, 0.3H), 6.72-6.59 (m, 2H), 6.08 (dd, J=16.8, 2.4 Hz, 1H), 5.70 (dd, J=10.5, 2.5 Hz, 1H), 4.95 (d, J=14.0 Hz, 0.24H), 4.81-4.69 (m, 0.76H), 4.54 (d, J=14.0 Hz, 0.74H), 4.41-4.32 (m, 0.26H), 4.00-3.86 (m, 1H), 3.69 (dd, J=14.2, 4.3 Hz, 1H), 3.30-3.20 (m, 4H), 3.02-2.88 (m, 1H), 2.72 (dt, J=12.5, 4.2 Hz, 1H), 2.01 (d, J=4.5 Hz, 3H), 1.47 (d, J=6.7 Hz, 3H), 1.15-1.06 (m, 3H), 1.04-0.94 (m, 3H).

MS (ESI) m/z (M+H)$^+$=649.2.

Compound 49B:
$^1$H NMR (400 MHz, DMSO-d$_6$) δ 10.16 (brs, 1H), 8.97 (s, 1H), 7.83 (s, 1H), 7.22 (d, J=7.8 Hz, 1H), 6.95 (dd, J=16.8, 10.6 Hz, 0.75H), 6.79 (dd, J=16.5, 10.6 Hz, 0.25H), 6.77-6.48 (m, 2H), 6.24-5.98 (m, 1H), 5.76-5.50 (m, 1H), 4.95 (d, J=14.0 Hz, 0.25H), 4.74 (t, J=5.2 Hz, 0.75H), 4.54 (d, J=14.1 Hz, 0.75H), 4.38 (s, 0.25H), 4.01-3.89 (m, 1H), 3.69 (dd, J=14.1, 4.3 Hz, 1H), 3.25-3.02 (m, 4H), 2.88-2.65 (m, 1H), 2.57-2.46 (m, 1H), 2.25 (s, 3H), 1.47 (d, J=6.8 Hz, 3H), 0.97 (d, J=6.6 Hz, 3H), 0.86 (d, J=6.7 Hz, 3H).

MS (ESI) m/z (M+H)$^+$=649.2.

Step 13: Separation of Isomer of Compound 49A

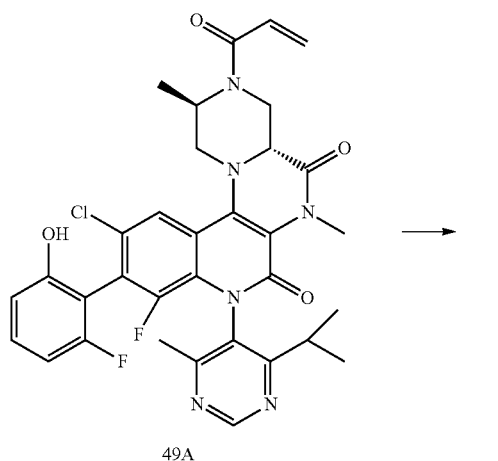

49A

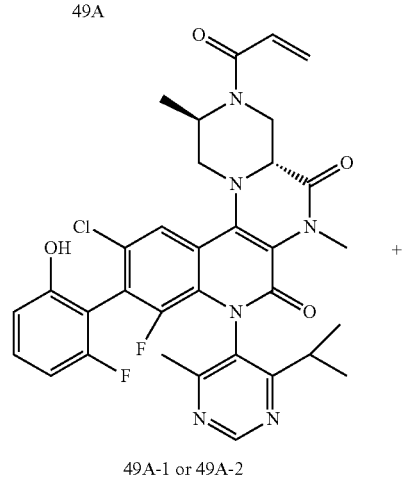

49A-1 or 49A-2

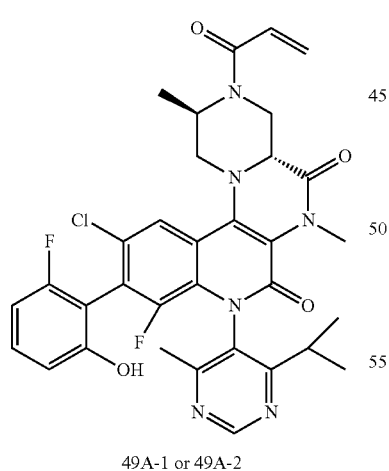

49A-1 or 49A-2

Diastereomeric compound 49A was purified by SFC (separation conditions: chromatographic column: «Column_3»; mobile phase: [CO₂-ethanol (0.1% ammonia)]; ethanol %: 30%-30%; flow rate: 70 mL/min). After concentration, compound 49A-1 and compound 49A-2 were obtained.

Compound 49A-1:

¹H NMR (400 MHz, DMSO-d₆) δ 10.18 (s, 1H), 8.97 (s, 1H), 8.18-7.75 (m, 1H), 7.21 (d, J=7.7 Hz, 1H), 6.95 (dd, J=16.8, 10.6 Hz, 0.75H), 6.79 (dd, J=16.5, 10.6 Hz, 0.25H), 6.72-6.60 (m, 2H), 6.22-5.97 (m, 1H), 5.81-5.60 (m, 1H), 4.95 (d, J=13.9 Hz, 0.24H), 4.74 (d, J=8.1 Hz, 0.74H), 4.54 (d, J=14.0 Hz, 0.73H), 4.37 (s, 0.23H), 3.97-3.84 (m, 1H), 3.69 (dd, J=14.2, 4.3 Hz, 1H), 3.23-3.14 (m, 4H), 3.01-2.82 (m, 1H), 2.72 (dd, J=12.5, 3.7 Hz, 1H), 2.00 (s, 3H), 1.47 (d, J=6.8 Hz, 3H), 1.17-0.91 (m, 6H).

MS (ESI) m/z (M+H)⁺=649.0.

HPLC retention time was 5.345 min.

Separation conditions: chromatographic column: Waters XBridge 4.6*100 mm, 3.5 μm; column temperature: 40° C.; mobile phase: water (10 mM NH₄HCO₃)-acetonitrile; acetonitrile: 5%-95% 7 min; flow rate: 1.2 mL/min.

SFC retention time was 4.426 min.

separation conditions: chromatographic column: Chiralcel OD-3 150×4.6 mm I.D., 3 μm; column temperature: 35° C.; mobile phase: CO₂-ethanol (0.05% DEA); ethanol: 5%-40% 5 min, 40% 2.5 min, 5% 2.5 min; flow rate: 2.5 mL/min.

Compound 49A-2:

¹H NMR (400 MHz, DMSO-d₆) δ 10.18 (s, 1H), 8.97 (s, 1H), 8.18-7.75 (m, 1H), 7.21 (d, J=7.7 Hz, 1H), 6.95 (dd, J=16.8, 10.6 Hz, 0.75H), 6.79 (dd, J=16.5, 10.6 Hz, 0.25H), 6.72-6.60 (m, 2H), 6.22-5.97 (m, 1H), 5.81-5.60 (m, 1H), 4.95 (d, J=13.9 Hz, 0.24H), 4.74 (d, J=8.1 Hz, 0.74H), 4.54 (d, J=14.0 Hz, 0.73H), 4.37 (s, 0.23H), 3.97-3.84 (m, 1H), 3.69 (dd, J=14.2, 4.3 Hz, 1H), 3.23-3.14 (m, 4H), 3.01-2.82 (m, 1H), 2.72 (dd, J=12.5, 3.7 Hz, 1H), 2.00 (s, 3H), 1.47 (d, J=6.8 Hz, 3H), 1.17-0.91 (m, 6H).

MS (ESI) m/z (M+H)⁺=649.2.

SFC retention time was 4.636 min.

separation conditions: chromatographic column: Chiralcel OD-3 150×4.6 mm I.D., 3 μm; column temperature: 35° C.; mobile phase: CO₂-ethanol (0.05% DEA); ethanol: 5%-40% 5 min, 40% 2.5 min, 5% 2.5 min; flow rate: 2.5 mL/min.

Embodiment 50: Preparation of Compound 50

Step 1: Preparation of Compound 50

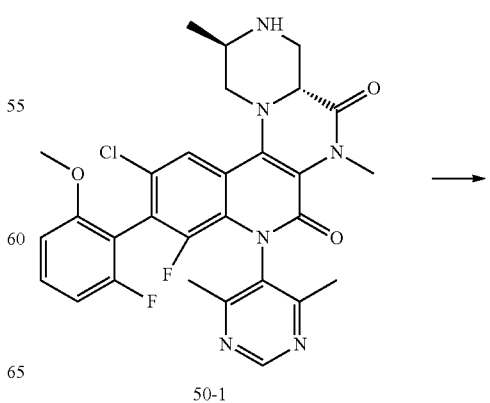

50-1

-continued

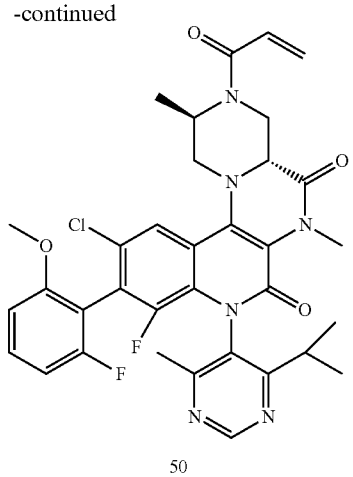

50

Compound 50-1 (100 mg, 0.168 mmol) was dissolved in dichloromethane (10 mL), and the system was cooled to 0° C., triethylamine (0.3 mL, 2.1 mmol) and acryloyl chloride (27 mg, 0.3 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (20 mL) and water (20 mL); and the organic phase was dried over anhydrous sodium sulfate, filtered, and the filtrate was concentrated to obtain a crude product, the crude product was purified by high performance liquid chromatography (separation conditions: chromatographic column Welch Xtimate® C18 21.2×250 mm, 10 μm; column temperature: 25° C., mobile phase: water (10 mM/L $NH_4HCO_3$)-acetonitrile; acetonitrile 35%-75% 18 min; flow rate 30 mL/min) to obtain compound 50.

MS (ESI) m/z (M+H)$^+$=663.0.

Step 2: Preparation of Compounds 50A, 50B, 50C and 50D

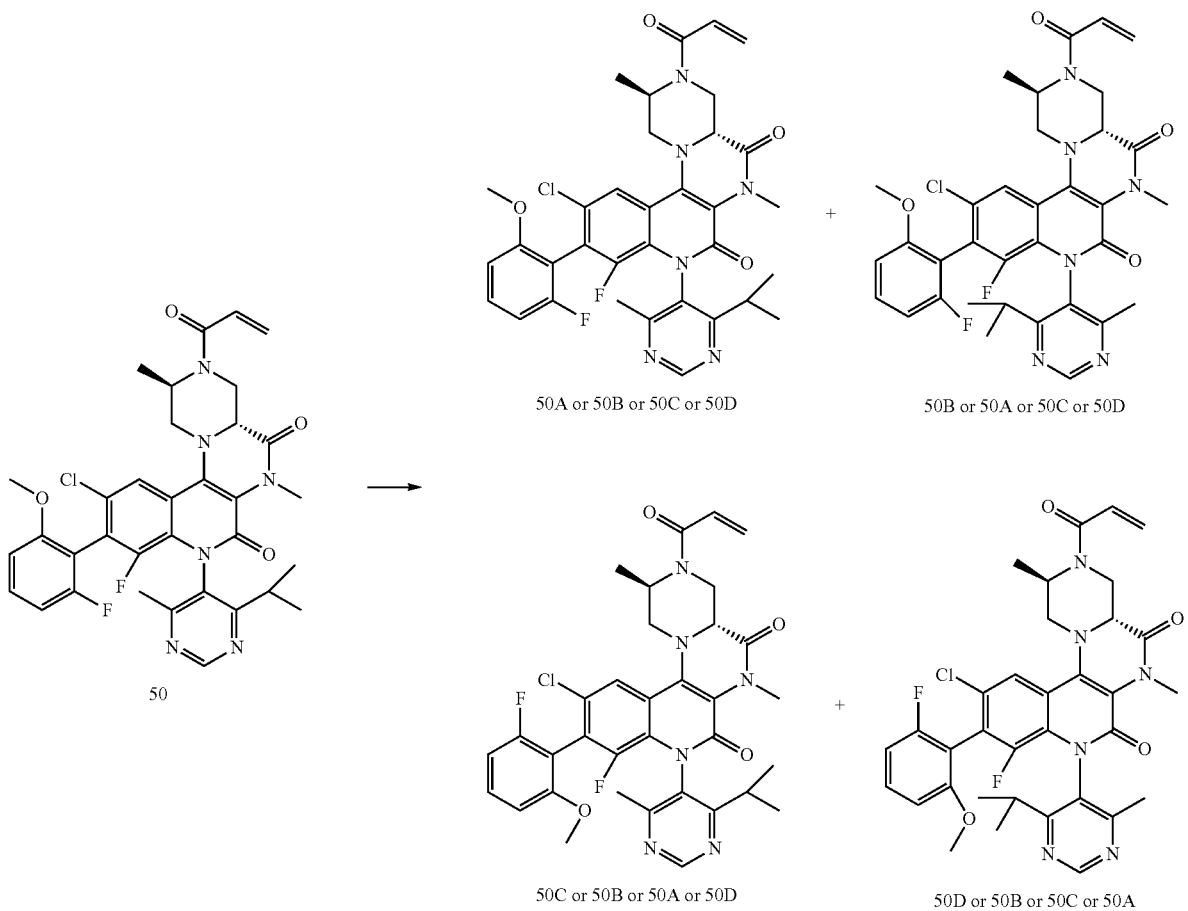 [SMILES: C=CC(=O)N1C[C@@H]2C(=O)N(C)c3c(c4cc(Cl)c(-c5c(F)cccc5OC)c(F)c4n(-c4c(C)ncnc4C(C)C)c3=O)N2C[C@H]1C ; C=CC(=O)N1C[C@@H]2C(=O)N(C)c3c(c4cc(Cl)c(-c5c(F)cccc5OC)c(F)c4n(-c4c(C)ncnc4C(C)C)c3=O)N2C[C@H]1C ; C=CC(=O)N1C[C@@H]2C(=O)N(C)c3c(c4cc(Cl)c(-c5c(F)cccc5OC)c(F)c4n(-c4c(C)ncnc4C(C)C)c3=O)N2C[C@H]1C ; C=CC(=O)N1C[C@@H]2C(=O)N(C)c3c(c4cc(Cl)c(-c5c(F)cccc5OC)c(F)c4n(-c4c(C)ncnc4C(C)C)c3=O)N2C[C@H]1C ; C=CC(=O)N1C[C@@H]2C(=O)N(C)c3c(c4cc(Cl)c(-c5c(F)cccc5OC)c(F)c4n(-c4c(C)ncnc4C(C)C)c3=O)N2C[C@H]1C]

Diasteromeric compound 50 was purified by SFC (separation conditions: chromatographic column: «Column_3»; mobile phase: [$CO_2$-isopropanol (0.1% ammonia)]; isopropanol %: 30%-30%; flow rate: 80 mL/min). After concentration, compounds 50A, 50B, 50C and 50D were obtained.

Compound 50A:

$^1$H NMR (400 MHz, DMSO-$d_6$) δ 8.97 (s, 1H), 7.83 (d, J=1.5 Hz, 1H), 7.42 (td, J=8.4, 7.0 Hz, 1H), 7.02-6.90 (m, 2H), 6.89-6.81 (m, 1H), 6.16-6.03 (m, 1H), 5.77-5.63 (m, 1H), 4.95 (d, J=14.0 Hz, 0.25H), 4.75 (s, 0.80H), 4.53 (d, J=14.0 Hz, 0.80H), 4.42-4.35 (m, 0.23H), 4.02-3.88 (m, 1H), 3.74-3.65 (m, 4H), 3.26-3.16 (m, 4H), 2.75-2.56 (m, 2H), 2.25 (d, J=2.0 Hz, 3H), 1.47 (d, J=6.8 Hz, 3H), 0.96 (d, J=6.6 Hz, 3H), 0.86 (d, J=6.7 Hz, 3H).

MS (ESI) m/z (M+H)$^+$=663.2.

HPLC retention time was 6.258 min.

Separation conditions: chromatographic column: Waters XBridge 4.6*100 mm, 3.5 µm; column temperature: 40° C.; mobile phase: water (10 mM $NH_4HCO_3$)-acetonitrile; acetonitrile: 5%-95% 7 min; flow rate: 1.2 mL/min.

SFC retention time was 3.951 min.

separation conditions: chromatographic column: Chiralpak AD-3 150×4.6 mm I.D., 3 µm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 50B:

$^1$H NMR (400 MHz, DMSO-$d_6$) δ 9.10 (s, 1H), 8.02-7.91 (m, 1H), 7.55 (td, J=8.5, 6.9 Hz, 1H), 7.21-6.83 (m, 3H), 6.29-6.12 (m, 1H), 5.87-5.74 (m, 1H), 5.08 (d, J=13.9 Hz, 0.25H), 4.91-4.78 (m, 0.75H), 4.67 (d, J=14.0 Hz, 0.75H), 4.55-4.42 (m, 0.25H), 4.18-4.00 (m, 1H), 3.81 (dd, J=13.9, 4.0 Hz, 1H), 3.71 (s, 3H), 3.43-3.25 (m, 4H), 2.99-2.62 (m, 2H), 2.37 (d, J=1.8 Hz, 3H), 1.59 (d, J=6.8 Hz, 3H), 1.11 (d, J=6.6 Hz, 3H), 1.04 (d, J=6.7 Hz, 3H).

MS (ESI) m/z (M+H)$^+$=663.2.

SFC retention time was 4.071 min.

separation conditions: chromatographic column: Chiralpak AD-3 150×4.6 mm I.D., 3 µm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 50C:

$^1$H NMR (400 MHz, DMSO-$d_6$) δ 8.97 (s, 1H), 7.83 (d, J=1.5 Hz, 1H), 7.43 (td, J=8.5, 7.0 Hz, 1H), 7.03-6.82 (m, 3H), 6.16-6.00 (m, 1H), 5.74-5.64 (m, 1H), 4.95 (d, J=13.9 Hz, 0.25H), 4.74 (d, J=7.9 Hz, 0.75H), 4.54 (d, J=14.1 Hz, 0.75H), 4.45-4.31 (m, 0.25H), 3.88 (d, J=3.8 Hz, 1H), 3.68 (dd, J=14.2, 4.2 Hz, 1H), 3.61 (s, 3H), 3.23-3.16 (m, 4H), 2.92 (p, J=6.7 Hz, 1H), 2.72 (dd, J=12.4, 3.6 Hz, 1H), 2.00 (s, 3H), 1.46 (d, J=6.8 Hz, 3H), 1.08 (d, J=6.6 Hz, 3H), 1.01 (d, J=6.7 Hz, 3H).

MS (ESI) m/z (M+H)$^+$=663.2.

HPLC retention time was 6.070 min.

Separation conditions: chromatographic column: Waters XBridge 4.6*100 mm, 3.5 µm; column temperature: 40° C.; mobile phase: water (10 mM $NH_4HCO_3$)-acetonitrile; acetonitrile: 5%-95% 7 min; flow rate: 1.2 mL/min.

SFC retention time was 5.963 min.

separation conditions: chromatographic column: Chiralpak AD-3 150×4.6 mm I.D., 3 µm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 50D:

$^1$H NMR (400 MHz, DMSO-$d_6$) δ 8.97 (s, 1H), 7.87-7.74 (m, 1H), 7.42 (td, J=8.5, 6.9 Hz, 1H), 7.06-6.81 (m, 3H), 6.19-6.01 (m, 1H), 5.75-5.62 (m, 1H), 4.95 (d, J=14.0 Hz, 0.25H), 4.80-4.70 (m, 0.75H), 4.54 (d, J=14.1 Hz, 0.75H), 4.41-4.33 (m, 0.25H), 3.95-3.83 (m, 1H), 3.76-3.62 (m, 4H), 3.29-3.16 (m, 4H), 2.94 (p, J=6.7 Hz, 1H), 2.76-2.57 (m, 1H), 2.02 (s, 3H), 1.46 (d, J=6.8 Hz, 3H), 1.08 (d, J=6.6 Hz, 3H), 0.97 (d, J=6.7 Hz, 3H).

MS (ESI) m/z (M+H)$^+$=663.2.

HPLC retention time was 6.112 min.

Separation conditions: chromatographic column: Waters XBridge 4.6*100 mm, 3.5 µm; column temperature: 40° C.; mobile phase: water (10 mM $NH_4HCO_3$)-acetonitrile; acetonitrile: 5%-95% 7 min; flow rate: 1.2 mL/min.

SFC retention time was 7.041 min.

separation conditions: chromatographic column: Chiralpak AD-3 150×4.6 mm I.D., 3 µm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Embodiment 51: Preparation of Compound 51

Step 1: Preparation of Compound 51-1

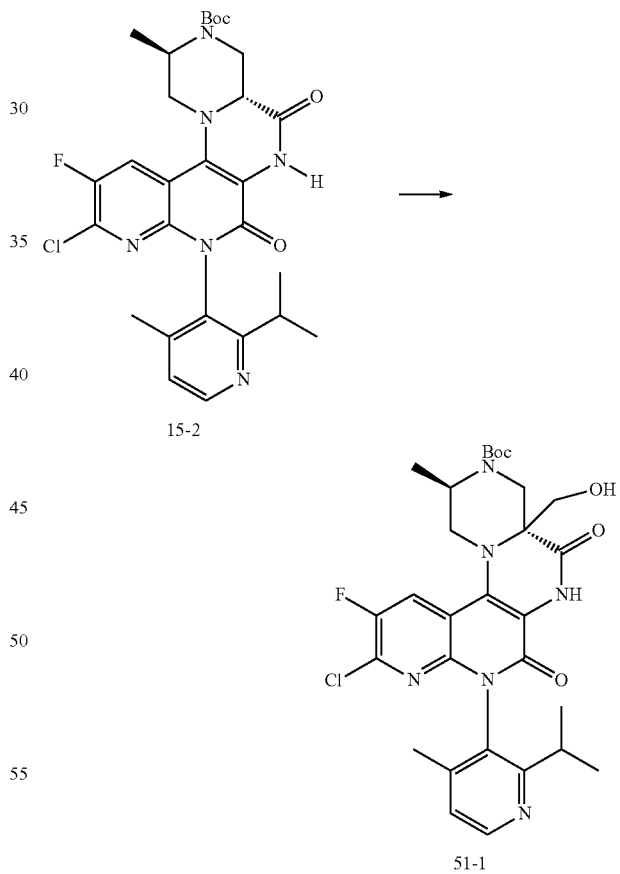

Compound 15-2 (0.10 g, 0.175 mmol), paraformaldehyde (50 mg, 1.66 mmol) were dissolved in N, N-dimethylformamide (2.0 mL), and potassium carbonate (0.05 g, 0.35 mmol) was added thereto at room temperature (25° C.). After the addition was completed, the system was heated to 80° C. and stirred for 1 hour. The system was cooled to room temperature, the reaction was quenched by adding water (8 mL), and the mixture was extracted with ethyl acetate (2 mL×2); the organic phases were combined, dried over anhydrous sodium sulfate, filtered, and the filtrate was concentrated to obtain compound 51-1, which was used directly in the next reaction without further purification.

MS (ESI) m/z (M+H)$^+$=601.0

Step 2: Preparation of Compound 51-2

Step 3: Preparation of Compound 51-3

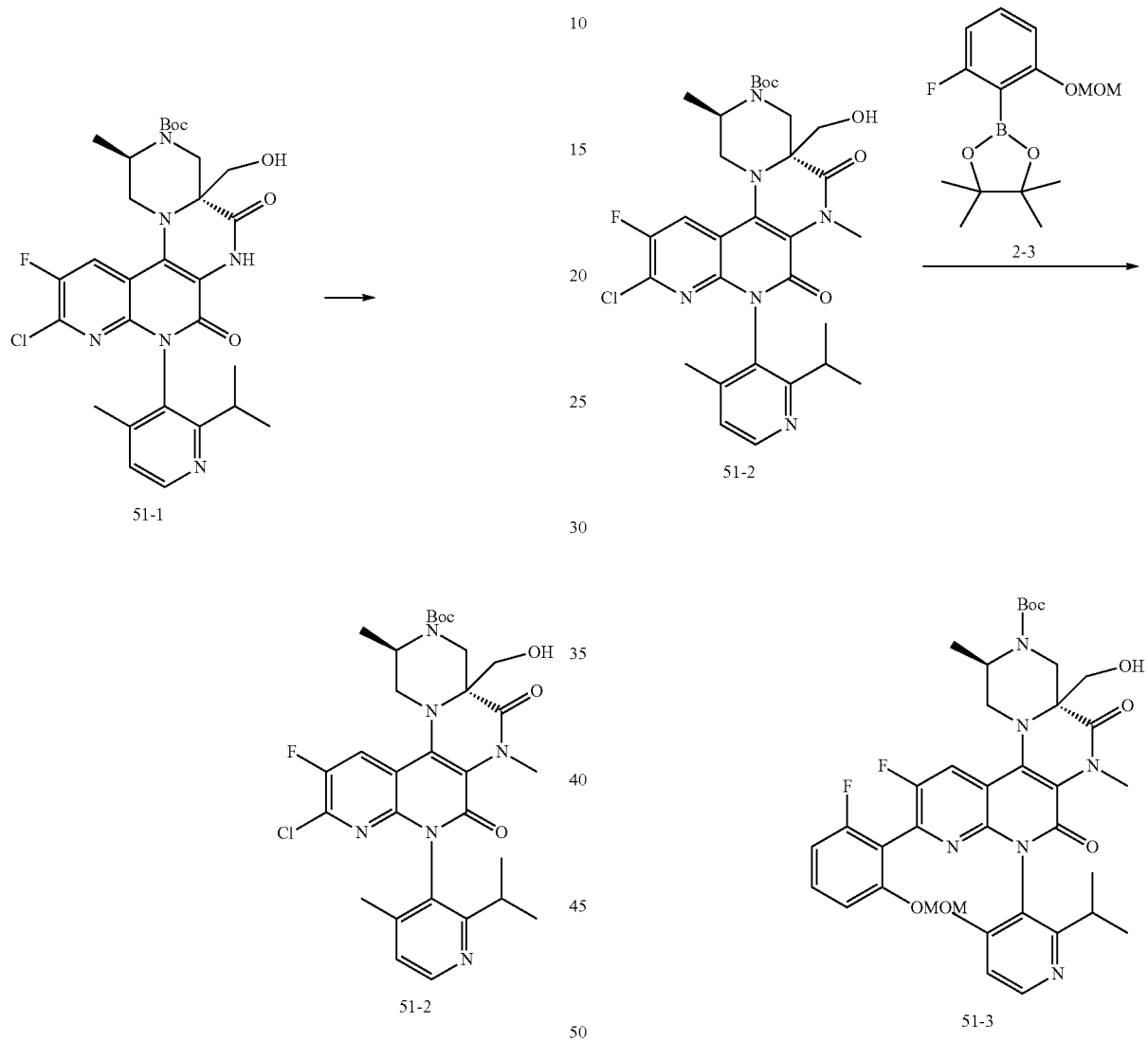

Compound 51-1 (75 mg, 0.125 mmol) and cesium carbonate (35 mg, 0.25 mmol) were dissolved in N,N-dimethylformamide (2 mL), iodomethane (53 mg, 0.375 mmol) was added thereto at room temperature (25° C.). After the addition was completed, under nitrogen atmosphere, the system was stirred at room temperature (25° C.) for 1 hour. Water was added to the system to quench the reaction, the mixture was extracted with ethyl acetate (2 mL×2), the combined organic phase was dried over anhydrous sodium sulfate, filtered, and the filtrate was concentrated to obtain a crude product. The crude product was purified by medium pressure column chromatography (ethyl acetate/petroleum ether (v/v)=0-60%) to obtain compound 51-2.

MS (ESI) m/z (M+H)$^+$=615.2.

Compound 51-2 (63 mg, 0.102 mmol), compound 2-3 (58.0 mg, 0.204 mmol), tetrakis(triphenylphosphine)palladium (30 mg, 0.025 mmol) and potassium carbonate (29.0 mg, 0.204 mmol) were dissolved in a mixed solution of dioxane and water (2 mL, 3:1). Under nitrogen atmosphere, the system was heated to 100° C. and stirred for 1 hour. The system was concentrated to obtain a crude product, the crude product was purified by medium pressure column chromatography (ethyl acetate/petroleum ether (v/v)=0-50%) to obtain compound 51-3.

MS (ESI) m/z (M+H)$^+$=735.1.

Step 4: Preparation of Compound 51-4

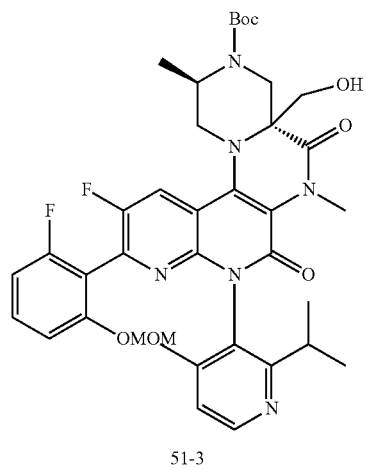

51-3

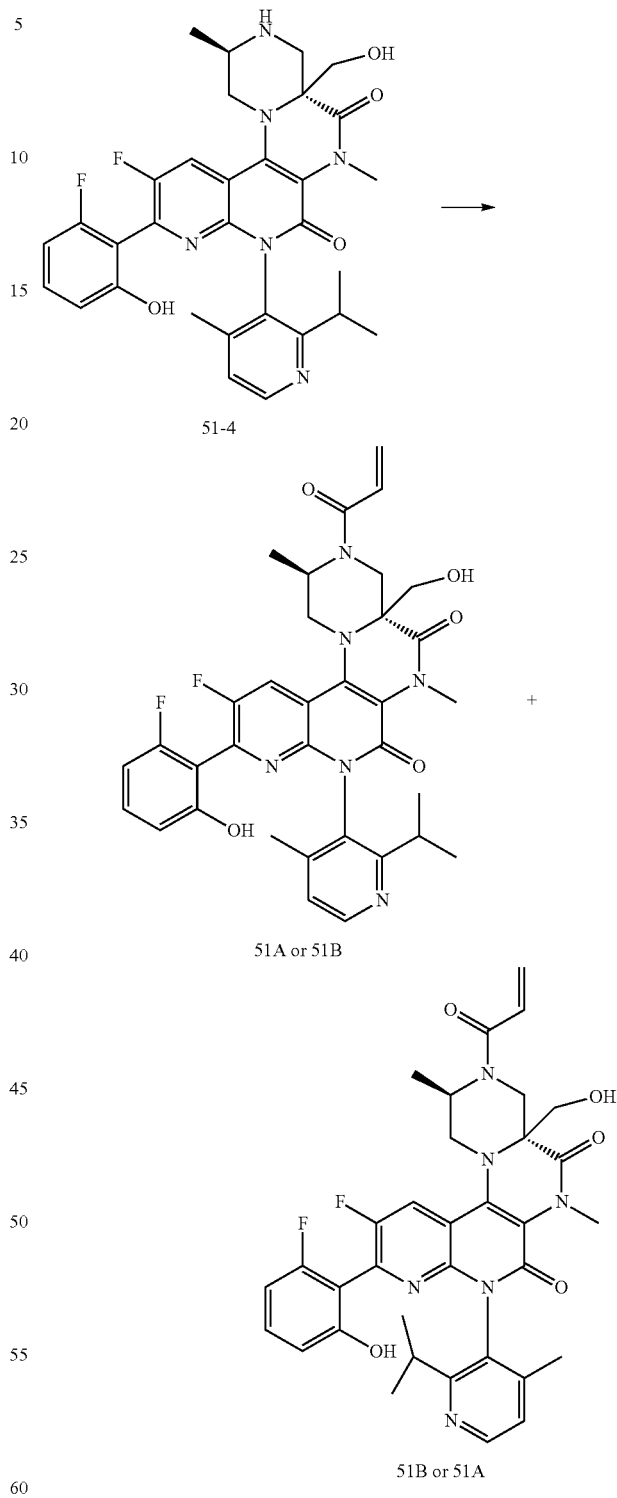

Step 5: Preparation of Compound 51

Compound 51-3 (55 mg, 0.075 mmol) was dissolved in a mixed solvent of hydrochloric acid (6 N) and methanol (2 mL, 1:1). The system was heated to 55° C. and stirred for 15 min. The system was concentrated to obtain crude product compound 51-4, which was directly used in the next reaction without further purification.

MS (ESI) m/z (M+H)$^+$=591.0.

Compound 51-4 (35 mg, 0.04 mmol) was dissolved in dichloromethane (3 mL), and the system was cooled to 0° C., triethylamine (22.7 mg, 0.225 mmol) and acryloyl chloride (6.8 mg, 0.075 mmol) were added dropwise thereto, the reaction was carried out at 0° C. for 0.5 hours. The system was separated and extracted with water (5 mL) and dichloromethane (3 mL), the organic phase was concentrated, and the residue was dissolved in a mixed solvent of tetrahydrofuran (2 mL) and water (1 mL), then lithium hydroxide (6 mg, 0.15 mmol) was added thereto. After the addition was completed, the system was stirred at room temperature (25° C.) for 30 min. The pH was adjusted to 6 with 1 N HCl; and the mixture was extracted with dichloromethane (2 mL×2); the organic phase were combined, dried over anhydrous sodium sulfate, filtered, and the filtrate was concentrated to obtain a crude product. The crude product was purified by preparative high performance liquid chromatography (separation conditions: chromatographic column Welch Xtimate® C18 21.2×250 mm, 10 μm; mobile phase: water (10 mM $NH_4HCO_3$)-acetonitrile; acetonitrile: 20%-50% in 16 min; flow rate 30/min) to obtain compound 51A and compound 51B.

Compound 51A:

$^1$H NMR (400 MHz, DMSO-$d_6$) δ 10.17 (s, 1H), 8.45 (s, 1H), 8.19-7.99 (m, 1H), 7.25 (s, 2H), 7.07-6.95 (m, 1H), 6.85-6.66 (m, 2H), 6.12 (d, J=17.3 Hz, 1H), 5.87-5.57 (m, 1H), 5.41-5.18 (m, 2H), 4.73 (d, J=14.0 Hz, 1H), 4.58-4.38 (m, 1H), 3.62 (d, J=31.2 Hz, 2H), 3.54-3.33 (m, 4H), 2.87-2.65 (m, 1H), 2.00 (s, 3H), 1.32-1.22 (m, 3H), 0.96 (dd, J=51.3, 7.4 Hz, 6H).

MS (ESI) m/z (M+H)$^+$=645.40.

HPLC retention time was 4.602 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

Compound 51B:

MS (ESI) m/z (M+H)$^+$=645.40.

HPLC retention time was 4.566 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

Embodiment 52: Preparation of Compound 52

Step 18: Preparation of Compound 52

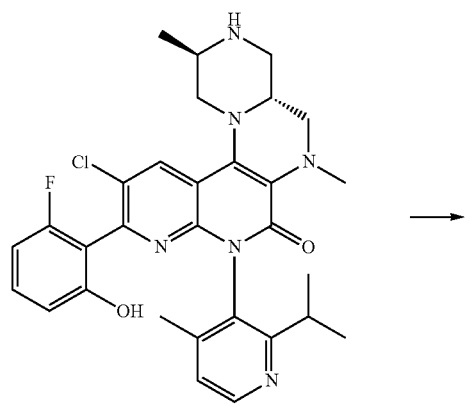

8-16

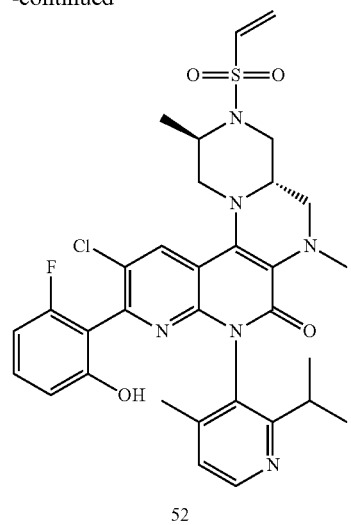

52

Compound 8-16 (50 mg) was dissolved in dichloromethane (4 mL), and triethylamine (14 mg, 0.14 mmol) and arylsulfonyl chloride (13 mg, 0.106 mmol) were added dropwise thereto at room temperature (20° C.). After the addition was completed, the system was stirred at room temperature (20° C.) for 2 hours. Tetrahydrofuran (4 mL), water (1 mL) and lithium hydroxide aqueous solution (31.74 mg, 756.47 μmol) were added to the system, and the mixture was stirred at room temperature (20° C.) for 2 hours. The pH of the system was adjusted to neutral with 1 N hydrochloric acid; and the mixture was extracted with ethyl acetate (10 mL×2), the organic phase was dried over anhydrous sodium sulfate, filtered, and the filtrate was concentrated to obtain a crude product. The crude product was purified by preparative high performance liquid chromatography (separation conditions: chromatographic column Welch Xtimate® C18 21.2×250 mm, 10 μm; column temperature: 25° C.; mobile phase: water (10 mM $NH_4HCO_3$)-acetonitrile; acetonitrile: 50%-70% 12 min; flow rate 30 mL/min) and then purified by SFC (separation conditions: chromatographic column: «Column_3»; mobile phase: [$CO_2$-isopropanol (0.1% ammonia)]; isopropanol %: 35%-35%) to obtain compounds 52A and 52B.

Compound 52A:

$^1$H NMR (400 MHz, DMSO-$d_6$) δ 9.88-9.80 (m, 1H), 8.34-8.32 (m, 1H), 7.93 (s, 1H), 7.13-7.07 (m, 2H), 6.89-6.81 (m, 1H), 6.62-6.53 (m, 2H), 6.11-6.04 (m, 2H), 4.05-3.95 (m, 1H), 3.68-3.59 (m, 1H), 3.53-3.43 (m, 2H), 3.10-2.92 (m, 4H), 2.60-2.54 (m, 1H), 2.29-2.23 (m, 1H), 1.73 (m, 3H), 1.73-1.70 (m, 3H), 1.55-1.49 (m, 3H), 1.00-0.98 (m, 3H), 0.83-0.75 (m, 3H).

MS (ESI) m/z (M+H)$^+$=653.0.

HPLC 92% purity; retention time was 5.876 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

SFC retention time was 4.766 min.

separation conditions: chromatographic column: Chiralpak AD-3 150×4.6 mm I.D., 3 μm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 52B:

¹H NMR (400 MHz, DMSO-d₆) δ ¹H NMR (400 MHz, DMSO) 9.85. (b, 1H), 8.34-8.31 (m, 1H), 7.94 (s, 1H), 7.15-7.09 (m, 2H), 6.88-6.82 (m, 1H), 6.63-6.53 (m, 2H), 6.13-6.04 (m, 2H), 4.03-3.98 (m, 1H), 3.66-3.60 (m, 1H), 3.52-3.04 (m, 2H), 3.14-3.10 (m, 1H), 3.05 (s, 3H), 291-2.87 (m, 1H), 2.29-2.25 (m, 2H), 1.83-1.78 (m, 3H), 1.53-1.51 (m, 3H), 0.96-0.94 (m, 3H), 0.83-0.75 (m, 3H).

MS (ESI) m/z (M+H)⁺=653.0.

HPLC 98% purity; retention time was 5.930 min.

Separation conditions: chromatographic column: Waters XBridge 4.6*100 mm, 3.5 μm; column temperature: 40° C.; mobile phase: water (10 mM NH₄HCO₃)-acetonitrile; acetonitrile: 5%-95% 7 min; flow rate: 1.2 mL/min.

SFC retention time was 5.380 min.

separation conditions: chromatographic column: Chiralpak AD-3 150×4.6 mm I.D., 3 μm; column temperature: 35° C.; mobile phase: CO₂-isopropanol (0.05% DEA); isopropanol: 5%-40% 5 min, 40% 2.5 min, 5% 2.5 min; flow rate: 2.5 mL/min.

Embodiment 53: Preparation of Compound 53

Step 1: Preparation of Compound 53-2

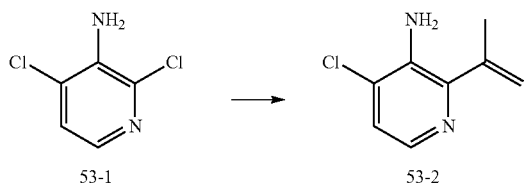

Compound 53-1 (16.3 g, 100 mmol), isopropenylboronic acid pinacol ester (20.16 g, 120 mmol) and sodium carbonate (31.8 g, 300 mmol) were dissolved in a mixed solvent of dioxane (200 mL) and water (50 mL), under the protection of nitrogen, [1,1'-bis(diphenylphosphino)ferrocene]palladium dichloride (7.32 g, 10 mmol) was added thereto. The reaction was heated to 95° C. and stirred for 16 hours. The reaction mixture was diluted with ethyl acetate (100 mL), filtered, the filtrate was concentrated under reduced pressure, and the crude product was purified by silica gel column chromatography (ethyl acetate/petroleum ether (v/v)=0-25%) to obtain compound 53-2.

¹H NMR (400 MHz, Chloroform-d) δ7.76-7.75 (m, 1H), 7.22-7.20 (m, 1H), 5.47-5.46 (m, 1H), 5.27-5.28 (m, 1H), 5.17 (brs, 2H), 2.06 (s, 3H).

MS (ESI) m/z (M+H)⁺=168.80.

Step 2: Preparation of Compound 53-3

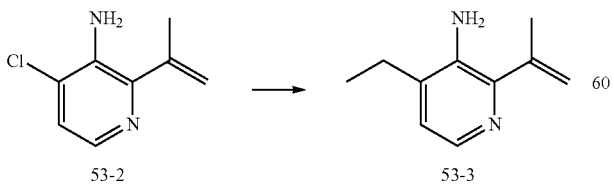

Compound 53-2 (13.4 g, 80 mmol), ethylboronic acid (29.52 g, 400 mmol) and cesium carbonate (104.32 g, 320 mmol) were dissolved in a mixed solvent of dioxane (200 mL) and water (50 mL), under the protection of nitrogen, [1,1'-bis(diphenylphosphino)ferrocene]palladium dichloride (5.85 g, 8 mmol) was added thereto. The reaction was heated to 100° C. and stirred for 4 hours. The reaction mixture was diluted with ethyl acetate (200 mL), filtered, the filtrate was concentrated under reduced pressure, and the crude product was purified by silica gel column chromatography (ethyl acetate/petroleum ether (v/v)=0-25%) to obtain compound 53-3.

¹H NMR (400 MHz, DMSO-d₆) δ 7.76 (d, J=4.7 Hz, 1H), 6.88 (d, J=4.8 Hz, 1H), 5.41 (t, J=1.7 Hz, 1H), 5.19 (dd, J=2.0, 1.0 Hz, 1H), 4.72 (brs, 2H), 2.62-2.43 (m, 2H), 2.06 (dd, J=1.5, 0.9 Hz, 3H), 1.16 (t, J=7.4 Hz, 3H).

MS (ESI) m/z (M+H)⁺=162.8.

Step 3: Preparation of Compound 53-4

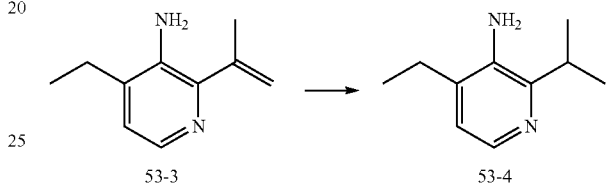

Compound 53-3 (6.2 g, 38.3 mmol) was dissolved in methanol (100 mL), and palladium/carbon (700 mg) was added thereto under the protection of nitrogen. After the addition was completed, under hydrogen atmosphere, the reaction was stirred at room temperature (20° C.) for 3 hours. The system was filtered, and the filtrate was concentrated to obtain compound 53-4, which was directly used in the next reaction without further purification.

MS (ESI) m/z (M+H)⁺=165.0.

Step 4: Preparation of Compound 53-5

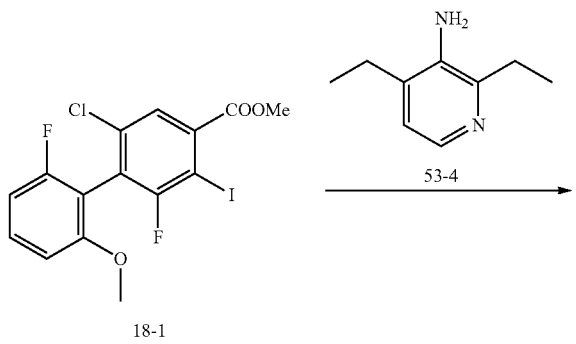

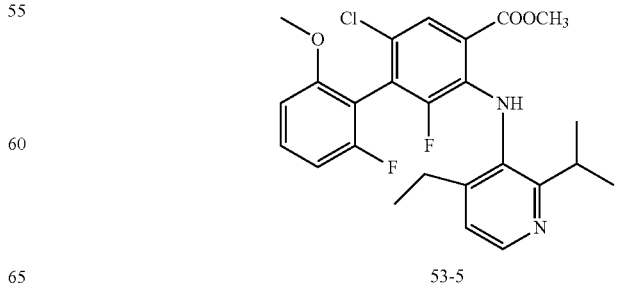

Under the protection of nitrogen, compound 18-1 (2.78 g, 6.35 mmol) and compound 53-4 (1.3 g, 7.62 mmol) were dissolved in toluene (30 mL), and 4,5-bis(diphenylphosphino)-9,9-dimethylxanthene (404 mg, 0.7 mmol), tris(dibenzylideneacetone)dipalladium (640 mg, 0.7 mmol) and cesium carbonate (6.21 g, 19.05 mmol) were added successively. After the addition was completed, the reaction was heated to 100° C. and stirred for 16 hours. The reaction mixture was diluted with ethyl acetate (100 mL), filtered, the filtrate was concentrated under reduced pressure, and the crude product was purified by silica gel column chromatography (ethyl acetate/petroleum ether (v/v)=0-50%) to obtain compound 53-5.

MS (ESI) m/z $(M+H)^+=475.0$.

Step 5: Preparation of Compound 53-6

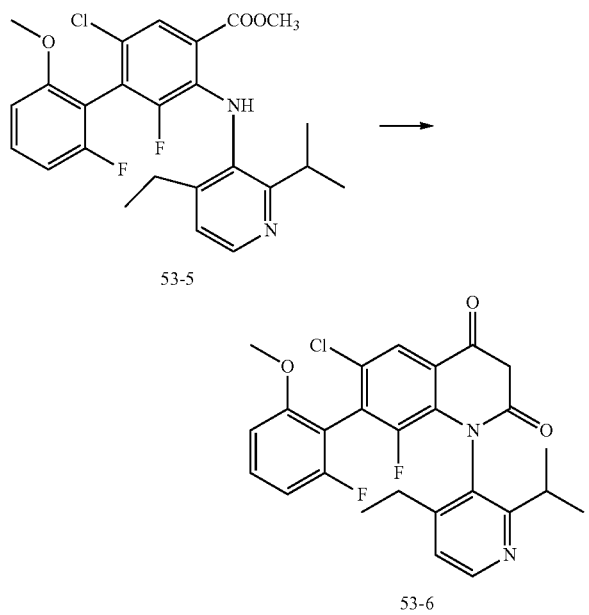

53-5

53-6

Compound 53-5 (3.2 g, 6.75 mmol) was dissolved in N,N-dimethylformamide (20 mL), and sodium hydride (1.35 g, 33.7 mmol, 60%) was added thereto at 0° C. After the addition was completed, the system was stirred at 0° C. for 20 min. The system was raised to room temperature (20° C.), and acetyl chloride (2.54 mL, 33.7 mmol) was added dropwise. After the addition was completed, the system was stirred at room temperature (20° C.) for 1 hour. The system was quenched with water (100 mL), extracted with ethyl acetate (100 mL×2); then the organic phases were combined, concentrated; methanol (50 mL) and potassium carbonate (5 g) were added thereto, and the mixture was stirred at room temperature (20° C.) for 1 hour. The system was concentrated, diluted with water (50 mL), the pH was adjusted to 7 with 1 N HCl; and the mixture was extracted with ethyl acetate (100 mL×2); then the organic phases were combined, dried over anhydrous sodium sulfate, filtered, and the filtrate was concentrated to obtain a crude product, the crude product was purified by reversed-phase silica gel column chromatography (acetonitrile/water (0.5% ammonium bicarbonate aqueous solution) (v/v)=5-95%) to obtain compound 53-6.

MS (ESI) m/z $(M+H)^+=485.0$.

Step 6: Preparation of Compound 53-7

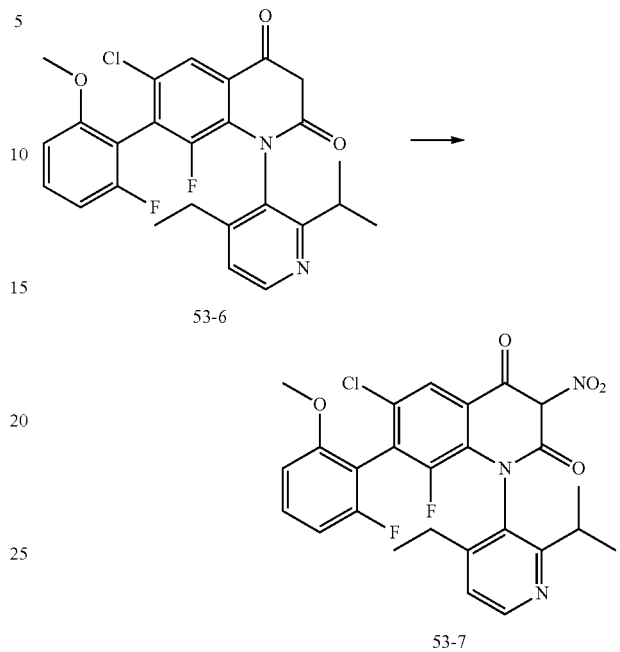

53-6

53-7

Under the protection of nitrogen, compound 53-6 (880 mg, 1.82 mmol) was dissolved in acetic acid (18 mL), and concentrated nitric acid (1.8 mL) was added thereto. After the addition was completed, the reaction was heated to 40° C. and stirred for 2 hours. The reaction mixture was concentrated under reduced pressure to remove most of the acetic acid, poured into ice water, the pH was adjusted to 6 with sodium hydroxide; and the mixture was extracted with ethyl acetate (100 mL×2); then the organic phases were combined, dried over anhydrous sodium sulfate, filtered, and the filtrate was concentrated to obtain a crude product, the crude product was purified by reversed-phase silica gel column chromatography (acetonitrile/water (0.5% ammonium bicarbonate aqueous solution) (v/v)=5-95%) to obtain compound 53-7.

MS (ESI) m/z $(M+H)^+=530.0$.

Step 7: Preparation of Compound 53-8

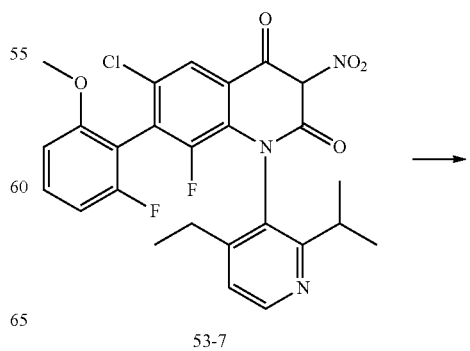

53-7

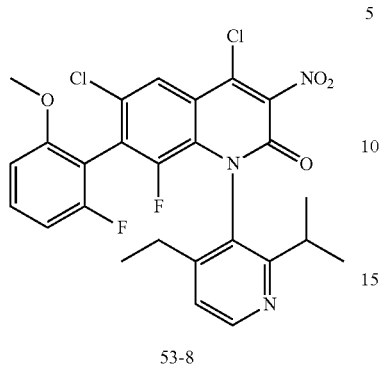

53-8

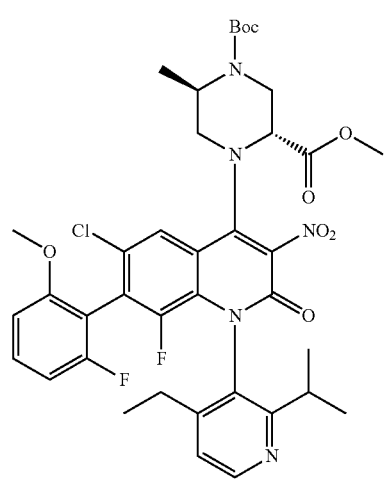

53-9

Under the protection of nitrogen, compound 53-7 (200 mg, 0.378 mmol) was dissolved in acetonitrile (6 mL), diisopropylethylamine (0.8 mL) and phosphorus oxychloride (0.5 mL) were added thereto sequentially. After the addition was completed, the reaction was heated to 80° C. and stirred for 2 hours. The reaction mixture was cooled to room temperature, concentrated under reduced pressure, the system was poured into ice water, the pH was adjusted to 8 with sodium hydroxide; and the mixture was extracted with ethyl acetate (100 mL×2); then the organic phases were combined, dried over anhydrous sodium sulfate, filtered, and the filtrate was concentrated to obtain a crude product, the crude product was purified by silica gel column chromatography (ethyl acetate/petroleum ether (v/v)=0-35%) to obtain compound 53-8.

MS (ESI) m/z (M+H)$^+$=548.0.

Step 8: Preparation of Compound 53-9

Compound 53-8 (140 mg, 0.306 mmol), compound 7-1 (102 mg, 0.398 mmol) and N,N-diisopropylethylamine (100 μL) were dissolved in acetonitrile (3 mL). Under airtight conditions, the system was heated to 100° C. and stirred for 4 hours. The system was concentrated to obtain a crude product, the crude product was purified by medium pressure column chromatography (ethyl acetate/petroleum ether (v/v) =0-35%) to obtain compound 53-9.

MS (ESI) m/z (M+H)$^+$=770.2.

Step 9: Preparation of Compound 53-10

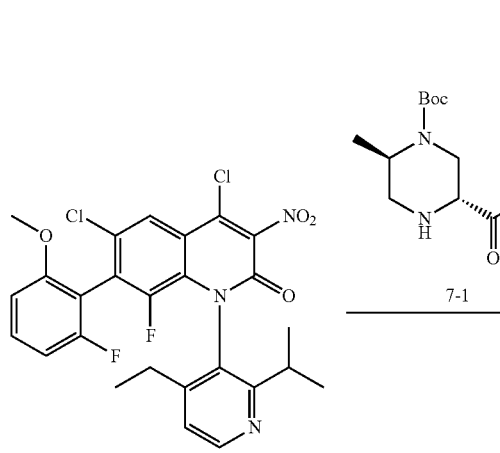

53-8

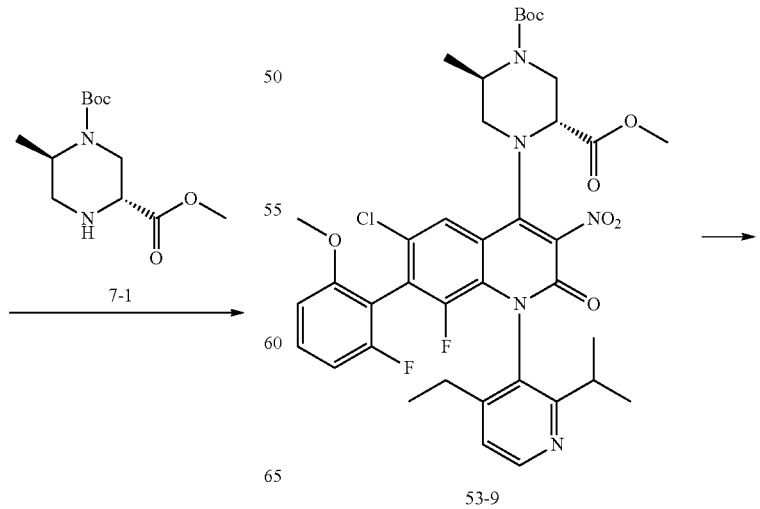

53-9

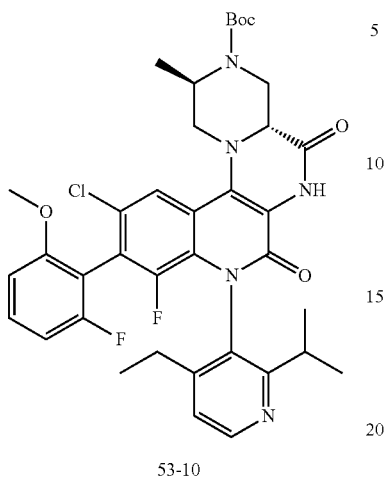

53-10

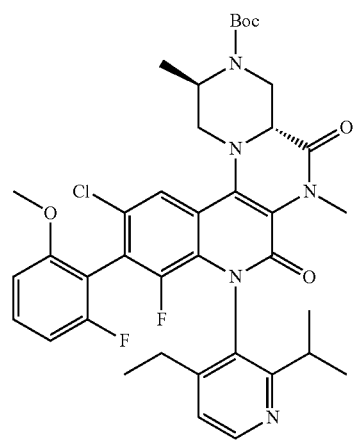

53-11

Compound 53-9 (166 mg, 0.216 mmol) and iron powder (42 mg, 0.755 mmol) were dissolved in acetic acid (3 mL), and the system was heated to 80° C. and stirred for 145 min under nitrogen atmosphere. The system was concentrated, diluted with dichloromethane (50 mL), filtered, the filtrate was washed with saturated sodium bicarbonate aqueous solution, dried over anhydrous sodium sulfate, filtered, and the filtrate was concentrated to obtain compound 53-10, which was directly used for the next reaction without further purification.

MS (ESI) m/z (M+H)$^+$=708.2.

Step 10: Preparation of Compound 53-11

Compound 53-10 (148 mg, 210 μmol) and potassium carbonate (87 mg, 630 μmol) were dissolved in acetone (105 mL), and methyl iodide (200 μL) was added thereto at room temperature (25° C.). After the addition was completed, under nitrogen atmosphere, the system was heated to 60° C. and stirred for 4 hours. The system was concentrated to obtain a crude product, the crude product was purified by medium pressure column chromatography (ethyl acetate/petroleum ether (v/v)=0-60%) to obtain compound 53-11.

Step 11: Preparation of Compound 53-12

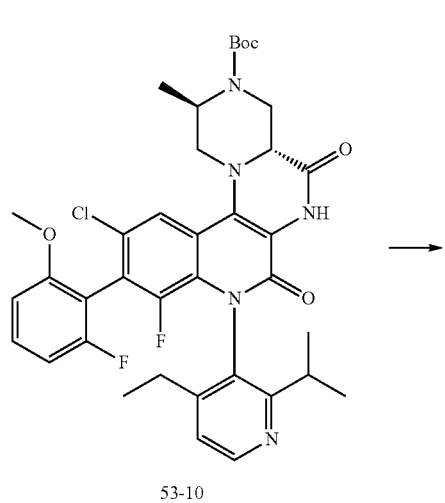

53-10

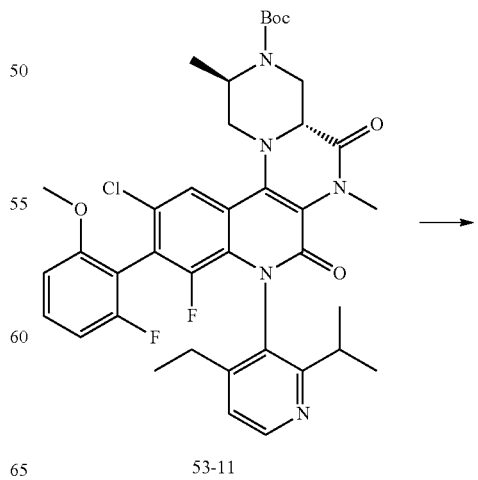

53-11

-continued

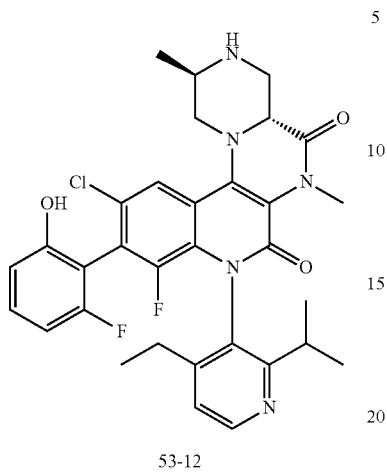

53-12

Compound 53-11 (140 mg, 194 μmol) was dissolved in dichloromethane (4 mL), and boron tribromide (1.5 mL) was added thereto, and the reaction was stirred at 25° C. for 2 hours. The reaction mixture was quenched with methanol (10 mL), stirred for 10 min, and concentrated under reduced pressure to obtain compound 53-12 (hydrobromide), which was directly used in the next reaction without further purification.

MS (ESI) m/z (M+H)$^+$=608.2.

Step 12: Preparation of Compound 53

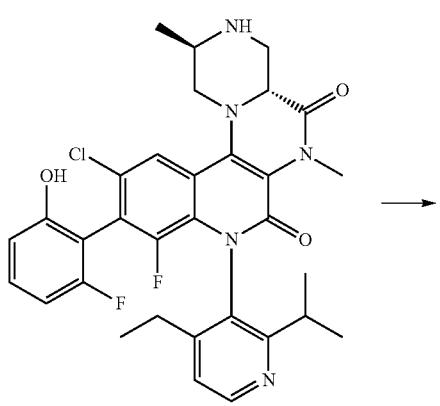

53-12

-continued

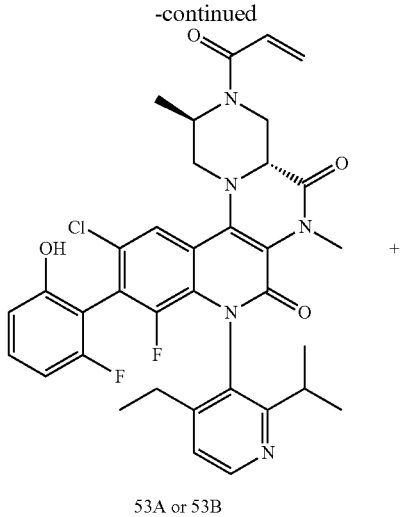

53A or 53B

+

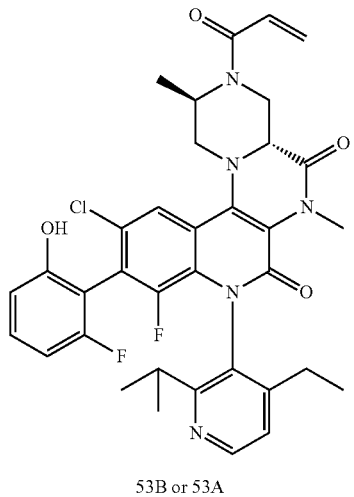

53B or 53A

Compound 53-12 (140 mg, 0.231 mmol) was dissolved in dichloromethane (10 mL), and the system was cooled to 0° C., triethylamine (0.3 mL, 0.462 mmol) and acryloyl chloride (27 mg, 0.3 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (20 mL) and water (20 mL); and the organic phase was dried over anhydrous sodium sulfate, filtered, and the filtrate was concentrated to obtain a crude product, the crude product was purified by high performance liquid chromatography (separation conditions: chromatographic column Agilent 10 Prep-C18 250×21.2 mm; column temperature: 25° C.; mobile phase: water (0.1% FA)-acetonitrile; acetonitrile: 40%-70% 12 min, flow rate: 30 mL/min to obtain compounds 53A and 53B.

MS (ESI) m/z (M+H)$^+$=662.2.

Step 13: Separation of Isomer of Compound 53A

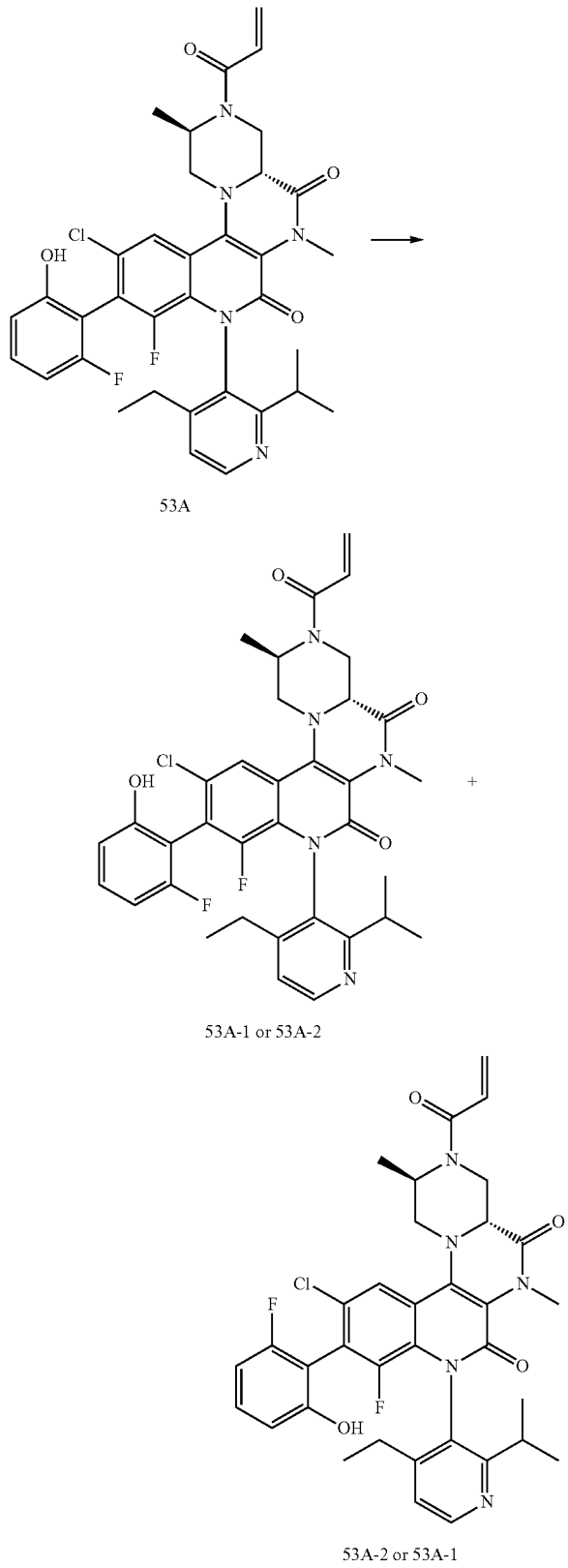

53A 53A-1 or 53A-2

53A-2 or 53A-1

Diastereoisomeric compound 53A was purified by SFC (separation conditions: chromatographic column: Phenomenex-Cellulose-2 (250 mm*30 mm, 10 μm); mobile phase: [$CO_2$-isopropanol (0.1% ammonia)]; isopropanol %: 30%-30%). After concentration, compound 53A-1 and compound 53A-2 were obtained.

Compound 53A-1:

$^1$H NMR (400 MHz, DMSO-$d_6$) δ 10.11 (brs, 1H), 8.45 (d, J=5.0 Hz, 1H), 7.81 (d, J=1.5 Hz, 1H), 7.19 (dd, J=6.2, 3.4 Hz, 2H), 6.95 (dd, J=16.8, 10.7 Hz, 0.75H), 6.79 (dd, J=16.5, 10.6 Hz, 0.25H), 6.69-6.58 (m, 2H), 6.20-6.01 (m, 1H), 5.75-5.63 (m, 1H), 4.95 (d, J=14.0 Hz, 0.25H), 4.76-4.69 (m, 0.75H), 4.53 (d, J=14.0 Hz, 0.75H), 4.41-4.31 (m, 0.25H), 4.02-3.87 (m, 1H), 3.68 (dd, J=14.0, 4.2 Hz, 1H), 3.25-3.18 (m, 4H), 2.87-2.74 (m, 1H), 2.74-2.53 (m, 1H), 2.21-1.97 (m, 2H), 1.46 (d, J=6.8 Hz, 3H), 1.04 (d, J=6.6 Hz, 3H), 0.96 (d, J=6.7 Hz, 3H), 0.91 (t, J=7.6 Hz, 3H).

MS (ESI) m/z (M+H)$^+$=662.2.

HPLC 92% purity; retention time was 5.48 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

SFC 90% ee. Retention time was 4.24 min separation conditions: chromatographic column: Chiralpak AD-3 150×4.6 mm I.D., 3 μm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Compound 53A-2:

$^1$H NMR (400 MHz, DMSO-$d_6$) δ 8.44 (d, J=4.9 Hz, 1H), 7.86-7.72 (m, 1H), 7.20 (d, J=5.0 Hz, 2H), 6.95 (dd, J=16.8, 10.6 Hz, 0.75H), 6.79 (dd, J=16.7, 10.3 Hz, 0.25H), 6.69-6.50 (m, 2H), 6.20-6.01 (m, 1H), 5.75-5.60 (m, 1H), 4.95 (d, J=14.1 Hz, 0.25H), 4.79-4.65 (m, 0.75H), 4.53 (d, J=14.0 Hz, 0.75H), 4.40-4.28 (m, 0.25H), 4.03-3.89 (m, 1H), 3.68 (dd, J=14.2, 4.3 Hz, 1H), 3.24-3.15 (m, 4H), 2.89-2.56 (m, 2H), 2.39-2.29 (m, 2H), 1.46 (d, J=6.8 Hz, 3H), 1.07-0.76 (m, 9H).

MS (ESI) m/z (M+H)$^+$=662.2.

HPLC 98% purity; retention time was 5.481 min

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

SFC 100% ee. Retention time was 4.643 min.

separation conditions: chromatographic column: Chiralpak AD-3 150×4.6 mm I.D., 3 μm; column temperature: 35° C.; mobile phase: $CO_2$-isopropanol (0.05% DEA); isopropanol: 5%-40% 5 min, 40% 2.5 min, 5% 2.5 min; flow rate: 2.5 mL/min.

Step 7: Separation of Isomer of Compound 53B

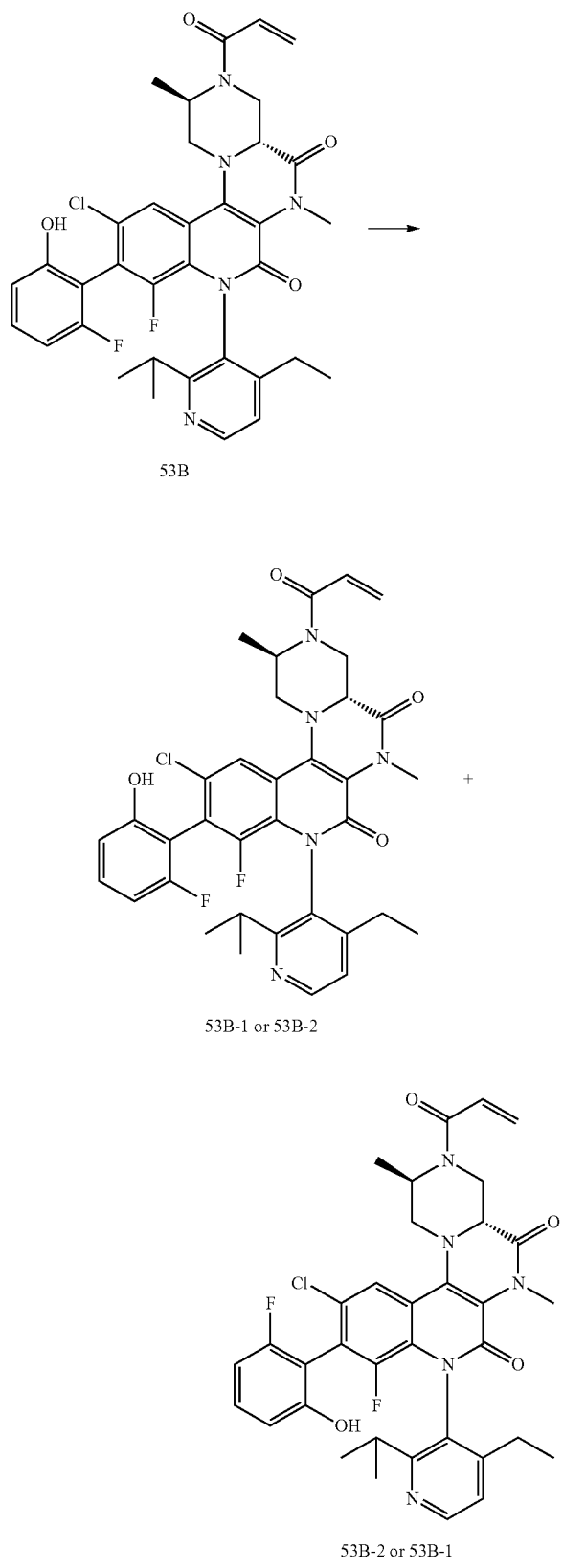

Diastereoisomeric compound 53B was purified by SFC (separation conditions: chromatographic column: DAICEL CHIRALPAK AD-H (250 mm*30 mm, 5 μm); mobile phase: [$CO_2$-ethanol (0.1% ammonia)]; ethanol %: 35%-35%). After concentration, compound 53B-1 and compound 53B-2 were obtained.

Compound 53B-1:

$^1$H NMR (400 MHz, DMSO-$d_6$) δ 10.14 (s, 1H), 8.44 (d, J=5.0 Hz, 1H), 7.87-7.71 (m, 1H), 7.29-7.14 (m, 2H), 6.95 (dd, J=16.8, 10.6 Hz, 0.75H), 6.79 (dd, J=16.4, 10.6 Hz, 0.25H), 6.70-6.57 (m, 2H), 6.19-6.00 (m, 1H), 5.79-5.57 (m, 1H), 4.95 (d, J=13.7 Hz, 0.25H), 4.79-4.69 (m, 0.75H), 4.53 (d, J=14.1 Hz, 0.75H), 4.40-4.31 (m, 0.25H), 4.02-3.85 (m, 1H), 3.68 (dd, J=14.0, 4.2 Hz, 1H), 3.25-3.15 (m, 4H), 2.91-2.64 (m, 2H), 2.23-1.94 (m, 2H), 1.47 (d, J=6.9 Hz, 3H), 1.02 (dd, J=17.9, 6.6 Hz, 6H), 0.87 (t, J=7.6 Hz, 3H).

MS (ESI) m/z (M+H)$^+$=662.1.

HPLC 99% purity; retention time was 5.78 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

SFC 100% ee. Retention time was 3.966 min.

separation conditions: chromatographic column: Chiralpak AD-3 150×4.6 mm I.D., 3 μm; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Compound 53B-2:

$^1$H NMR (400 MHz, DMSO-$d_6$) δ 10.12 (brs, 1H), 8.45 (d, J=5.0 Hz, 1H), 7.87-7.66 (m, 1H), 7.26-7.14 (m, 2H), 6.96 (dd, J=16.8, 10.6 Hz, 0.75H), 6.79 (dd, J=16.6, 10.7 Hz, 0.25H), 6.68-6.53 (m, 2H), 6.15-6.00 (m, 1H), 5.77-5.58 (m, 1H), 4.95 (d, J=13.9 Hz, 0.25H), 4.79-4.69 (m, 0.75H), 4.53 (d, J=14.1 Hz, 0.75H), 4.39-4.32 (m, 0.25H), 4.02-3.93 (m, 1H), 3.69 (dd, J=14.1, 4.3 Hz, 1H), 3.26-3.16 (m, 4H), 2.88-2.61 (m, 2H), 2.41-2.26 (m, 2H), 1.47 (d, J=6.8 Hz, 3H), 1.00 (t, J=7.6 Hz, 3H), 0.95 (d, J=6.6 Hz, 3H), 0.84 (d, J=6.7 Hz, 3H).

MS (ESI) m/z (M+H)$^+$=662.1.

HPLC 99% purity; retention time was 5.702 min.

Separation conditions: chromatographic column: Waters XBridge 4.6*100 mm, 3.5 μm; column temperature: 40° C.; mobile phase: water (10 mM $NH_4HCO_3$)-acetonitrile; acetonitrile: 5%-95% 7 min; flow rate: 1.2 mL/min.

SFC 100% ee. Retention time was 4.777 min separation conditions: chromatographic column: Chiralpak AD-3 150×4.6 mm I.D., 3 μm; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Embodiment 54: Preparation of Compound 54

Step 1: Preparation of Compound 54-1

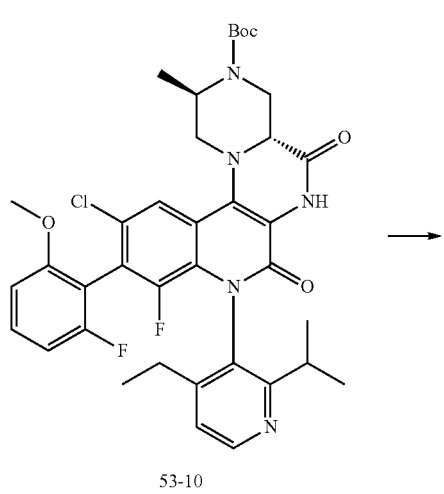

53-10

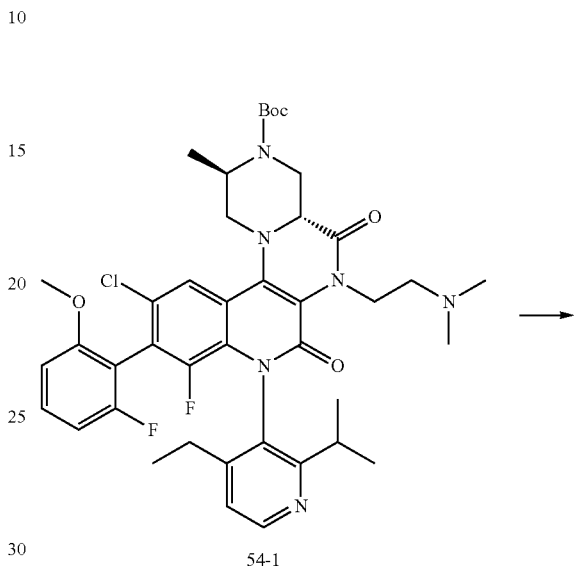

54-1

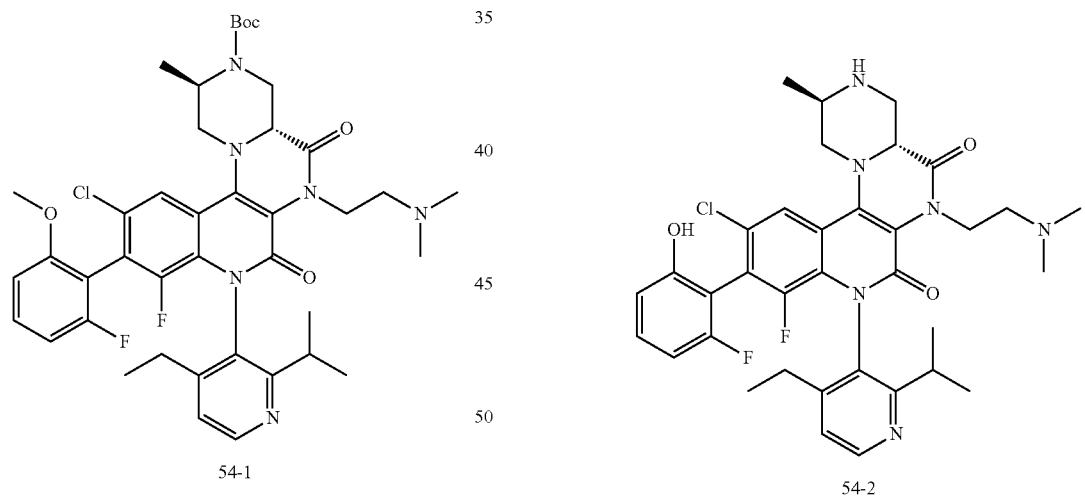

54-1          54-2

Compound 53-10 (156 mg, 220 μmol), 2-chloro-N,N-dimethylethylamine hydrochloride (104 mg, 660 μmol), cesium carbonate (224 mg, 660 μmol) and potassium iodide (40 mg, 220 μmol) were dissolved in DMF (2 mL), and the system was stirred at 120° C. for 3 hours under nitrogen atmosphere. The system was poured into ice water, extracted with EA (50 mL×3); the organic phases were combined, dried over anhydrous sodium sulfate, filtered, and the filtrate was concentrated to obtain a crude product. The crude product was purified by medium pressure column chromatography (ethyl acetate/petroleum ether (v/v)=0-90%) to obtain compound 54-1.

MS (ESI) m/z (M+H)$^+$=779.24.

Step 2: Preparation of Compound 54-2

Compound 54-1 (115 mg, 148 μmol) was dissolved in dichloromethane (4 mL), and boron tribromide (1.5 mL) was added thereto, and the reaction was stirred at 25° C. for 2 hours. The reaction mixture was quenched with methanol (10 mL), stirred for 10 min, and concentrated under reduced pressure to obtain compound 54-2 (hydrobromide), which was directly used in the next reaction without further purification.

MS (ESI) m/z (M+H)$^+$=665.2.

Step 3: Preparation of Compounds 54A and 54B

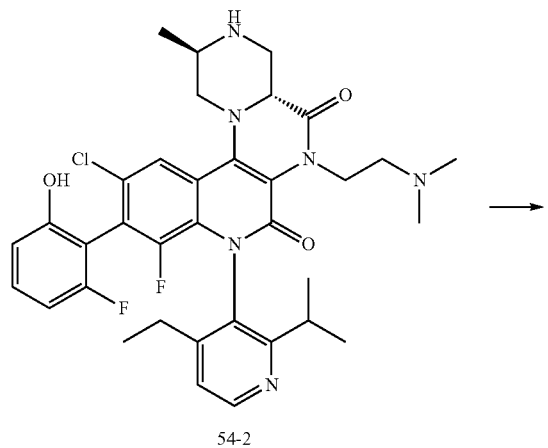

54-2

Compound 54-2 (40 mg, 0.06 mmol) was dissolved in dichloromethane (10 mL), and the system was cooled to 0° C., triethylamine (0.3 mL, 0.462 mmol) and acryloyl chloride (10 mg, 0.3 mmol) were added dropwise thereto, the reaction was carried out at 0° C. for 0.5 hours. The system was quenched with methanol and then concentrated to obtain a crude product. The crude product was dissolved in methanol (5 mL), potassium carbonate (140 mg) was added thereto, after the addition was completed, the system was stirred at room temperature (20° C.) for 30 min. The pH of the system was adjusted to 6 with hydrochloric acid, the mixture was extracted with dichloromethane (20 mL) and water (20 mL); and the organic phase was dried over anhydrous sodium sulfate, filtered, and the filtrate was concentrated to obtain a crude product, the crude product was purified by high performance liquid chromatography (separation conditions: Welch Xtimate® C18 21.2×250 mm, 10 μm; column temperature: 25° C.; mobile phase: water (10 mM/L NH$_4$HCO$_3$)-acetonitrile; acetonitrile: 45%-65% 9 min; flow rate 30 mL/min) to obtain compounds 54A and 54B.

MS (ESI) m/z (M+H)$^+$=719.2.

Step 4: Separation of Isomer of Compound 54A

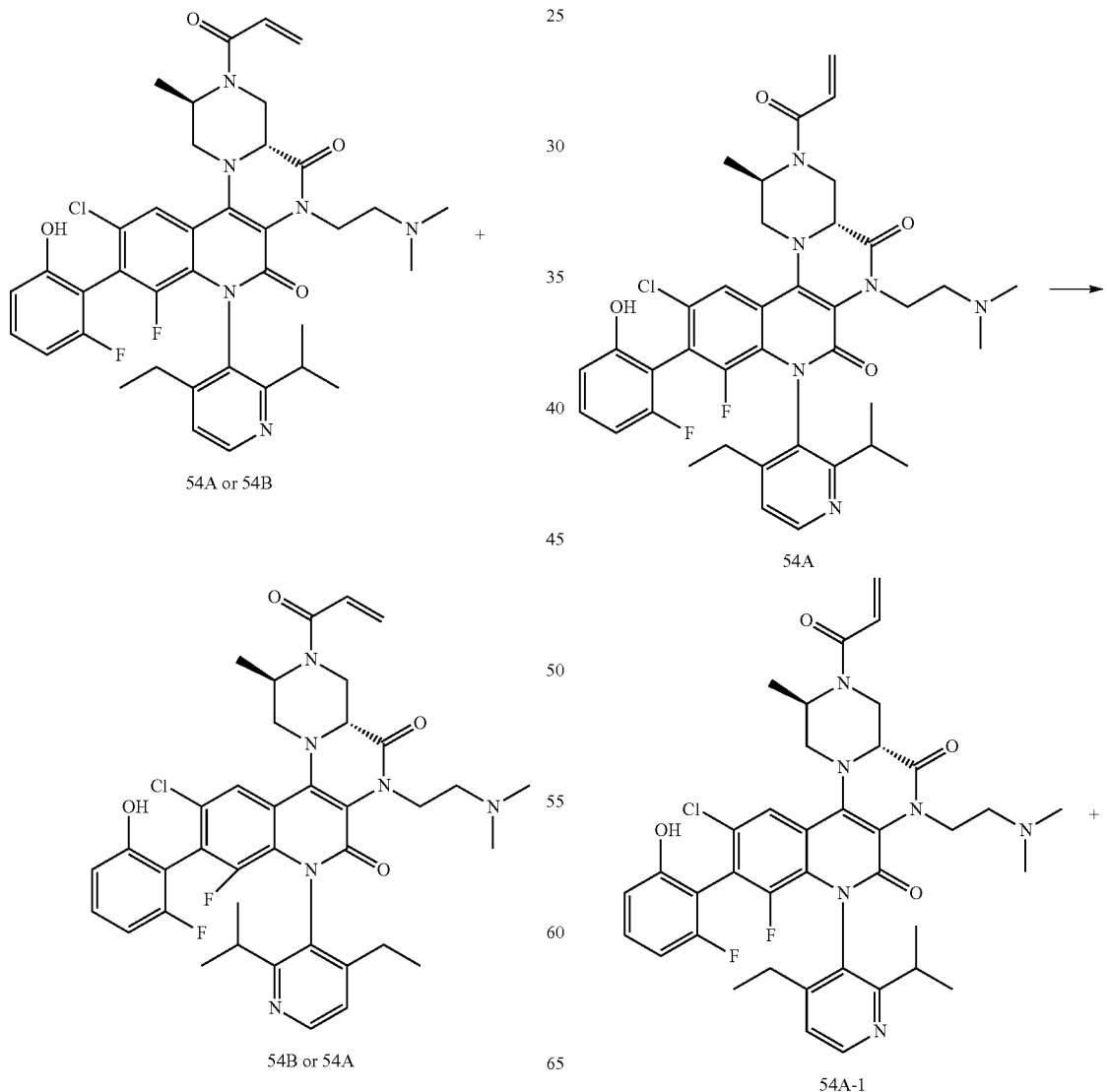

669

-continued

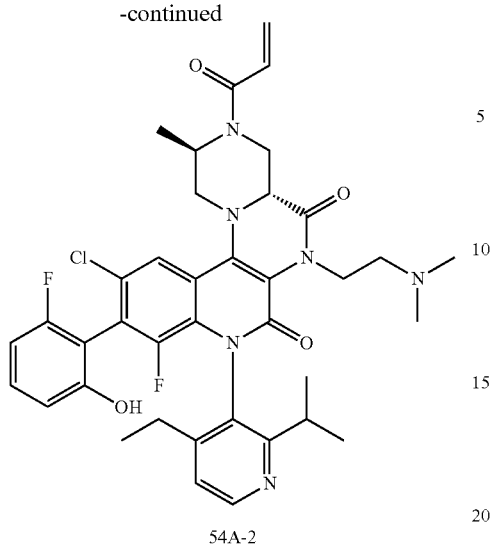

54A-2

Diastereoisomeric compound 54A was purified by SFC (separation conditions: chromatographic column: Phenomenex-Cellulose-2 (250 mm*30 mm, 10 μm); mobile phase: [CO$_2$-isopropanol (0.1% ammonia)]; isopropanol %: 30%-30%). After concentration, compound 54A-1 and compound 54A-2 were obtained.

Compound 54A-1:

MS (ESI) m/z (M+H)$^+$=719.0.

HPLC 92% purity; retention time was 5.734 min.

Separation conditions: chromatographic column: Waters XBridge 4.6*100 mm, 3.5 μm; column temperature: 40° C.; mobile phase: water (10 mM NH$_4$HCO$_3$)-acetonitrile; acetonitrile: 5%-95% 7 min; flow rate: 1.2 mL/min.

SFC 90% ee. Retention time was 4.098 min.

Separation conditions: chromatographic column: «Column_2»; column temperature: 35° C.; mobile phase: CO$_2$-isopropanol (0.05% DEA); isopropanol: 5%-40%; flow rate: 2.5 mL/min.

Compound 54A-2:

$^1$H NMR (400 MHz, DMSO-d$_6$) δ 10.16 (brs, 1H), 8.45 (d, J=4.9 Hz, 1H), 7.95-7.63 (m, 1H), 7.33-7.14 (m, 2H), 6.96 (dd, J=16.8, 10.6 Hz, 0.75H), 6.85-6.73 (m, 0.25H), 6.74-6.57 (m, 2H), 6.07 (dd, J=16.9, 2.2 Hz, 1H), 5.82-5.58 (m, 1H), 4.95 (d, J=14.0 Hz, 0.25H), 4.80-4.70 (m, 0.75H), 4.53 (d, J=14.1 Hz, 0.75H), 4.43-4.33 (m, 0.25H), 4.31-4.03 (m, 2H), 3.99-3.85 (m, 1H), 3.75-3.63 (m, 1H), 3.24-3.15 (m, 1H), 2.83-2.71 (m, 1H), 2.21-2.01 (m, 2H), 1.99-1.80 (m, 6H), 1.47 (d, J=6.8 Hz, 3H), 1.05 (d, J=6.6 Hz, 3H), 1.00 (d, J=6.7 Hz, 3H), 0.87 (t, J=7.6 Hz, 3H).

MS (ESI) m/z (M+H)$^+$=719.0.

HPLC 98% purity; retention time was 5.786 min.

Separation conditions: chromatographic column: Waters XBridge 4.6*100 mm, 3.5 μm; column temperature: 40° C.; mobile phase: water (10 mM NH$_4$HCO$_3$)-acetonitrile; acetonitrile: 5%-95% 7 min; flow rate: 1.2 mL/min.

SFC 100% ee. Retention time was 4.706 min

Separation conditions: chromatographic column: «Column_2»; column temperature: 35° C.; mobile phase: CO$_2$-isopropanol (0.05% DEA); isopropanol: 5%-40%; flow rate: 2.5 mL/min.

670

Step 5: Separation of Isomer of Compound 54B

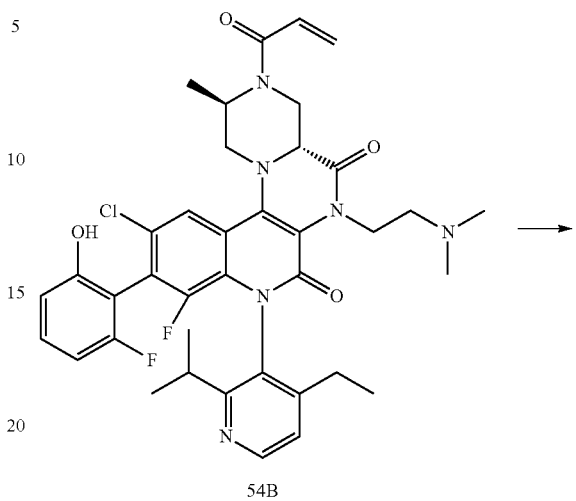

54B

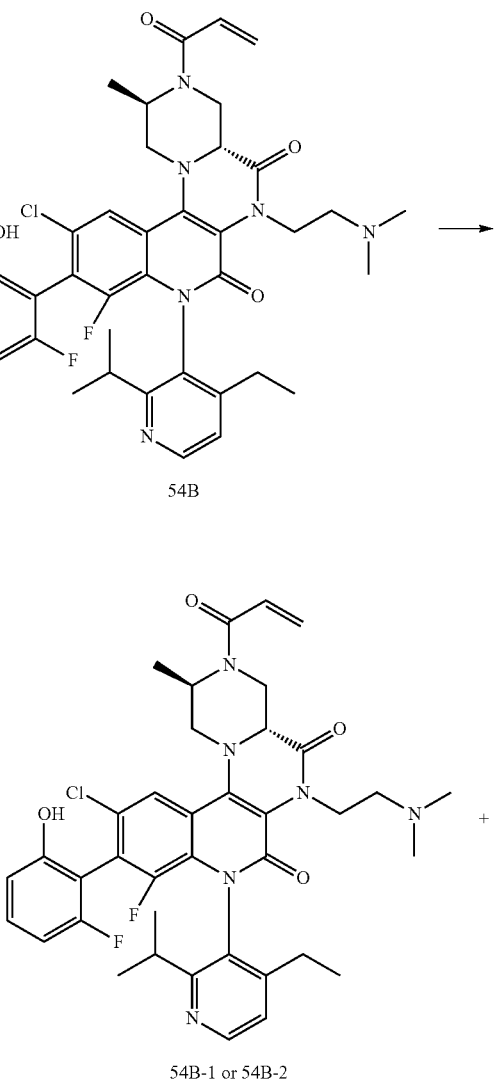

54B-1 or 54B-2

+

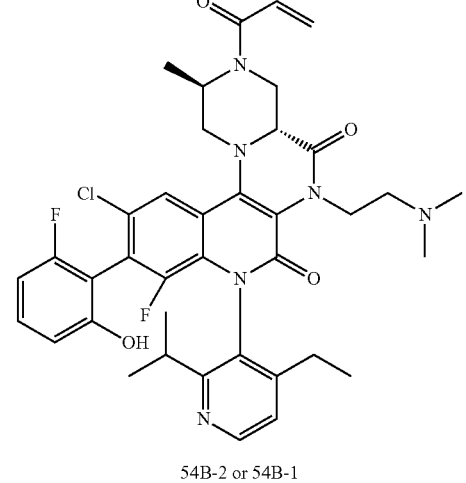

54B-2 or 54B-1

Diastereoisomeric compound 54B was purified by SFC (separation conditions: chromatographic column: DAICEL CHIRALPAK AD-H (250 mm*30 mm, 5 μm); mobile phase: [CO₂-isopropanol (0.1% ammonia)]; isopropanol %: 30%-30%). After concentration, compound 54B-1 and compound 54B-2 were obtained.

Compound 54B-1:

¹H NMR (400 MHz, DMSO-d₆) δ 10.12 (brs, 1H), 8.45 (d, J=4.9 Hz, 1H), 7.86-7.76 (m, 1H), 7.28-7.14 (m, 2H), 6.96 (dd, J=16.8, 10.6 Hz, 0.75H), 6.78 (dd, J=16.5, 10.7 Hz, 0.25H), 6.71-6.59 (m, 2H), 6.07 (dd, J=16.9, 2.6 Hz, 1H), 5.75-5.63 (m, 1H), 4.94 (d, J=13.8 Hz, 0.25H), 4.81-4.72 (m, 0.75H), 4.53 (d, J=14.0 Hz, 0.75H), 4.40-4.33 (m, 0.25H), 4.32-4.21 (m, 1H), 4.21-4.11 (m, 1H), 4.03-3.86 (m, 1H), 3.68 (dd, J=14.2, 4.3 Hz, 1H), 3.24-3.16 (m, 1H), 3.01-2.90 (m, 1H), 2.35-2.06 (m, 5H), 2.01-1.90 (m, 6H), 1.47 (d, J=6.9 Hz, 3H), 1.04-0.94 (m, 6H), 0.91 (d, J=6.7 Hz, 3H).

MS (ESI) m/z (M+H)⁺=719.0.

HPLC 98% purity; retention time was 5.60 min.

Separation conditions: chromatographic column: Waters XBridge 4.6*100 mm, 3.5 μm; column temperature: 40° C.; mobile phase: water (10 mM NH₄HCO₃)-acetonitrile; acetonitrile: 5%-95% 7 min; flow rate: 1.2 mL/min.

SFC 100% ee. Retention time was 4.845 min.

Separation conditions: chromatographic column: «Column_2»; column temperature: 35° C.; mobile phase: CO₂-isopropanol (0.05% DEA); isopropanol: 5%-40%; flow rate: 2.5 mL/min.

Compound 54B-2:

¹H NMR (400 MHz, DMSO-d₆) δ 8.45 (d, J=5.0 Hz, 1H), 7.82 (s, 1H), 7.19 (d, J=5.0 Hz, 2H), 6.96 (dd, J=16.9, 10.6 Hz, 0.75H), 6.85-6.73 (m, 0.25H), 6.67-6.50 (m, 2H), 6.07 (dd, J=16.9, 2.6 Hz, 1H), 5.68 (dd, J=10.5, 2.4 Hz, 1H), 4.94 (d, J=13.8 Hz, 0.25H), 4.81-4.71 (m, 0.75H), 4.53 (d, J=14.0 Hz, 0.75H), 4.41-4.35 (m, 0.25H), 4.34-4.21 (m, 1H), 4.17-4.05 (m, 1H), 3.97-3.82 (m, 1H), 3.72-3.57 (m, 1H), 3.04 (d, J=10.4 Hz, 1H), 2.80-2.64 (m, 1H), 2.27-2.05 (m, 5H), 1.96 (d, J=9.6 Hz, 6H), 1.46 (d, J=6.8 Hz, 3H), 1.04 (d, J=6.7 Hz, 3H), 0.99-0.83 (m, 6H).

MS (ESI) m/z (M+H)⁺=719.2.

HPLC 98% purity; retention time was 5.587 min.

Separation conditions: chromatographic column: Waters XBridge 4.6*100 mm, 3.5 μm; column temperature: 40° C.; mobile phase: water (10 mM NH₄HCO₃)-acetonitrile; acetonitrile: 5%-95% 7 min; flow rate: 1.2 mL/min.

SFC 100% ee. Retention time was 5.083 min

Separation conditions: chromatographic column: «Column_2»; column temperature: 35° C.; mobile phase: CO₂-isopropanol (0.05% DEA); isopropanol: 5%-40%; flow rate: 2.5 mL/min.

Embodiment 55: Preparation of Compound 55

Step 1: Preparation of Compound 55

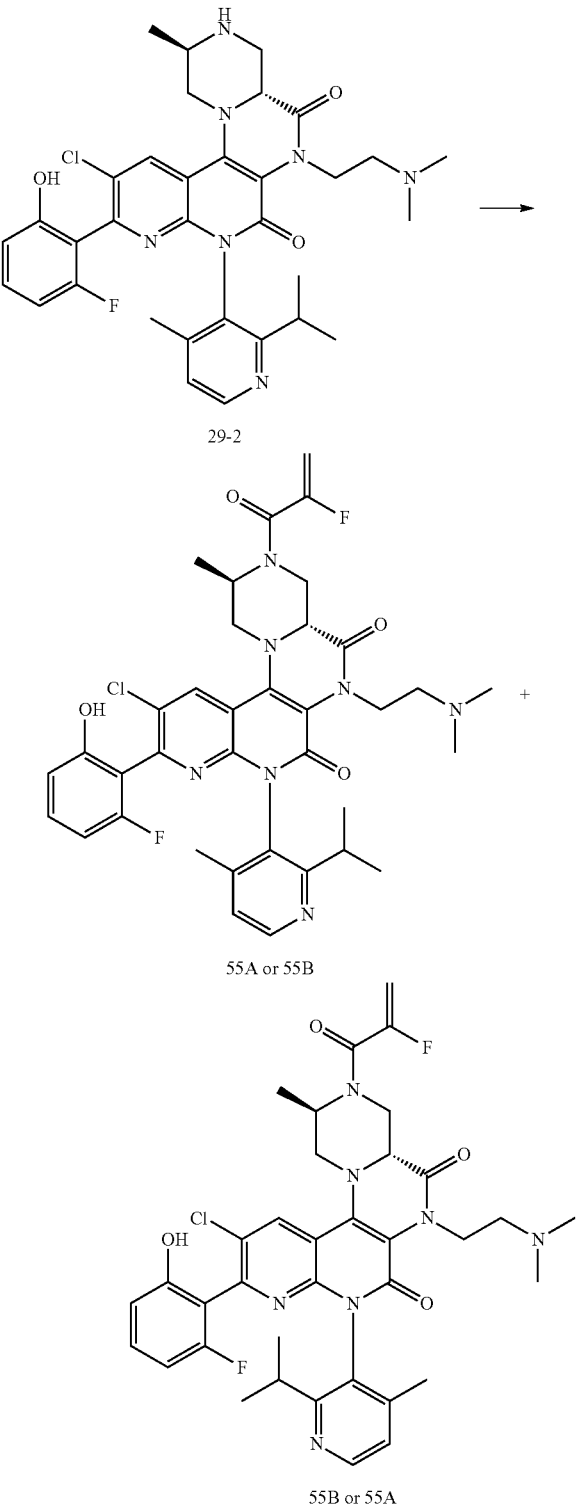

Compound 29-2 (25.0 mg, 0.039 mmol), 2-fluoroacrylic acid (3.5 mg, 0.039 mmol), 2-(7-azabenzotriazol-1-yl)-N,N,N',N'-tetramethyluronium hexafluorophosphate (22.0 mg, 0.059 mmol) and triethylamine (7.9 mg, 0.078 mmol) were dissolved in dichloromethane (1.5 mL), and the system was stirred at room temperature (25° C.) for 2 hours. Water (2 mL) was added to quench the reaction; then the mixture was extracted with dichloromethane (1.5 mL×2). The organic phases were combined, dried over anhydrous sodium sulfate, filtered, and the filtrate was concentrated to obtain a crude product. The crude product was purified by preparative high performance liquid chromatography (separation conditions: Agilent 10 Prep-C18 250×21.2 mm; column temperature: 25° C.; mobile phase: water (0.1% FA)-acetonitrile; acetonitrile: 20%-40% 12 min, flow rate 30 mL/min), and then purified by SFC (separation conditions: chromatographic column: «Column_3»; mobile phase: [$CO_2$-ethanol (0.1% ammonia)]; ethanol %: 20%-20%). After concentration, compound 55A and compound 55B were obtained.

Compound 55A:

$^1$H NMR (400 MHz, DMSO-$d_6$) δ10.09 (d, J=12 Hz, 1H), 8.44 (d, J=4 Hz, 1H), 8.25 (s, 1H), 7.34-7.16 (m, 2H), 6.77-6.59 (m, 2H), 5.49-5.24 (m, 2H), 4.79-4.58 (m, 2H), 4.43-4.16 (m, 2H), 4.07-3.96 (m, 2H), 3.26-3.11 (m, 2H), 2.39-2.19 (m, 2H), 2.12-1.91 (m, 10H), 1.72-1.50 (m, 3H), 1.18-0.81 (m, 6H).

SFC retention time was 3.33 min.

Separation conditions: chromatographic column: «Column_2»; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Compound 55B:

$^1$H NMR (400 MHz, DMSO-$d_6$) δ 10.12 (d, J=16 Hz, 1H), 8.45 (d, J=4 Hz, 1H), 8.27 (s, 1H), 7.31-7.15 (m, 2H), 6.76-6.61 (m, 2H), 5.50-5.27 (m, 2H), 4.76-4.56 (m, 2H), 4.37-4.17 (m, 2H), 4.08-3.83 (m, 4H), 2.87-2.63 (m, 3H), 2.43-2.14 (m, 6H), 1.92-1.74 (m, 3H), 1.69-1.51 (m, 3H), 1.19-1.07 (m, 3H), 1.05-0.97 (m, 3H).

SFC retention time was 3.81 min.

Separation conditions: chromatographic column: «Column_2»; column temperature: 35° C.; mobile phase: $CO_2$-ethanol (0.05% DEA); ethanol: 5%-40% 5 min, 40% 2.5 min, 5% 2.5 min; flow rate: 2.5 mL/min.

Embodiment 56: Preparation of Compound 56

Step 1: Preparation of Compound 56-1

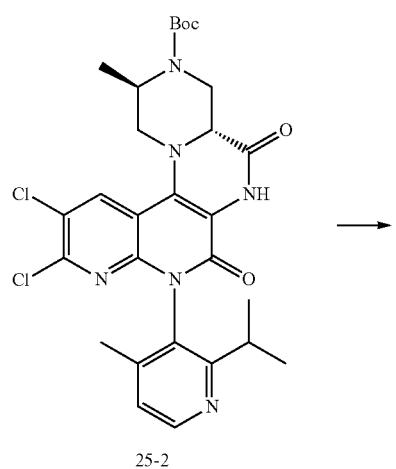

25-2

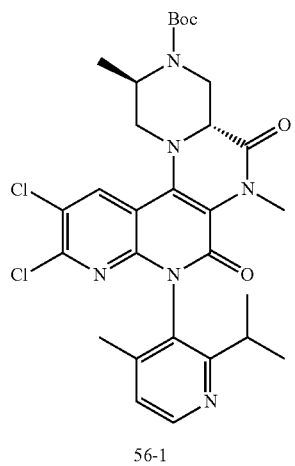

56-1

Compound 25-2 (1.17 g, 2 mmol) and potassium carbonate (552 mg, 4 mmol) were dissolved in acetone (10 mL), and methyl iodide (2.84 g, 20 mmol) was added thereto at room temperature (20° C.). After the addition was completed, under nitrogen atmosphere, the system was stirred at room temperature 20° C. for 2 hours. The system was concentrated to obtain a crude product. The crude product was directly used in the next reaction without further purification.

MS (ESI) m/z (M+H)$^+$=601.0.

Step 2: Preparation of Compound 56-3

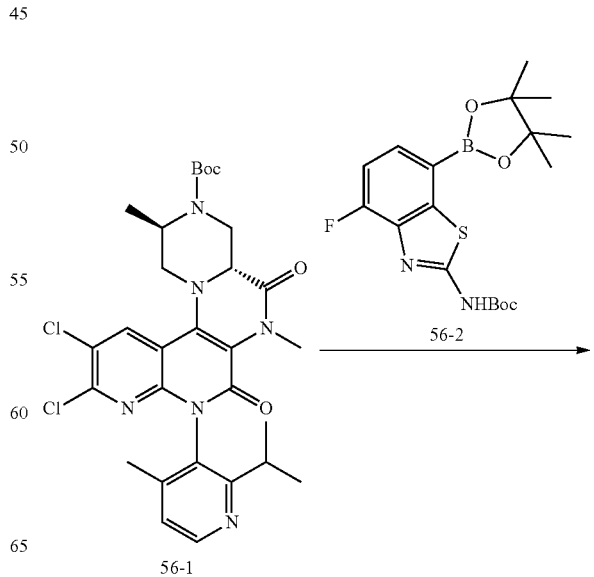

56-1          56-2

-continued

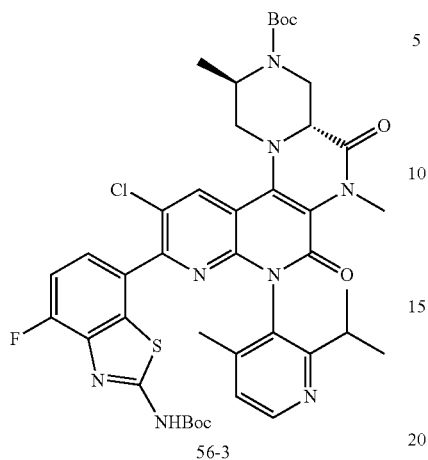

56-3

Compound 56-1 (1.25 g, 2.08 mmol), compound 56-2 (1.22 g, 3.12 mmol), 1,1'-bis(diphenylphosphino)ferrocene palladium dichloride (304 mg, 0.416 mmol), potassium phosphate (880 mg, 4.16 mmol) were dissolved in a mixed solution of tetrahydrofuran (25 mL) and water (6 mL). Under nitrogen atmosphere, the system was heated to 100° C. and stirred for 6 hours. The system was concentrated, then separated and extracted with ethyl acetate (200 mL×2) and water (100 mL); the organic phases were combined, dried over anhydrous sodium sulfate, filtered and the filtrate was concentrated to obtain a crude product, the crude product was purified by medium pressure column chromatography (ethyl acetate/petroleum ether (v/v)=0-70%) to obtain compound 56-3.

MS (ESI) m/z (M+H)$^+$=833.2.

Step 3: Preparation of Compound 56-4

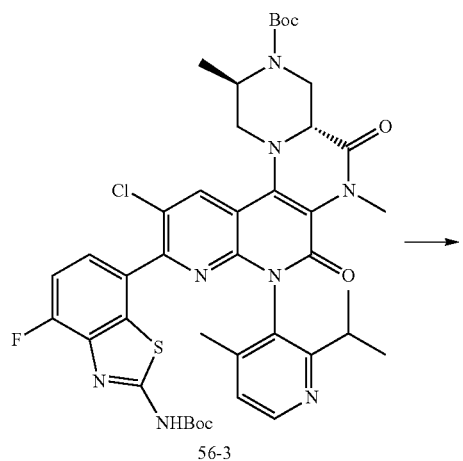

56-3

-continued

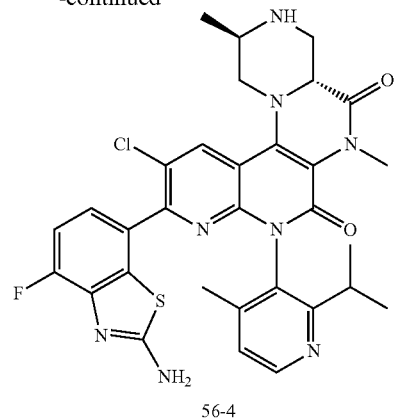

56-4

Compound 56-3 (200 mg, 0.240 mmol) was dissolved in a mixed solvent of methanol (2.6 mL) and tetrahydrofuran (3 mL), and hydrochloric acid/dioxane solution (3 mL) was added thereto at 0° C. The system was heated to room temperature (25° C.) and stirred for 10 min. The system was concentrated to obtain crude product compound 56-4, which was directly used in the next reaction without further purification.

MS (ESI) m/z (M+H)$^+$=633.2.

Step 4: Preparation of Compound 56-6

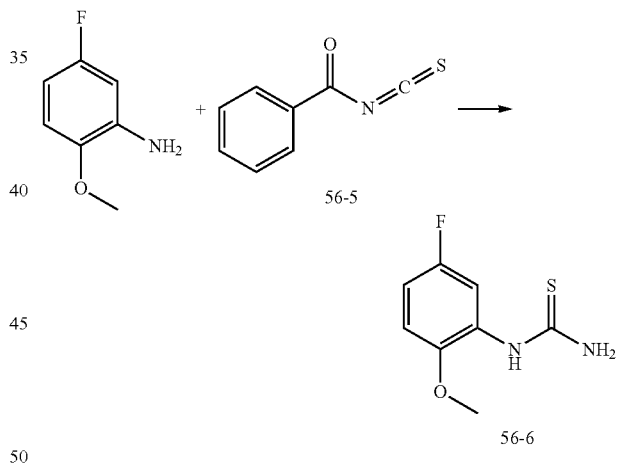

56-6

2-Methoxy-5-fluoro-aniline (23.12 g, 141.70 mmol, 19.11 mL) was dissolved in tetrahydrofuran (200 mL) at 5° C., and tetrahydrofuran solution (20 mL) of compound 56-5 (20 g, 141.70 mmol) was added thereto, then the system was raised to room temperature (25° C.) and the reaction was carried out for 20 min. Sodium hydroxide aqueous solution (2 M, 85.02 mL) was added to the system, and the system was raised to 80° C. and the reaction was carried out for 3 hours. Water (200 mL) and tert-butyl methyl ether (500 mL) were added to the system, and the pH was adjusted to 5 with 1 N hydrochloric acid, and the system was separated and extracted; and the organic phases were combined and dried over anhydrous sodium sulfate, filtered, and the filtrate was concentrated to obtain a crude product. At 0° C., the crude product was slurried with petroleum ether (100 mL) and filtered, the filter cake was washed with petroleum ether (2×10 mL) and dried to obtain compound 56-6, which was directly used in the next reaction without further purification.

$^1$H NMR (400 MHz, DMSO-d$_6$) δ=9.16 (s, 1H), 8.16 (br d, J=10.8 Hz, 1H), 8.01-7.37 (br, 2H), 7.03 (dd, J=5.3, 9.0 Hz, 1H), 6.91 (dt, J=3.0, 8.5 Hz, 1H), 3.83 (s, 3H).

Step 5: Preparation of Compound 56-7

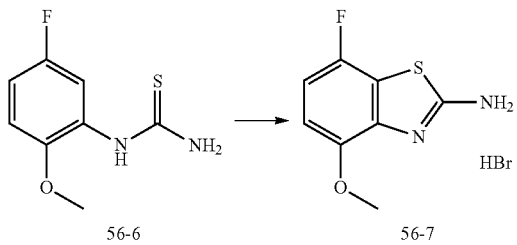

Compound 56-6 (26 g, 12.85 mmol) was dissolved in chloroform (500 mL) at 0-5° C., and liquid bromine (21.17 g, 132.45 mmol, 6.83 mL) was added thereto, the reaction was carried out at 0° C. for 30 min, and then raised to 70° C. and the reaction was carried out for 2 hours. The system was cooled to room temperature, filtered, the filter cake was washed with chloroform (3×10 mL), and then dried to obtain compound 56-7.

$^1$H NMR (400 MHz, DMSO-d$_6$) δ=8.42 (br s, 1H), 7.06-6.87 (m, 2H), 3.87 (s, 3H).

Step 6: Preparation of Compound 56-8

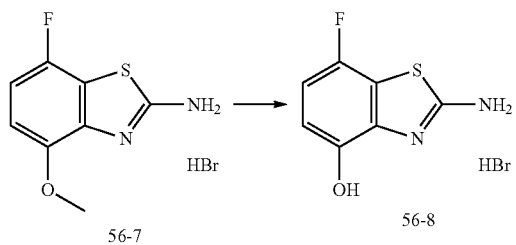

Compound 56-7 (36 g, 128.97 mmol, HBr salt) was dissolved in dichloromethane (500 mL) at 0-10° C., and boron tribromide (96.93 g, 386.92 mmol, 37.28 mL) was added dropwise thereto. After the dropwise addition was completed, the system was heated to room temperature (20° C.) and the reaction was carried out for 20 hours. The system was cooled to 0° C. and the reaction was quenched by adding methanol (10 mL) dropwise thereto; the system was filtered and the filter cake was washed with dichloromethane (10 mL×2), and dried to obtain compound 56-8.

$^1$H NMR (400 MHz, DMSO-d$_6$) δ=9.13-8.32 (br s, 4H), 6.89 (t, J=9.0 Hz, 1H), 6.74 (dd, J=4.4, 8.8 Hz, 1H)

Step 7: Preparation of Compound 56-9

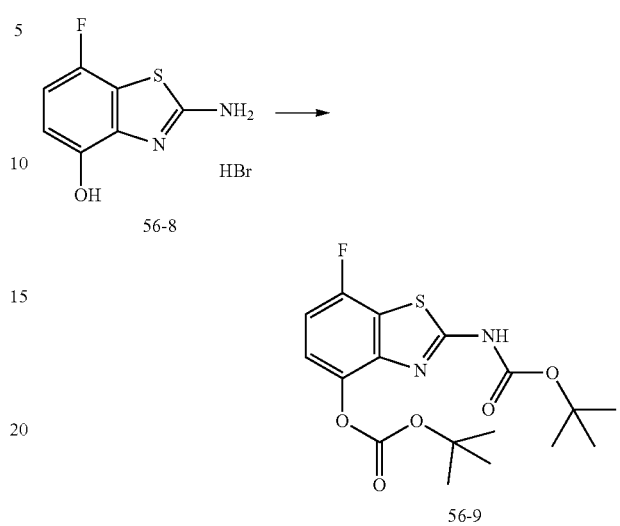

Compound 56-8 (15 g, 52.76 mmol) was dissolved in dioxane (150 mL) at 10-15° C., di-tert-butyl dicarbonate (26.48 g, 121.35 mmol, 27.88 mL), 4-dimethylaminopyridine (322.28 mg, 2.64 mmol) and N,N-diisopropylethylamine (14.32 g, 110.80 mmol, 19.30 mL) were added thereto. After the addition was completed, the system was heated to room temperature (20° C.) and the reaction was carried out for 20 hours. The system was concentrated, added with water (200 mL), and extracted with ethyl acetate (3×100); the organic phases were combined, dried over anhydrous sodium sulfate, filtered and the filtrate was concentrated to obtain a crude product, the crude product was purified by medium pressure column chromatography (ethyl acetate/petroleum ether (v/v)=0-30%) to obtain compound 56-9.

MS (ESI) m/z (M+1)$^+$=685.0

Step 8: Preparation of Compound 56-10

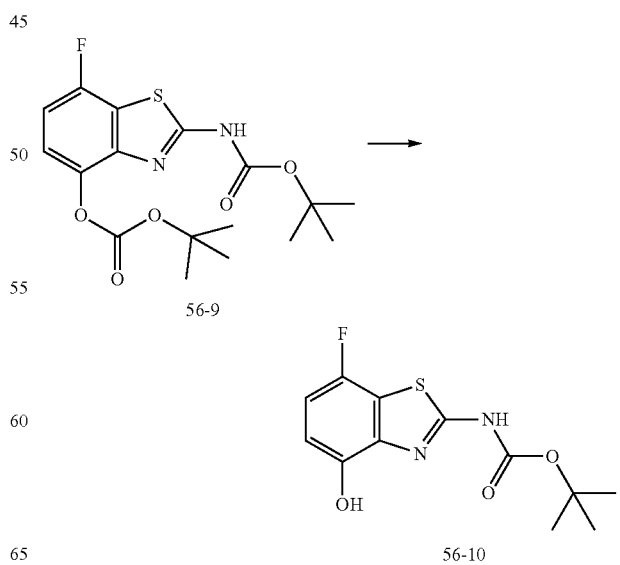

Compound 56-9 (20 g, 52.03 mmol) was dissolved in methanol (15 mL), and sodium methoxide (4.22 g, 78.04 mmol) was added thereto at 10-15° C. After the addition was completed, the system was heated to room temperature (20° C.) and the reaction was carried out for 20 hours. The system was concentrated, added with water (200 mL), and extracted with ethyl acetate (3×100); the organic phases were combined, dried over anhydrous sodium sulfate, filtered and the filtrate was concentrated to obtain a crude product, the crude product was purified by medium pressure column chromatography (ethyl acetate/petroleum ether (v/v)=0-30%) to obtain compound 56-10.

$^1$H NMR (400 MHz, CHLOROFORM-d) δ=6.98-6.72 (m, 2H), 1.55 (s, 9H).

Step 8: Preparation of Compound 56-11

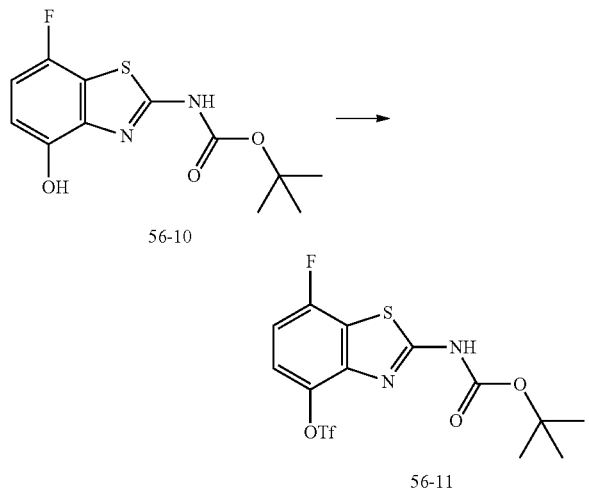

Compound 56-10 (14 g, 49.24 mmol) was dissolved in pyridine (200 mL), and trifluoromethanesulfonic anhydride (16.67 g, 59.09 mmol, 9.75 mL) was added thereto at 10° C. After the addition was completed, the system was heated to room temperature (20° C.) and the reaction was carried out for 2 hours. Water (200 mL) and 10% citric acid (100 mL) were added to the system, the mixture was extracted with dichloromethane (3×100 mL); and the organic phases were combined, dried over anhydrous sodium sulfate, filtered and the filtrate was concentrated to obtain a crude product, the crude product was purified by medium pressure column chromatography (ethyl acetate/petroleum ether (v/v)=0-15%) to obtain compound 56-11.

$^1$H NMR (400 MHz, CHLOROFORM-d) δ=8.99 (br s, 1H), 7.26-7.22 (m, 1H), 6.98 (t, J=8.6 Hz, 1H), 1.54 (s, 9H)

Step 9: Preparation of Compound 56-2

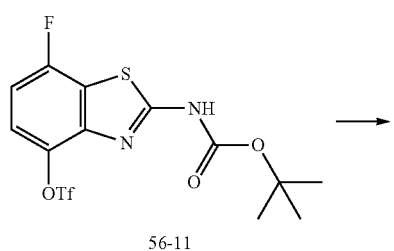

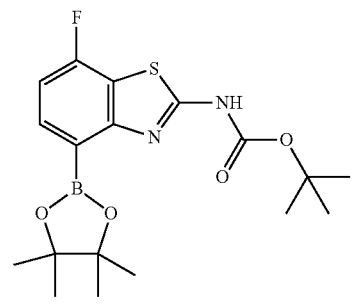

Compound 56-11 (18 g, 43.23 mmol), bis(pinacolato)diboron (65.87 g, 259.39 mmol), tetrakis(triphenylphosphine)palladium (5.00 g, 4.32 mmol), and potassium acetate (12.73 g, 129.69 mmol) were dissolved in dioxane (200 mL). Under nitrogen atmosphere, the system was heated to 100° C. and stirred for 20 hours. The system was concentrated, and the residue was separated and extracted with ethyl acetate (200 mL×3) and water (100 mL); and the organic phases were combined, dried over anhydrous sodium sulfate, filtered, and the filtrate was concentrated; acetone (500 mL), water (500 mL), ammonium acetate (105 g) and sodium periodate (250 g) were added thereto, the reaction was carried out at room temperature (20° C.) for 16 hours. The system was added with ethyl acetate (500 mL), filtered, the filtrate was separated and extracted; the organic phases were combined, dried over anhydrous sodium sulfate, filtered, and the filtrate was concentrated to obtain a crude product, the crude product was slurried with petroleum ether (100 mL) and filtered to obtain compound 56-2.

$^1$H NMR (400 MHz, DMSO-d$_6$) δ=7.78-7.74 (m, 1H), 7.17-7.11 (m, 1H), 1.51 (s, 9H), 1.32 (s, 12H).

Step 10: Preparation of Compound 56

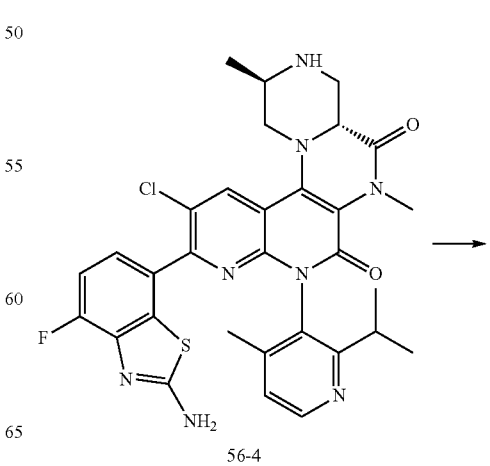

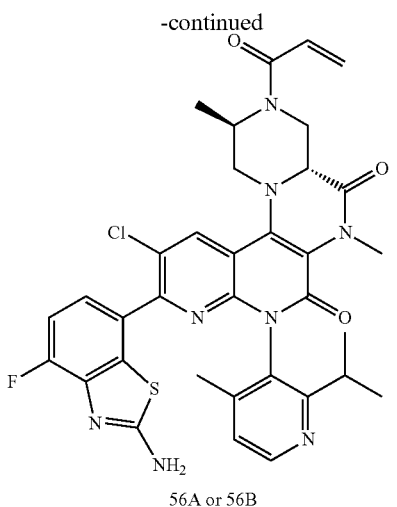

56A or 56B

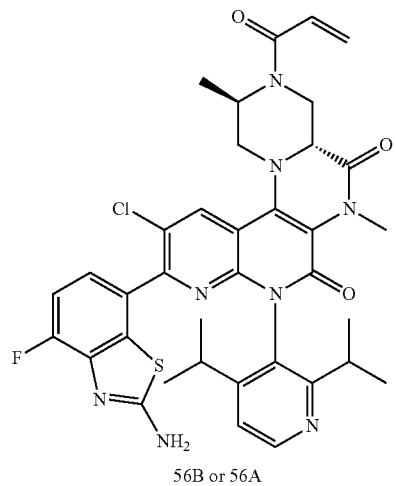

56B or 56A

Compound 56-4 (150 mg, 0.237 mmol) was dissolved in N,N-dimethylformamide (2 mL), acrylic acid (25.6 mg, 0.356 mmol), 2-(7-azabenzotriazol-1-yl)-N,N,N',N'-tetramethyluronium hexafluorophosphate (135 mg, 0.356 mmol), N,N-diisopropyl ethylamine (61 mg, 0.474 mmol) were added thereto, the reaction was carried out at room temperature (25° C.) for 2 hours. The system was concentrated to obtain a crude product, the crude product was purified by preparative high performance liquid chromatography (separation conditions: chromatographic column Welch Xtimate® C18 21.2×250 mm, 10 μm; mobile phase: water (10 mM/L ammonium bicarbonate)-acetonitrile; acetonitrile 50%-70% 12 min; flow rate 30 mL/min) and then purified by SFC («Column_3»; mobile phase: [CO$_2$-ethanol (0.1% ammonia)]; ethanol %: 40%; flow rate: 80 mL/min; column temperature: 38° C.). After concentration, compound 56A and compound 56B were obtained.

Compound 56A $^1$H NMR (400 MHz, DMSO-d$_6$) δ 8.44-8.43 (m, 1H), 8.19-8.17 (m, 1H), 7.90-7.84 (s, 2H), 7.24-7.23 (m, 1H), 7.07-6.82 (m, 3H), 6.19-6.12 (m, 1H), 5.78-5.72 (m, 1H), 4.85-4.79 (m, 1H), 4.64-4.59 (m, 1H), 4.60-3.59 (m, 1H), 3.78-3.73 (m, 1H), 3.31-3.20 (m, 4H), 2.86-2.68 (m, 1H), 2.33 (s, 1H), 1.99 (s, 3H), 1.54-1.54 (m, 3H), 1.05-1.03 (m, 6H).

MS (ESI) m/z (M+H)$^+$=687.2.

HPLC retention time was 5.619 min.

Separation conditions: chromatographic column: Waters XBridge 4.6*100 mm, 3.5 μm; column temperature: 40° C.; mobile phase: water (10 mM ammonium bicarbonate)-acetonitrile; acetonitrile: 5%-95% 7 min; flow rate: 1.2 mL/min.

SFC retention time was 2.324 min.

Separation conditions: chromatographic column: «Column_2»; mobile phase: [CO$_2$-isopropanol (0.05% DEA)]; isopropanol %: 5%-40% 5 min; flow rate: 2.5 mL/min; column temperature: 35° C.

Compound 56B $^1$H NMR (400 MHz, DMSO-d$_6$) δ 8.44-8.43 (m, 1H), 8.18-8.16 (m, 1H), 7.87 (s, 2H), 7.24-7.22 (m, 1H, J=Hz), 7.06-6.94 (m, 3H), 6.18-6.13 (m, 1H), 5.78-5.75 (m, 1H), 5.00-4.82 (m, 1H), 4.64-4.60 (m, 1H), 4.02-3.96 (m, 1H), 3.78-3.75 (m, 1H), 3.40-3.31 (m, 4H), 2.89-2.86 (m, 1H), 2.78-2.75 (m, 1H), 1.84 (s, 3H), 1.57-1.52 (m, 3H), 1.11-1.09 (m, 3H), 0.97 (m, 3H).

MS (ESI) m/z (M+H)$^+$=687.2.

HPLC retention time was 5.516 min.

Separation conditions: chromatographic column: Waters XBridge 4.6*100 mm, 3.5 μm; column temperature: 40° C.; mobile phase: water (10 mM ammonium bicarbonate)-acetonitrile; acetonitrile: 5%-95% 7 min; flow rate: 1.2 mL/min.

SFC retention time was 3.063 min.

Separation conditions: chromatographic column: «Column_2»; mobile phase: [CO$_2$-isopropanol (0.05% DEA)]; isopropanol %: 5%-40% 5 min; flow rate: 2.5 mL/min; column temperature: 35° C.

Embodiment 57: Preparation of Compound 57

Step 1: Preparation of Compound 57-1

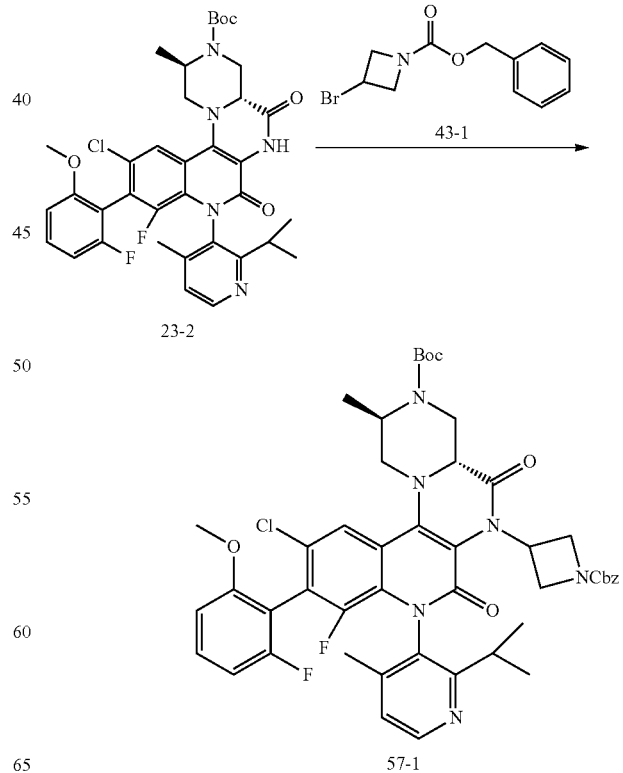

57-1

Compound 23-2 (400 mg, 576.23 µmol) and cesium carbonate (318.56 mg, 2.30 mmol) were dissolved in N,N-dimethylformamide (2 mL), and compound 43-1 (466.96 mg, 1.73 mmol) and potassium iodide (95.65 mg, 576.23 µmol) were added thereto at room temperature (25° C.). After the addition was completed, under nitrogen atmosphere, the system was heated to 100° C. and stirred for 16 hours. The system was concentrated, then separated and extracted with ethyl acetate (10 mL×2) and water (10 mL); the organic phases were combined, dried over anhydrous sodium sulfate, filtered and the filtrate was concentrated to obtain a crude product, the crude product was purified by silica gel column chromatography (dichloromethane/methanol (v/v)=1/7) to obtain compound 57-1.

MS (ESI) m/z (M+H)$^+$=883.4.

Step 2: Preparation of Compound 57-2

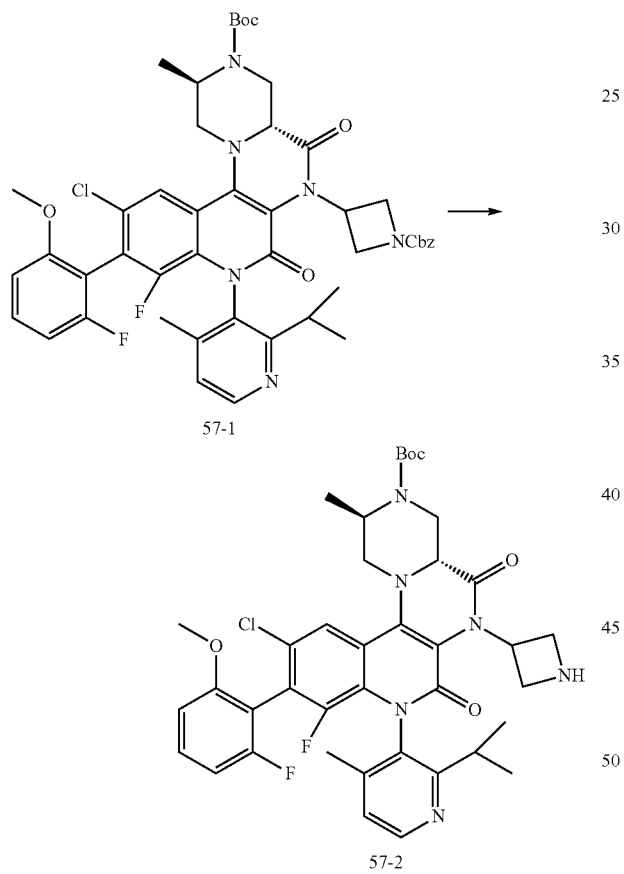

Compound 57-1 (150 mg, 169.80 µmol) was dissolved in dichloromethane (6 mL), and under hydrogen atmosphere, palladium chloride (105.39 mg, 594.31 µmol) and triethylamine (429.56 mg, 4.25 mmol, 590.87 µL) were added thereto. Under hydrogen atmosphere, the reaction was stirred at 25° C. for 5 hours. The reaction mixture was filtered and concentrated to obtain a crude product, the crude product was purified by silica gel column chromatography (dichloromethane/methanol (v/v)=1/7) to obtain compound 57-2.

MS (ESI) m/z (M+H)$^+$=749.4.

Step 3: Preparation of Compound 57-3

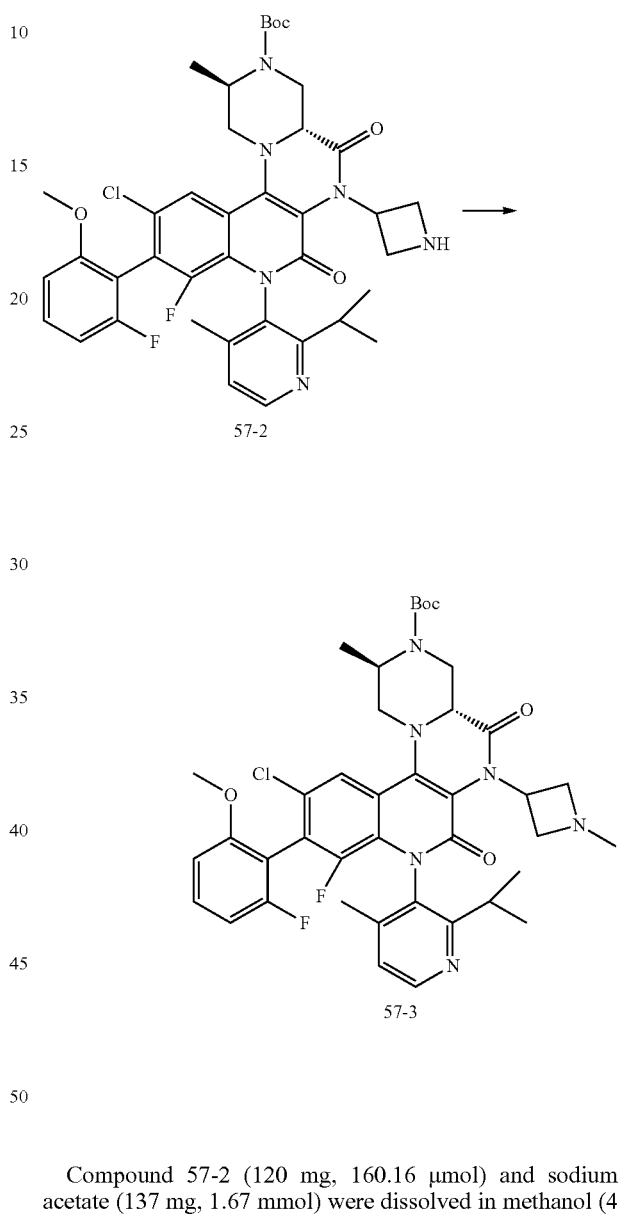

Compound 57-2 (120 mg, 160.16 µmol) and sodium acetate (137 mg, 1.67 mmol) were dissolved in methanol (4 mL), formaldehyde aqueous solution (872.00 mg, 10.74 mmol, 0.8 mL, 37% purity) was added thereto, and the reaction was stirred at 25° C. for 0.5 hours. Tetrahydrofuran solution (2 mL) of sodium cyanoborohydride (110 mg, 1.75 mmol) was added thereto, and the reaction was stirred at 25° C. for 4 hours. The system was diluted with ethyl acetate (40 mL), washed with saturated saline (20 mL); and the organic phase was dried over anhydrous sodium sulfate, filtered, and the filtrate was concentrated to obtain a crude product, the crude product was purified by silica gel column chromatography (dichloromethane/methanol (v/v)=1/10) to obtain compound 57-3.

MS (ESI) m/z (M+H)$^+$=763.4.

Step 4: Preparation of Compound 57-4

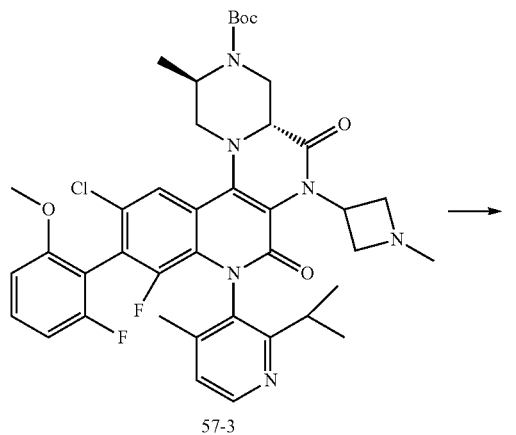

Compound 57-3 (80 mg, 104.81 μmol) was dissolved in dichloromethane (5 mL), trifluoroacetic acid (1.54 g, 13.51 mmol, 1 mL) was added thereto, after the addition was completed, and the system was stirred at room temperature (25° C.) for 2 hours. The system was concentrated, the residue was dissolved in dichloromethane (30 mL), washed with saturated sodium bicarbonate aqueous solution (10 mL); the organic phases were combined, dried over anhydrous sodium sulfate, filtered, and the filtrate was concentrated to obtain compound 57-4, which was directly used in the next reaction without further purification.

MS (ESI) m/z (M+H)$^+$=663.0.

Step 5: Preparation of Compound 57

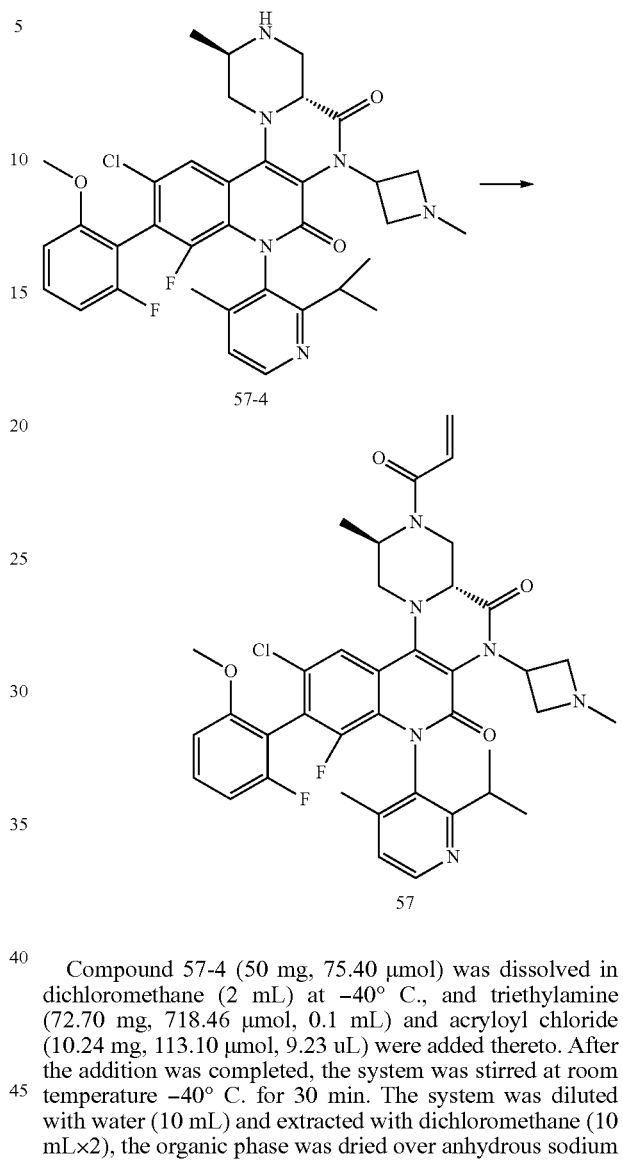

Compound 57-4 (50 mg, 75.40 μmol) was dissolved in dichloromethane (2 mL) at −40° C., and triethylamine (72.70 mg, 718.46 μmol, 0.1 mL) and acryloyl chloride (10.24 mg, 113.10 μmol, 9.23 uL) were added thereto. After the addition was completed, the system was stirred at room temperature −40° C. for 30 min. The system was diluted with water (10 mL) and extracted with dichloromethane (10 mL×2), the organic phase was dried over anhydrous sodium sulfate, filtered, and the filtrate was concentrated to obtain a crude product. The crude product was purified by preparative high performance liquid chromatography (separation conditions: chromatographic column: Phenomenex Gemini-NX 80*30 mm*3 μm; mobile phase: [water (10 mM ammonium bicarbonate aqueous solution)-acetonitrile]; acetonitrile %: 48%-78% 9 min) to obtain compound 57.

$^1$H NMR (400 MHz, Methanol-$d_4$) δ 8.44 (br d, J=4.4 Hz, 1H), 8.01 (br s, 1H), 7.48-7.35 (m, 1H), 7.25 (br dd, J=4.9, 16.6 Hz, 1H), 7.07 (dd, J=10.7, 16.8 Hz, 1H), 6.94-6.85 (m, 1H), 6.80 (br t, J=8.5 Hz, 1H), 6.31-6.18 (m, 1H), 5.81 (dd, J=1.7, 10.8 Hz, 1H), 4.98 (br s, 1H), 4.72 (br d, J=13.5 Hz, 1H), 4.60 (br s, 2H), 4.16-4.02 (m, 1H), 3.99-3.80 (m, 2H), 3.78-3.63 (m, 4H), 3.43-3.35 (m, 1H), 3.27-3.09 (m, 2H), 3.06-2.97 (m, 1H), 2.34-2.19 (m, 3H), 2.09-1.84 (m, 3H), 1.77-1.60 (m, 3H), 1.26-0.97 (m, 6H). MS (ESI) m/z (M+H)$^+$=717.2.

HPLC retention time was 4.512 min.

Separation conditions: chromatographic column Xbridge C18, 5 μm, 2.1*50 mm; column temperature: 50° C.; mobile phase: water (0.2 mL/L ammonia)-acetonitrile; acetonitrile: 10%-80% 6 min, 80% 2 min; flow rate: 0.8 mL/min.

Experimental Embodiment 1: Inhibition of RAS-Mediated Signal Transduction

The ability of the compounds disclosed herein to inhibit RAS-mediated signal transduction was evaluated and demonstrated as follows. Cell NCI-H358 (ATCC catalogue number CRL-5807) expressing mutant RAS(G12C) was cultured in RPMI medium containing 10% fetal bovine serum and penicillin/streptomycin double antibody. 40,000 cells per well were spread in a 96-well plate (Corning catalogue number 3699), and the cells were left to stand overnight to adhere to the plate bottom. The cells were treated with or without the compound of the present disclosure (dimethyl sulfoxide, DMSO), and the final concentration of DMSO was guaranteed to be 0.5%. After 2 hours of treatment, the medium was removed and 4% paraformaldehyde (Beyotime catalog number E672002-0100) was added and left to stand for 20 minutes. Cells were washed with PBS after fixation and incubated with precooled methanol for 10 min to permeabilize the cell membrane. 1× blocking buffer (Thermo catalogue number 37520) was added and incubated for 1 hour to block the binding of nonspecific antibody.

The level of phosphorylated ERK was detected using an enzyme linked immunosorbent assay (ELISA) method. Phosphorylated ERK antibody (Cell Signal Technology catalogue number 4370) was diluted 1:400 with 1× blocking solution containing 0.05% Tween-20, then the mixture was added to a 96-well plate and incubated overnight at 4° C. The plates were washed 5 times with PBS containing 0.05% Tween 20. The secondary antibody coupled to HRP (Thermo catalogue number 31460) was diluted 1:10,000 with 1× blocking solution containing 0.05% Tween 20, the mixture was added to a 96-well plate and incubated at room temperature for 2 hours. The plate was washed 5 times with PBS containing 0.05% Tween, and TMB (Thermo catalogue number 4816) was added and incubated at room temperature for 15 minutes. The reaction was stopped by adding 1 mol/L H2SO4, and the OD value was read at 450 nm by EnVision (PerkinElmer).

The total number of cells per well was detected by Janus Green B staining method. After detecting the level of phosphorylated ERK, the 96-well plate was washed with PBS until colorless, and 0.1% Janus Green B (Abcam catalogue number ab111622) was added to incubate for 10 minutes. After the 96-well plate was washed with double distilled water, 0.1 mol/L HCl was added, then the mixture was shaked and incubated for 10 minutes. The OD value was read at 595 nm by EnVision (PerkinElmer).

The signal of pERK (Thr202/Tyr204) was normalized by the signal value of Janus Green B, and the inhibition percentage after drug treatment relative to DMSO reference was calculated. The percentage values were fitted by a four-parameter dose-response curve and generated IC50 values. The experimental results were shown in Table 1.

TABLE 1

| Compound number | p-ERK IC50 (NCI H358, μM) |
| --- | --- |
| ARS-1620 | 0.325 |
| Compound 1A | 0.173 |
| Compound 1B | 8.511 |
| Compound 2A | 0.066 |

TABLE 1-continued

| Compound number | p-ERK IC50 (NCI H358, μM) |
| --- | --- |
| Compound 2B | 8.511 |
| Compound 3A | 0.474 |
| Compound 3B | 0.008 |
| Compound 3A-1 | 3.014 |
| Compound 3A-2 | 5.240 |
| Compound 3B-1 | 0.026 |
| Compound 3B-2 | 0.006 |
| Compound 4A | 0.159 |
| Compound 5A | 0.061 |
| Compound 5B | 0.128 |
| Compound 6A | 0.065 |
| Compound 6B | 0.691 |
| Compound 7B | 0.098 |
| Compound 8: | 0.024 |
| Compound 9: | 1.96 |
| Compound 10A | 0.063 |
| Compound 11A | 1.117 |
| Compound 12A | 0.604 |
| Compound 13A | 0.040 |
| Compound 13B | 5.671 |
| Compound 16A | 0.017 |
| Compound 16A-1 | 0.011 |
| Compound 16A-2 | 0.084 |
| Compound 16B | 1.252 |
| Compound 16B-1 | 0.648 |
| Compound 17: | 0.275 |
| Compound 18A | 0.005 |
| Compound 18A-1 | 0.004 |
| Compound 18A-2 | 0.013 |
| Compound 18B | 0.151 |
| Compound 18B-1 | 0.036 |
| Compound 18B-2 | 0.102 |
| Compound 19A | 0.008 |
| Compound 19B | 0.936 |
| Compound 20A | 0.004 |
| Compound 20B | 0.264 |
| Compound 21A | 0.013 |
| Compound 21A-1 | 0.104 |
| Compound 21A-2 | 0.015 |
| Compound 21B | 0.306 |
| Compound 21B-1 | 2.238 |
| Compound 22A | 0.016 |
| Compound 22A-1 | 0.060 |
| Compound 22A-2 | 0.054 |
| Compound 22B | 0.548 |
| Compound 22B-1 | 0.213 |
| Compound 23A-1 | 0.111 |
| Compound 23A-2 | 0.003 |
| Compound 23B-1 | 0.150 |
| Compound 23B-2 | 0.749 |
| Compound 24A | 3.817 |
| Compound 24B | 0.075 |
| Compound 24C | 0.012 |
| Compound 24D | 0.246 |
| Compound 25A | 0.014 |
| Compound 25B | 0.245 |
| Compound 26A | 0.203 |
| Compound 26B | 0.019 |
| Compound 26C | 0.002 |
| Compound 26D | 0.068 |
| Compound 27A | 0.087 |
| Compound 27C | 0.004 |
| Compound 27D | 0.124 |
| Compound 28A | 0.006 |
| Compound 28C | 6.909 |
| Compound 29A | 0.124 |
| Compound 29B | 0.009 |
| Compound 30A | 0.170 |
| Compound 30B | 0.017 |
| Compound 31A | 2.156 |
| Compound 31B | 0.062 |
| Compound 32A | 0.274 |
| Compound 32B | 0.010 |
| Compound 32C | 0.151 |
| Compound 32D | 1.362 |
| Compound 33A-1 | 0.717 |
| Compound 33A-2 | 0.023 |

TABLE 1-continued

| Compound number | p-ERK IC50 (NCI H358, μM) |
|---|---|
| Compound 33B-2 | 0.333 |
| Compound 34A | 0.503 |
| Compound 35A | 0.068 |
| Compound 35A-1 | 0.313 |
| Compound 35A-2 | 0.052 |
| Compound 36A-1 | 0.016 |
| Compound 36A-2 | 0.240 |
| Compound 37A | 0.070 |
| Compound 38B | 0.064 |
| Compound 38A-1 | 0.242 |
| Compound 38A-2 | 0.035 |
| Compound 38B-1 | 1.127 |
| Compound 39A | 0.798 |
| Compound 39A-1 | 1.641 |
| Compound 39A-2 | 0.789 |
| Compound 40A | 0.052 |
| Compound 40A-1 | 0.042 |
| Compound 40A-2 | 0.142 |
| Compound 41A | 0.942 |
| Compound 42A | 0.009 |
| Compound 42B | 0.182 |
| Compound 43 | 1.921 |
| Compound 44A | 0.580 |
| Compound 45A | 1.539 |
| Compound 46A | 2.047 |
| Compound 46B | 0.037 |
| Compound 47A | 1.565 |
| Compound 47B | 0.150 |
| Compound 48A-1 | 0.294 |
| Compound 48B-1 | 0.662 |
| Compound 48B-2 | 0.024 |
| Compound 49A | 0.004 |
| Compound 49A-1 | 0.005 |
| Compound 49A-2 | 0.249 |
| Compound 49B | 1.164 |
| Compound 50 | 0.041 |
| Compound 50B | 0.121 |
| Compound 50C | 0.630 |
| Compound 50D | 0.014 |
| Compound 51A | 1.277 |
| Compound 53A-1 | 0.003 |
| Compound 53A-2 | 0.011 |
| Compound 54A-1 | 0.641 |
| Compound 54A-2 | 0.844 |
| Compound 54B-1 | 0.012 |
| Compound 54B-2 | 0.004 |
| Compound 56A | 0.183 |
| Compound 56B | 0.011 |

The compounds of the present disclosure exhibit excellent ability to inhibit RAS-mediated signal transduction.

Experimental Embodiment 2: Growth Ability Experiment of Inhibition of Tumor Cell Lines Expressing KRAS-G12C The ability of the compounds of the present disclosure to inhibit the growth of cells expressing KRAS-G12C was evaluated by measuring the cell viability and calculating the GI50 values.

The tumor cell line NCI-H358 (ATCC catalogue number CRL-5807) expressing KRAS-G12C was cultured in RPMI medium supplemented with 10% fetal bovine serum and penicillin/streptomycin, and the tumor cell line MIA PaCa2 (ATCC CRL-1420) expressing KRAS-G12C was cultured in DMEM medium supplemented with 10% fetal bovine serum, 2.5% horse serum, and penicillin/streptomycin.

Cells NCI-H358 and MIA-Paca2 were inoculated into black transparent bottom 384-well plate (PerkinElmer catalogue number 6007460) with cell density of 1000 and 800 respectively, and the cells were allowed to adhere to the wall overnight (8-12 hours). After the cells adhered to the wall, the experimental group was added with the compound of the present disclosure diluted 5 times the concentration of the working solution (final concentration containing 0.1% dimethyl sulfoxide, i.e. DMSO); the control group was added with the same dilution as the experimental group (final concentration containing 0.1% DMSO). After 72 hours, Cell Titer Glo reagent (Promega catalogue number G7572) was used to detect ATP content according to the instruction method to determine the amount of cell proliferation. The brief operation steps were as follows: the cell plate was taken out and kept at normal temperature for equilibrium for 30 minutes; Cell Titer Glo reagent with the same volume as the culture was added; the culture plate was placed on a shaker for shaking and cracking for 2 minutes; the culture plate was left to stand at room temperature for 10 minutes; then the light signal value was read by microplate reader EnVision (PerkinElmer).

Data from all experimental groups were used to calculate the respective percent inhibition using the DMSO group, and the GI50 was calculated using the data processing software GraphPad to analyze the inhibition rates produced by the 9 compound dose concentrations diluted at ⅓-fold ratio. The experimental results were shown in Table 2.

TABLE 2

| Compound number | $GI_{50}$(NCI-H358, μM) | $GI_{50}$(MIA-Paca2, μM) |
|---|---|---|
| ARS-1620 | 0.51 | 1.21 |
| Compound 2A | 0.143 | 1.024 |
| Compound 3B | 0.008 | 0.039 |
| Compound 3B-1 | 0.027 | 0.166 |
| Compound 3B-2 | 0.005 | 0.031 |
| Compound 4A | 0.523 | 2.405 |
| Compound 5A | 0.089 | 0.252 |
| Compound 5B | 0.210 | 3.132 |
| Compound 6A | 0.041 | 0.230 |
| Compound 7B | 0.148 | 0.328 |
| Compound 8: | 0.022 | 0.037 |
| Compound 10A | 0.184 | 0.496 |
| Compound 13A | 0.059 | 0.265 |
| Compound 16A | 0.020 | 0.211 |
| Compound 16A-1 | 0.012 | 0.055 |
| Compound 16A-2 | 0.074 | 0.146 |
| Compound 18A | 0.006 | 0.013 |
| Compound 18A-1 | 0.002 | 0.010 |
| Compound 18A-2 | 0.012 | 0.024 |
| Compound 18B | 0.138 | 0.468 |
| Compound 18B-1 | 0.021 | 0.066 |
| Compound 18B-2 | 0.149 | 0.172 |
| Compound 19A | 0.008 | 0.014 |
| Compound 20A | 0.004 | 0.010 |
| Compound 20B | 0.413 | 1.595 |
| Compound 21A-1 | 0.091 | 0.156 |
| Compound 21A-2 | 0.010 | 0.034 |
| Compound 22A | 0.010 | 0.024 |
| Compound 22A-1 | 0.028 | 0.085 |
| Compound 22A-2 | 0.042 | 0.119 |
| Compound 23A-1 | 0.104 | 0.281 |
| Compound 23A-2 | 0.003 | 0.014 |
| Compound 24B | 0.068 | 0.112 |
| Compound 24C | 0.011 | 0.023 |
| Compound 24D | 0.232 | 0.407 |
| Compound 25A | 0.010 | 0.029 |
| Compound 26A | 0.152 | 0.724 |
| Compound 26B | 0.022 | 0.028 |
| Compound 26C | 0.002 | 0.001 |
| Compound 26D | 0.082 | 0.079 |
| Compound 27A | 0.147 | 0.152 |
| Compound 27C | 0.005 | 0.003 |
| Compound 27D | 0.085 | 0.117 |
| Compound 28A | 0.007 | 0.009 |
| Compound 29A | 0.044 | 0.067 |
| Compound 29B | 0.007 | 0.004 |
| Compound 30A | 0.208 | 0.231 |

TABLE 2-continued

| Compound number | GI$_{50}$(NCI-H358, μM) | GI$_{50}$(MIA-Paca2, μM) |
|---|---|---|
| Compound 30B | 0.012 | 0.013 |
| Compound 31B | 0.090 | 0.299 |
| Compound 32A | 0.442 | 0.604 |
| Compound 32B | 0.022 | 0.021 |
| Compound 32C | 0.258 | 1.523 |
| Compound 33A-2 | 0.018 | 0.062 |
| Compound 35A | 0.053 | 2.141 |
| Compound 35A-1 | 0.163 | 2.599 |
| Compound 35A-2 | 0.046 | 0.511 |
| Compound 36A-1 | 0.032 | 0.235 |
| Compound 37A | 0.066 | 0.392 |
| Compound 38B | 0.077 | 0.535 |
| Compound 38A-2 | 0.063 | 0.201 |
| Compound 39A-2 | 0.512 | 1.649 |
| Compound 40A | 0.062 | 0.056 |
| Compound 40A-1 | 0.043 | 0.221 |
| Compound 40A-2 | 0.112 | 0.483 |
| Compound 41A | 0.530 | 2.235 |
| Compound 42A | 0.009 | 0.228 |
| Compound 42B | 0.214 | 0.510 |
| Compound 44A | 0.424 | 1.566 |
| Compound 46B | 0.049 | 0.168 |
| Compound 47B | 0.106 | 0.332 |
| Compound 48B-2 | 0.015 | 0.020 |
| Compound 49A | 0.004 | 0.009 |
| Compound 49A-1 | 0.003 | 0.007 |
| Compound 50: | 0.062 | 0.094 |
| Compound 50B | 0.093 | 0.112 |
| Compound 50D | 0.011 | 0.073 |
| Compound 53A-1 | 0.002 | 0.004 |
| Compound 53A-2 | 0.007 | 0.010 |
| Compound 54B-1 | 0.007 | 0.006 |
| Compound 54B-2 | 0.002 | 0.003 |
| Compound 56A | 0.223 | 0.448 |
| Compound 56B | 0.012 | 0.025 |

Experimental Embodiment 3: Pharmacokinetic Experiment

In this experimental embodiment, in vivo pharmacokinetic evaluation was performed in mice by intravenous injection and oral administration.

Experimental methods and conditions: Male ICR mice were given a single dose of 1 mg/Kg (intravenous injection, solvent 5% DMSO+15% Solutol+80% saline) and 5 mg/Kg (intragastric administration, solvent 1% Tween80/2% HPMC/97% water) of the compound to be tested, respectively; 5 min, 15 min, 30 min, 1 hour, 2 hours, 4 hours, 6 hours, 8 hours, 24 hours after administration, blood was collected from the orbital vein, and each sample was collected at approximately 0.20 mL, anticoagulated with sodium heparin, placed on ice after collection, and centrifuged within 1 hour to separate the plasma for measurement. Plasma drug concentration in plasma was detected by liquid chromatography tandem mass spectrometry (LC/MS/MS) to calculate pharmacokinetic parameters. The results are shown in Tables 17 and 18.

TABLE 17

Pharmacokinetics of intravenous administration (1 mg/kg)

| Compound | T$_{1/2}$ (hr) | AUC$_{inf}$ (ng*hr/mL) | Vz (mL/Kg) | Cl (mL/min/kg) |
|---|---|---|---|---|
| AMG 510 | 0.26 | 176.19 | 2159.04 | 94.59 |
| Compound 3B-2 | 5.99 | 2333.44 | 3706.60 | 7.14 |
| Compound 29B | 1.43 | 368.33 | 5615.42 | 45.25 |
| Compound 27C | 1.76 | 519.01 | 4893.44 | 32.11 |

TABLE 18

Pharmacokinetics of intragastric administration (5 mg/kg)

| Compound | T$_{1/2}$ (hr) | C$_{max}$ (ng/mL) | AUC$_{inf}$ (ng*hr/mL) | F (%) |
|---|---|---|---|---|
| AMG 510 | 0.57 | 177.00 | 155.14 | 17.61 |
| Compound 3B-2 | 3.96 | 746.67 | 1984.18 | 17.01 |
| Compound 29B | 1.06 | 108.72 | 421.20 | 22.87 |
| Compound 27C | 1.78 | 133.67 | 526.88 | 20.30 |

Conclusion: It can be seen that the compound of the present disclosure has good pharmacokinetic absorption in mice and has pharmacokinetic advantages.

Experiment Embodiment 4 Xenograft Experiments

Nu/Nu Nude female mice (n=7-10) were housed with five animals per cage and given free access to tap water and commercial rat food (Harlan Teklad 22/5 Rodent Feed-8640). Cell line xenograft experiments were performed to make NCI-H358 tumor grow in mice. Once the tumor size reached 300 mm$^3$, the animals were randomly divided and treated with vehicle control (1% Tween80+1% HPMC) or compound (the doses were 10 mg/kg/day, 30 mg/kg/day and 100 mg/kg/day, respectively, orally). The tumor volume was calculated using equation) 0.5× length×width×width. At the end of the experiment, the animals were killed, the tumors were collected, weighed, and stored for additional analysis.

Figure 2:
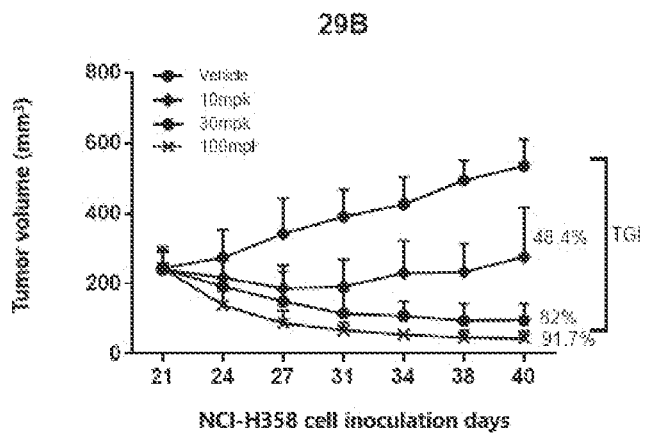
FIG. 2 is a graph showing the relationship between the inoculation days of NCI-H358 cells and the change of tumor volume after administration of compound 29B of embodiment according to an embodiment of the present disclosure.

Wherein, the results of body weight changes in mice after the administration of compound 29B were shown in FIG. 1, and the results of tumor volume changes were shown in FIG. 2.

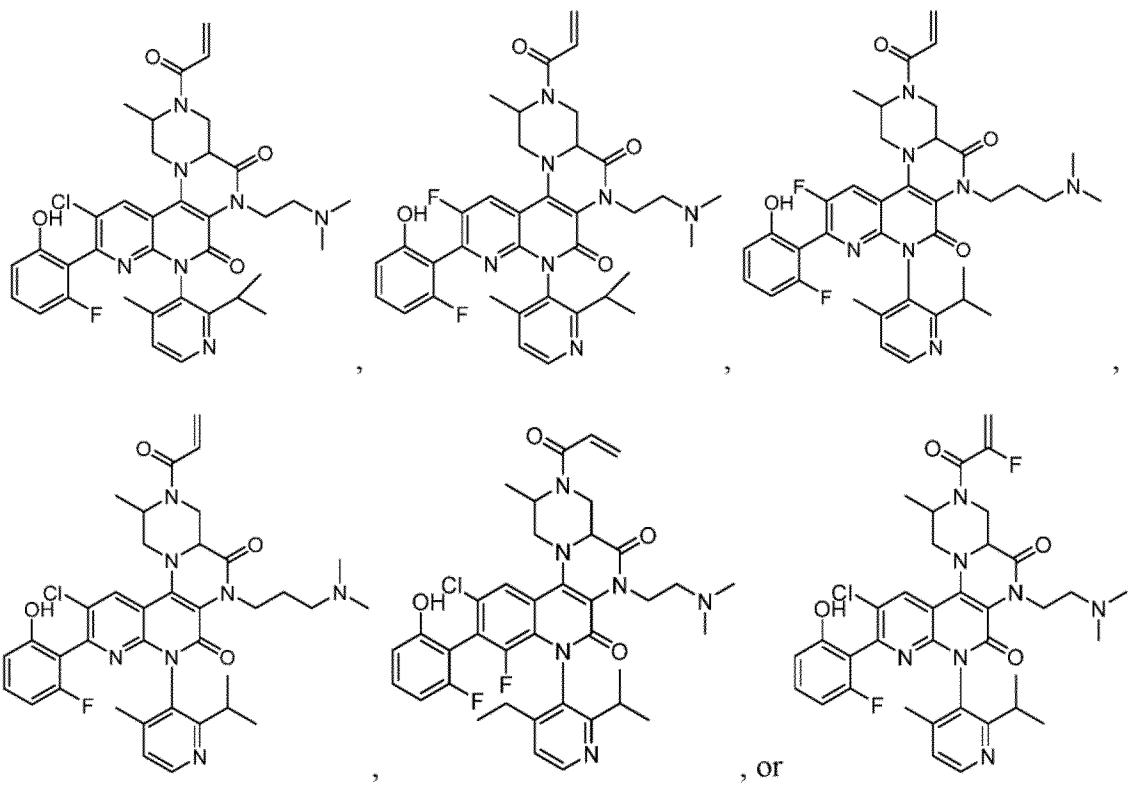

What is claimed is:

1. A compound, an optical isomer thereof or the pharmaceutically acceptable salt thereof, the compound having a structure of formula I-1:

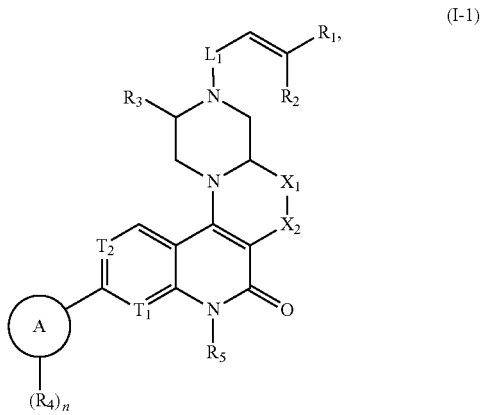

(I-1)

693
-continued (I-2)

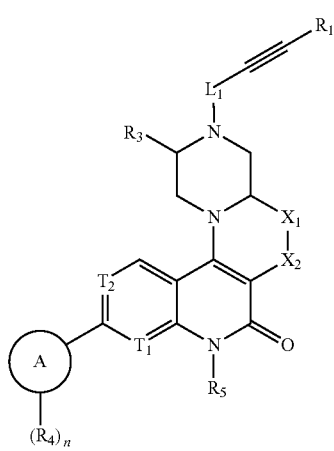

wherein,
$R_1$, $R_2$ are H;
$R_3$ is $CH_3$;
$R_4$ is H, halogen, OH, and $C_{1-6}$ alkyl;
$R_5$ is selected from phenyl, naphthyl, and 5-10 membered heteroaryl, wherein the phenyl, naphthyl, or 5-10 membered heteroaryl is optionally substituted by 1, 2 or 3 R;
$L_1$ is selected from —C(=O)—, —S(=O)- and —S(=O)$_2$—;
$T_1$ is N;
$T_2$ is —C($R_8$)—;
$R_8$ is halogen;
ring A is $C_{6-10}$ aryl;
n is 0, 1, 2, 3 or 4;
$X_1$ is —C(=O)—, and $X_2$ is —N($R_6$);
$R_6$ is selected from

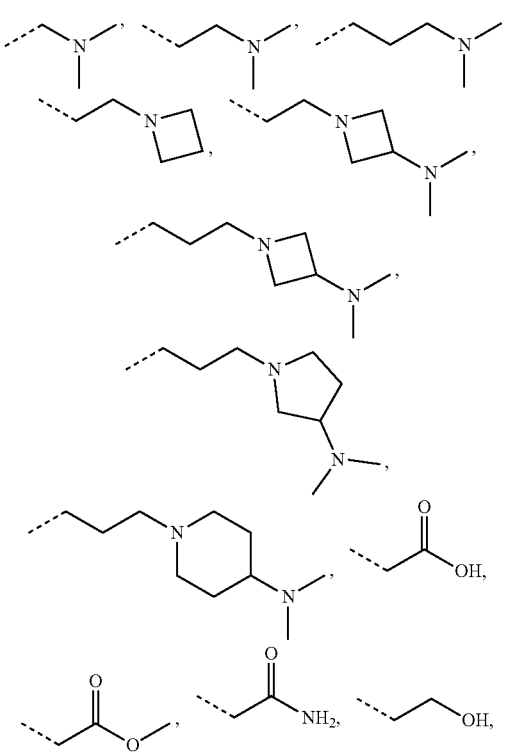

694
-continued

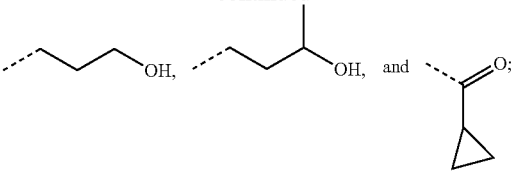

each R is independently selected from halogen, OH, $C_{1-6}$ alkyl, optionally substituted by 1, 2 or 3 R', wherein R' is selected from F, Cl, Br, I, OH, $NH_2$ and $CH_3$;
the 5-10 membered heteroaryl of $R^5$ comprises 1, 2, or 3 heteroatoms or heteroatomic groups independently selected from —O—, —NH—, —S—, and N.

2. The compound, the optical isomer thereof or the pharmaceutically acceptable salt thereof of claim 1, wherein, each R is independently halogen or $C_{1-3}$ alkyl.

3. The compound, the optical isomer thereof or the pharmaceutically acceptable salt thereof of claim 2, wherein, each R is independently selected from F, Cl, Br, I, and $CH_3$.

4. The compound, the optical isomer thereof or the pharmaceutically acceptable salt thereof of claim 1, wherein, each $R_4$ is independently selected from F, Cl, Br, I, OH, and $CH_3$.

5. The compound, the optical isomer thereof or the pharmaceutically acceptable salt thereof of claim 1, wherein, ring A is phenyl, naphthyl, pyridinyl, pyrimidinyl, pyridazinyl, or pyrazinyl, wherein the phenyl, naphthyl, pyridinyl, pyrimidinyl, pyridazinyl, or pyrazinyl is optionally substituted by 1, 2, 3 or 4 $R_4$.

6. The compound, the optical isomer thereof or the pharmaceutically acceptable salt thereof of claim 1, wherein, the structural moiety

is selected from

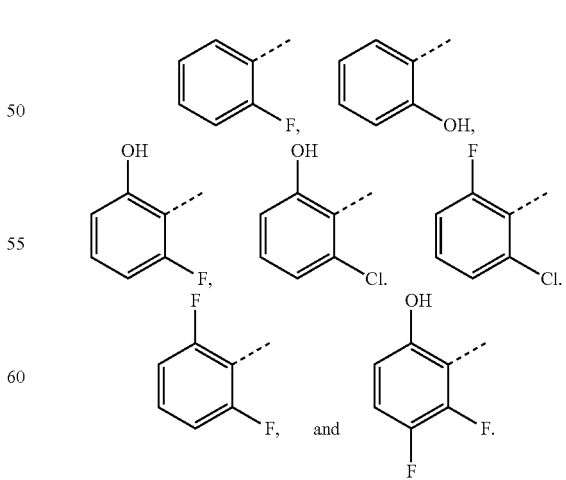

7. The compound, the optical isomer thereof or the pharmaceutically acceptable salt thereof of claim 1, wherein, R₅ is pyridinyl or pyrimidinyl, and the pyridinyl or pyrimidinyl is substituted by 1, 2 or 3 R.

8. The compound, the optical isomer thereof or the pharmaceutically acceptable salt thereof of claim 7, wherein, R₅ is selected from

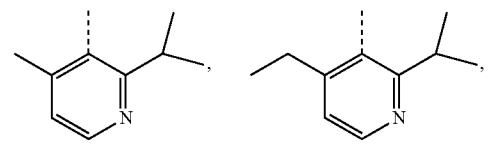

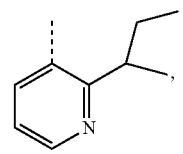

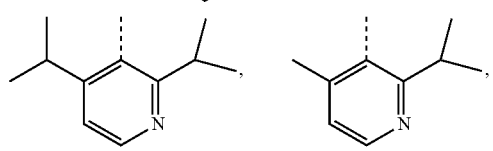

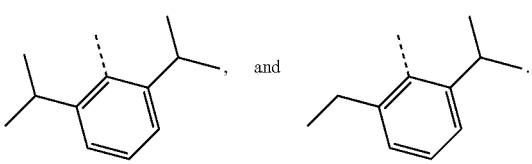

9. The compound, the optical isomer thereof or the pharmaceutically acceptable salt thereof of claim 1, wherein, the structural moiety

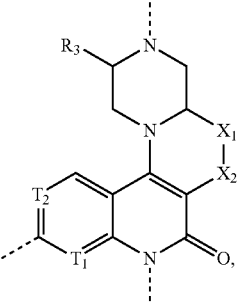

is selected from

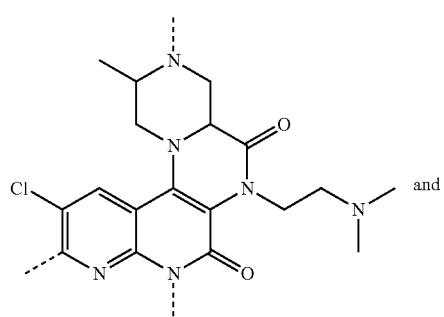

and

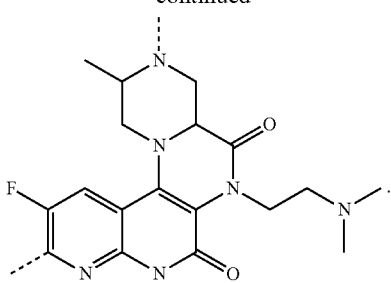

10. The compound of claim 1, or an optical isomer or pharmaceutically acceptable salt thereof, wherein the compound has one of the structures:

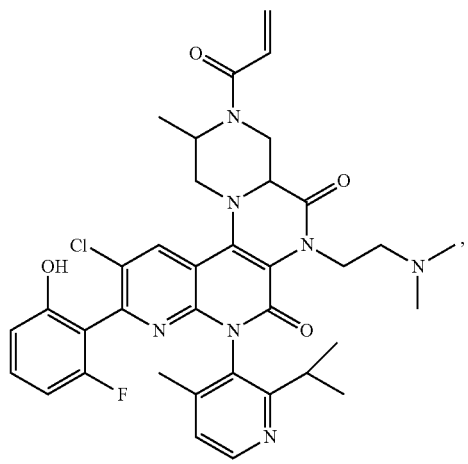

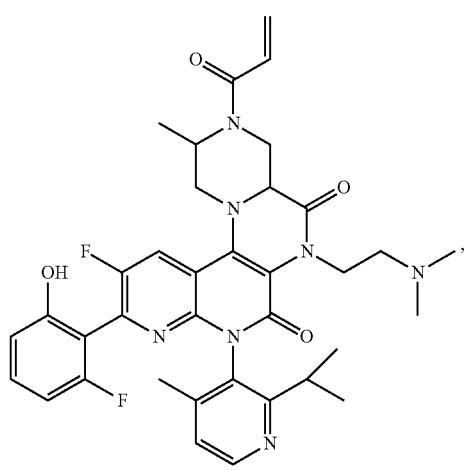

697

-continued

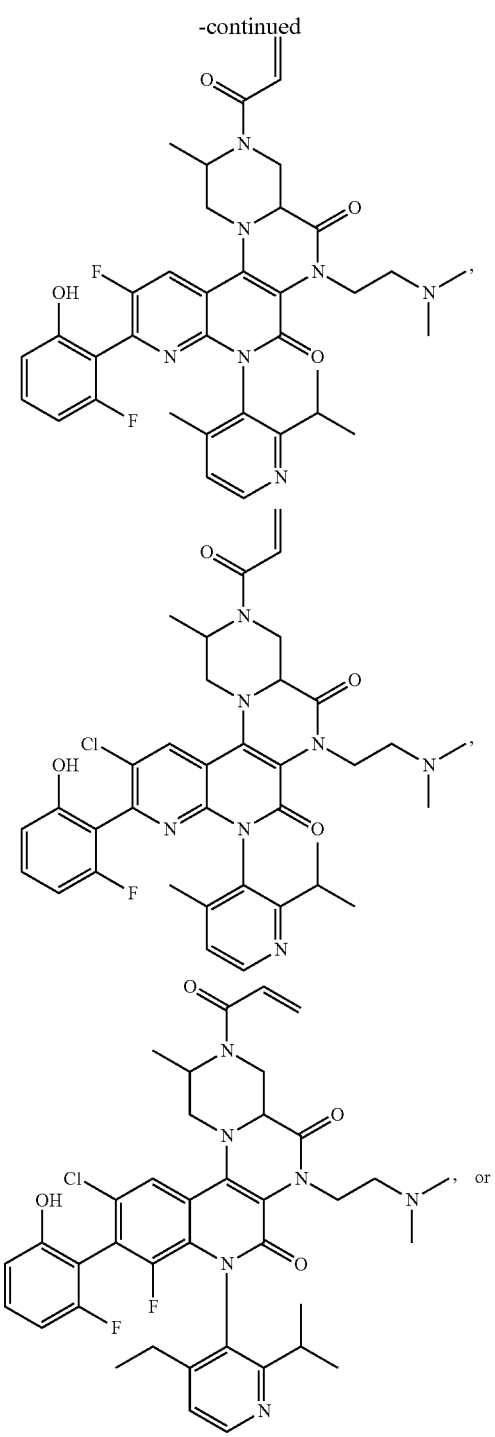

698

-continued

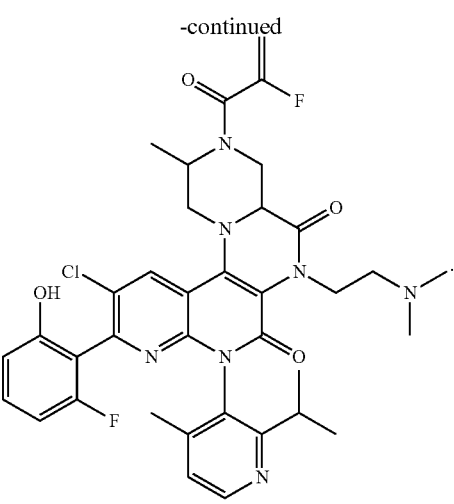

11. The compound of claim 1, wherein the compound has the structure:

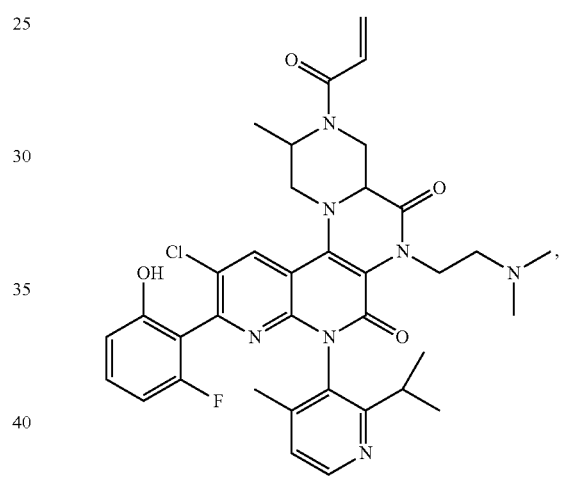

or an optical isomer or pharmaceutically acceptable salt thereof.

12. A pharmaceutical composition comprising the compound, the optical isomer or the pharmaceutically acceptable salt thereof as defined in claim 11, and one or more pharmaceutically acceptable carriers, diluents or excipients.

13. A pharmaceutical composition, comprising the compound, the optical isomer or the pharmaceutically acceptable salt thereof as defined in claim 1, and one or more pharmaceutically acceptable carriers, diluents or excipients.

* * * * *

UNITED STATES PATENT AND TRADEMARK OFFICE
CERTIFICATE OF CORRECTION

Page 1 of 4

PATENT NO.       : 12,122,787 B2
APPLICATION NO.  : 18/101515
DATED            : October 22, 2024
INVENTOR(S)      : Shuchun Guo et al.

It is certified that error appears in the above-identified patent and that said Letters Patent is hereby corrected as shown below:

In the Claims

Column 692, Line 41, cancel the text beginning with "1. A compound, an optical isomer thereof or the" to and ending with "selected from —O—, —NH—, —S—, and N." in Column 694, Line 15, replace Claim 1 with the following claim:

1. A compound, an optical isomer thereof or the pharmaceutically acceptable salt thereof, the compound having a structure of formula I-1:

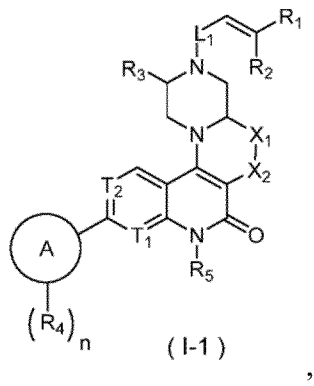

wherein,
$R_1$, $R_2$ are H;
$R_3$ is $CH_3$;
$R_4$ is independently selected from H, halogen, OH, and $C_{1-6}$ alkyl,
$R_5$ is selected from phenyl, naphthyl, and 5-10 membered heteroaryl, wherein the phenyl, naphthyl, or 5-10 membered heteroaryl is optionally substituted by 1, 2 or 3 R;
$L_1$ is selected from -C(=O)-, -S(=O)- and -S(=O)$_2$-;
$T_1$ is N;
$T_2$ is -C($R_8$) -;
$R_8$ is halogen;
ring A is $C_{6-10}$ aryl;
n is 0, 1, 2, 3 or 4;

Signed and Sealed this
Twenty-fifth Day of February, 2025

Coke Morgan Stewart
*Acting Director of the United States Patent and Trademark Office*

$X_1$ is –C(=O)–, and $X_2$ is -N($R_6$)-;
$R_6$ is selected from

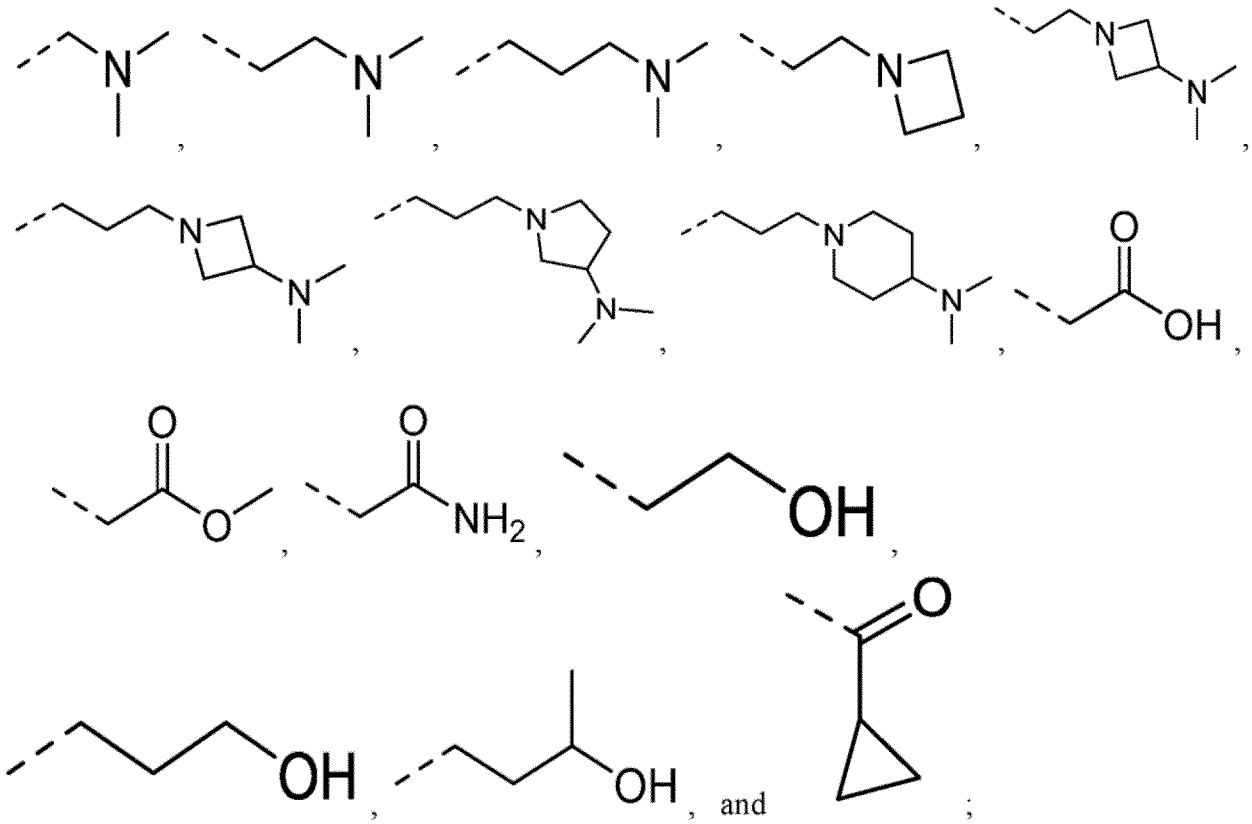

and each R is independently selected from halogen, OH, C1-6 alkyl, optionally substituted by 1, 2 or 3 R', wherein
R' is selected from F, Cl, Br, I, OH, $NH_2$ and $CH_3$;
the 5-10 membered heteroaryl of $R_5$ comprises 1, 2, or 3 heteroatoms or heteroatomic groups independently selected from -O-, -NH-, -S-, and N.

Column 695, Line 3, cancel the text beginning with "8. The compound, the optical isomer thereof or the pharmaceutically acceptable salt thereof of claim 7, wherein, $R_5$ is selected from" to and ending with " 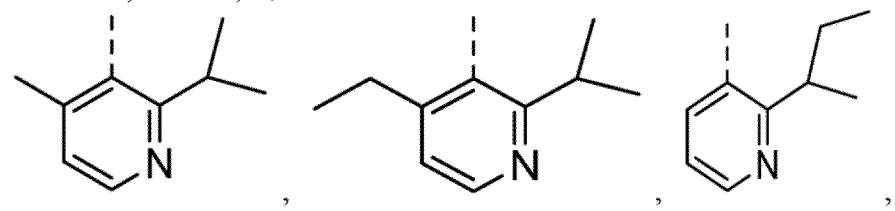 " in Column 695, Line 30, replace Claim 8 with the following claim:

8. The compound, the optical isomer thereof or the pharmaceutically acceptable salt thereof of claim 7, wherein, $R_5$ is selected from

CERTIFICATE OF CORRECTION (continued)
U.S. Pat. No. 12,122,787 B2

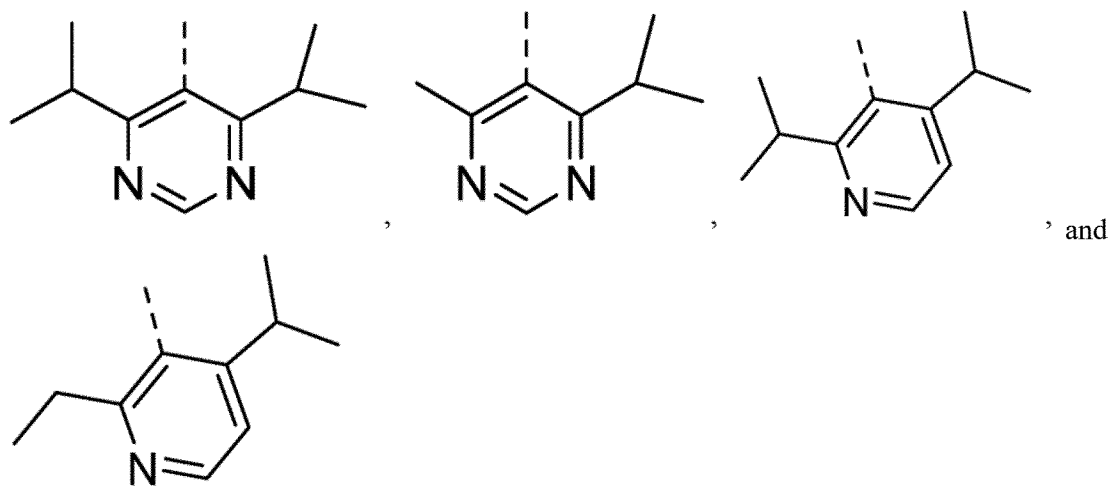

Column 696, Line 15, cancel the text beginning with "10. The compound of claim 1, or an optical isomer or pharmaceutically acceptable salt thereof, wherein the compound has one of the structures:"

to and ending with " 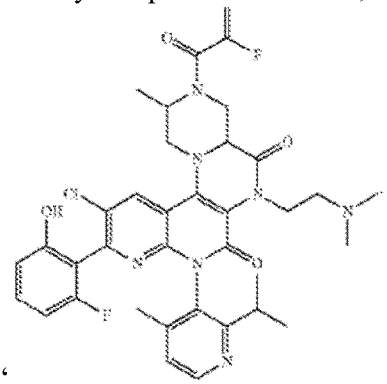 " in Column 698, Line 20, replace Claim 10 with the following claim:

10. The compound of claim 1, or an optical isomer or pharmaceutically acceptable salt thereof, wherein the compound has one of the structures:

CERTIFICATE OF CORRECTION (continued)
U.S. Pat. No. 12,122,787 B2